US011495747B2

(12) United States Patent
Lee et al.

(10) Patent No.: US 11,495,747 B2
(45) Date of Patent: Nov. 8, 2022

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Yun Suk Lee, Cheonan-si (KR); Yu Ri Kim, Cheonan-si (KR); Min Ji Jo, Cheonan-si (KR); Jung Hwan Park, Cheonan-si (KR); Bum Sung Lee, Cheonan-si (KR); Sun Hee Lee, Cheonan-si (KR); Soung Yun Mun, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 372 days.

(21) Appl. No.: 16/720,758

(22) Filed: Dec. 19, 2019

(65) Prior Publication Data

US 2020/0203623 A1 Jun. 25, 2020

(30) Foreign Application Priority Data

Dec. 20, 2018 (KR) ........................ 10-2018-0166463
Apr. 29, 2019 (KR) ........................ 10-2019-0049991
Apr. 29, 2019 (KR) ........................ 10-2019-0050099

(51) Int. Cl.
*H01L 51/00* (2006.01)
*C07D 405/10* (2006.01)
(Continued)

(52) U.S. Cl.
CPC ........ *H01L 51/0067* (2013.01); *C07D 405/10* (2013.01); *C07D 405/14* (2013.01);
(Continued)

(58) Field of Classification Search
None
See application file for complete search history.

(56) References Cited

U.S. PATENT DOCUMENTS 10,361,380 B2 7/2019 Kim et al.
2014/0225072 A1 8/2014 Kim et al.
(Continued)

FOREIGN PATENT DOCUMENTS

CN 106749132 A 5/2017
CN 106946859 A 7/2017
(Continued)

OTHER PUBLICATIONS

Machine translation of CN-108912063, translation generated Jan. 2022, 17 pages. (Year: 2022).*
(Continued)

*Primary Examiner* — Robert S Loewe
(74) *Attorney, Agent, or Firm* — Vorys, Sater, Seymour and Pease LLP; Mih Suhn Koh

(57) ABSTRACT

Provided are a compound of Formula 1; an organic electric element comprising a first electrode, a second electrode, and an organic material layer formed between the first electrode and the second electrode, comprising a mixture of a compound of Formula 1 and a compound of Formula 2, or comprising a compound of Formula 3, a subgenus of Formula 1, in the organic material layer; and an electronic device comprising the element, which has lowered driving voltage and increased luminous efficiency and life time.

27 Claims, 3 Drawing Sheets

(51) Int. Cl.

| | |
|---|---|
| ***C07D 405/14*** | (2006.01) |
| ***C07D 409/14*** | (2006.01) |
| ***C09K 11/02*** | (2006.01) |
| *H01L 51/50* | (2006.01) |

(52) U.S. Cl.

CPC .......... *C07D 409/14* (2013.01); *C09K 11/025* (2013.01); *H01L 51/006* (2013.01); *H01L 51/0059* (2013.01); *H01L 51/0061* (2013.01); *H01L 51/0073* (2013.01); *H01L 51/0074* (2013.01); *H01L 51/0056* (2013.01); *H01L 51/5016* (2013.01); *H01L 51/5056* (2013.01); *H01L 51/5072* (2013.01)

(56) References Cited

U.S. PATENT DOCUMENTS

| | | | | |
|---|---|---|---|---|
| 2015/0001489 | A1* | 1/2015 | Lee | H01L 51/0067 257/40 |
| 2015/0034923 | A1* | 2/2015 | Kim | H01L 27/3209 257/40 |
| 2015/0076459 | A1* | 3/2015 | Choi | H01L 51/0087 257/40 |
| 2015/0318508 | A1* | 11/2015 | Kim | H01L 51/5072 257/40 |
| 2016/0079546 | A1 | 3/2016 | Park et al. | |
| 2016/0133880 | A1* | 5/2016 | Lee | H01L 51/5281 257/40 |
| 2016/0149141 | A1* | 5/2016 | Jung | H01L 51/0073 257/40 |
| 2018/0097184 | A1* | 4/2018 | Lee | C07D 401/12 |
| 2018/0166644 | A1* | 6/2018 | Youn | H01L 51/0097 |
| 2020/0251659 | A1* | 8/2020 | Lee | H01L 51/0074 |

FOREIGN PATENT DOCUMENTS

| | | | | |
|---|---|---|---|---|
| CN | 108912063 | A * | 11/2018 | C07D 251/24 |
| CN | 108912063 | A | 11/2018 | |
| EP | 3 020 708 | A1 | 5/2016 | |
| EP | 3 351 537 | A1 | 7/2018 | |
| JP | 2018-65798 | A | 4/2018 | |
| KR | 10-2016-0055556 | A | 5/2016 | |
| KR | 10-1789998 | B1 | 10/2017 | |
| KR | 10-2017-0130737 | A | 11/2017 | |
| KR | 10-2017-0134264 | A | 12/2017 | |
| KR | 10-2018-0022574 | A | 3/2018 | |
| KR | 10-1847347 | B1 | 4/2018 | |
| KR | 10-1857632 | B1 | 5/2018 | |
| KR | 10-2019-0038246 | A | 4/2019 | |
| WO | 2018/038463 | A1 | 3/2018 | |

OTHER PUBLICATIONS

Japanese Office Action dated Dec. 8, 2020, 6 pages, for corresponding JP application No. 2019-230549.

Partial European Search Report for EP 19217541 2, 12 pages, dated Apr. 17, 2020.

Prioritized Examination Report for KR 10-2020-0015902, 8 pages, dated Feb. 18, 2020.

Notice of Allowance issued in corresponding Japanese Patent Application No. 2019-230549 dated Mar. 30, 2021, 2 pages.

Notice of Allowance dated Sep. 5, 2019, in corresponding KR Patent Application No. 10-2019-0050099, three pages.

Prioritized Examination Report dated May 13, 2019, in corresponding KR Patent Application No. 10-2019-0050099, two pages.

Notice of Allowance from corresponding KR Application No. 10-2019-0049991, dated May 6, 2022, 2 pages.

* cited by examiner

[Table 11]

| |
|---|
| 4-naphthobenzofuran derivative |
|  |
| 1-naphthobenzofuran derivative (the present invention) |
|  |

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This application is a Non-Provisional Application which claims the benefit of priority from Korean Patent Application No. 10-2018-0166463, filed on Dec. 20, 2018, Korean Patent Application Nos. 10-2019-0049991 and 10-2019-0050099, filed on Apr. 29, 2019, the contents of each of which are incorporated herein by reference in its entirety.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure each composed of different materials in order to improve efficiency and stability of an organic electric element, and for example, may include a hole injection layer, a hole transport layer, a light emitting layer, an electron transport layer, an electron injection layer, or the like.

A material used in an organic material layer of an organic electric element may be classified into a light emitting material and a charge transport material, such as a hole injection material, a hole transport material, an electron transport material, an electron injection material and the like depending on its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to the deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more and more as size of display becomes larger and larger in the portable display market. Therefore, the power consumption is a very important factor in the portable display with a limited power source of the battery, and the situation is such that efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective organic material layer is given.

Therefore it is required to develop a light emitting material that has high thermal stability and can achieve efficiently a charge balance in the light-emitting layer. That is, in order to allow an organic electric element to fully exhibit the above-mentioned excellent features, the material consisting an organic material layer of the element such as a hole injection material, a hole transport material, a light emitting material, an electron transport material, an electron injection material, or the like should be prerequisite to support by a stable and efficient material, and among them, it is necessary to develop host material for a light emitting layer.

Object, Technical Solution and Effects of the Invention

The present invention is to provide a compound lowering driving voltage of the element, improving luminous efficiency and lifetime of the element, an organic electric element comprising the same, and an electronic device thereof.

In an aspect of the present invention, the present invention provides an organic electric element comprising the compounds represented by the following formulas 1 and 2 and an electric device thereof.

<Formula 1>

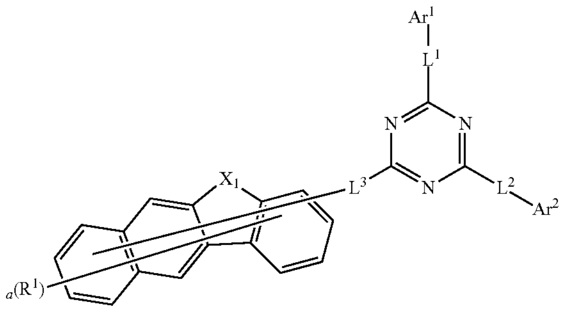

-continued

<Formula 2>

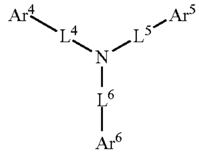

In another aspect of the present invention, the present invention provides the compound represented by the following formula 3, an organic electric element comprising the compound and an electric device thereof.

<Formula 3>

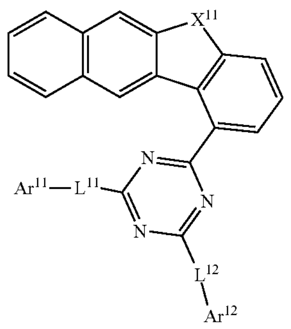

Further, in another aspect of the present invention, the present invention provides an organic electric element comprising the compound represented by formula 3 above and the compound represented by the following formula 4 and an electric device thereof.

<Formula 4>

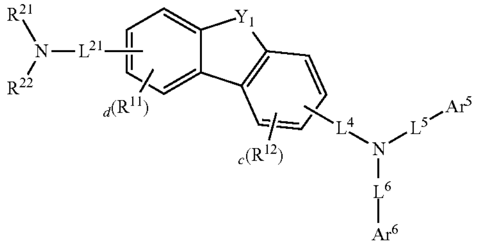

By using the mixture of the compounds represented by formulas 1 and 2 above or by using the compound represented by formula 3, wherein formula 3 is comprised in formula 1, as host of a light emitting layer, the driving voltage of an element can be lowered and the luminous efficiency and lifetime of an element can be improved.

BRIEF DESCRIPTION OF THE DRAWINGS

The FIGS. 1 to 3 illustrate an example of an organic electroluminescent element according to an embodiment of the present invention: 100, 200, 300 are an organic electric element, 110 is a first electrode, 120 is a hole injection layer, 130 is a hole transport layer, 140 is a light emitting layer, 150 is an electron transport layer, 160 is an electron injection layer, 170 is a second electrode, 180 is a light efficiency improving layer, 210 is a buffer layer, 220 is an emission-auxiliary layer, 320 is a first hole injection layer, 330 is a first hole transport layer, 340 is a first light emitting layer, 350 is a first electron transport layer, 360 is a first charge generation layer, 361 is a second charge generation layer, 420 is a second hole injection layer, 430 is a second hole transport layer, 440 is a second light emitting layer, 450 is a second electron transport layer, CGL is a charge generation layer, ST1 is a first stack and ST2 is a second stack.

DETAILED DESCRIPTION

Figure 1:
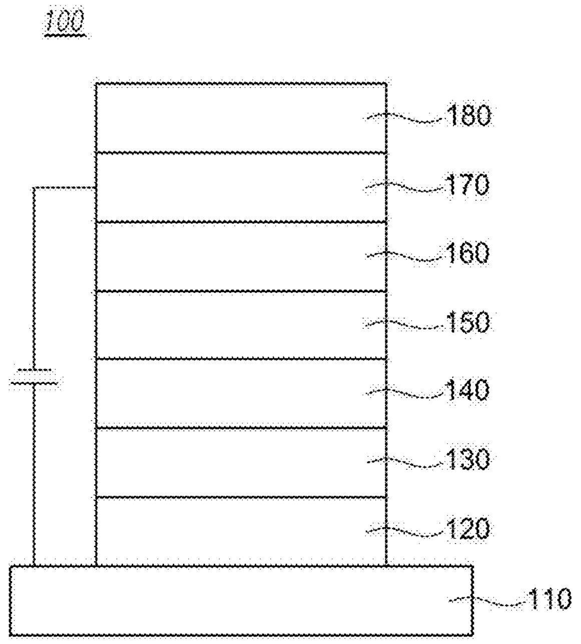

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, Spiro compounds and the like. In addition, unless otherwise stated, a fluorenyl group may be comprised in an aryl group and a fluorenylene group may be comprised in an arylene group Unless otherwise stated, the term "fluorenyl group" or "fluorenylene group" as used herein means "substituted or unsubstituted fluorenyl group" "substituted or unsubstituted fluorenylene group", respectively. "Fluorenyl group" or "fluorenylene group" as used herein may be represented by the following formula, wherein R, R' and R" may be hydrogen or a substituent other than hydrogen and R and R' are linked to each other to form the spiro compound together with the carbon to which they are bonded.

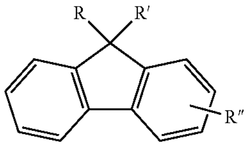

The term "spiro compound" as used herein has a Spiro union which means union having one atom as the only common member of two rings. The common atom is designated as 'Spiro atom'. The compounds are defined as 'monospiro-', 'dispiro' or 'trispiro-' depending on the number of Spiro atoms in one compound.

The term "heterocyclic group" as used herein means a non-aromatic ring as well as an aromatic ring like "heteroaryl group" or "heteroarylene group", and unless otherwise stated, it means a ring comprising one or more heteroatoms and having 2 to 60 carbon atoms, but not limited thereto. Unless otherwise stated, the term "hetero atom" as used herein represents N, O, S, P or Si, and the heterocyclic group means a monocytic form, ring assemblies, a fused polycyclic system or a spiro compound comprising heteroatom(s). Also, "heterocyclic group" may comprise the compound comprising a heteroatom group such as $SO_2$, P═O etc. instead of carbon forming a ring, such as the following compound.

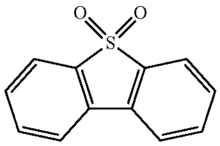 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, Spiro compounds, and the like, and unless otherwise specified, it means a ring of 3 to 60 carbon atoms, but not limited thereto.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

In addition, in the present specification, the numbers and alphabets indicating a position may be omitted when describing a compound name or a substituent name, For example, pyrido[4,3-d]pyrimidine, benzopuro[2,3-d]pyrimidine and 9,9-dimethyl-9H-fluorene can be described as pyridopyrimidine, benzofurropyrimidine and dimethylfluorene, respectively. Therefore, both benzo[g]quinoxaline and benzo[f] quinoxaline can be described as benzoquinoxaline.

In addition, unless otherwise expressed, where any formula of the present invention is represented by the following formula, the substituent according to the index may be defined as follows.

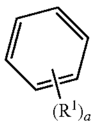

In the above formula, where a is an integer of zero, the substituent $R^1$ is absent, that is, hydrogen atoms are bonded to all the carbon constituting the benzene ring. Here, chemical formulas or compounds may be written without explicitly describing the hydrogen. In addition, one substituent $R^1$ is bonded to any carbon of the carbons forming the benzene ring when "a" is an integer of 1. Similarly, where "a" is an integer of 2 or 3, substituents $R^1$s may be bonded to the carbon of the benzene ring, for example, as followings. Also, where "a" is an integer of 4 to 6, substituents $R^1$s are bonded to the carbon of the benzene ring in a similar manner. Further, where "a" is an integer of 2 or more, $R^1$s may be the same or different from each other.

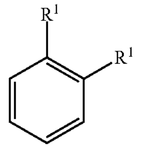

(a = 2)

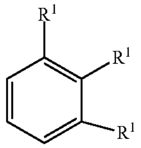

(a = 3)

In addition, unless otherwise stated, the ring formed by combining adjacent groups to each other may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring formed by a $C_3$-$C_{60}$ aliphatic ring and a $C_6$-$C_{60}$ aromatic ring group and a combination thereof.

Hereinafter, referring to FIGS. 1-3, a lamination structure of an organic electric element including the compound of the present invention will be described.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It will be understood that the expression "one component is "connected," "coupled" or "joined" to another component" comprises the case where a third component may be "connected," "coupled," and "joined" between the first and second components as well as the case where the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

Figure 2:
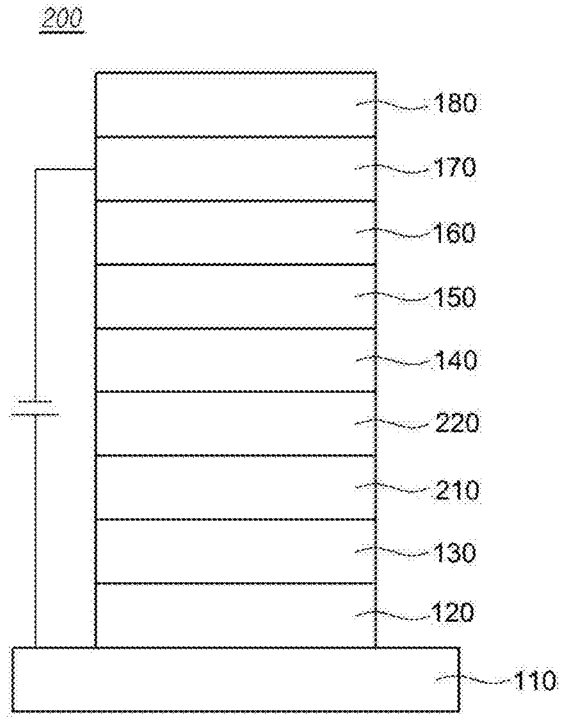
Figure 3:
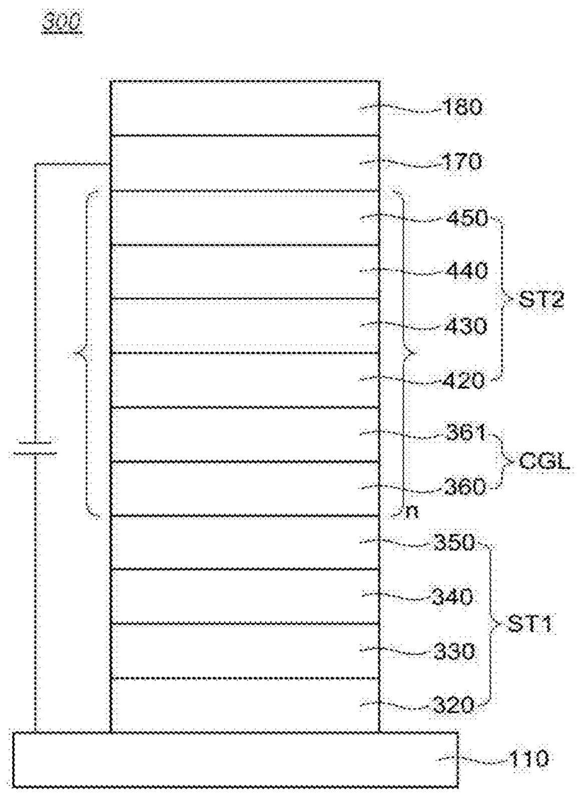

The FIGS. 1-3 are laminated structures for showing an example of an organic electric element according to an embodiment of the present invention, respectively.

Referring to the FIG. 1, an organic electric element 100 according to an embodiment of the present invention includes a first electrode 110 formed on a substrate (not shown), a second electrode 170, and an organic material layer formed between the first electrode 110 and the second electrode 170.

The first electrode 110 may be an anode (positive electrode), and the second electrode 170 may be a cathode (negative electrode). In the case of an inverted organic electric element, the first electrode may be a cathode, and the second electrode may be an anode.

The organic material layer may comprised a hole injection layer 120, a hole transport layer 130, a light emitting layer 140, an electron transport layer 150, and an electron injection layer 160. Specifically, a hole injection layer 120, a hole transport layer 130, a light emitting layer 140, an electron transport layer 150, and an electron injection layer 160 are formed on the first electrode 110 in sequence.

Preferably, a layer for improving the luminous efficiency 180 may be formed one side of sides of the first electrode 110 and the second electrode 170, wherein one side is not facing the organic material layer, as a result the luminous efficiency of an organic electric element can be improved.

For example, the light efficiency improving layer 180 may be formed on the second electrode 170, as a result, in the case of a top emission organic light emitting diode, the optical energy loss due to surface plasmon polaritons (SPPs) at the second electrode 170 may be reduced and in the case of a bottom emission organic light emitting diode, the light efficiency improving layer 180 may serve as a buffer for the second electrode 170.

Meanwhile, a buffer layer 210 or an emission-auxiliary layer 220 may be further formed between the hole transport layer 130 and the light emitting layer 140, which will be described with reference to FIG. 2.

Referring to FIG. 2, the organic electric element 200 according to another embodiment of the present invention may comprise a hole injection layer 120, a hole transport layer 130, a buffer layer 210, an emission-auxiliary layer 220, a light emitting layer 140, the electron transport layer 150, the electron injection layer 160, and a second electrode 170 formed on a first electrode 110 in sequence, and a light efficiency improving layer 180 is formed on the second electrode 170.

Although not shown in FIG. 2, an electron transport auxiliary layer may be further formed between the light emitting layer 140 and the electron transport layer 150.

In addition, according to another embodiment of the present invention, the organic material layer may be a form formed by a plurality of stacks, wherein the stacks comprise a hole transport layer, a light emitting layer, and an electron transport layer, respectively. This will be described with reference to FIG. 3.

Referring to FIG. 3, two or more sets of stacks of the organic material layers ST1 and ST2 may be formed between the first electrode 110 and the second electrode 170 in the organic electric element 300 according to another embodiment of the present invention, wherein the organic material layers are consisted of multiple layers, respectively, and the charge generation layer CGL may be formed between the stacks of the organic material layer.

Specifically, the organic electric element according to the embodiment of the present invention may comprise the first electrode 110, the first stack ST1, the charge generation layer CGL, the second stack ST2, and the second electrode 170 and the light efficiency improving layer 180.

The first stack ST1 is an organic layer formed on the first electrode 110, and the first stack ST1 may comprise the first hole injection layer 320, the first hole transport layer 330, the first light emitting layer 340 and the first electron transport layer 350 and the second stack ST2 may comprise a second hole injection layer 420, a second hole transport layer 430, a second light emitting layer 440 and a second electron transport layer 450. As such, the first stack and the second stack may be the organic layers having the same or different stacked structures.

The charge generation layer CGL may be formed between the first stack ST1 and the second stack ST2. The charge generation layer CGL may comprise a first charge generation layer 360 and a second charge generation layer 361. The charge generating layer CGL is formed between the first light emitting layer 340 and the second light emitting layer 440 to increase the current efficiency generated in each light emitting layer and to smoothly distribute charges.

The first light emitting layer 340 may comprise a light emitting material comprising a blue host doped with a blue fluorescent dopant and the second light emitting layer 440 may comprise a light emitting material comprising a green host doped with a greenish yellow dopant and a red dopant together, but the material of the first light emitting layer 340 and the second light emitting layer 440 according to an embodiment of the present invention is not limited thereto.

In FIG. 3, n may be an integer of 1 to 5 and the charge generation layer CGL and the third stack may be further stacked on the second stack ST2 when n is 2.

When a plurality of light emitting layers are formed in a multi-layer stack structure as shown in FIG. 3, it is possible to manufacture an organic electroluminescent element that emits not only white light but also various colors, wherein the white light is emitted by the mixing effect of light emitted from each light emitting layer.

The mixture of the compound represented by Formula 1 and the compound represented by Formula 2, or the compound represented by Formula 3 comprised in Formula 1 can be used as material of a hole injection layer 120, 320, 420, a hole transport layer 130, 330, 430, a buffer layer 210, an emission-auxiliary layer 220, an electron transport layer 150, 350, 450, an electron injection layer 160, a light emitting layer 140, 340, 440, or a layer for improving luminous efficiency 180, preferably as material of an emission-auxiliary layer 220, a light emitting layer 140, 340, 440 or a layer for improving luminous efficiency 180, more preferably, as host material of a light emitting layer 140, 340, 440.

Even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, energy level and $T_1$ value between the respective layers of the organic material layer, inherent material properties (mobility, interfacial properties, etc.) and the like can be optimized by using the mixture of the compound represented by Formula 1 and the compound represented by Formula 2, or by using the compound represented by Formula 3 comprised in Formula 1 as material of a light emitting layer 140, 340, 440 and/or an emission-auxiliary layer 220, and thus it is possible to simultaneously improve the lifetime and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 110, forming the organic material layer comprising the hole injection layer 120, the hole transport layer 130, the light emitting layer 140, the electron transport layer 150, and the electron injection layer 160 thereon, and then depositing a material, which can be used as the cathode 170, thereon. Also, an emission-auxiliary layer 220 may be formed between a hole transport layer 130 and a light emitting layer 140, and an electron transport auxiliary layer (not shown) may be further formed between a light emitting layer 140 and an electron transport layer 150 and, as described above, a stack structure may be formed.

Also, the organic material layer may be manufactured in such a manner that the fewer layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to an embodiment of the present invention may be selected from the group consisting of an organic light emitting diode, an organic solar cell, an organic photo conductor, an organic transistor, an element for monochromatic illumination and an element for quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the organic electric element and the compound according to an aspect of the present invention will be described.

The organic electric element according to an aspect of the present invention comprises a first electrode, a second electrode, and an organic material layer formed between the first electrode and the second electrode, wherein the organic material layer comprises a phosphorescent light emitting layer, and the host of the phosphorescent light emitting layer comprises a first compound represented by the following Formula 1 and a second compound represented by the following Formula 2.

<Formula 1>

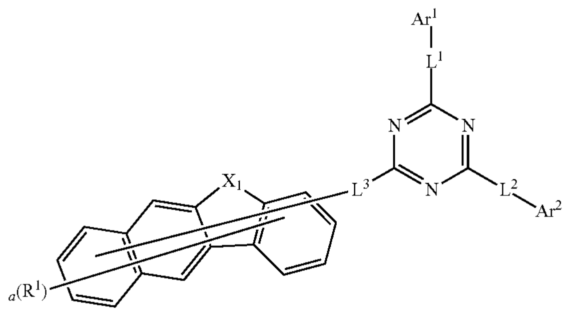

<Formula 2>

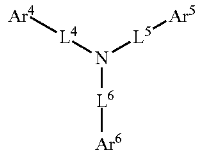

First, Formula 1 will be described.

In the formula 1, each of symbols may be defined as follows.

$X_1$ is O or S.

$Ar^1$ and $Ar^2$ may be each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring group, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group.

Where $Ar^1$ and $Ar^2$ are an aryl group, $Ar^1$ and $Ar^2$ may be preferably a $C_6$-$C_{30}$ aryl group, more preferably a $C_6$-$C_{18}$ aryl group, for example, phenyl, biphenyl, naphthyl, terphenyl, phenanthrene, pyrene, triphenylene, anthracene or the like.

When $Ar^1$ and $Ar^2$ are a heterocyclic group, $Ar^1$ and $Ar^2$ may be preferably a $C_2$-$C_{30}$ heterocyclic group, more preferably a $C_2$-$C_{18}$ heterocyclic group, for example, dibenzothiophene, dibenzofuran, carbazole, phenylcarbazole, benzonaphthofuran, benzonaphthothiophene or the like.

When $Ar^1$ and $Ar^2$ is a fluorenyl group, $Ar^1$ and $Ar^2$ may be 9,9-diphenylfluorene, 9,9-dimethylfluorene or the like.

Where $Ar^1$ and $Ar^2$ are an aliphatic ring group, $Ar^1$ and $Ar^2$ may be preferably a $C_3$-$C_{30}$ aliphatic ring group, more preferably a $C_5$-$C_{12}$ aliphatic ring group, for example, cyclohexane, cyclohexylcyclohexane or the like.

Where $Ar^1$ and $Ar^2$ are an alkyl group, $Ar^1$ and $Ar^2$ may be preferably a $C_1$-$C_{10}$ alkyl group, for example, methyl, t-butyl or the like. Where $Ar^1$ and $Ar^2$ are an alkenyl group, $Ar^1$ and $Ar^2$ may be preferably a $C_2$-$C_{10}$ alkenyl group, for example, ethene, propene or the like.

$L^1$ to $L^3$ may be each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring and a combination thereof.

Where $L^1$ to $L^3$ are each arylene group, $L^1$ to $L^3$ may be preferably a $C_6$-$C_{30}$ arylene group, more preferably a $C_6$-$C_{18}$ arylene group, for example, phenyl, biphenyl, naphthyl, terphenyl or the like. Where $L^1$ to $L^3$ are a heterocyclic group, $L^1$ to $L^3$ may be preferably a $C_2$-$C_{30}$ heterocyclic group, more preferably a $C_2$-$C_{18}$ heterocyclic group, for example, carbazole, phenylcarbazole, dibenzofuran, dibenzothiophene or the like.

$R^1$ may be selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may optionally be linked to each other to form a ring.

a is an integer of 0-9, and where a is an integer of 2 or more, each of a plurality of $R^1$ is the same as or different from each other.

The ring formed by bonding adjacent $R^1$s to each other may be a $C_6$-$C_{60}$ aromatic ring group, a fluorenyl group, a $C_2$-$C_{60}$ heterocyclic group containing at least one heteroatom selected from the group consisting of O, N, S, Si, and P, or a $C_3$-$C_{60}$ aliphatic ring or the like. Where adjacent $R^1$ groups are linked together to each other to form an aromatic ring group, the ring may be preferably a $C_6$-$C_{30}$ aromatic ring group, more preferably a $C_6$-$C_{14}$ aromatic ring group, for example, benzene ring, naphthalene, phenanthrene or the like.

Where $R^1$ is an aryl group, $R^1$ may be preferably a $C_6$-$C_{30}$ aryl group, more preferably a $C_6$-$C_{18}$ aryl group, for example, phenyl, naphthyl, biphenyl, terphenyl, phenanthrene or the like.

L' may be each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof.

$R_a$ and $R_b$ may be each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a combination thereof.

$Ar^1$, $Ar^2$, $L^1$~$L^3$, $R^1$, L', $R_a$, $R_b$, and the ring formed by bonding adjacent $R^1$s to each other may be each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group.

Formula 1 may be represented by one of the following Formula 1-A to Formula 1-G:

<Formula 1-A>

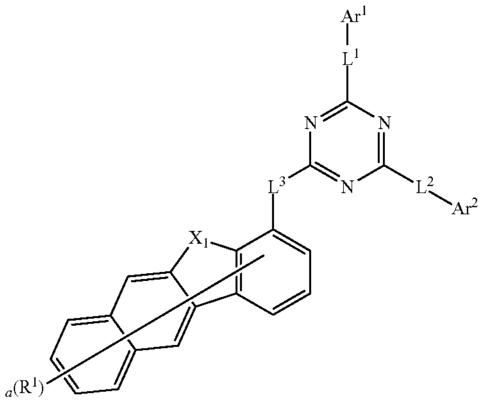

<Formula 1-B>

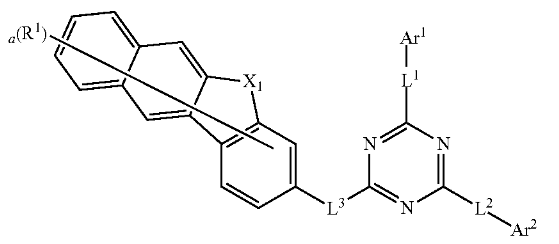

<Formula 1-C>

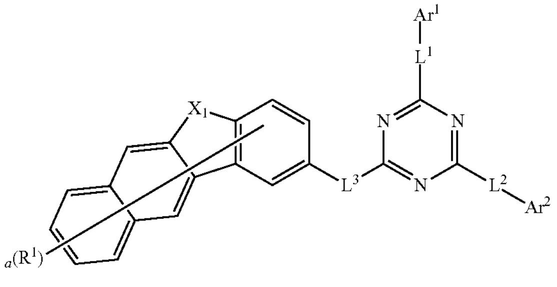

-continued

<Formula 1-D>

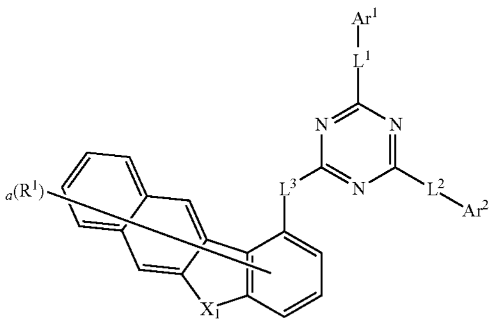

<Formula 1-E>

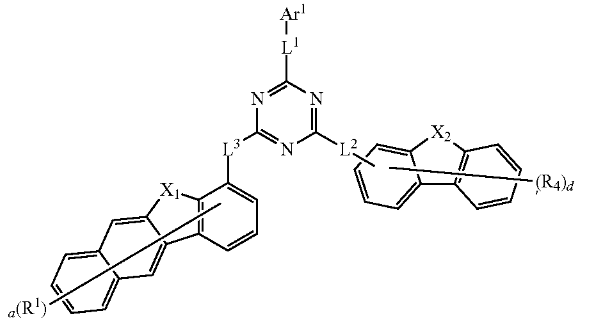

<Formula 1-F>

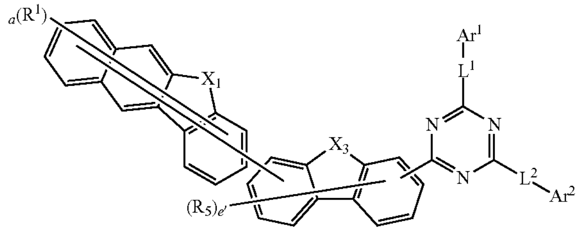

<Formula 1-G>

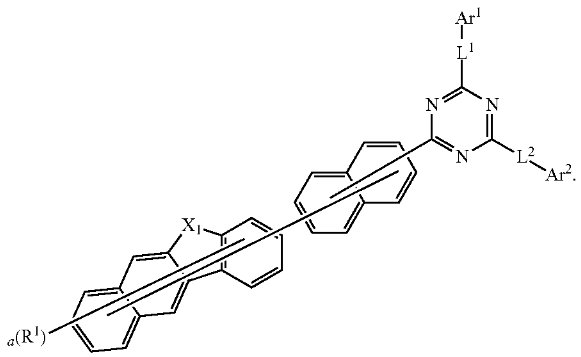

In the formulas 1-A to 1-G, each of symbols may be defined as follows.

$Ar^1$, $Ar^2$, $L^1$~$L^3$, $X_1$, $R^1$ and a are the same as defined in Formula 1. Preferably, in the formulas 1-F and 1-G, $Ar^1$ and $Ar^2$ are different from each other, and preferably, $Ar^1$ and $Ar^2$ may be each independently an aryl group, more preferably naphthyl.

$X_2$ and $X_3$ are each independently O or S.

$R_4$ and $R_5$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, and a $C_6$-$C_{30}$ aryloxy group, and adjacent groups may optionally be linked to each other to form a ring.

The ring formed by bonding adjacent groups to each other' may be a $C_6$-$C_{60}$ aromatic ring group, a fluorenyl group, a $C_2$-$C_{60}$ heterocyclic group containing at least one heteroatom selected from the group consisting of O, N, S, Si, and P, or a $C_3$-$C_{60}$ aliphatic ring or the like. Where adjacent $R_4$ groups or adjacent $R_5$ groups are linked to each other to form an aromatic ring group, the ring may be preferably a $C_6$-$C_{30}$ aromatic ring group, more preferably a $C_6$-$C_{14}$ aromatic ring group, for example, benzene, naphthalene, phenanthrene or the like.

d' is an integer of 0-7, e' is an integer of 0-6, and where they are an integer of 2 or more, respectively, each of a plurality of $R_4$ and each of a plurality of $R_5$ are the same as or different from each other.

Preferably, in the formulas 1-A to 1-G or the like, $Ar^1$, $Ar^2$, $L^1$~$L^3$, $R^1$, $R_4$, $R_5$, and the ring formed by bonding adjacent groups to each other may be each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group.

In addition, preferably, Formula 1 may be represented by the following Formula 3.

<Formula 3>

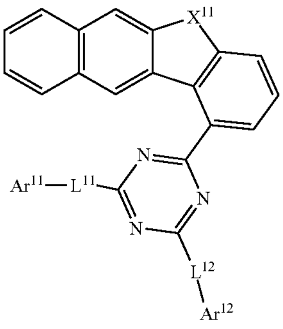

In the formula 3, $X^{11}$ is O or S, $L^{11}$ and $L^{12}$ are each independently a single bond or a $C_6$-$C_{30}$ arylene group, and $Ar^{11}$ and $Ar^{12}$ are each independently $C_6$-$C_{30}$ aryl group.

Where $L^{11}$ and $L^{12}$ are each independently an arylene group, preferably, a $C_6$-$C_{20}$, a $C_6$-$C_{19}$, a $C_6$-$C_{18}$, a $C_6$-$C_{17}$, a $C_6$~$C_{16}$, a $C_6$-$C_{15}$, a $C_6$~$C_{14}$, a $C_6$-$C_{13}$, a $C_6$~$C_{12}$, a $C_6$-$C_{11}$, a $C_6$~$C_{10}$, a $C_6$, a $C_{10}$, a $C_{11}$, a $C_{12}$, a $C_{13}$, a $C_{14}$, a $C_{15}$, a $C_{16}$ or a $C_{18}$ arylene group.

Where $Ar^{11}$ and $Ar^{12}$ are each independently an aryl group, preferably, a $C_6$-$C_{20}$, a $C_6$-$C_{19}$, a $C_6$-$C_{18}$, a $C_6$-$C_{17}$, a $C_6$-$C_{16}$, a $C_6$-$C_{15}$, a $C_6$~$C_{14}$, a $C_6$-$C_{13}$, a $C_6$~$C_{12}$, a $C_6$-$C_{11}$, a $C_6$~$C_{10}$, a $C_6$, a $C_{10}$, a $C_{11}$, a $C_{12}$, a $C_{13}$, a $C_{14}$, a $C_{15}$, a $C_{16}$ or a $C_{18}$ aryl group.

Preferably, dimethylcyclopentaphenanthrene being a $C_{17}$ aryl group is excluded from the Formula 3.

In the formula 3, $L^{11}$, $L^{12}$, $Ar^{11}$ and $Ar^{12}$ may be each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group.

In the formula 3, where $X^{11}$ is O, Formula 3 may be represented by the following Formula 3-1.

<Formula 3-1>

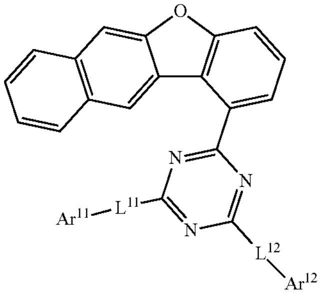

In the formula 3-1, each of symbols may be the same as defined in Formula 3.

Formula 3-1 may be represented by the following Formulas 3-A or 3-B.

<Formula 3-A>

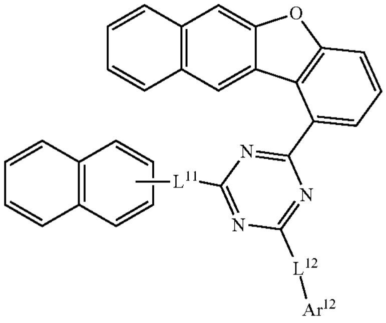

<Formula 3-B>

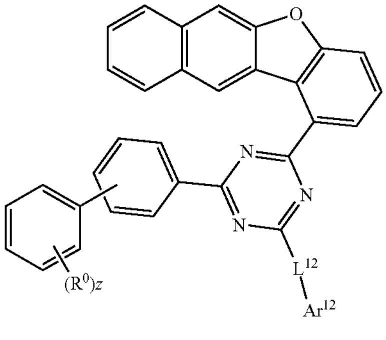

In Formulas 3-A and 3-B, each of symbols may be the same as defined in Formula 3, and $R^0$ is the same as $Ar^{11}$ in Formula 3. z is an integer of 0-5, and where z is an integer of 2 or more, each of a plurality of $R^0$ is the same as or different from each other, and adjacent groups may optionally be linked to each other to form a ring. Preferably, $R^0$ is hydrogen or a $C_6$-$C_2$ aryl group, or adjacent $R^0$s may optionally be linked to each other to form a benzene or naphthalene ring.
Specifically, the compound represented by formula 1 may be one of the following compounds.
1-1
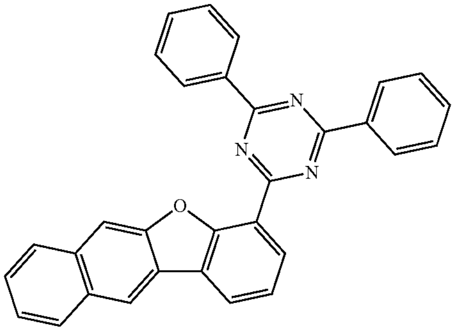
1-2
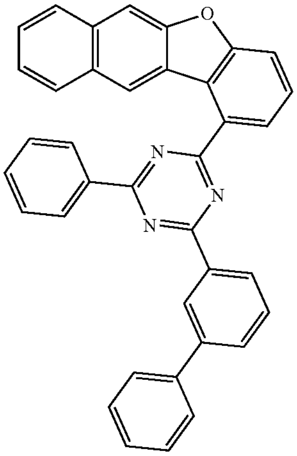
1-3
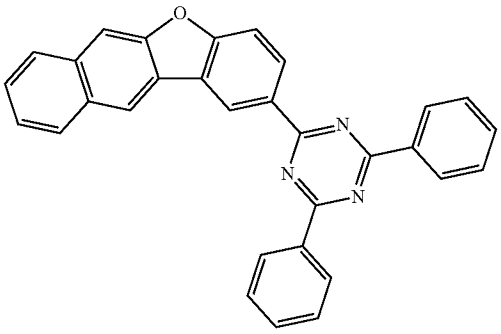
-continued
1-4
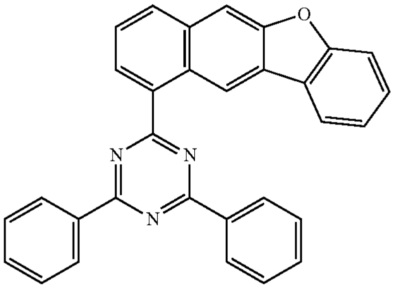
1-5
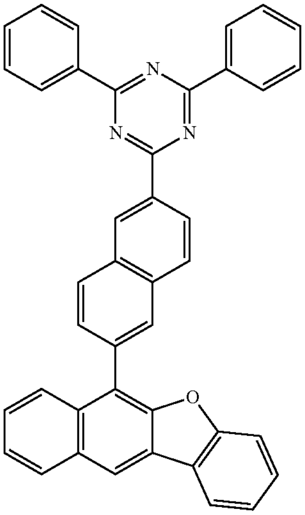
1-6
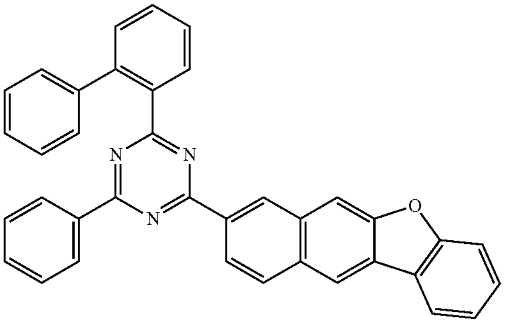
1-7
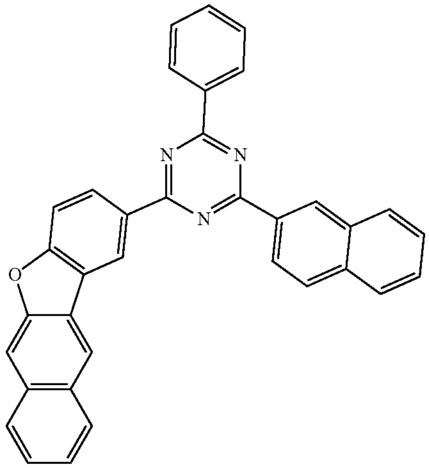

-continued
1-8
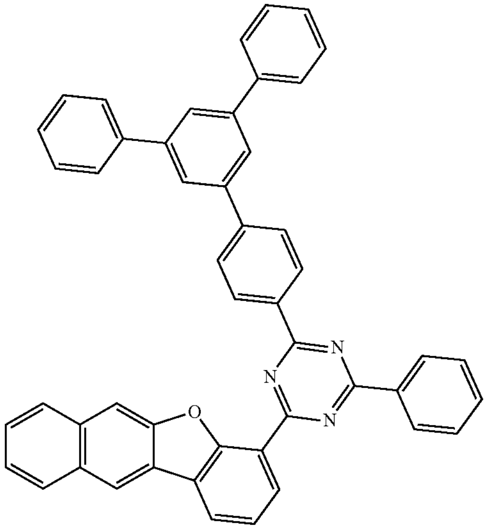
1-9
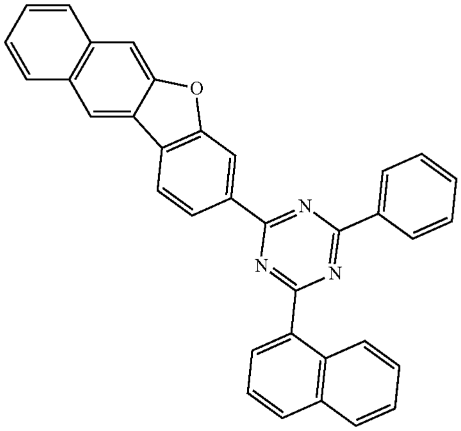
1-10
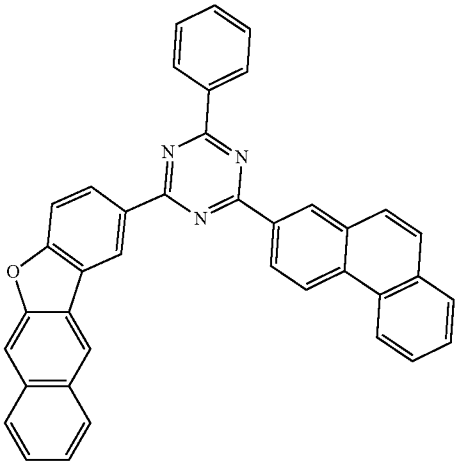
-continued
1-11
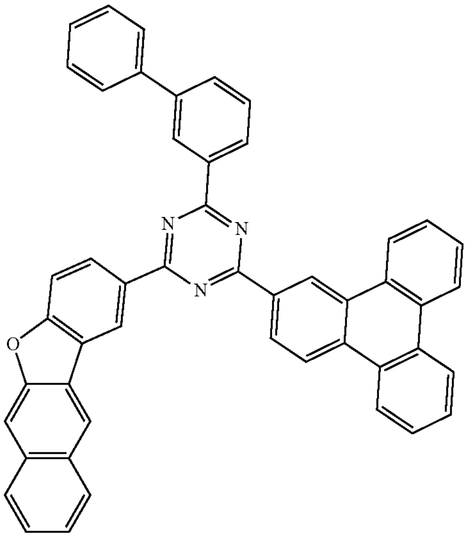
1-12
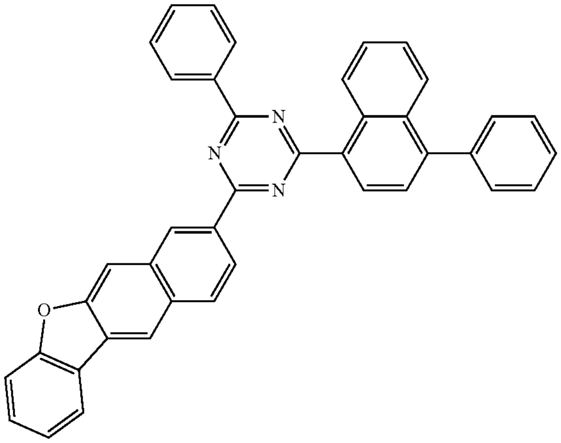
1-13
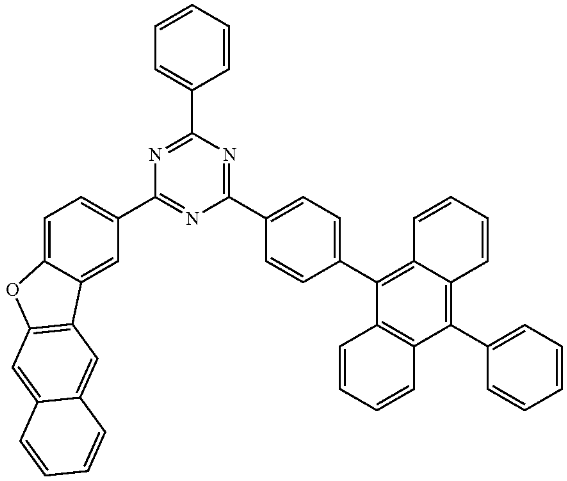

-continued
1-14
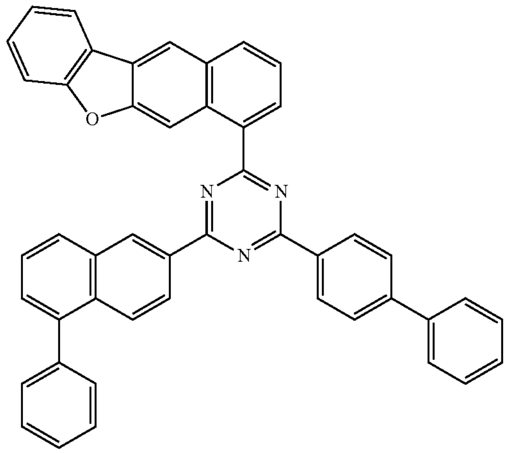
1-15
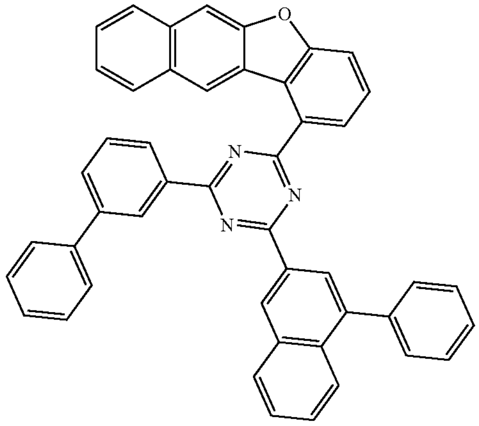
1-16
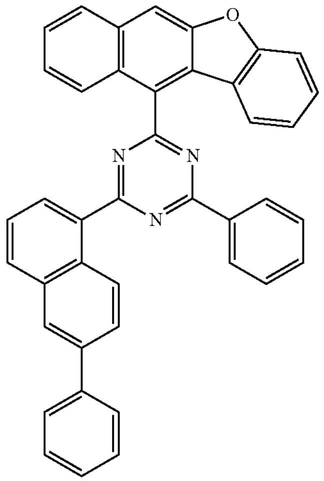
-continued
1-17
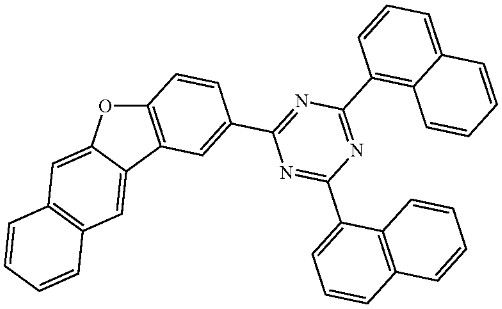
1-18
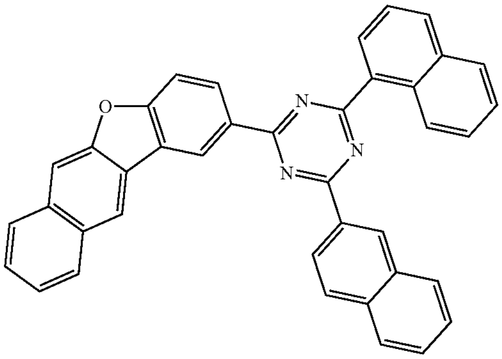
1-19
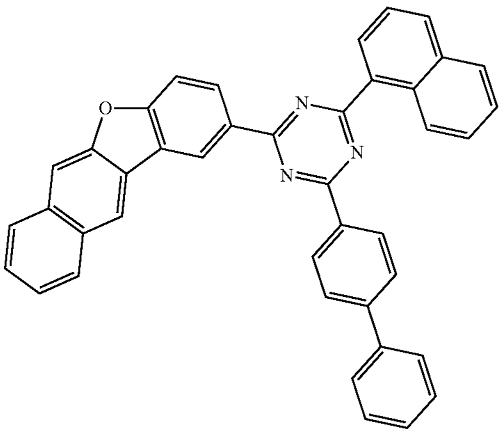
1-20
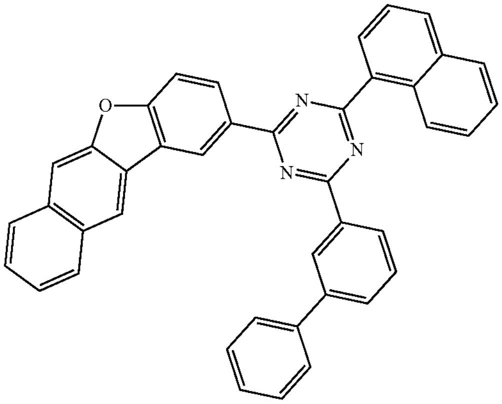

-continued
1-21
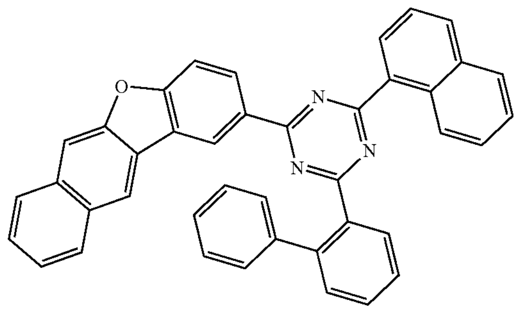
1-22
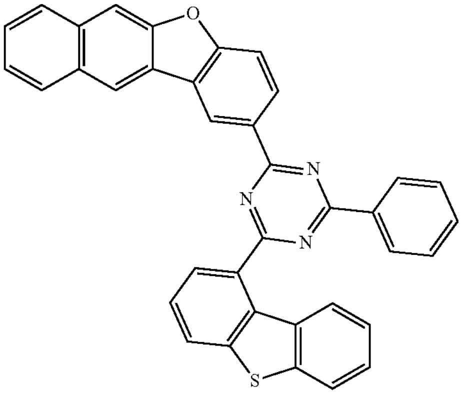
1-23
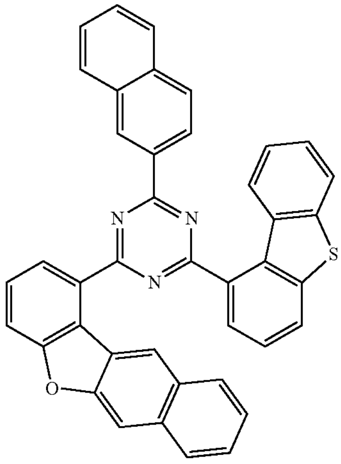
1-24
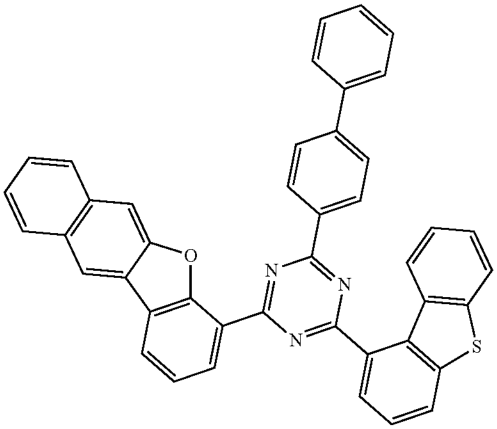
-continued
1-25
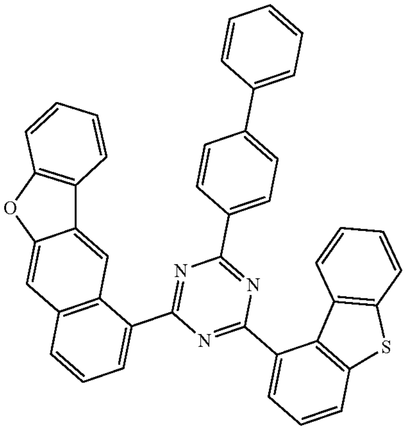
1-26
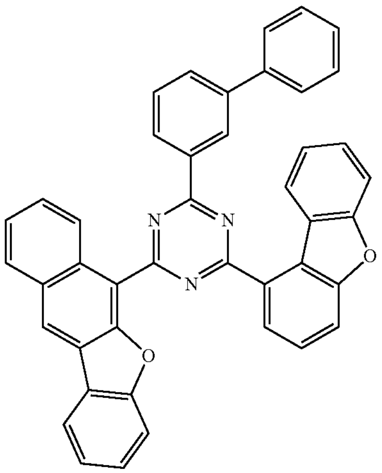
1-27
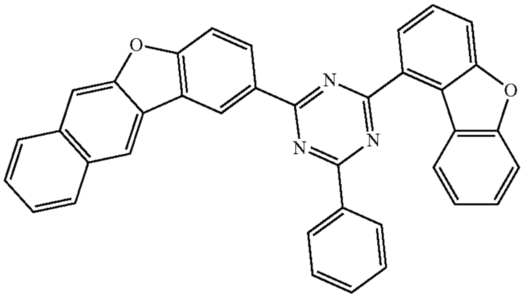
1-28
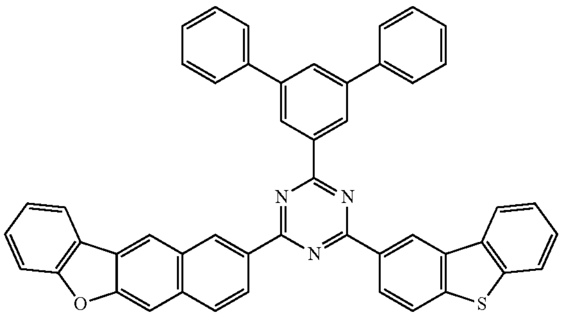

-continued
1-29
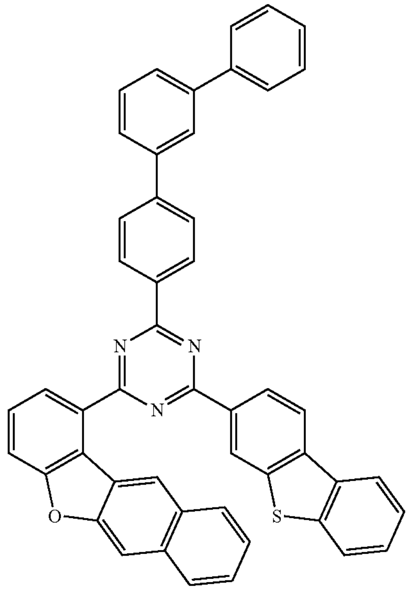
1-30
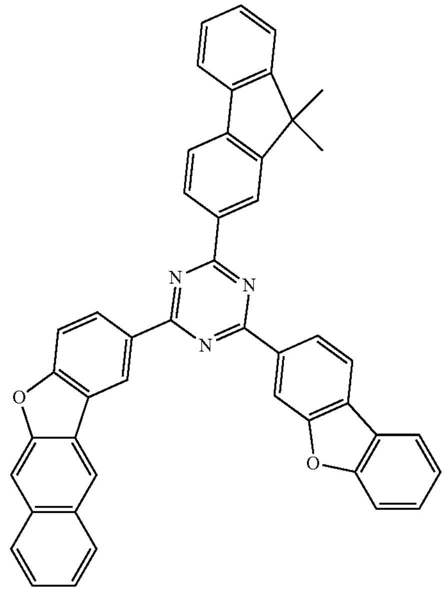
1-31
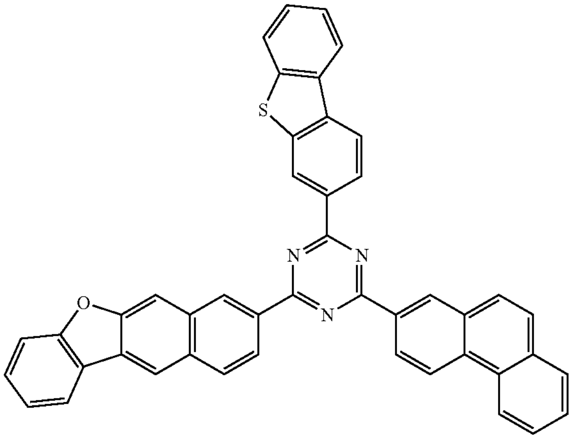
-continued
1-32
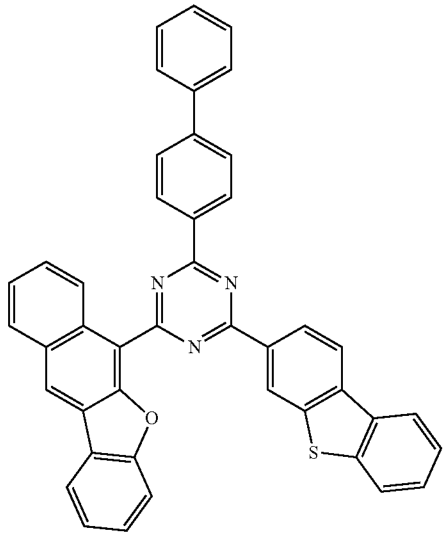
1-33
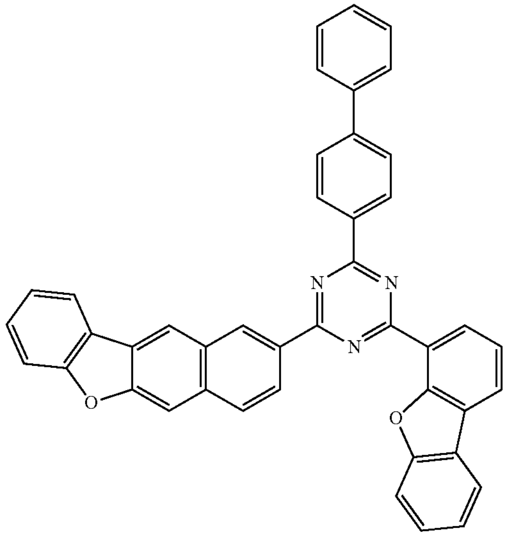
1-34
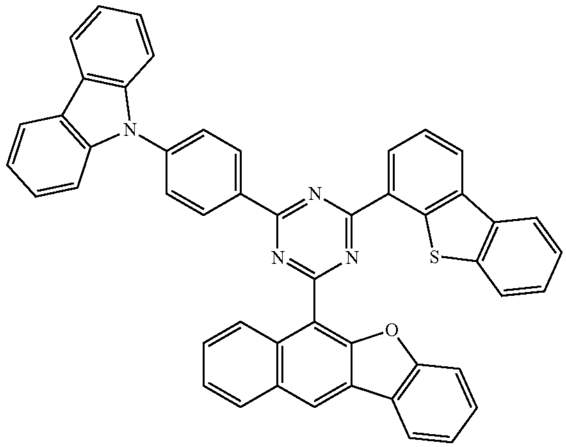

-continued
1-35
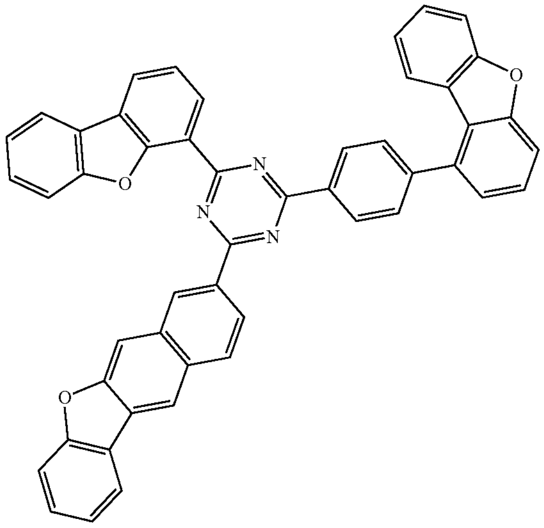
1-36
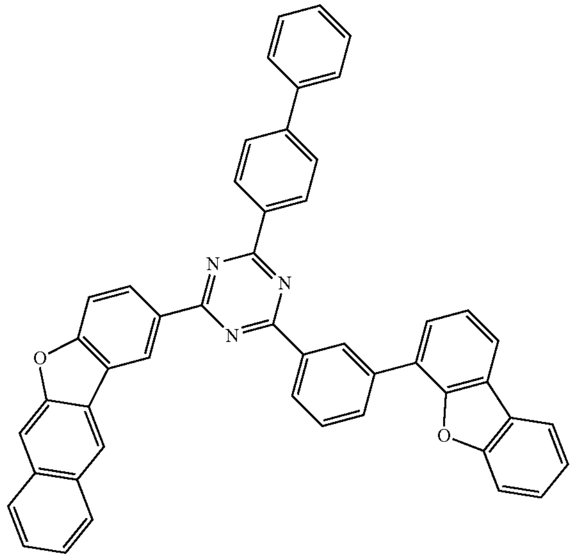
-continued
1-37
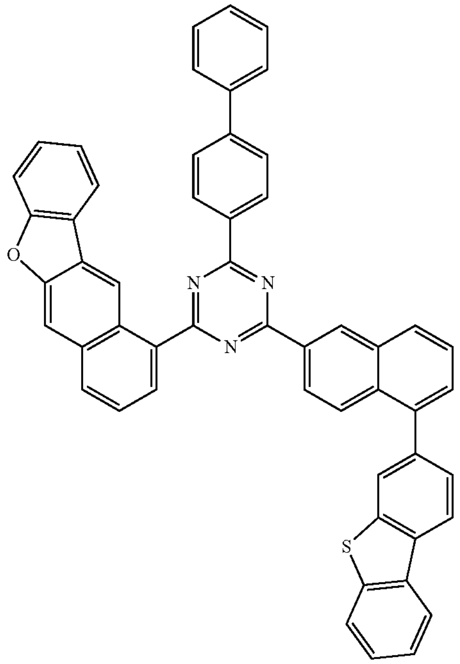
1-38
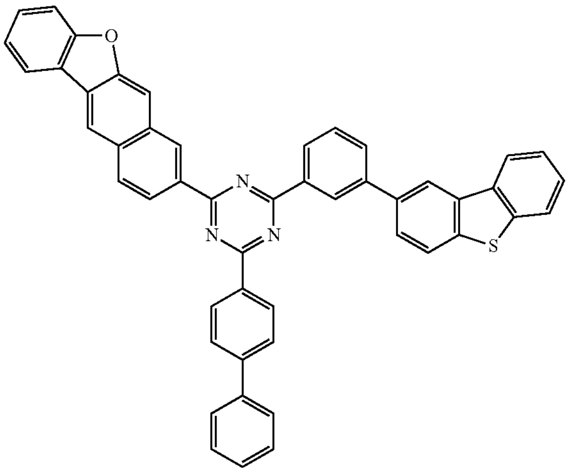

-continued
1-39
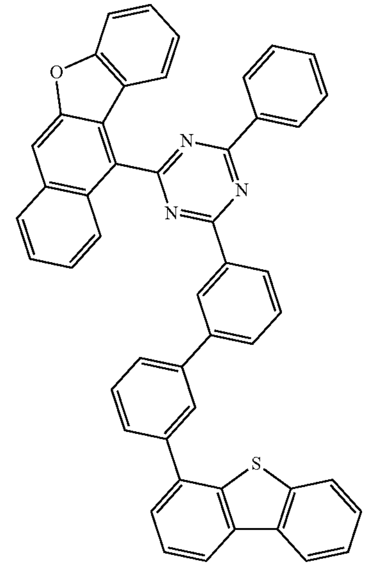
1-40
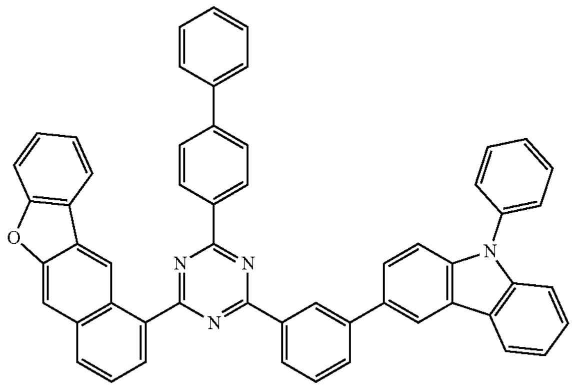
1-41
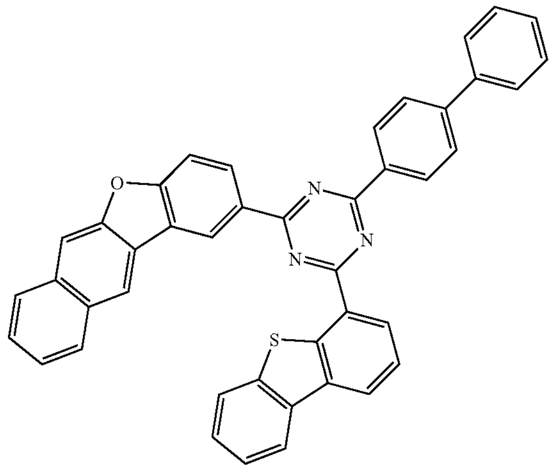
-continued
1-42
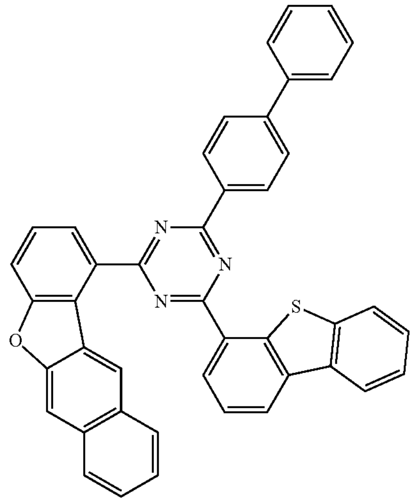
1-43
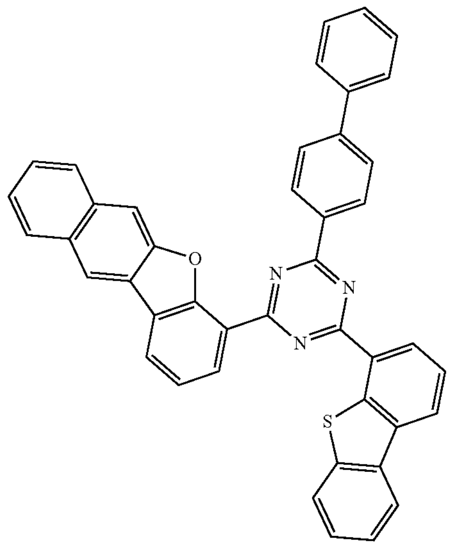
1-44
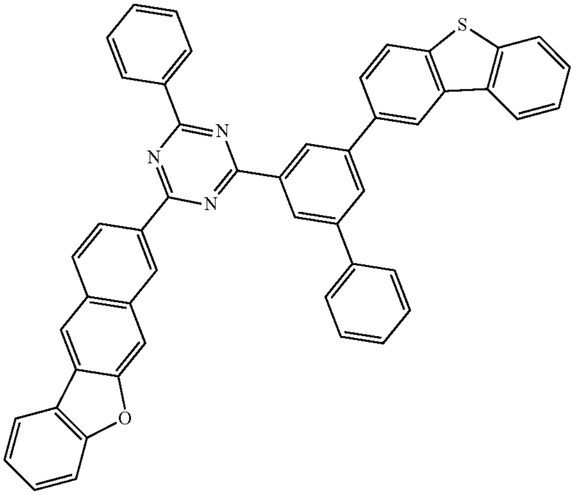

-continued
1-45
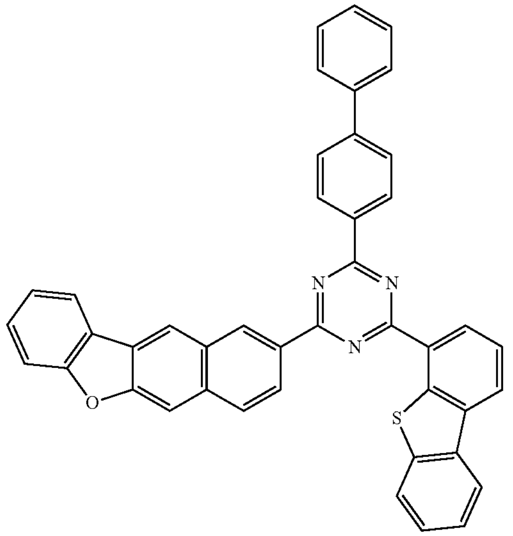
1-46
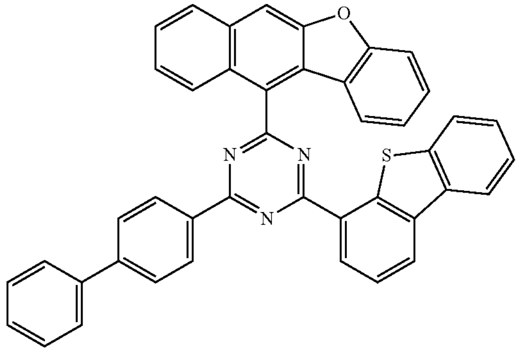
1-47
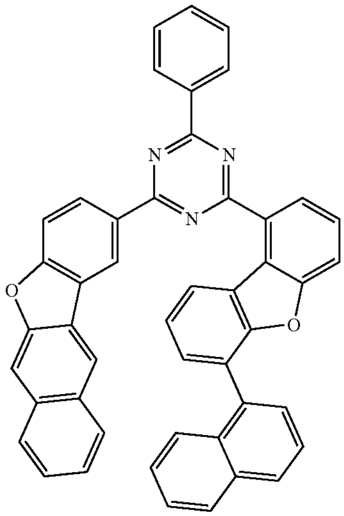
-continued
1-48
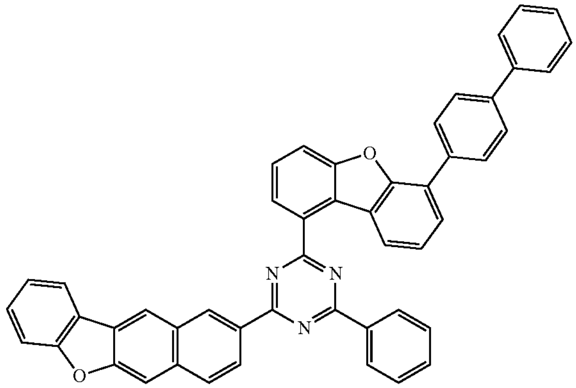
1-49
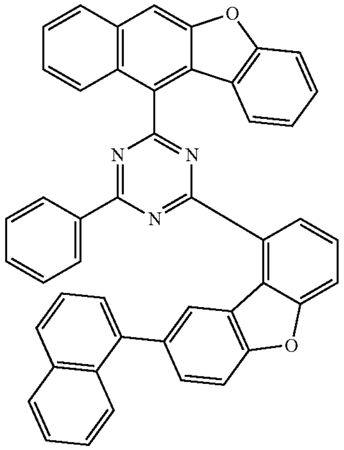
1-50
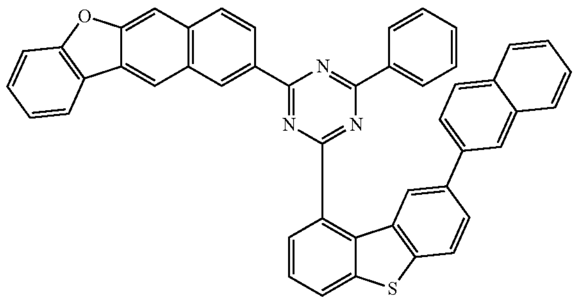
1-51
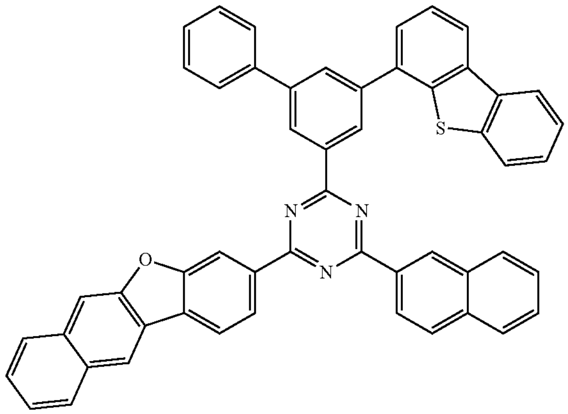

-continued
1-52
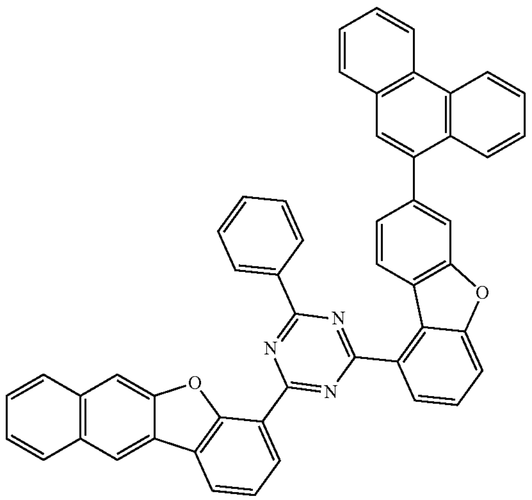
1-53
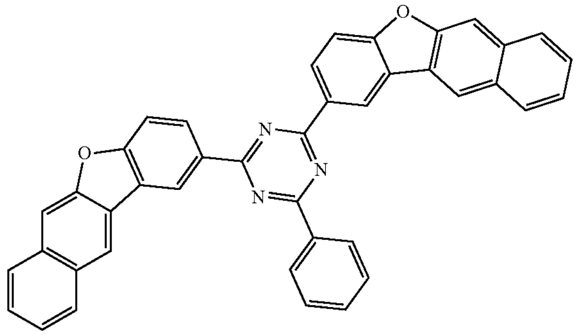
1-54
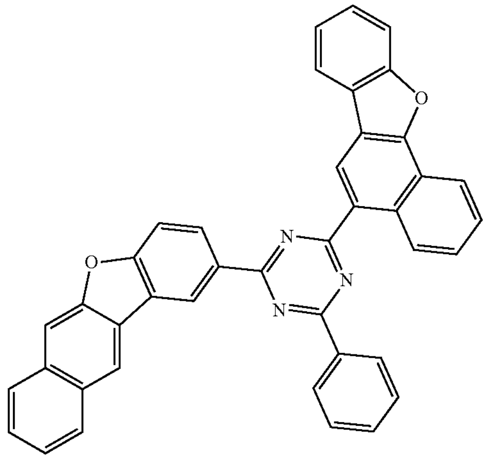
-continued
1-55
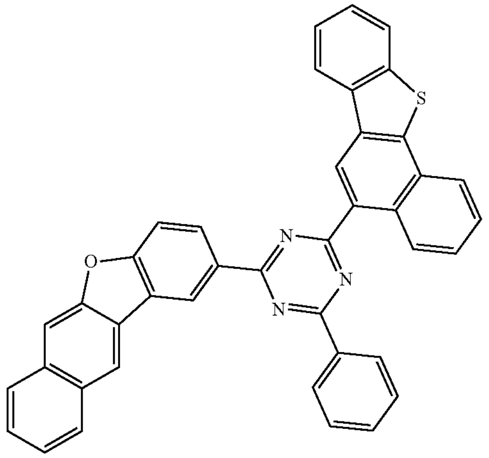
1-56
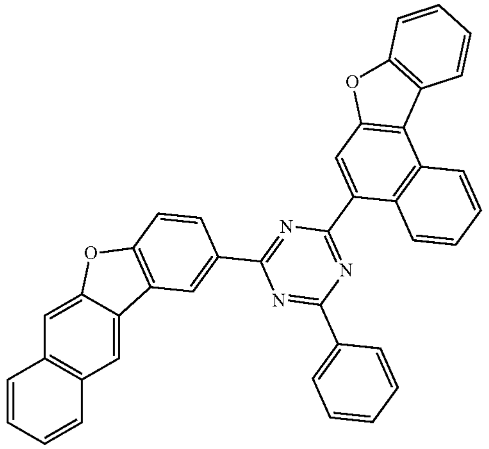
1-57
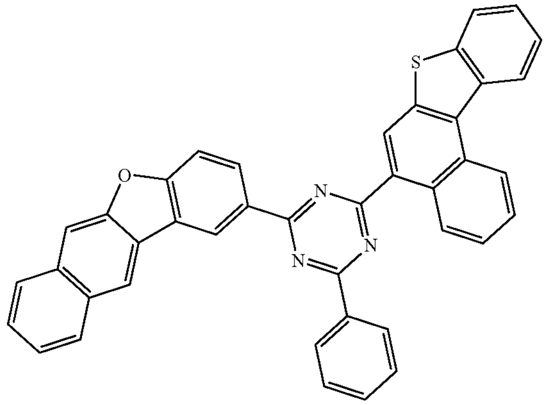

-continued
1-58
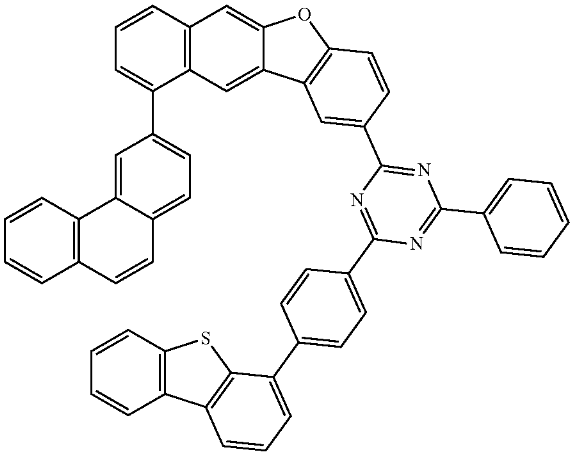
1-59
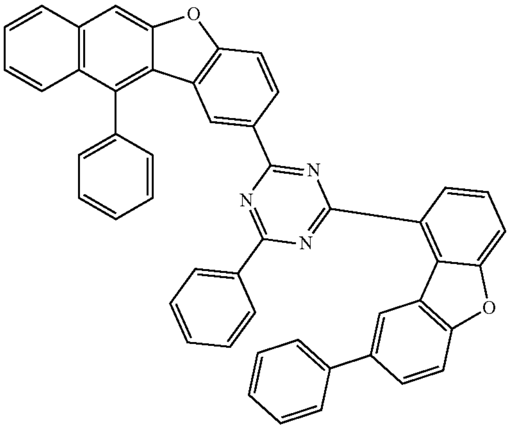
1-60
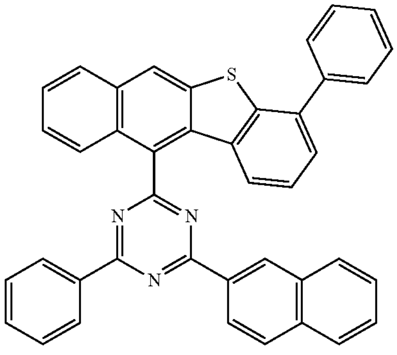
1-61
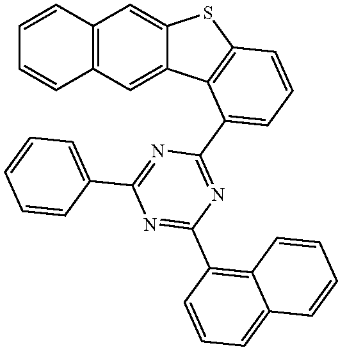
-continued
1-62
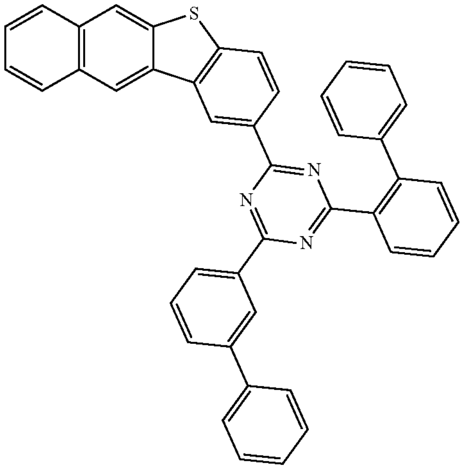
1-63
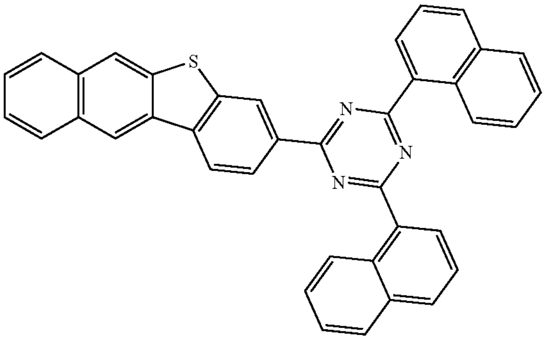
1-64
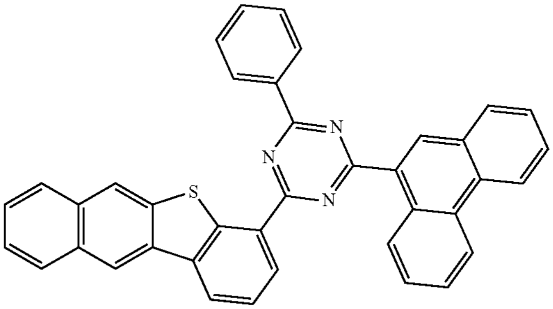
1-65
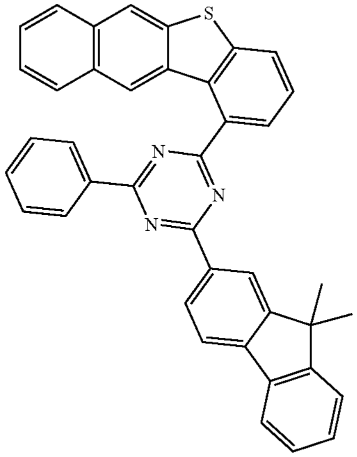

-continued
1-66
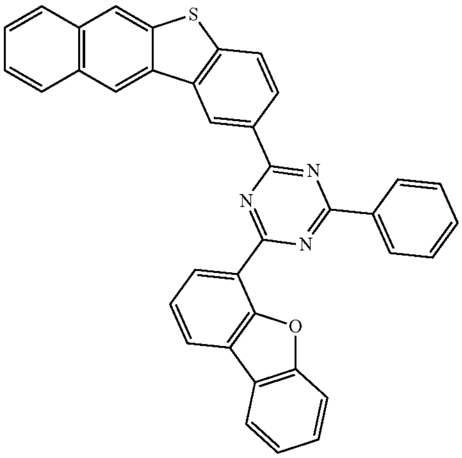
1-67
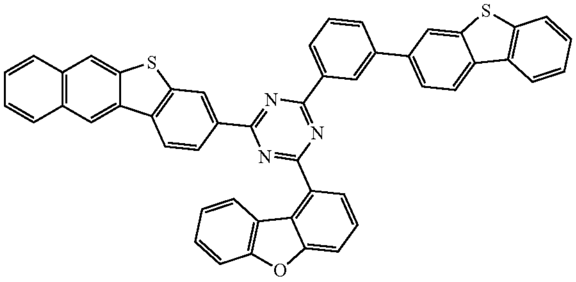
1-68
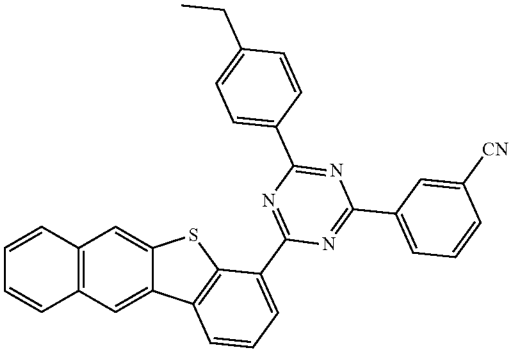
1-69
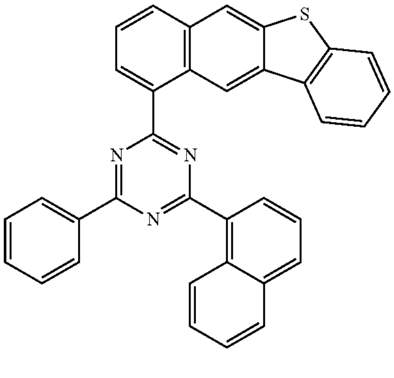
-continued
1-70
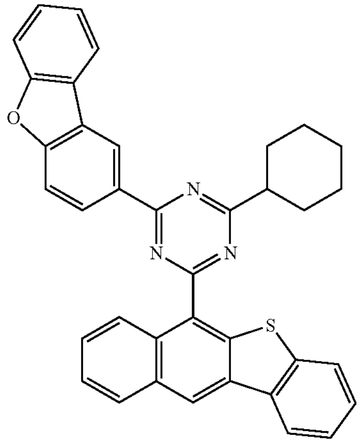
1-71
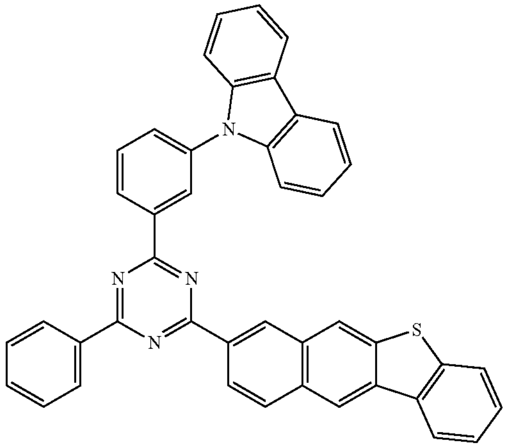
1-72
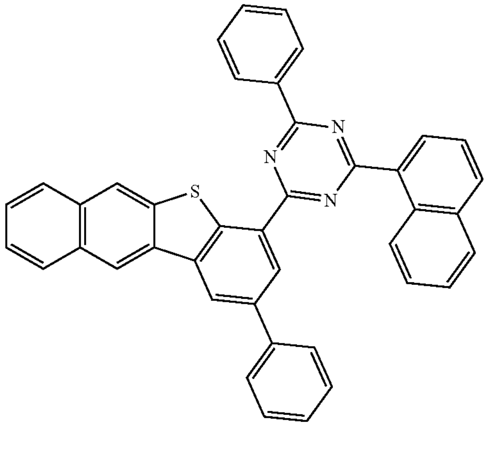

-continued
1-73
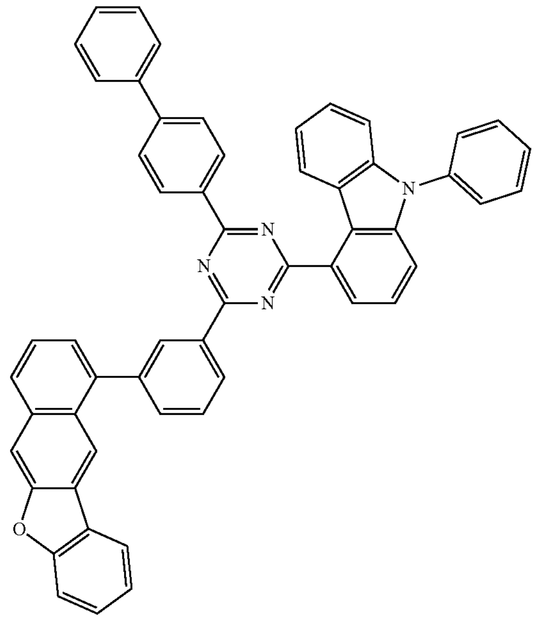
1-74
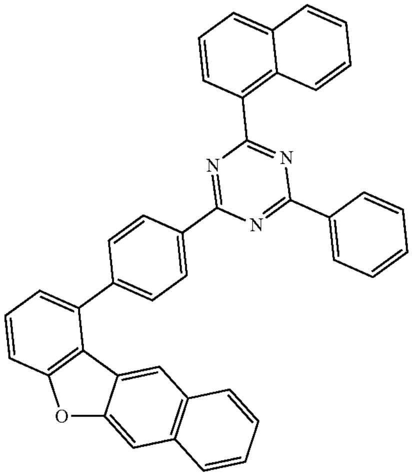
1-75
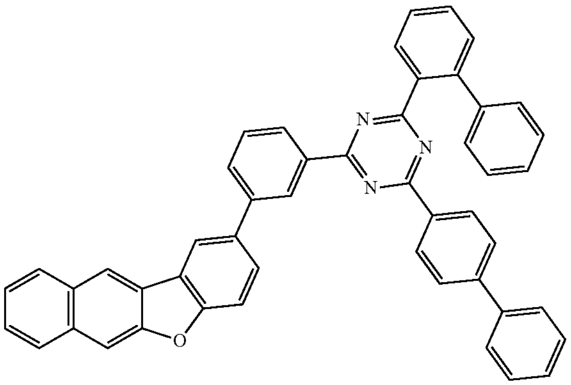
-continued
1-76
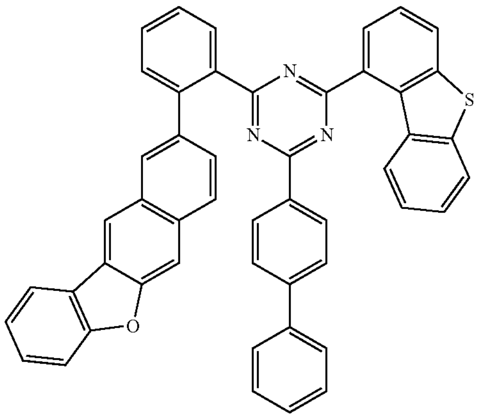
1-77
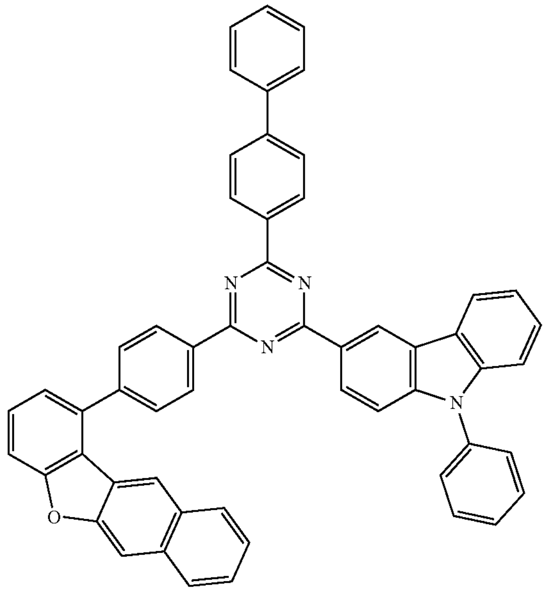
1-78
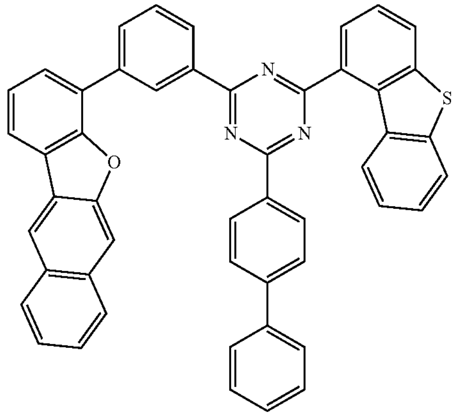

-continued
1-79
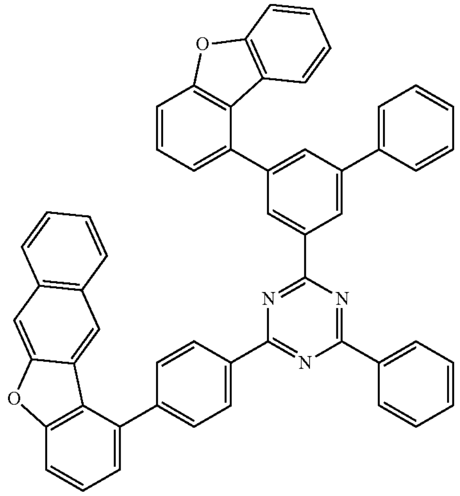
1-80
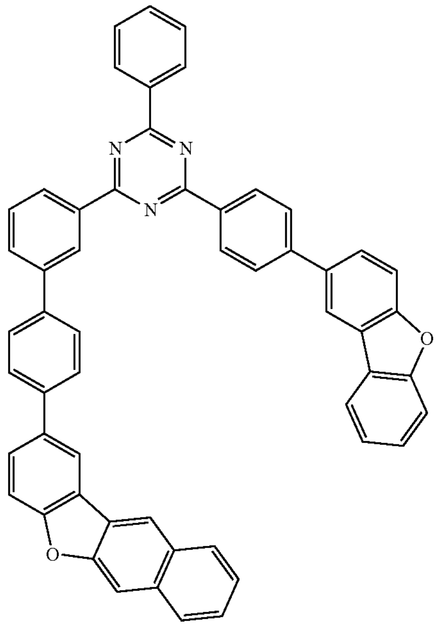
1-81
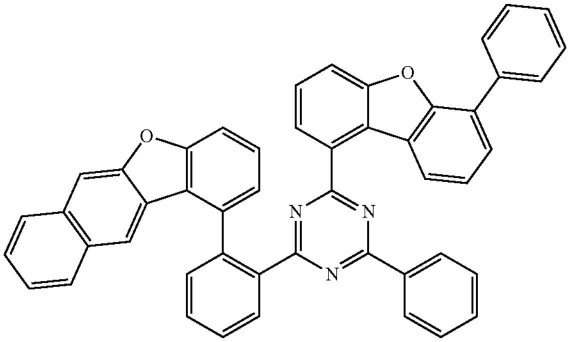
-continued
1-82
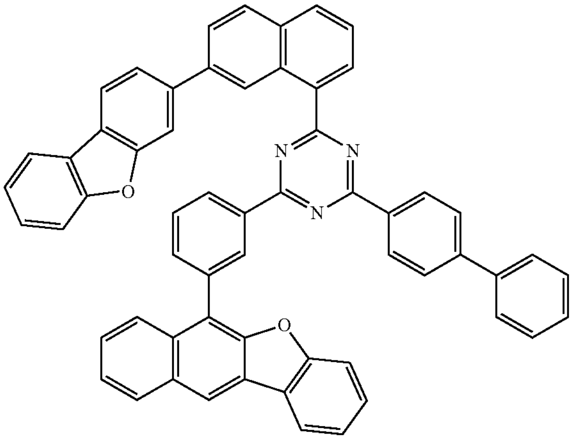
1-83
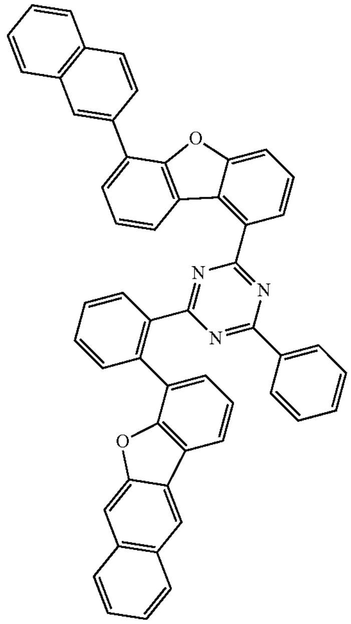
1-84
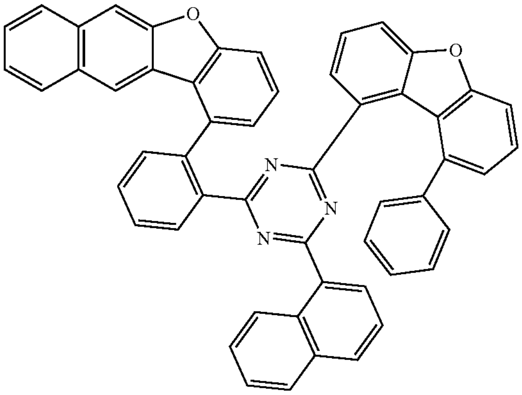

-continued
1-85
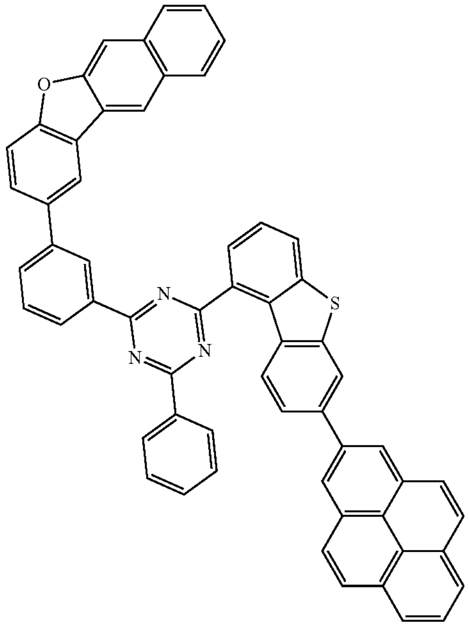
1-86
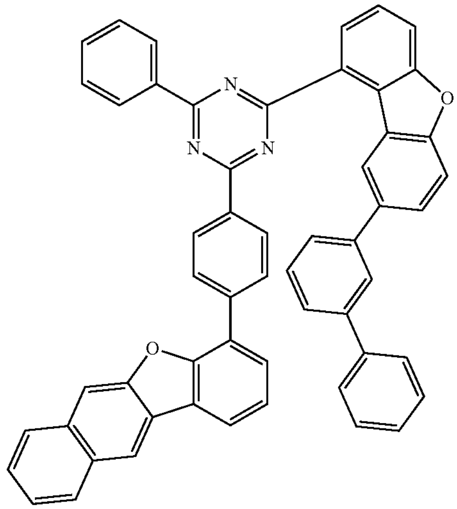
1-87
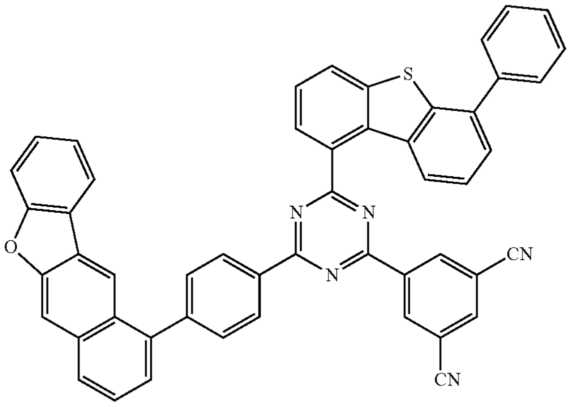
-continued
1-88
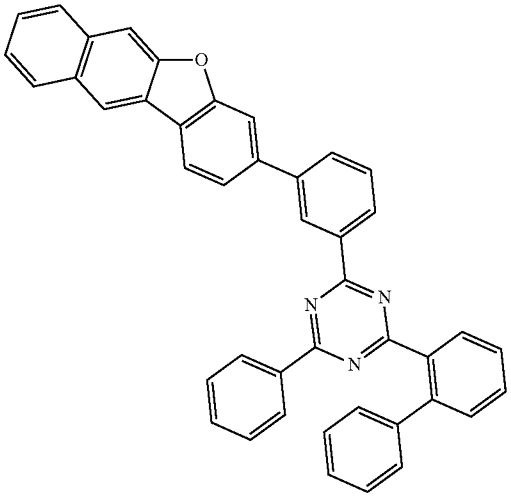
1-89
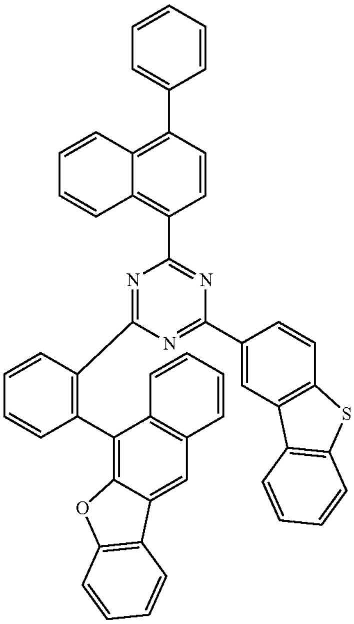

-continued
1-90
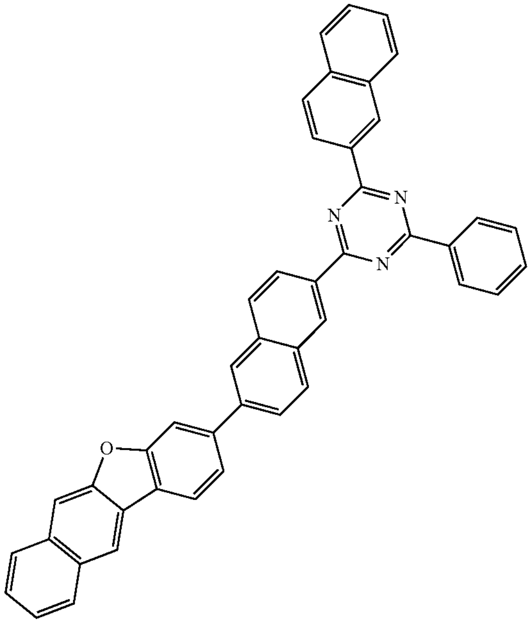
1-91
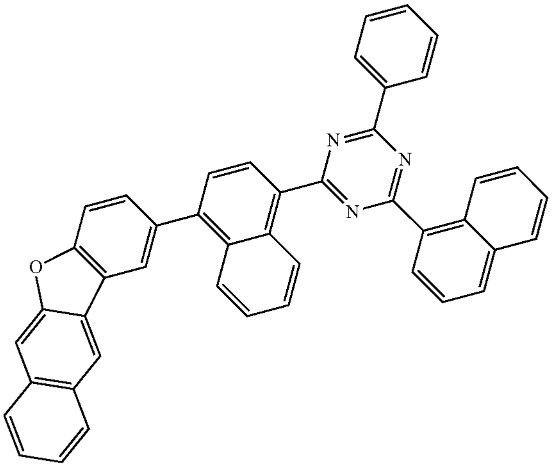
1-92
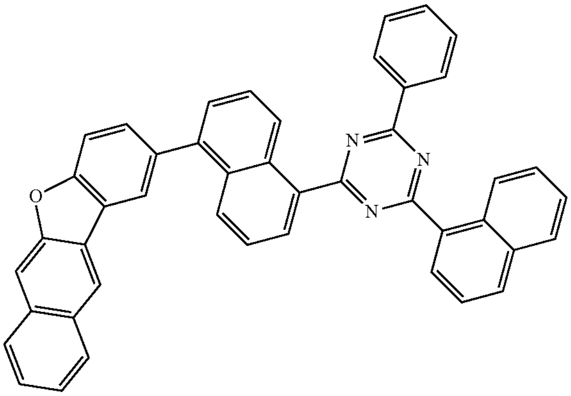
-continued
1-93
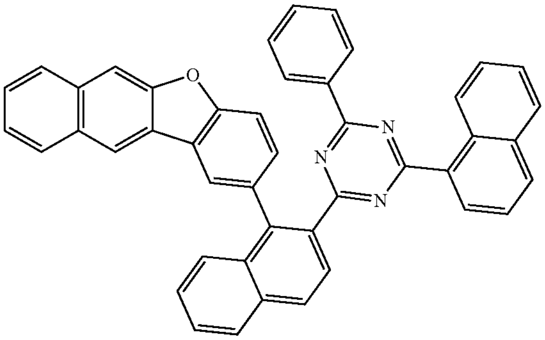
1-94
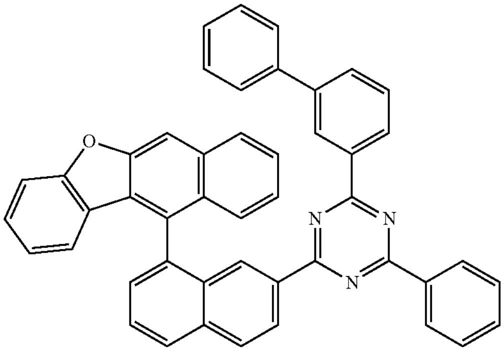
1-95
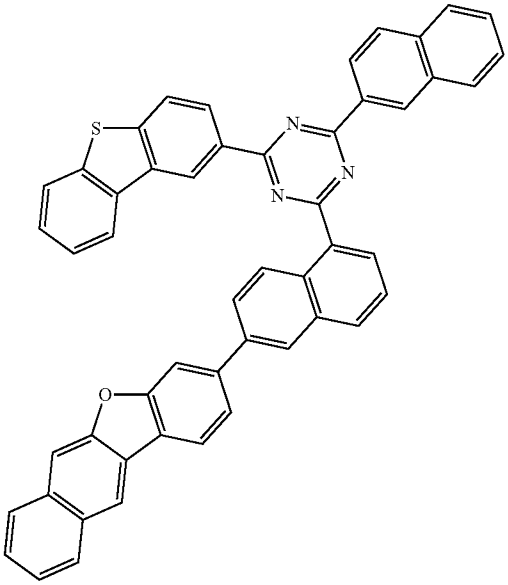

-continued
1-96
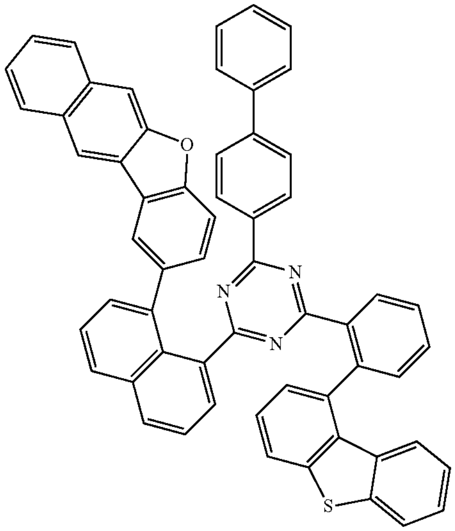
1-97
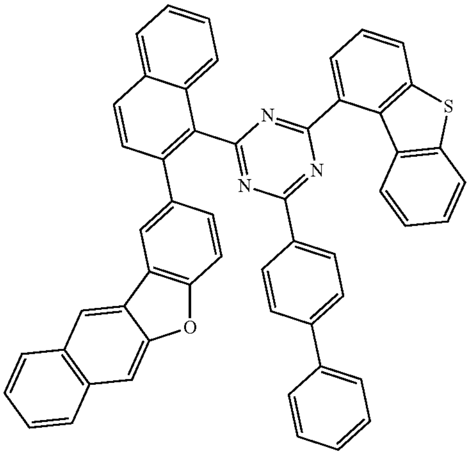
1-98
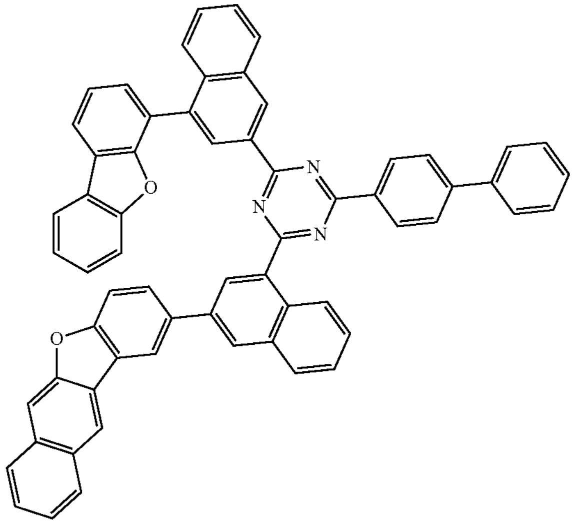
-continued
1-99
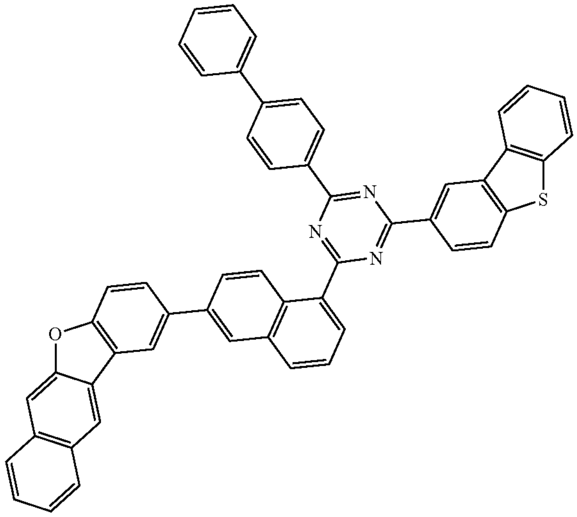
1-100
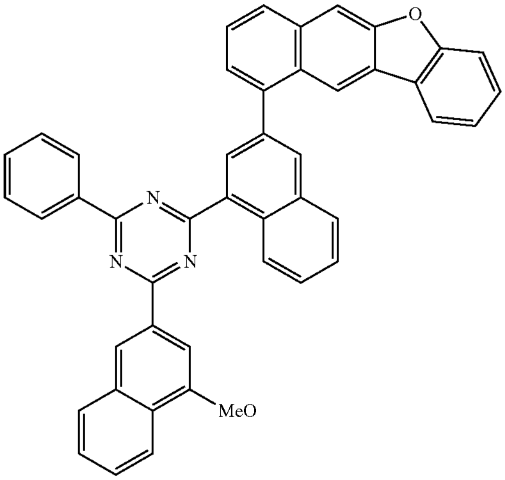
1-101
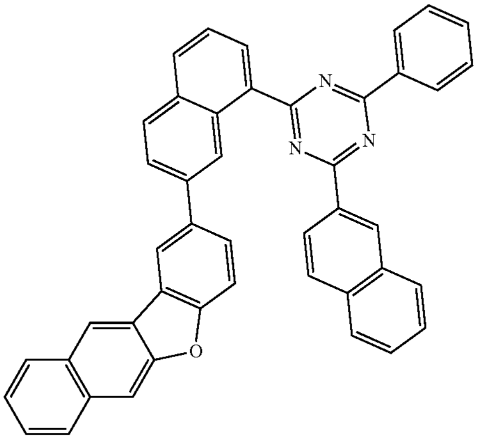

-continued
1-102
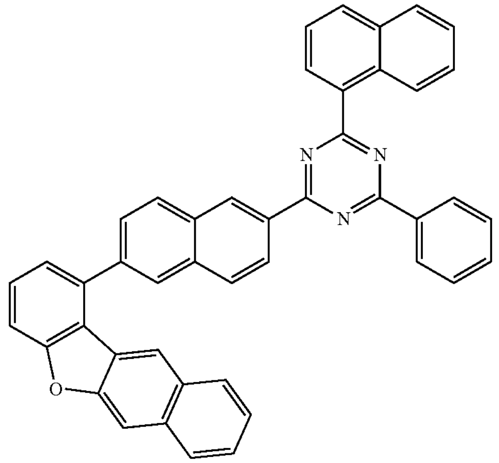
1-103
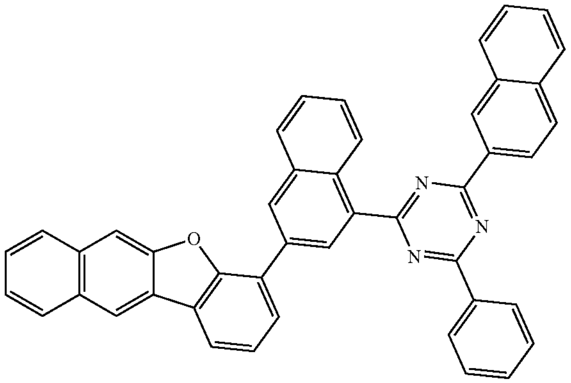
1-104
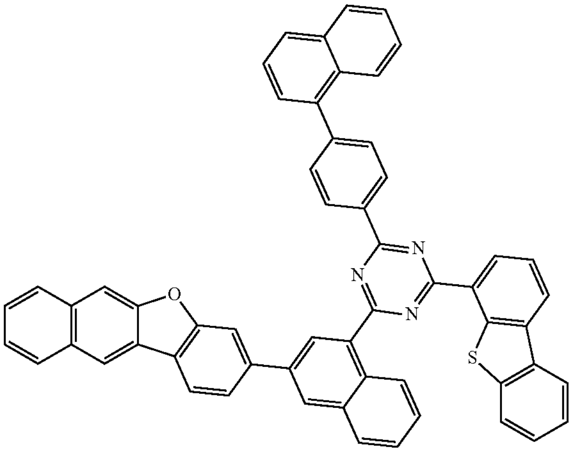
-continued
1-105
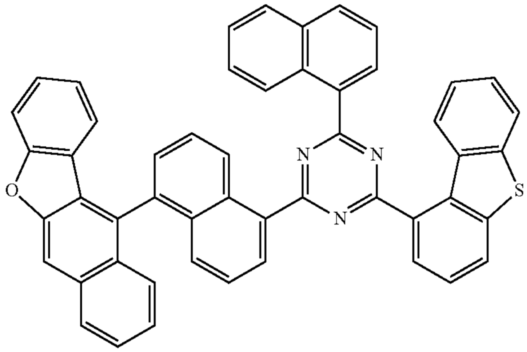
1-106
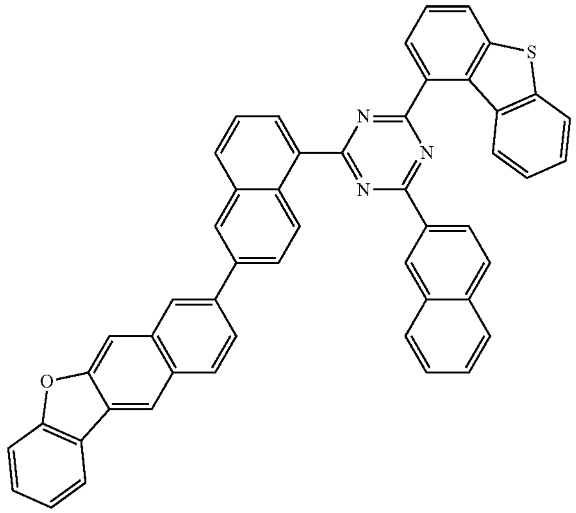
1-107
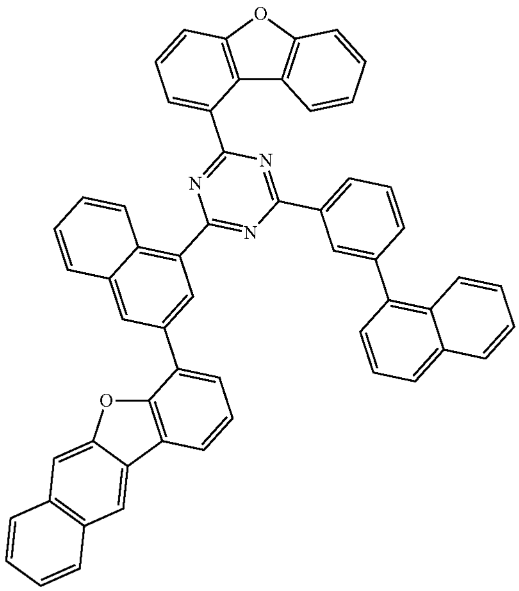

-continued
1-108
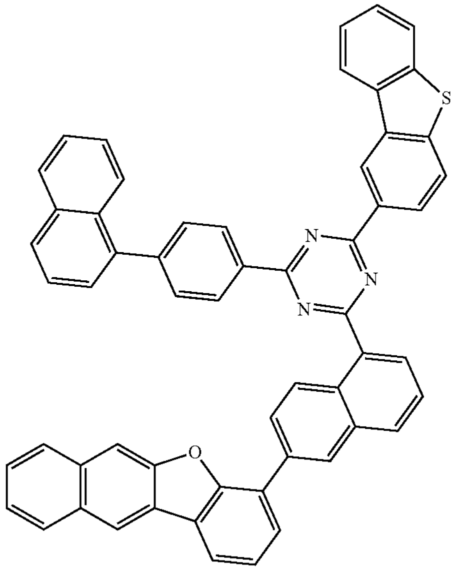
1-109
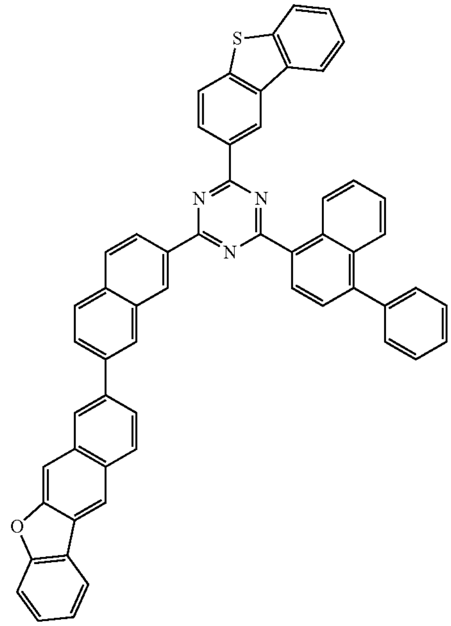
1-110
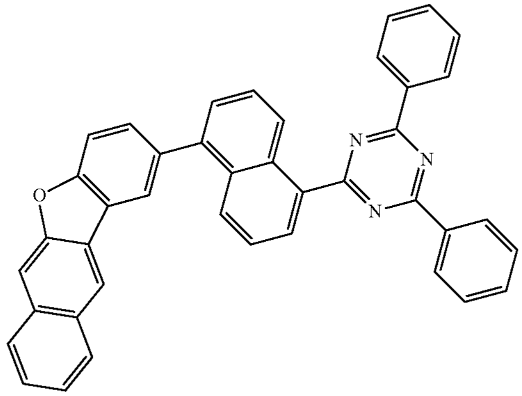
-continued
1-111
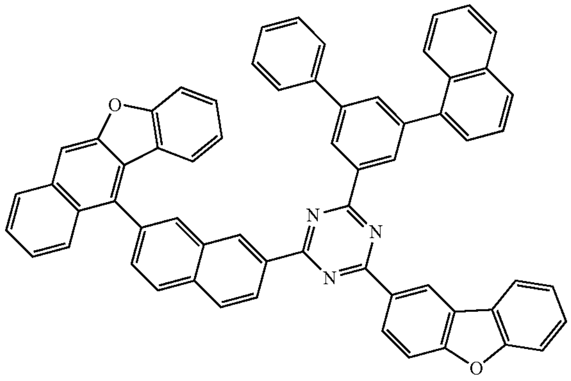
1-112
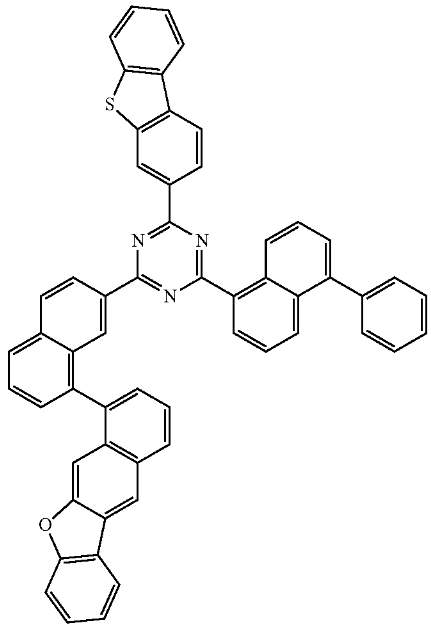
1-113
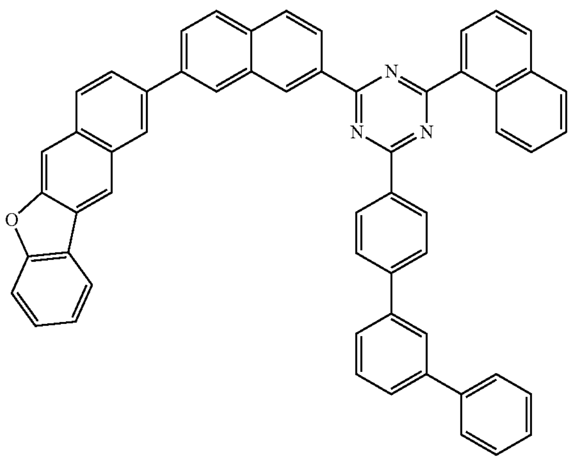

-continued
1-114
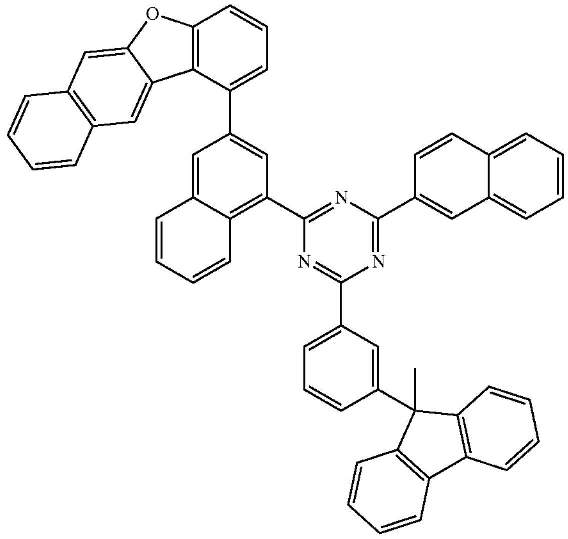
1-115
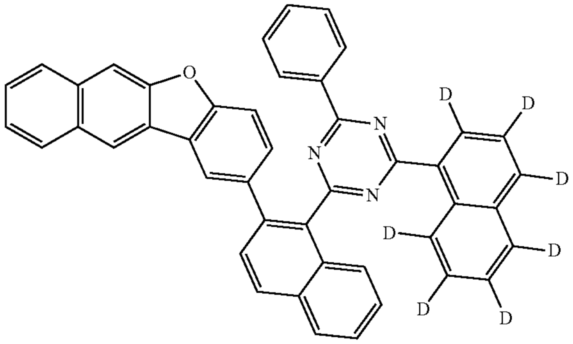
1-116
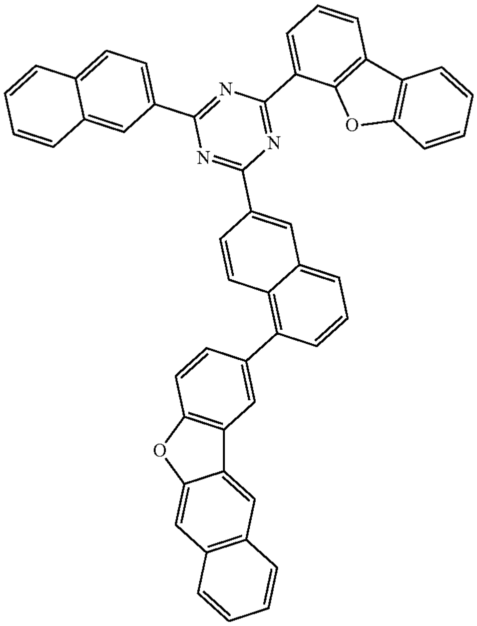
-continued
1-117
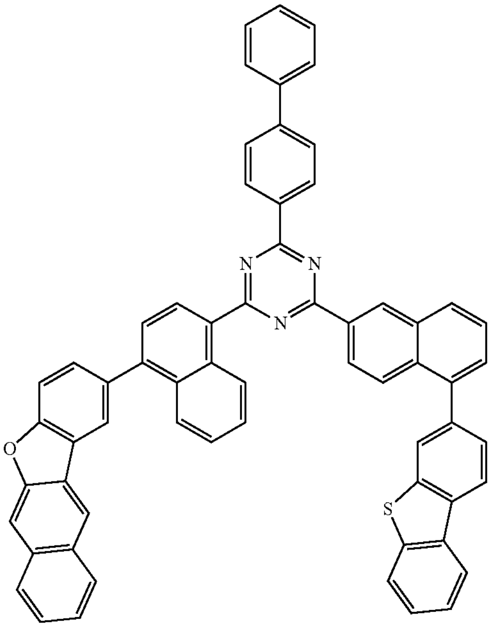
1-118
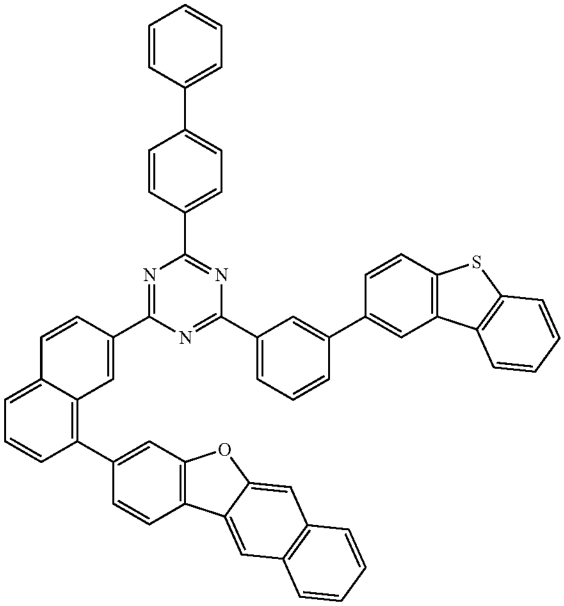

-continued
1-119
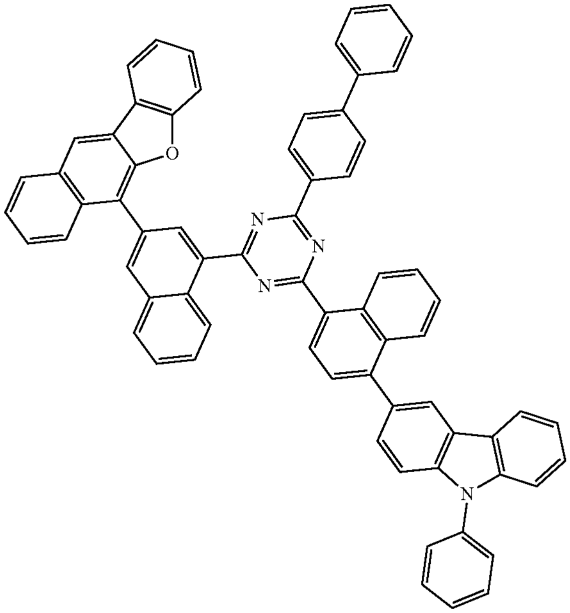
1-120
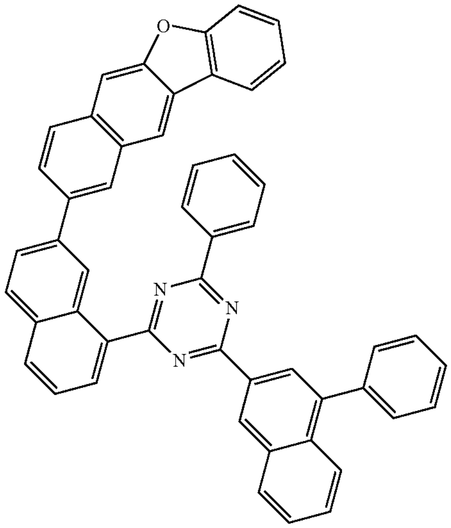
1-121
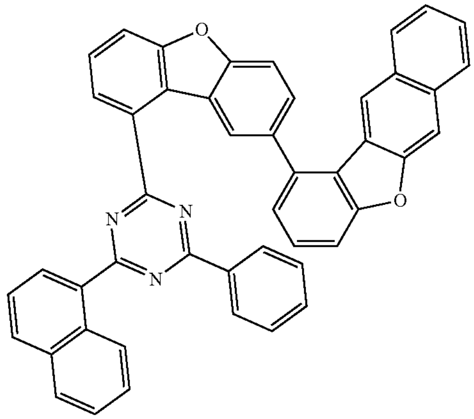
-continued
1-122
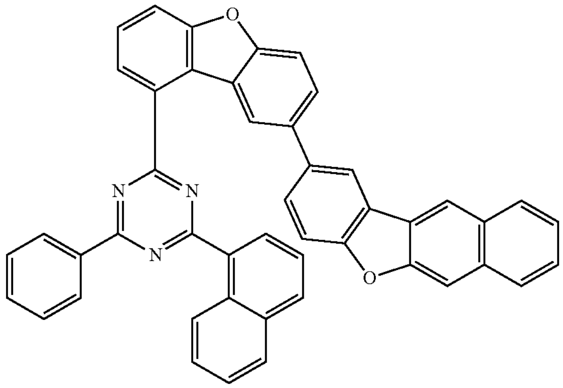
1-123
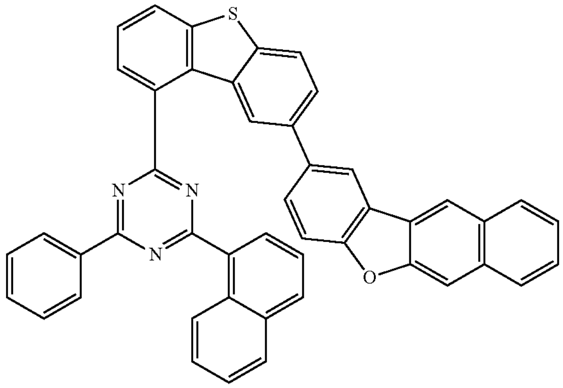
1-124
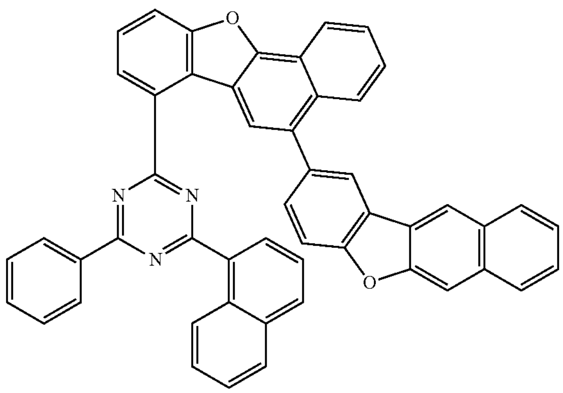

-continued
1-125
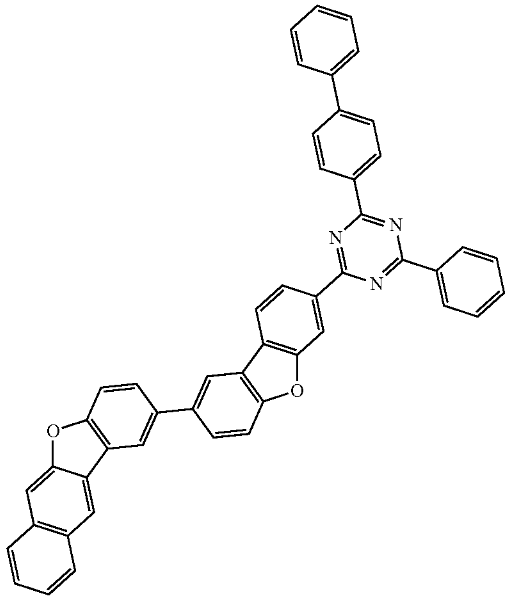
1-126
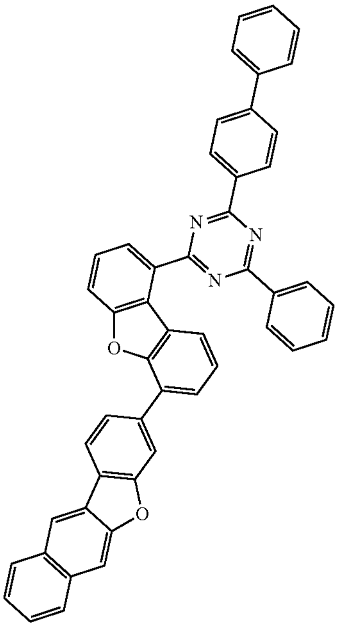
-continued
1-128
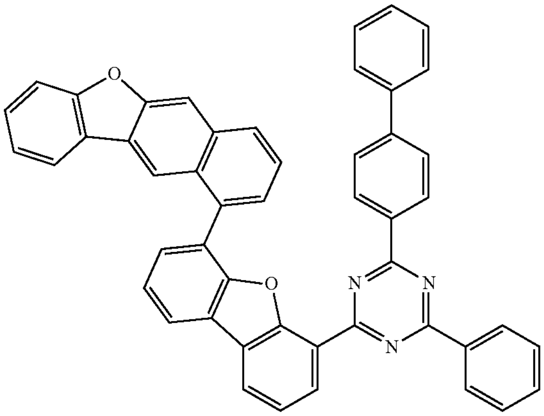
1-129
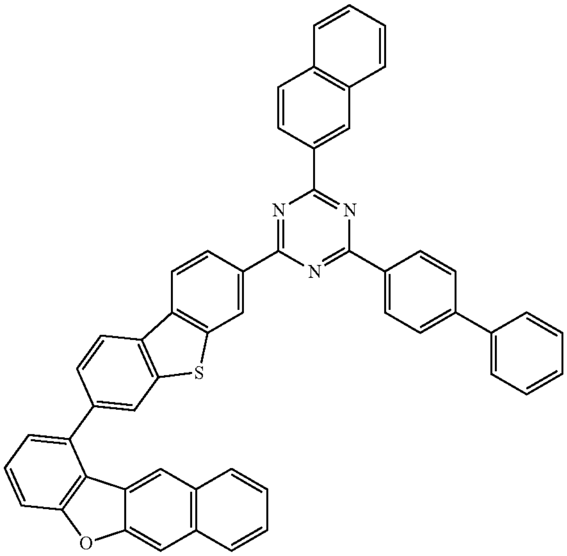
1-130
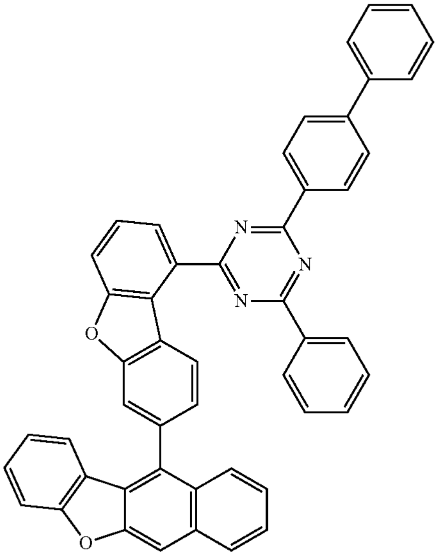

-continued
1-131
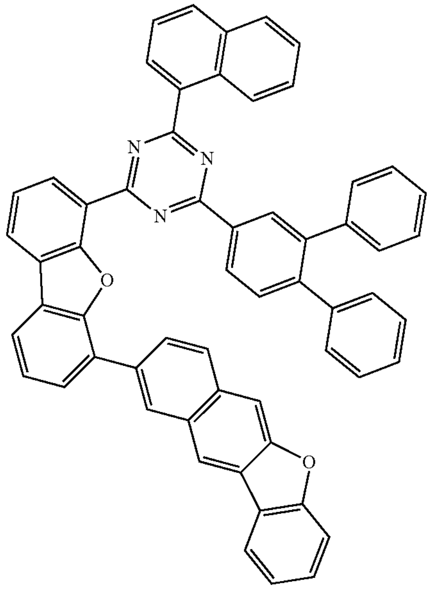
1-132
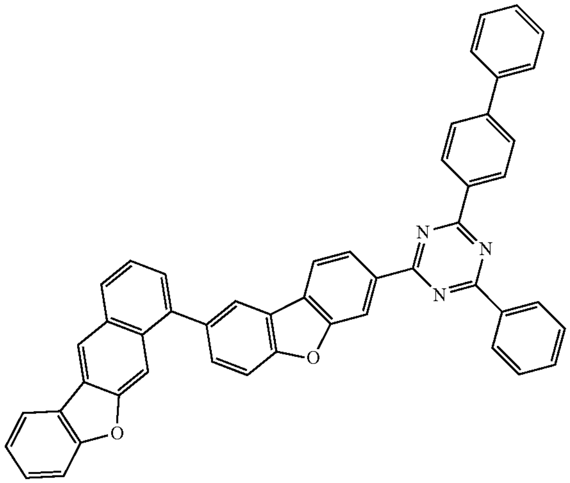
-continued
1-133
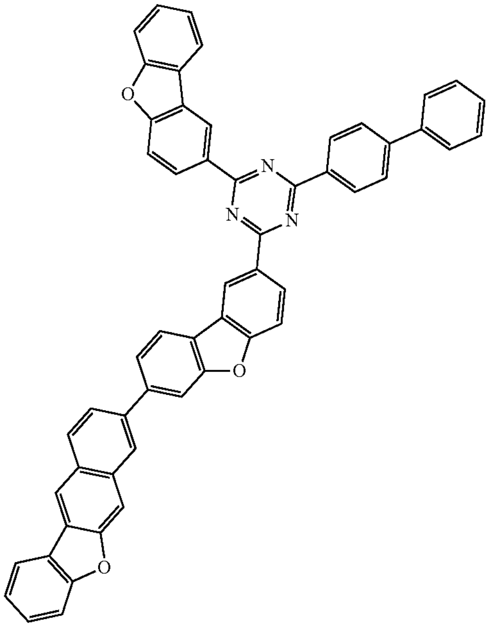
1-134
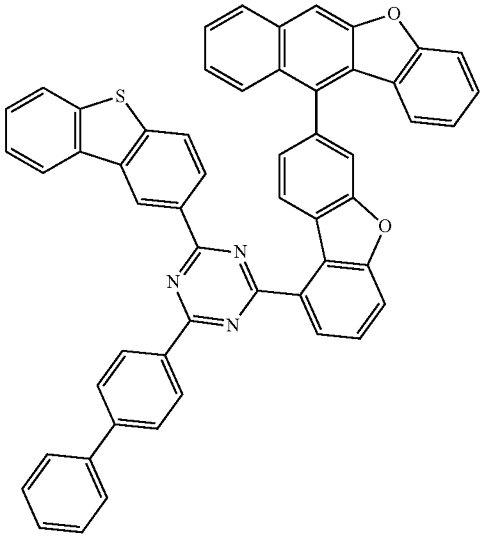

-continued
1-136
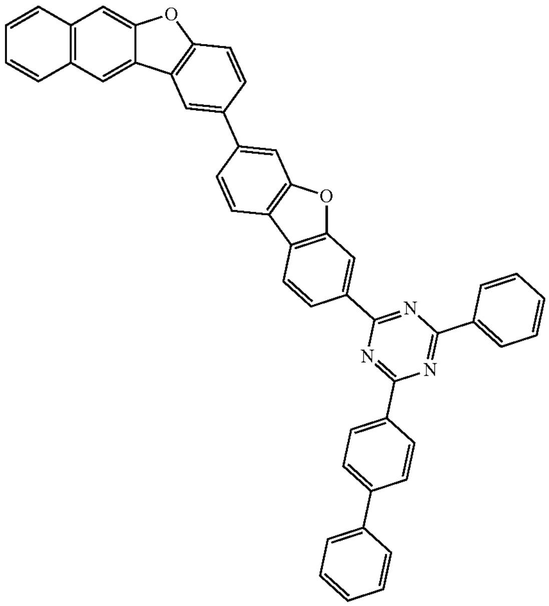
1-137
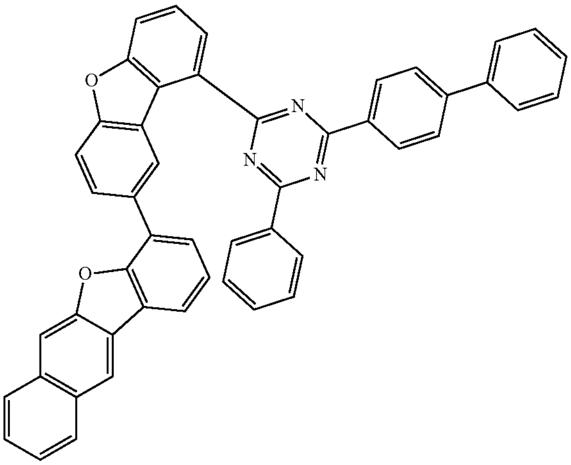
1-138
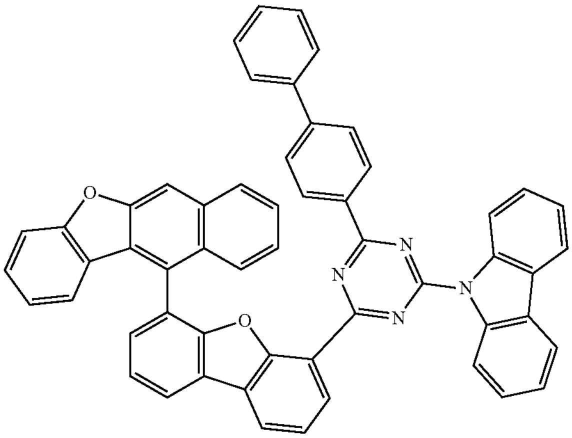
-continued
1-139
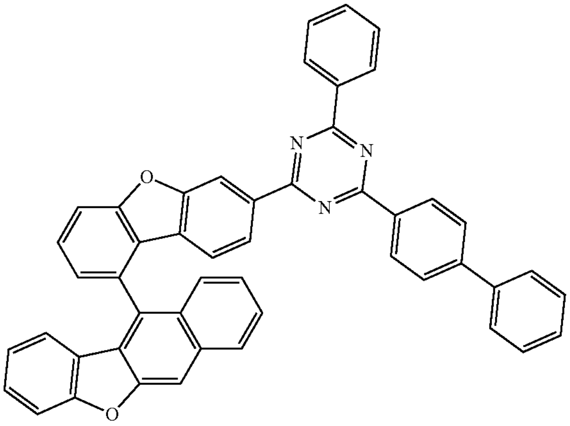
1-140
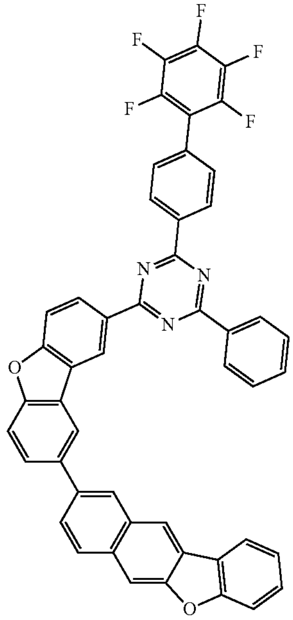
1-141
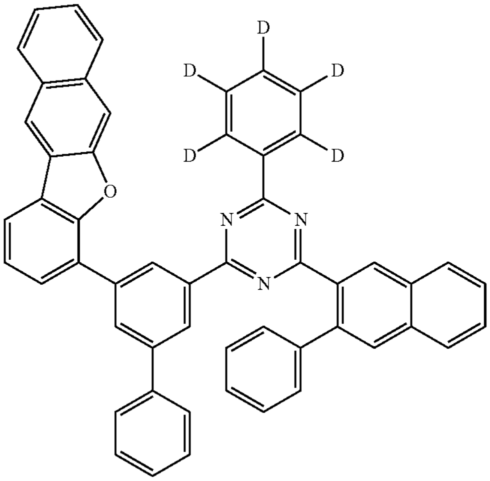

1-142
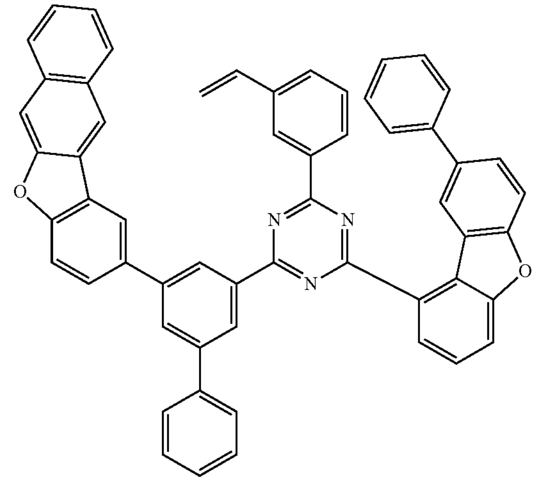
1-143
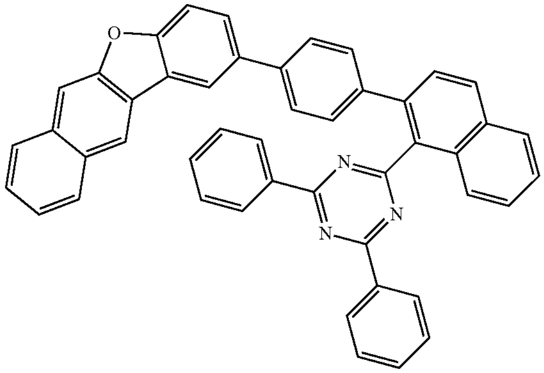
1-144
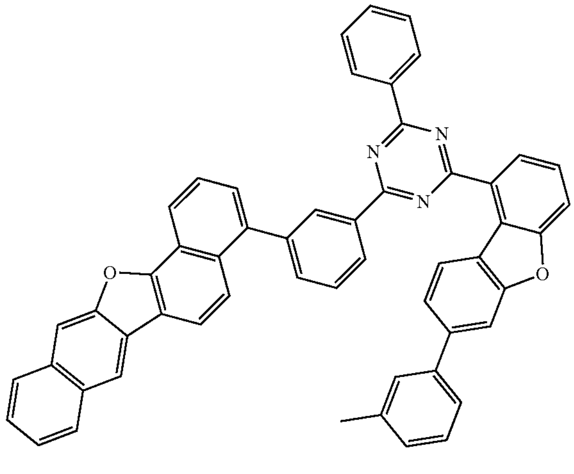
1-145
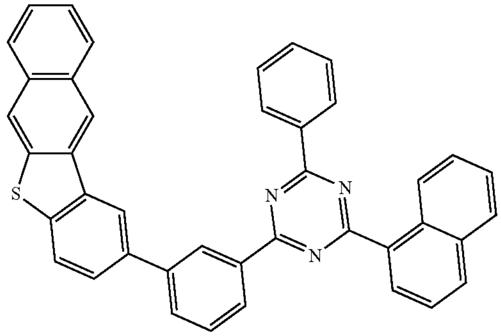
1-146
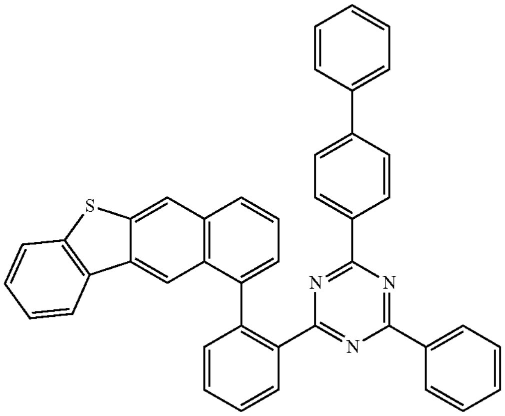
1-147
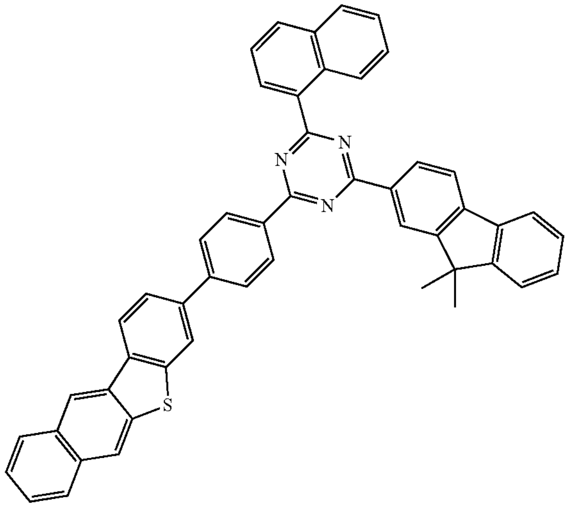

-continued
1-148
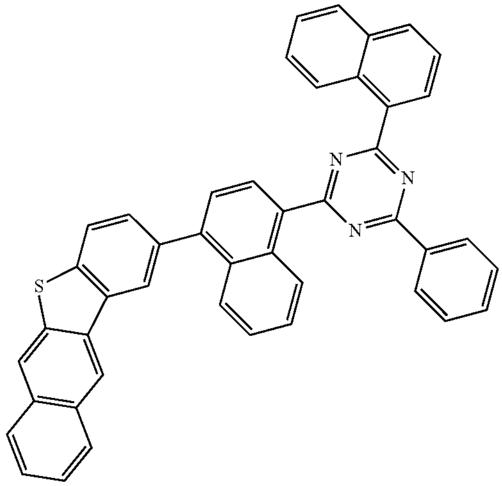
1-149
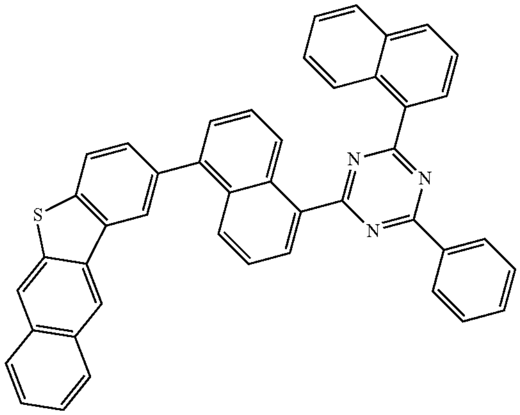
1-150
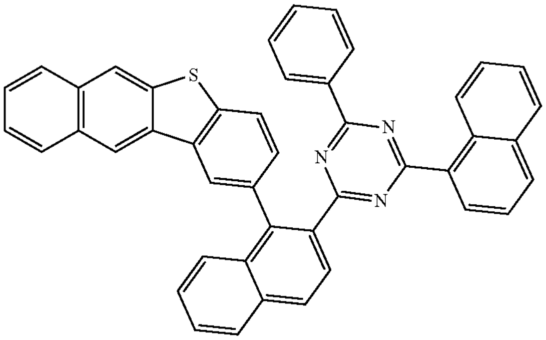
-continued
1-151
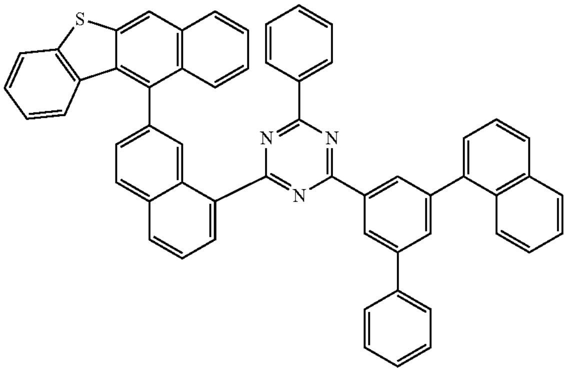
1-152
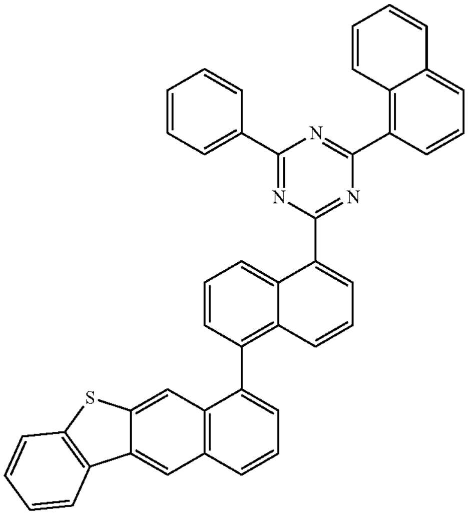
1-153
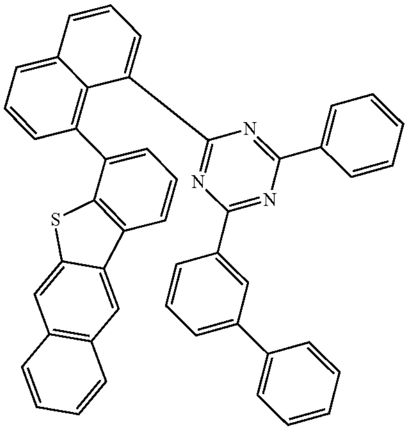

-continued
1-154
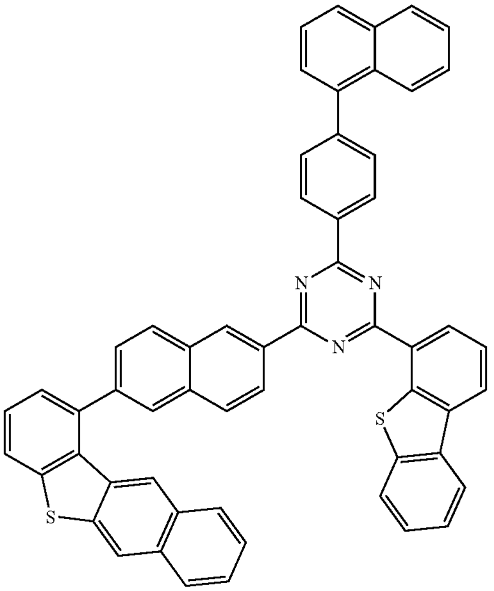
1-155
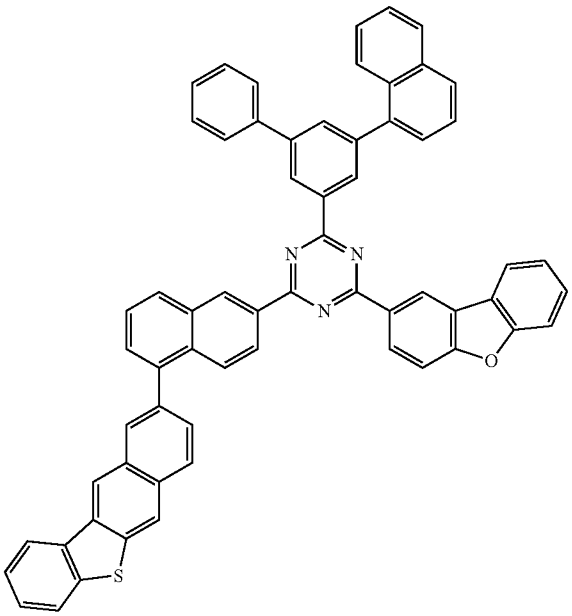
1-156
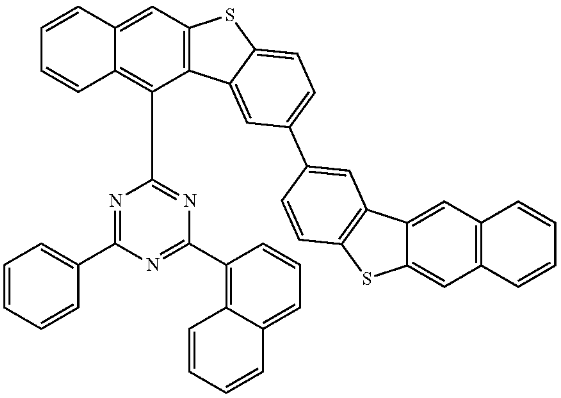
-continued
1-157
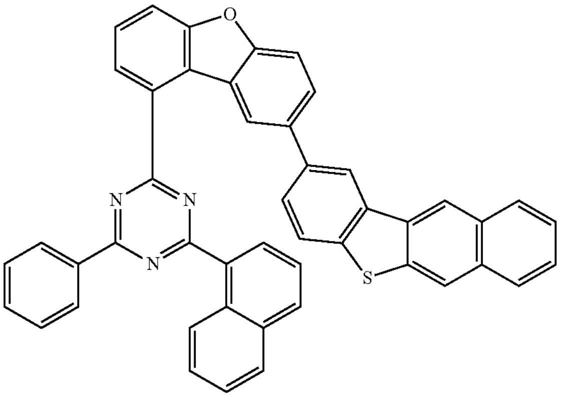
1-158
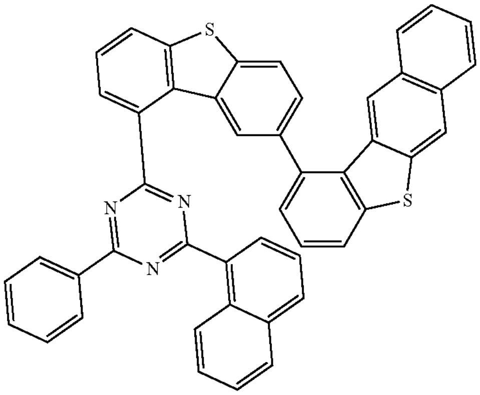
1-159
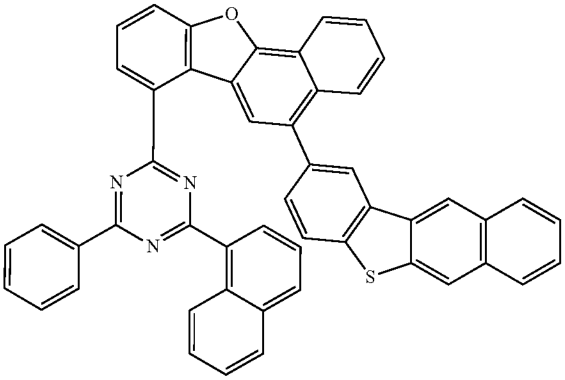
1-160
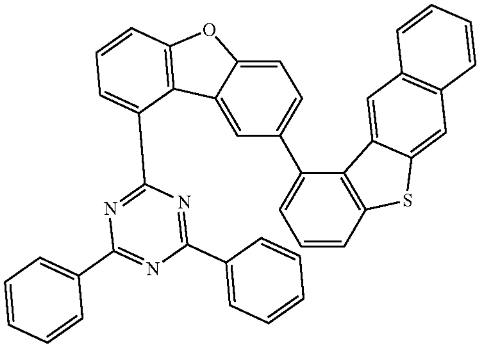

-continued
1-162
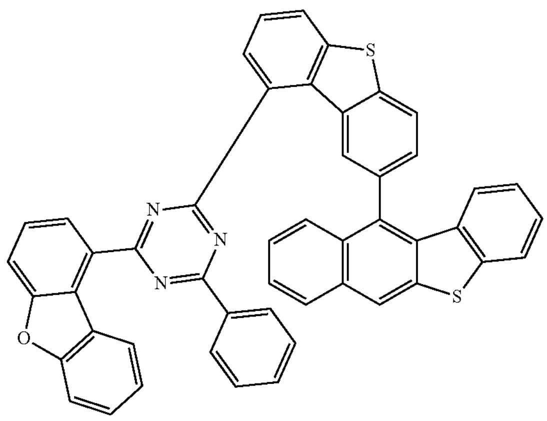
1-163
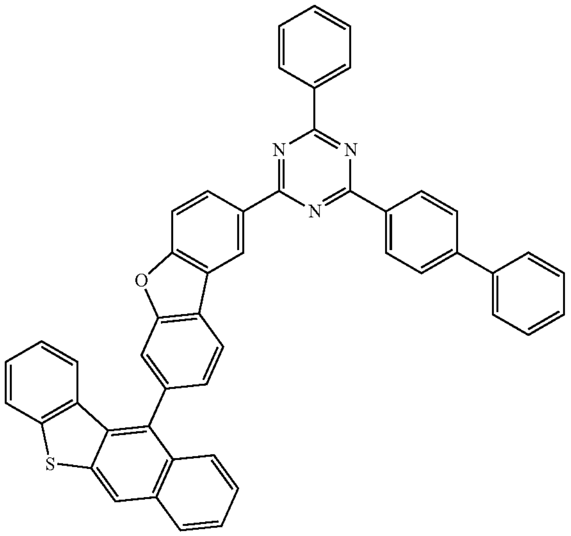
1-164
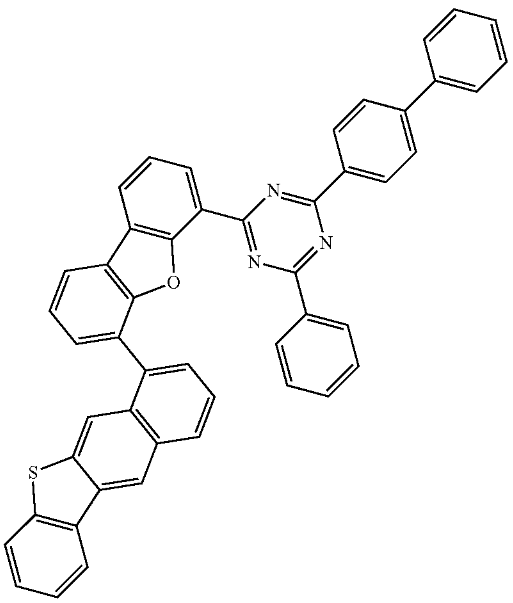
-continued
1-165
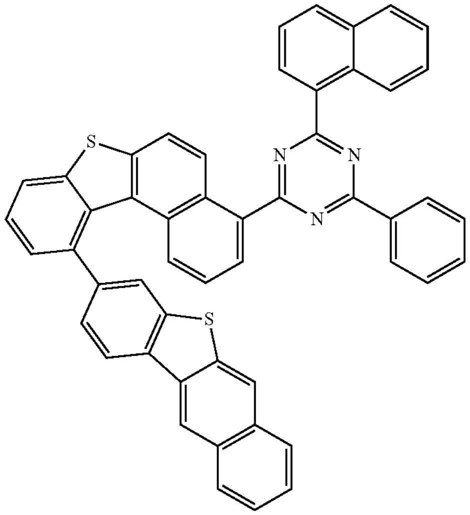
1-166
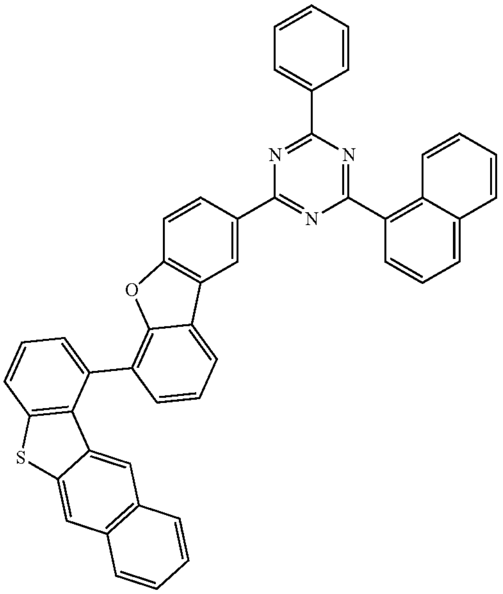

-continued
1-167
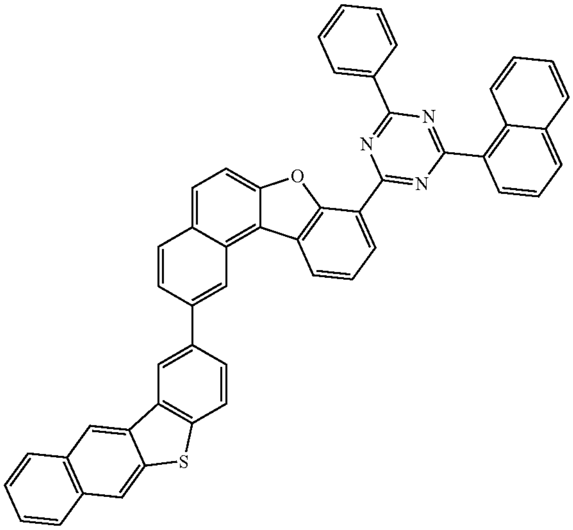
1-168
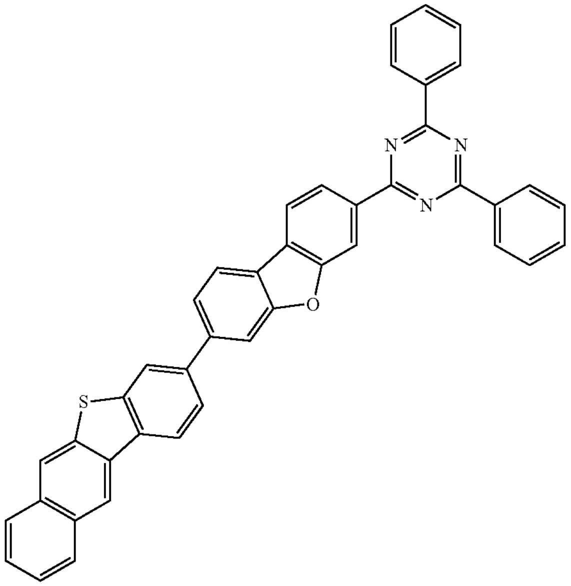
1-169
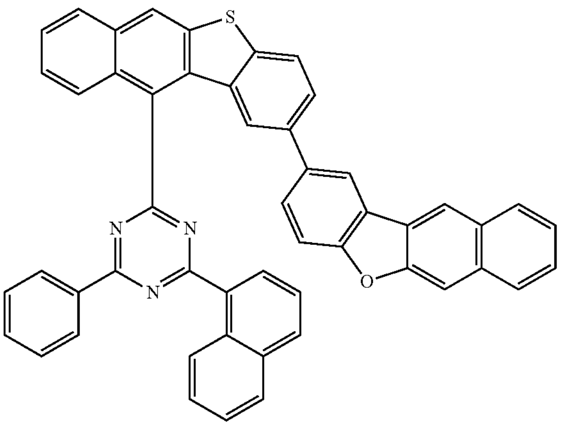
-continued
1-170
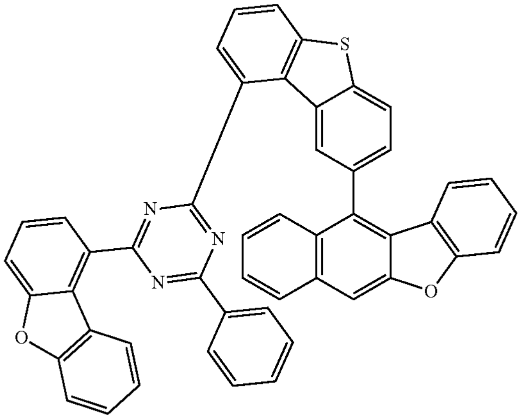
1-171
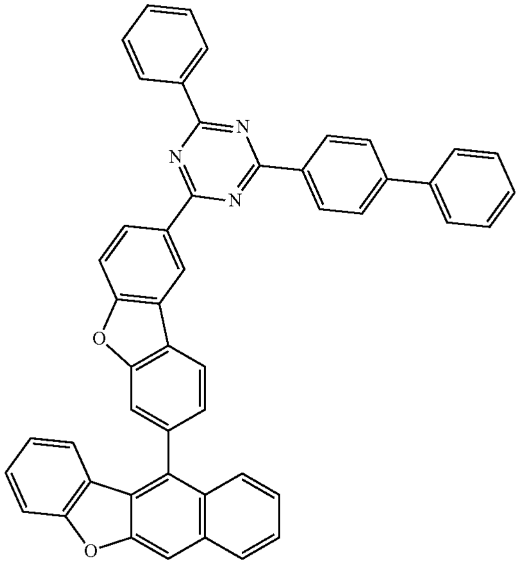
1-172
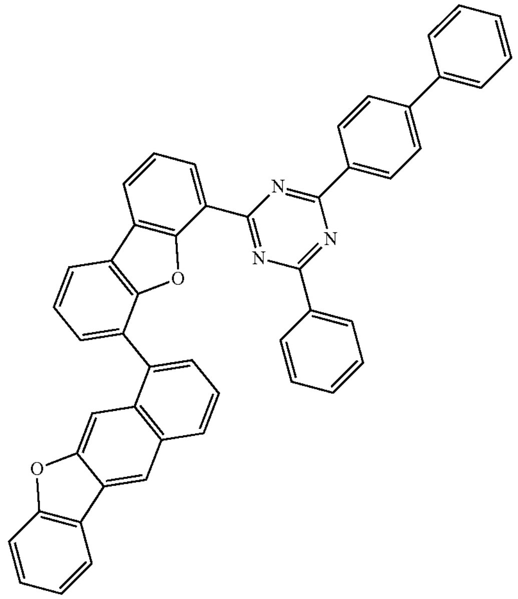

-continued
1-173
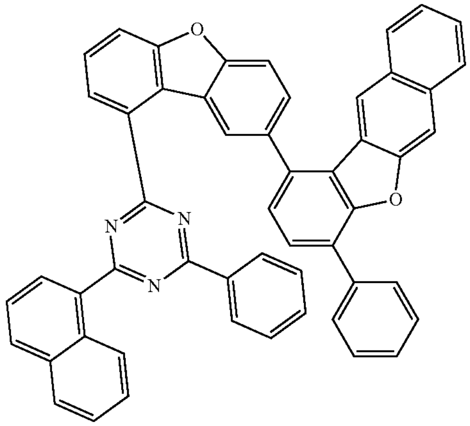
1-174
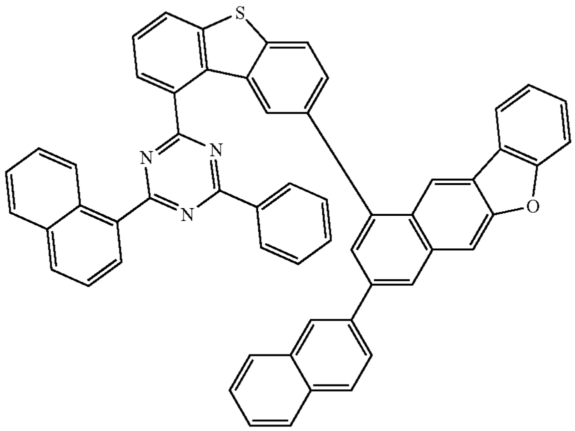
1-175
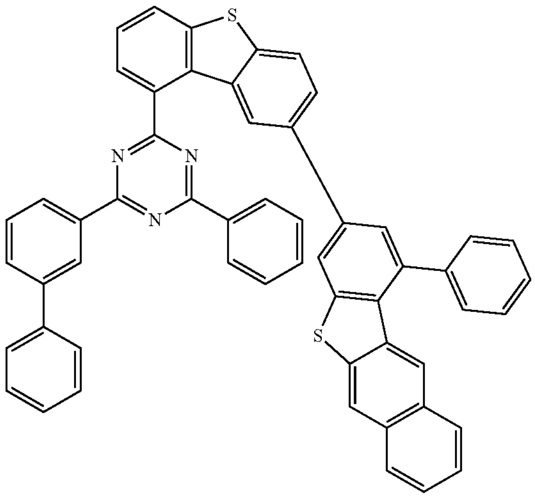
-continued
1-176
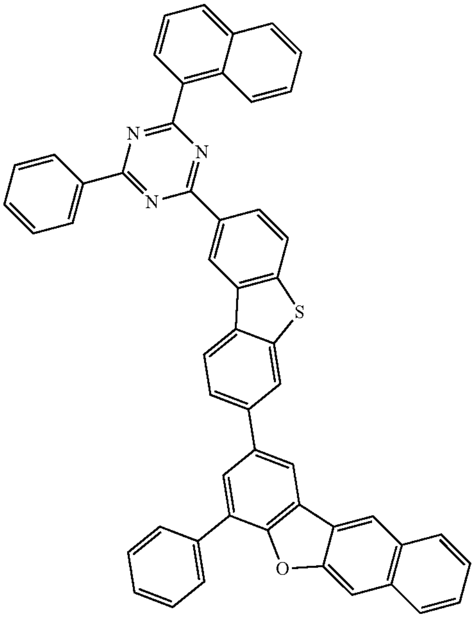
2-101
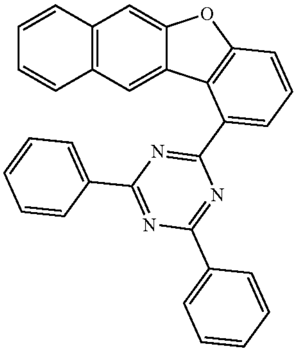
2-102
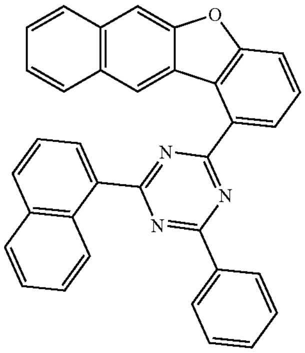

-continued
2-103
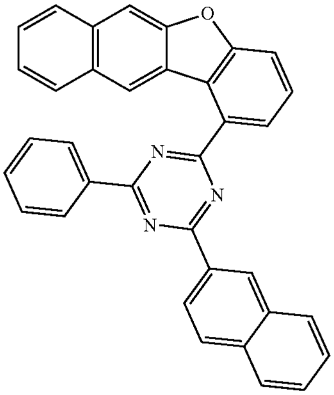
2-104
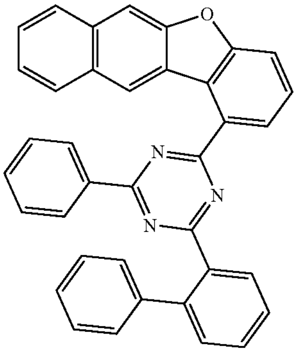
2-105
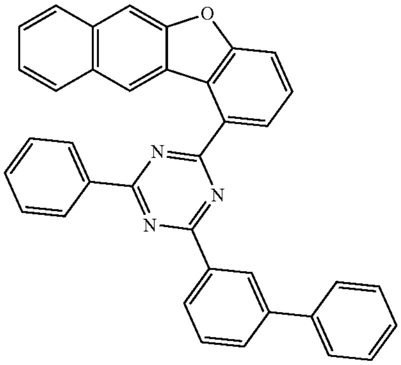
2-106
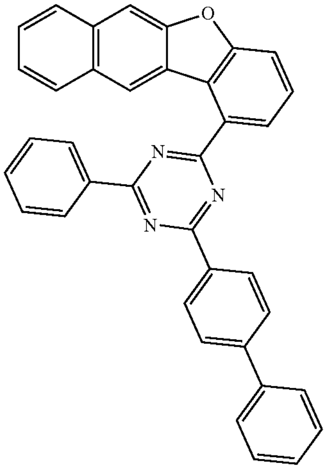
-continued
2-107
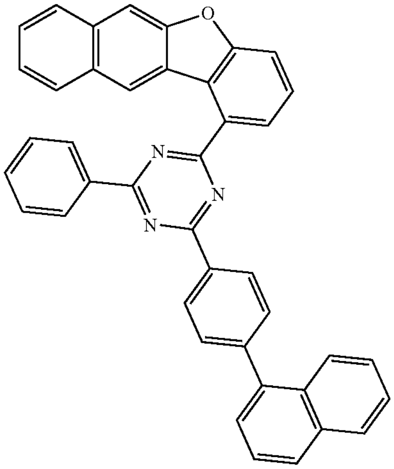
2-108
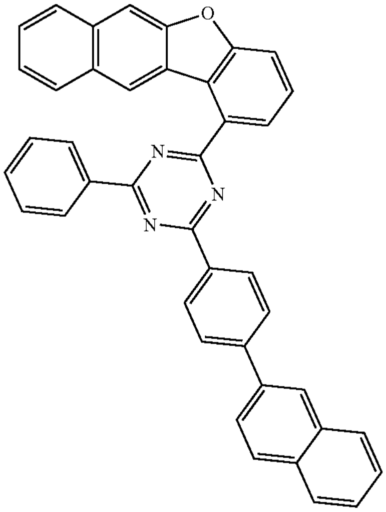
2-109
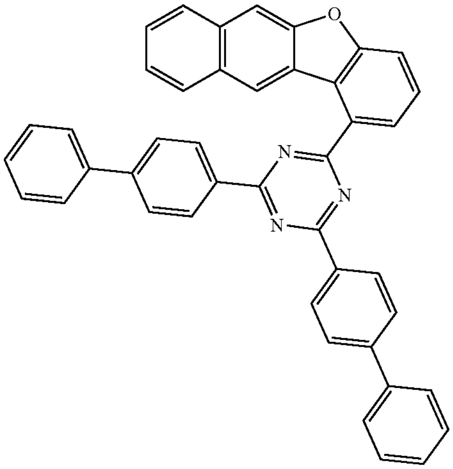

-continued
2-110
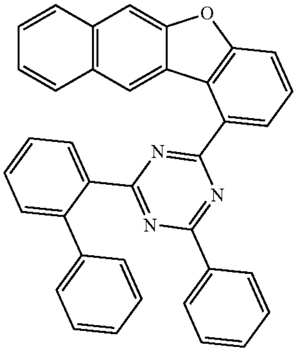
2-111
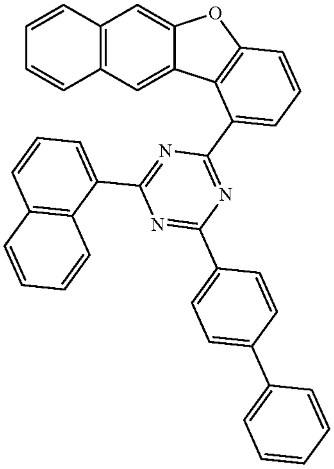
2-112
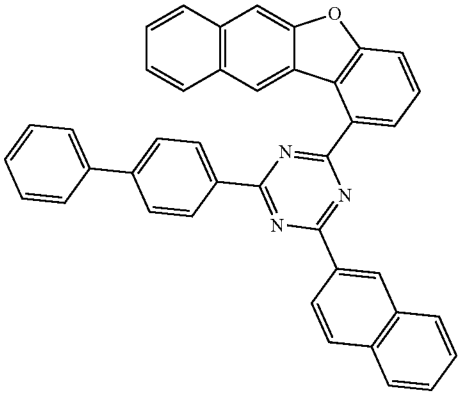
2-113
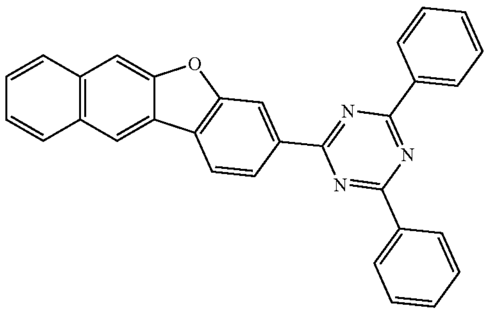
-continued
2-114
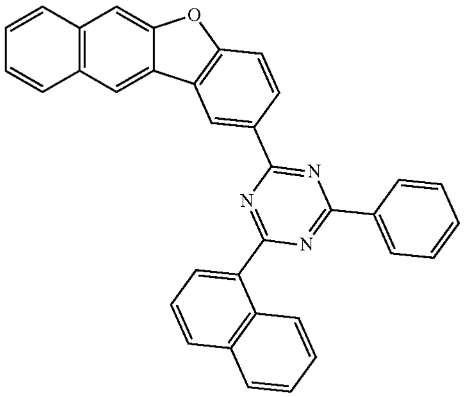
2-115
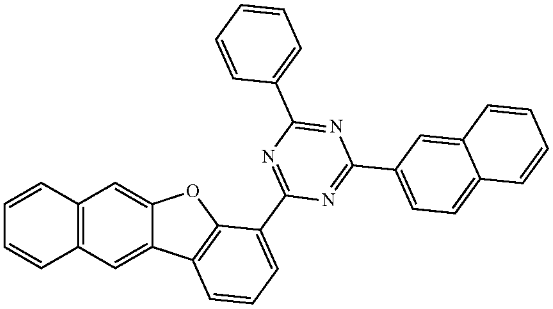
2-116
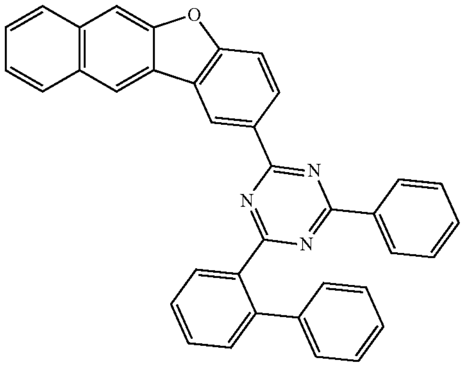
2-117
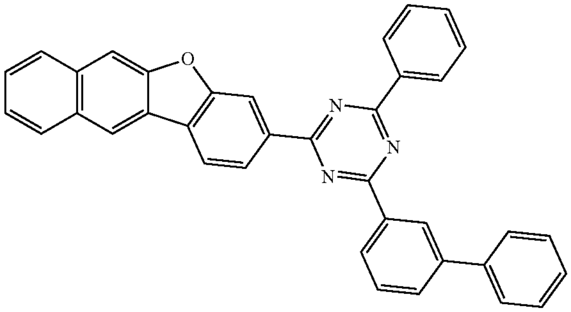

-continued
2-118
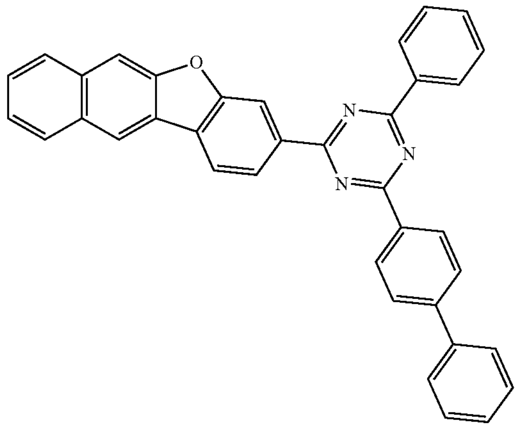
2-119
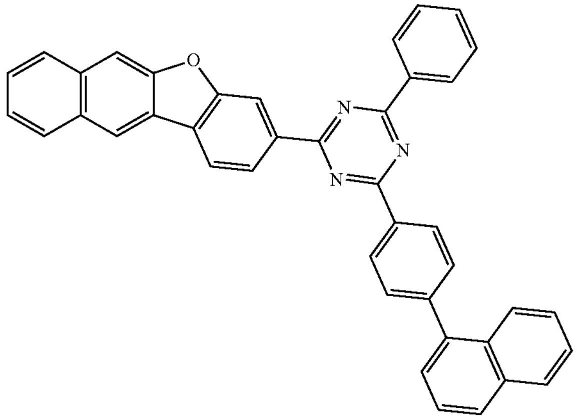
2-120
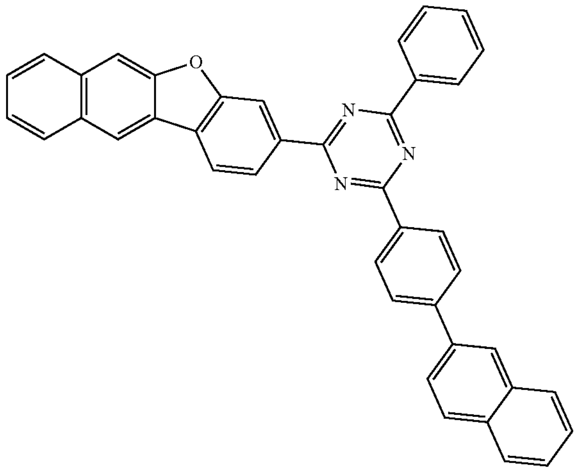
-continued
2-121
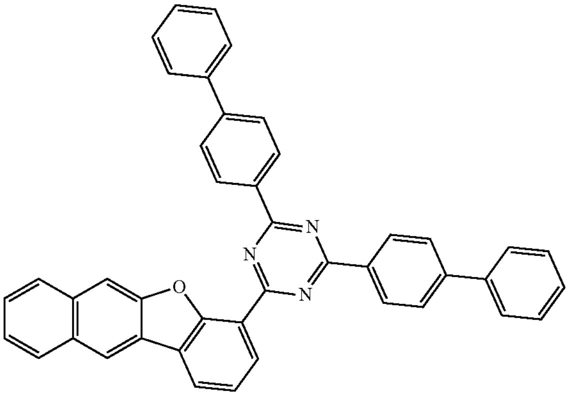
2-122
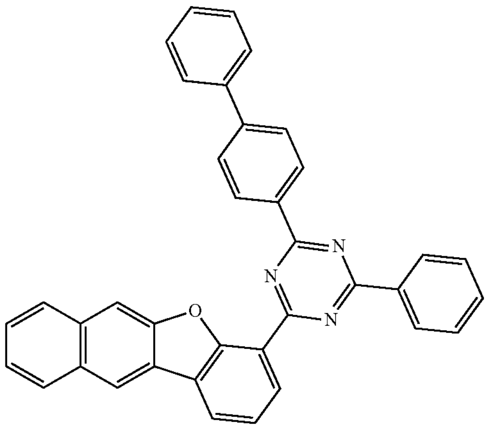
2-123
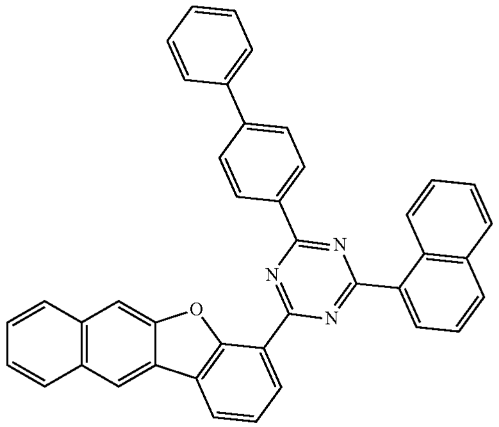

-continued 2-124

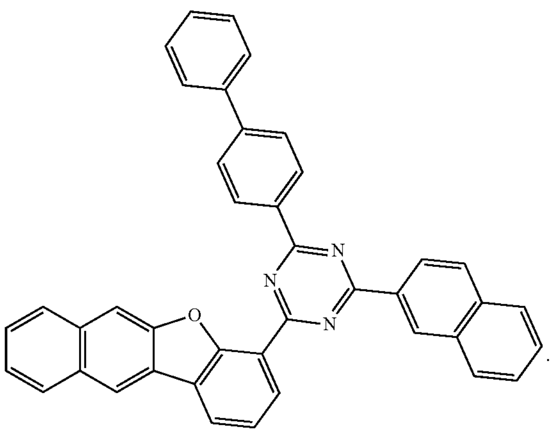

Next, the following Formula 2 will be described.

<Formula 2>

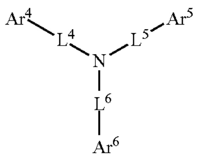

In the formula 2, each of symbols may be defined as follows.

$Ar^4$ to $Ar^6$ may be each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group.

Where $Ar^4$ to $Ar^6$ are an aryl group, $Ar^4$ to $Ar^6$ may be preferably a $C_6$-$C_{30}$ aryl group, more preferably a $C_6$-$C_{18}$ aryl group, for example, phenyl, biphenyl, naphthyl, terphenyl, phenanthrene or the like.

When $Ar^4$ to $Ar^6$ are a heterocyclic group, $Ar^4$ to $Ar^6$ may be preferably a $C_2$-$C_{30}$ heterocyclic group, more preferably a $C_2$-$C_{20}$ heterocyclic group, for example, dibenzothiophene, dibenzofuran, benzothienopyrimidine, carbazole, phenylcarbazole, benzonaphthothiophene, benzofurothiophene, dinaphthothiophene, dinaphthofuran or the like.

When $Ar^4$ to $Ar^6$ are a fluorenyl group, $Ar^4$ to $Ar^6$ may be 9,9-dimethyl-9H-fluorene, 9,9-diphenyl-9H-fluorene, 9,9'-spirobifluorene or the like.

$L^4$ to $L^6$ may be each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof, Where $L^4$ to $L^6$ are each an arylene group, $L^4$ to $L^6$ may be preferably a $C_6$-$C_{30}$ arylene group, more preferably a $C_6$-$C_{18}$ arylene group, for example, phenylene, biphenyl, naphthyl, terphenyl or the like.

When $L^4$ to $L^6$ are a fluorenyl group, $L^4$ to $L^6$ may be 9,9-dimethyl-9H-fluorene, 9,9-diphenyl-9H-fluorene, 9,9'-spirobifluorene or the like.

$Ar^4$~$Ar^6$ may be each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group, a $C_8$-$C_{20}$ arylalkenyl group and -L'-N($R_a$)($R_b$).

L' may be selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof.

$R_a$ and $R_b$ may be each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a combination thereof.

$L^4$~$L^6$, $R^1$, L', $R_a$ and $R_b$ may be each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group Formula 2 may be represented by one of the following Formula 2-A to Formula 2-L.

<Formula 2-A>

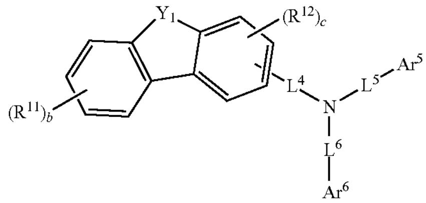

<Formula 2-B>

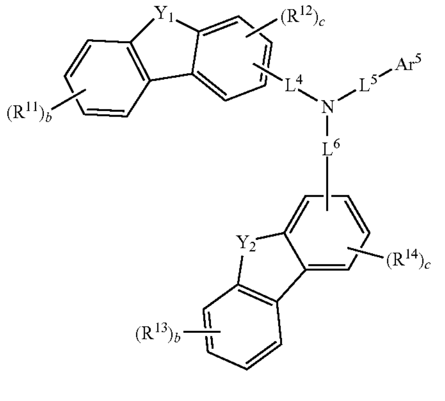

-continued

<Formula 2-C>

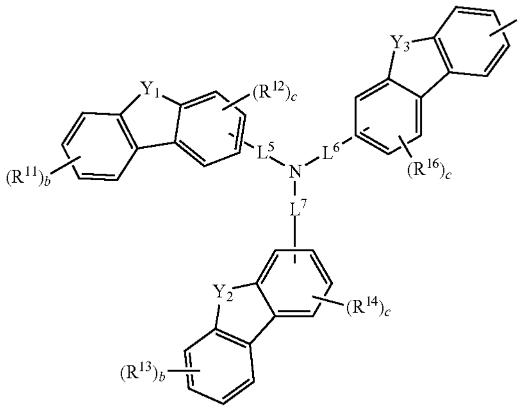

<Formula 2-D>

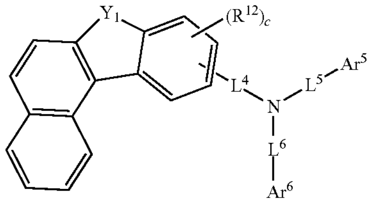

<Formula 2-E>

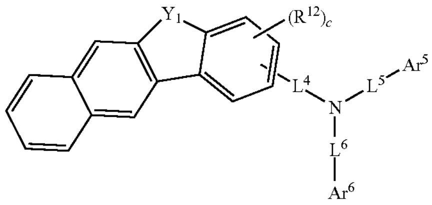

<Formula 2-F>

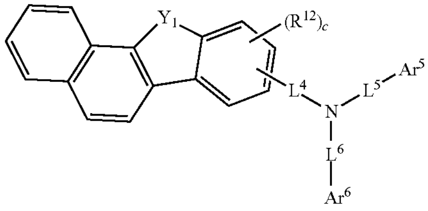

<Formula 2-G>

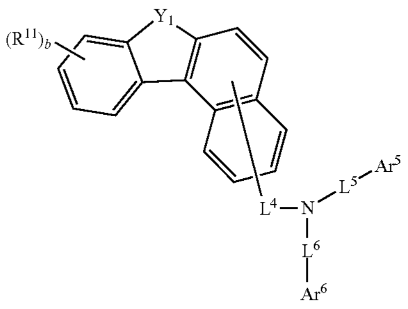

-continued

<Formula 2-H>

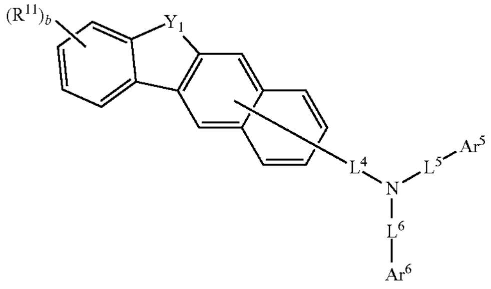

<Formula 2-I>

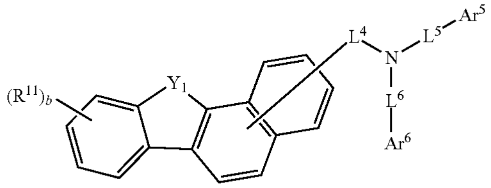

<Formula 2-J>

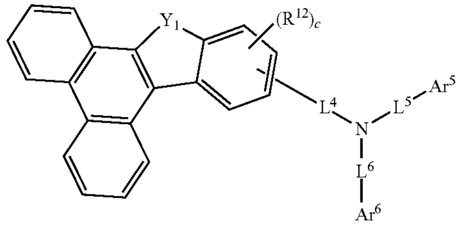

<Formula 2-K>

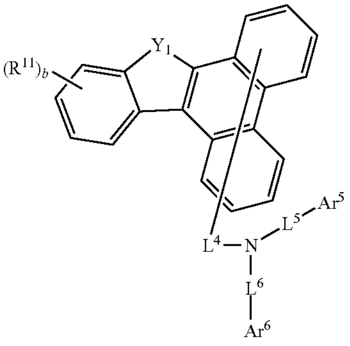

<Formula 2-L>

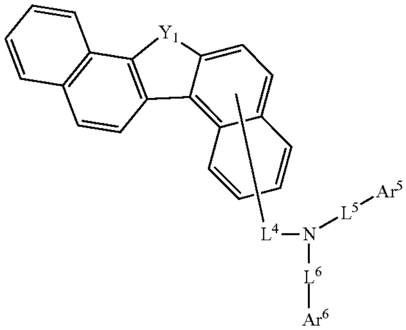

In Formulas 2-A to 2-L, Ary, $Ar^6$, and $L^4$~$L^6$ are the same as defined in Formula 2, and $Y_1$~$Y_3$ are each independently O, S, or C(R')(R").

$R^{11}$~$R^{16}$, R' and R" are each independently selected from the group consisting of hydrogen, deuterium, halogen, a silane group substituted or unsubstituted with $C_1$-$C_{20}$ alkyl group or $C_6$-$C_{20}$ aryl group, a cyano group, a nitro group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and -L'-N($R_a$)($R_b$), and adjacent groups may optionally be linked to each other to form a ring. Here, L', $R_a$ and $R_b$ are the same as defined in Formula 2.

The ring formed by bonding adjacent groups to each other may be a $C_6$-$C_{60}$ aromatic ring group, a fluorenyl group, a $C_2$-$C_{60}$ heterocyclic group containing at least one heteroatom selected from the group consisting of O, N, S, Si, and P, or a $C_3$-$C_{60}$ aliphatic ring or the like. For example, where adjacent $R^{11}$ groups, adjacent $R^{12}$ groups, adjacent $R^{13}$ groups, adjacent $R^{14}$ groups, adjacent $R^{15}$ groups, adjacent $R^{16}$ groups, and/or R' and R" groups, respectively, are linked to each other to form an aromatic ring group, the ring may be preferably a $C_6$-Cso aromatic ring group, more preferably a $C_6$-$C_{14}$ aromatic ring group, for example, benzene, naphthalene, phenanthrene or the like.

b is an integer of 0-4, and where b is an integer of 2 or more, each of a plurality of $R^{11}$, each of a plurality of $R^{13}$ and each of a plurality of $R^{15}$ are the same as or different from each other, c is an integer of 0-3, and where c is an integer of 2 or more, each of a plurality of $R^{12}$, each of a plurality of $R^{14}$ and each of a plurality of $R^{16}$ are the same as or different from each other.

In addition, preferably, Formula 2 may be represented by the following Formula 4. The following Formula 4 may be the case where one of $R^{11}$s in Formula 2-A is -L'-N($R_a$)($R_b$) or the case where $Ar^4$ is a 3-fused (condensed) ring comprising $Y_1$ and the 3-fused ring is further substituted with -L'-N($R_a$)($R_b$) in Formula 2.

Therefore, in the following Formula 4, $Y_1$, $R^{11}$, $R^{12}$, $L^4$, $L^5$, $L^6$, $Ar^5$, $Ar^6$, c and the like are the same as defined in Formula 2-A, $L^{21}$ is defined to be the same n as L' of Formula 2 or Formula 2-A, $R^{21}$ and $R^{22}$ are each defined to be the same n as $R_a$ and $R_b$ of Formula 2 or Formula 2-A, and d is an integer of 0-3. Each of a plurality of $R^{11}$ is the same as or different from each other and adjacent groups may optionally be linked to each other to form a ring, where d is an integer of 2 or more.

<Formula 4>

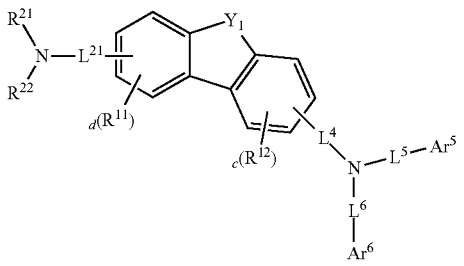

Where $R^{11}$ and $R^{12}$ are an aryl group, $R^{11}$ and $R^{12}$ may be preferably a $C_6$-$C_{18}$ aryl group, for example, phenyl, naphthyl, biphenyl, terphenyl, phenanthrene or the like.

Where $R^{11}$ and $R^{12}$ are a heterocyclic group, $R^{11}$ and $R^{12}$ may be preferably a $C_2$-$C_{12}$ heterocyclic group, for example, a heterocyclic ring containing N such as pyridine, pyrimidine, triazine, quinazoline, quinoline, isoquinoline and the like, or dibenzothiophene, dibenzofuran and the like.

Where $R^{11}$ and $R^{12}$ are an alkyl group, $R^{11}$ and $R^{12}$ may be preferably a $C_1$-$C_{10}$ alkyl group, for example, methyl, t-butyl and the like.

The ring formed by bonding adjacent $R^{11}$ groups and/or adjacent $R^{12}$ groups to each other may be a $C_6$-$C_{20}$ aromatic ring group, a fluorenyl group, a $C_2$-$C_{20}$ heterocyclic group containing at least one heteroatom selected from the group consisting of O, N, S, Si, and P, or a $C_3$-$C_{20}$ aliphatic ring or the like. Where adjacent groups are linked to each other to form an aromatic ring group, the ring may be preferably a $C_6$-$C_{14}$ aromatic ring group, for example, benzene, naphthalene, anthracene, phenanthrene or the like.

Where $L^{21}$ is an arylene group, $L^{21}$ may be preferably a $C_6$-$C_{30}$ arylene group, more preferably a $C_6$-$C_{18}$ arylene group, for example, phenylene, naphthylene, biphenyl, terphenyl or the like.

Where $R^{21}$ and $R^{22}$ are an aryl group, $R^{21}$ and $R^{22}$ may be preferably a $C_6$-$C_{18}$ aryl group, for example, phenyl, naphthyl, biphenyl, terphenyl, phenanthrene, triphenylene or the like.

Where $R^{21}$ and $R^{22}$ are a heterocyclic group, $R^{21}$ and $R^{22}$ may be preferably a $C_2$-$C_{18}$ heterocyclic group, for example, benzothiophene, benzofuran, dibenzothiophene, dibenzofuran, benzonaphthothiophene, benzonaphthofuran, carbazole, phenylcarbazole and the like.

When $R^{21}$ and $R^{22}$ is a fluorenyl group, $R^{21}$ and $R^{22}$ may be 9,9-dimethylfluorene, 9,9-diphenyifluorene, 9,9'-bispirofluorene or the like.

Preferably, Formula 4 may be represented by one of the following Formulas 4-1 to 4-9.

<Formula 4-1>

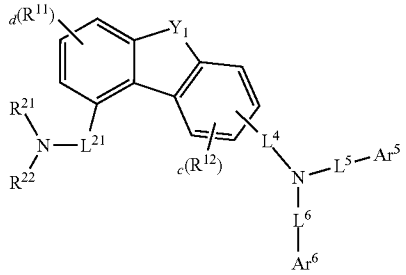

<Formula 4-2>

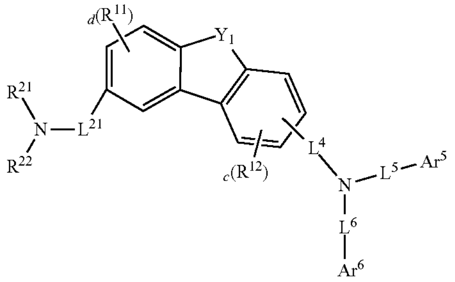

<Formula 4-3>

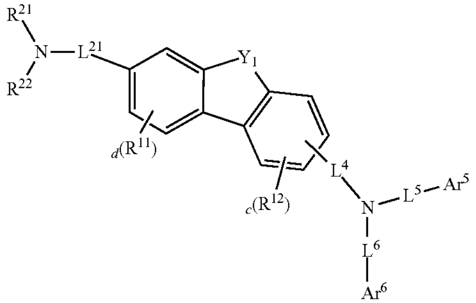

-continued

<Formula 4-4>

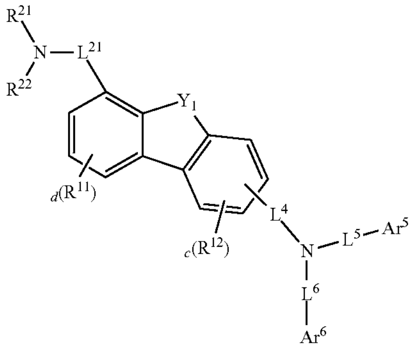

<Formula 4-5>

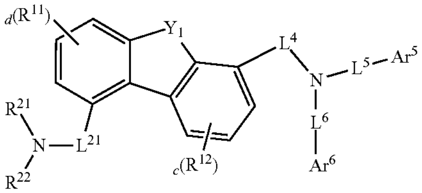

<Formula 4-6>

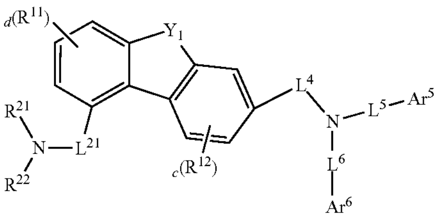

<Formula 4-7>

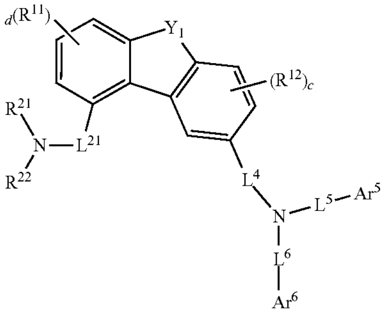

<Formula 4-8>

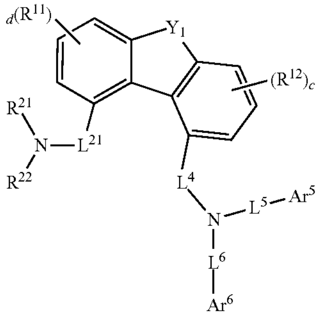

-continued

<Formula 4-9>

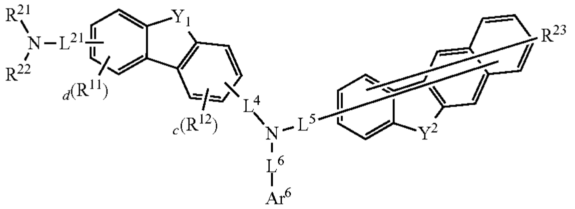

In Formulas 4-1 to 4-9, the symbols such as $Y_1$, $L^4$, $L^5$, $L^6$, $Ar^5$, $Ar^6$, $R^{11}$, $R^{12}$, $L^{21}$, $R^{21}$, $R^{22}$, c, d and the like are the same as defined in Formula 4, $Y^2$ is O or S, and $R^{23}$ may be defined to be the same as $R^{11}$.

Specifically, the compound represented by formula 2 may be one of the following compounds, but it is not limited thereto.

2-1

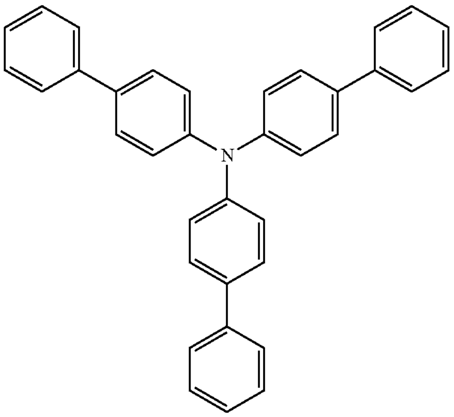

2-2

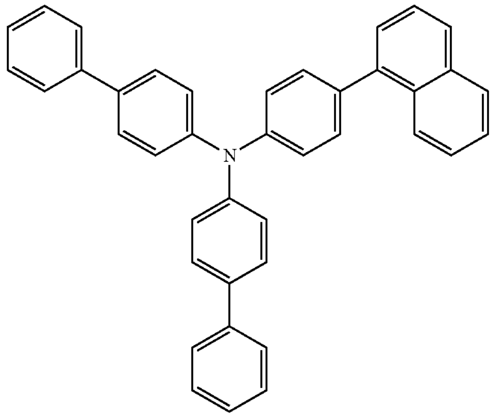

2-3

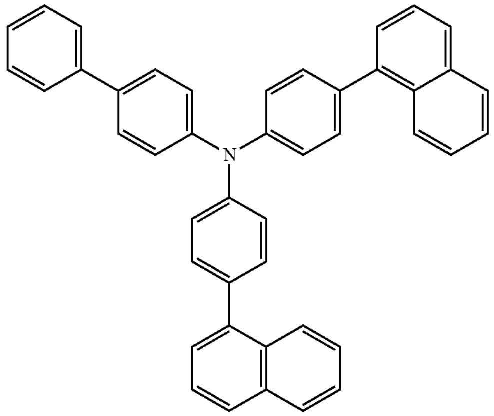

-continued
2-4
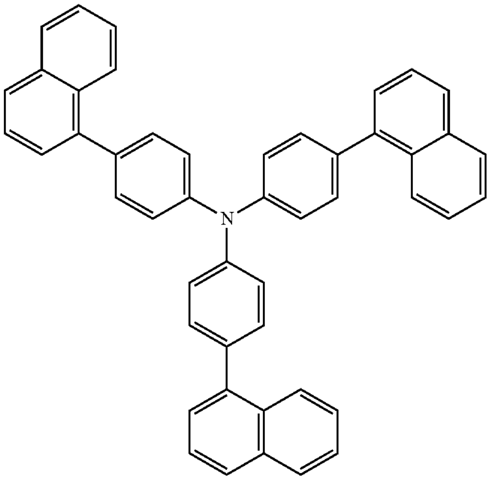
2-5
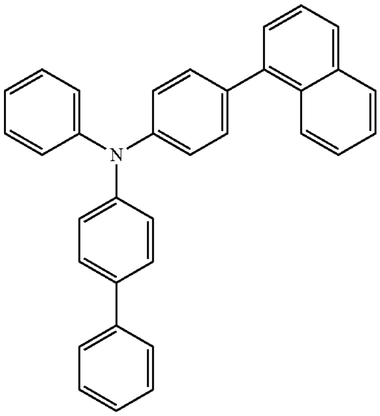
2-6
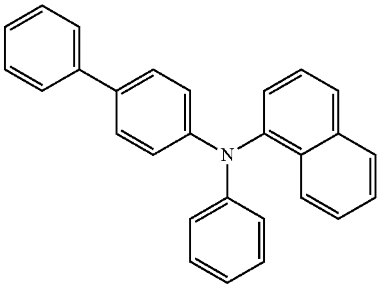
2-7
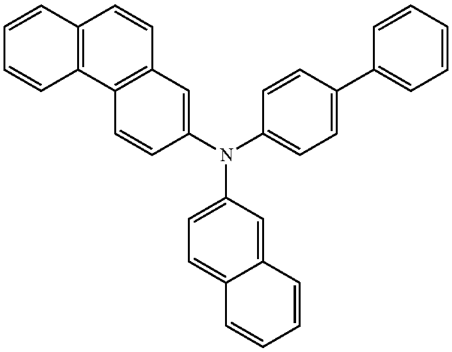
-continued
2-8
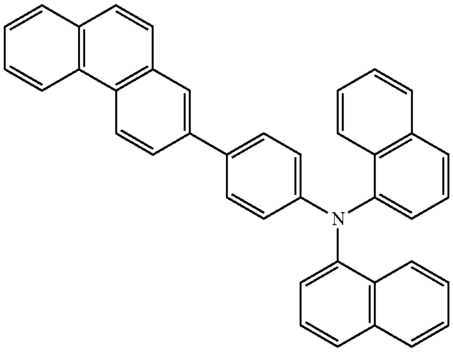
2-9
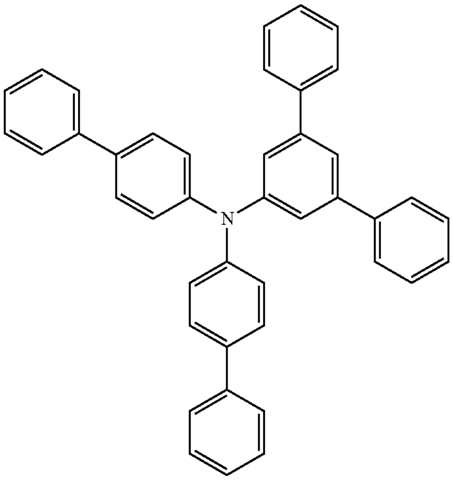
2-10
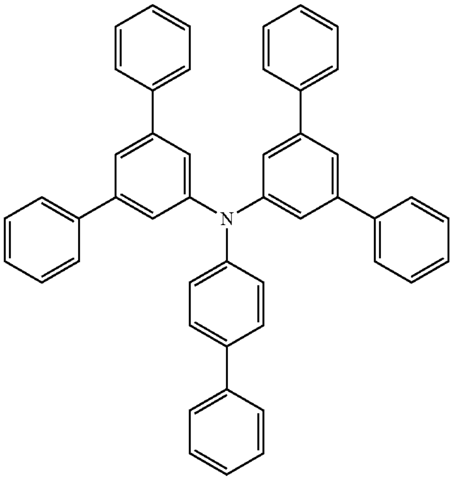

-continued
2-11
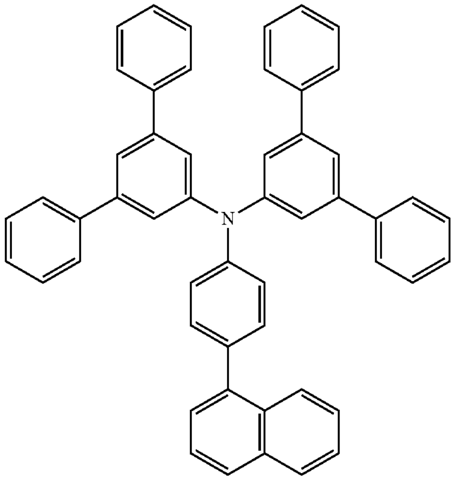
2-12
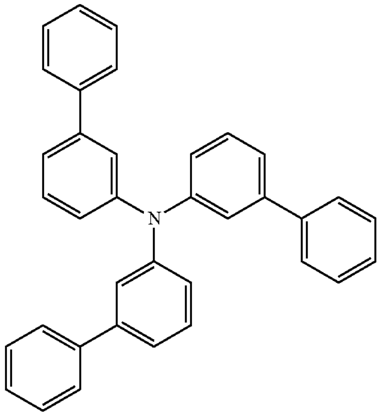
2-13
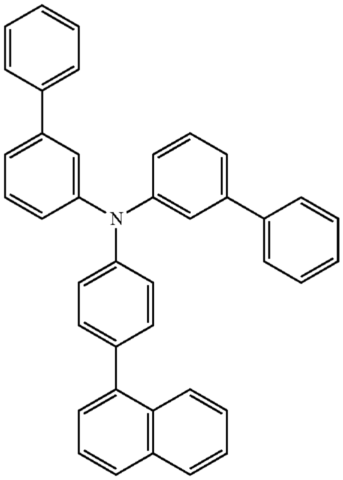
-continued
2-14
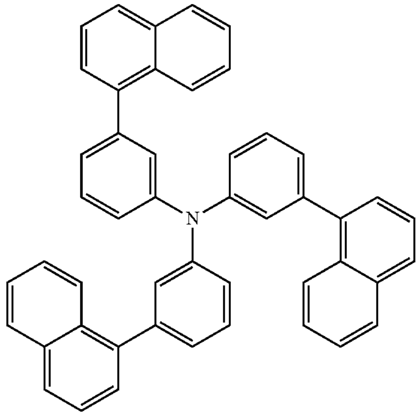
2-15
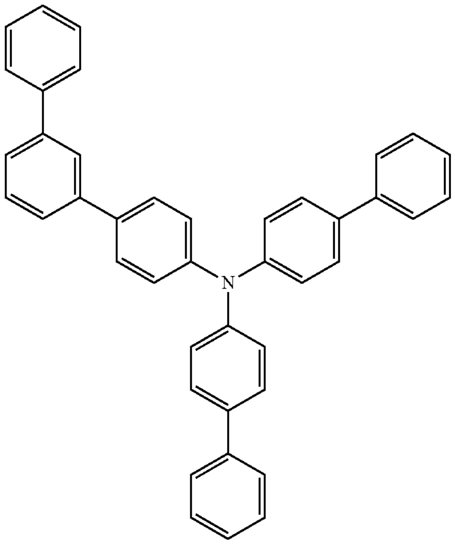
2-16
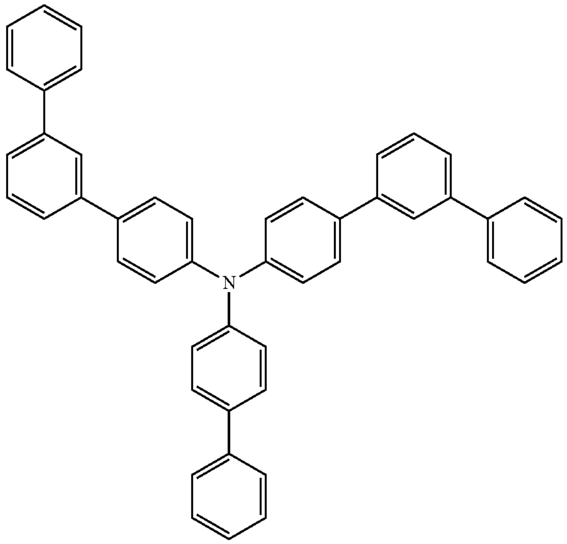

-continued
2-17
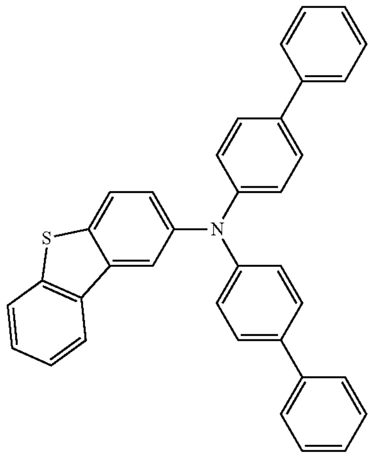
2-18
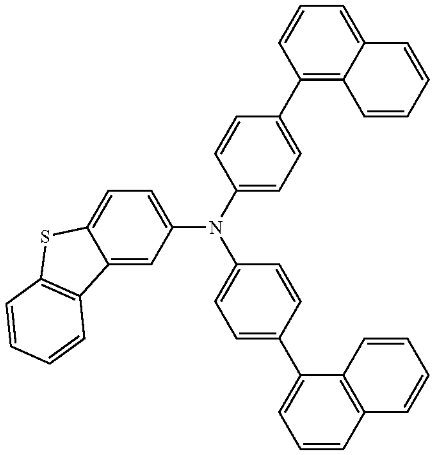
2-19
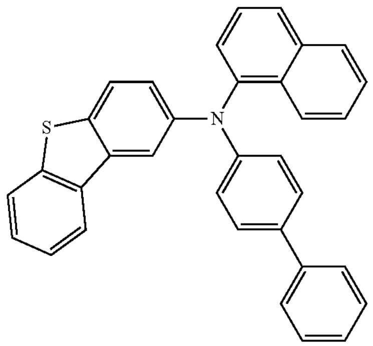
2-20
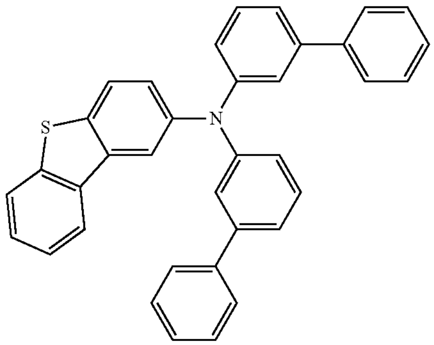
-continued
2-21
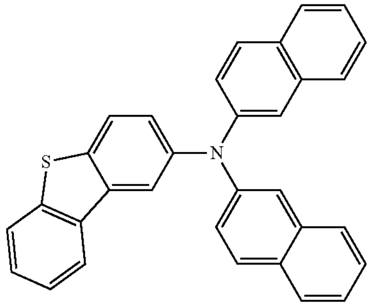
2-22
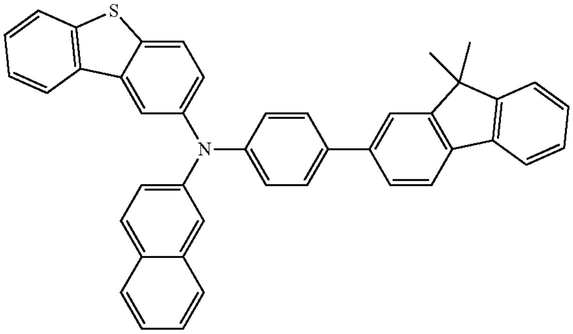
2-23
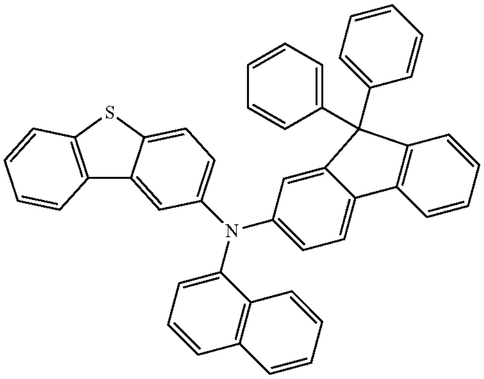
2-24
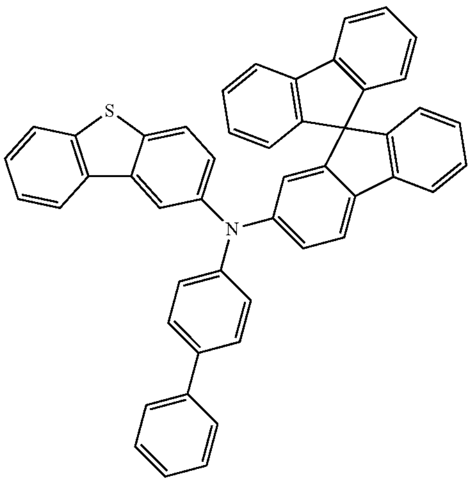

-continued
2-25
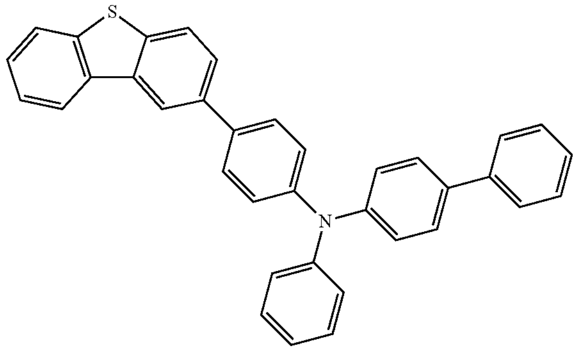
2-26
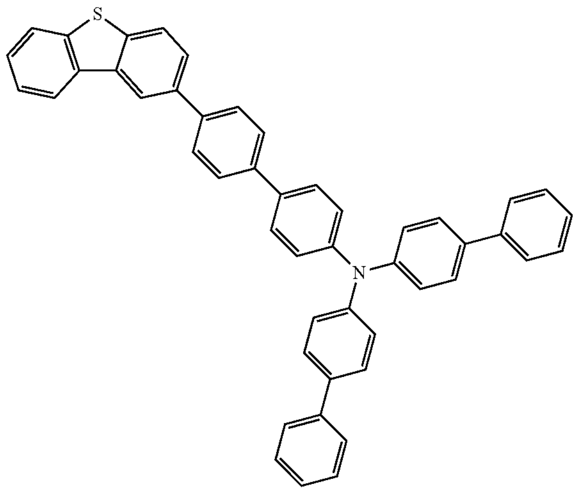
2-27
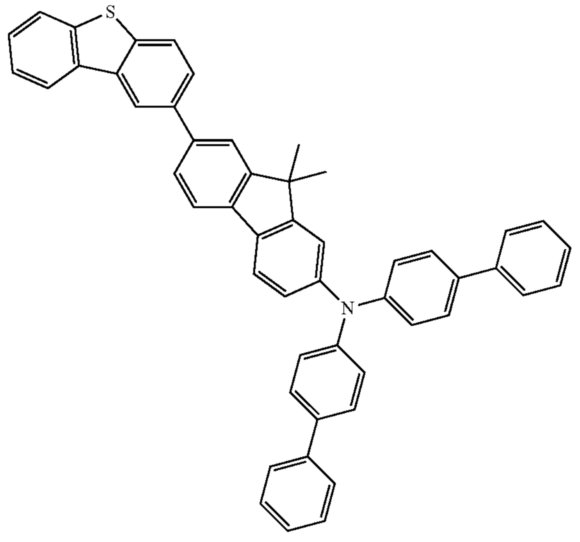
-continued
2-28
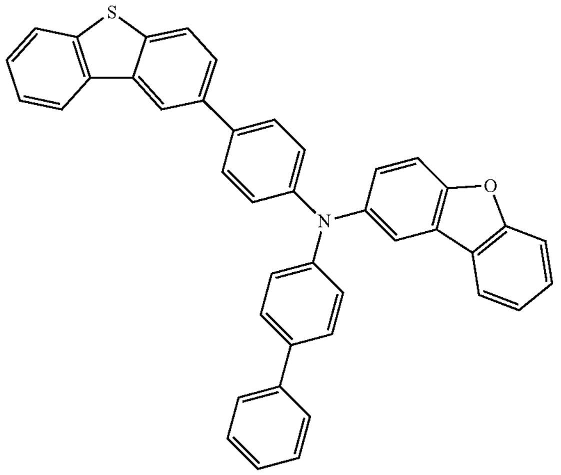
2-29
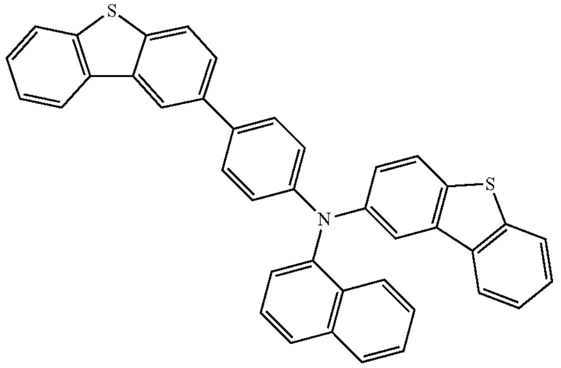
2-30
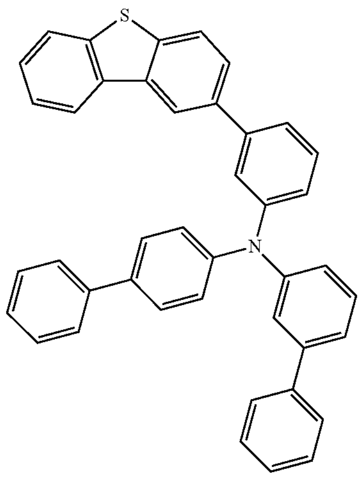

-continued
2-31
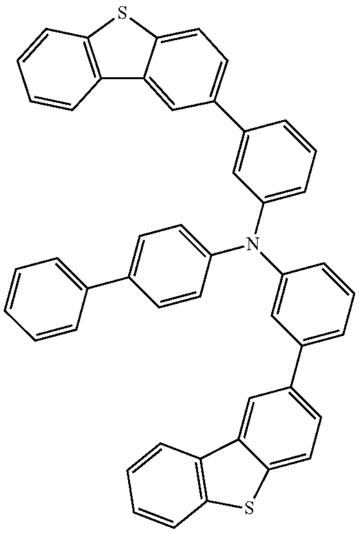
2-32
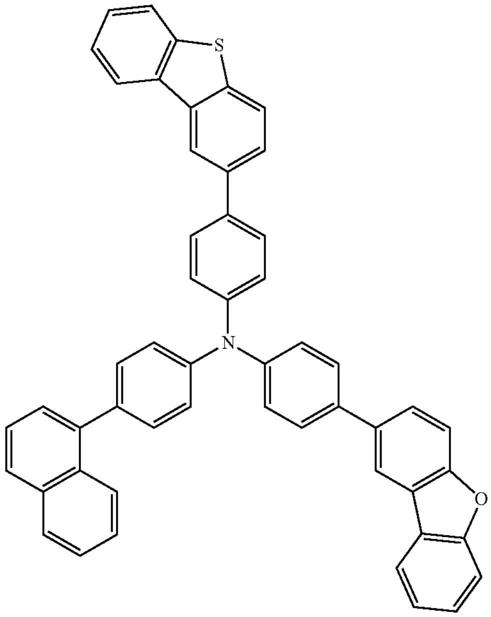
2-33
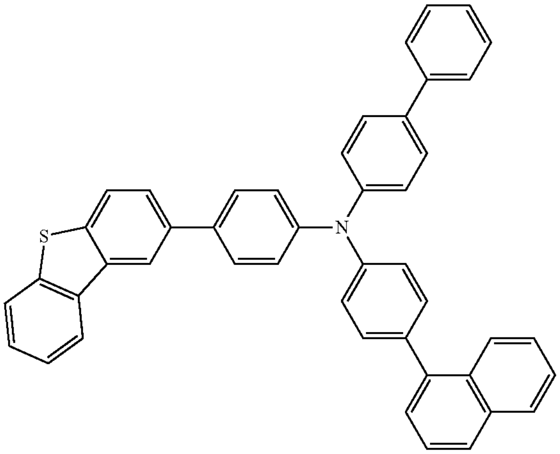
-continued
2-34
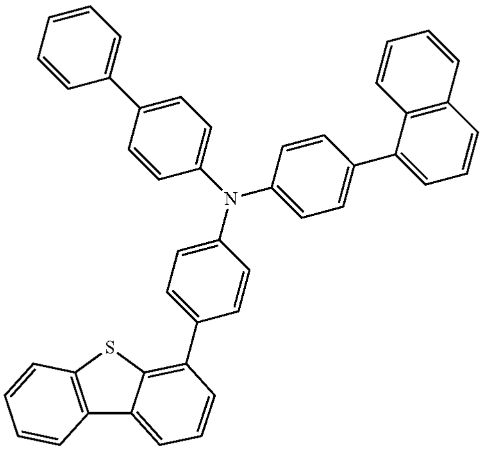
2-35
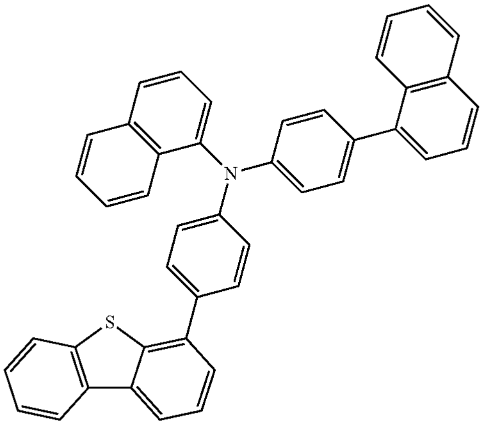
2-36
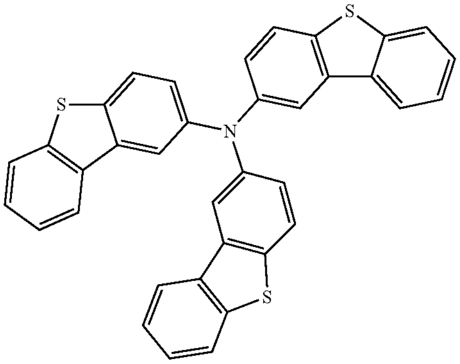

-continued
2-37
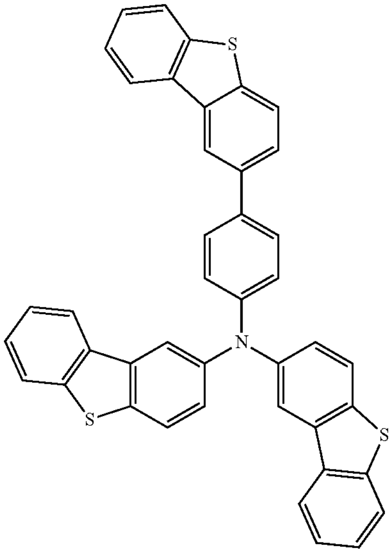
2-38
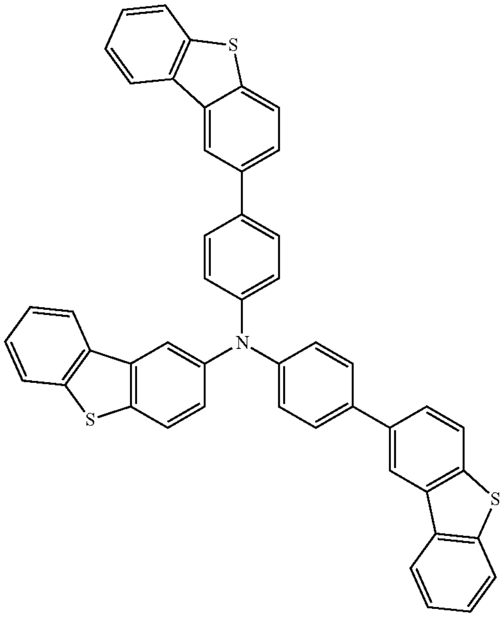
-continued
2-39
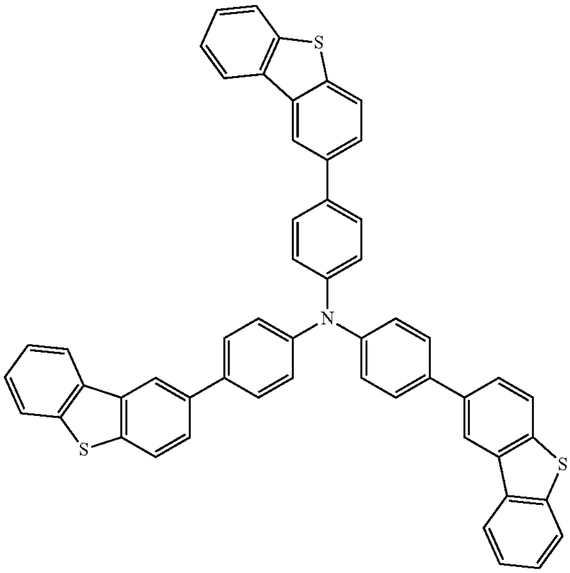
2-40
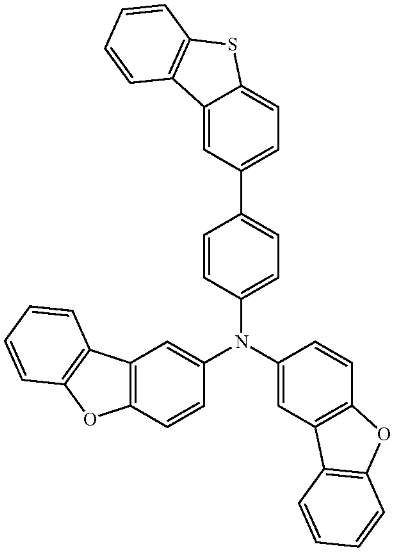
2-41
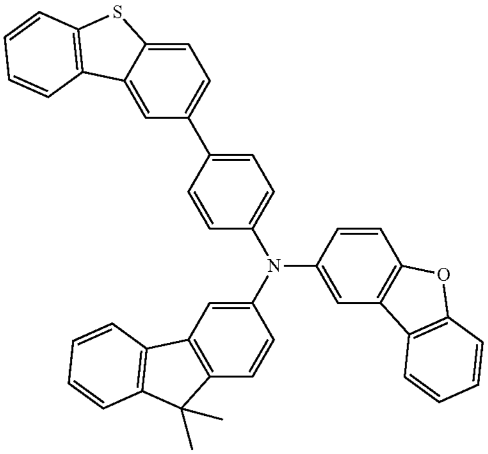

-continued
2-42
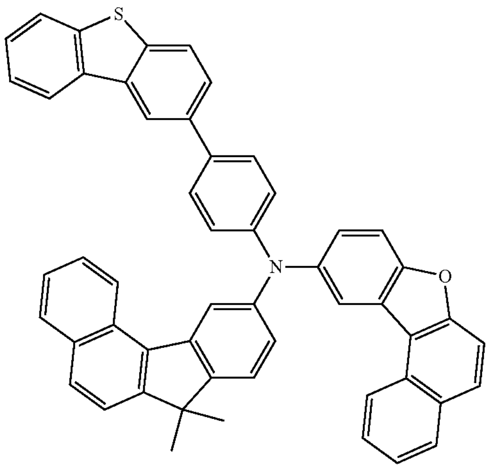
2-43
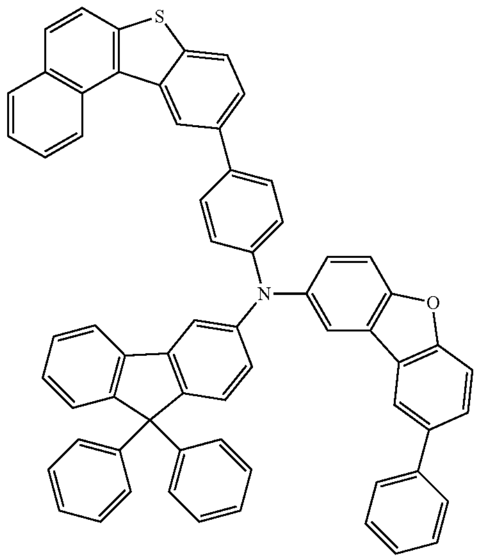
2-44
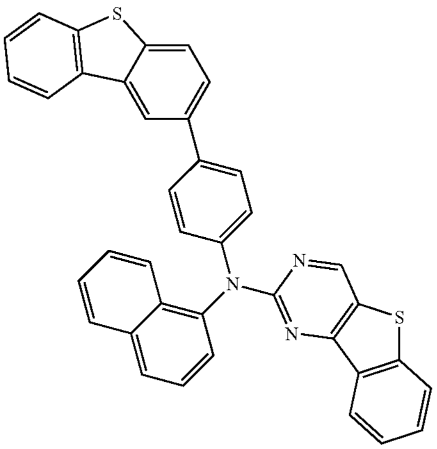
-continued
2-45
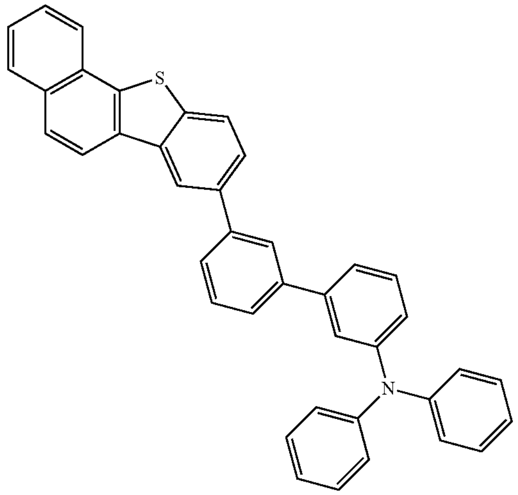
2-46
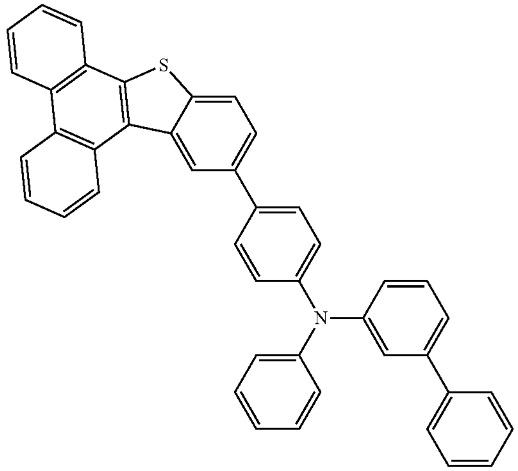
2-47
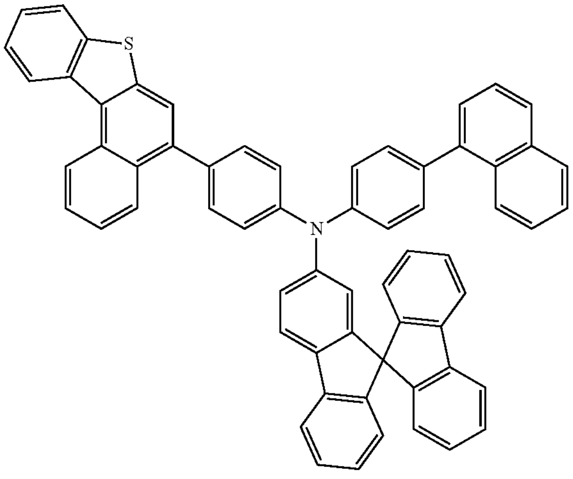

-continued
2-48
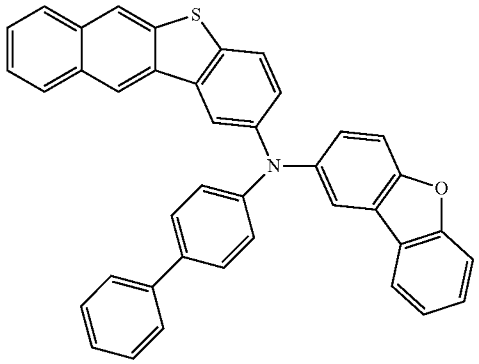
2-49
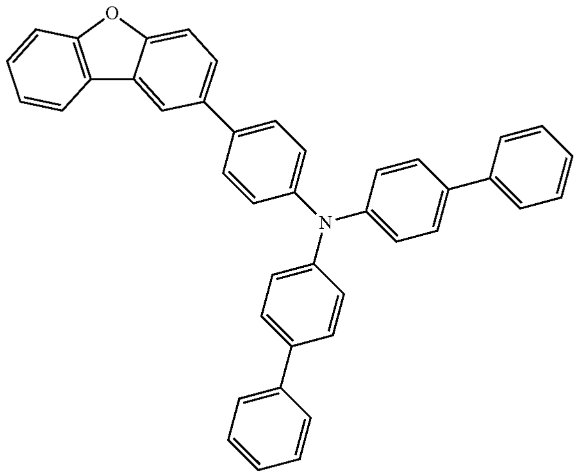
2-50
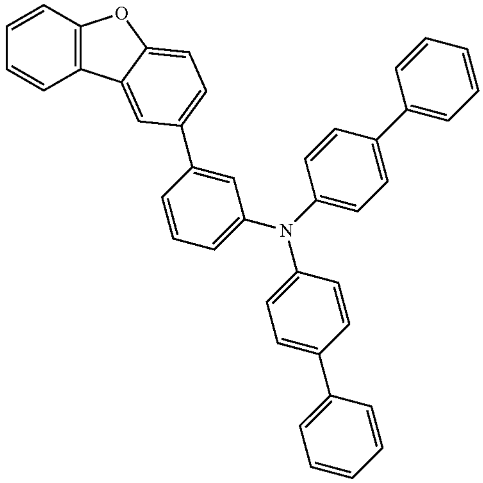
-continued
2-51
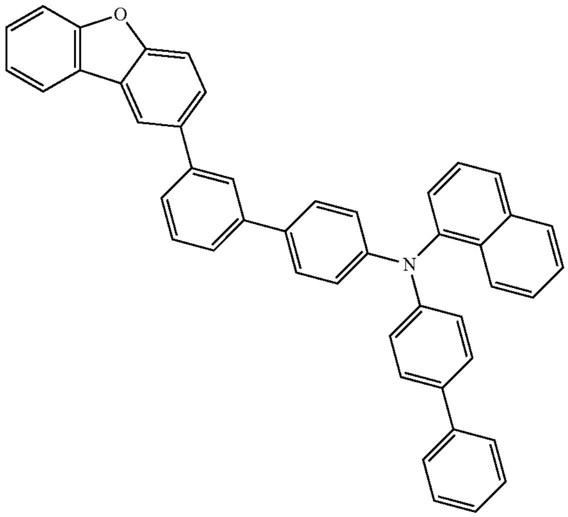
2-52
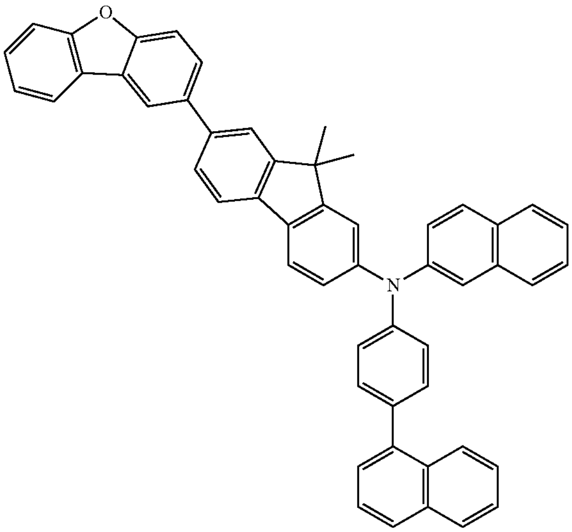
2-53
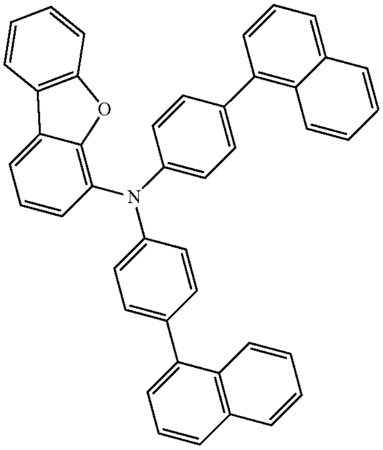

-continued
2-54
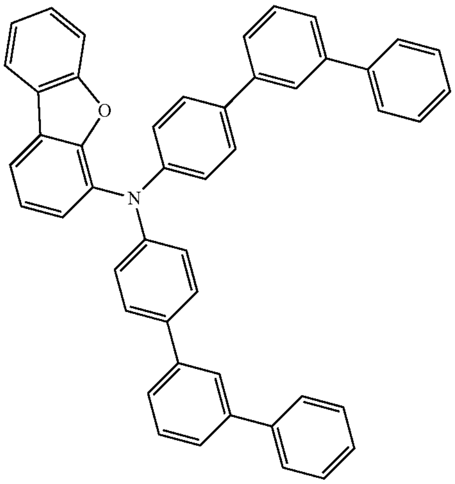
2-55
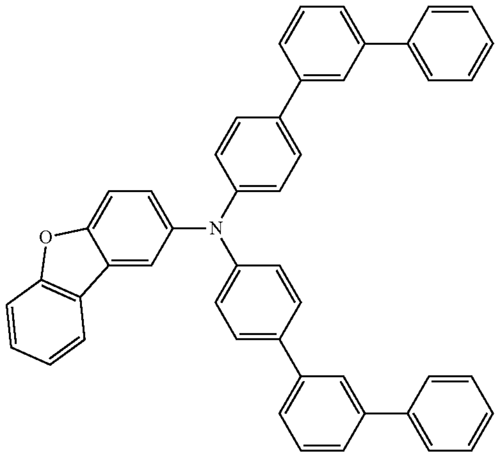
2-56
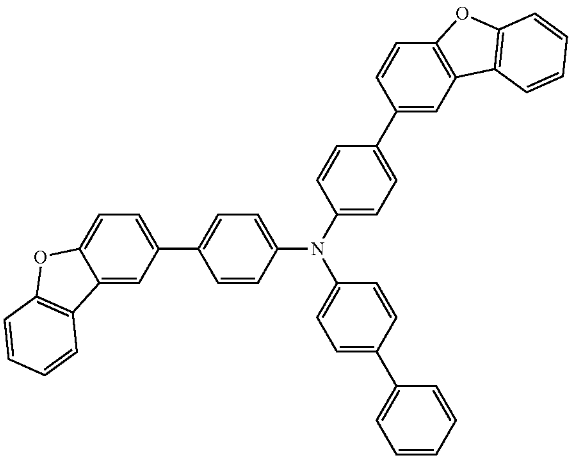
-continued
2-57
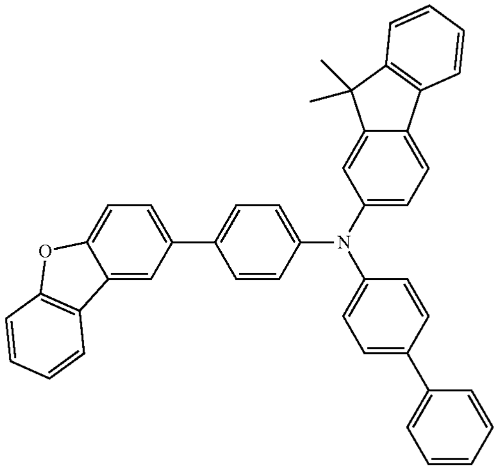
2-58
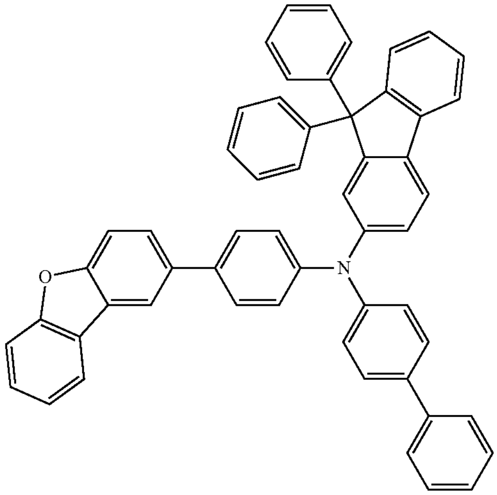
2-59
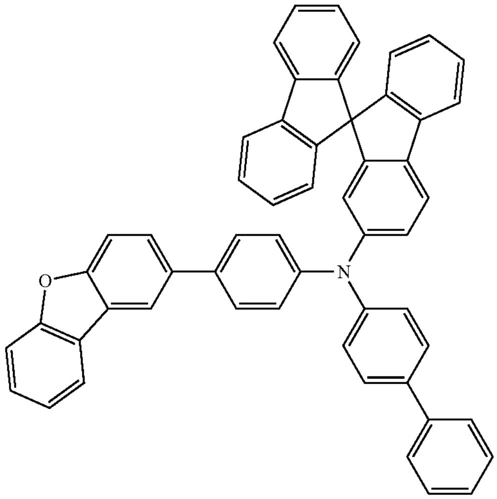

-continued
2-60
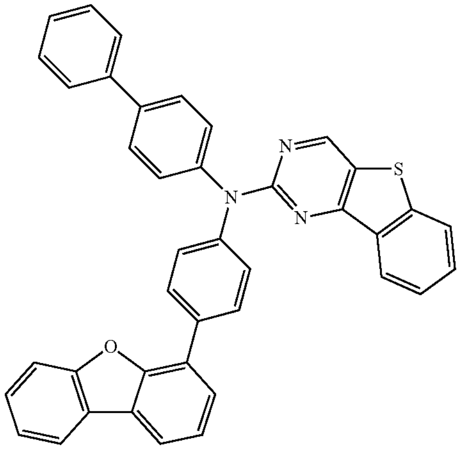
2-61
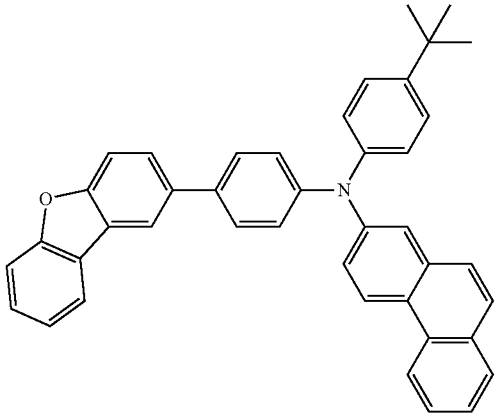
2-62
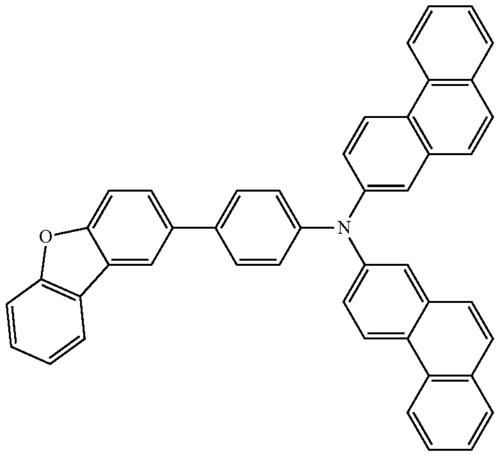
-continued
2-63
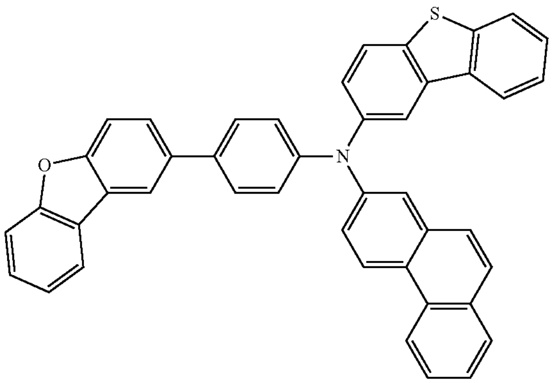
2-64
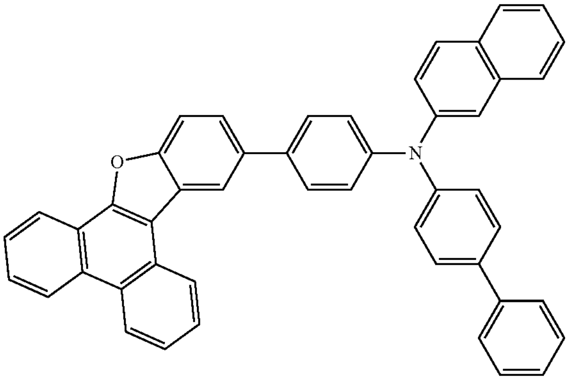
2-65
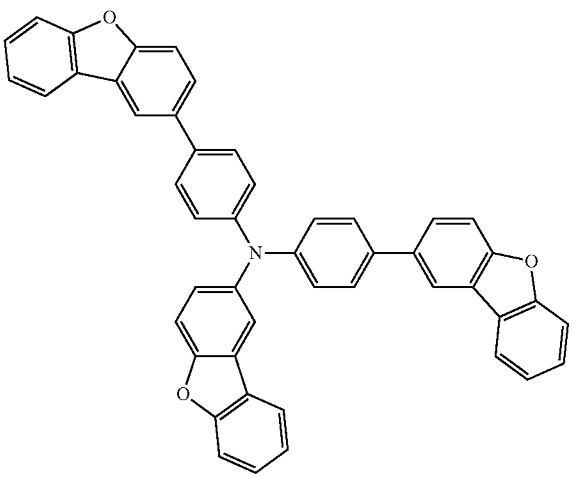

-continued
2-66
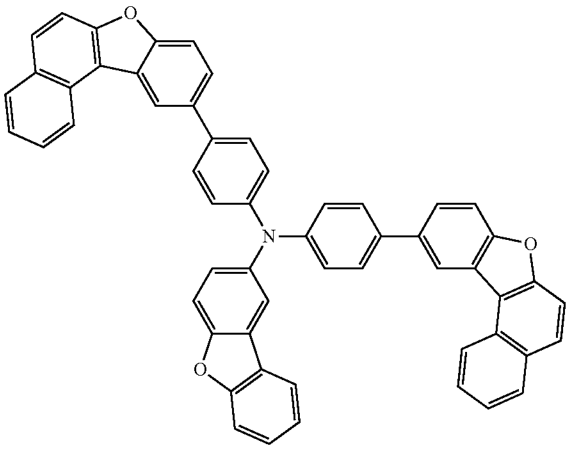
2-67
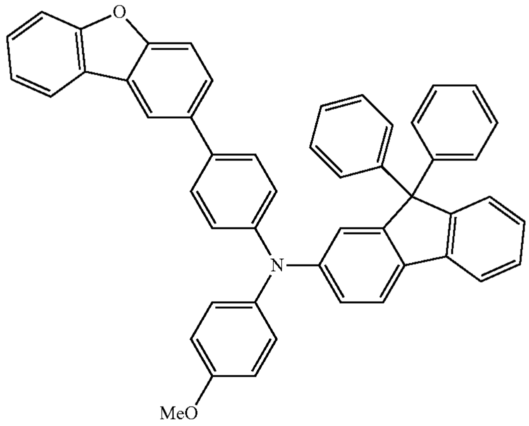
2-68
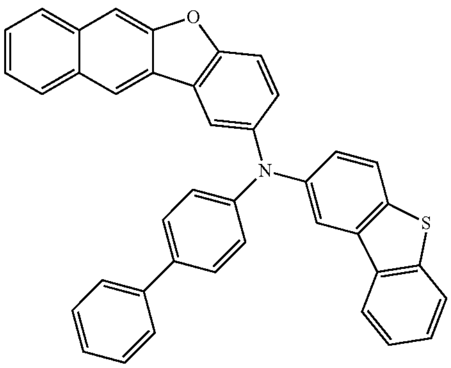
-continued
2-69
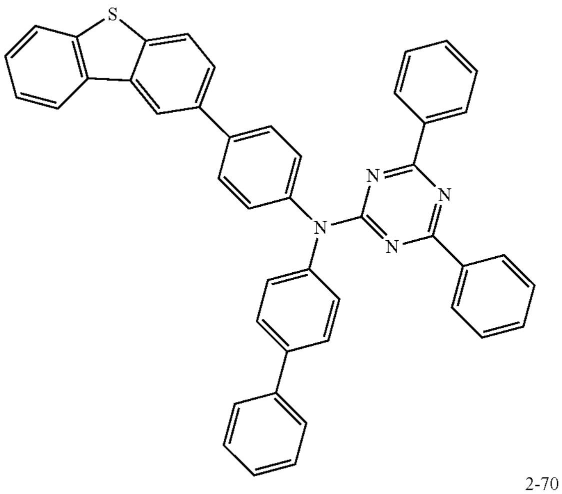
2-70
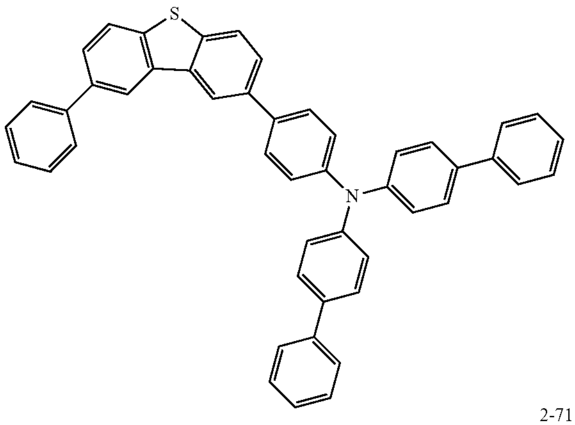
2-71
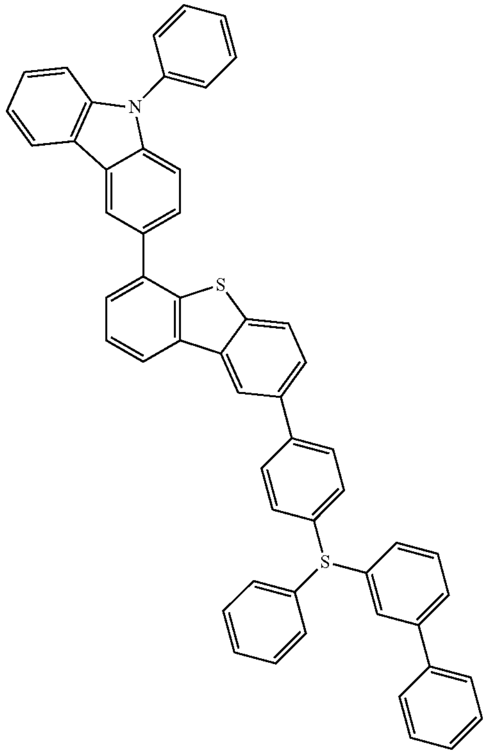

-continued
2-72
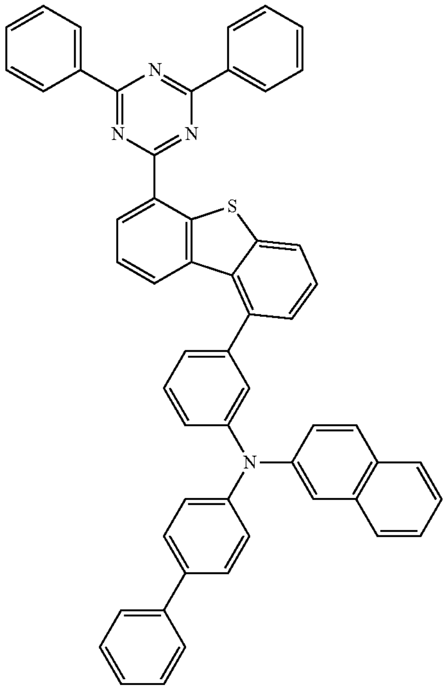
2-73
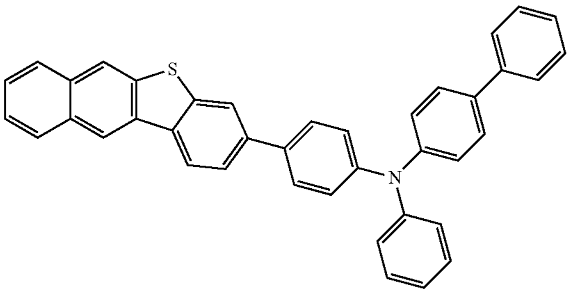
2-74
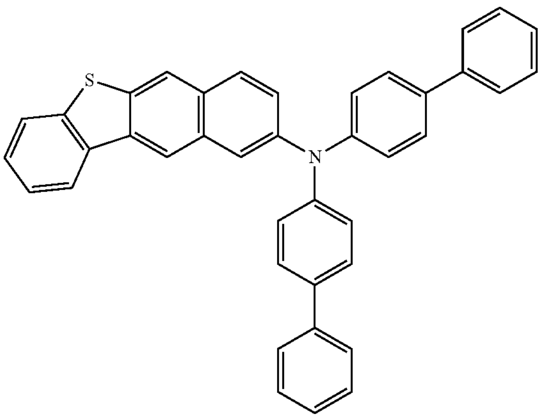
-continued
2-75
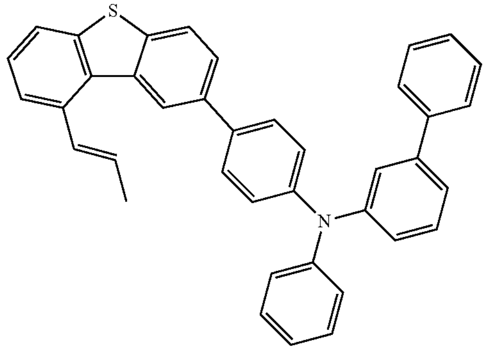
2-76
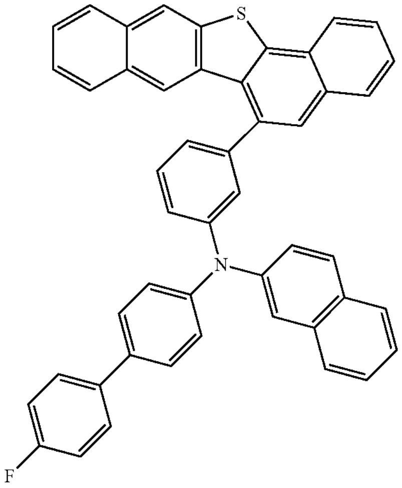
2-77
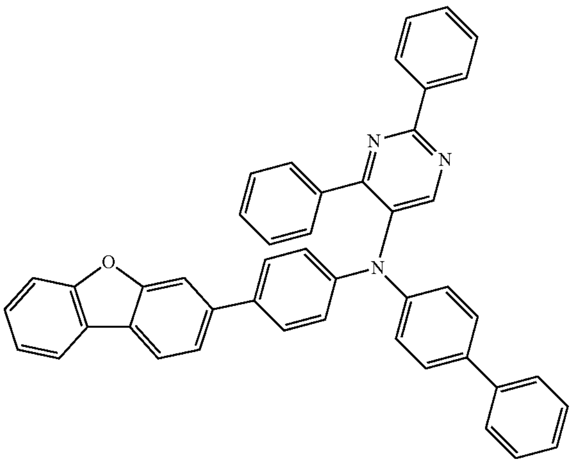

-continued
2-78
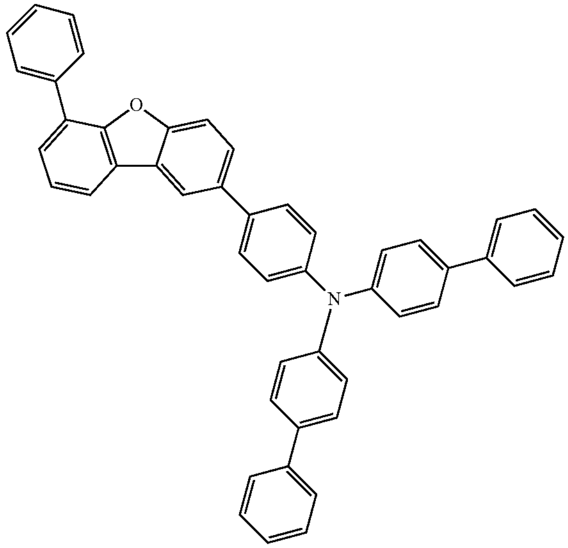
2-79
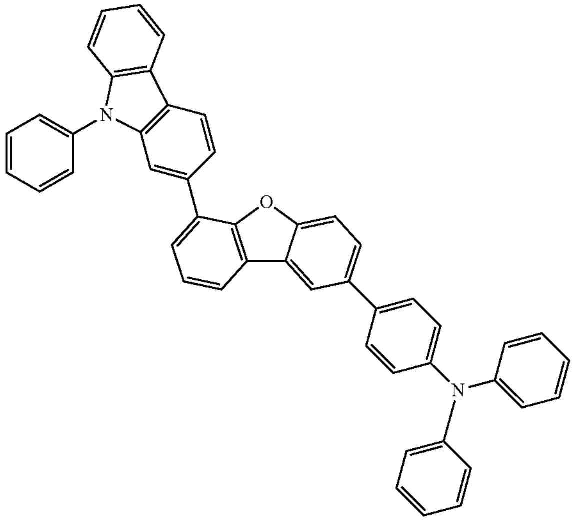
2-80
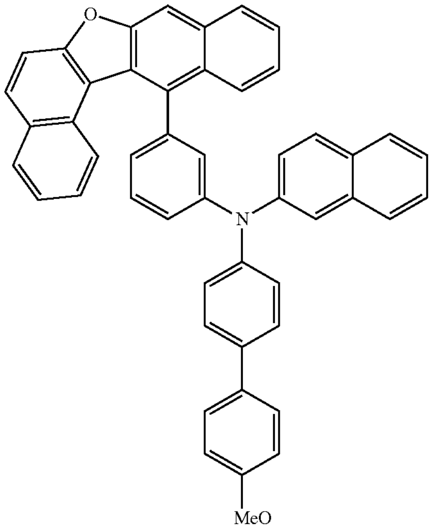
-continued
2-81
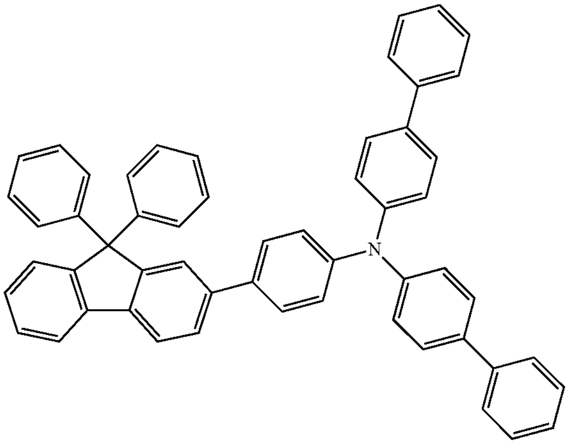
2-82
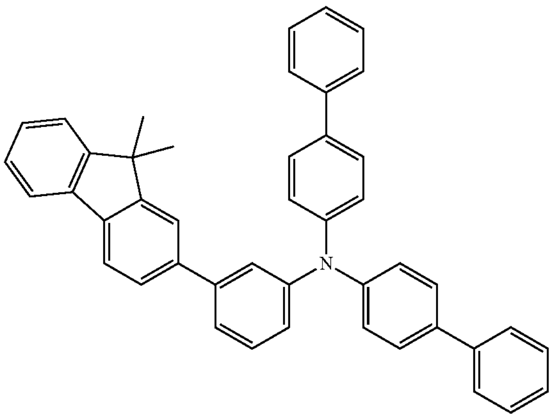
2-83
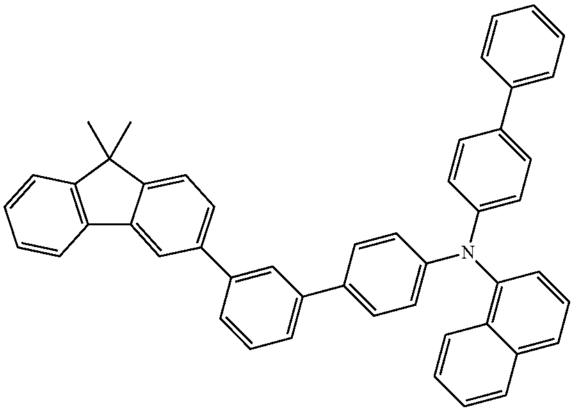

-continued
2-84
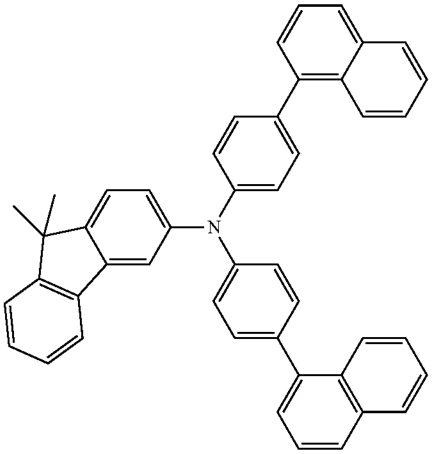
2-85
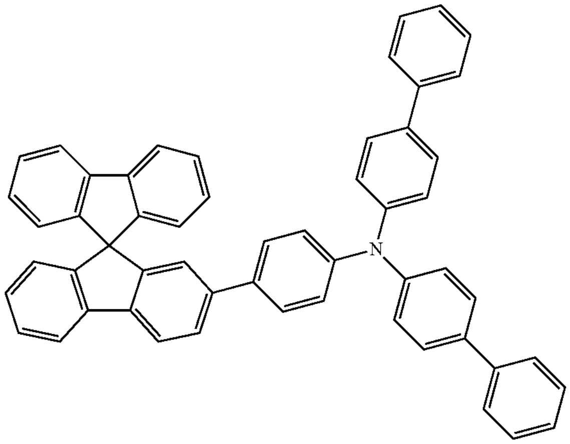
2-86
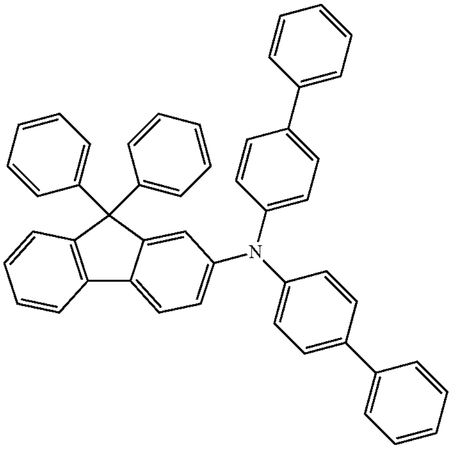
-continued
2-87
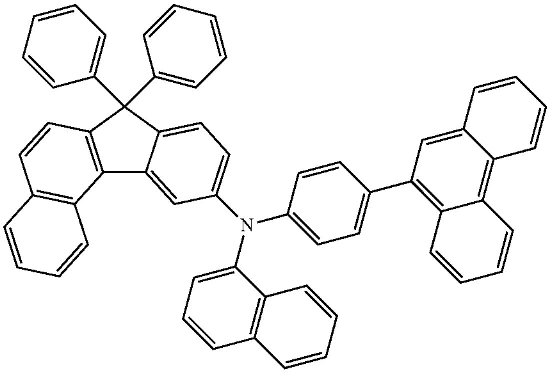
2-88
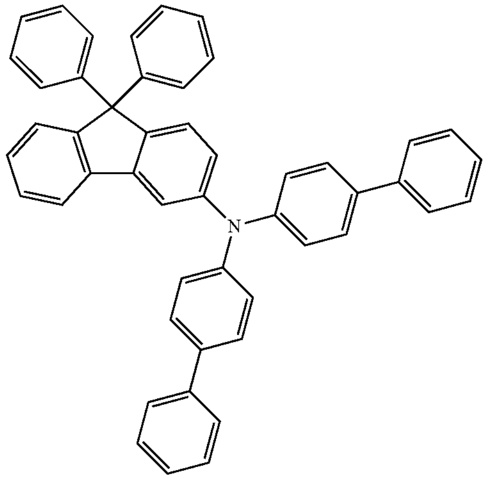
2-89
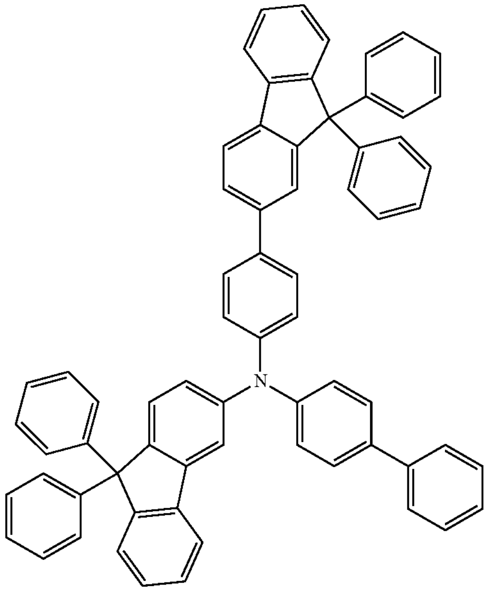

-continued
2-90
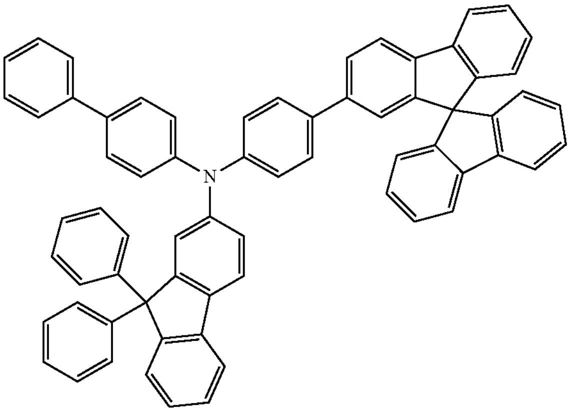
2-91
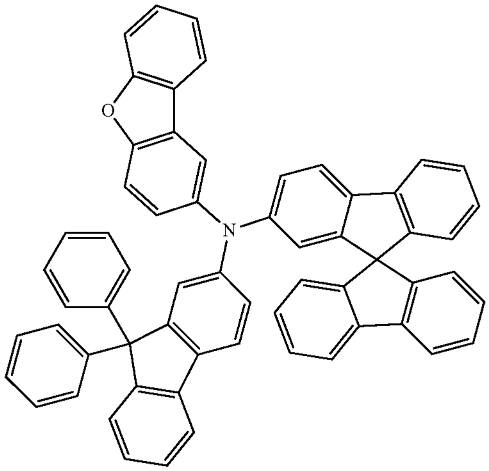
2-92
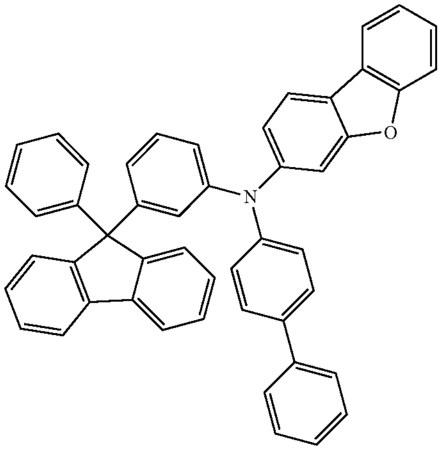
-continued
2-93
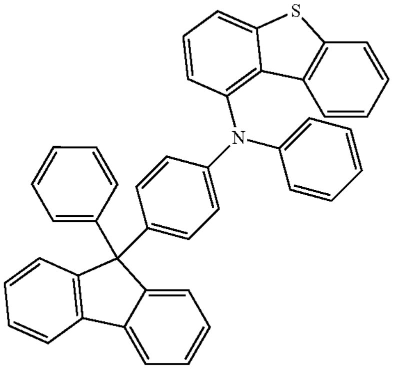
2-94
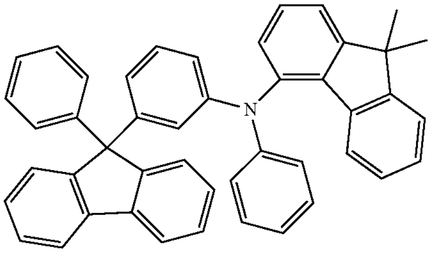
2-95
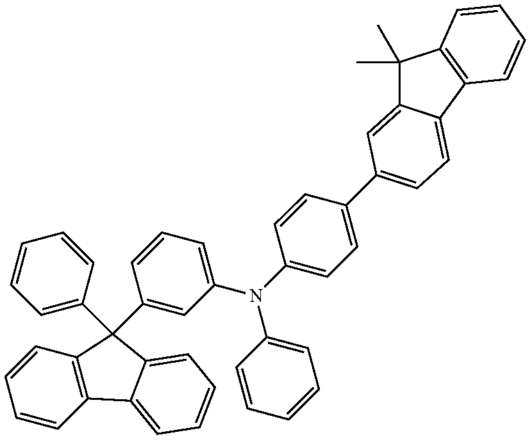
2-96
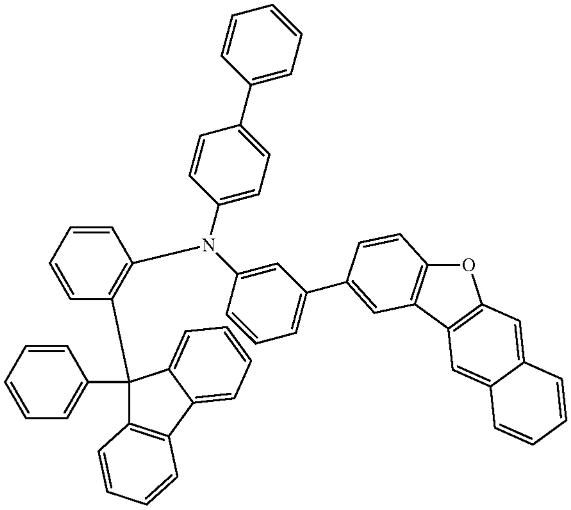

-continued
2-97
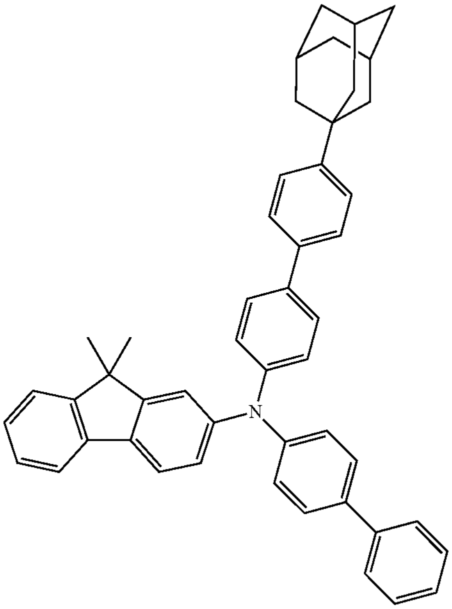
3-1
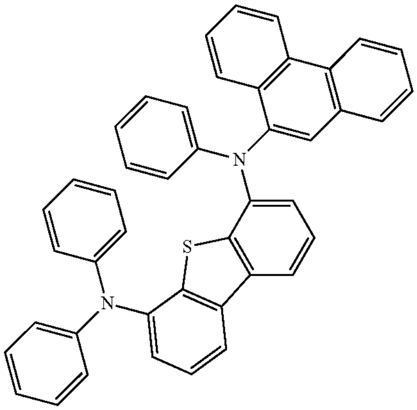
3-2
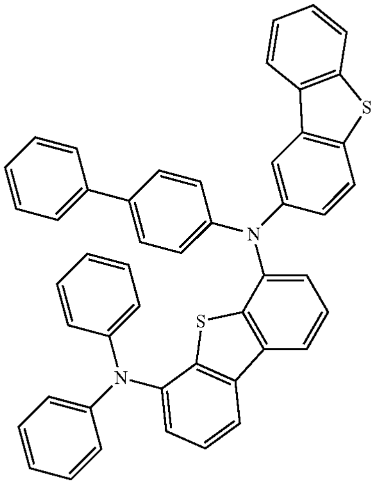
-continued
3-3
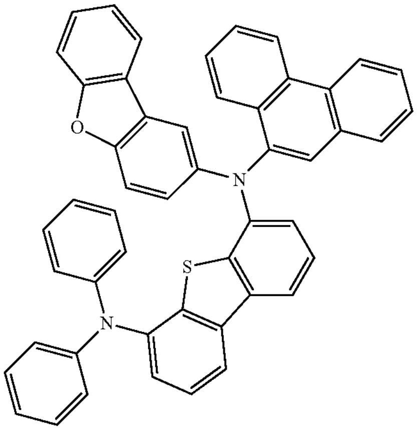
3-4
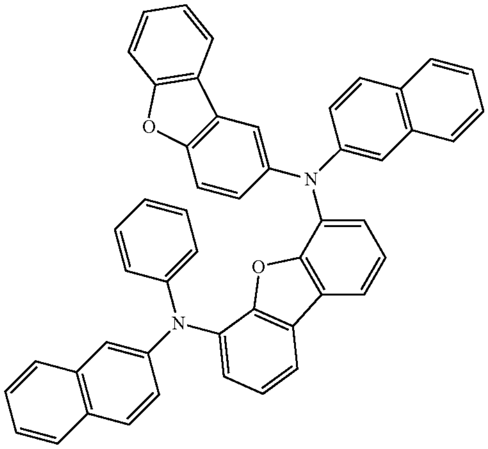
3-5
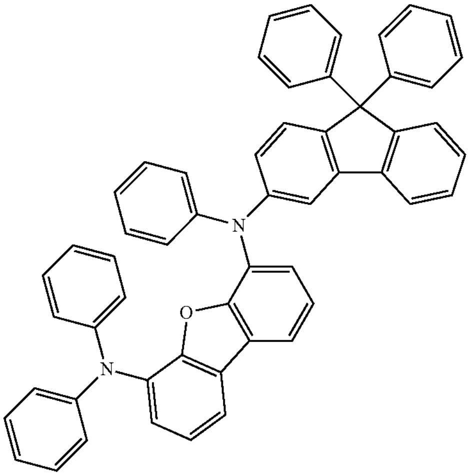

3-6
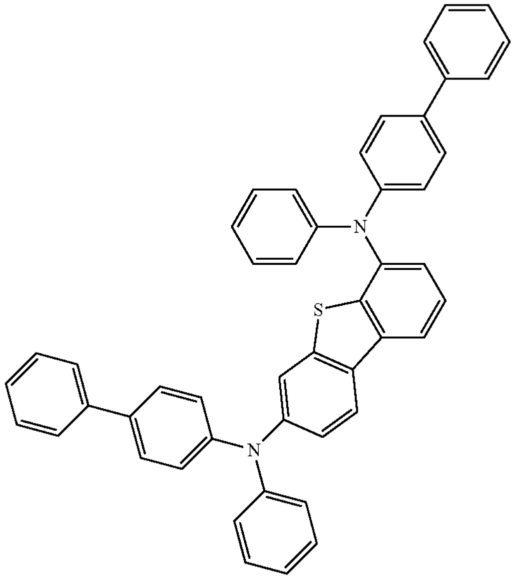
3-7
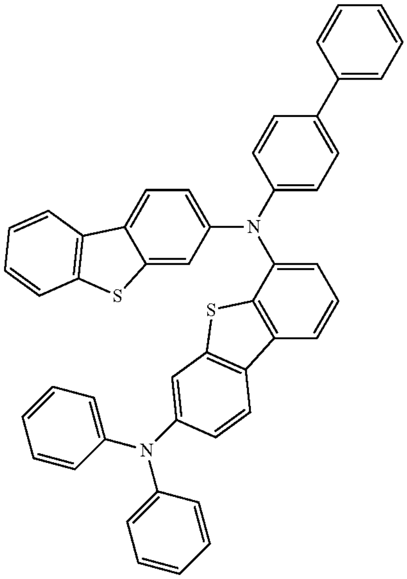
3-8
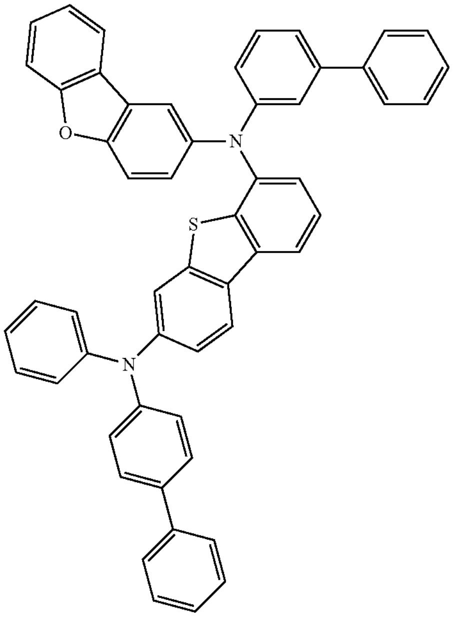
3-9
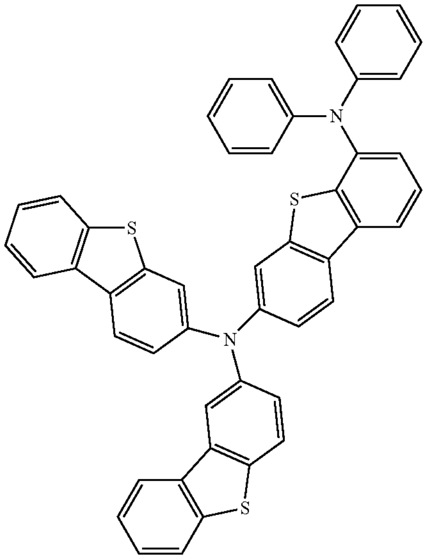

-continued
3-10
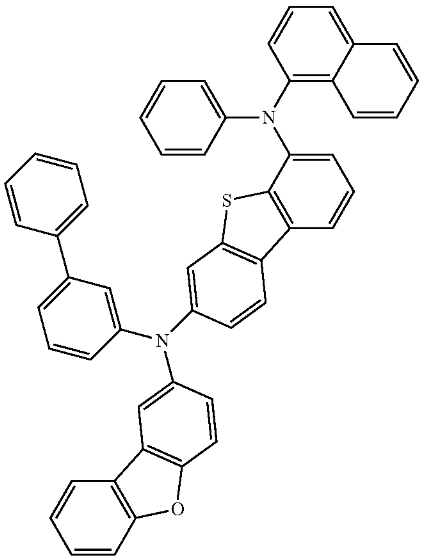
3-11
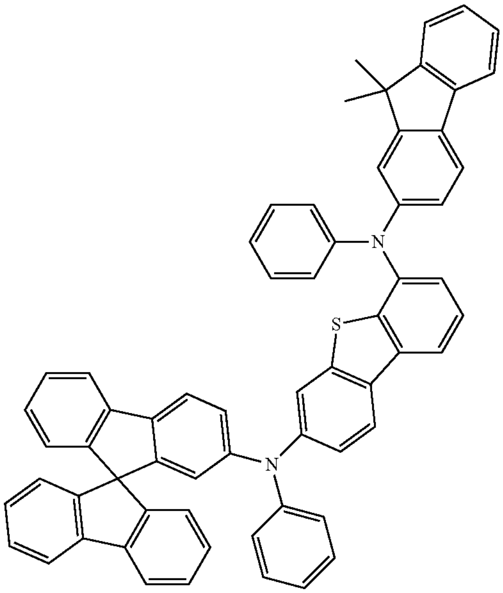
-continued
3-12
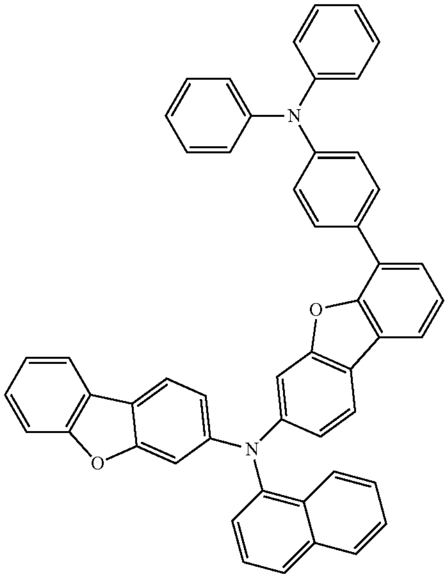
3-13
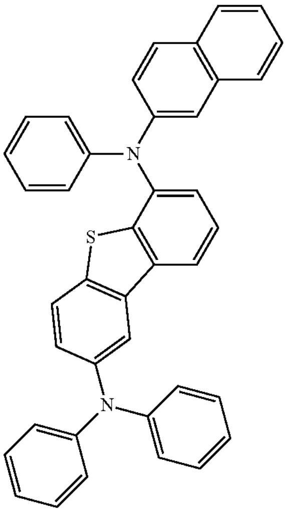
3-14
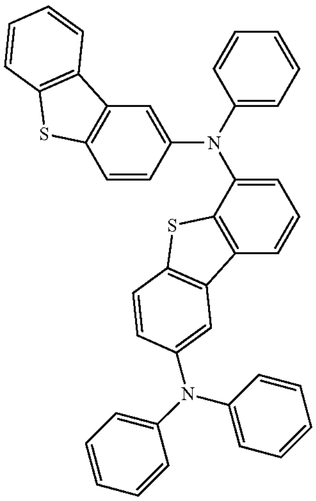

-continued
3-15
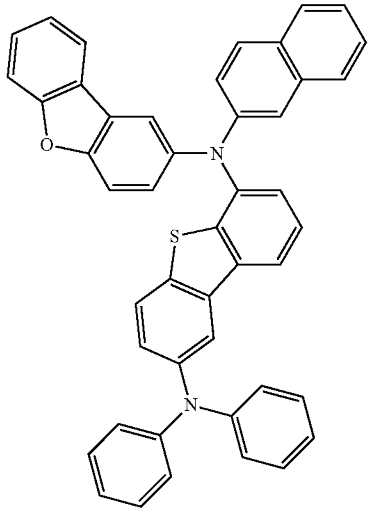
3-16
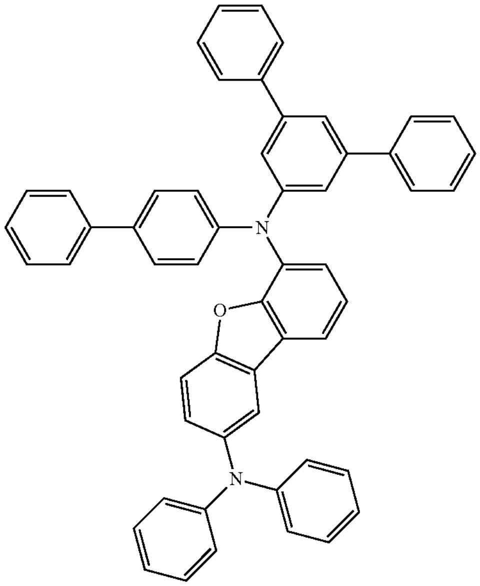
-continued
3-17
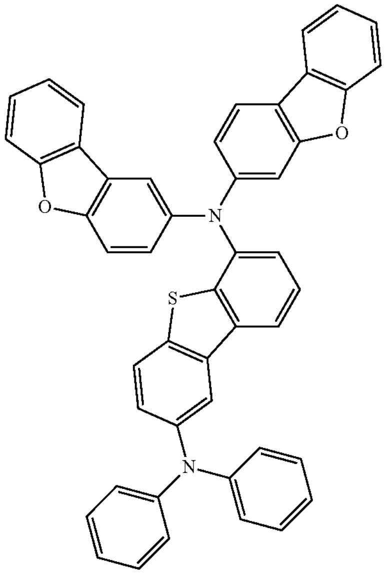
3-18
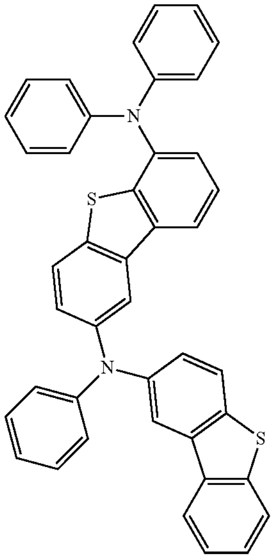

-continued
3-19
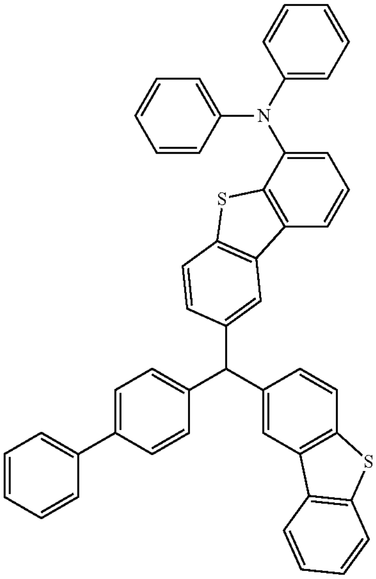
3-20
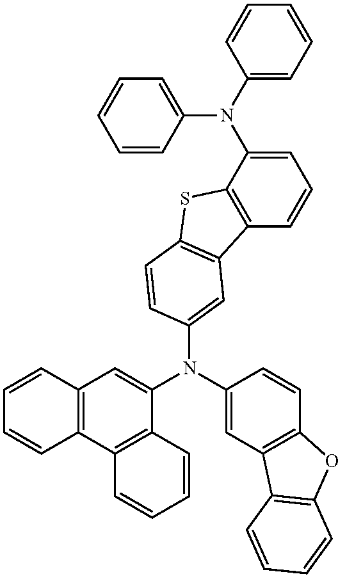
-continued
3-21
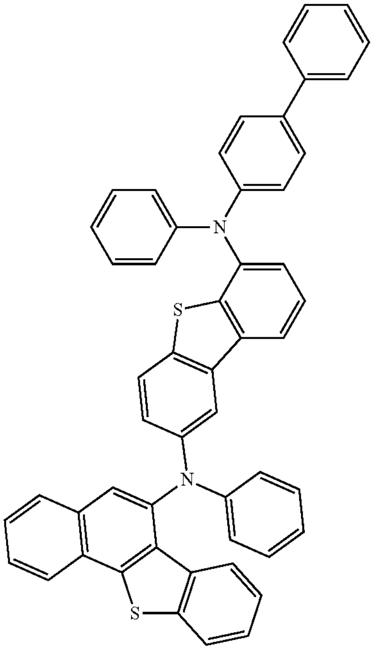
3-22
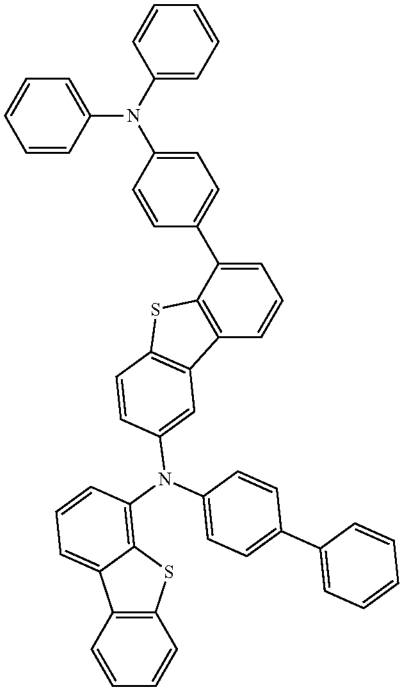

-continued
3-23
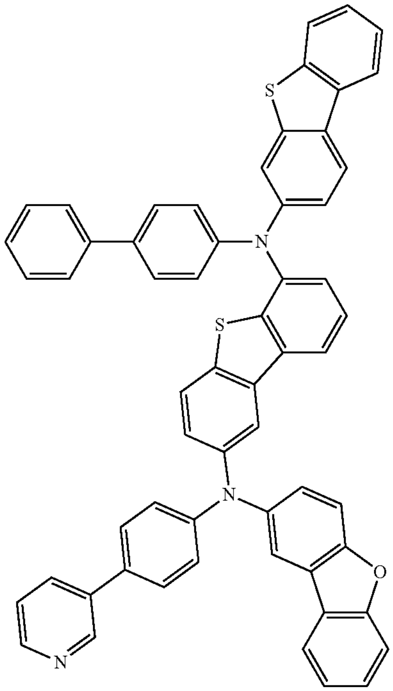
3-24
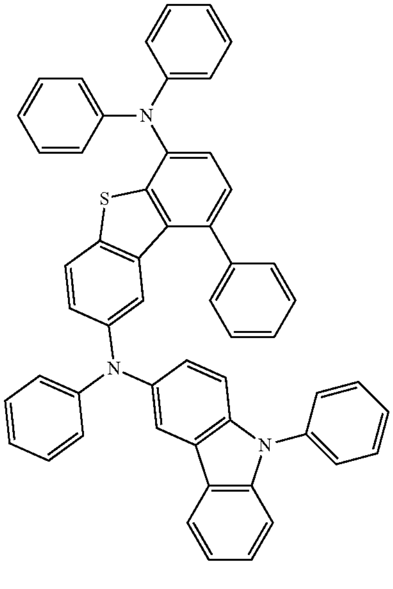
-continued
3-25
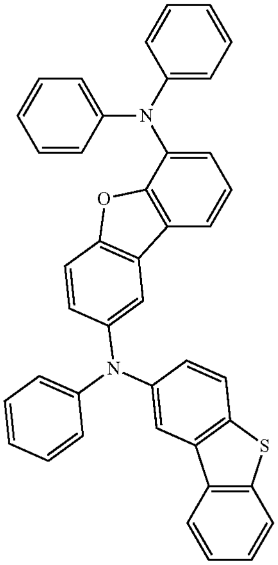
3-26
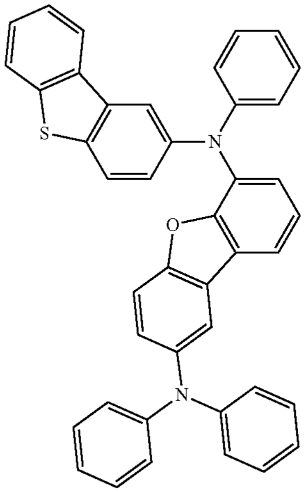
3-27
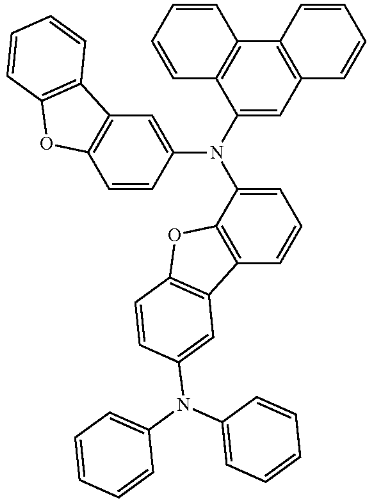

-continued
3-28
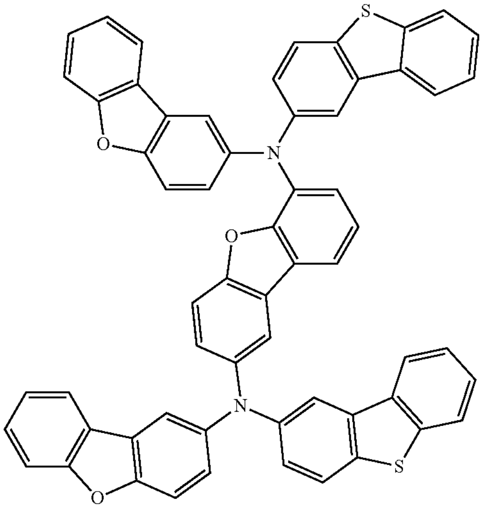
3-29
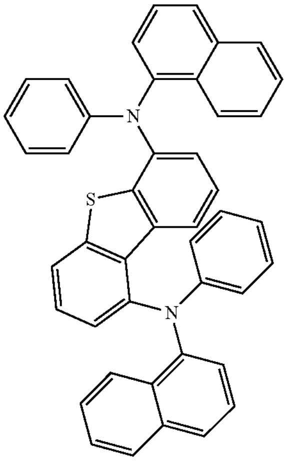
3-30
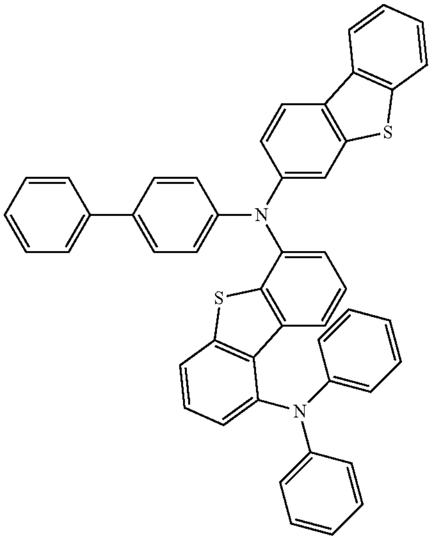
-continued
3-31
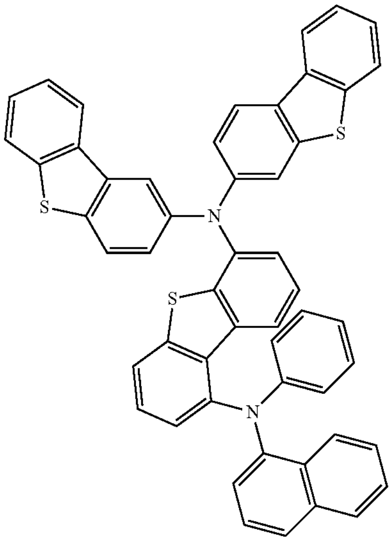
3-32
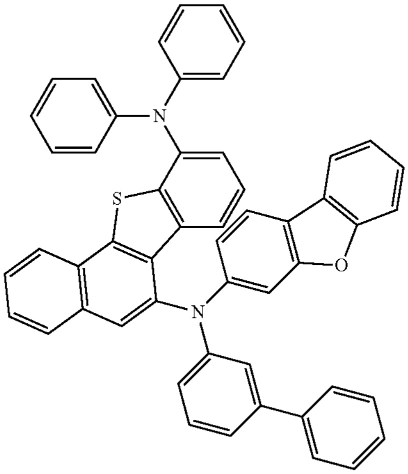
3-33
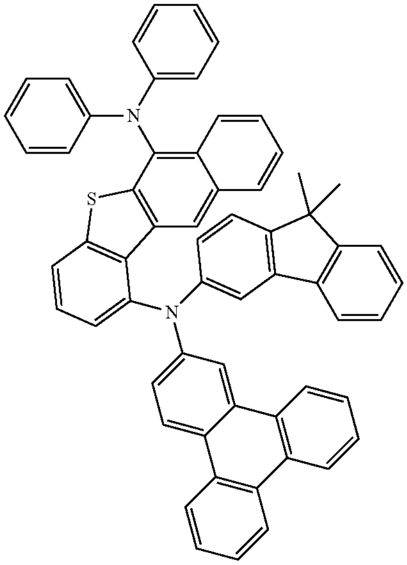

-continued
3-34
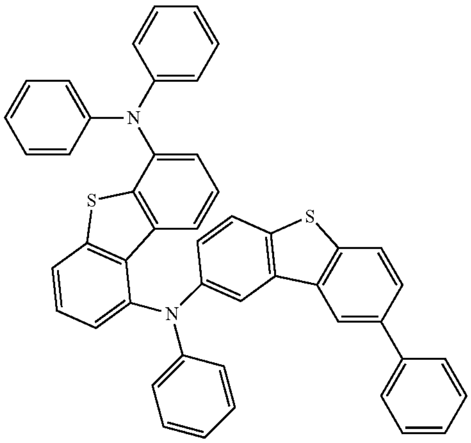
3-35
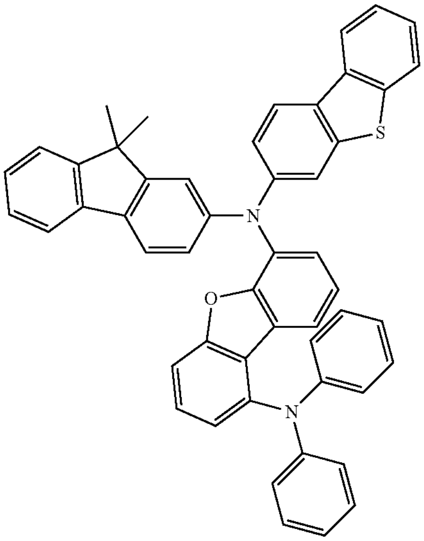
3-36
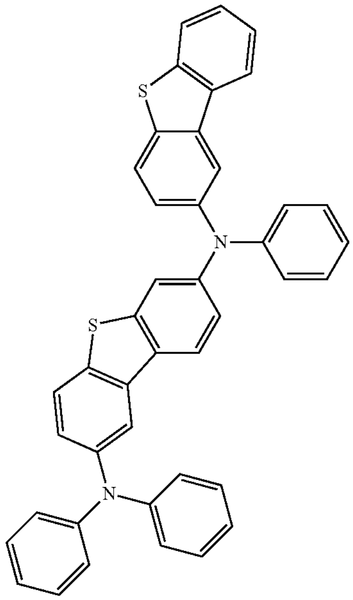
-continued
3-37
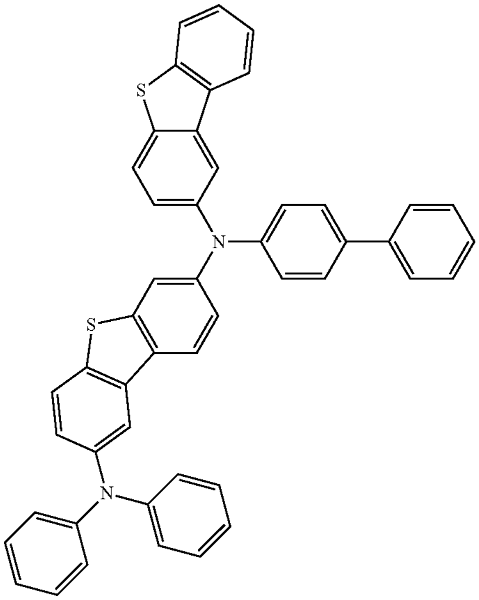
3-38
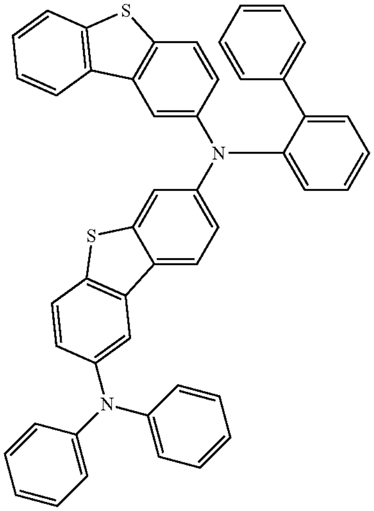

-continued
3-39
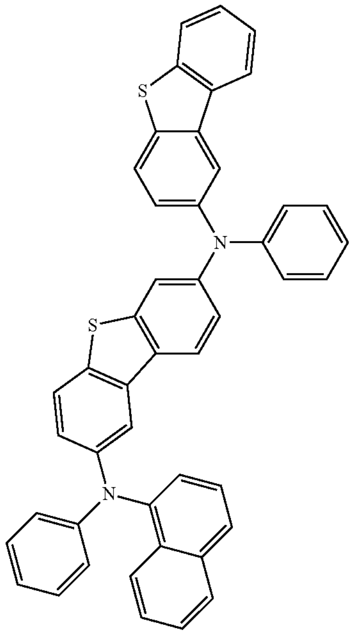
3-40
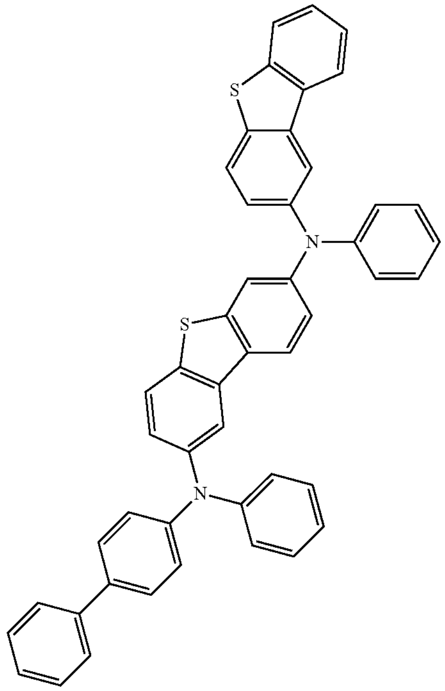
-continued
3-41
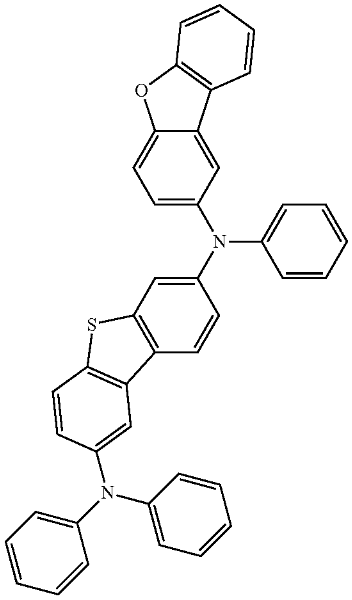
3-42
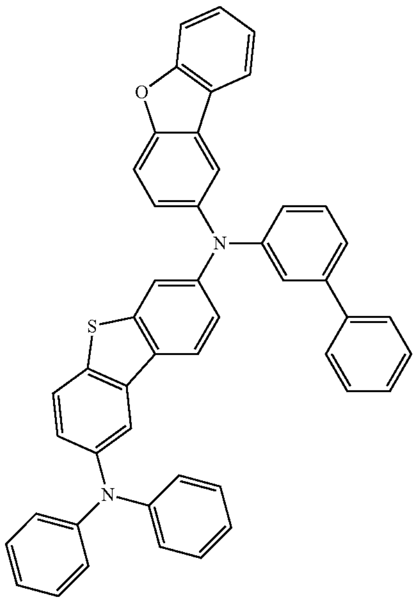

-continued
3-43
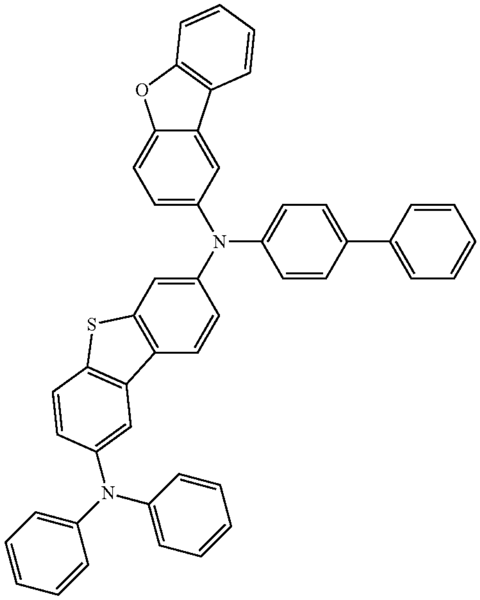
3-45
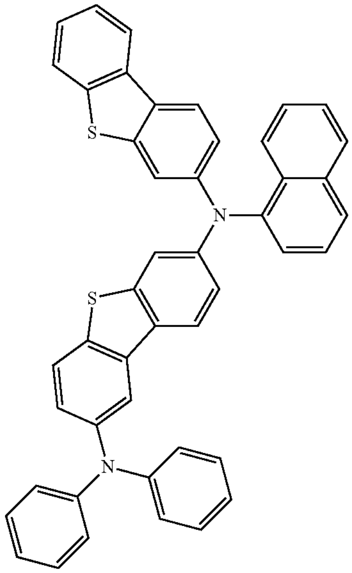
3-44
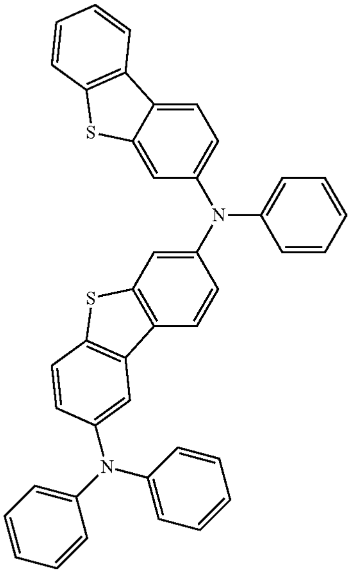
3-46
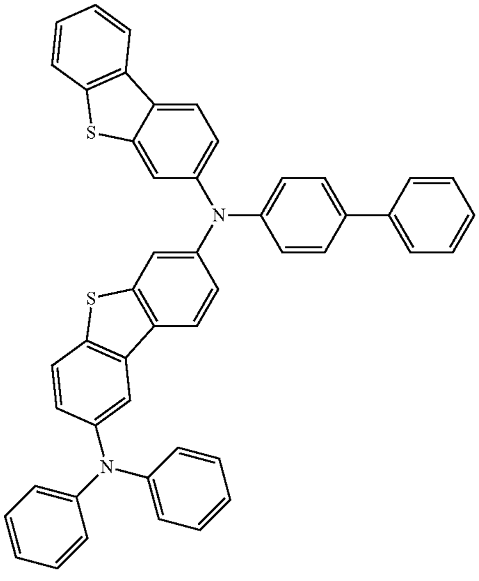

-continued
3-47
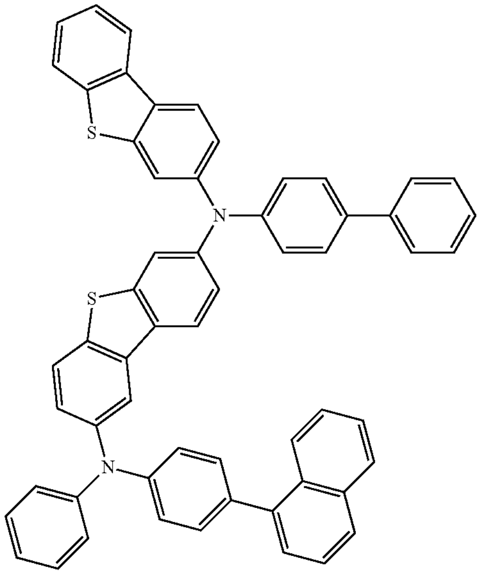
3-48
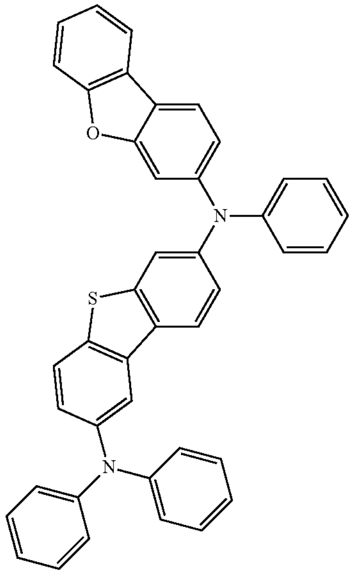
3-49
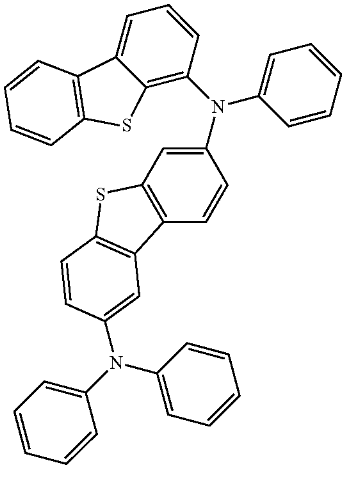
-continued
3-50
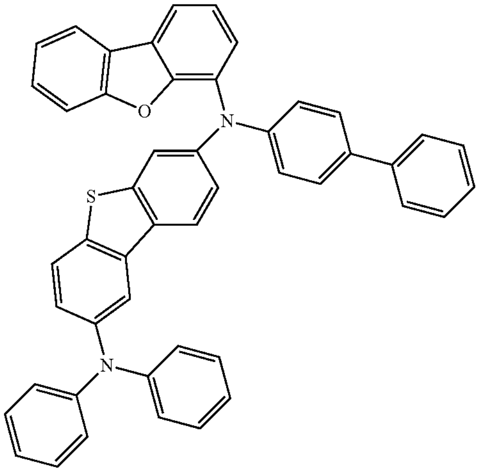
3-51
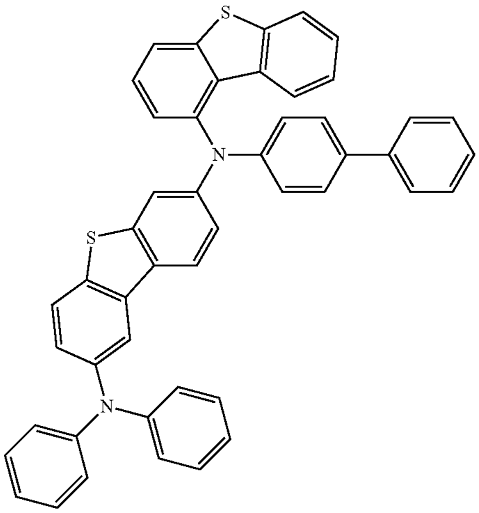
3-52
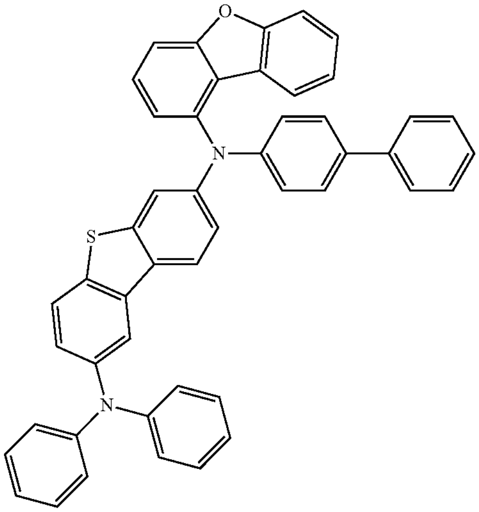

-continued
3-53
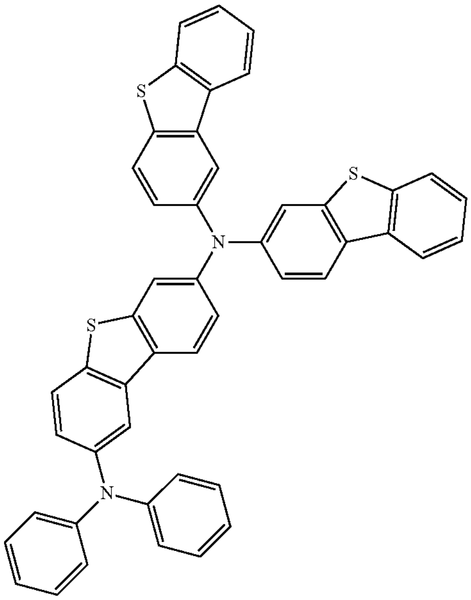
3-54
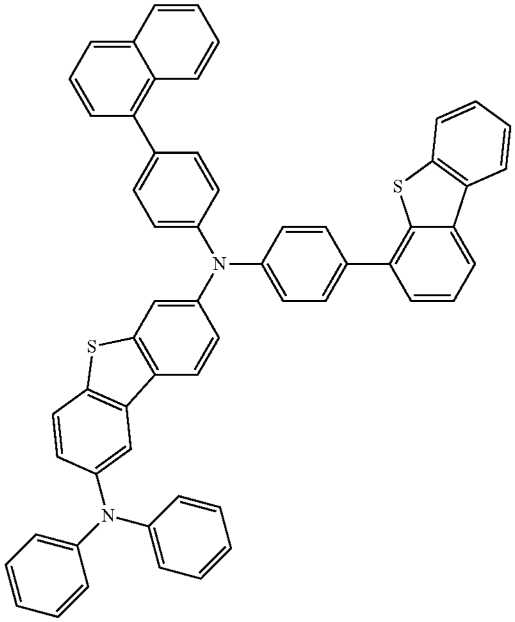
-continued
3-55
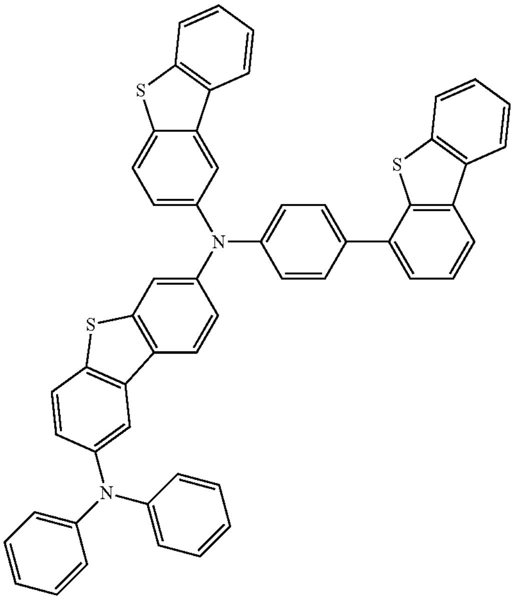
3-56
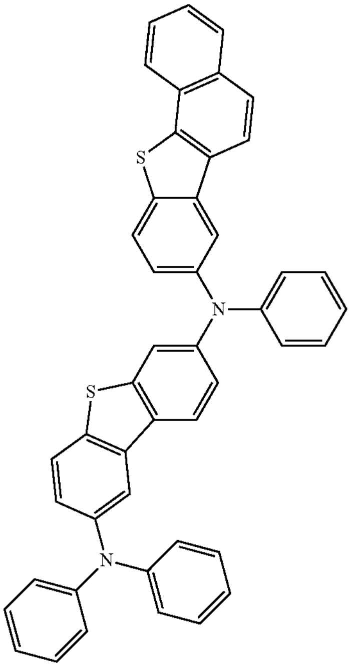

-continued
3-57
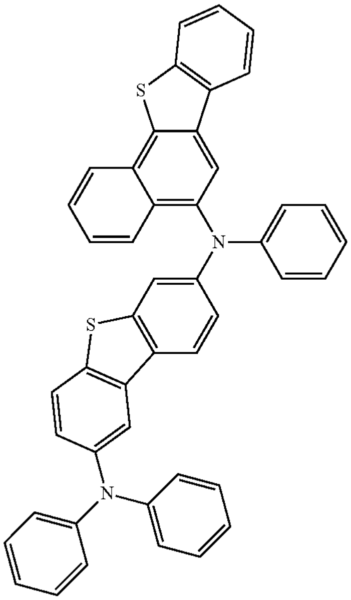
3-58
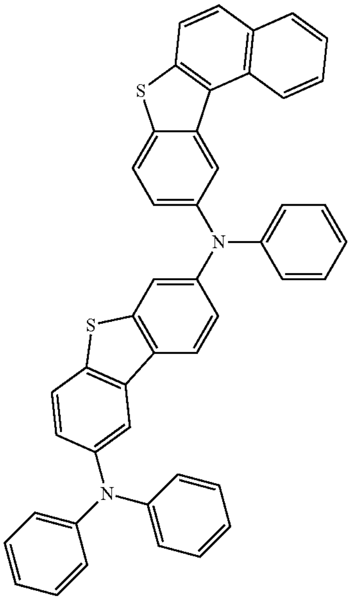
-continued
3-59
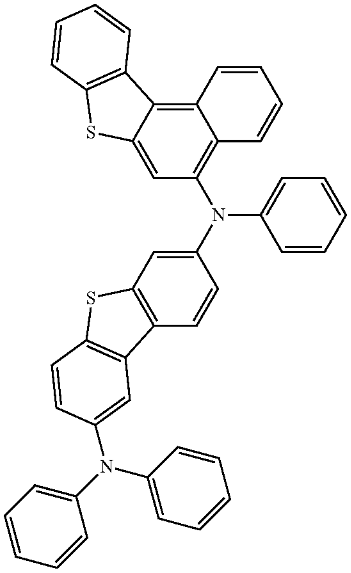
3-60
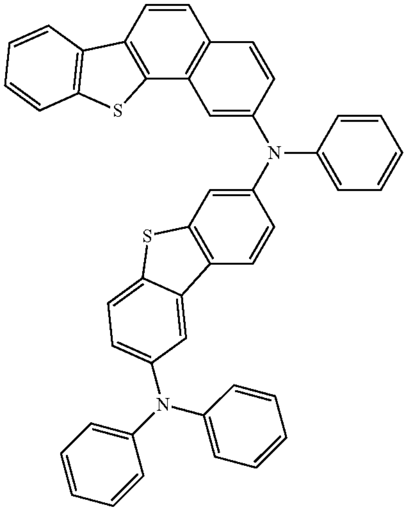

-continued
3-61
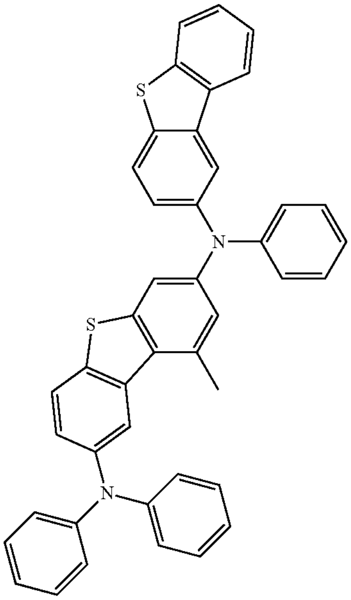
3-62
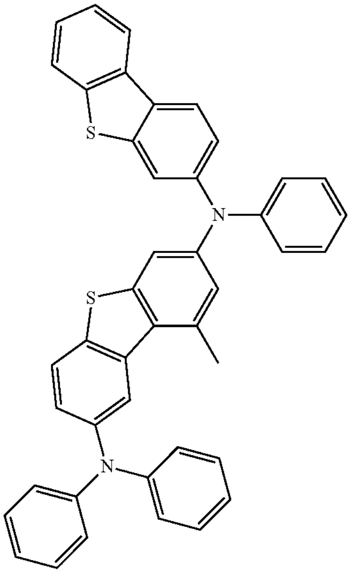
-continued
3-63
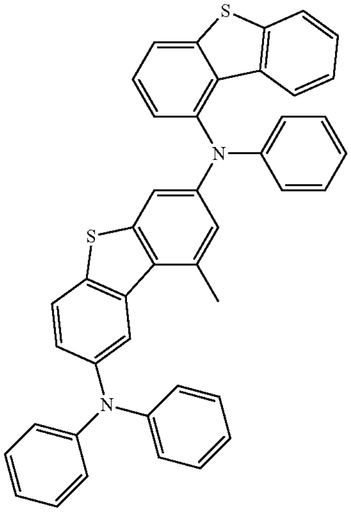
3-64
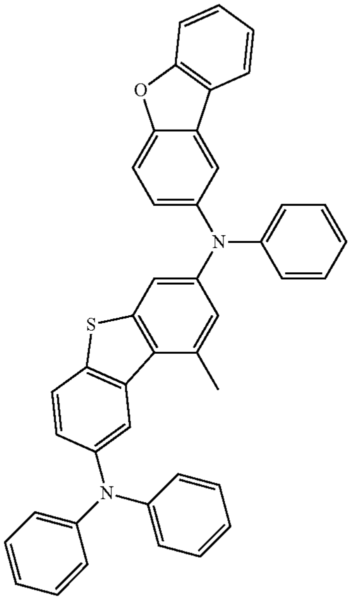

-continued
3-65
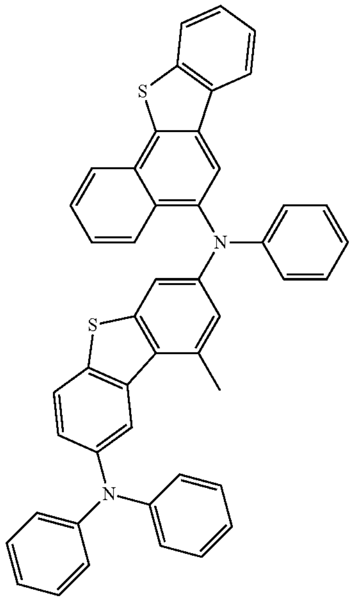
3-66
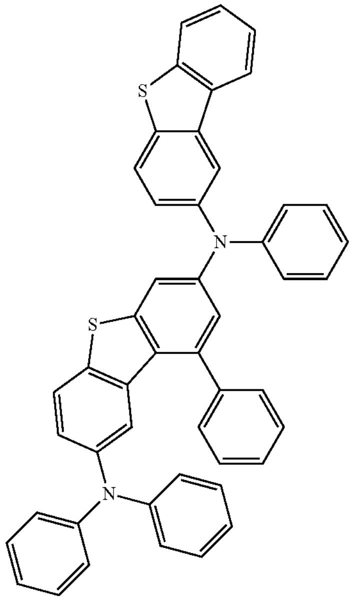
-continued
3-67
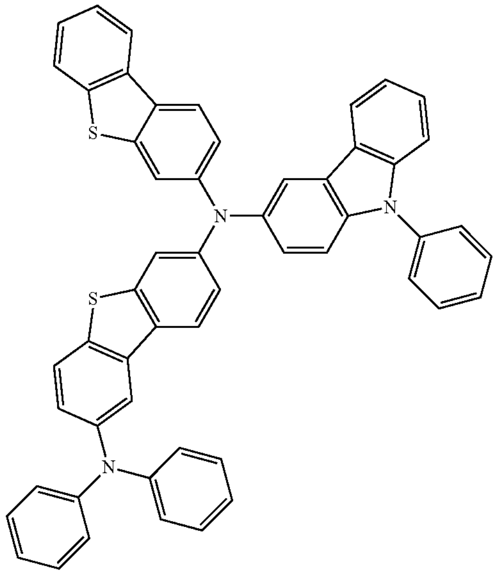
3-68
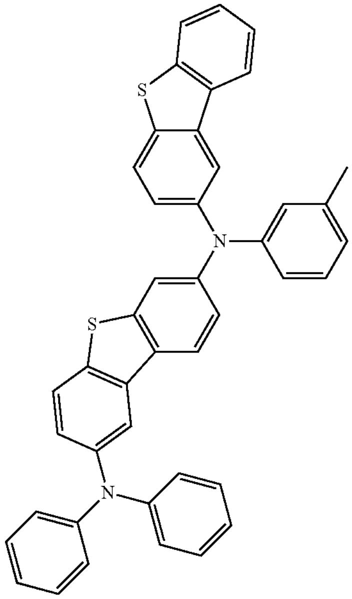

-continued
3-69
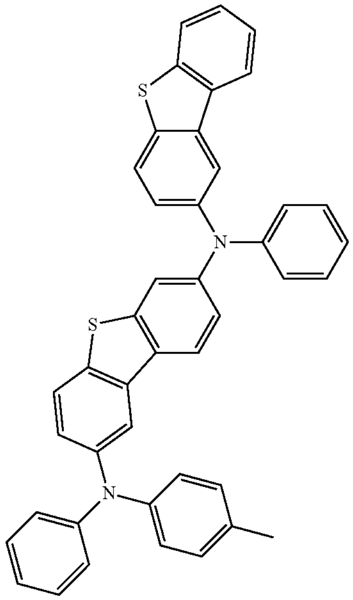
3-70
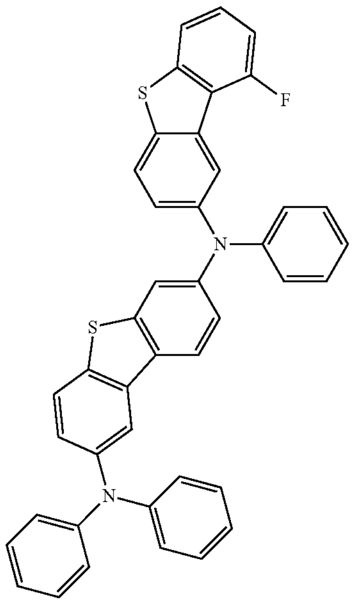
-continued
3-71
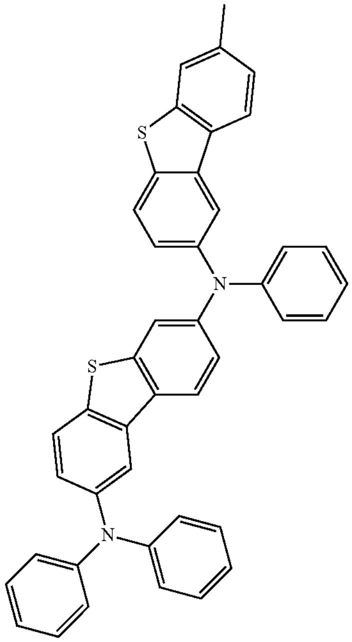
3-72
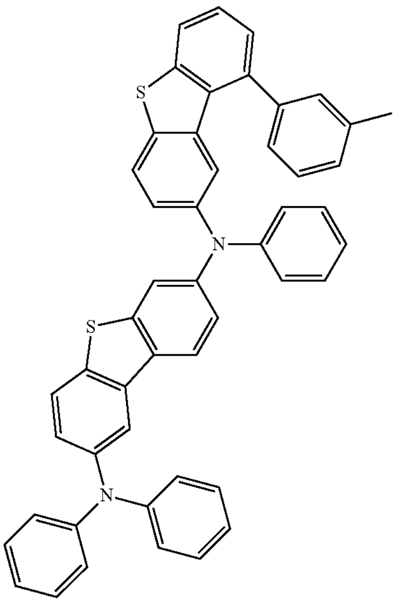

-continued
3-73
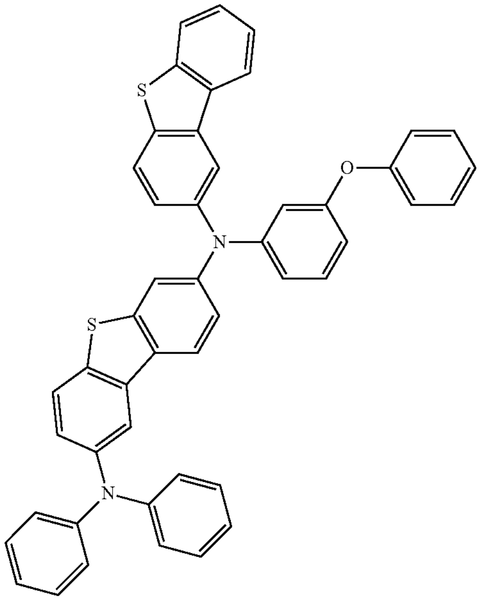
3-74
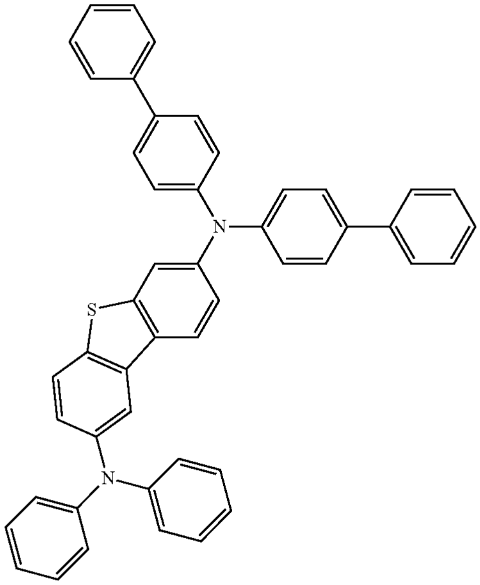
3-75
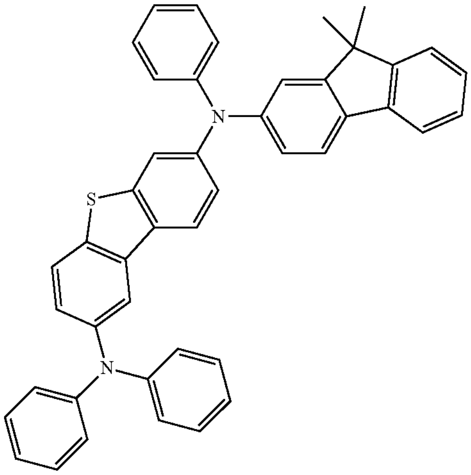
-continued
3-76
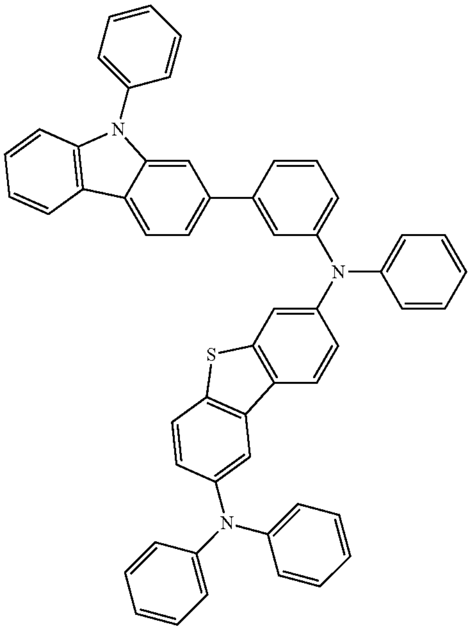
3-77
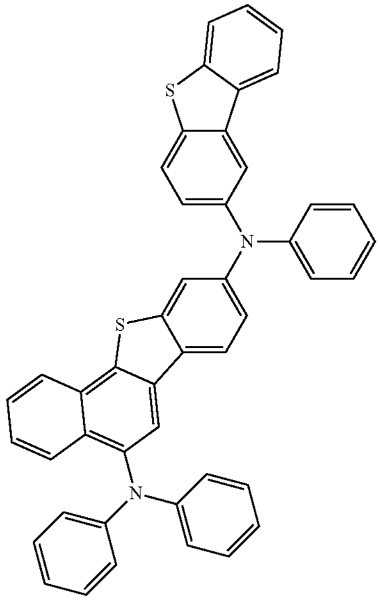

3-78
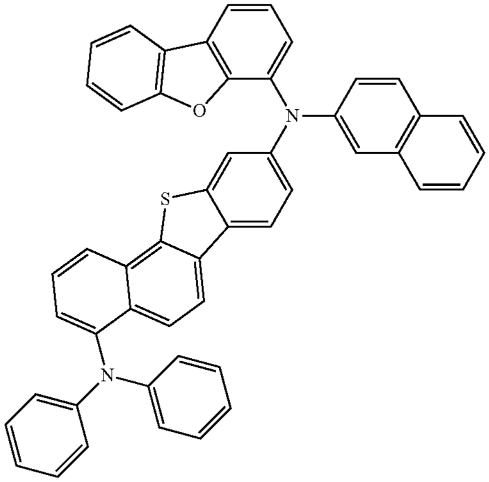
3-79
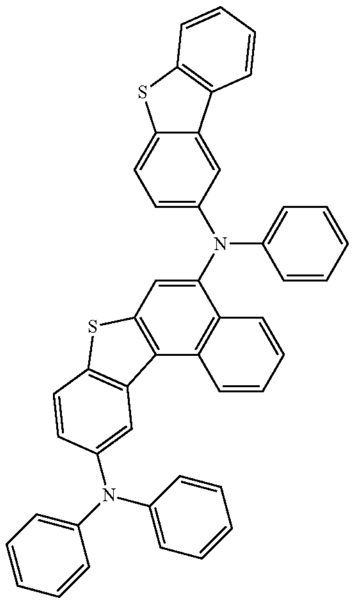
3-80
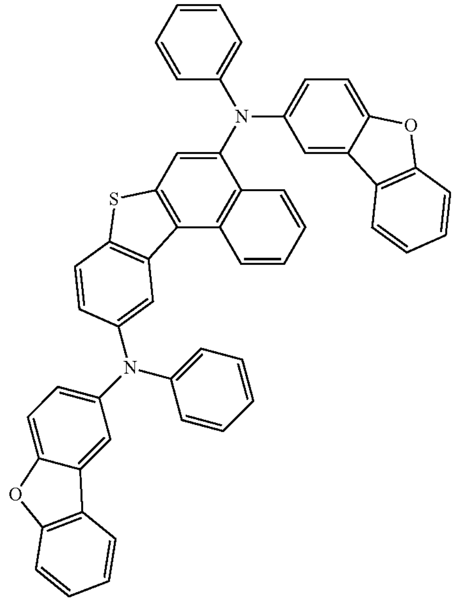
3-81
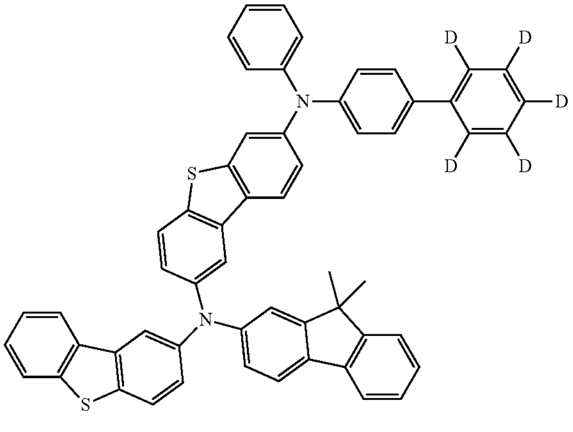
3-82
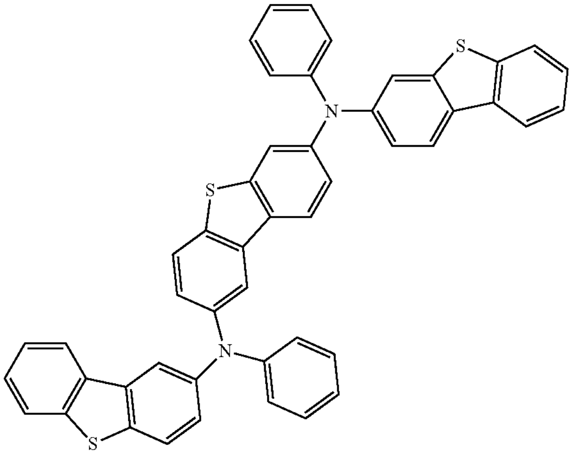

-continued
3-83
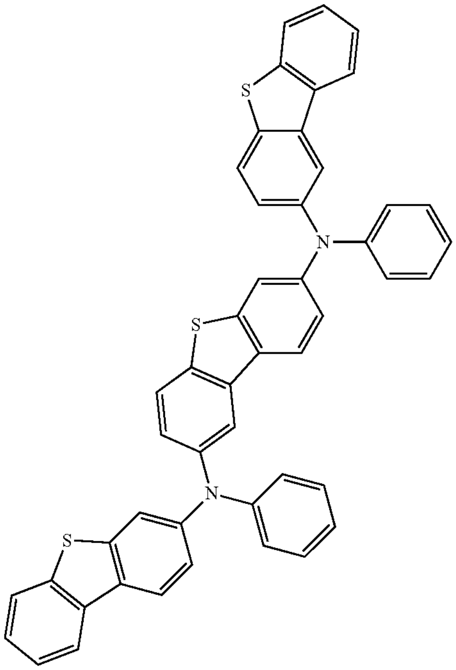
3-84
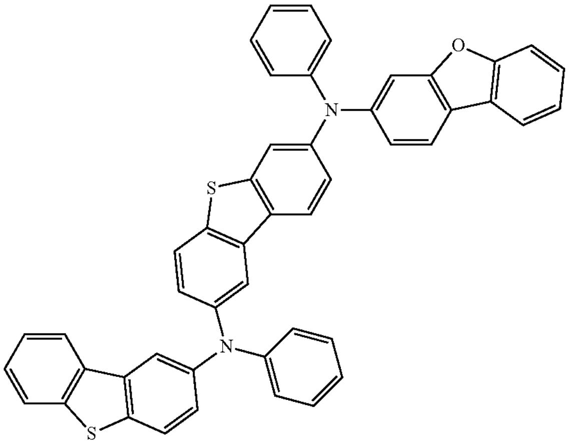
-continued
3-85
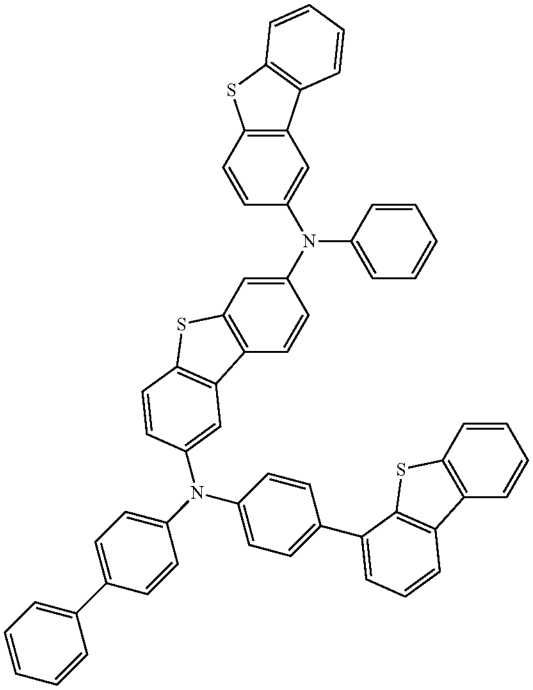
3-86
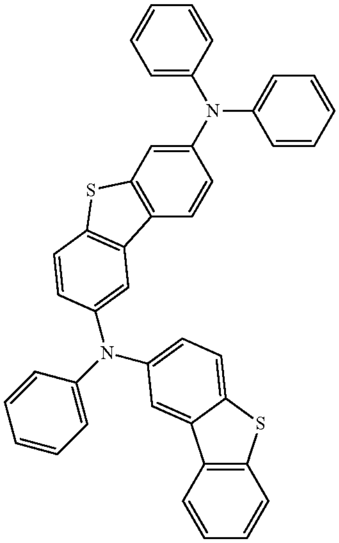

-continued
3-87
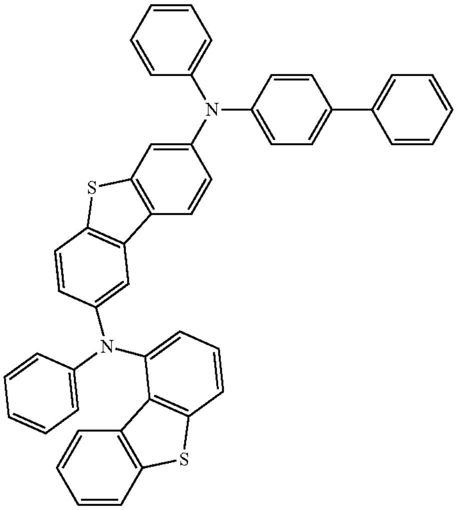
3-88
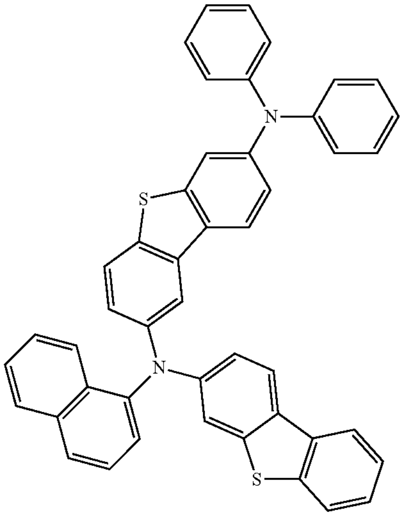
3-89
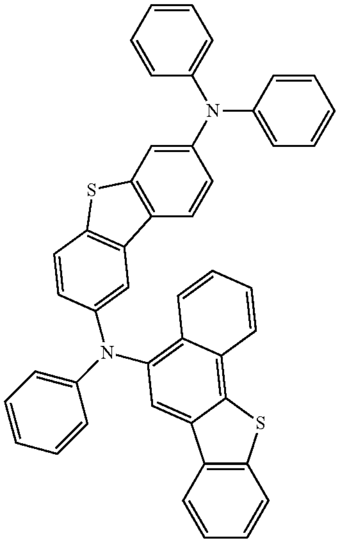
-continued
3-90
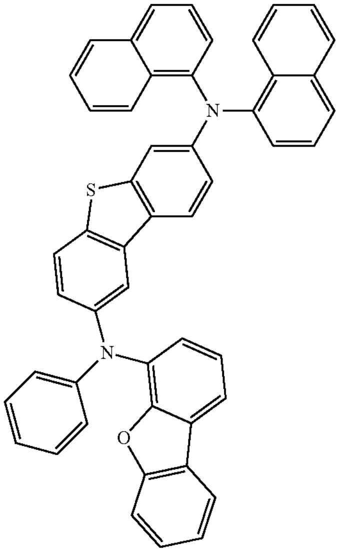
3-91
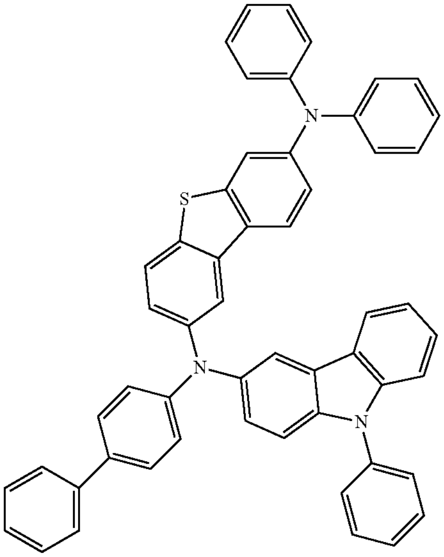
3-92
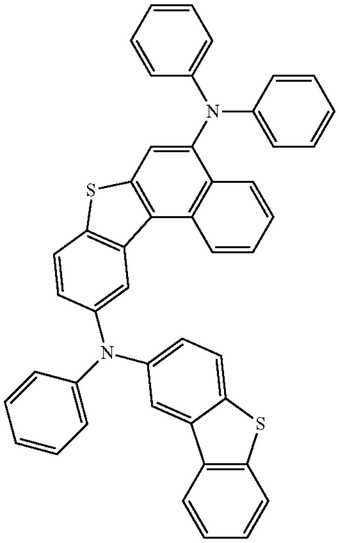

-continued
3-93
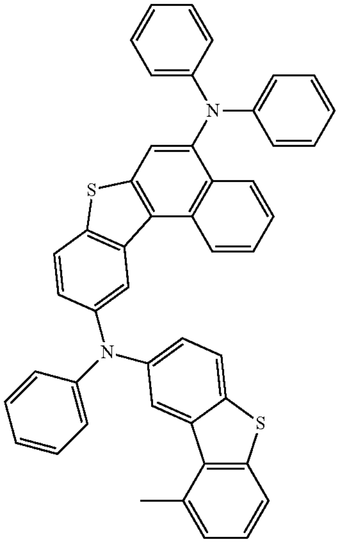
3-94
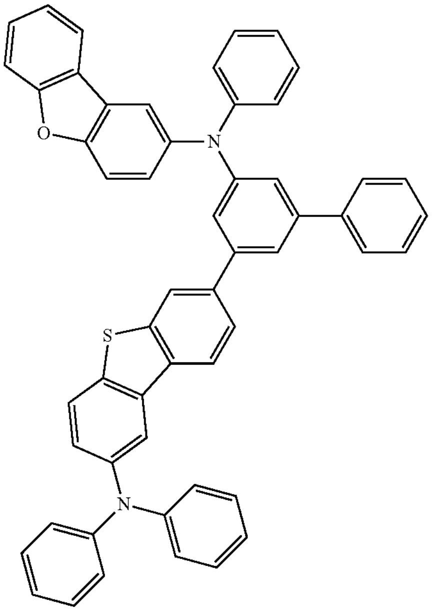
-continued
3-95
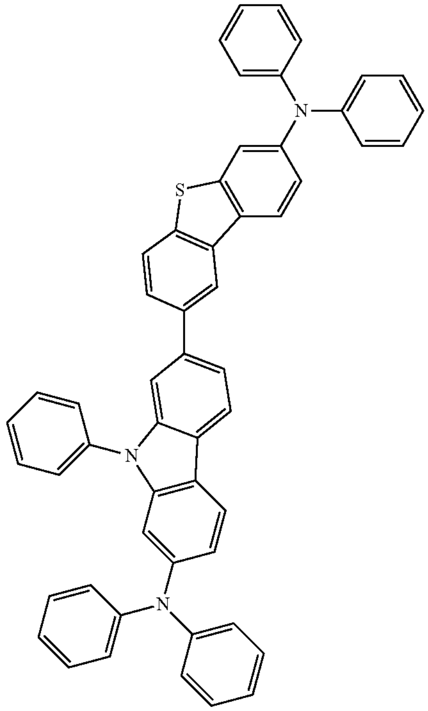
3-96
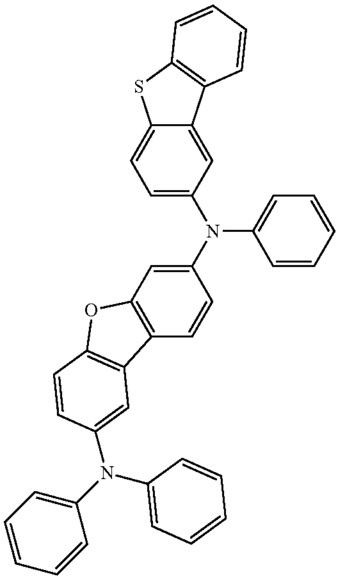

-continued
3-97
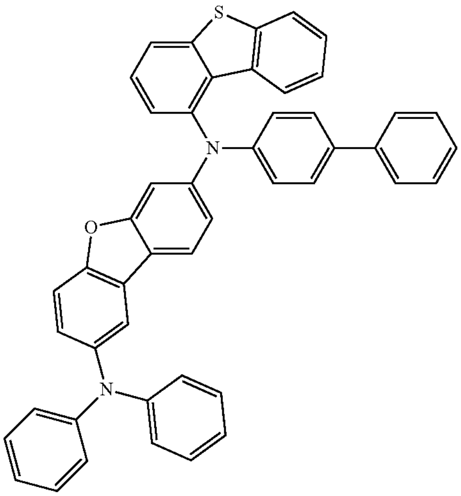
3-98
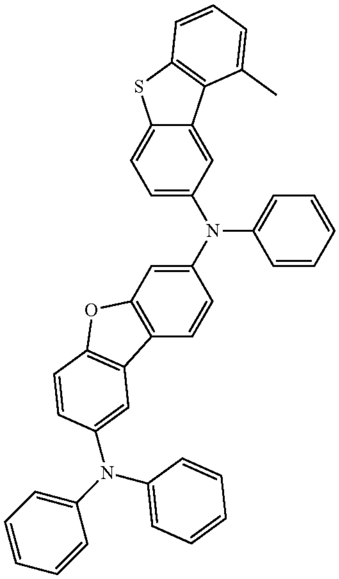
-continued
3-99
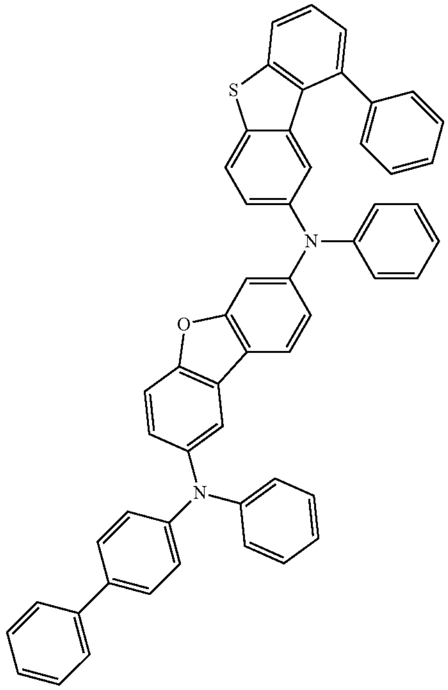
3-100
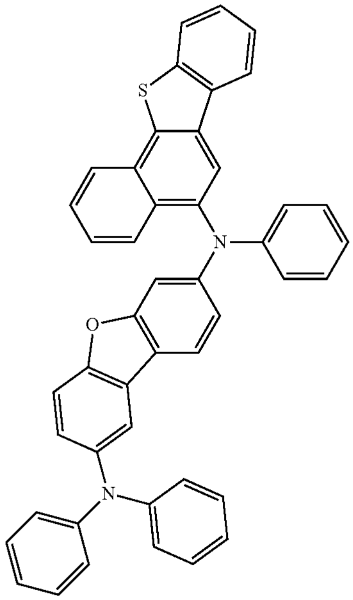

-continued
3-101
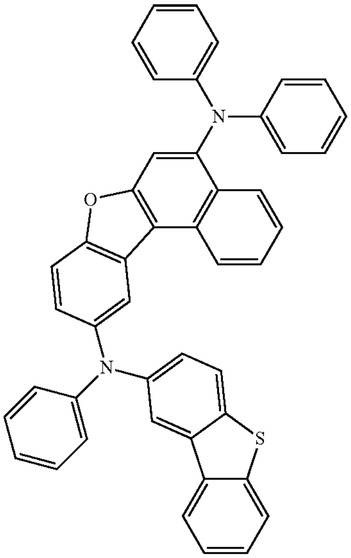
3-102
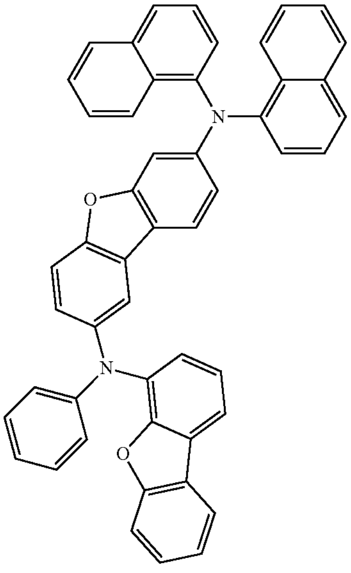
-continued
3-103
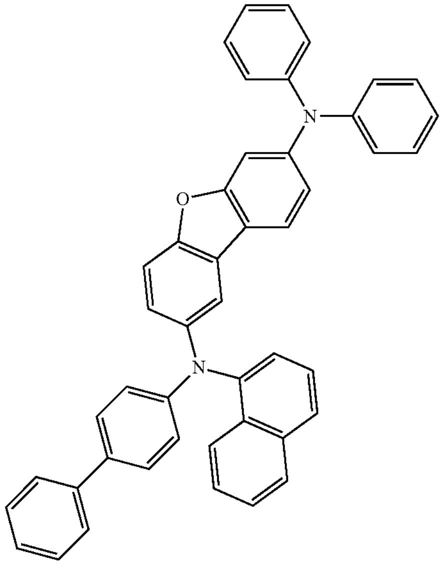
3-104
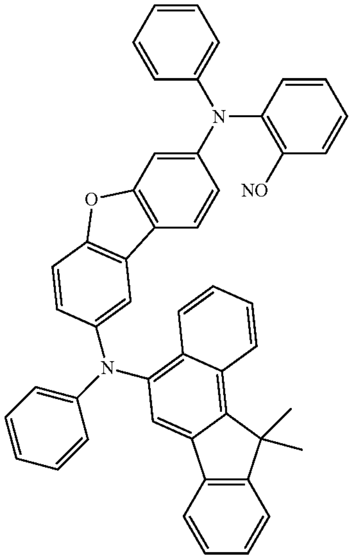

-continued
3-105
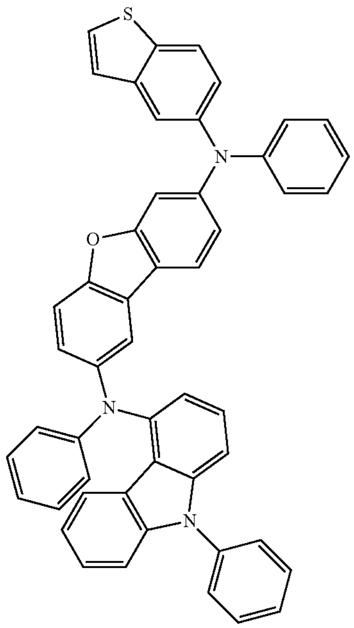
3-106
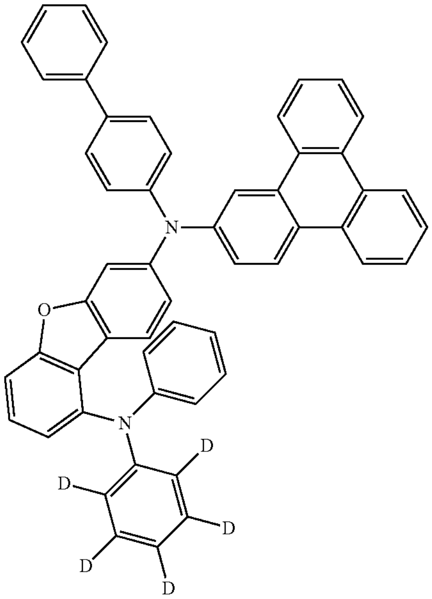
-continued
3-107
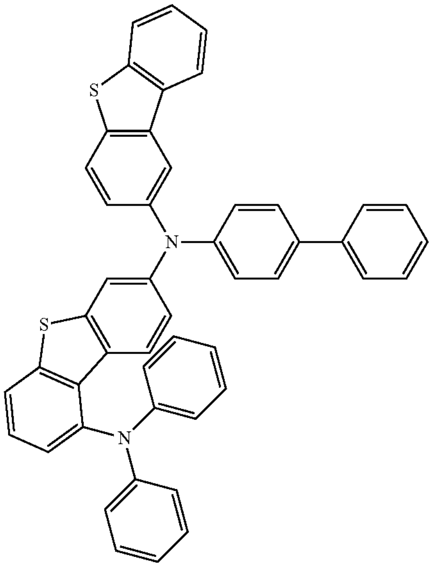
3-108
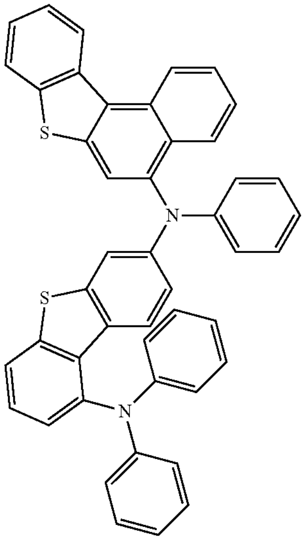
3-109
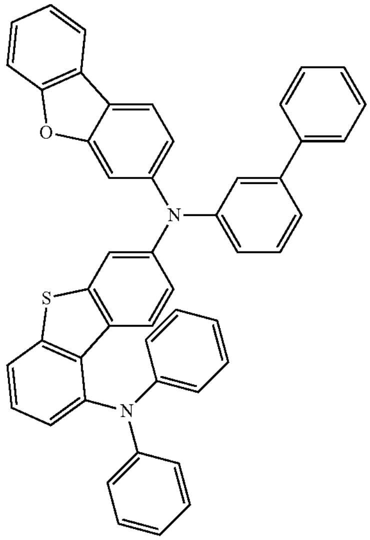

-continued
3-110
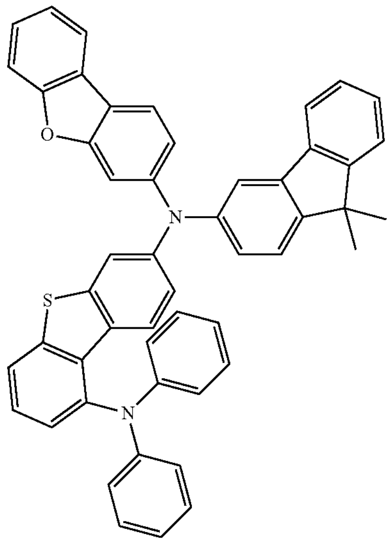
3-111
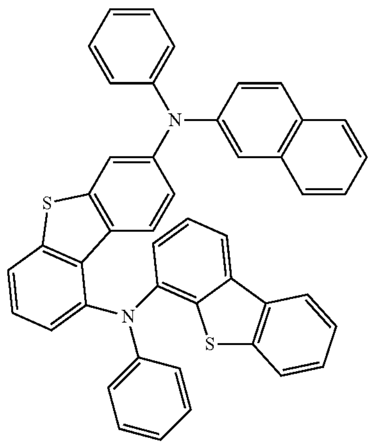
3-112
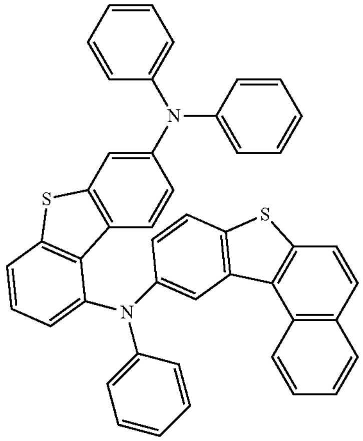
-continued
3-113
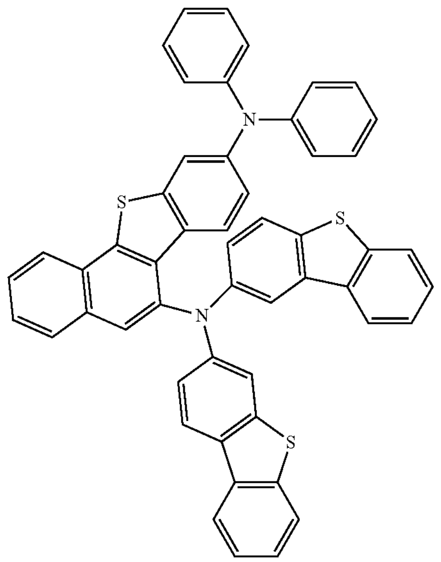
3-114
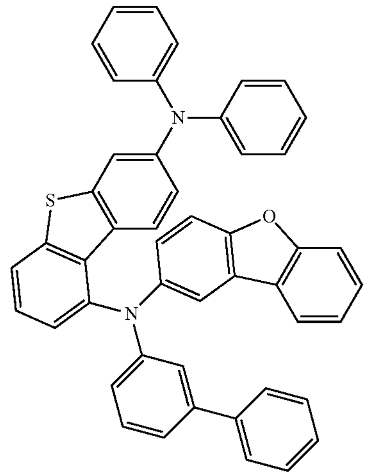
3-115
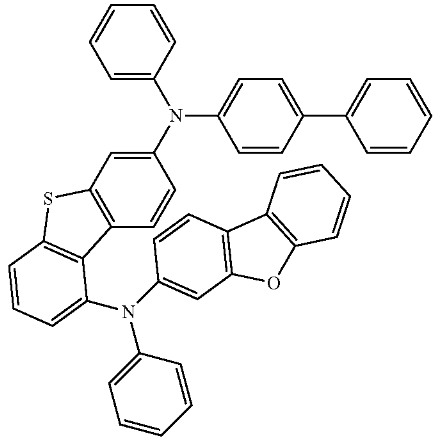

-continued
3-116
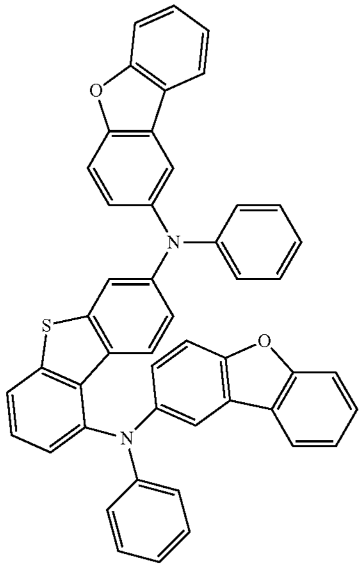
3-117
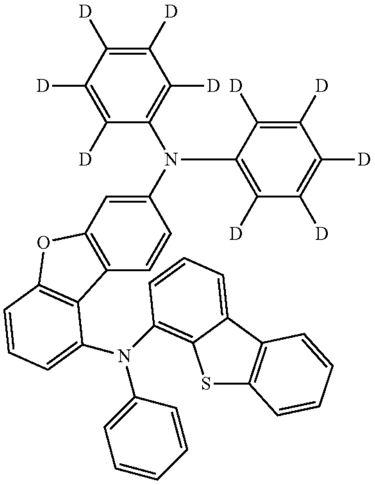
3-118
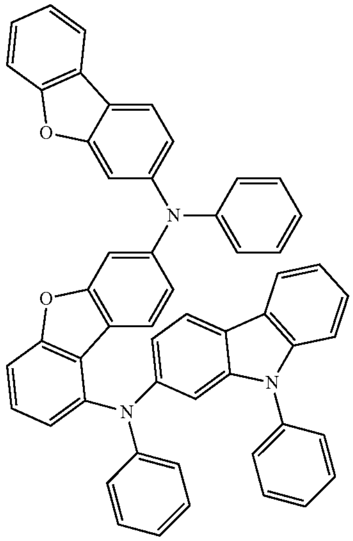
-continued
3-119
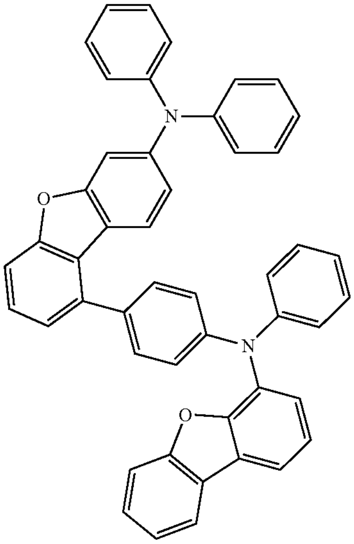
3-120
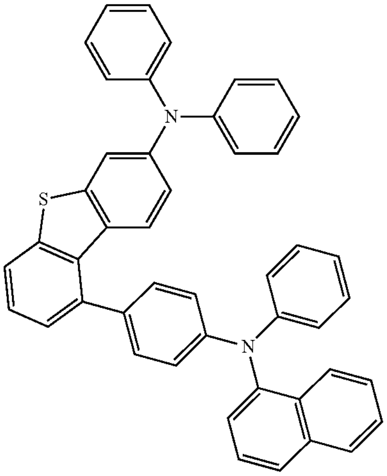
3-121
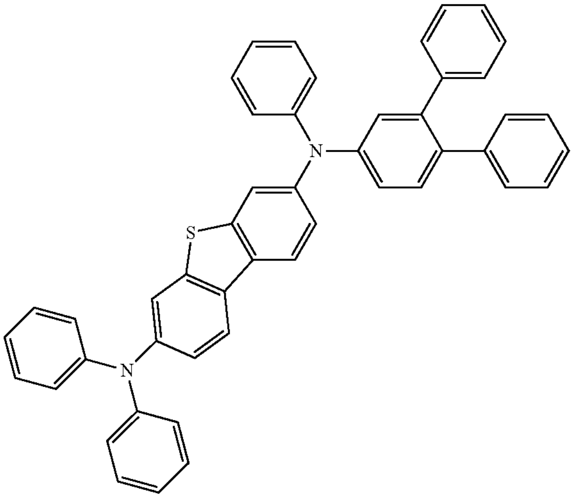

-continued
3-122
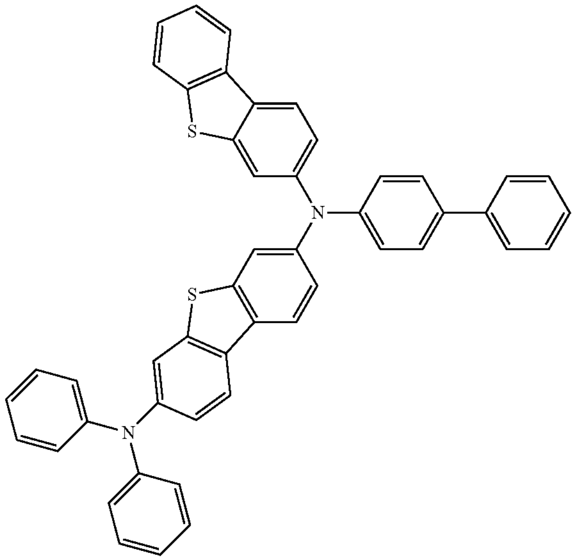
3-123
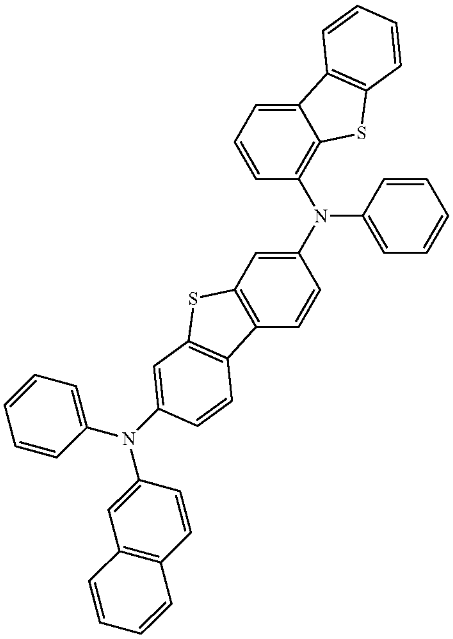
-continued
3-124
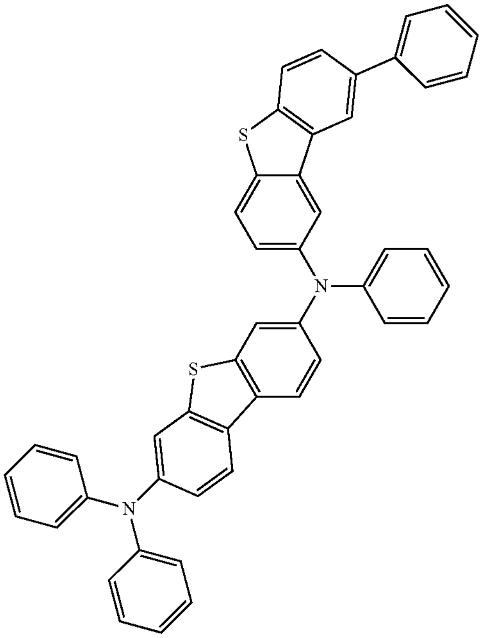
3-125
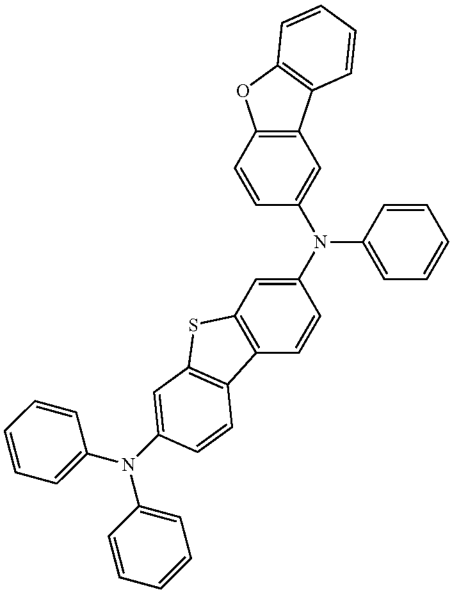

-continued
3-126
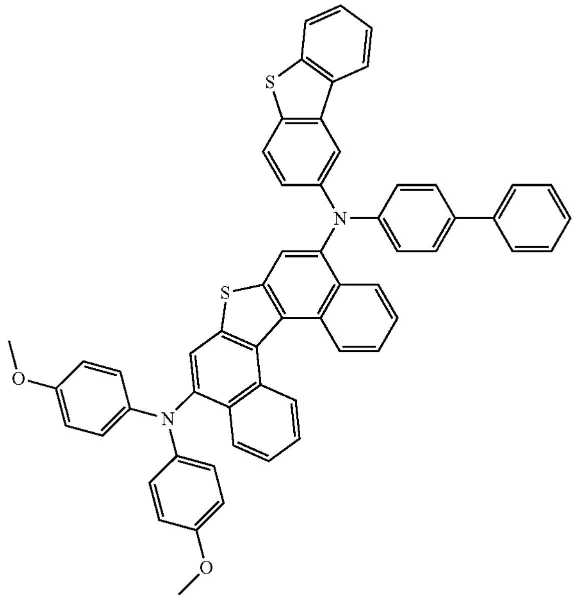
3-127
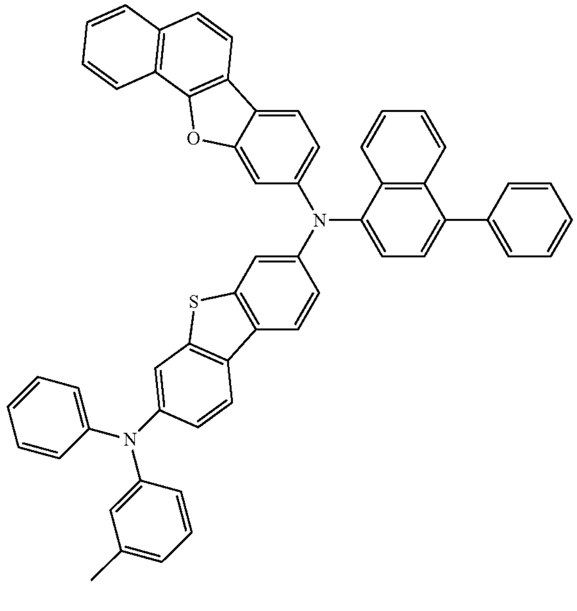
-continued
3-128
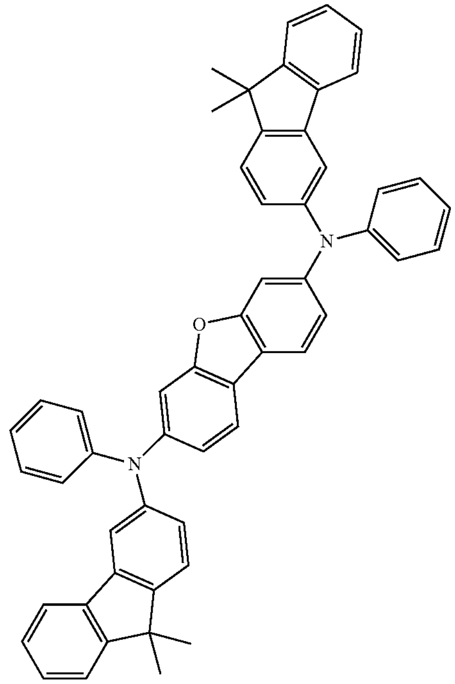
3-129
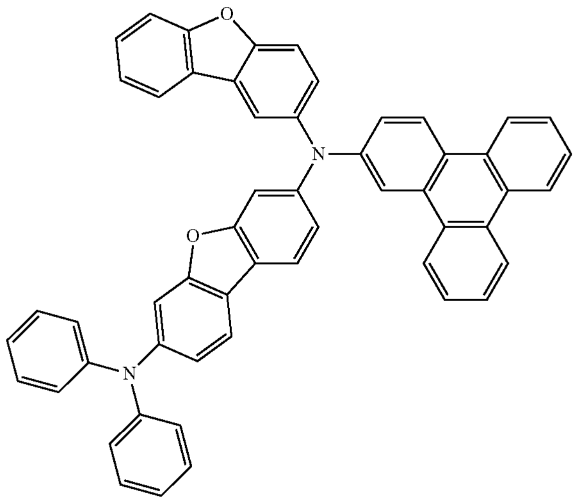

-continued
3-130
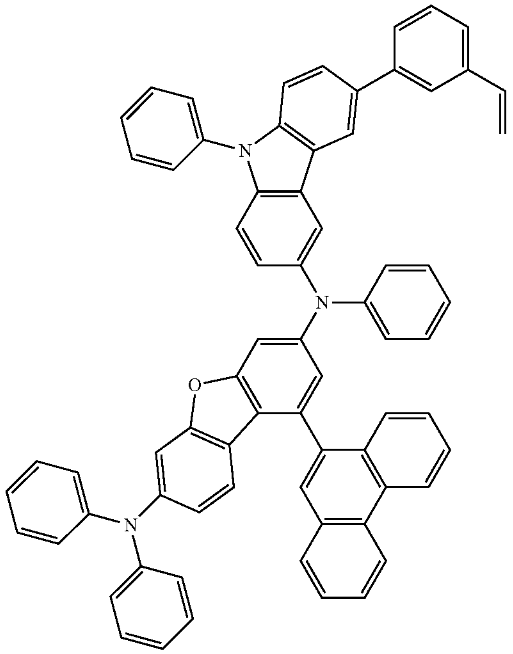
3-131
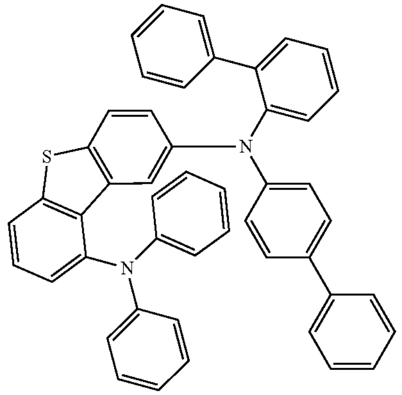
3-132
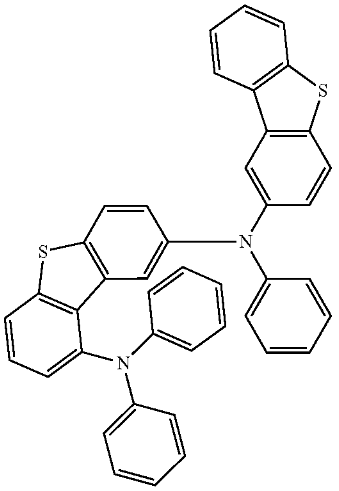
-continued
3-133
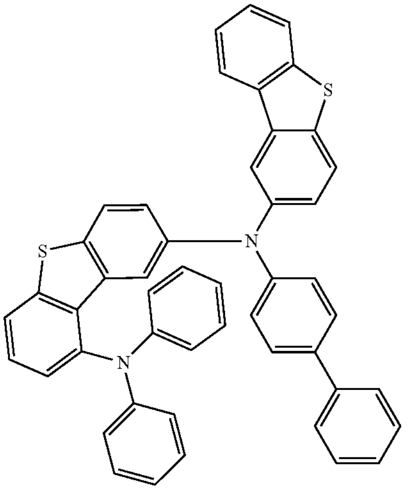
3-134
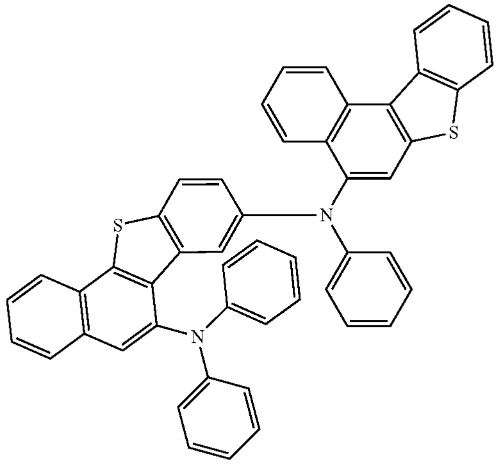
3-135
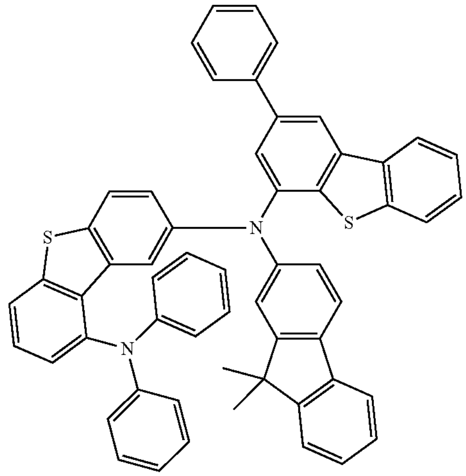

-continued
3-136
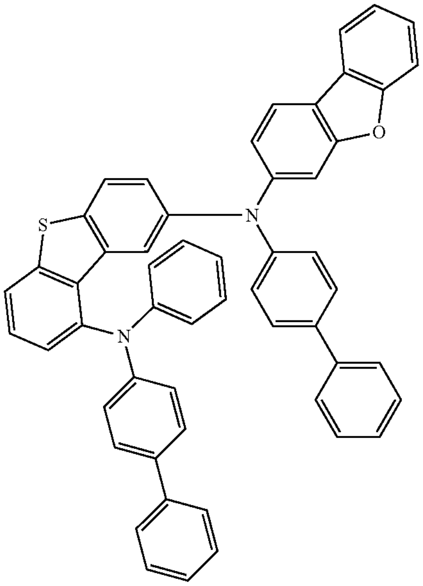
3-137
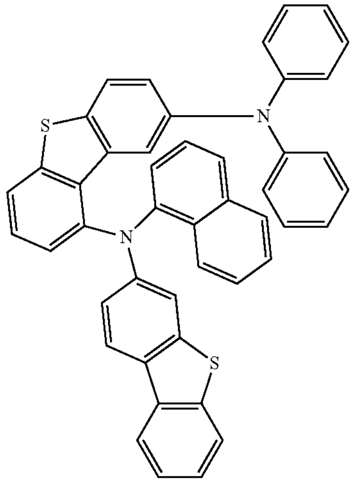
3-138
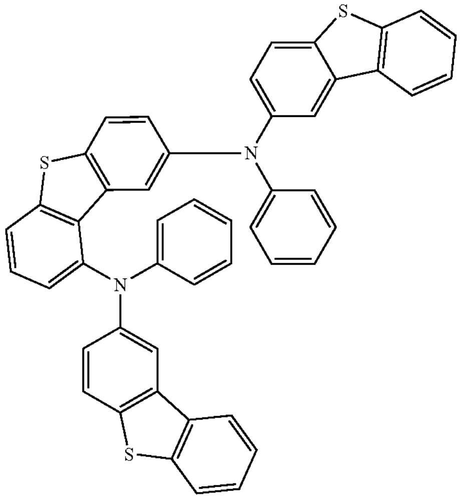
-continued
3-139
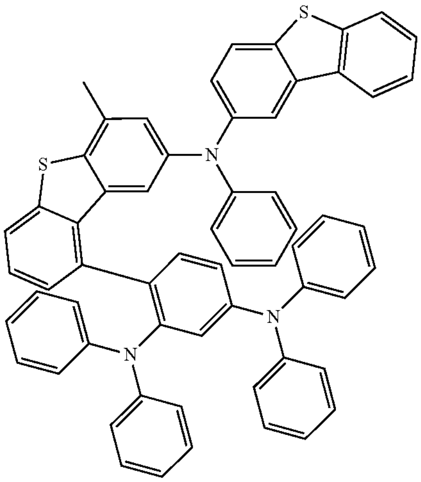
3-140
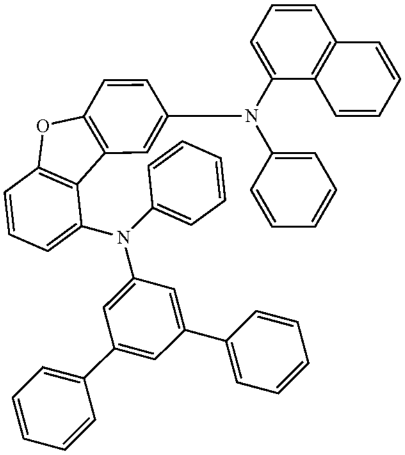
3-141
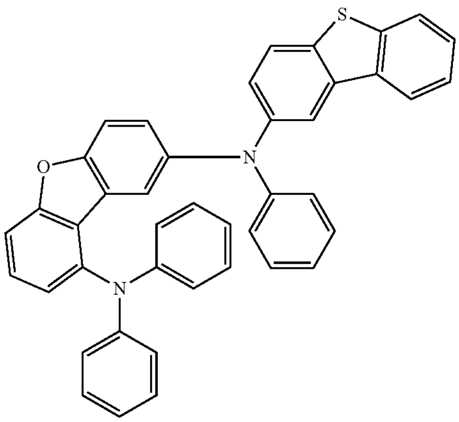

-continued
3-142
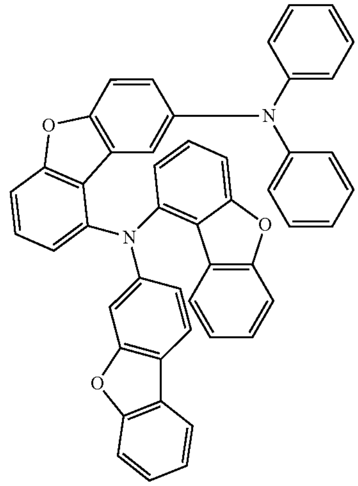
3-143
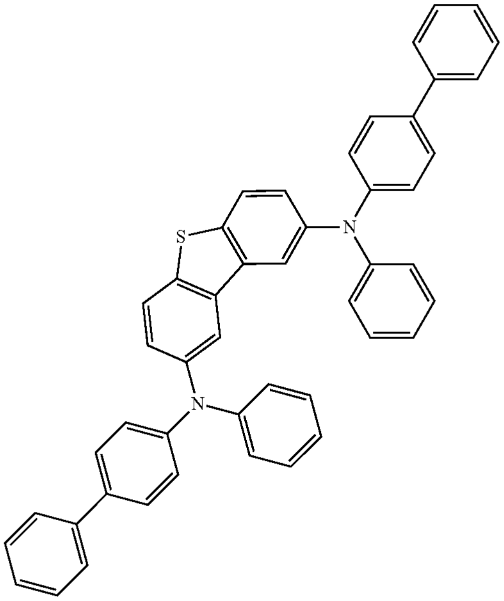
3-144
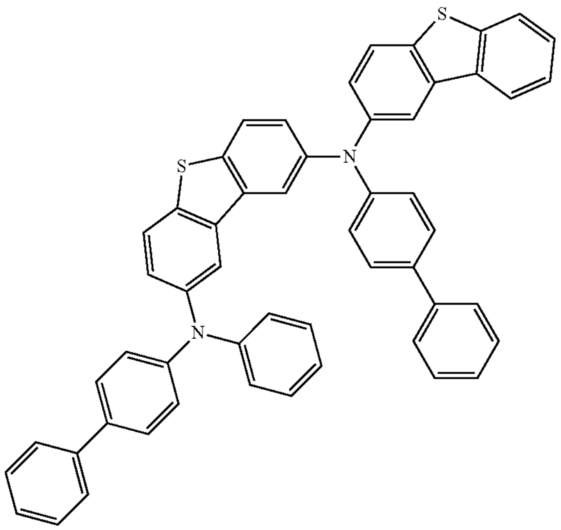
-continued
3-145
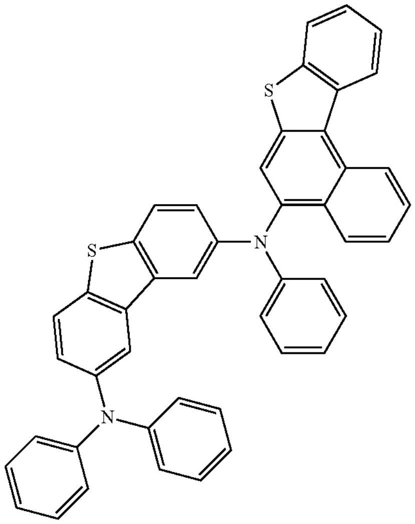
3-146
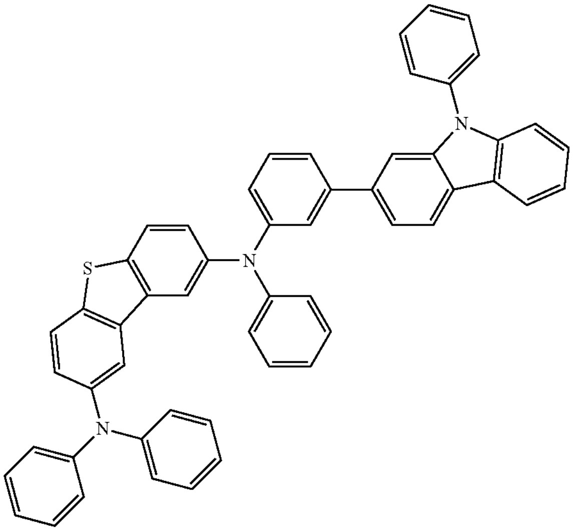
3-147
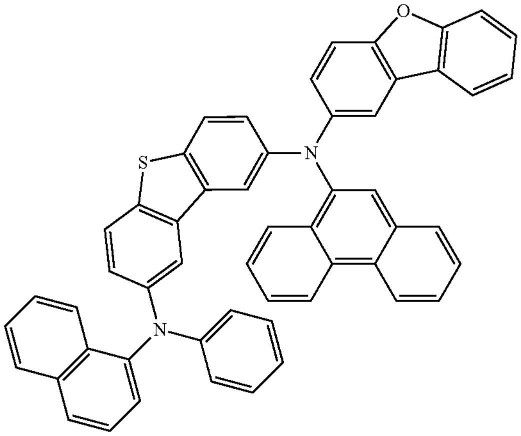

-continued
3-148
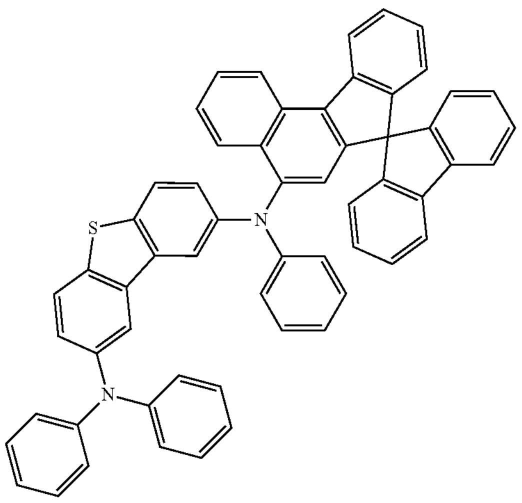
3-149
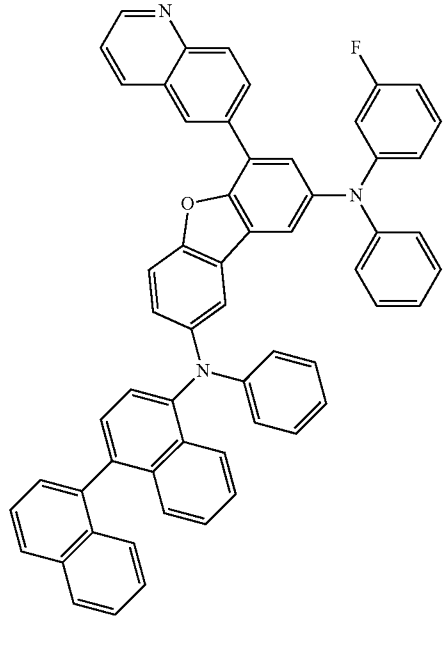
-continued
3-150
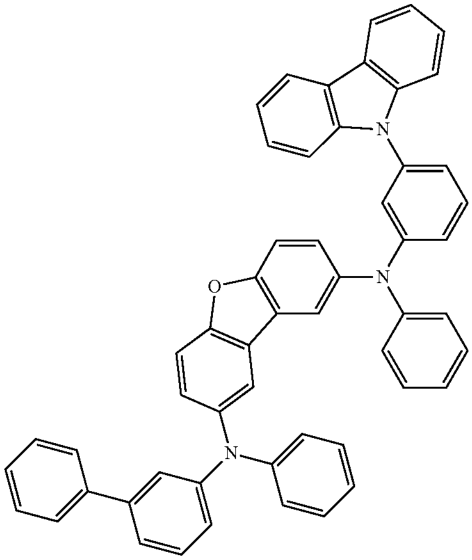
3-151
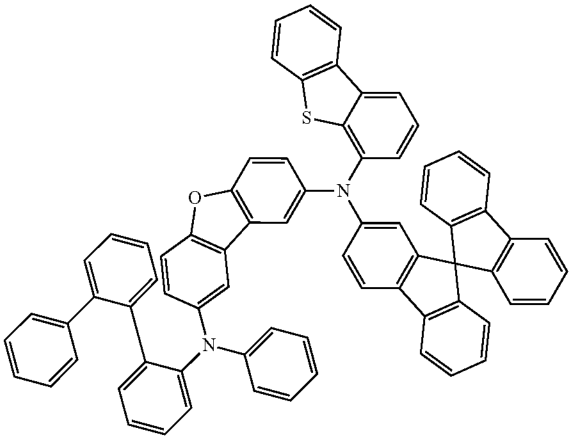
3-152
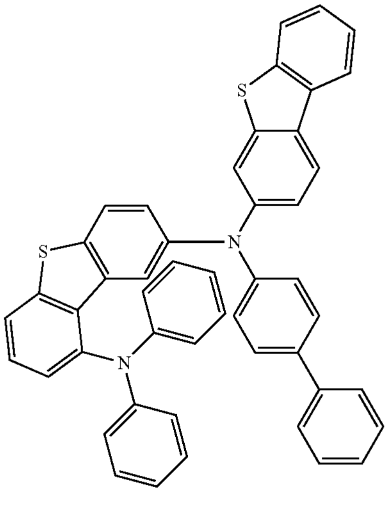

-continued
3-153
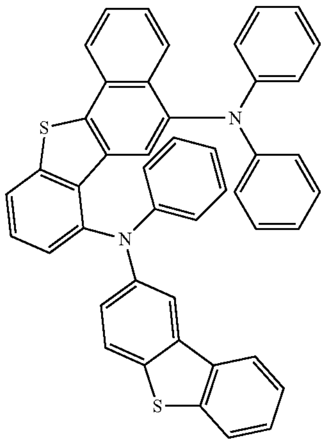
3-154
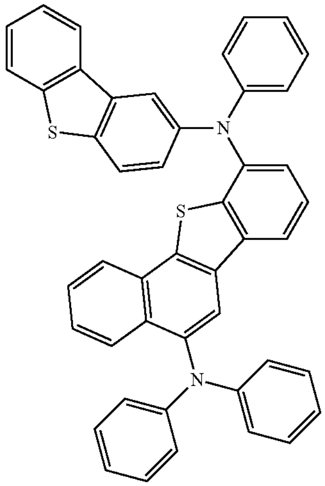
3-155
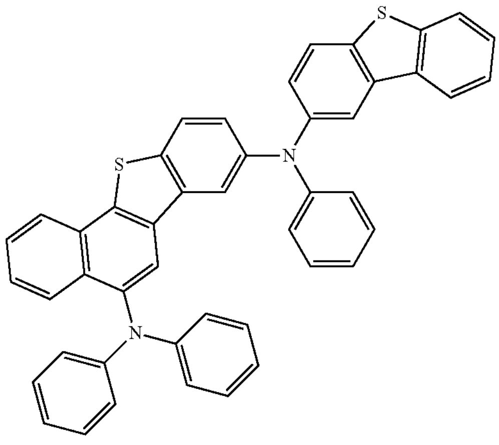
-continued
3-156
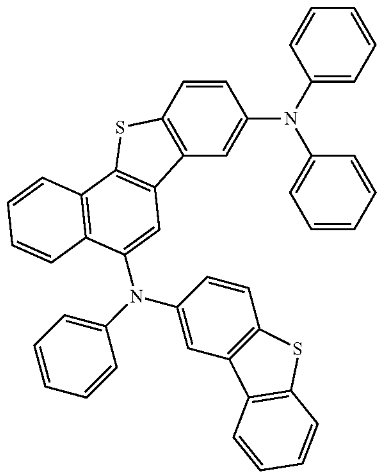
3-157
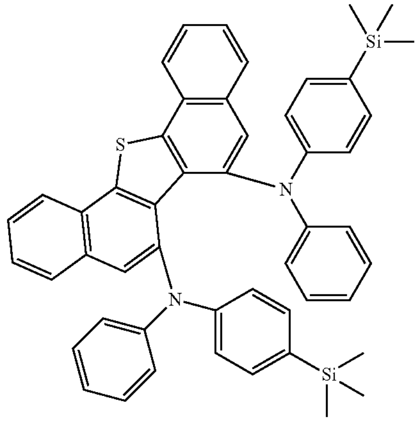
3-158
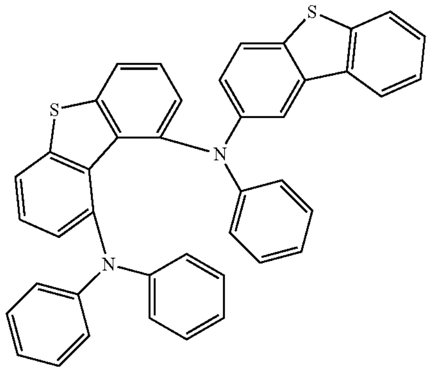

-continued
3-159
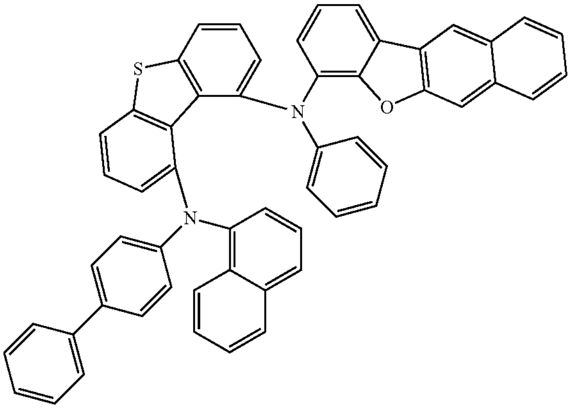
3-160
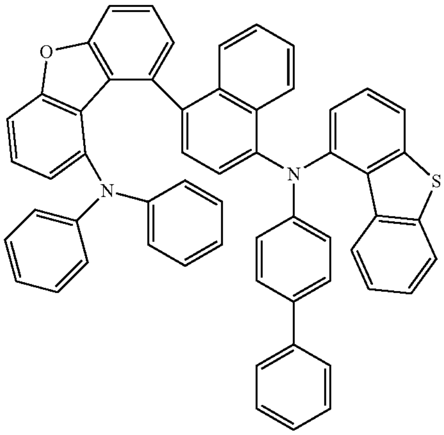
3-161
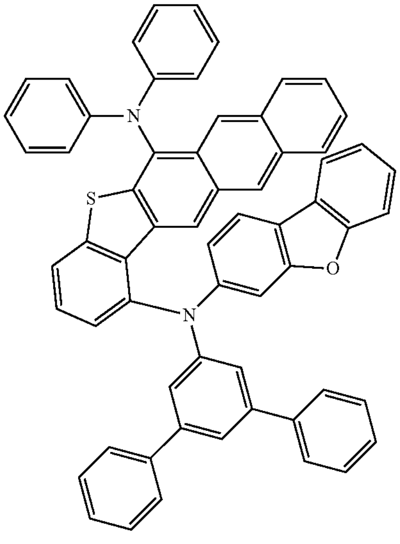
-continued
3-162
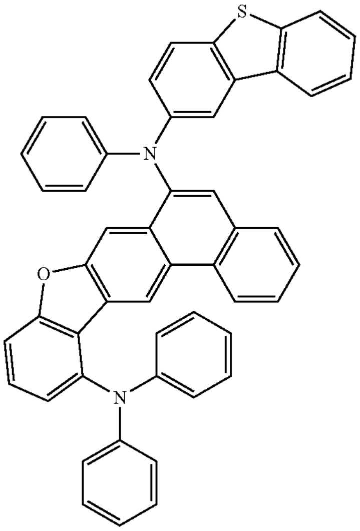
3-163
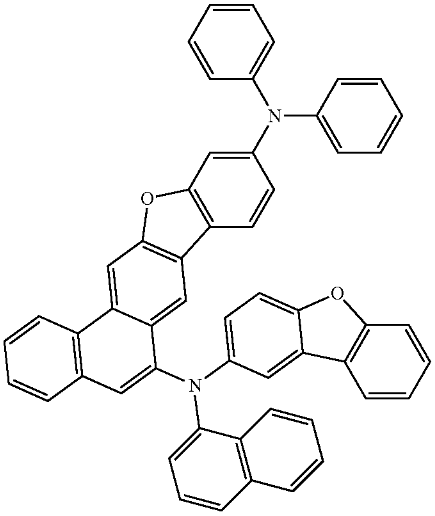
3-164
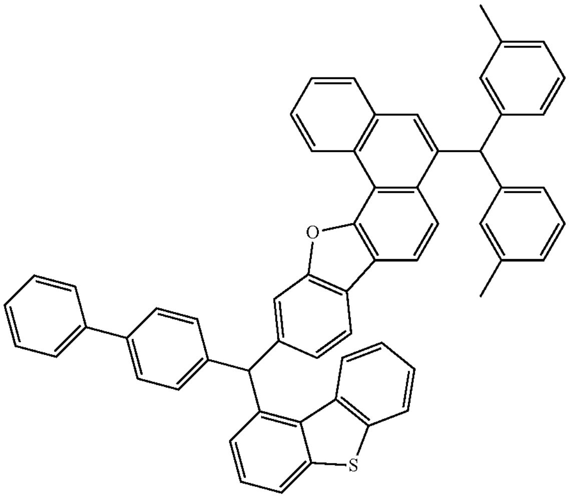

3-165
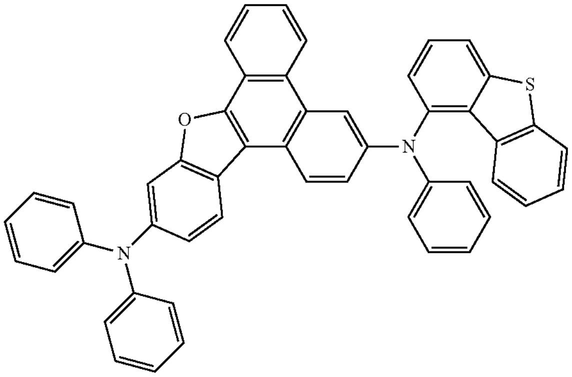
3-166
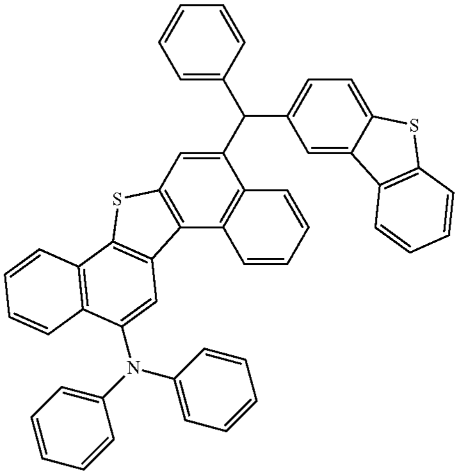
3-167
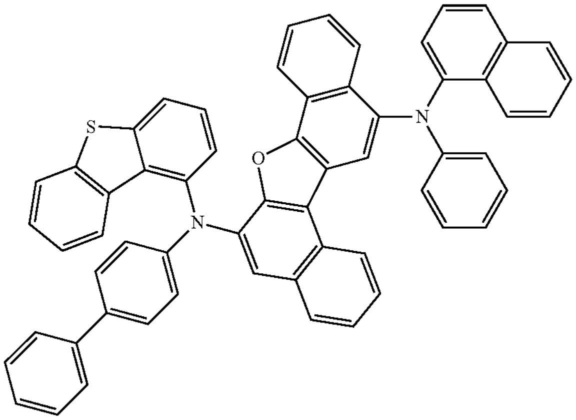
3-168
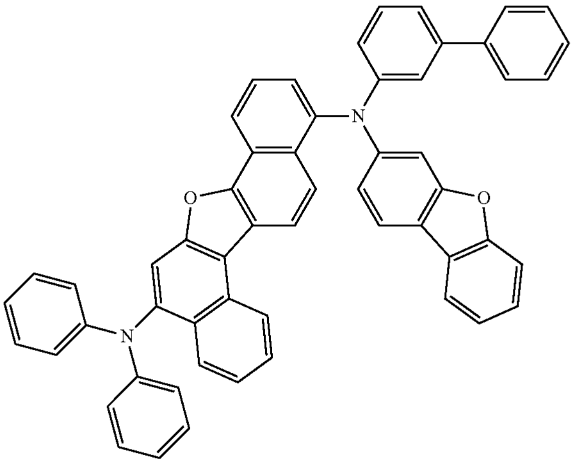
3-169
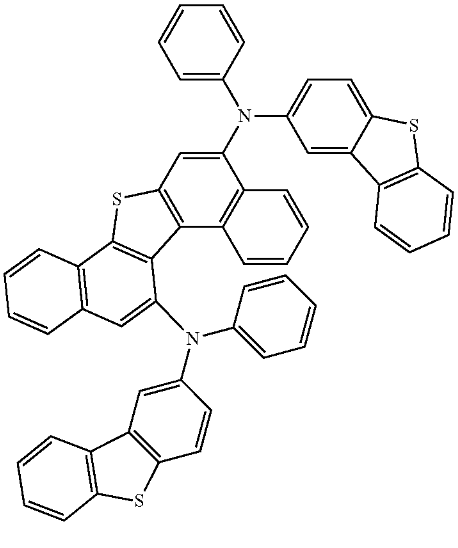
3-170
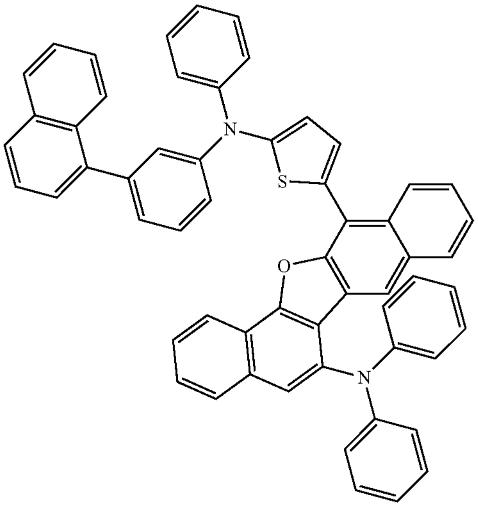

-continued
3-171
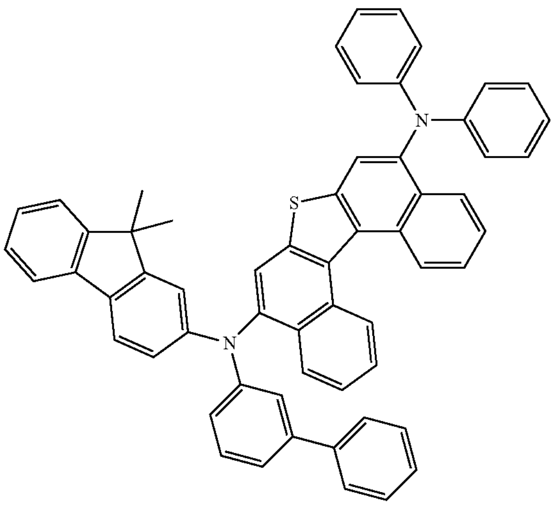
3-172
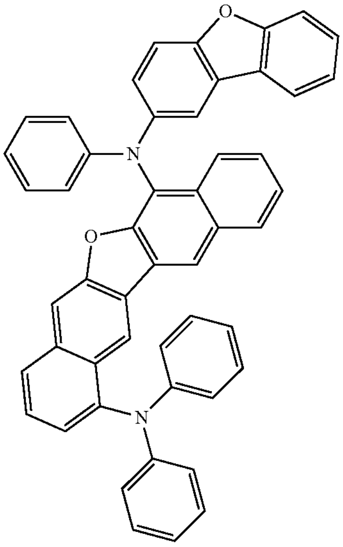
3-173
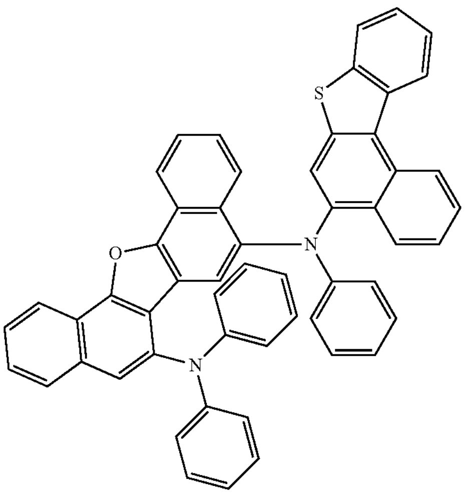
-continued
3-174
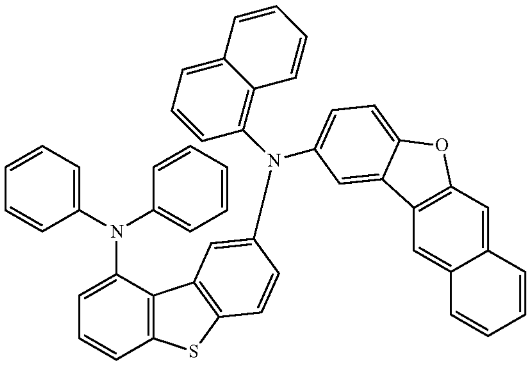
3-175
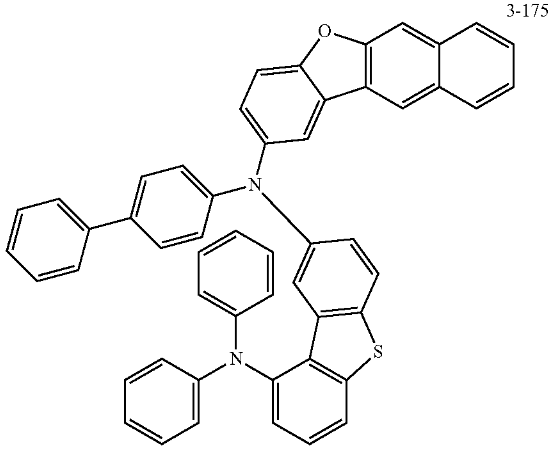
Preferably, in Formulas 1 and 2, $L^1$ to $L^6$ may be each independently one of the following Formulas b-1 to b-13.
<Formula b-1>
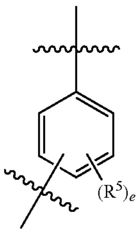
<Formula b-2>
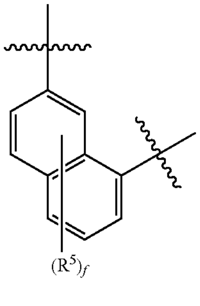

-continued

<Formula b-3>

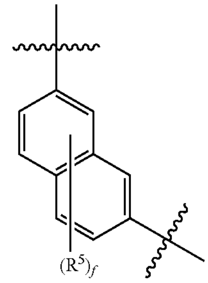

<Formula b-4>

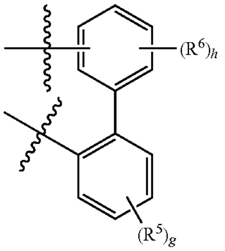

<Formula b-5>

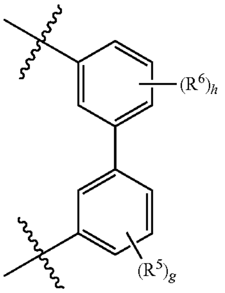

<Formula b-6>

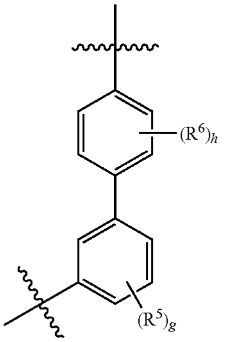

<Formula b-7>

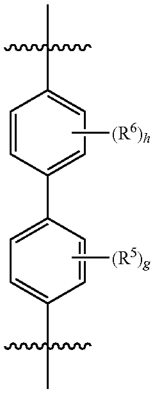

-continued

<Formula b-8>

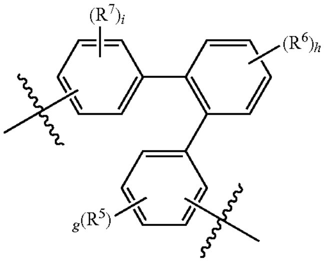

<Formula b-9>

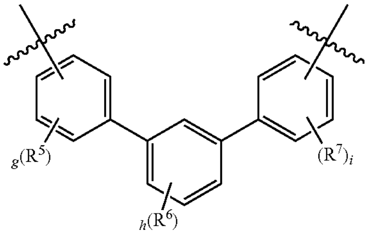

<Formula b-10>

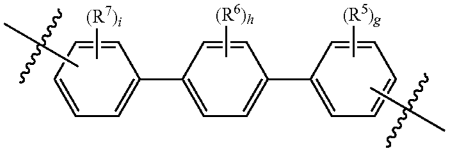

<Formula b-11>

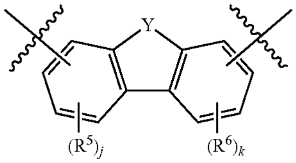

<Formula b-12>

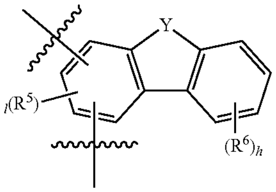

<Formula b-13>

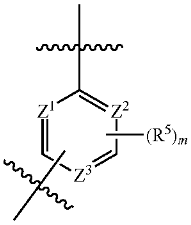

In Formulas b-1 to b-13, each of symbols may be defined as follows.

$R^5$ to $R^7$ may be each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, and a $C_6$-$C_{20}$ aryloxy group, and adjacent groups may optionally be linked to each other to form a ring.

The ring formed by bonding adjacent groups to each other may be a $C_6$-$C_{60}$ aromatic ring group, a fluorenyl group, a $C_2$-$C_{60}$ heterocyclic group containing at least one heteroatom selected from the group consisting of O, N, S, Si, and P, or a $C_3$-$C_{60}$ aliphatic ring or the like. Where adjacent groups are linked to each other to form an aromatic ring group, the ring may be preferably a $C_6$-$C_{30}$ aromatic ring group, more preferably a $C_6$-$C_{14}$ aromatic ring group, for example, benzene, naphthalene, phenanthrene or the like.

Y is N-($L^a$-$Ar^a$), O, S or C(R')(R").

$Z^1$ to $Z^3$ are each independently C, C(R') or N, and at least one of $Z^1$ to $Z^3$ is N.

f is an integer of 0-6, e, g, h and i are each an integer of 0-4, j and k are each an integer of 0-3, l is an integer of 0-2, m is an integer of 0-3, and where they are an integer of 2 or more, respectively, each of a plurality of $R^5$, each of a plurality of $R^6$, and each of a plurality of $R^7$ are the same as or different from each other.

R' and R" may be each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group, and -$L^a$-N($R_a$)($R_b$).

R' and R" of C(R')(R") may optionally be linked to each other to form a ring, and adjacent R's of C(R') may optionally be linked to each other to form a ring.

$Ar^a$ may be selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$L^a$ may be selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R_b$ may be each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^5$ to $R^7$, $L^a$, $Ar^a$, R', R", $R^a$, $R^b$, and the ring formed by bonding adjacent groups to each other may be each optionally further substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_6$-$C_{20}$ arylalkenyl group.

In one embodiment of the present invention, it is preferable to use a mixture of the compound represented by Formula 1 and the compound represented by Formula 2 in a weight ratio of 2:8 to 8:2 as a host material.

In another embodiment of the present invention, the compound represented by Formula 3 of the present invention may be comprised in a light emitting layer and/or an emission-auxiliary layer, preferably used as a host of a light emitting layer or a material of an emission-auxiliary layer.

In another embodiment of the present invention, a mixture of the compound represented by Formula 3 and the compound represented by Formula 4 of the present invention may be used as a host material of a light emitting layer.

Hereinafter, synthesis examples of the compounds represented by Formulas 1 and 2, respectively, and preparation method of an organic electric element according to one embodiment of the present invention will be described in detail by way of examples. However, the present invention is not limited to the following examples.

[Synthesis Example 1] Formula 1

As shown in Reaction Scheme 1 below, the compound (final product) represented by Formula 1 according to the present invention can be synthesized by reacting Sub 1 with Sub 2, but there is no limitation thereto.

<Reaction Scheme 1>

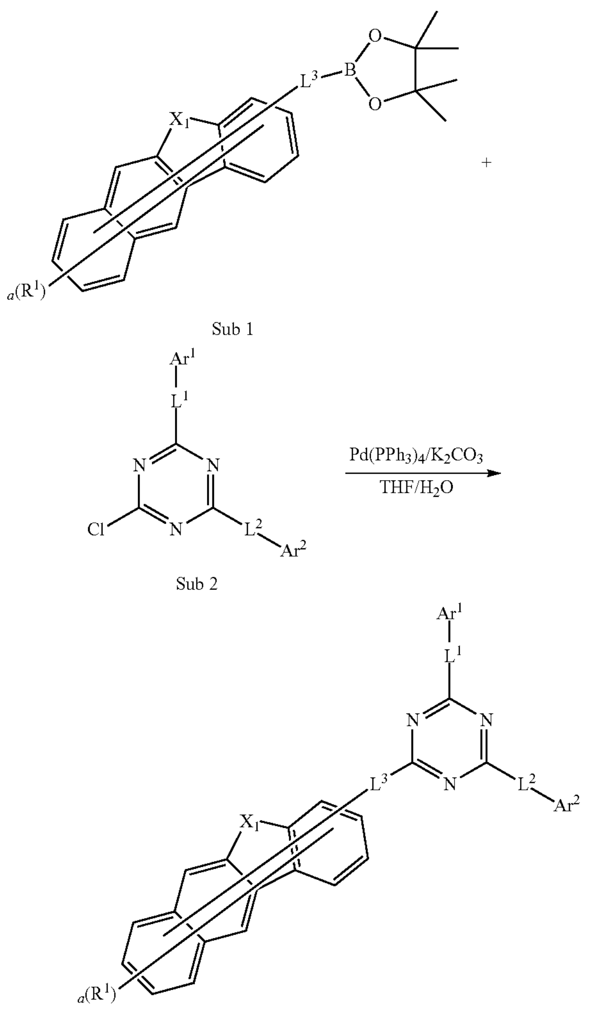

Sub 1

Sub 2

Final product 1

1. Exemplary Compounds of Sub 1 and Synthesis Example

The compound belonging to Sub 1 may be, but not limited to, the following compounds.

Sub 1-1
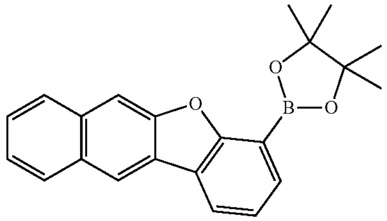
Sub 1-2
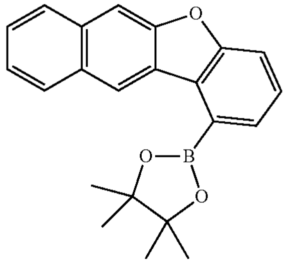
Sub 1-3
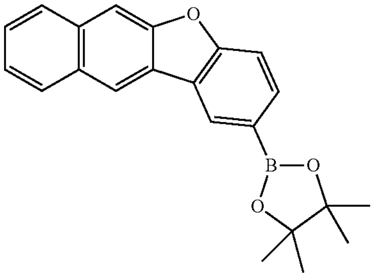
Sub 1-4
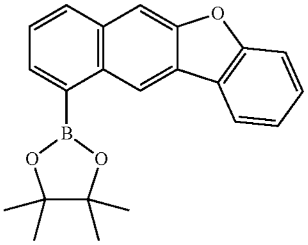
Sub 1-5
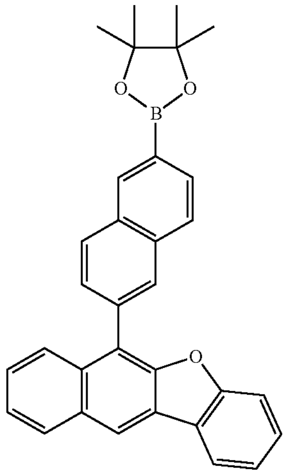
-continued
Sub 1-6
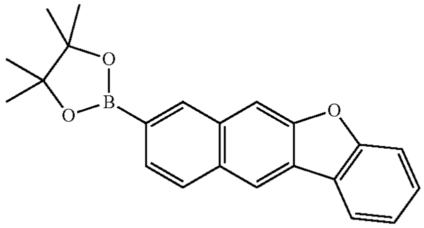
Sub 1-7
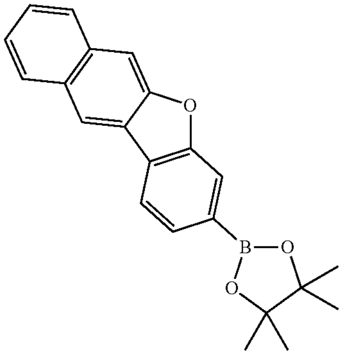
Sub 1-8
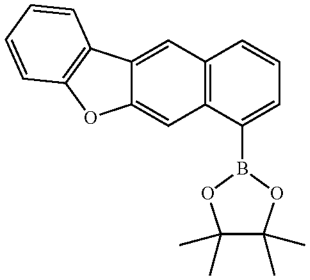
Sub 1-9
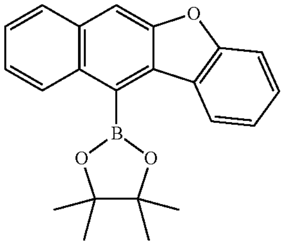
Sub 1-10
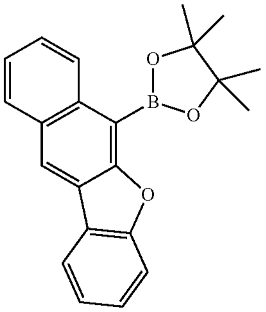

-continued
Sub 1-11
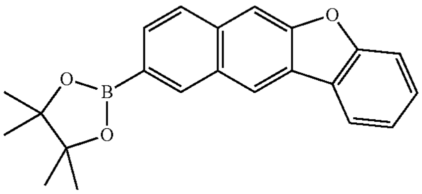
Sub 1-12
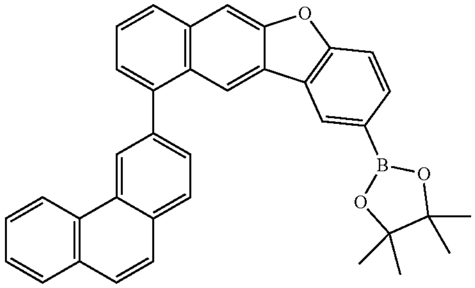
Sub 1-13
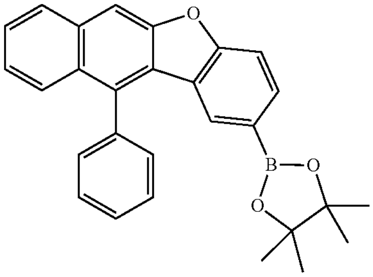
Sub 1-14
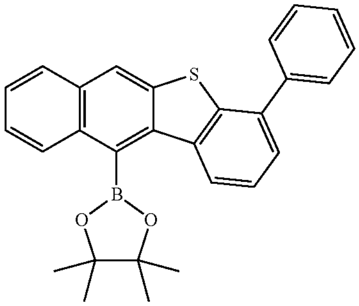
Sub 1-15
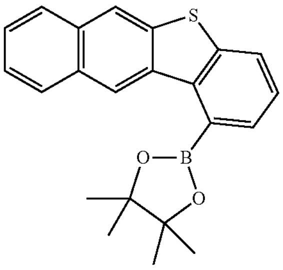
-continued
Sub 1-16
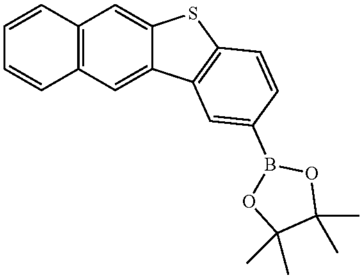
Sub 1-17
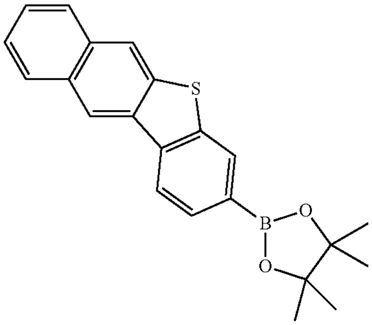
Sub 1-18
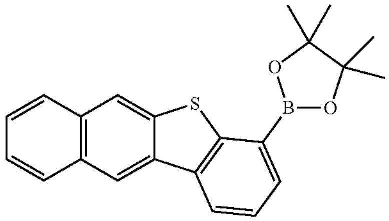
Sub 1-19
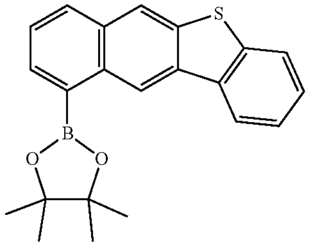
Sub 1-20
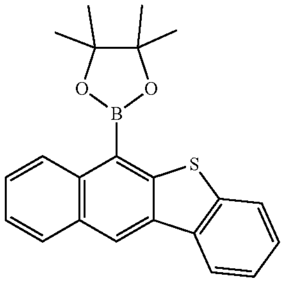
Sub 1-21
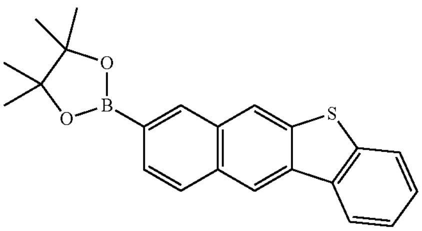

-continued
Sub 1-22
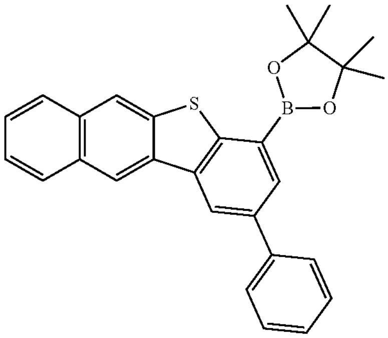
Sub 1-23
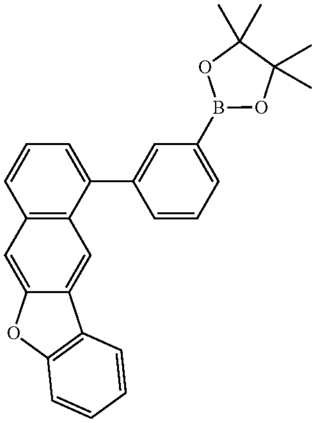
Sub 1-24
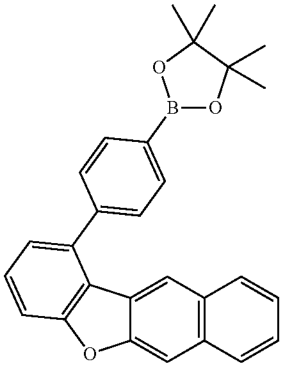
Sub 1-25
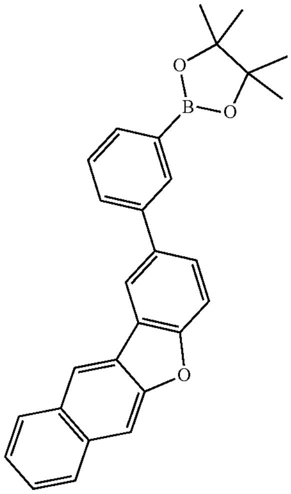
-continued
Sub 1-26
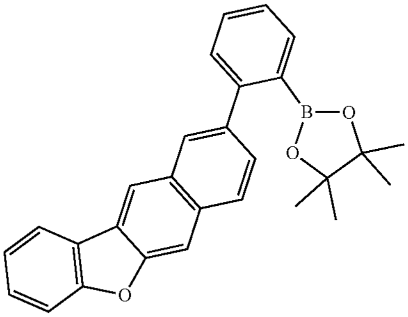
Sub 1-27
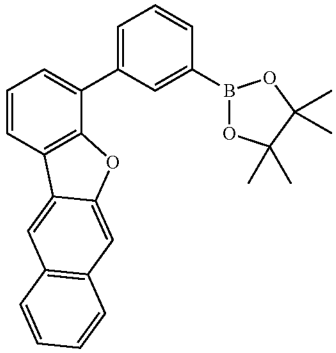
Sub 1-28
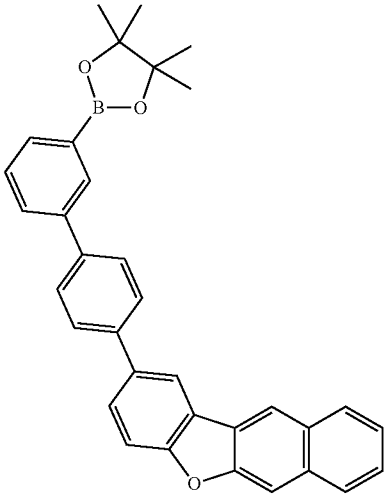
Sub 1-29
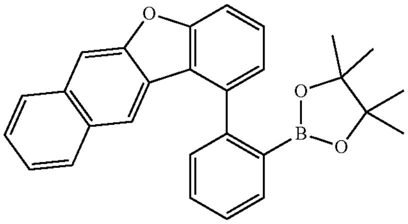

-continued
Sub 1-30
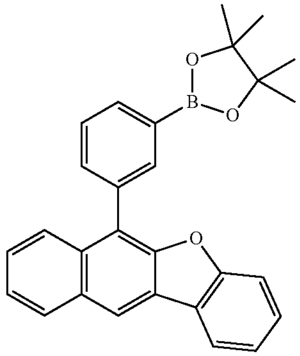
Sub 1-31
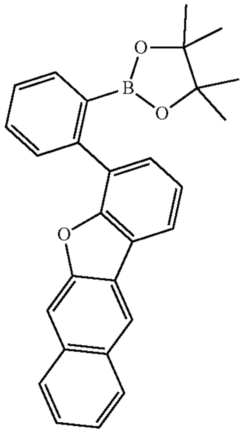
Sub 1-32
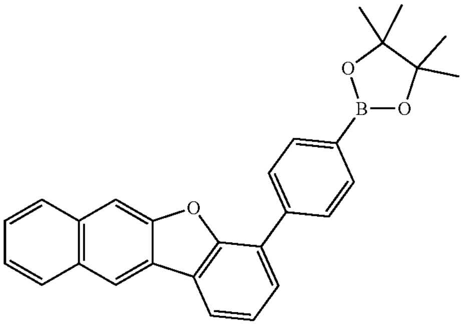
Sub 1-33
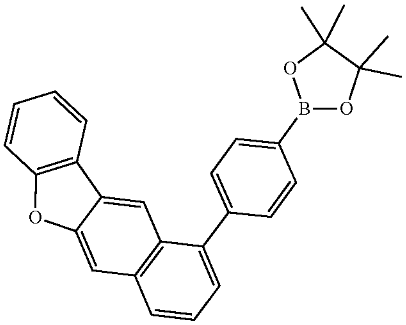
-continued
Sub 1-34
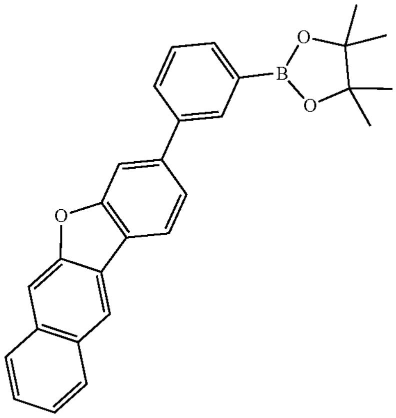
Sub 1-35
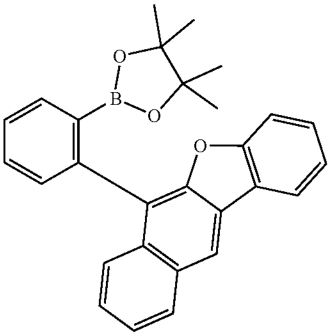
Sub 1-36
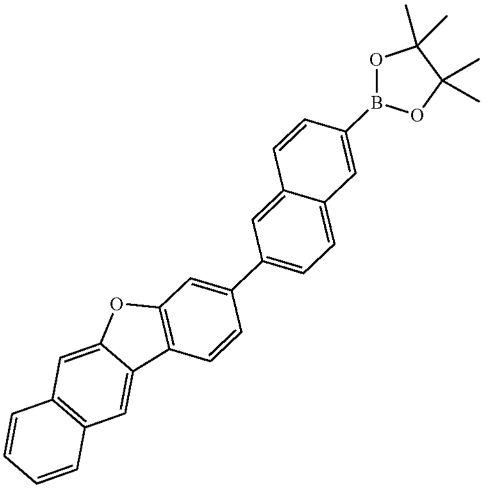
Sub 1-37
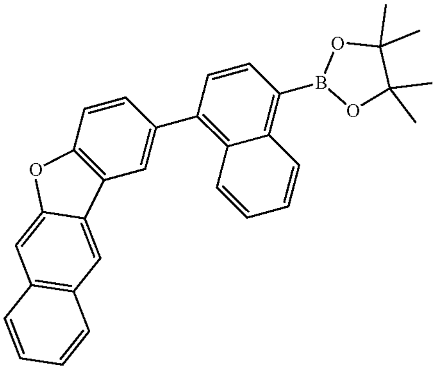

-continued
Sub 1-38
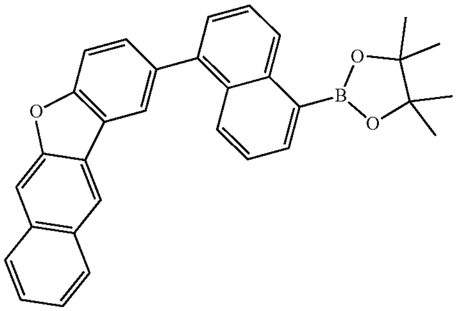
Sub 1-39
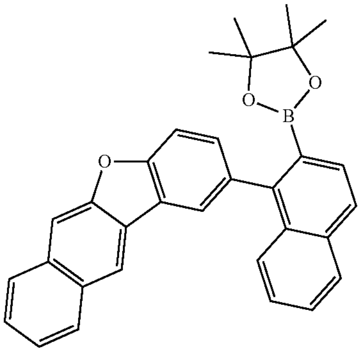
Sub 1-40
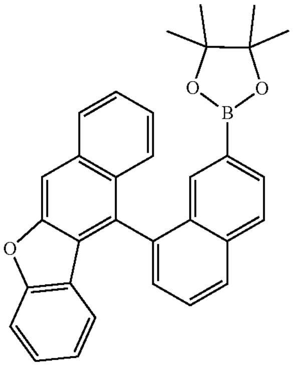
Sub 1-41
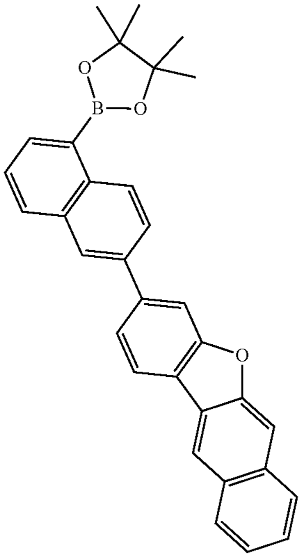
-continued
Sub 1-42
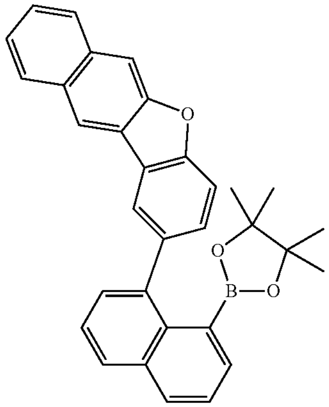
Sub 1-43
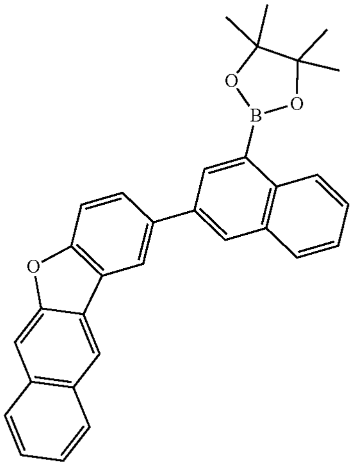
Sub 1-44
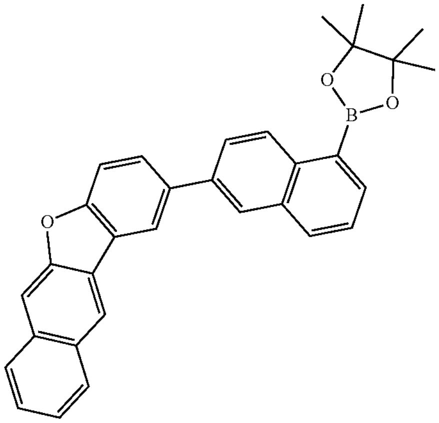
Sub 1-45
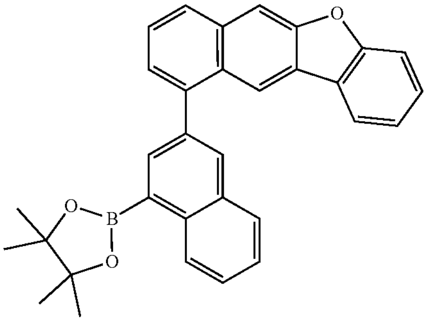

-continued
Sub 1-46
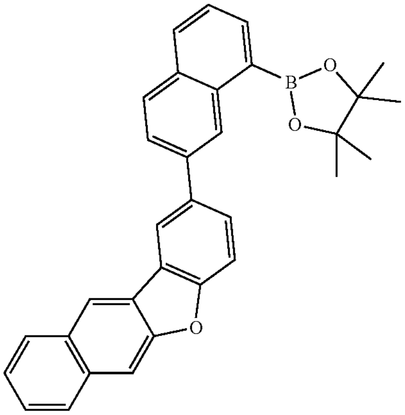
Sub 1-47
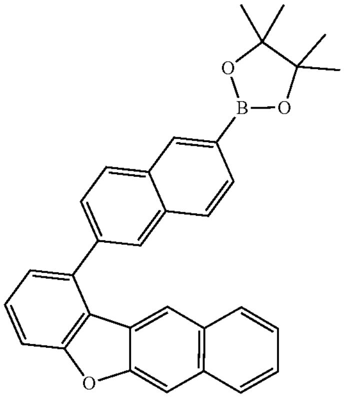
Sub 1-48
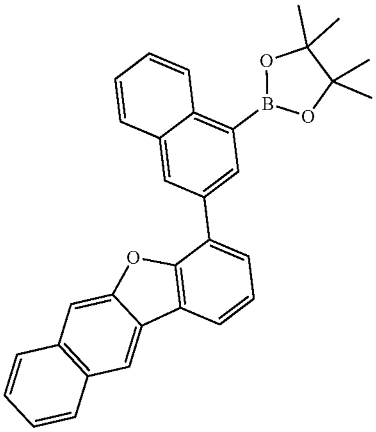
-continued
Sub 1-49
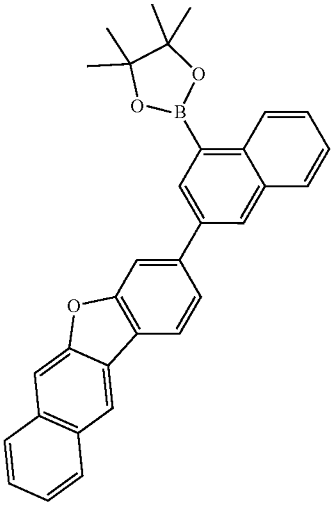
Sub 1-50
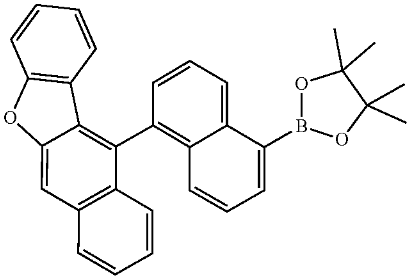
Sub 1-51
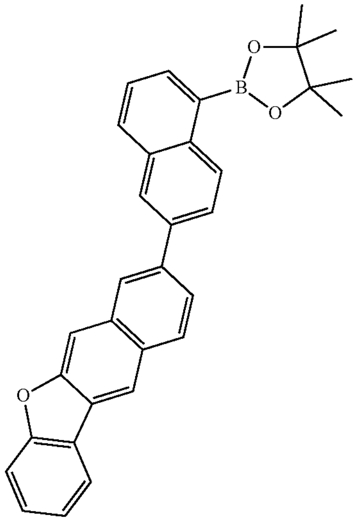

-continued
Sub 1-52
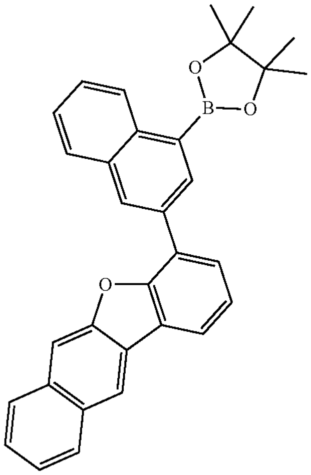
Sub 1-53
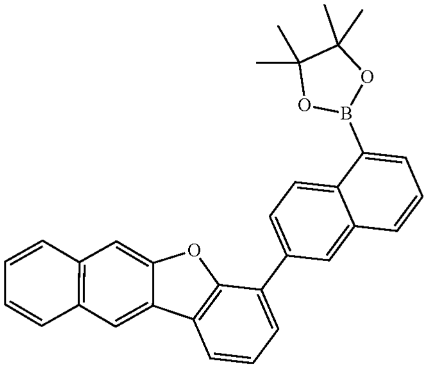
Sub 1-54
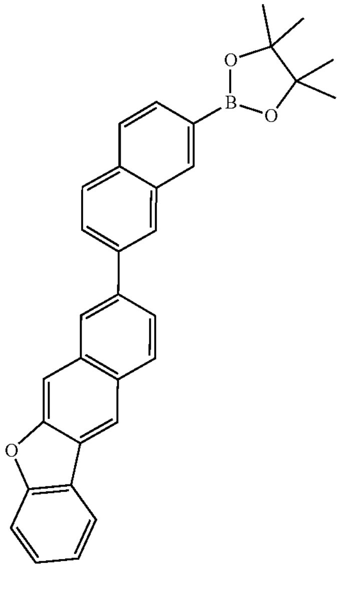
-continued
Sub 1-55
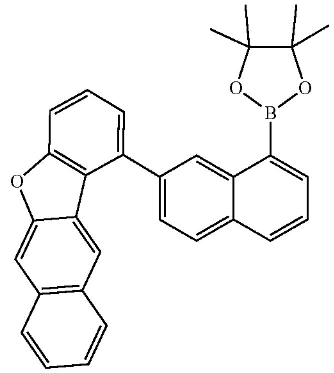
Sub 1-56
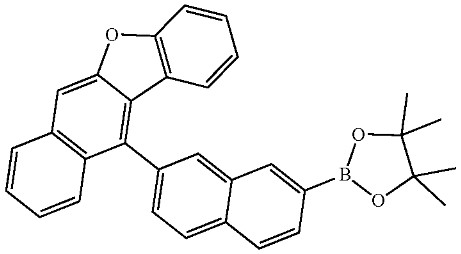
Sub 1-57
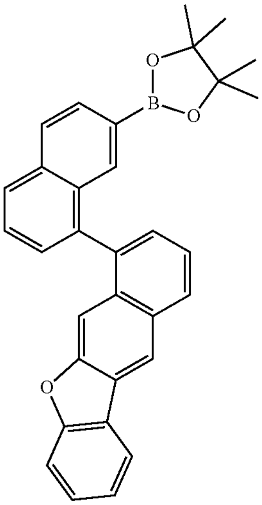
Sub 1-58
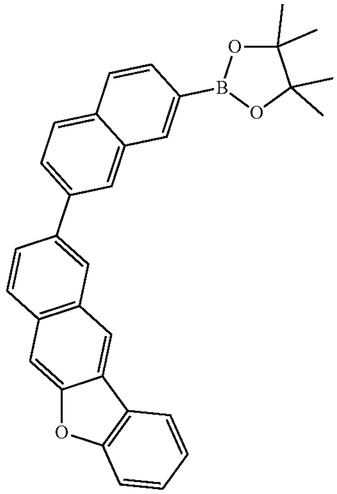

-continued
Sub 1-59
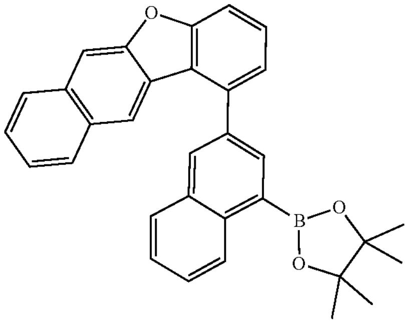
Sub 1-60
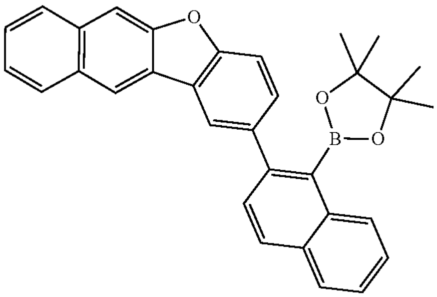
Sub 1-61
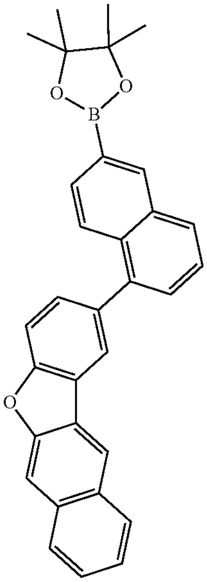
-continued
Sub 1-62
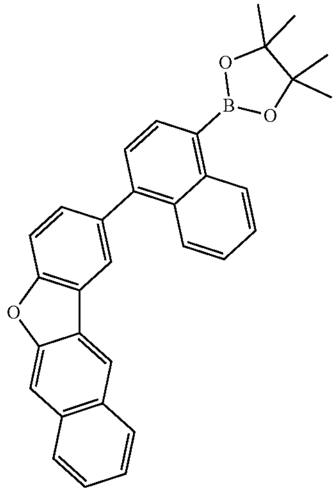
Sub 1-63
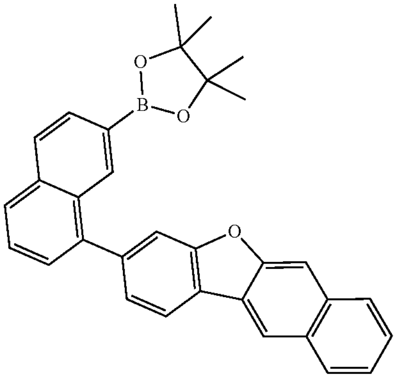
Sub 1-64
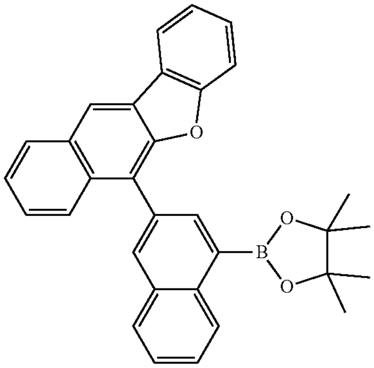
Sub 1-65
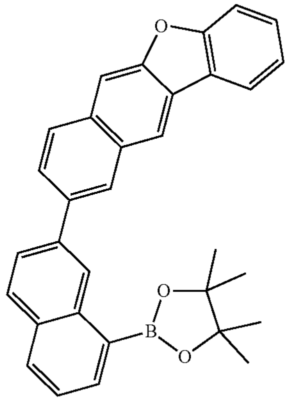

-continued
Sub 1-66
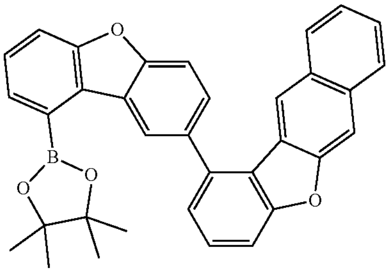
Sub 1-67
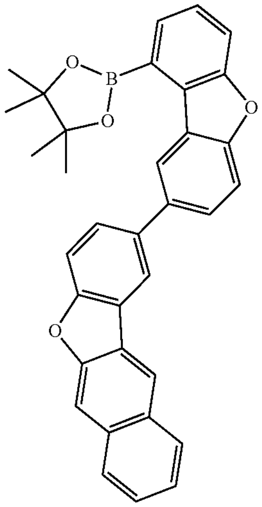
Sub 1-68
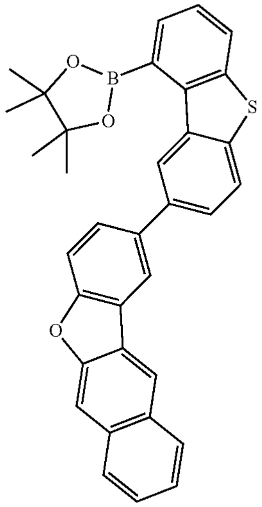
-continued
Sub 1-69
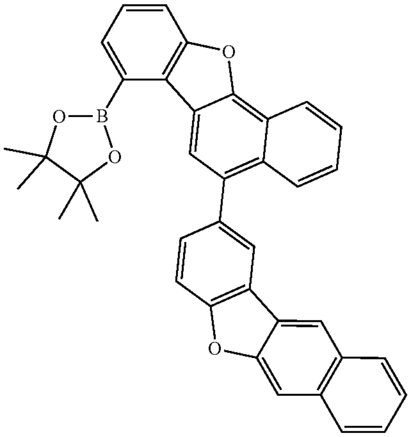
Sub 1-70
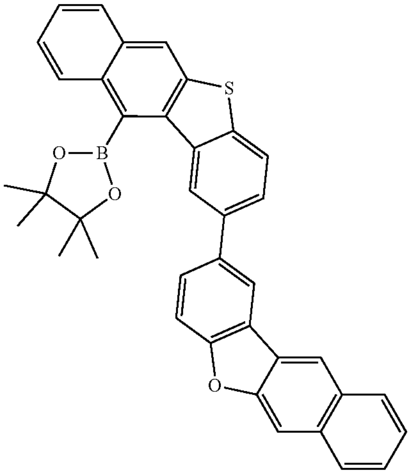
Sub 1-71
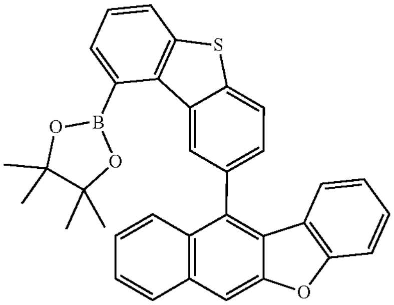

-continued
Sub 1-72
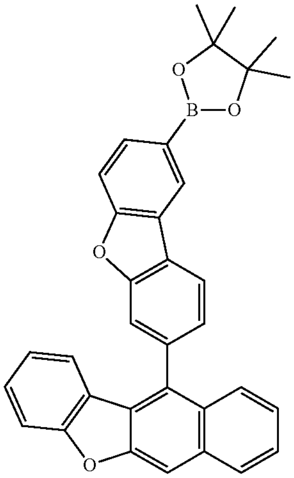
Sub 1-73
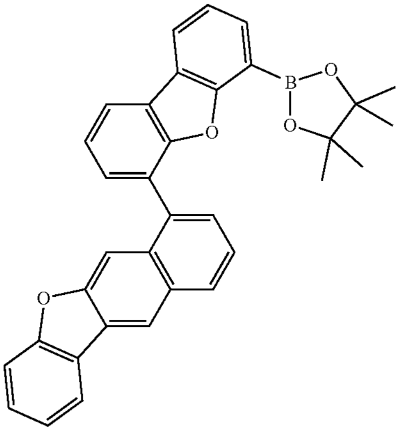
Sub 1-74
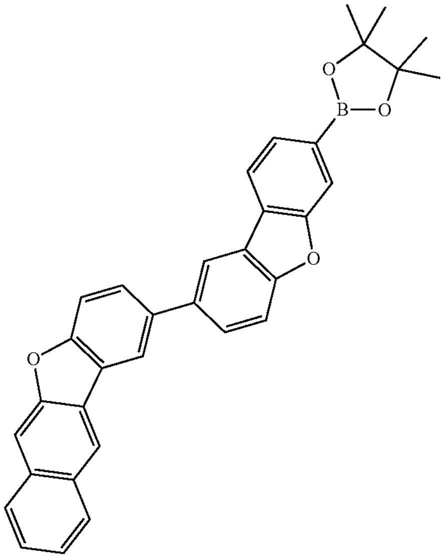
-continued
Sub 1-75
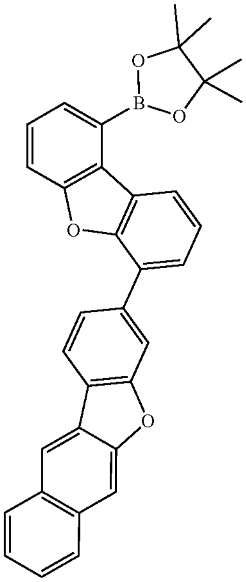
Sub 1-76
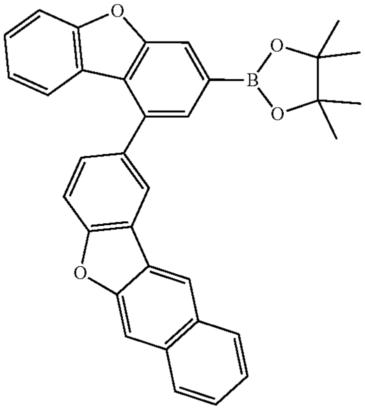
Sub 1-77
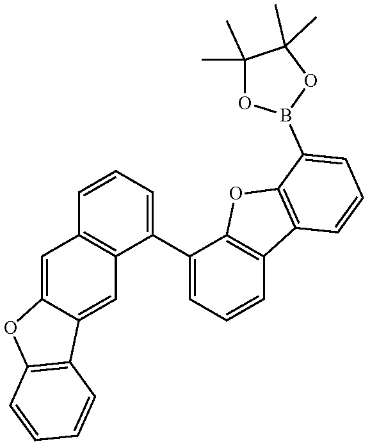

-continued
Sub 1-78
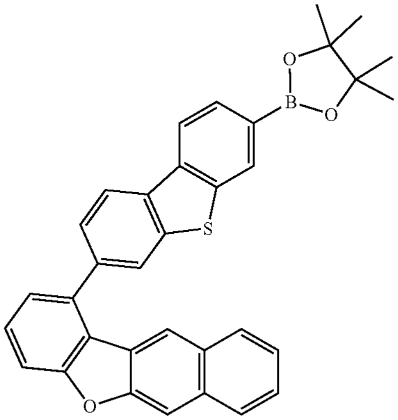
Sub 1-79
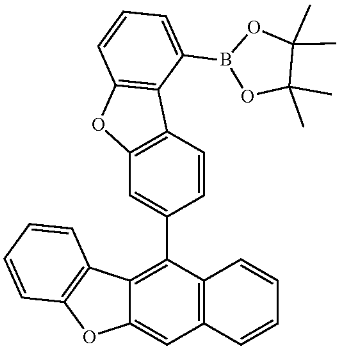
Sub 1-80
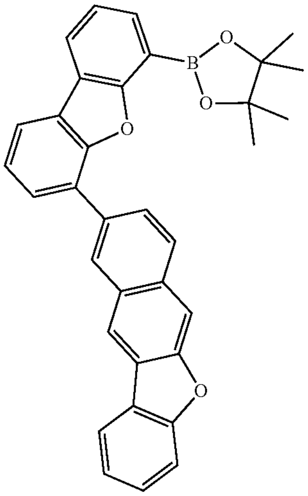
-continued
Sub 1-81
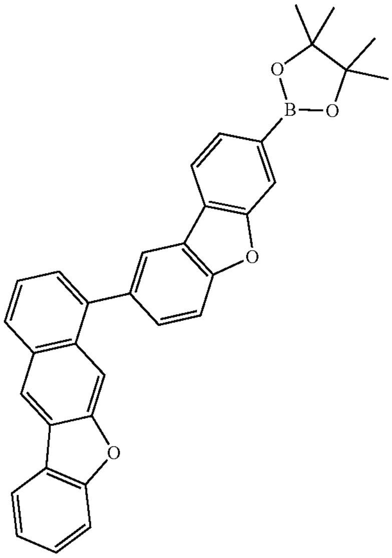
Sub 1-82
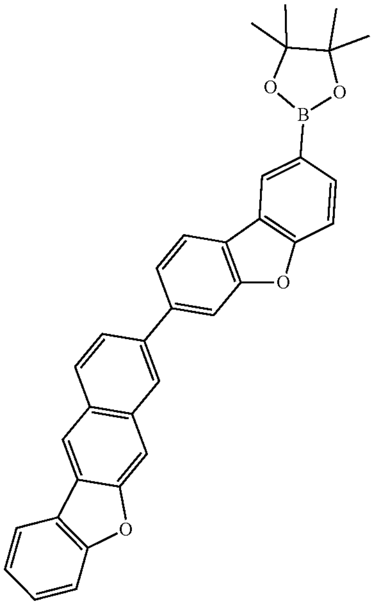
Sub 1-83
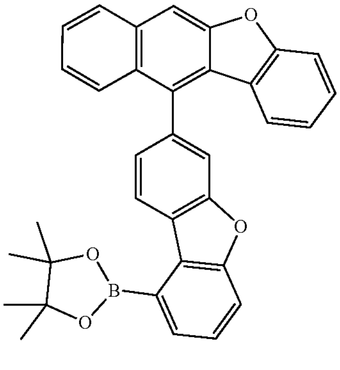

Sub 1-84
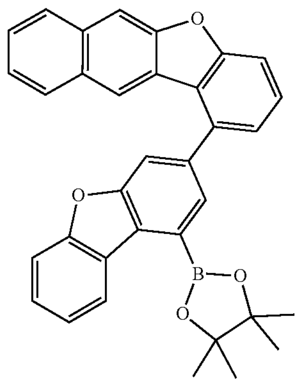
Sub 1-85
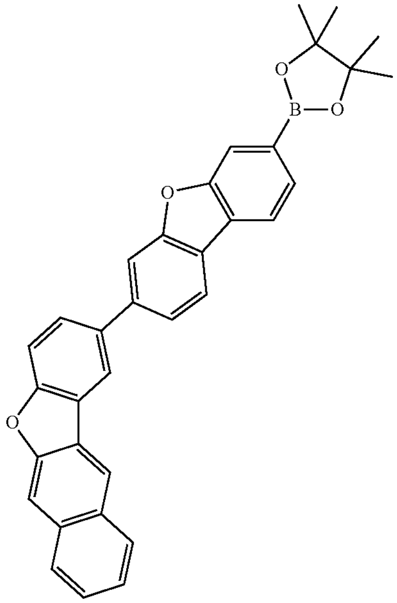
Sub 1-86
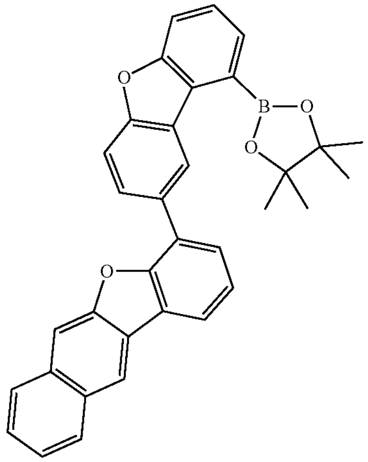
Sub 1-87
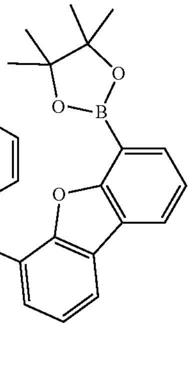
Sub 1-88
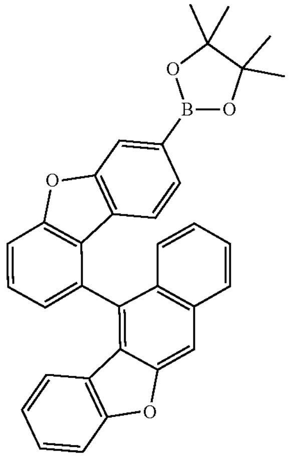
Sub 1-89
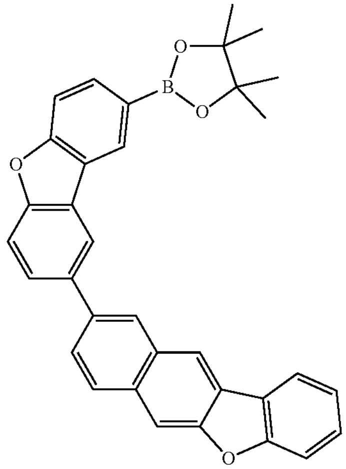

-continued
Sub 1-90
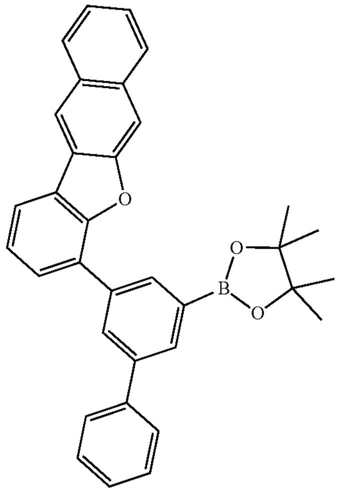
Sub 1-91
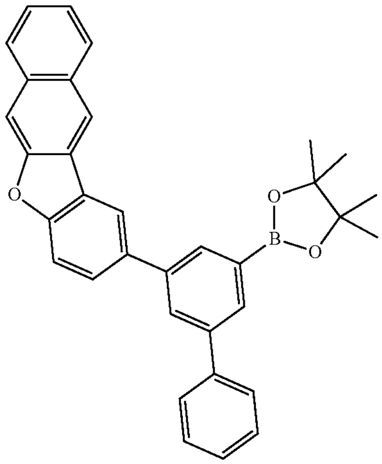
Sub 1-92
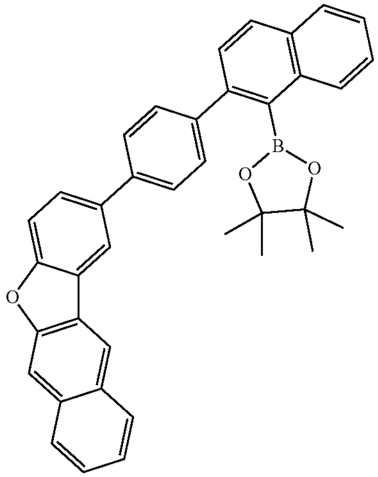
-continued
Sub 1-93
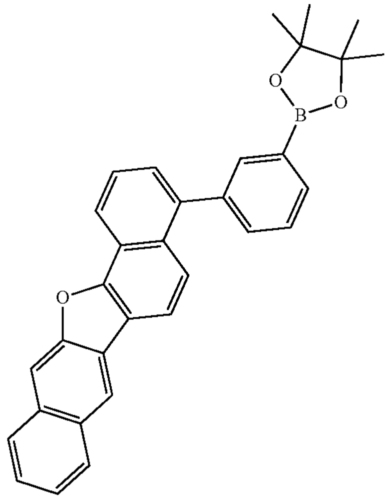
Sub 1-94
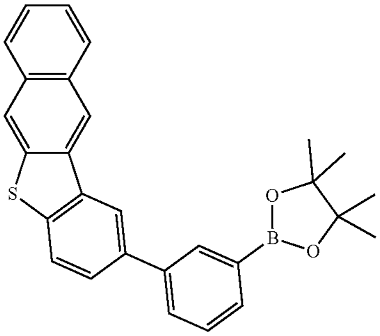
Sub 1-95
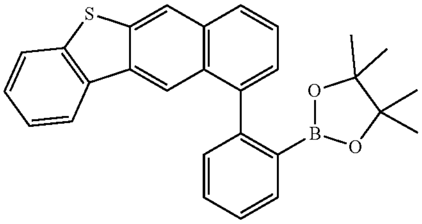
Sub 1-96
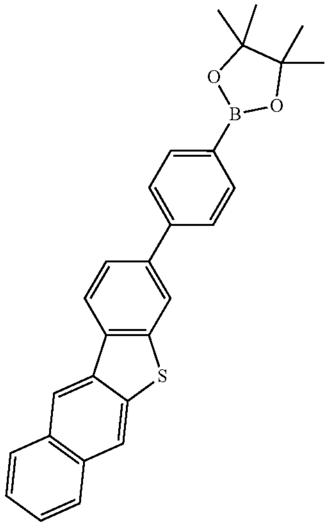

-continued
Sub 1-97
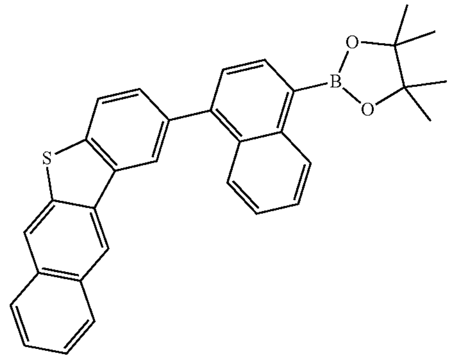
Sub 1-98
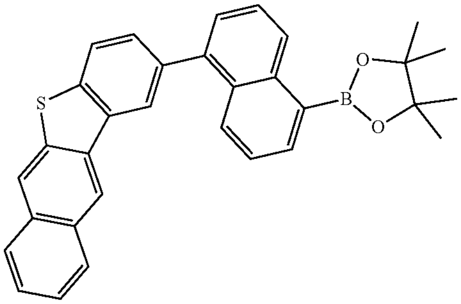
Sub 1-99
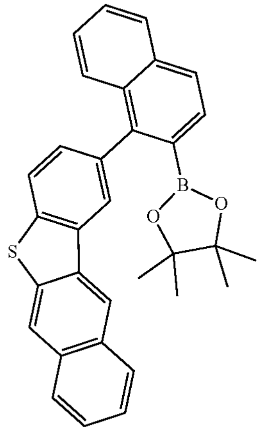
Sub 1-100
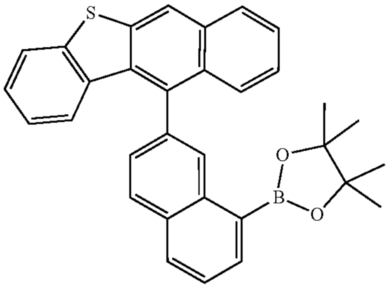
-continued
Sub 1-101
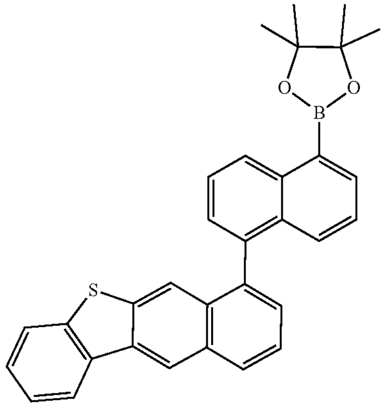
Sub 1-102
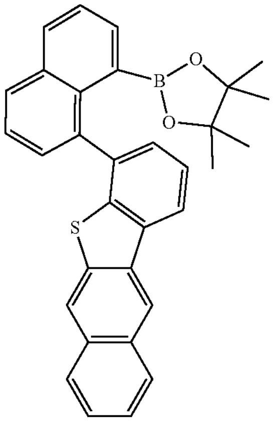
Sub 1-103
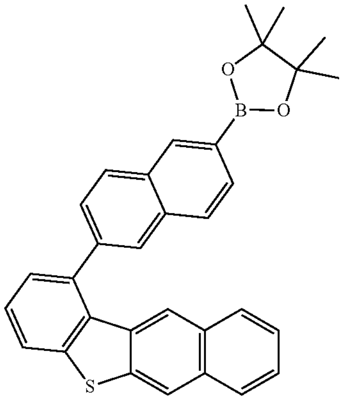

-continued
Sub 1-104
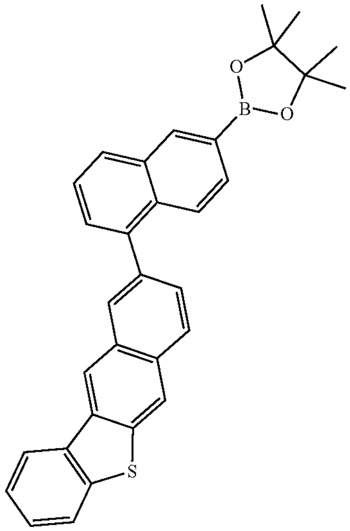
Sub 1-105
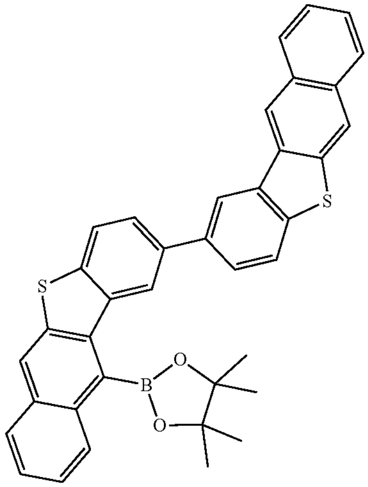
Sub 1-106
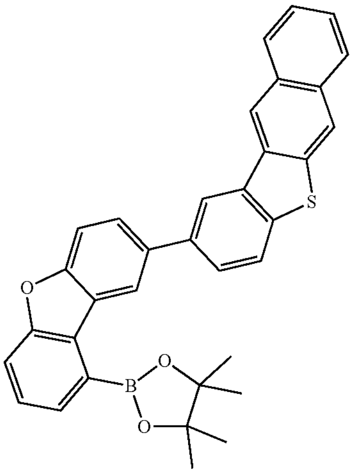
-continued
Sub 1-107
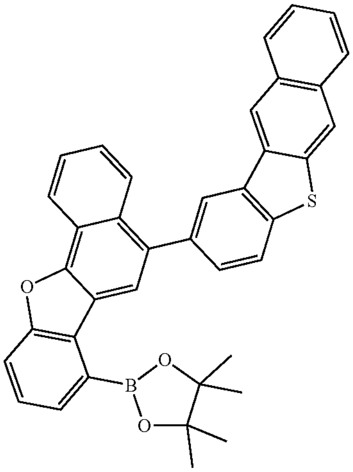
Sub 1-108
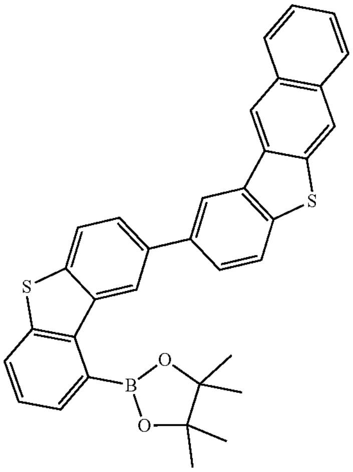
Sub 1-109
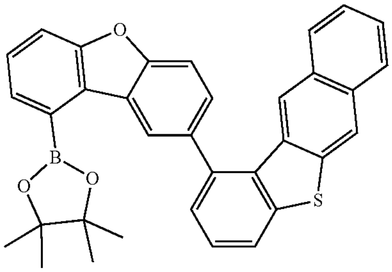
Sub 1-110
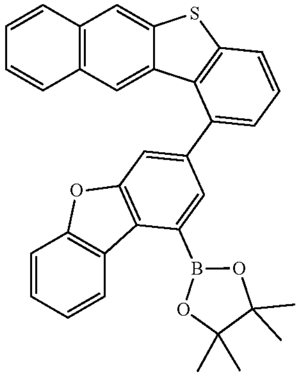

-continued
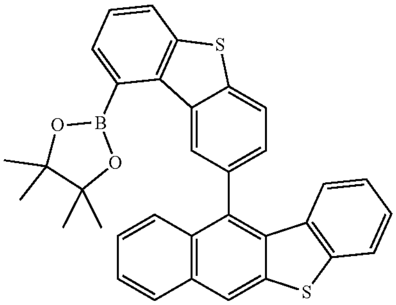
Sub 1-111
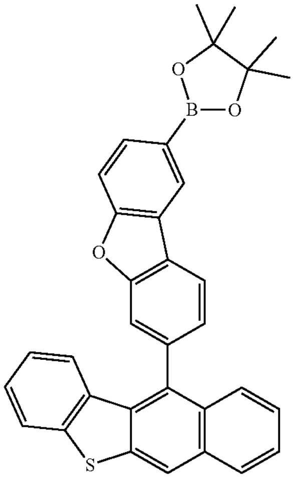
Sub 1-112
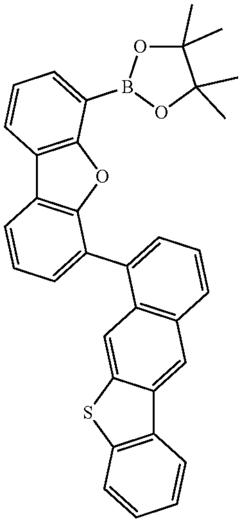
Sub 1-113
-continued
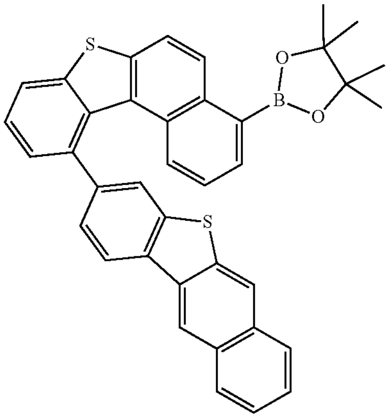
Sub 1-114
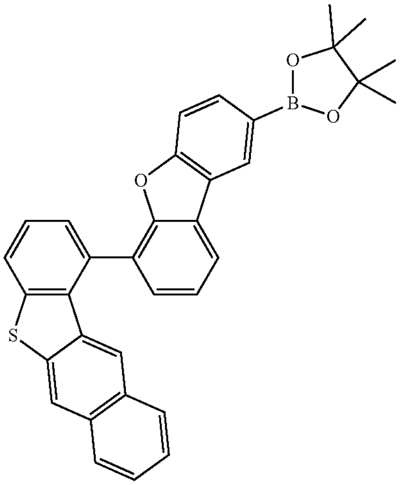
Sub 1-115
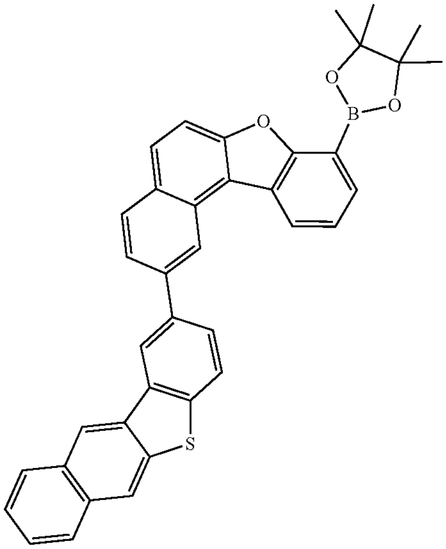
Sub 1-116

-continued

Sub 1-117

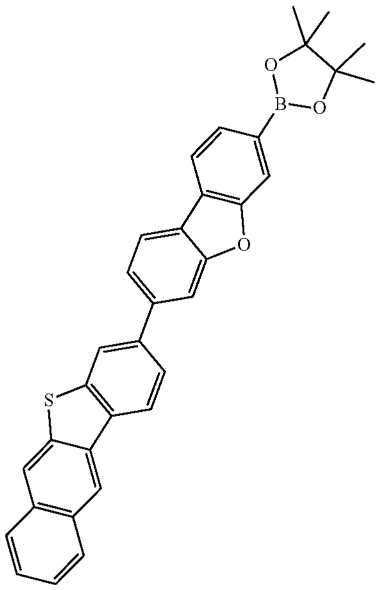

Sub 1-118

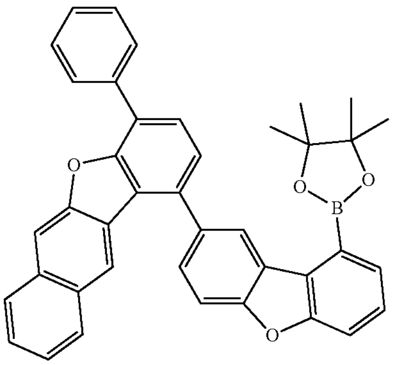

Sub 1-119

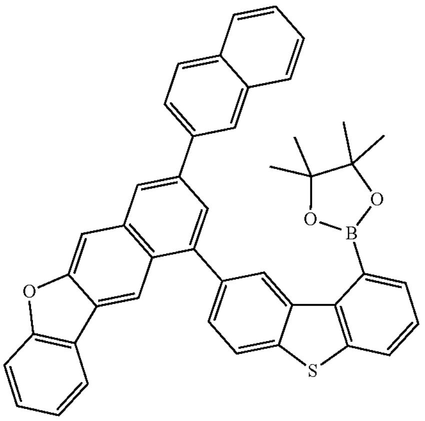

-continued

Sub 1-120

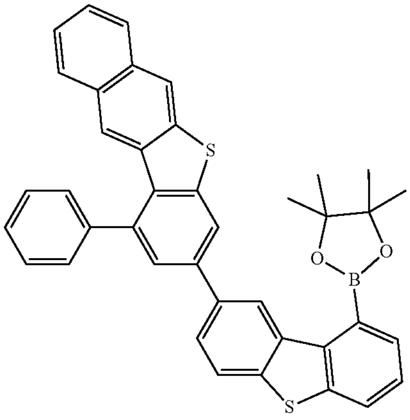

Sub 1-121

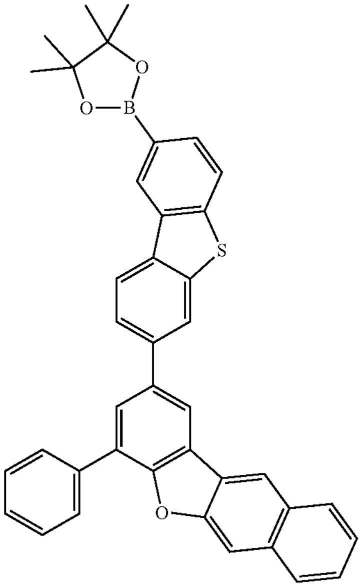

The FD-MS (Field Desorption-Mass Spectrometry) values of the above compounds belonging to Sub 1 are shown in the following Table 1.

TABLE 1

| compound | FD-MS |
|---|---|
| Sub 1-1 | m/z = 344.16($C_{22}H_{21}BO_3$ = 344.22) |
| Sub 1-2 | m/z = 344.16($C_{22}H_{21}BO_3$ = 344.22) |
| Sub 1-3 | m/z = 344.16($C_{22}H_{21}BO_3$ = 344.22) |
| Sub 1-4 | m/z = 344.16($C_{22}H_{21}BO_3$ = 344.22) |
| Sub 1-5 | m/z = 470.21($C_{32}H_{27}BO_3$ = 470.38) |
| Sub 1-6 | m/z = 344.16($C_{22}H_{21}BO_3$ = 344.22) |
| Sub 1-7 | m/z = 344.16($C_{22}H_{21}BO_3$ = 344.22) |
| Sub 1-8 | m/z = 344.16($C_{22}H_{21}BO_3$ = 344.22) |
| Sub 1-9 | m/z = 344.16($C_{22}H_{21}BO_3$ = 344.22) |
| Sub 1-10 | m/z = 344.16($C_{22}H_{21}BO_3$ = 344.22) |
| Sub 1-11 | m/z = 344.16($C_{22}H_{21}BO_3$ = 344.22) |
| Sub 1-12 | m/z = 520.22($C_{36}H_{29}BO_3$ = 520.44) |
| Sub 1-13 | m/z = 420.19($C_{28}H_{25}BO_3$ = 420.32) |
| Sub 1-14 | m/z = 436.17($C_{28}H_{25}BO_2S$ = 436.38) |
| Sub 1-15 | m/z = 360.14($C_{22}H_{21}BO_2S$ = 360.28) |
| Sub 1-16 | m/z = 360.14($C_{22}H_{21}BO_2S$ = 360.28) |
| Sub 1-17 | m/z = 360.14($C_{22}H_{21}BO_2S$ = 360.28) |
| Sub 1-18 | m/z = 360.14($C_{22}H_{21}BO_2S$ = 360.28) |
| Sub 1-28 | m/z = 496.22($C_{34}H_{29}BO_3$ = 496.41) |
| Sub 1-30 | m/z = 420.19($C_{28}H_{25}BO_3$ = 420.32) |
| Sub 1-36 | m/z = 470.21($C_{32}H_{27}BO_3$ = 470.38) |

TABLE 1-continued

| compound | FD-MS |
|---|---|
| Sub 1-66 | m/z = 510.2($C_{34}H_{27}BO_4$ = 510.4) |
| Sub 1-68 | m/z = 526.18($C_{34}H_{27}BO_3S$ = 526.46) |
| Sub 1-69 | m/z = 560.22($C_{38}H_{29}BO_4$ = 560.46) |
| Sub 1-70 | m/z = 576.19($C_{38}H_{29}BO_3S$ = 576.52) |
| Sub 1-90 | m/z = 496.22($C_{34}H_{29}BO_3$ = 496.41) |
| Sub 1-92 | m/z = 546.24($C_{38}H_{31}BO_3$ = 546.47) |
| Sub 1-93 | m/z = 470.21($C_{32}H_{27}BO_3$ = 470.38) |
| Sub 1-94 | m/z = 436.17($C_{28}H_{25}BO_2S$ = 436.38) |
| Sub 1-97 | m/z = 486.18($C_{32}H_{27}BO_2S$ = 486.44) |
| Sub 1-105 | m/z = 592.17($C_{38}H_{29}BO_2S_2$ = 592.58) |
| Sub 1-106 | m/z = 526.18($C_{34}H_{27}BO_3S$ = 526.46) |
| Sub 1-107 | m/z = 576.19($C_{38}H_{29}BO_3S$ = 576.52) |
| Sub 1-108 | m/z = 542.15($C_{34}H_{27}BO_2S_2$ = 542.52) |
| Sub 1-118 | m/z = 586.23($C_{40}H_{31}BO_4$ = 586.49) |
| Sub 1-119 | m/z = 652.22($C_{44}H_{33}BO_3S$ = 652.62) |
| Sub 1-120 | m/z = 618.19($C_{40}H_{31}BO_2S_2$ = 618.62) |
| Sub 1-121 | m/z = 602.21($C_{40}H_{31}BO_3S$ = 602.56) |

Sub 1 of the Reaction Scheme 1 can be synthesized according to the reaction route of the following Reaction Scheme 2, but there is no limitation thereto.

<Reaction Scheme 2>

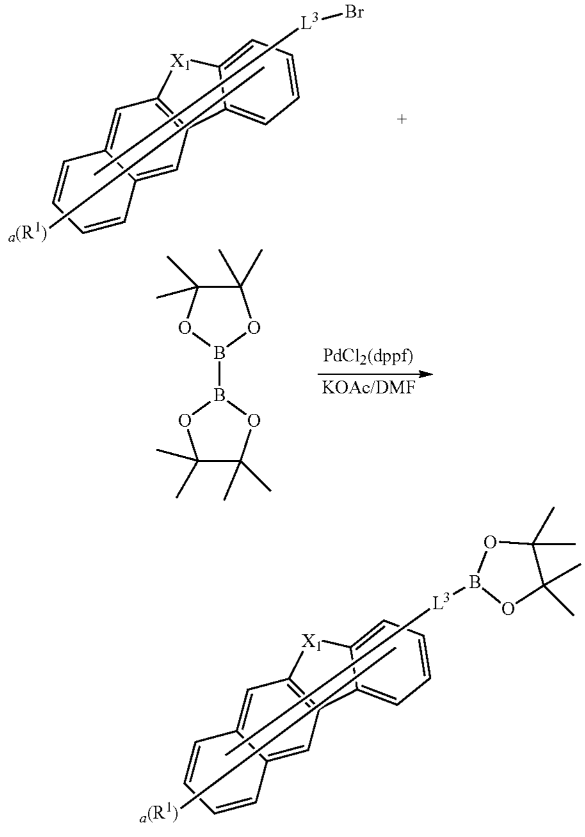

Sub 1

Synthesis Example of Sub 1-3

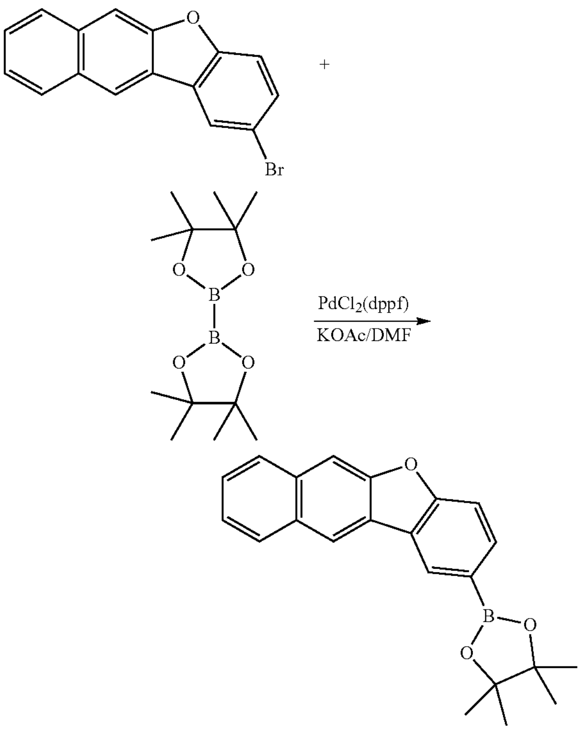

Sub 1-3

Bis(pinacolato)diboran (CAS Registry Number: 73183-34-3) (33.28 g, 131.04 mmol), $PdCl_2$(dppf) (2.92 g, 3.57 mmol), KOAc (35.07 g, 357.40 mmol) and DMF (596 ml) were added to 2-bromonaphtho[2,3-b]benzofuran (35.4 g, 119.13 mmol) and the mixture was stirred under reflux. When the reaction was completed, the reaction product was extracted with $CH_2Cl_2$ and water, and then the organic layer was dried with $MgSO_4$ and concentrated. Then, the concentrate was applied to silica gel column and recrystallized to obtain 34.86 g (yield: 85%) of the product.

Synthesis Example of Sub 1-21

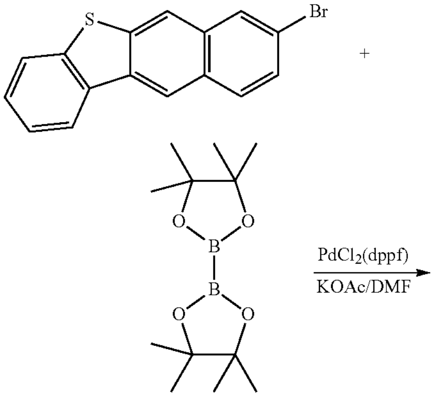

-continued

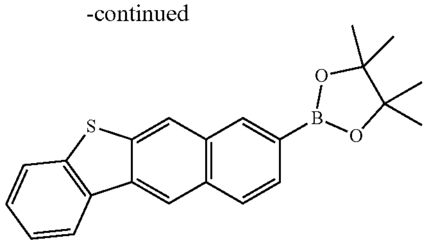

Sub 1-21

After bis(pinacolato)diboran (CAS Registry Number: 73183-34-3) (31.57 g, 124.33 mmol), $PdCl_2$(dppf) (2.77 g, 3.39 mmol), KOAc (33.28 g, 339.07 mmol) and DMF (565 ml) were added to 8-bromobenzo[b]naphtho[2,3-d]thiophene (35.40 g, 113.02 mmol), the reaction was carried out in the same manner as in the synthesis method of 1-3 to obtain 33.39 g (yield: 82%) of product.

Synthesis Example of Sub 1-37

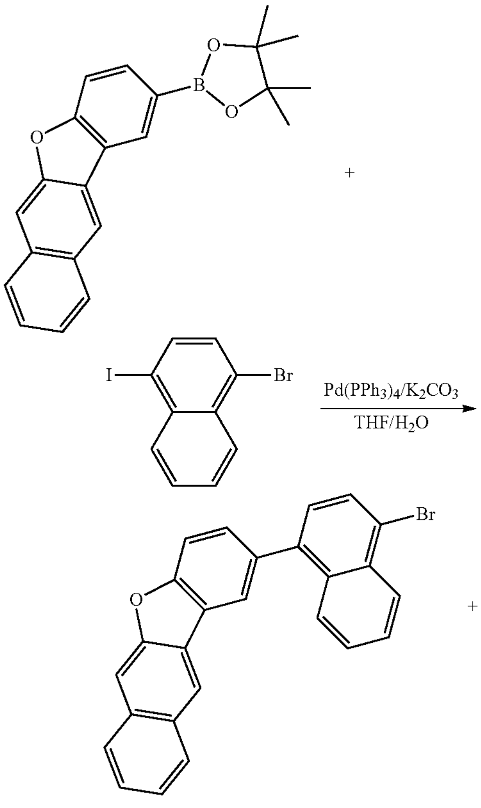

Sub 1-37a

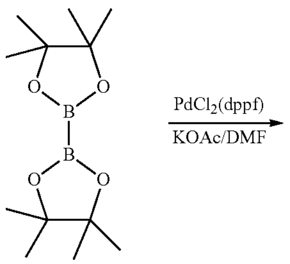

-continued

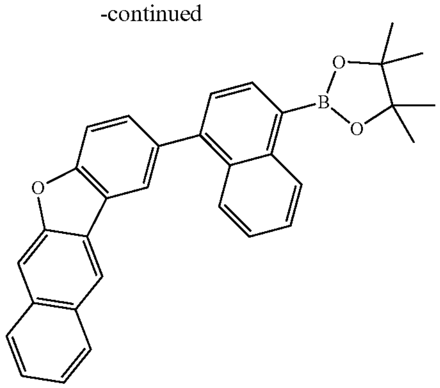

Sub 1-37

(1) Synthesis of Sub 1-37a 1-bromo-4-iodonaphthalene (69.65 g, 209.17 mmol), $Pd(PPh_3)_4$ (8.06 g, 6.97 mmol), $K_2CO_3$ (72.27 g, 522.92 mmol), THF (639 ml) and water (320 ml) were added to 4,4,5,5-tetramethyl-2-(naphtho[2,3-b]benzofuran-2-yl)-1,3,2-dioxaborolane (60 g, 174.31 mmol) and the mixture was stirred under reflux. When the reaction was completed, the reaction product was extracted with ether and water. Then the organic layer was concentrated, dried with $MgSO_4$ and concentrated. Finally, the concentrate was applied to silica gel column and recrystallized to obtain 45.01 g (yield: 61% of the product.

(2) Synthesis of Sub 1-37

After bis(pinacolato)diboran (CAS Registry Number: 73183-34-3) (29.70 g, 116.96 mmol), $PdCl_2$ (dppf) (2.60 g, 3.19 mmol), KOAc (31.31 g, 318.99 mmol) and DMF (532 ml) were added to Sub 1-37a (45.01 g, 106.33 mmol), the reaction was carried out in the same manner as in the synthesis method of 1-3 to obtain 39.01 g (yield: 78%) of product.

Synthesis Example of Sub 1-68

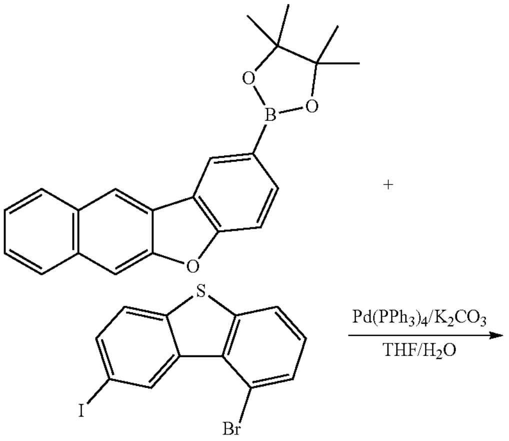

-continued

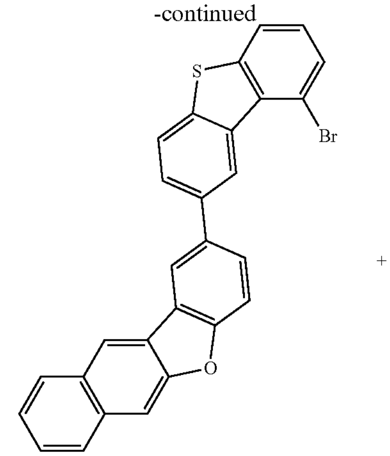

Sub 1-68a

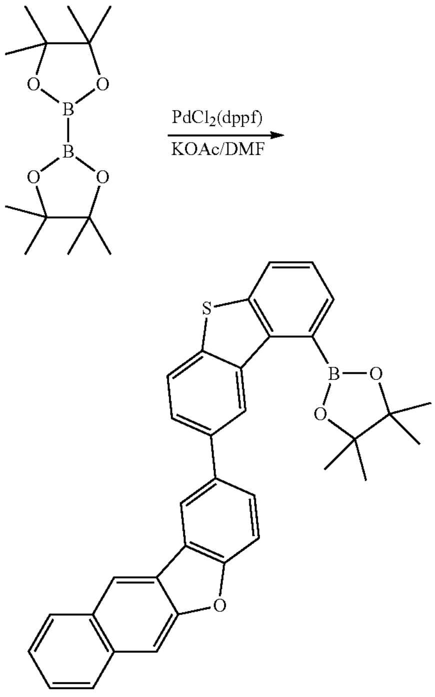

Sub 1-68

(1) Synthesis of Sub 1-68a After 1-bromo-8-iododibenzo[b,d]thiophene (81.38 g, 209.17 mmol), $Pd(PPh_3)_4$ (8.06 g, 6.97 mmol), $K_2CO_3$ (72.27 g, 522.92 mmol), THF (639 ml) and water (320 ml) were added to 4,4,5,5-tetramethyl-2-(naphtho[2,3-b]benzofuran-2-yl)-1,3,2-dioxaborolane (60 g, 174.31 mmol), the reaction was carried out in the same manner as in the synthesis method of Sub 1-37a to obtain 56.82 g (yield: 68%) of product.

(2) Synthesis of Sub 1-68

After bis(pinacolato)diboran (CAS Registry Number: 73183-34-3) (33.11 g, 130.38 mmol), $PdCl_2$ (dppf) (2.90 g, 3.56 mmol), KOAc (34.90 g, 355.58 mmol) and DMF (593 ml) were added to Sub 1-68a (56.82 g, 118.53 mmol), the reaction was carried out in the same manner as in the synthesis method of 1-3 to obtain 46.80 g (yield: 75%) of product.

Synthesis Example of Sub 1-98

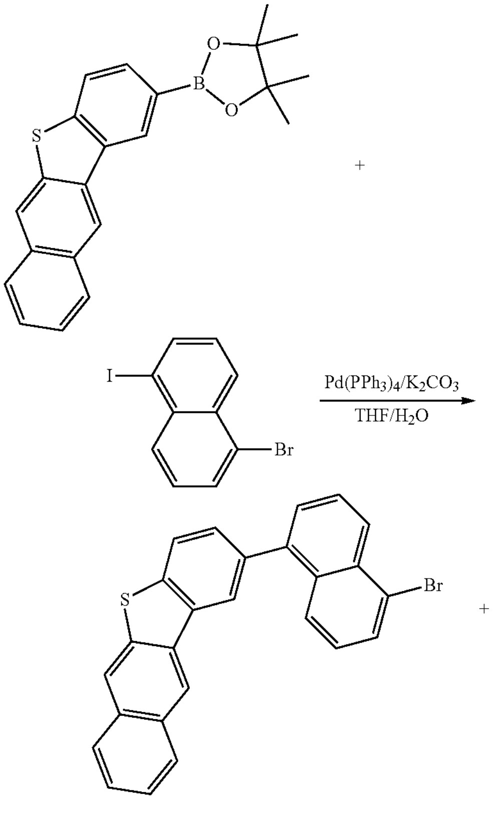

Sub 1-98a

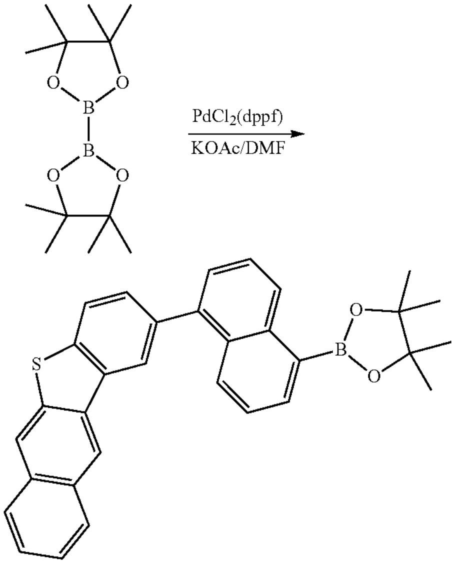

Sub 1-98

(1) Synthesis of Sub 1-98a

After 1-bromo-5-iodonaphthalene (66.54 g, 199.84 mmol), $Pd(PPh_3)_4$ (7.70 g, 6.66 mmol), $K_2CO_3$ (69.05 g, 499.61 mmol), THF (611 ml) and water (305 ml) were added to 2-(benzo[b]naphtho[2,3-d]thiophen-2-yl)-4,4,5,5-tetramethyl-1,3,2-dioxaborolane (60 g, 166.54 mmol), the reaction was carried out in the same manner as in the synthesis method of Sub 1-37a to obtain 46.83 g (yield: 64%) of product.

(2) Synthesis of Sub 1-98

After bis(pinacolato)diboran (CAS Registry Number: 73183-34-3) (29.77 g, 117.24 mmol), $PdCl_2$ (dppf) (2.61 g, 3.20 mmol), KOAc (31.38 g, 319.75 mmol) and DMF (533 ml) were added to 1-98a (46.83 g, 106.58 mmol), the reaction was carried out in the same manner as in the synthesis method of 1-3 to obtain 37.33 g (yield: 72%) of product.

Synthesis Example of Sub 1-111

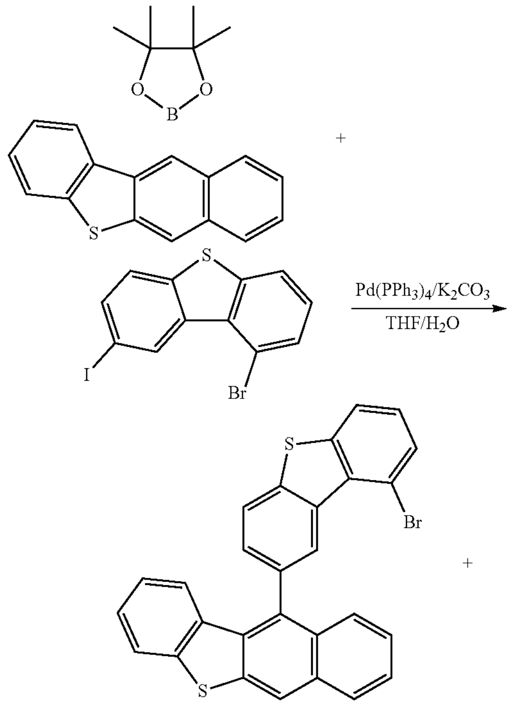

Sub 1-111a

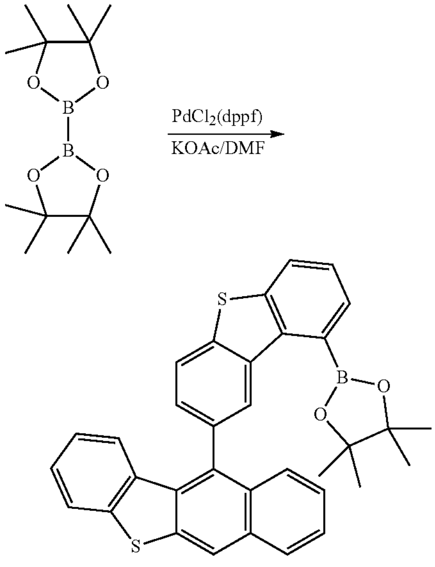

Sub 1-111

(1) Synthesis of Sub 1-111a

After 1-bromo-8-iododibenzo[b,d]thiophene (77.75 g, 199.84 mmol), $Pd(PPh_3)_4$ (7.70 g, 6.66 mmol), $K_2CO_3$ (69.05 g, 499.61 mmol), THF (611 ml) and water (305 ml) were added to 2-(benzo[b]naphtho[2,3-d]thiophen-11-yl)-4,4,5,5-tetramethyl-1,3,2-dioxaborolane (60 g, 166.54 mmol), the reaction was carried out in the same manner as in the synthesis method of Sub 1-37a to obtain 54.46 g (yield: 66%) of product.

(2) Synthesis of Sub 1-111

After bis(pinacolato)diboran (CAS Registry Number: 73183-34-3) (30.70 g, 120.91 mmol), $PdCl_2$ (dppf) (2.69 g, 3.30 mmol), KOAc (32.36 g, 329.76 mmol) and DMF (550 ml) were added to Sub 1-111a (54.46 g, 109.92 mmol), the reaction was carried out in the same manner as in the synthesis method of 1-3 to obtain 41.15 g (yield: 69%) of product.

2. Exemplary Compounds of Sub 2 and Synthesis Example

The compounds belonging to Sub 2 of Reaction Scheme 1 may be, but not limited to, the following compounds.

Sub 2-1

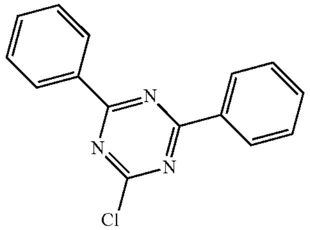

Sub 2-2

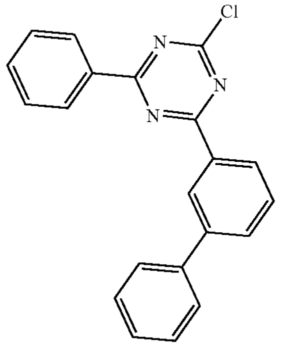

Sub 2-3

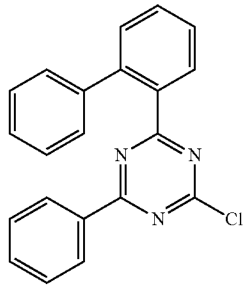

-continued
Sub 2-4
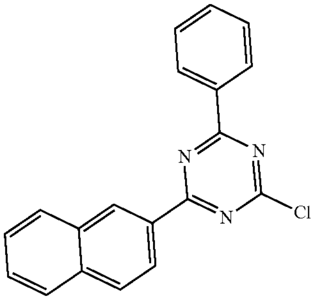
Sub 2-5
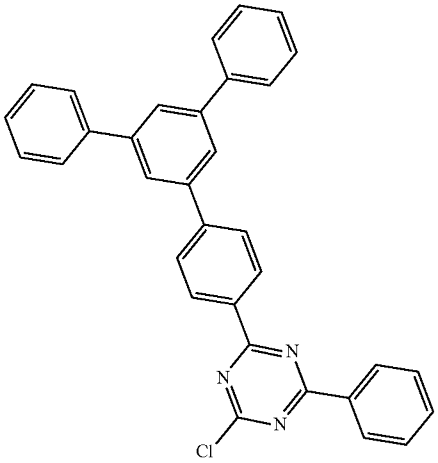
Sub 2-6
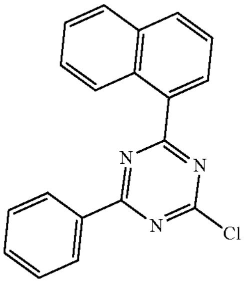
Sub 2-7
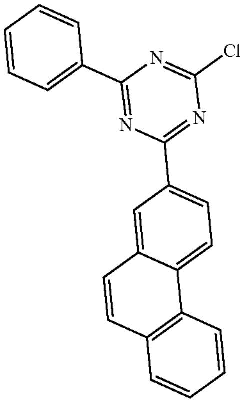
-continued
Sub 2-8
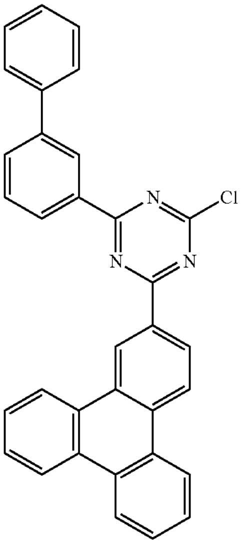
Sub 2-9
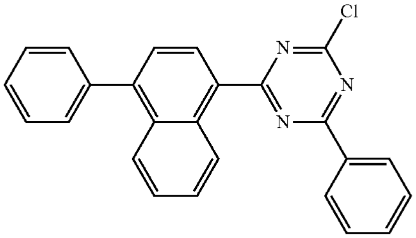
Sub 2-10
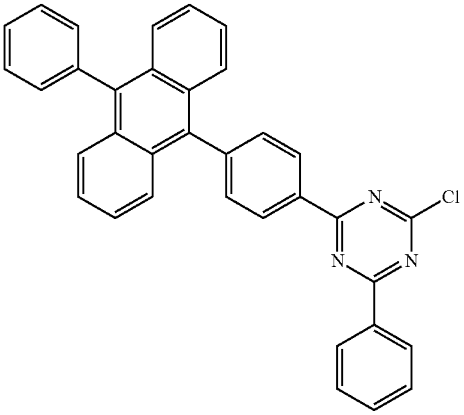

-continued
Sub 2-11
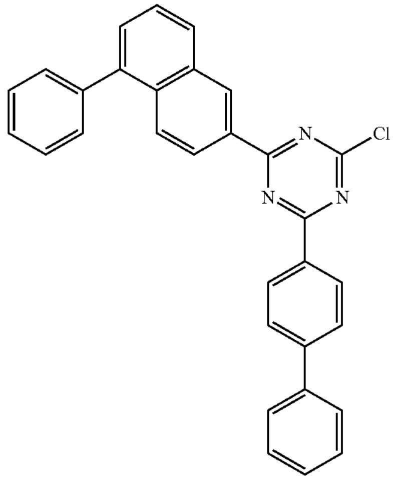
Sub 2-12
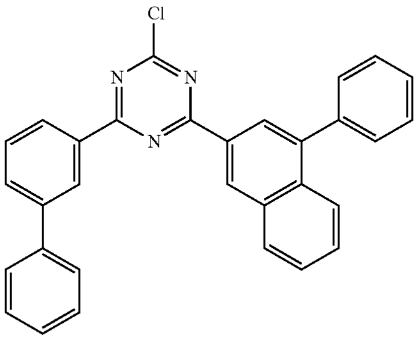
Sub 2-13
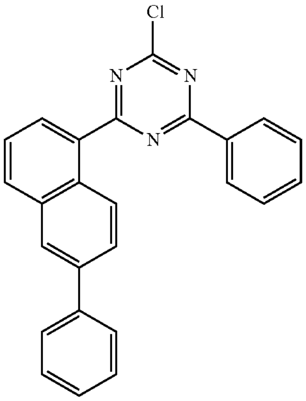
Sub 2-14
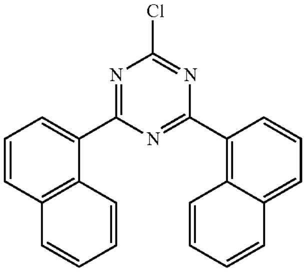
-continued
Sub 2-15
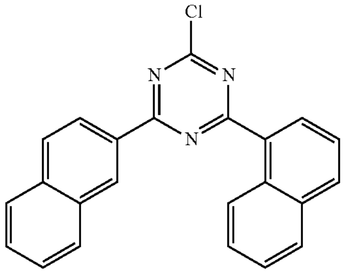
Sub 2-16
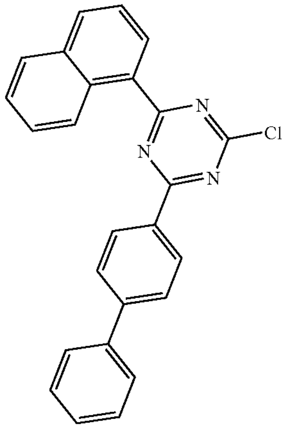
Sub 2-17
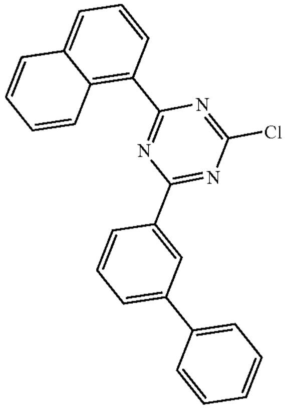
Sub 2-18
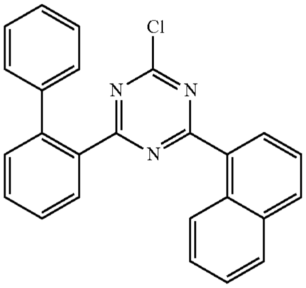

-continued
Sub 2-19
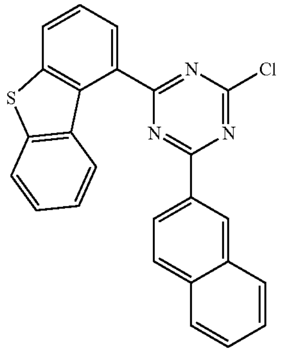
Sub 2-20
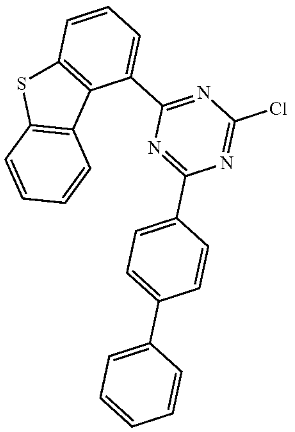
Sub 2-21
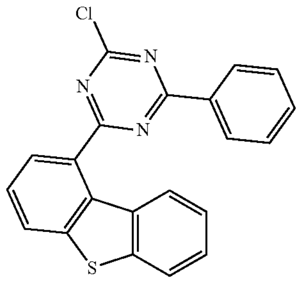
Sub 2-22
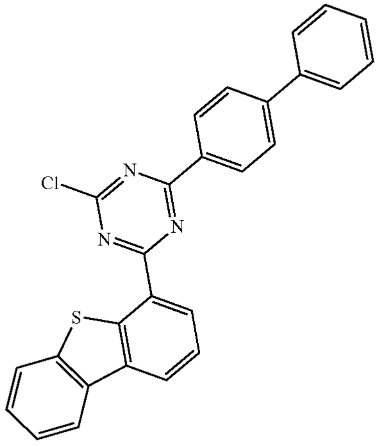
-continued
Sub 2-23
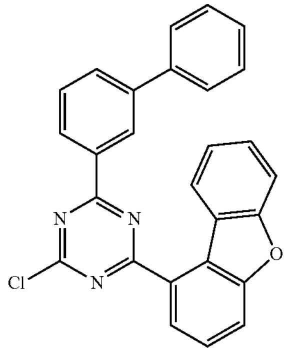
Sub 2-24
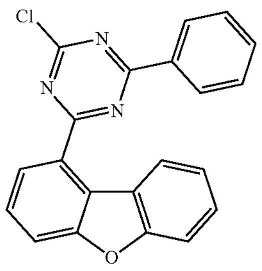
Sub 2-25
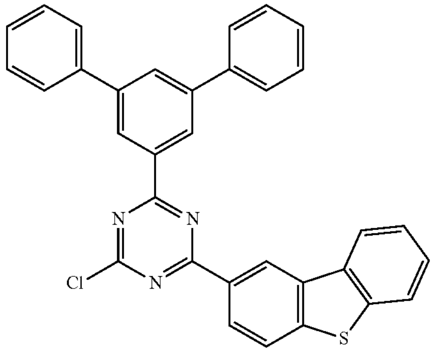
Sub 2-26
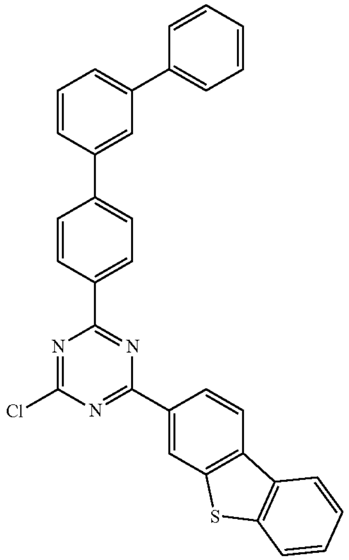

-continued
Sub 2-27
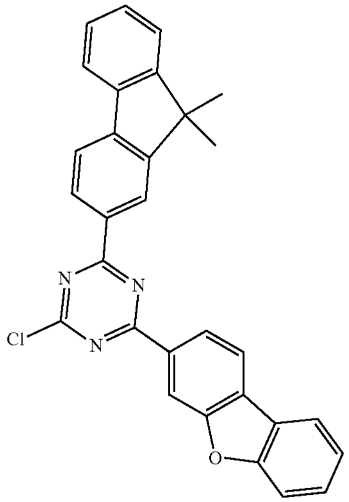
Sub 2-28
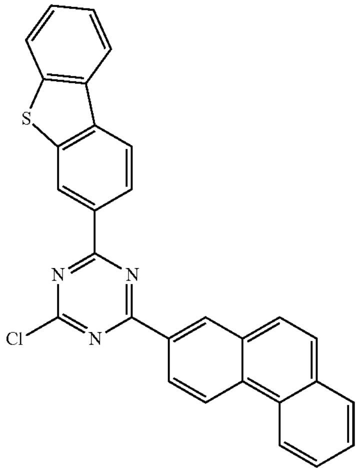
Sub 2-29
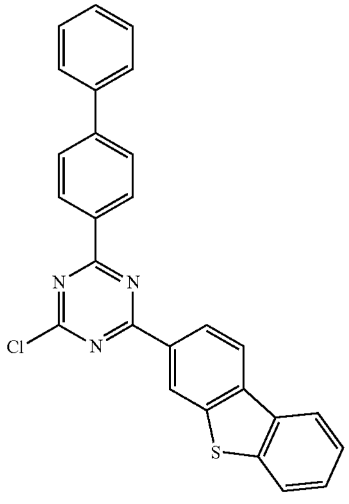
-continued
Sub 2-30
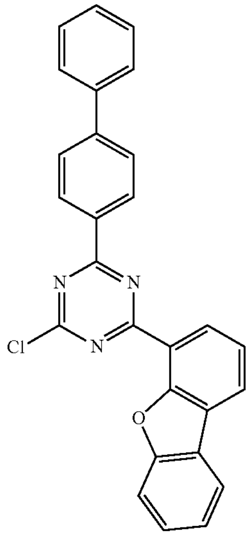
Sub 2-31
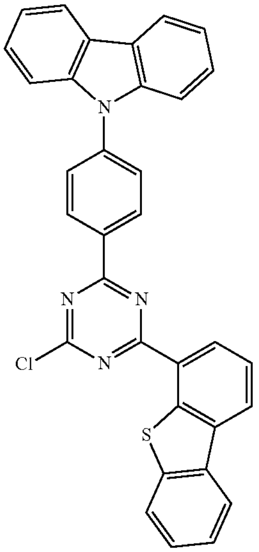
Sub 2-32
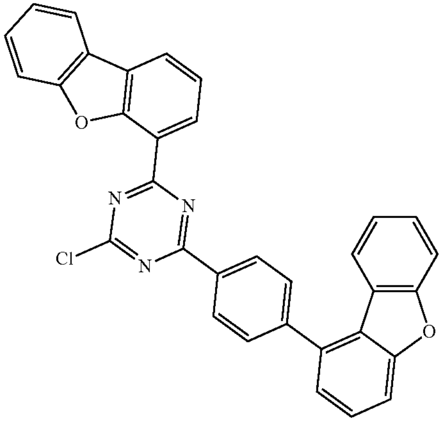

-continued
Sub 2-33
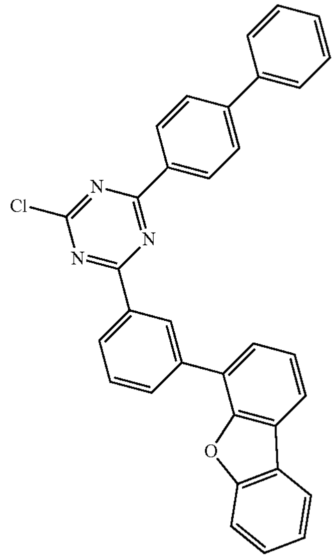
Sub 2-34
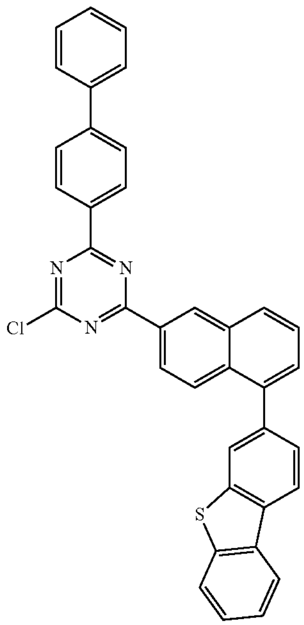
Sub 2-35
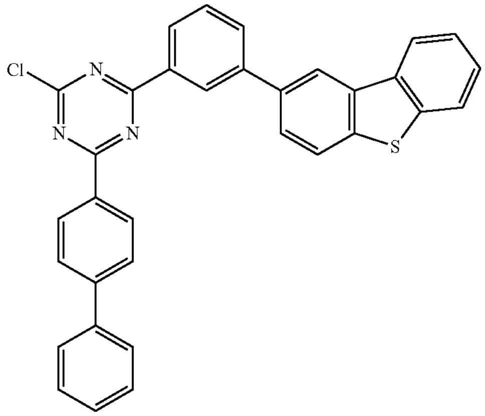
-continued
Sub 2-36
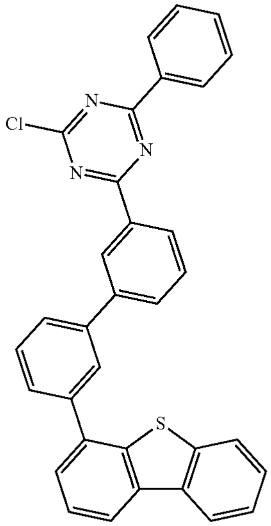
Sub 2-37
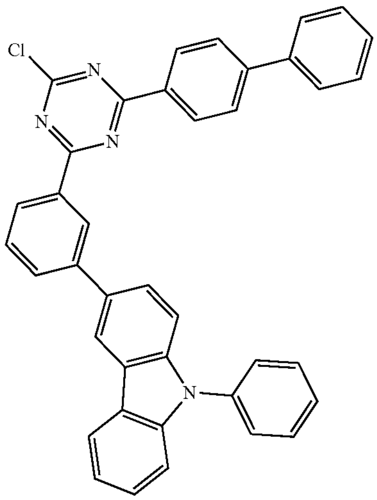
Sub 2-38
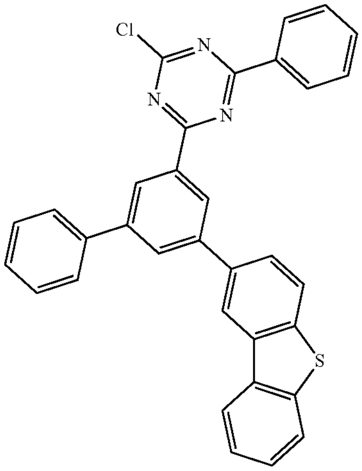

-continued
Sub 2-39
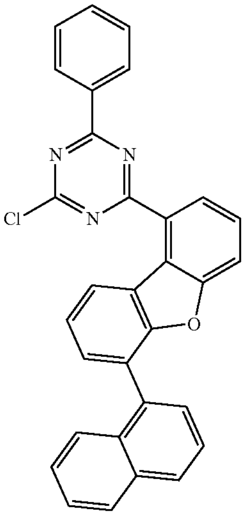
Sub 2-40
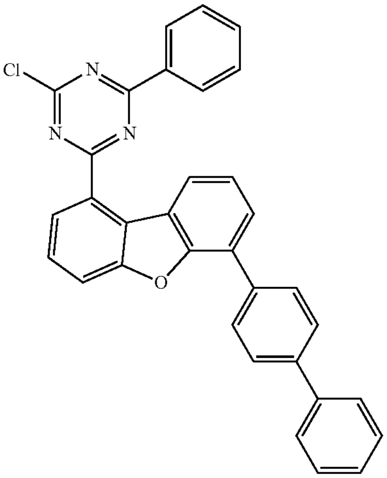
Sub 2-41
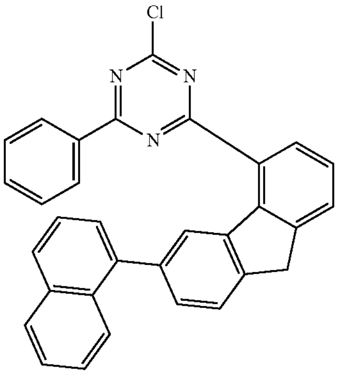
-continued
Sub 2-42
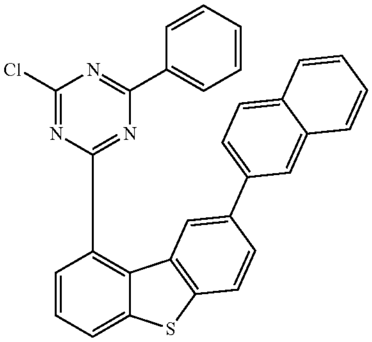
Sub 2-43
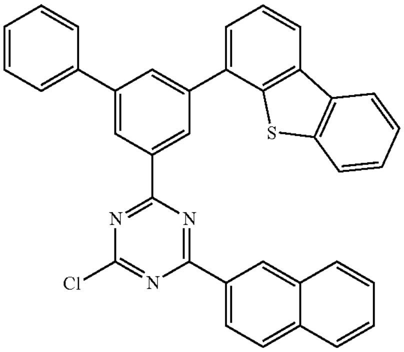
Sub 2-44
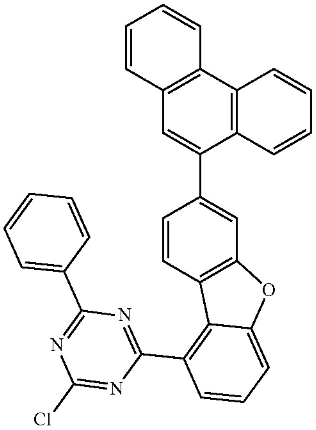
Sub 2-45
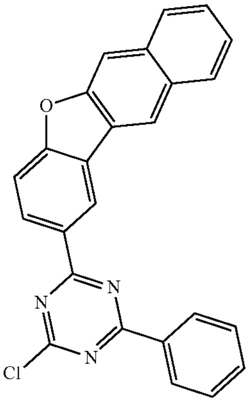

-continued
Sub 2-46
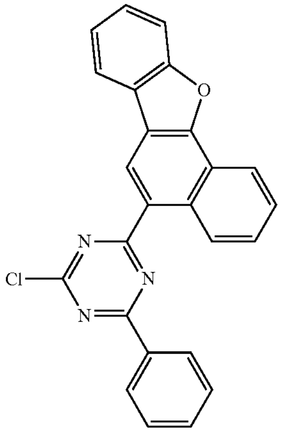
Sub 2-47
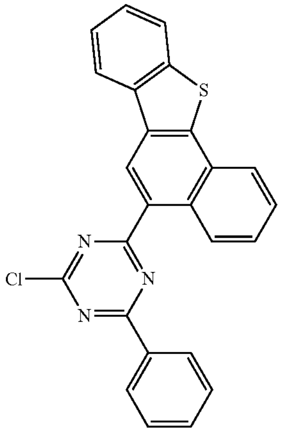
Sub 2-48
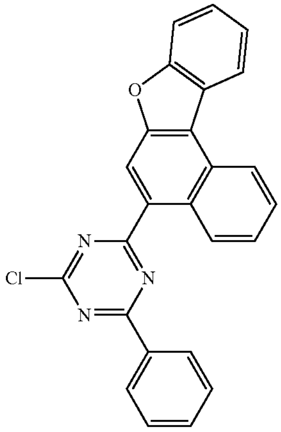
-continued
Sub 2-49
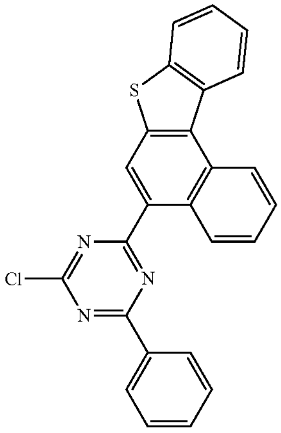
Sub 2-50
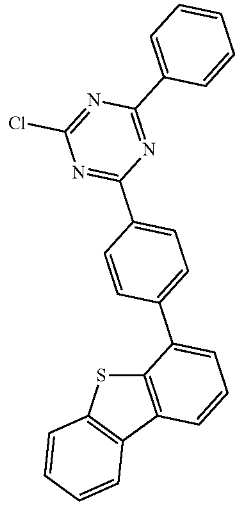
Sub 2-51
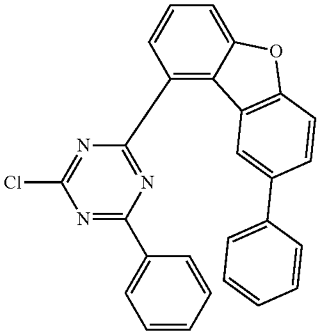

-continued
Sub 2-52
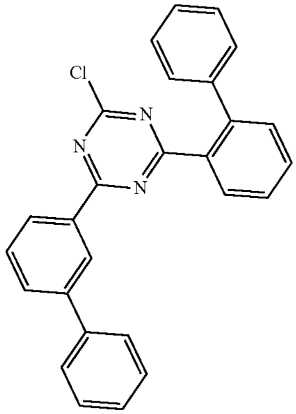
Sub 2-53
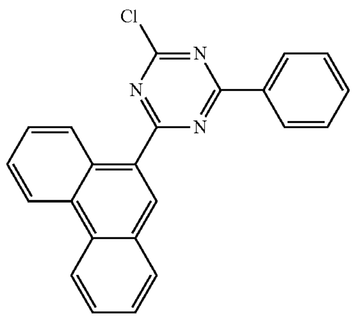
Sub 2-54
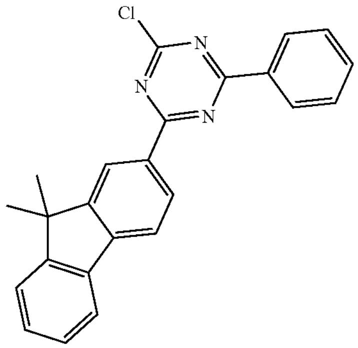
Sub 2-55
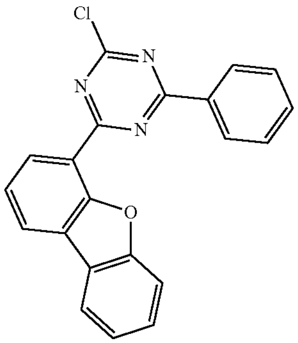
-continued
Sub 2-56
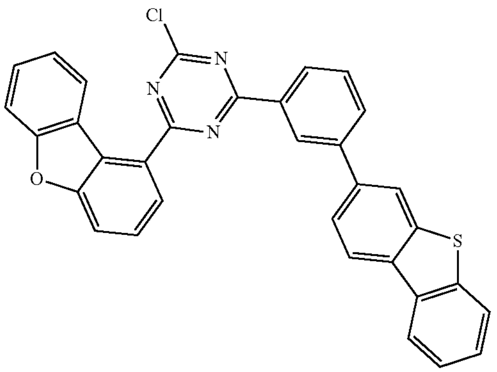
Sub 2-57
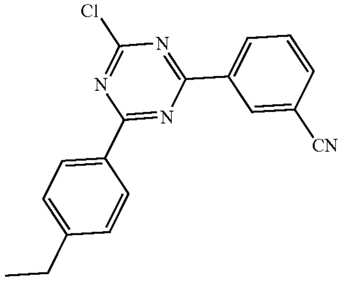
Sub 2-58
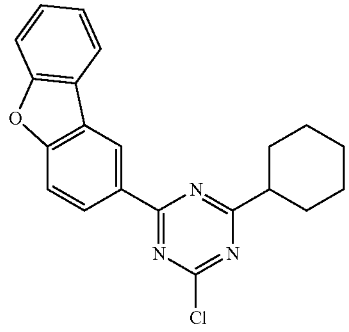
Sub 2-59
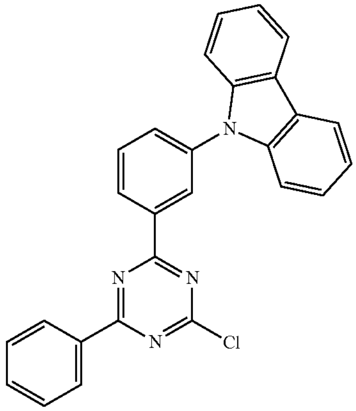

-continued
Sub 2-60
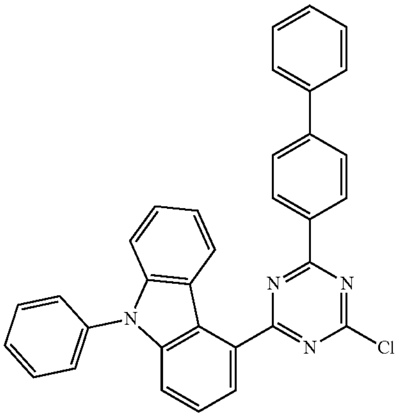
Sub 2-61
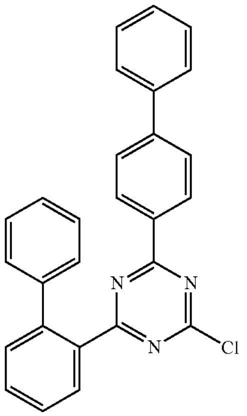
Sub 2-62
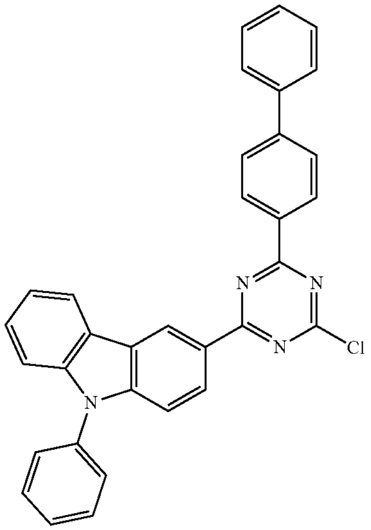
-continued
Sub 2-63
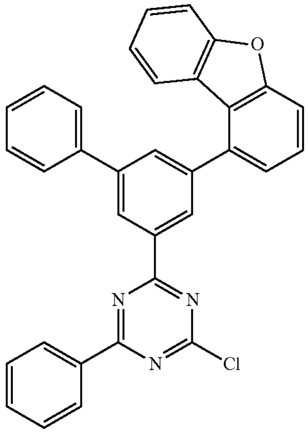
Sub 2-64
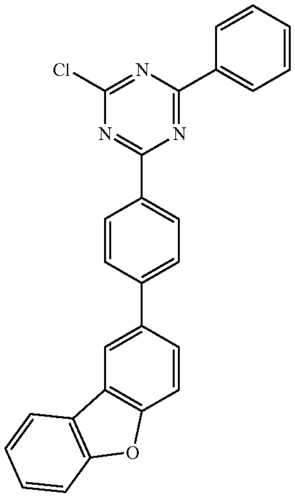
Sub 2-65
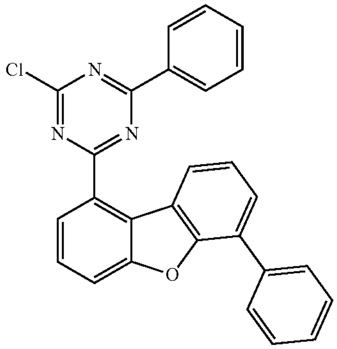

-continued
Sub 2-66
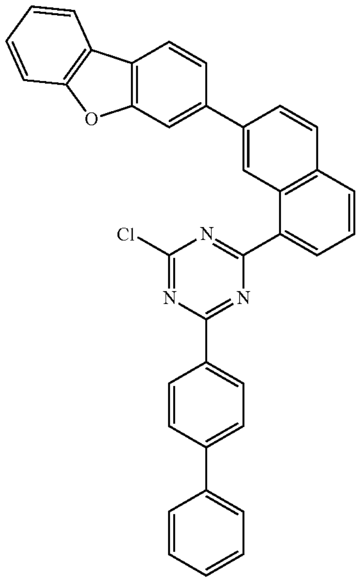
Sub 2-67
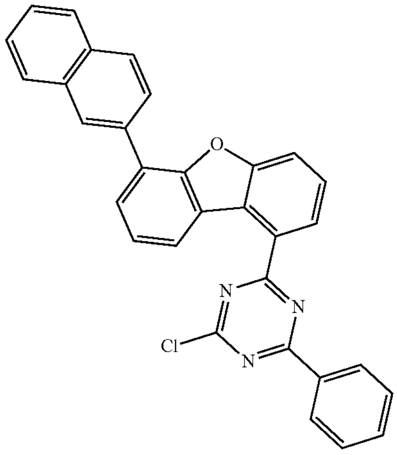
Sub 2-68
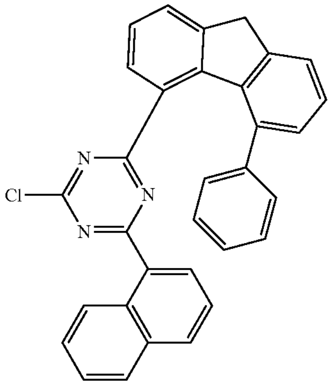
-continued
Sub 2-69
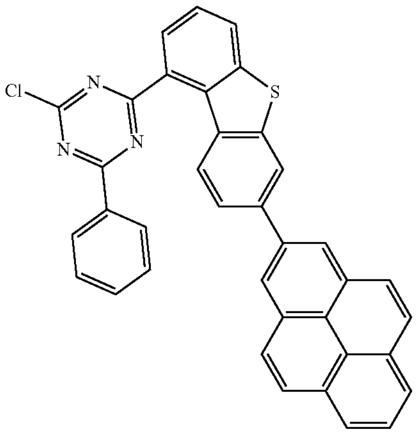
Sub 2-70
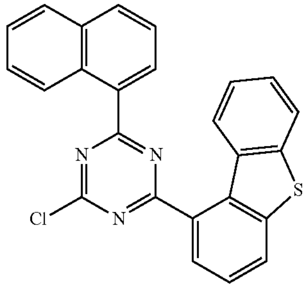
Sub 2-71
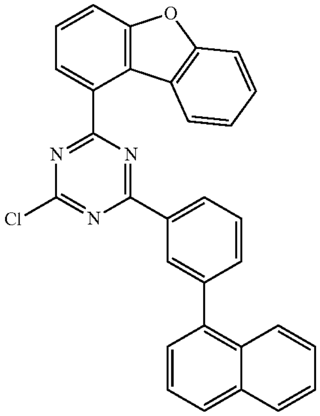
Sub 2-72
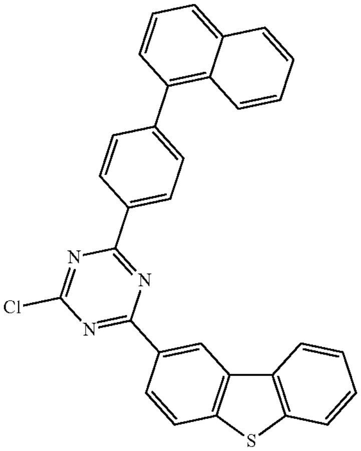

-continued
Sub 2-73
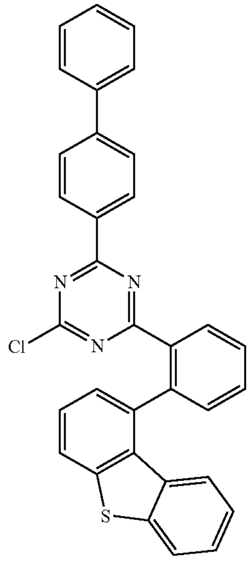
Sub 2-74
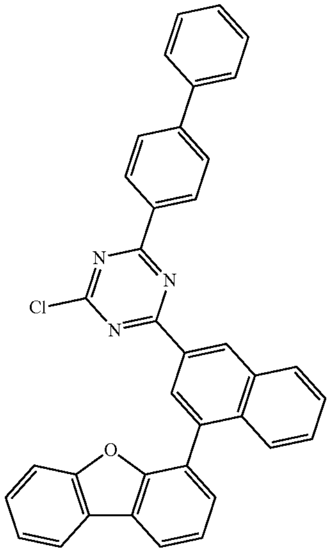
Sub 2-75
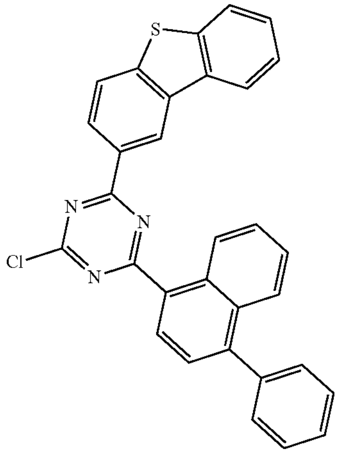
-continued
Sub 2-76
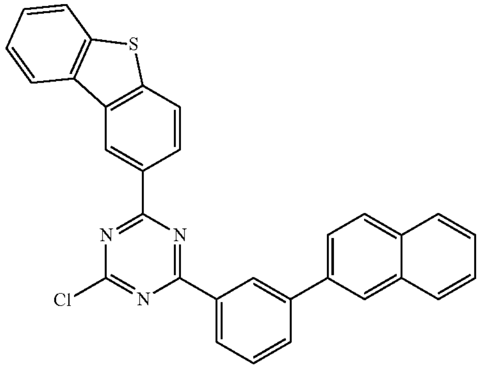
Sub 2-77
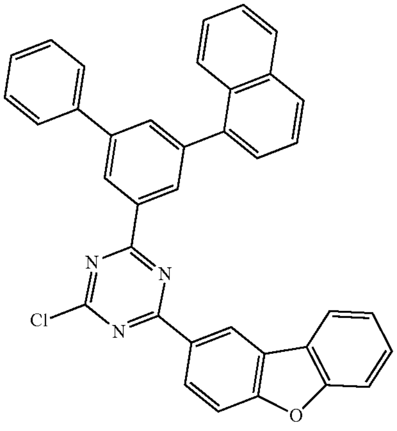
Sub 2-78
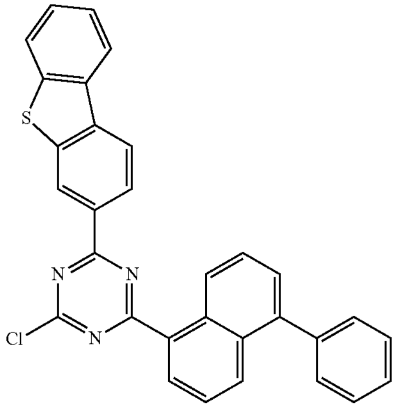

-continued
Sub 2-79
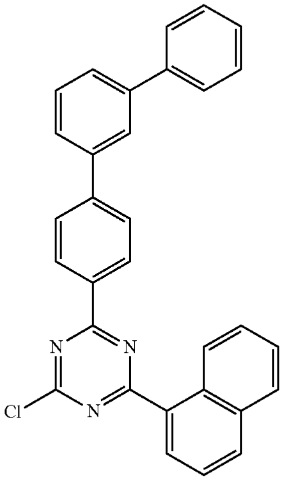
Sub 2-80
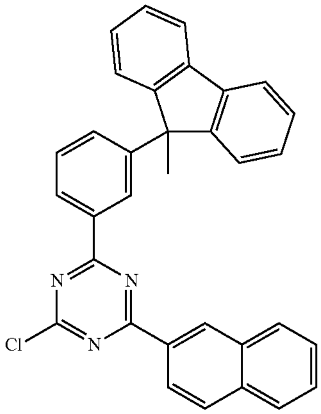
Sub 2-81
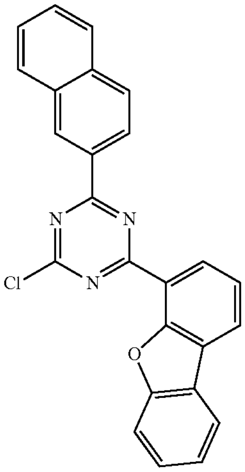
-continued
Sub 2-82
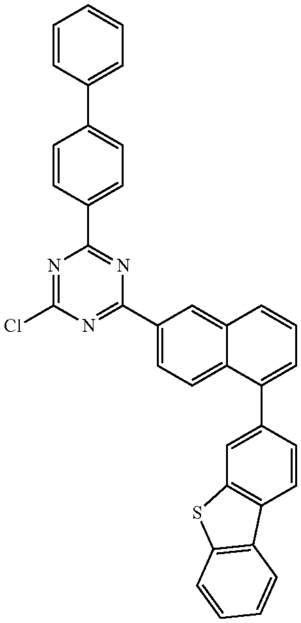
Sub 2-83
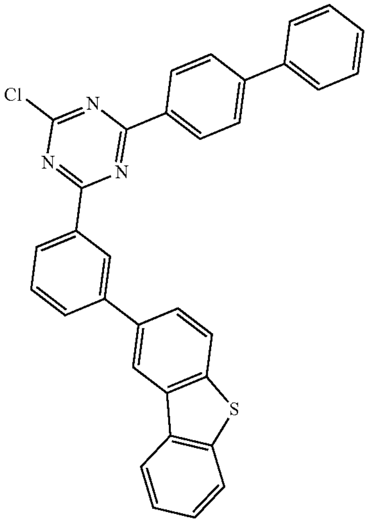

Sub 2-84
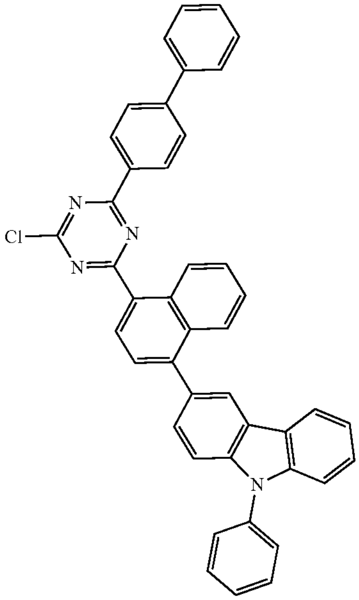
Sub 2-85
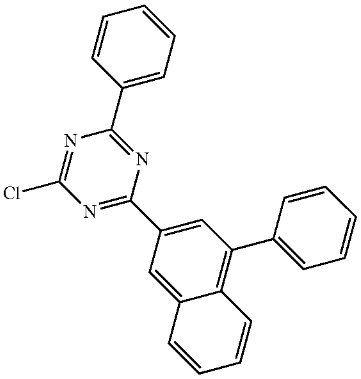
Sub 2-86
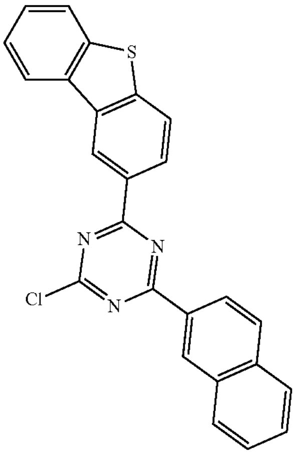
Sub 2-87
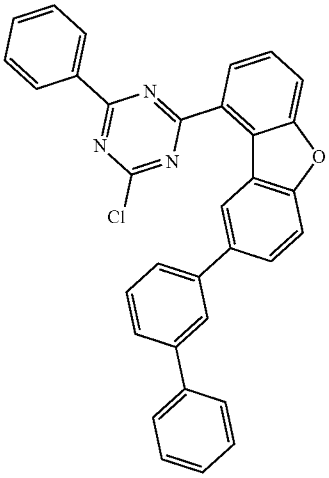
Sub 2-88
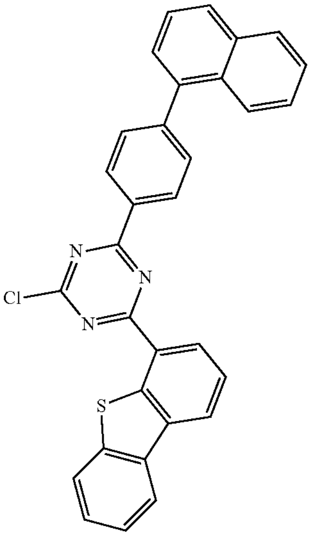
Sub 2-89
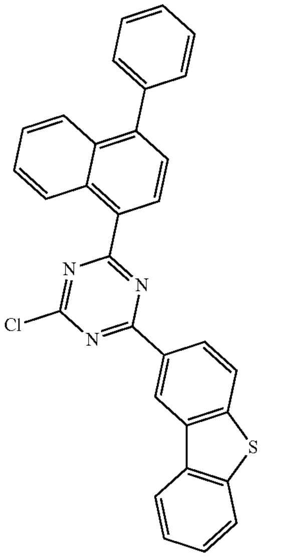

-continued
Sub 2-90
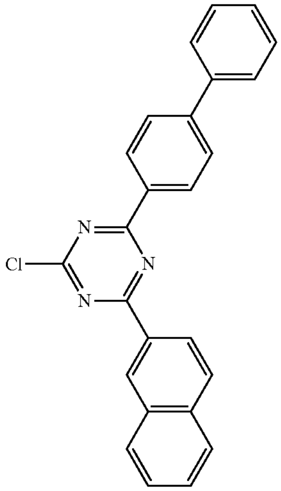
Sub 2-91
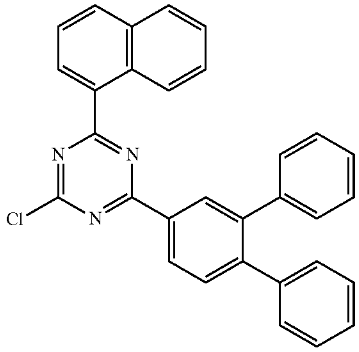
Sub 2-92
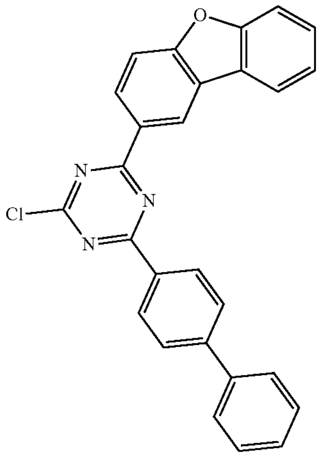
-continued
Sub 2-93
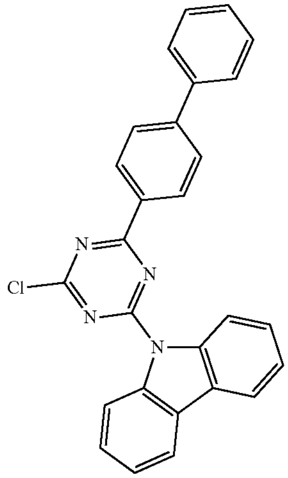
Sub 2-94
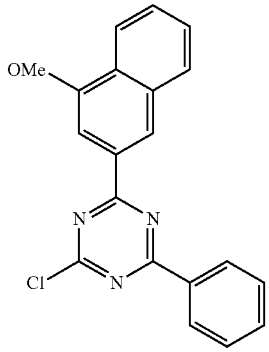
Sub 2-95
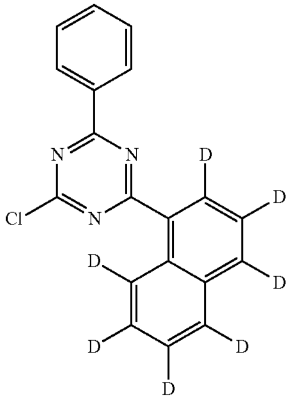
Sub 2-96
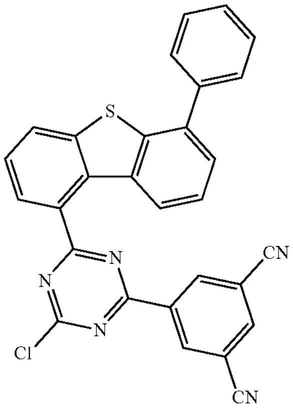

-continued
Sub 2-97
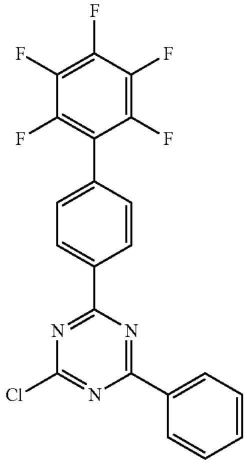
Sub 2-98
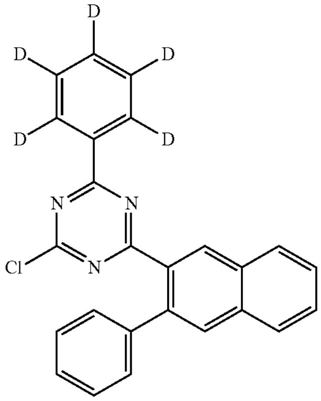
Sub 2-99
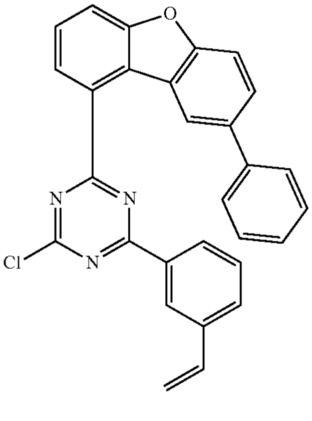
-continued
Sub 2-100
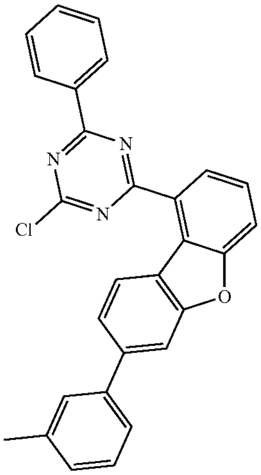
Sub 2-101
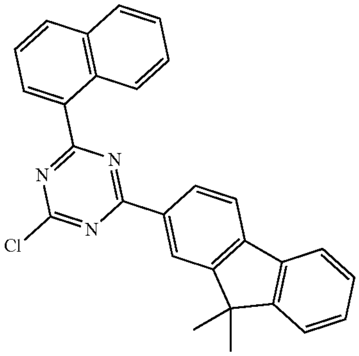
Sub 2-102
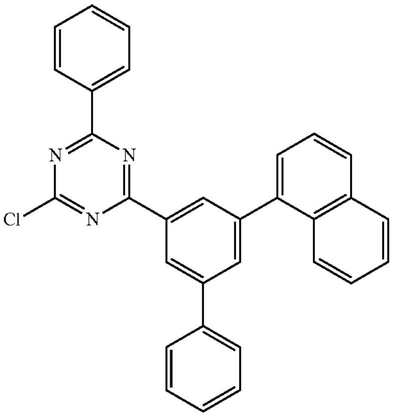

-continued

Sub 2-103

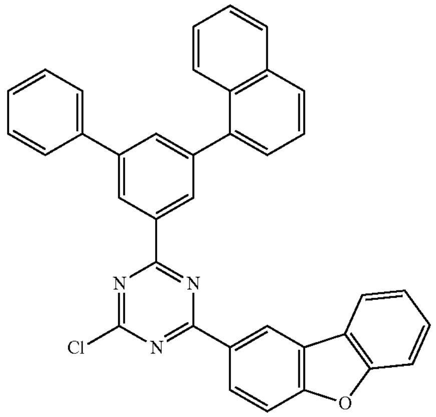

The FD-MS values of the above compounds belonging to Sub 2 are shown in the following Table 2.

TABLE 2

| compound | FD-MS |
|---|---|
| Sub 2-1 | m/z = 267.06($C_{15}H_{10}ClN_3$ = 267.72) |
| Sub 2-2 | m/z = 343.09($C_{21}H_{14}ClN_3$ = 343.81) |
| Sub 2-4 | m/z = 317.07($C_{19}H_{12}ClN_3$ = 317.78) |
| Sub 2-5 | m/z = 495.15($C_{33}H_{22}ClN_3$ = 496.01) |
| Sub 2-7 | m/z = 367.09($C_{23}H_{14}ClN_3$ = 367.84) |
| Sub 2-8 | m/z = 493.13($C_{33}H_{20}ClN_3$ = 493.99) |
| Sub 2-9 | m/z = 393.1($C_{25}H_{16}ClN_3$ = 393.87) |
| Sub 2-10 | m/z = 519.15($C_{35}H_{22}ClN_3$ = 520.03) |
| Sub 2-11 | m/z = 469.13($C_{31}H_{20}ClN_3$ = 469.97) |
| Sub 2-12 | m/z = 393.1($C_{25}H_{16}ClN_3$ = 393.87) |
| Sub 2-14 | m/z = 367.09($C_{23}H_{14}ClN_3$ = 367.84) |
| Sub 2-19 | m/z = 423.06($C_{25}H_{14}ClN_3S$ = 423.92) |
| Sub 2-20 | m/z = 449.08($C_{27}H_{16}ClN_3S$ = 449.96) |
| Sub 2-21 | m/z = 373.04($C_{21}H_{12}ClN_3S$ = 373.86) |
| Sub 2-22 | m/z = 433.1($C_{27}H_{16}ClN_3O$ = 433.9) |
| Sub 2-24 | m/z = 357.07($C_{21}H_{12}ClN_3O$ = 357.8) |
| Sub 2-25 | m/z = 525.11($C_{33}H_{20}ClN_3S$ = 526.05) |
| Sub 2-27 | m/z = 473.13($C_{30}H_{20}ClN_3O$ = 473.96) |
| Sub 2-28 | m/z = 473.08($C_{29}H_{16}ClN_3S$ = 473.98) |
| Sub 2-31 | m/z = 538.1($C_{33}H_{19}ClN_4S$ = 539.05) |
| Sub 2-32 | m/z = 523.11($C_{33}H_{18}ClN_3O_2$ = 523.98) |
| Sub 2-33 | m/z = 509.13($C_{33}H_{20}ClN_3O$ = 509.99) |
| Sub 2-34 | m/z = 575.12($C_{37}H_{22}ClN_3S$ = 576.11) |
| Sub 2-37 | m/z = 584.18($C_{39}H_{25}ClN_4$ = 585.11) |
| Sub 2-39 | m/z = 483.11($C_{31}H_{18}ClN_3O$ = 483.96) |
| Sub 2-40 | m/z = 509.13($C_{33}H_{20}ClN_3O$ = 509.99) |
| Sub 2-42 | m/z = 499.09($C_{31}H_{18}ClN_3S$ = 500.02) |
| Sub 2-43 | m/z = 575.12($C_{37}H_{22}ClN_3S$ = 576.11) |
| Sub 2-44 | m/z = 533.13($C_{35}H_{20}ClN_3O$ = 534.02) |
| Sub 2-45 | m/z = 407.08($C_{25}H_{14}ClN_3O$ = 407.86) |
| Sub 2-47 | m/z = 423.06($C_{25}H_{14}ClN_3S$ = 423.92) |
| Sub 2-50 | m/z = 449.08($C_{27}H_{16}ClN_3S$ = 449.96) |
| Sub 2-51 | m/z = 433.1($C_{27}H_{16}ClN_3O$ = 433.9) |
| Sub 2-52 | m/z = 419.12($C_{27}H_{18}ClN_3$ = 419.91) |
| Sub 2-54 | m/z = 383.12($C_{24}H_{18}ClN_3$ = 383.88) |
| Sub 2-55 | m/z = 357.07($C_{21}H_{12}ClN_3O$ = 357.8) |
| Sub 2-56 | m/z = 539.09($C_{33}H_{18}ClN_3OS$ = 540.04) |
| Sub 2-57 | m/z = 320.08($C_{18}H_{13}ClN_4$ = 320.78) |
| Sub 2-58 | m/z = 363.11($C_{21}H_{18}ClN_3O$ = 363.85) |
| Sub 2-59 | m/z = 432.11($C_{27}H_{17}ClN_4$ = 432.91) |
| Sub 2-60 | m/z = 508.15($C_{33}H_{21}ClN_4$ = 509.01) |
| Sub 2-64 | m/z = 433.1($C_{27}H_{16}ClN_3O$ = 433.9) |
| Sub 2-66 | m/z = 559.15($C_{37}H_{22}ClN_3O$ = 560.05) |
| Sub 2-67 | m/z = 483.11($C_{31}H_{18}ClN_3O$ = 483.96) |
| Sub 2-69 | m/z = 573.11($C_{37}H_{20}ClN_3S$ = 574.1) |
| Sub 2-80 | m/z = 495.15($C_{33}H_{22}ClN_3$ = 496.01) |
| Sub 2-84 | m/z = 634.19($C_{43}H_{27}ClN_4$ = 635.17) |
| Sub 2-94 | m/z = 347.08($C_{20}H_{14}ClN_3O$ = 347.8) |
| Sub 2-95 | m/z = 324.12($C_{19}H_5D_7ClN_3$ = 324.82) |
| Sub 2-96 | m/z = 499.07($C_{29}H_{14}ClN_5S$ = 499.98) |
| Sub 2-97 | m/z = 433.04($C_{21}H_9ClF_5N_3$ = 433.77) |
| Sub 2-98 | m/z = 398.13($C_{25}H_{11}D_5ClN_3$ = 398.9) |

TABLE 2-continued

| compound | FD-MS |
|---|---|
| Sub 2-99 | m/z = 459.11($C_{29}H_{18}ClN_3O$ = 459.93) |
| Sub 2-100 | m/z = 447.11($C_{28}H_{18}ClN_3O$ = 447.92) |
| Sub 2-101 | m/z = 433.13($C_{28}H_{20}ClN_3$ = 433.94) |
| Sub 2-102 | m/z = 469.13($C_{31}H_{20}ClN_3$ = 469.97) |
| Sub 2-103 | m/z = 559.15($C_{37}H_{22}ClN_3O$ = 560.05) |

Sub 2 of the Reaction Scheme 1 can be synthesized according to the reaction route of the following Reaction Scheme 3, but there is no limitation thereto.

<Reaction Scheme 3>

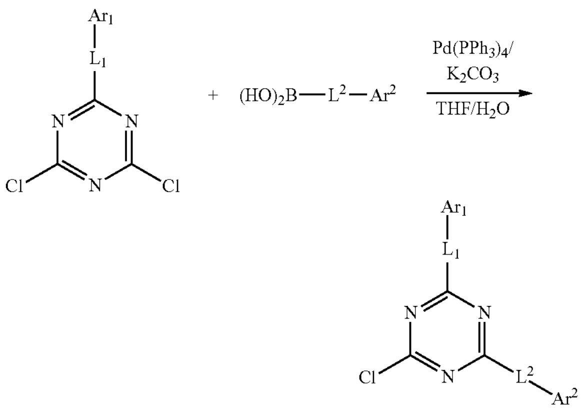

Sub2

Synthesis Example of Sub 2-2

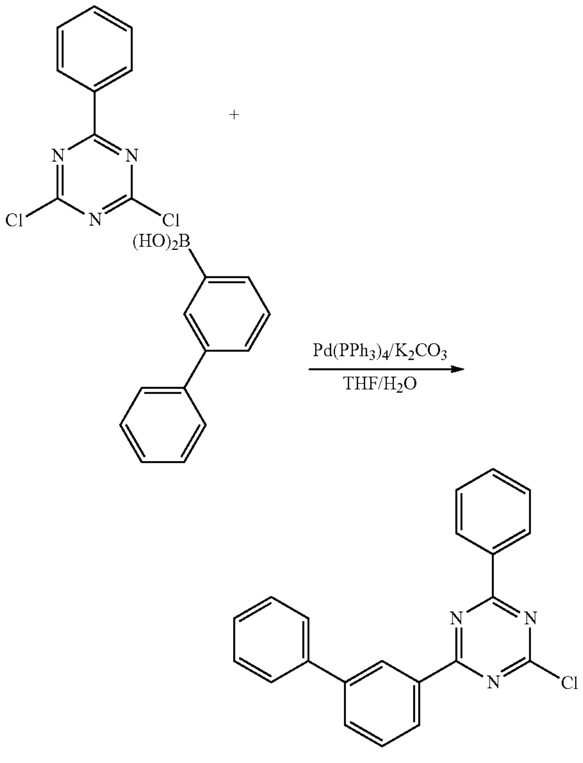

Sub 2-2

[1,1'-biphenyl]-3-ylboronic acid (31.01 g, 156.60 mmol), $Pd(PPh_3)_4$ (7.24 g, 6.26 mmol), $K_2CO_3$ (64.93 g, 469.79 mmol), THF (522 ml) and water (261 ml) were added to 2,4-dichloro-6-phenyl-1,3,5-triazine (35.4 g, 156.60 mmol) and the mixture was stirred under reflux. When the reaction was completed, the reaction product was extracted with ether and water. Then the organic layer was concentrated, dried with $MgSO_4$ and concentrated. Finally, the concentrate was applied to silica gel column and recrystallized to obtain 43.07 g (yield: 80%) of the product.

Synthesis Example of Sub 2-6

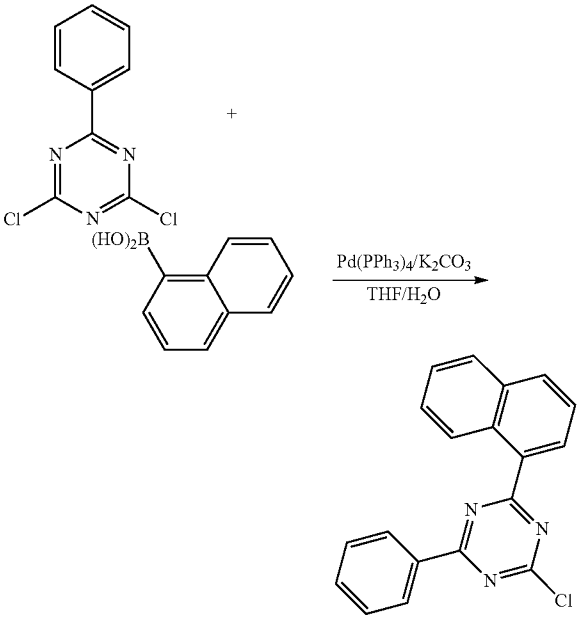

Sub 2-6

After naphthalen-1-ylboronic acid (26.93 g, 156.60 mmol), $Pd(PPh_3)_4$ (7.24 g, 6.26 mmol), $K_2CO_3$ (64.93 g, 469.79 mmol), THF (522 ml) and water (261 ml) were added to 2,4-dichloro-6-phenyl-1,3,5-triazine (35.4 g, 156.60 mmol), the reaction was carried out in the same manner as in the synthesis method of Sub 2-2 to obtain 36.82 g (yield: 74%) of product.

Synthesis Example of Sub 2-22

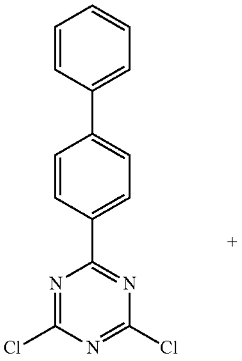

-continued

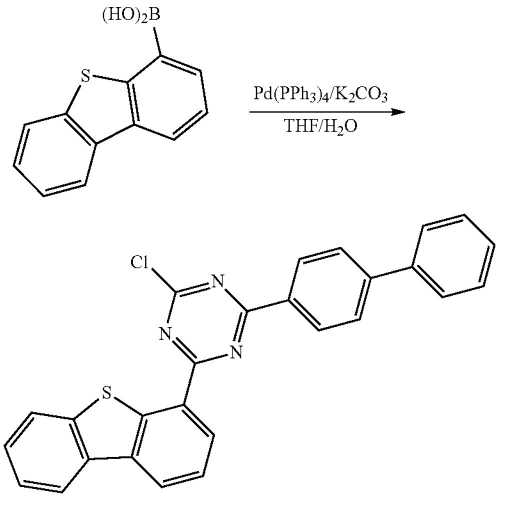

Sub 2-22

After dibenzo[b,d]thiophen-4-ylboronic acid (26.72 g, 117.16 mmol), $Pd(PPh_3)_4$ (5.42 g, 4.69 mmol), $K_2CO_3$ (48.58 g, 351.47 mmol), THF (391 ml) and water (195 ml) were added to 2-([1,1'-biphenyl]-4-yl)-4,6-dichloro-1,3,5-triazine (35.4 g, 117.16 mmol), the reaction was carried out in the same manner as in the synthesis method of Sub 2-2 to obtain 40.06 g (yield: 76%) of product.

Synthesis Example of Sub 2-24

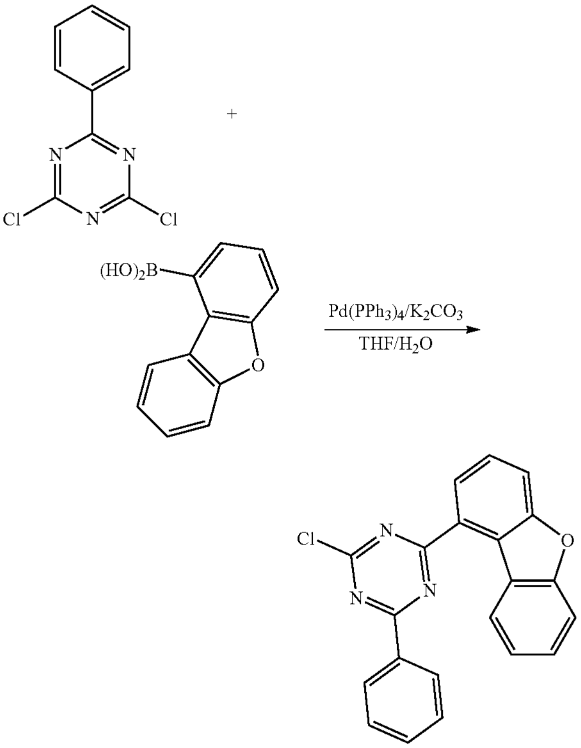

Sub 2-24

After dibenzo[b,d]furan-1-ylboronic acid (33.20 g, 156.60 mmol), $Pd(PPh_3)_4$ (7.24 g, 6.26 mmol), $K_2CO_3$ (64.93 g, 469.79 mmol), THF (522 ml) and water (261 ml) were added to 2,4-dichloro-6-phenyl-1,3,5-triazine (35.4 g, 156.60 mmol), the reaction was carried out in the same manner as in the synthesis method of Sub 2-2 to obtain 38.66 g (yield: 69%) of product.

Synthesis Example of Sub 2-47

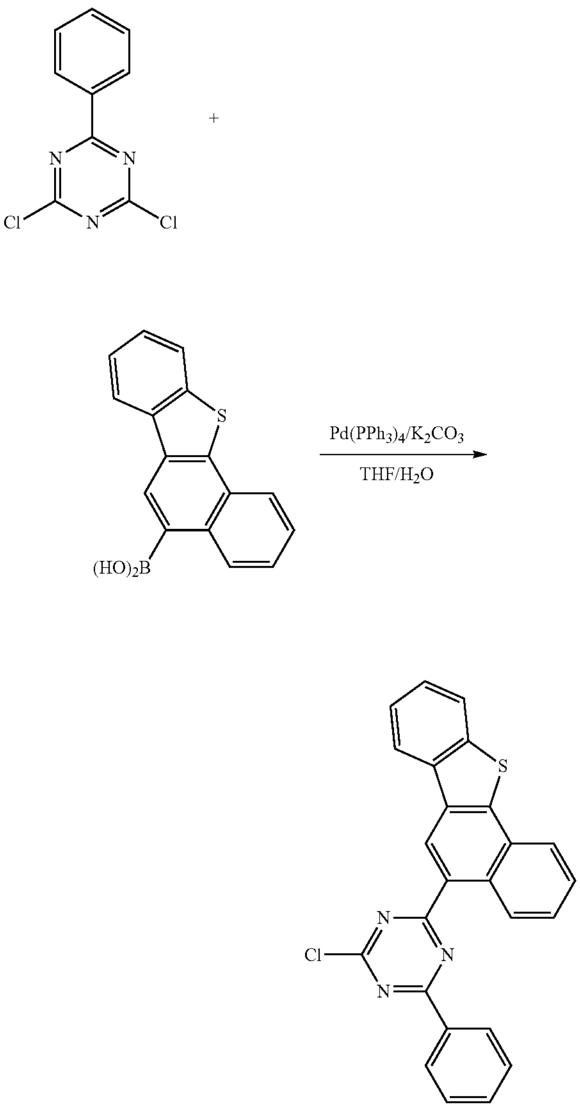

Sub 2-47

After benzo[b]naphtho[2,1-d]thiophen-5-ylboronic acid (43.55 g, 156.60 mmol), $Pd(PPh_3)_4$ (7.24 g, 6.26 mmol), $K_2CO_3$ (64.93 g, 469.79 mmol), THF (522 ml) and water (261 ml) were added to 2,4-dichloro-6-phenyl-1,3,5-triazine (35.4 g, 156.60 mmol), the reaction was carried out in the same manner as in the synthesis method of Sub 2-2 to obtain 19.58 g (yield: 45%) of product.

3. Synthesis Example of Final Product

Synthesis Example of 1-6

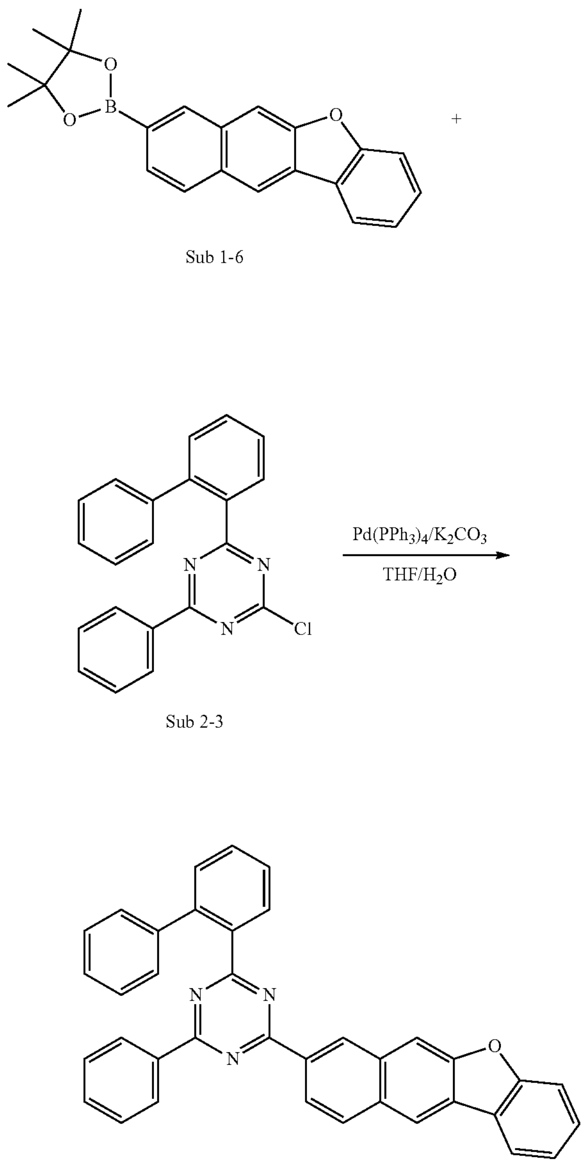

Sub 1-6

Sub 2-3

1-6

After Sub 1-6 (56.7 g, 164.72 mmol) was dissolved in THF (604 mL) in a round bottom flask, Sub 2-3 (67.96 g, 197.66 mmol), $Pd(PPh_3)_4$ (7.61 g, 6.59 mmol), $K_2CO_3$ (68.30 g, 494.16 mmol) and water (302 mL) were added thereto and the mixture was stirred under reflux. When the reaction was completed, the reaction product was extracted with ether and water. Then the organic layer was dried with $MgSO_4$ and concentrated. Finally, the concentrate was applied to silica gel column and recrystallized to obtain 64.93 (yield: 75%) of the product.

Synthesis Example of 1-46

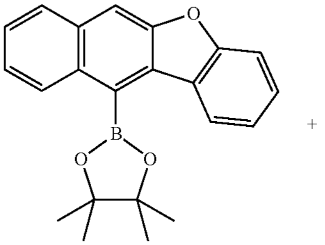
Sub 1-9

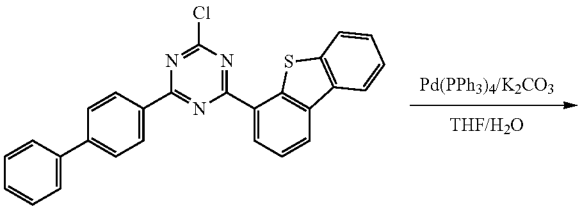

Sub 2-22

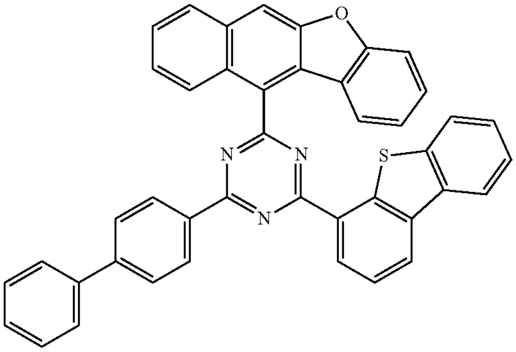
1-46

After THF (604 mL), Sub 2-22 (88.94 g, 197.66 mmol), $Pd(PPh_3)_4$ (7.61 g, 6.59 mmol), $K_2CO_3$ (68.30 g, 494.16 mmol) and water (302 mL) were added to Sub 1-9 (56.7 g, 164.72 mmol), the reaction was carried out in the same manner as in the synthesis method of 1-6 to obtain 81.17 g (yield: 73%) of product.

Synthesis Example of 1-81

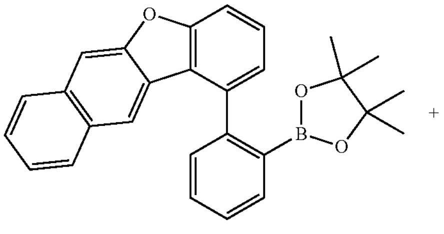
Sub 1-29

-continued

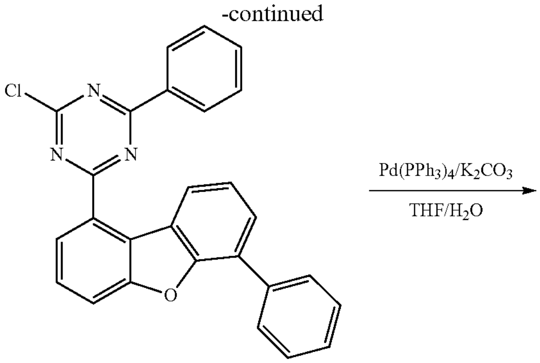

Sub 2-65

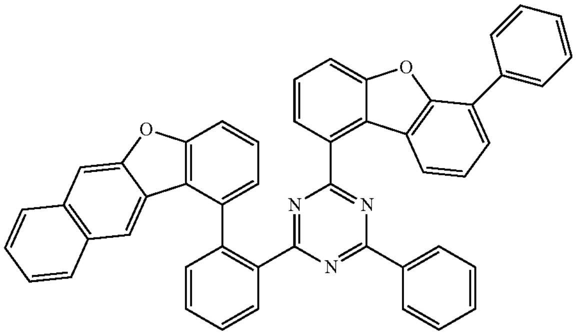
I-81

After THF (495 mL), Sub 2-65 (70.24 g, 161.88 mmol), $Pd(PPh_3)_4$ (6.24 g, 5.40 mmol), $K_2CO_3$ (55.93 g, 404.69 mmol) and water (247 mL) were added to Sub 1-29 (56.7 g, 134.90 mmol), the reaction was carried out in the same manner as in the synthesis method of 1-6 to obtain 59.73 g (yield: 64%) of product.

Synthesis Example of 1-92

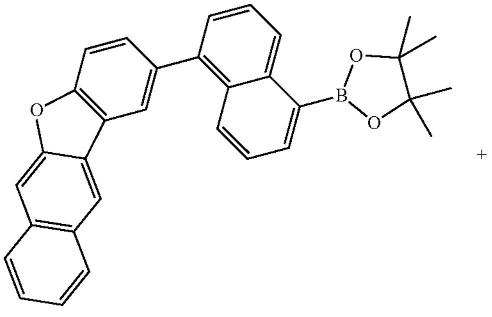
Sub 1-38

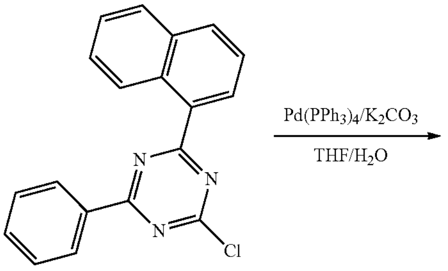

Sub 2-6

-continued

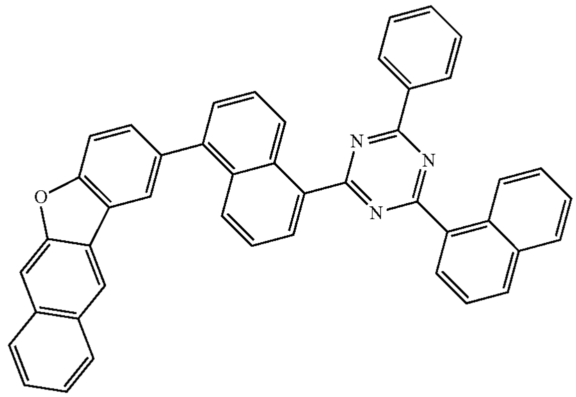

1-92

After THF (442 mL), Sub 2-6 (45.97 g, 144.65 mmol), $Pd(PPh_3)_4$ (5.57 g, 4.82 mmol), $K_2CO_3$ (49.98 g, 361.62 mmol) and water (221 mL) were added to Sub 1-38 (56.7 g, 120.54 mmol), the reaction was carried out in the same manner as in the synthesis method of 1-6 to obtain 65.62 g (yield: 87%) of product.

Synthesis Example of 1-122

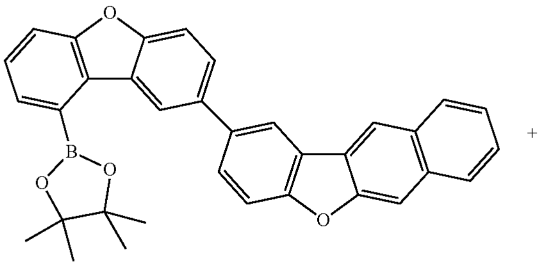

Sub 1-67

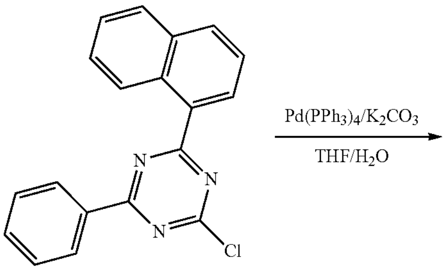

Sub 2-6

-continued

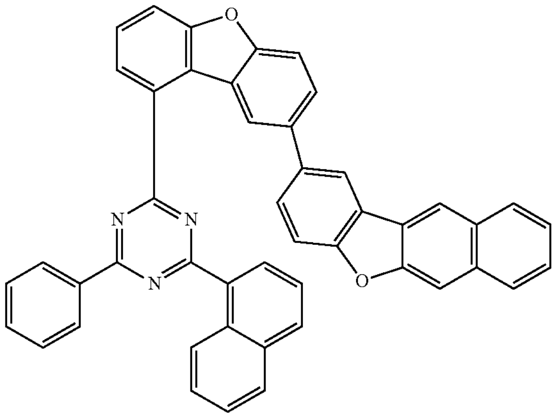

1-122

After THF (407 mL), Sub 2-6 (42.36 g, 133.31 mmol), $Pd(PPh_3)_4$ (5.13 g, 4.44 mmol), $K_2CO_3$ (46.06 g, 333.27 mmol) and water (204 mL) were added to Sub 1-67 (56.7 g, 111.09 mmol), the reaction was carried out in the same manner as in the synthesis method of 1-6 to obtain 59.17 g (yield: 80%) of product.

Synthesis Example of 1-148

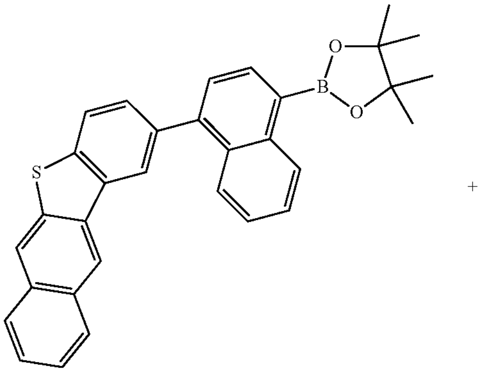

Sub 1-97

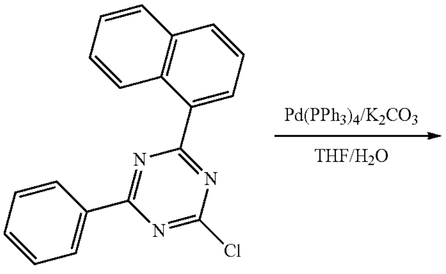

Sub 2-6

-continued

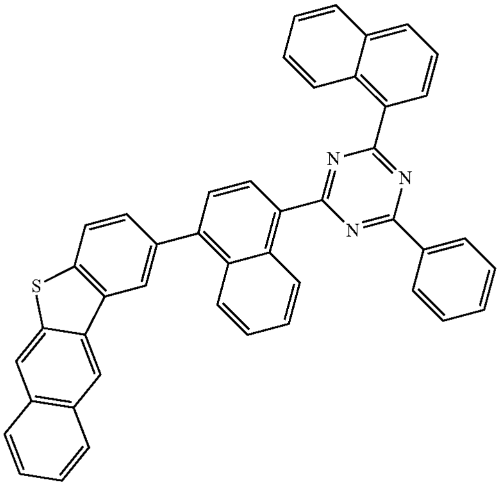

1-148

After THF (427 mL), Sub 2-6 (44.45 g, 139.87 mmol), $Pd(PPh_3)_4$ (5.39 g, 4.66 mmol), $K_2CO_3$ (48.33 g, 349.68 mmol) and water (214 mL) were added to Sub 1-97 (56.7 g, 116.56 mmol), the reaction was carried out in the same manner as in the synthesis method of 1-6 to obtain 62.84 g (yield: 84%) of product.

Synthesis Example of 1-157

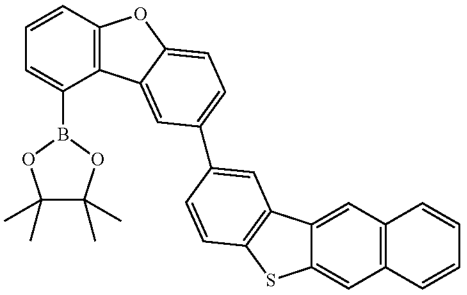

Sub 1-106

+

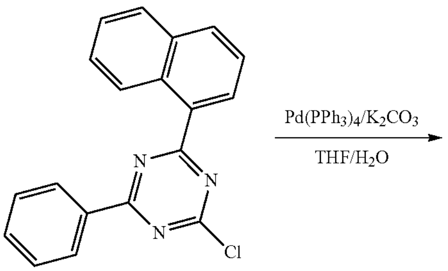

Sub 2-6

-continued

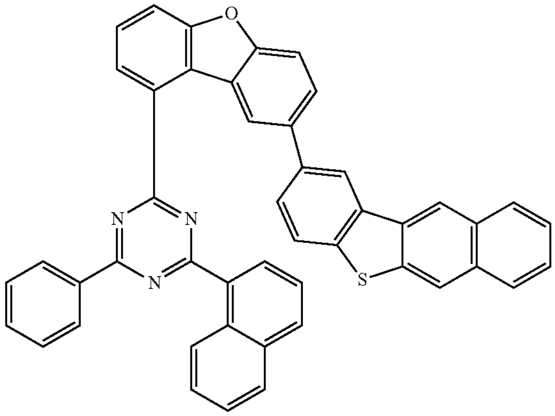

1-157

After THF (395 mL), Sub 2-6 (41.07 g, 129.24 mmol), $Pd(PPh_3)_4$ (4.98 g, 4.31 mmol), $K_2CO_3$ (44.66 g, 323.10 mmol) and water (197 mL) were added to Sub 1-106 (56.7 g, 107.70 mmol), the reaction was carried out in the same manner as in the synthesis method of 1-6 to obtain 59.48 (yield: 81%) of product.

Synthesis Example of 2-109

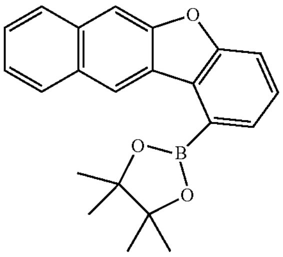

Sub 1-2

+

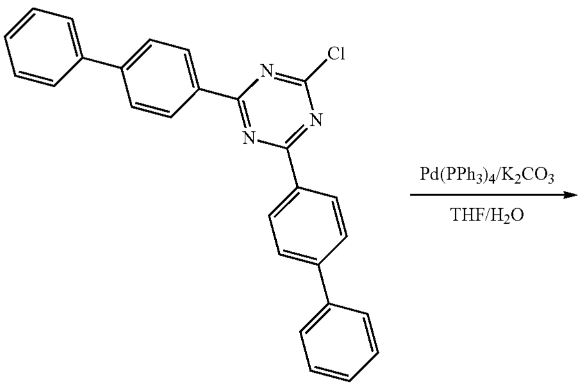

Sub 2-104

-continued

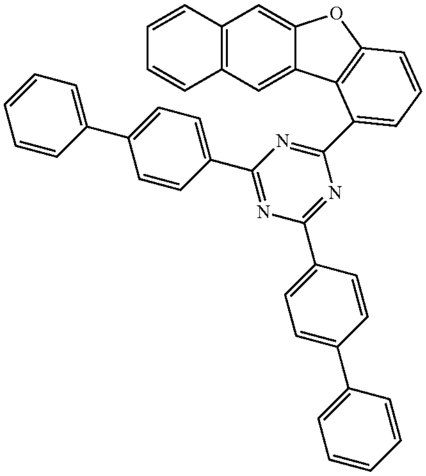

2-109

-continued

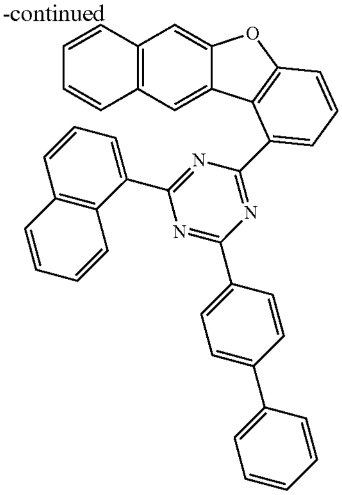

2-111

After THF (395 mL), Sub 2-104 (54.3 g, 129.24 mmol), $Pd(PPh_3)_4$ (4.98 g, 4.31 mmol), $K_2CO_3$ (44.66 g, 323.10 mmol) and water (197 mL) were added to Sub 1-2 (37.1 g, 107.7 mmol), the reaction was carried out in the same manner as in the synthesis method of 1-6 to obtain 55.5 g (yield: 81%) of product.

Synthesis Example of 2-111

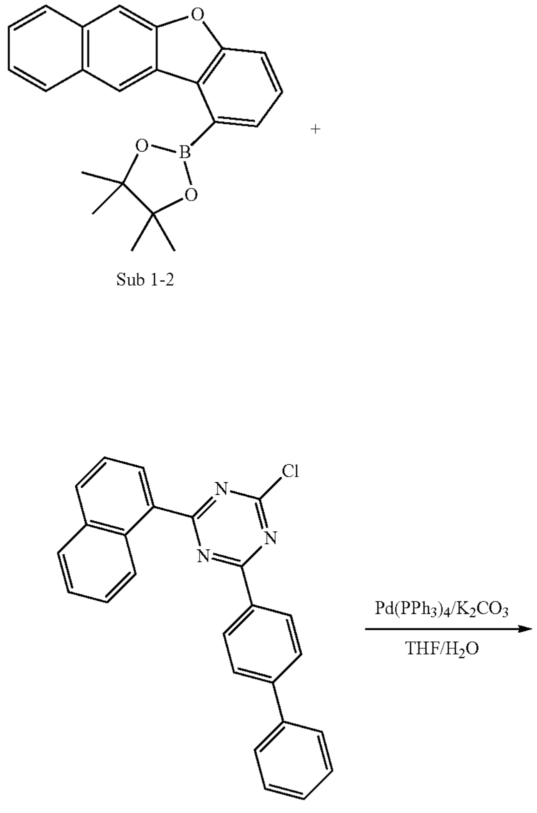

Sub 1-2

Sub 2-16

After THF (395 mL), Sub 2-16 (50.9 g, 129.24 mmol), $Pd(PPh_3)_4$ (4.98 g, 4.31 mmol), $K_2CO_3$ (44.66 g, 323.10 mmol) and water (197 mL) were added to Sub 1-2 (37.1 g, 107.7 mmol), the reaction was carried out in the same manner as in the synthesis method of 1-6 to obtain 50.8 g (yield: 82%) of product.

The FD-MS values of the compounds 1-1 to 1-176 and compounds 2-101 to 2-124 of the present invention prepared according to the above synthesis examples are shown in Table 3 below.

TABLE 3

| compound | FD-MS |
|---|---|
| 1-1 | m/z = 449.15($C_{31}H_{19}N_3O$ = 449.51) |
| 1-2 | m/z = 525.18($C_{37}H_{23}N_3O$ = 525.61) |
| 1-3 | m/z = 449.15($C_{31}H_{19}N_3O$ = 449.51) |
| 1-4 | m/z = 449.15($C_{31}H_{19}N_3O$ = 449.51) |
| 1-5 | m/z = 575.2($C_{41}H_{25}N_3O$ = 575.67) |
| 1-6 | m/z = 525.18($C_{37}H_{23}N_3O$ = 525.61) |
| 1-7 | m/z = 499.17($C_{35}H_{21}N_3O$ = 499.57) |
| 1-8 | m/z = 677.25($C_{49}H_{31}N_3O$ = 677.81) |
| 1-9 | m/z = 499.17($C_{35}H_{21}N_3O$ = 499.57) |
| 1-10 | m/z = 549.18($C_{39}H_{23}N_3O$ = 549.63) |
| 1-11 | m/z = 675.23($C_{49}H_{29}N_3O$ = 675.79) |
| 1-12 | m/z = 575.2($C_{41}H_{25}N_3O$ = 575.67) |
| 1-13 | m/z = 701.25($C_{51}H_{31}N_3O$ = 701.83) |
| 1-14 | m/z = 651.23($C_{47}H_{29}N_3O$ = 651.77) |
| 1-15 | m/z = 651.23($C_{47}H_{29}N_3O$ = 651.77) |
| 1-16 | m/z = 575.2($C_{41}H_{25}N_3O$ = 575.67) |
| 1-17 | m/z = 549.18($C_{39}H_{23}N_3O$ = 549.63) |
| 1-18 | m/z = 549.18($C_{39}H_{23}N_3O$ = 549.63) |
| 1-19 | m/z = 575.2($C_{41}H_{25}N_3O$ = 575.67) |
| 1-20 | m/z = 575.2($C_{41}H_{25}N_3O$ = 575.67) |
| 1-21 | m/z = 575.2($C_{41}H_{25}N_3O$ = 575.67) |
| 1-22 | m/z = 555.14($C_{37}H_{21}N_3OS$ = 555.66) |
| 1-23 | m/z = 605.16($C_{41}H_{23}N_3OS$ = 605.72) |
| 1-24 | m/z = 631.17($C_{43}H_{25}N_3OS$ = 631.75) |
| 1-25 | m/z = 631.17($C_{43}H_{25}N_3OS$ = 631.75) |
| 1-26 | m/z = 615.19($C_{43}H_{25}N_3OS$ = 615.69) |
| 1-27 | m/z = 539.16($C_{37}H_{21}N_3OS$ = 539.59) |
| 1-28 | m/z = 707.2($C_{49}H_{29}N_3OS$ = 707.85) |
| 1-29 | m/z = 707.2($C_{49}H_{29}N_3OS$ = 707.85) |
| 1-30 | m/z = 655.23($C_{46}H_{29}N_3OS$ = 655.76) |
| 1-31 | m/z = 655.17($C_{45}H_{25}N_3OS$ = 655.78) |
| 1-32 | m/z = 631.17($C_{43}H_{25}N_3OS$ = 631.75) |
| 1-33 | m/z = 615.19($C_{43}H_{25}N_3O_2$ = 615.69) |
| 1-34 | m/z = 720.2($C_{49}H_{28}N_4OS$ = 720.85) |
| 1-35 | m/z = 705.21($C_{49}H_{27}N_3O_3$ = 705.77) |
| 1-36 | m/z = 691.23($C_{49}H_{29}N_3O_2$ = 691.79) |
| 1-37 | m/z = 757.22($C_{53}H_{31}N_3OS$ = 757.91) |

TABLE 3-continued

| compound | FD-MS |
|---|---|
| 1-38 | m/z = 707.2($C_{49}H_{29}N_3OS$ = 707.85) |
| 1-39 | m/z = 707.2($C_{49}H_{29}N_3OS$ = 707.85) |
| 1-40 | m/z = 766.27($C_{55}H_{34}N_4O$ = 766.9) |
| 1-41 | m/z = 631.17($C_{43}H_{25}N_3OS$ = 631.75) |
| 1-42 | m/z = 631.17($C_{43}H_{25}N_3OS$ = 631.75) |
| 1-43 | m/z = 631.17($C_{43}H_{25}N_3OS$ = 631.75) |
| 1-44 | m/z = 707.2($C_{49}H_{29}N_3OS$ = 707.85) |
| 1-45 | m/z = 631.17($C_{43}H_{25}N_3OS$ = 631.75) |
| 1-46 | m/z = 631.17($C_{43}H_{25}N_3OS$ = 631.75) |
| 1-47 | m/z = 665.21($C_{47}H_{27}N_3O_2$ = 665.75) |
| 1-48 | m/z = 691.23($C_{49}H_{29}N_3O_2$ = 691.79) |
| 1-49 | m/z = 665.21($C_{47}H_{27}N_3O_2$ = 665.75) |
| 1-50 | m/z = 681.19($C_{47}H_{27}N_3OS$ = 681.81) |
| 1-51 | m/z = 757.22($C_{53}H_{31}N_3OS$ = 757.91) |
| 1-52 | m/z = 715.23($C_{51}H_{29}N_3O_2$ = 715.81) |
| 1-53 | m/z = 589.18($C_{41}H_{23}N_3O_2$ = 589.65) |
| 1-54 | m/z = 589.18($C_{41}H_{23}N_3O_2$ = 589.65) |
| 1-55 | m/z = 605.16($C_{41}H_{23}N_3OS$ = 605.72) |
| 1-56 | m/z = 589.18($C_{41}H_{23}N_3O_2$ = 589.65) |
| 1-57 | m/z = 605.16($C_{41}H_{23}N_3OS$ = 605.72) |
| 1-58 | m/z = 807.23($C_{57}H_{33}N_3OS$ = 807.97) |
| 1-59 | m/z = 691.23($C_{49}H_{29}N_3O_2$ = 691.79) |
| 1-60 | m/z = 591.18($C_{41}H_{25}N_3S$ = 591.73) |
| 1-61 | m/z = 515.15($C_{35}H_{21}N_3S$ = 515.63) |
| 1-62 | m/z = 617.19($C_{43}H_{27}N_3S$ = 617.77) |
| 1-63 | m/z = 565.16($C_{39}H_{23}N_3S$ = 565.69) |
| 1-64 | m/z = 565.16($C_{39}H_{23}N_3S$ = 565.69) |
| 1-65 | m/z = 581.19($C_{40}H_{27}N_3S_2$ = 581.74) |
| 1-66 | m/z = 555.14($C_{37}H_{21}N_3OS$ = 555.66) |
| 1-67 | m/z = 737.16($C_{49}H_{27}N_3OS_2$ = 737.9) |
| 1-68 | m/z = 518.16($C_{34}H_{22}N_4S$ = 518.64) |
| 1-69 | m/z = 515.15($C_{35}H_{21}N_3S$ = 515.63) |
| 1-70 | m/z = 561.19($C_{37}H_{27}N_3OS$ = 561.7) |
| 1-71 | m/z = 630.19($C_{43}H_{26}N_4S$ = 630.77) |
| 1-72 | m/z = 591.18($C_{41}H_{25}N_3S$ = 591.73) |
| 1-73 | m/z = 766.27($C_{55}H_{34}N_4O$ = 766.9) |
| 1-74 | m/z = 575.2($C_{41}H_{25}N_3O$ = 575.67) |
| 1-75 | m/z = 677.25($C_{49}H_{31}N_3O$ = 677.81) |
| 1-76 | m/z = 707.2($C_{49}H_{29}N_3OS$ = 707.85) |
| 1-77 | m/z = 766.27($C_{55}H_{34}N_4O$ = 766.9) |
| 1-78 | m/z = 707.2($C_{49}H_{29}N_3OS$ = 707.85) |
| 1-79 | m/z = 767.26($C_{55}H_{33}N_3O_2$ = 767.89) |
| 1-80 | m/z = 767.26($C_{55}H_{33}N_3O_2$ = 767.89) |
| 1-81 | m/z = 691.23($C_{49}H_{29}N_3O_2$ = 691.79) |
| 1-82 | m/z = 817.27($C_{59}H_{35}N_3O_2$ = 817.95) |
| 1-83 | m/z = 741.24($C_{53}H_{31}N_3O_2$ = 741.85) |
| 1-84 | m/z = 741.24($C_{53}H_{31}N_3O_2$ = 741.85) |
| 1-85 | m/z = 831.23($C_{59}H_{33}N_3OS$ = 831.99) |
| 1-86 | m/z = 767.26($C_{55}H_{33}N_3O_2$ = 767.89) |
| 1-87 | m/z = 757.19($C_{51}H_{27}N_5OS$ = 757.87) |
| 1-88 | m/z = 601.22($C_{43}H_{27}N_3O$ = 601.71) |
| 1-89 | m/z = 757.22($C_{53}H_{31}N_3OS$ = 757.91) |
| 1-90 | m/z = 625.22($C_{45}H_{27}N_3O$ = 625.73) |
| 1-91 | m/z = 625.22($C_{45}H_{27}N_3O$ = 625.73) |
| 1-92 | m/z = 625.22($C_{43}H_{27}N_3O$ = 625.73) |
| 1-93 | m/z = 625.22($C_{45}H_{27}N_3O$ = 625.73) |
| 1-94 | m/z = 651.23($C_{47}H_{29}N_3O$ = 651.77) |
| 1-95 | m/z = 731.2($C_{51}H_{29}N_3OS$ = 731.87) |
| 1-96 | m/z = 833.25($C_{59}H_{35}N_3OS$ = 834.01) |
| 1-97 | m/z = 757.22($C_{53}H_{31}N_3OS$ = 757.91) |
| 1-98 | m/z = 867.29($C_{63}H_{37}N_3O_2$ = 868.01) |
| 1-99 | m/z = 757.22($C_{53}H_{31}N_3OS$ = 757.91) |
| 1-100 | m/z = 655.23($C_{46}H_{29}N_3O_2$ = 655.76) |
| 1-101 | m/z = 625.22($C_{45}H_{27}N_3O$ = 625.73) |
| 1-102 | m/z = 625.22($C_{45}H_{27}N_3O$ = 625.73) |
| 1-103 | m/z = 625.22($C_{45}H_{27}N_3O$ = 625.73) |
| 1-104 | m/z = 807.23($C_{57}H_{33}N_3OS$ = 807.97) |
| 1-105 | m/z = 731.2($C_{51}H_{29}N_3OS$ = 731.87) |
| 1-106 | m/z = 731.2($C_{51}H_{29}N_3OS$ = 731.87) |
| 1-107 | m/z = 791.26($C_{57}H_{33}N_3O_2$ = 791.91) |
| 1-108 | m/z = 807.23($C_{37}H_{33}N_3OS$ = 807.97) |
| 1-109 | m/z = 807.23($C_{57}H_{33}N_3OS$ = 807.97) |
| 1-110 | m/z = 575.20($C_{41}H_{25}N_3O$ = 575.67) |
| 1-111 | m/z = 867.29($C_{63}H_{37}N_3O_2$ = 868.01) |
| 1-112 | m/z = 807.23($C_{57}H_{33}N_3OS$ = 807.97) |
| 1-113 | m/z = 777.28($C_{57}H_{35}N_3O$ = 777.93) |
| 1-114 | m/z = 803.29($C_{59}H_{37}N_3O$ = 803.97) |
| 1-115 | m/z = 632.26($C_{45}H_{20}D_7N_3O$ = 632.77) |

TABLE 3-continued

| compound | FD-MS |
|---|---|
| 1-116 | m/z = 715.23($C_{51}H_{29}N_3O_2$ = 715.81) |
| 1-117 | m/z = 883.27($C_{63}H_{37}N_3OS$ = 884.07) |
| 1-118 | m/z = 833.25($C_{59}H_{35}N_3OS$ = 834.01) |
| 1-119 | m/z = 942.34($C_{69}H_{42}N_4O$ = 943.12) |
| 1-120 | m/z = 701.25($C_{51}H_{31}N_3O$ = 701.83) |
| 1-121 | m/z = 615.19($C_{43}H_{25}N_3O_2$ = 615.69) |
| 1-122 | m/z = 665.21($C_{47}H_{27}N_3O_2$ = 665.75) |
| 1-123 | m/z = 681.19($C_{47}H_{27}N_3OS$ = 681.81) |
| 1-124 | m/z = 715.23($C_{51}H_{29}N_3O_2$ = 715.81) |
| 1-125 | m/z = 691.23($C_{49}H_{29}N_3O_2$ = 691.79) |
| 1-126 | m/z = 691.23($C_{49}H_{29}N_3O_2$ = 691.79) |
| 1-128 | m/z = 691.23($C_{49}H_{29}N_3O_2$ = 691.79) |
| 1-129 | m/z = 757.22($C_{53}H_{31}N_3OS$ = 757.91) |
| 1-130 | m/z = 691.23($C_{49}H_{29}N_3O_2$ = 691.79) |
| 1-131 | m/z = 817.27($C_{59}H_{35}N_3O_2$ = 817.95) |
| 1-132 | m/z = 691.23($C_{49}H_{29}N_3O_2$ = 691.79) |
| 1-133 | m/z = 781.24($C_{55}H_{31}N_3O_3$ = 781.87) |
| 1-134 | m/z = 797.21($C_{55}H_{31}N_3O_2S$ = 797.93) |
| 1-136 | m/z = 691.23($C_{49}H_{29}N_3O_2$ = 691.79) |
| 1-137 | m/z = 691.23($C_{49}H_{29}N_3O_2$ = 691.79) |
| 1-138 | m/z = 780.25($C_{55}H_{32}N_4O_2$ = 780.89) |
| 1-139 | m/z = 691.23($C_{49}H_{29}N_3O_2$ = 691.79) |
| 1-140 | m/z = 781.18($C_{49}H_{24}F_5N_3O_2$ = 781.74) |
| 1-141 | m/z = 732.29($C_{53}H_{28}D_5N_3O$ = 732.9) |
| 1-142 | m/z = 793.27($C_{57}H_{35}N_3O_2$ = 793.93) |
| 1-143 | m/z = 651.23($C_{47}H_{29}N_3O$ = 651.77) |
| 1-144 | m/z = 755.26($C_{54}H_{33}N_3O_2$ = 755.88) |
| 1-145 | m/z = 591.18($C_{41}H_{25}N_3S$ = 591.73) |
| 1-146 | m/z = 617.19($C_{43}H_{27}N_3S$ = 617.77) |
| 1-147 | m/z = 707.24($C_{50}H_{33}N_3S$ = 707.9) |
| 1-148 | m/z = 641.19($C_{45}H_{27}N_3S$ = 641.79) |
| 1-149 | m/z = 641.19($C_{45}H_{27}N_3S$ = 641.79) |
| 1-150 | m/z = 641.19($C_{45}H_{27}N_3S$ = 641.79) |
| 1-151 | m/z = 793.26($C_{57}H_{35}N_3S$ = 793.99) |
| 1-152 | m/z = 641.19($C_{45}H_{27}N_3S$ = 641.79) |
| 1-153 | m/z = 667.21($C_{47}H_{29}N_3S$ = 667.83) |
| 1-154 | m/z = 823.21($C_{57}H_{33}N_3S_2$ = 824.03) |
| 1-155 | m/z = 883.27($C_{63}H_{37}N_3OS$ = 884.07) |
| 1-156 | m/z = 747.18($C_{51}H_{29}N_3S_2$ = 747.93) |
| 1-157 | m/z = 681.19($C_{47}H_{27}N_3OS$ = 681.81) |
| 1-158 | m/z = 697.16($C_{47}H_{27}N_3S_2$ = 697.87) |
| 1-159 | m/z = 731.2($C_{51}H_{29}N_3OS$ = 731.87) |
| 1-160 | m/z = 631.17($C_{43}H_{25}N_3OS$ = 631.75) |
| 1-162 | m/z = 737.16($C_{49}H_{27}N_3OS_2$ = 737.9) |
| 1-163 | m/z = 707.2($C_{49}H_{29}N_3OS$ = 707.85) |
| 1-164 | m/z = 707.2($C_{49}H_{29}N_3OS$ = 707.85) |
| 1-165 | m/z = 747.18($C_{51}H_{29}N_3S_2$ = 747.93) |
| 1-166 | m/z = 681.19($C_{47}H_{27}N_3OS$ = 681.81) |
| 1-167 | m/z = 731.2($C_{51}H_{29}N_3OS$ = 731.87) |
| 1-168 | m/z = 631.17($C_{43}H_{25}N_3OS$ = 631.75) |
| 1-169 | m/z = 731.2($C_{51}H_{29}N_3OS$ = 731.87) |
| 1-170 | m/z = 721.18($C_{49}H_{27}N_3O_2S$ = 721.83) |
| 1-171 | m/z = 691.23($C_{49}H_{29}N_3O_2$ = 691.79) |
| 1-172 | m/z = 691.23($C_{49}H_{29}N_3O_2$ = 691.79) |
| 1-173 | m/z = 741.24($C_{53}H_{31}N_3O_2$ = 741.85) |
| 1-174 | m/z = 807.23($C_{57}H_{33}N_3OS$ = 807.97) |
| 1-175 | m/z = 799.21($C_{55}H_{33}N_3S_2$ = 800.01) |
| 1-176 | m/z = 757.22($C_{53}H_{31}N_3OS$ = 757.91) |
| 2-101 | m/z = 449.15($C_{31}H_{19}N_3O$ = 449.51) |
| 2-102 | m/z = 499.17($C_{35}H_{21}N_3O$ = 499.57) |
| 2-103 | m/z = 499.17($C_{35}H_{21}N_3O$ = 499.57) |
| 2-104 | m/z = 525.18($C_{37}H_{23}N_3O$ = 525.61) |
| 2-105 | m/z = 525.18($C_{37}H_{23}N_3O$ = 525.61) |
| 2-106 | m/z = 525.18($C_{37}H_{23}N_3O$ = 525.61) |
| 2-107 | m/z = 575.20($C_{41}H_{25}N_3O$ = 575.67) |
| 2-108 | m/z = 575.20($C_{41}H_{25}N_3O$ = 575.67) |
| 2-109 | m/z = 601.22($C_{43}H_{27}N_3O$ = 601.71) |
| 2-110 | m/z = 525.18($C_{37}H_{23}N_3O$ = 525.61) |
| 2-111 | m/z = 575.20($C_{41}H_{25}N_3O$ = 575.67) |
| 2-112 | m/z = 575.20($C_{41}H_{25}N_3O$ = 575.67) |
| 2-113 | m/z = 449.15($C_{31}H_{19}N_3O$ = 449.51) |
| 2-114 | m/z = 499.17($C_{35}H_{21}N_3O$ = 499.57) |
| 2-115 | m/z = 499.17($C_{35}H_{21}N_3O$ = 499.57) |
| 2-116 | m/z = 525.18($C_{37}H_{23}N_3O$ = 525.61) |
| 2-117 | m/z = 525.18($C_{37}H_{23}N_3O$ = 525.61) |
| 2-118 | m/z = 525.18($C_{37}H_{23}N_3O$ = 525.61) |
| 2-119 | m/z = 575.20($C_{41}H_{25}N_3O$ = 575.67) |
| 2-120 | m/z = 575.20($C_{41}H_{25}N_3O$ = 575.67) |

TABLE 3-continued

| compound | FD-MS |
|---|---|
| 2-121 | m/z = 601.22($C_{43}H_{27}N_3O$ = 601.71) |
| 2-122 | m/z = 525.18($C_{37}H_{23}N_3O$ = 525.61) |
| 2-123 | m/z = 575.20($C_{41}H_{25}N_3O$ = 575.67) |
| 2-124 | m/z = 575.20($C_{41}H_{25}N_3O$ = 575.67) |

[Synthesis Example 2] Formula 2

As shown in Reaction Scheme 4 below, the compounds (final product 2) represented by Formula 2 according to the present invention can be synthesized by reacting Sub 3 with Sub 4, but there is no limitation thereto.

<Reaction Scheme 4>

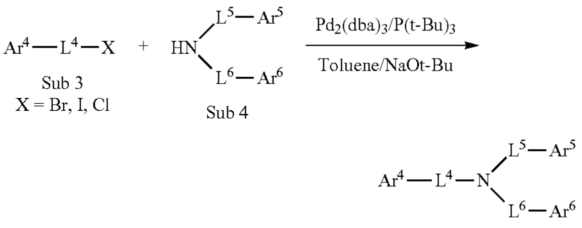

1. Exemplary Compounds of Sub 3

Sub 3 of the Reaction Scheme 4 can be synthesized according to the reaction route of the following Reaction Scheme 5, but there is no limitation thereto.

<Reaction Scheme 5>

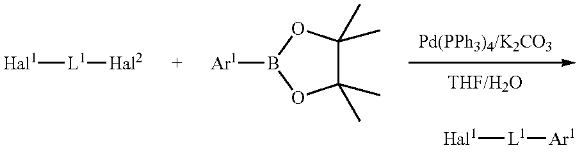

The compounds belonging to Sub 3 of the Reaction Scheme 4 may be, but not limited to, the following compounds.

Sub 3-1

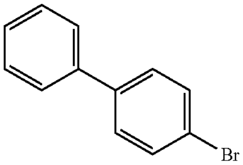

-continued

Sub 3-2

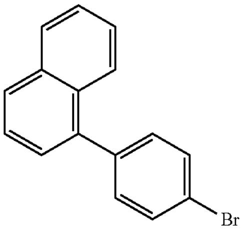

Sub 3-3

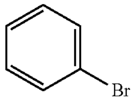

Sub 3-4

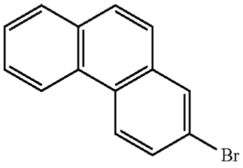

Sub 3-5

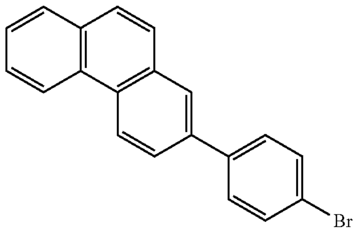

Sub 3-6

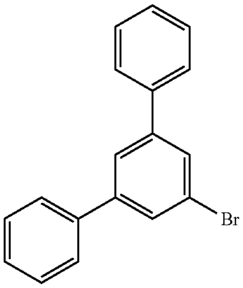

Sub 3-7

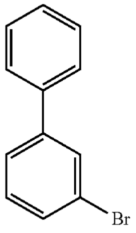

Sub 3-8

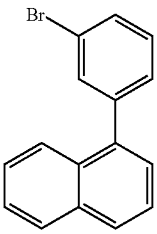

-continued
Sub 3-9
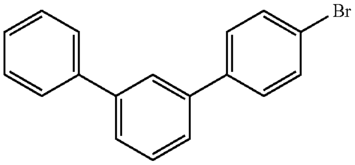
Sub 3-10
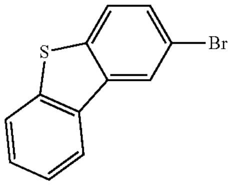
Sub 3-11
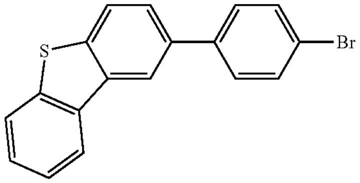
Sub 3-12
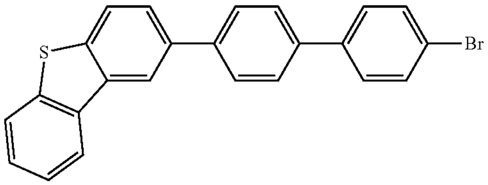
Sub 3-13
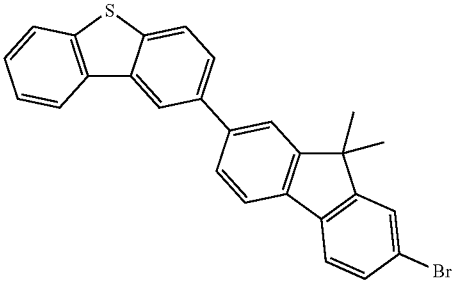
Sub 3-14
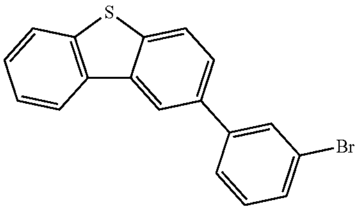
Sub 3-15
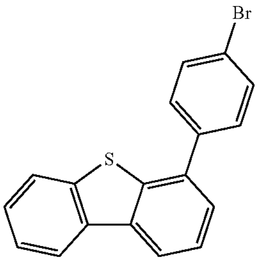
-continued
Sub 3-16
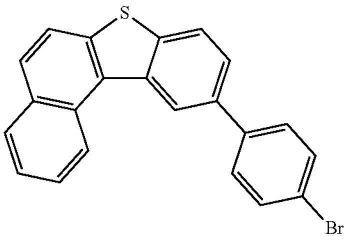
Sub 3-17
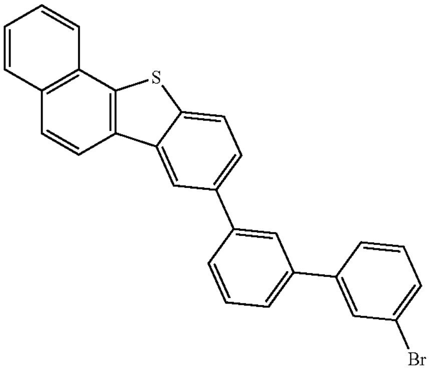
Sub 3-18
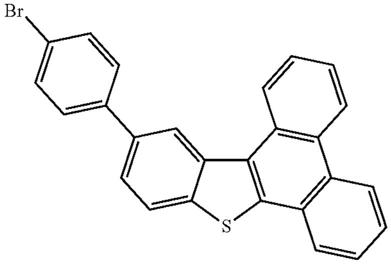
Sub 3-19
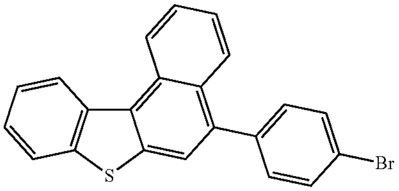
Sub 3-20
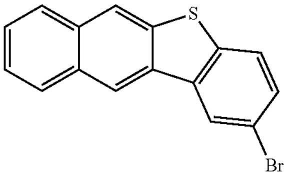
Sub 3-21
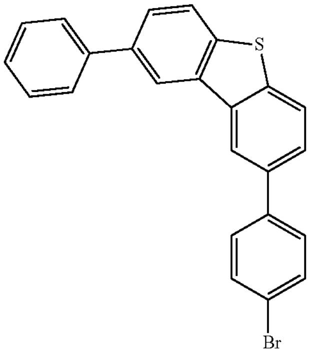

-continued
Sub 3-22
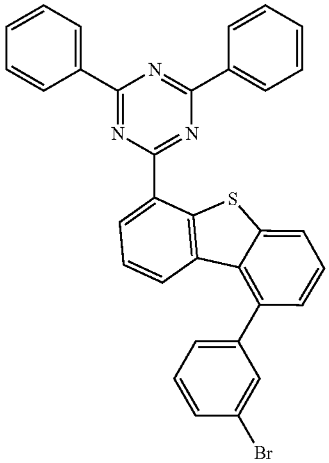
Sub 3-23
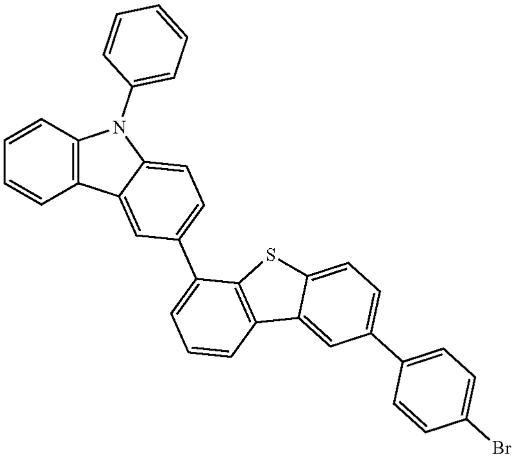
Sub 3-24
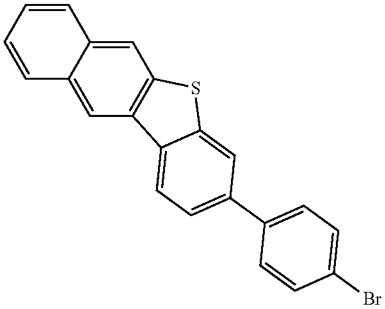
Sub 3-25
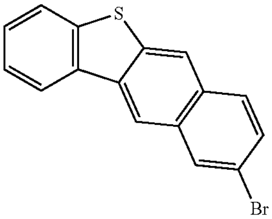
-continued
Sub 3-26
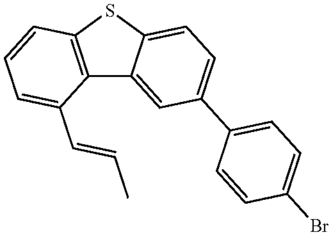
Sub 3-27
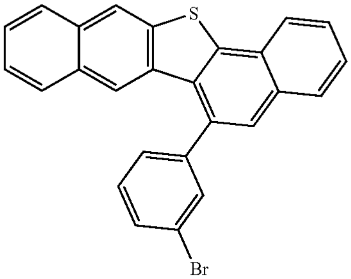
Sub 3-28
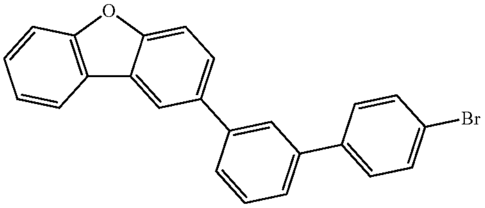
Sub 3-29
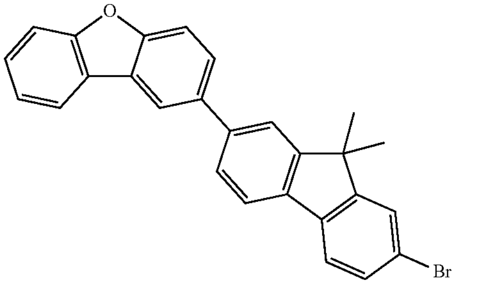
Sub 3-30
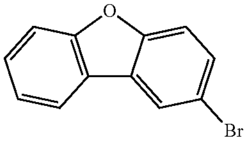
Sub 3-31
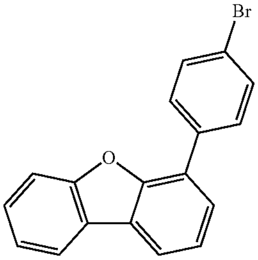

-continued
Sub 3-32
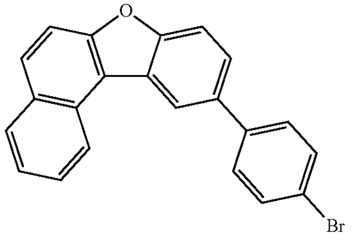
Sub 3-33
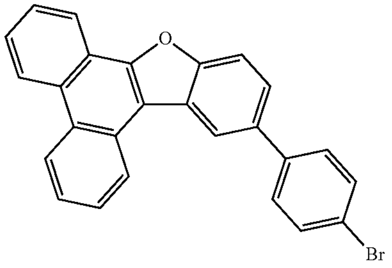
Sub 3-34
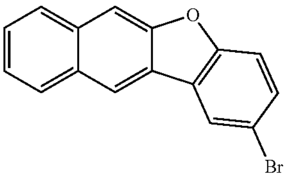
Sub 3-35
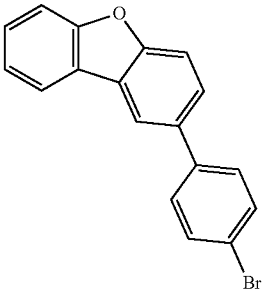
Sub 3-36
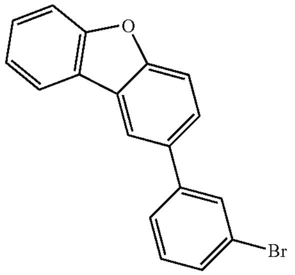
Sub 3-37
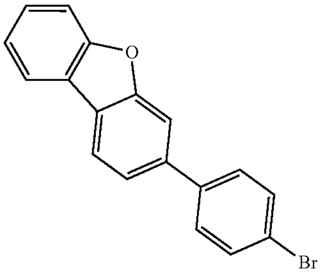
-continued
Sub 3-38
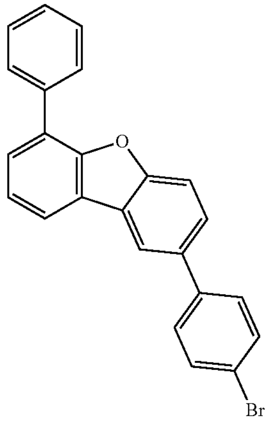
Sub 3-39
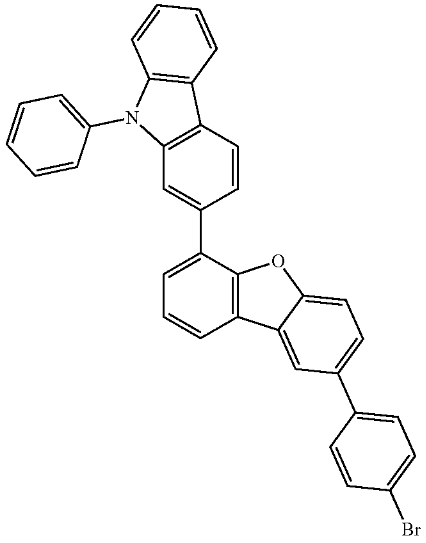
Sub 3-40
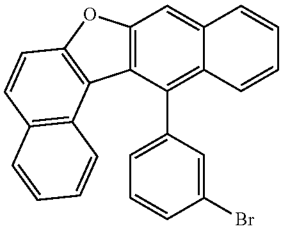
Sub 3-41
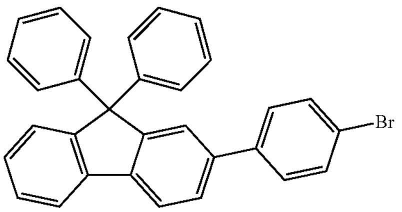
Sub 3-42
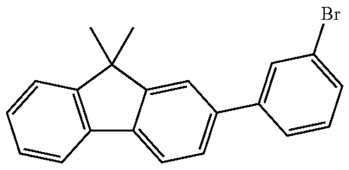

-continued

Sub 3-43

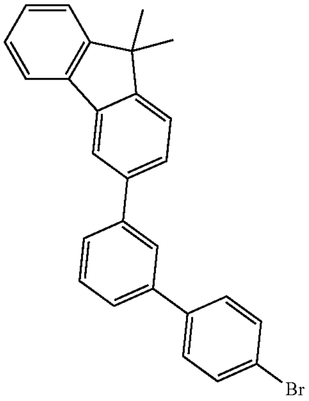

Sub 3-44

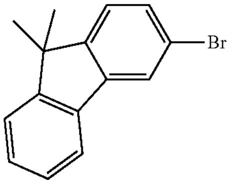

Sub 3-45

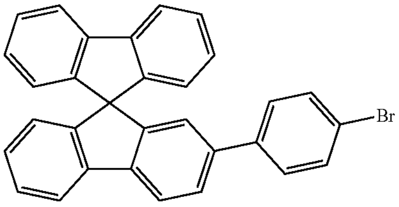

Sub 3-46

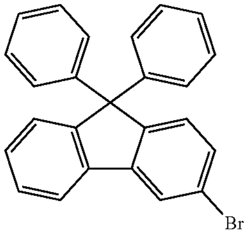

Sub 3-47

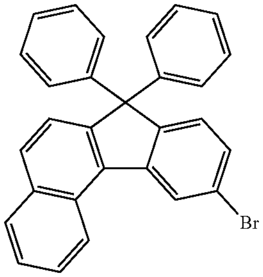

Sub 3-48

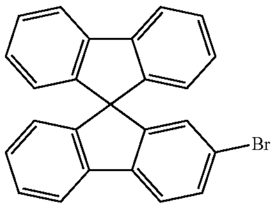

-continued

Sub 3-49

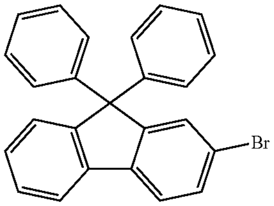

Sub 3-50

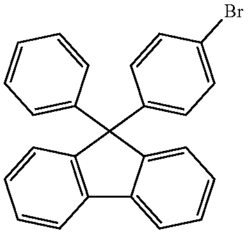

Sub 3-51

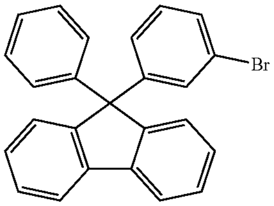

Sub 3-52

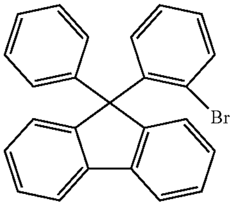

Table 4 shows FD-MS values of the compounds belonging to Sub 3.

TABLE 4

| compound | FD-MS |
|---|---|
| Sub 3-1 | m/z = 231.99($C_{12}H_9Br$ = 233.11) |
| Sub 3-2 | m/z = 282($C_{16}H_{11}Br$ = 283.17) |
| Sub 3-3 | m/z = 155.96($C_6H_5Br$ = 157.01) |
| Sub 3-4 | m/z = 255.99($C_{14}H_9Br$ = 257.13) |
| Sub 3-5 | m/z = 332.02($C_{20}H_{13}Br$ = 333.23) |
| Sub 3-6 | m/z = 308.02($C_{18}H_{13}Br$ = 309.21) |
| Sub 3-7 | m/z = 231.99($C_{12}H_9Br$ = 233.11) |
| Sub 3-8 | m/z = 282($C_{16}H_{11}Br$ = 283.17) |
| Sub 3-9 | m/z = 306.02($C_{18}H_{13}Br$ = 309.21) |
| Sub 3-10 | m/z = 261.95($C_{12}H_7BrS$ = 263.15) |
| Sub 3-11 | m/z = 337.98($C_{18}H_{13}BrS$ = 339.25) |
| Sub 3-12 | m/z = 414.01($C_{24}H_{15}BrS$ = 415.35) |
| Sub 3-13 | m/z = 454.04($C_{27}H_{19}BrS$ = 455.41) |
| Sub 3-14 | m/z = 337.98($C_{18}H_{11}BrS$ = 339.25) |
| Sub 3-15 | m/z = 337.98($C_{18}H_{11}BrS$ = 339.25) |
| Sub 3-16 | m/z = 387.99($C_{22}H_{13}BrS$ = 389.31) |
| Sub 3-17 | m/z = 464.02($C_{28}H_{17}BrS$ = 465.41) |
| Sub 3-18 | m/z = 438.01($C_{26}H_{15}BrS$ = 439.37) |
| Sub 3-19 | m/z = 387.99($C_{22}H_{13}BrS$ = 389.31) |
| Sub 3-20 | m/z = 311.96($C_{16}H_9BrS$ = 313.21) |
| Sub 3-21 | m/z = 414.01($C_{24}H_{15}BrS$ = 415.35) |
| Sub 3-22 | m/z = 569.06($C_{33}H_{20}BrN_3S$ = 570.51) |
| Sub 3-23 | m/z = 579.07($C_{36}H_{22}BrNS$ = 580.54) |
| Sub 3-24 | m/z = 387.99($C_{22}H_{13}BrS$ = 389.31) |
| Sub 3-25 | m/z = 311.96($C_{16}H_9BrS$ = 313.21) |
| Sub 3-26 | m/z = 378.01($C_{21}H_{15}BrS$ = 379.32) |
| Sub 3-27 | m/z = 438.01($C_{26}H_{15}BrS$ = 439.37) |

TABLE 4-continued

| compound | FD-MS |
|---|---|
| Sub 3-28 | m/z = 398.03($C_{24}H_{15}BrO$ = 399.29) |
| Sub 3-29 | m/z = 438.06($C_{27}H_{19}BrO$ = 439.35) |
| Sub 3-30 | m/z = 245.97($C_{12}H_7BrO$ = 247.09) |
| Sub 3-31 | m/z = 322($C_{18}H_{11}BrO$ = 323.19) |
| Sub 3-32 | m/z = 372.01($C_{22}H_{13}BrO$ = 373.25) |
| Sub 3-33 | m/z = 422.03($C_{26}H_{15}BrO$ = 423.31) |
| Sub 3-34 | m/z = 295.98($C_{16}H_9BrO$ = 297.15) |
| Sub 3-35 | m/z = 322($C_{18}H_{11}BrO$ = 323.19) |
| Sub 3-36 | m/z = 322($C_{18}H_{11}BrO$ = 323.19) |
| Sub 3-37 | m/z = 322($C_{18}H_{11}BrO$ = 323.19) |
| Sub 3-38 | m/z = 398.03($C_{24}H_{15}BrO$ = 399.29) |
| Sub 3-39 | m/z = 563.09($C_{36}H_{22}BrNO$ = 564.48) |
| Sub 3-40 | m/z = 422.03($C_{26}H_{15}BrO$ = 423.31) |
| Sub 3-41 | m/z = 472.08($C_{31}H_{21}Br$ = 473.41) |
| Sub 3-42 | m/z = 348.05($C_{21}H_{17}Br$ = 349.27) |
| Sub 3-43 | m/z = 424.08($C_{27}H_{21}Br$ = 425.37) |
| Sub 3-44 | m/z = 272.02($C_{15}H_{13}Br$ = 273.17) |
| Sub 3-45 | m/z = 470.07($C_{31}H_{19}Br$ = 471.4) |
| Sub 3-46 | m/z = 396.05($C_{25}H_{17}Br$ = 397.32) |
| Sub 3-47 | m/z = 448.07($C_{29}H_{19}Br$ = 447.38) |
| Sub 3-48 | m/z = 394.04($C_{25}H_{15}Br$ = 395.3) |
| Sub 3-49 | m/z = 396.05($C_{25}H_{17}Br$ = 397.32) |
| Sub 3-50 | m/z = 396.05($C_{25}H_{17}Br$ = 397.32) |
| Sub 3-51 | m/z = 396.05($C_{25}H_{17}Br$ = 397.32) |
| Sub 3-52 | m/z = 396.05($C_{25}H_{17}Br$ = 397.32) |

2. Exemplary Compounds of Sub 4 and Synthesis Example

Sub 4-1

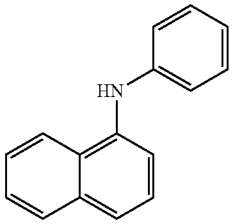

Sub 4-2

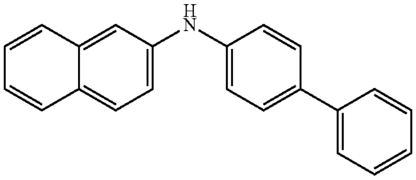

Sub 4-3

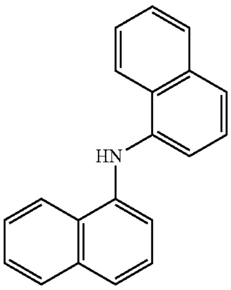

Sub 4-4

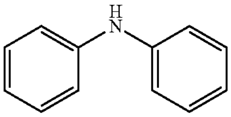

-continued

Sub 4-5

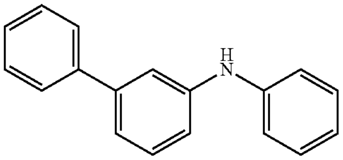

Sub 4-6

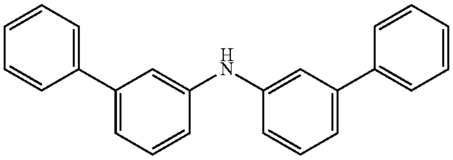

Sub 4-7

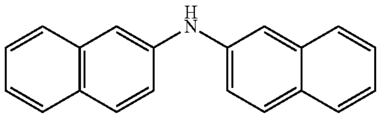

Sub 4-8

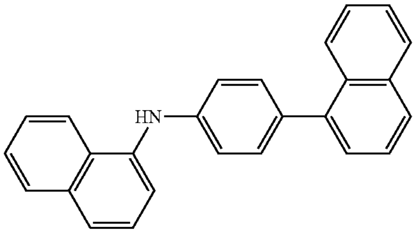

Sub 4-9

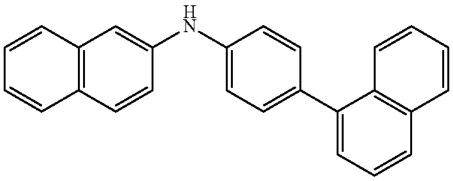

Sub 4-10

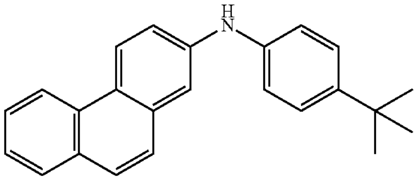

Sub 4-11

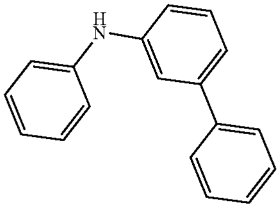

Sub 4-12

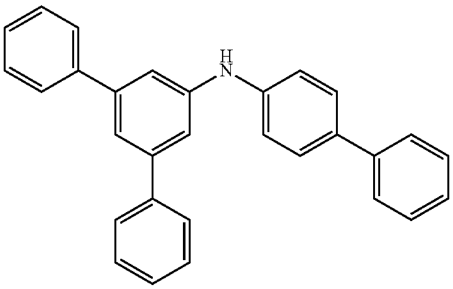

-continued
Sub 4-13
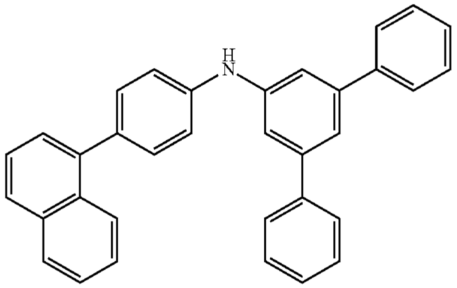
Sub 4-14
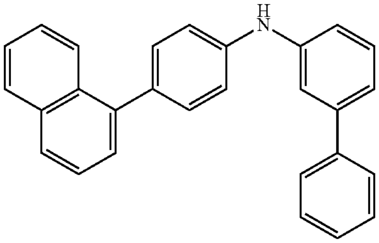
Sub 4-15
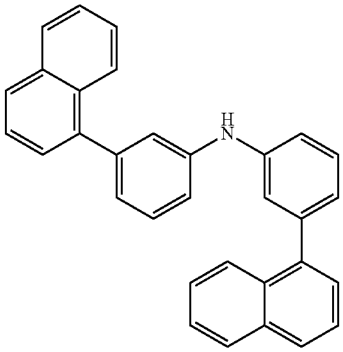
Sub 4-16
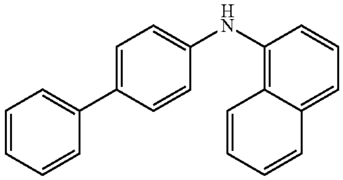
Sub 4-17
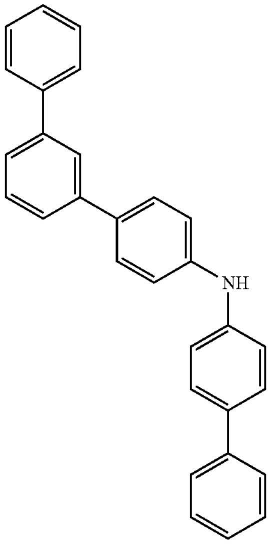
-continued
Sub 4-18
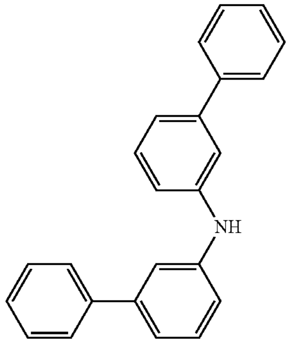
Sub 4-19
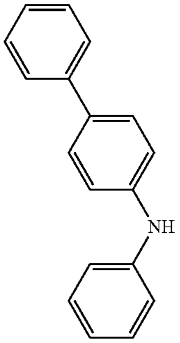
Sub 4-20
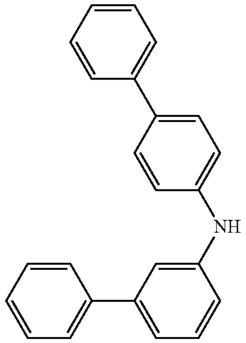
Sub 4-21
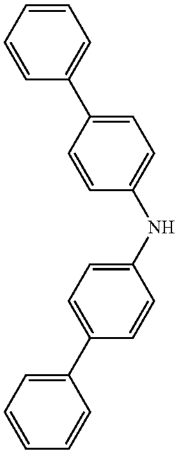

-continued
Sub 4-22
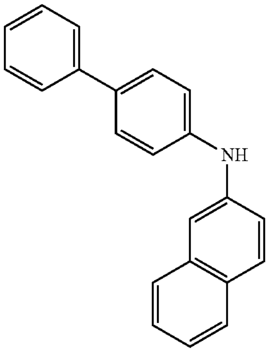
Sub 4-23
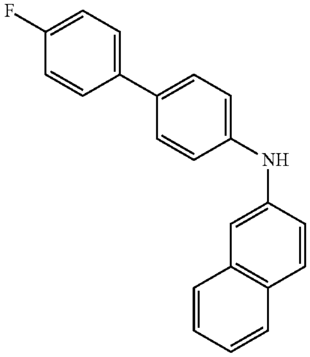
Sub 4-24
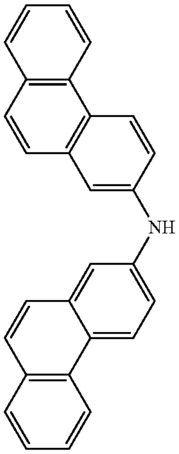
Sub 4-25
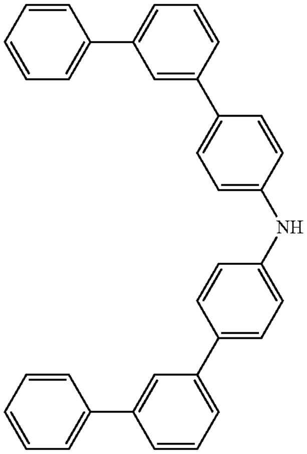
-continued
Sub 4-26
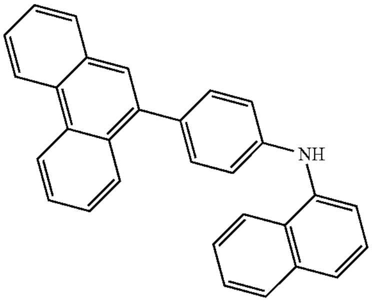
Sub 4-27
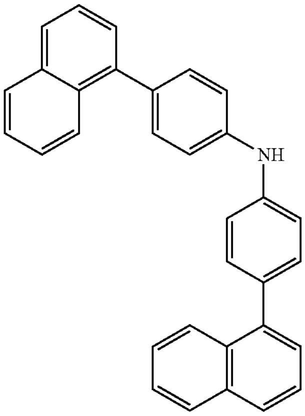
Sub 4-28
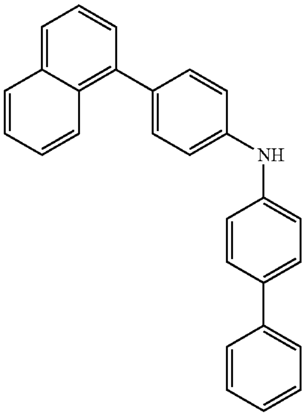
Sub 4-29
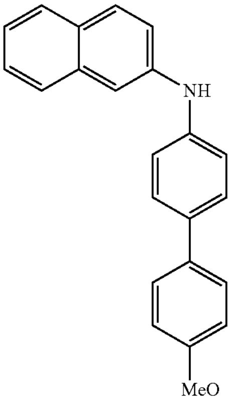

-continued
Sub 4-30
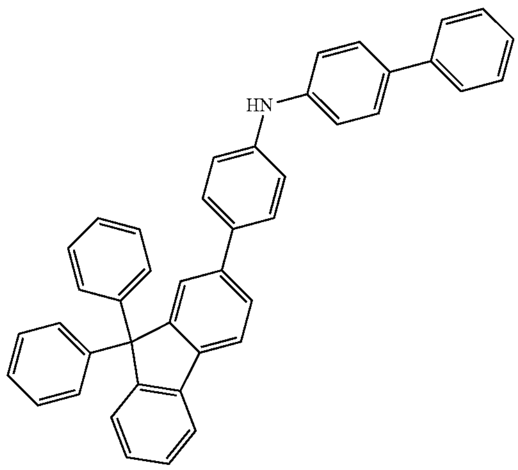
Sub 4-31
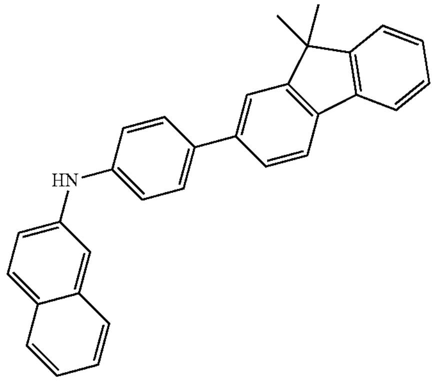
Sub 4-32
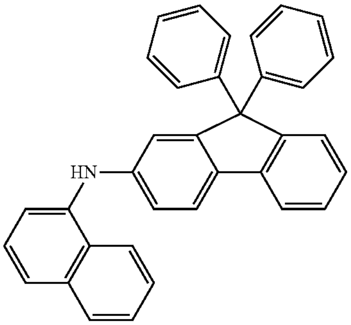
Sub 4-33
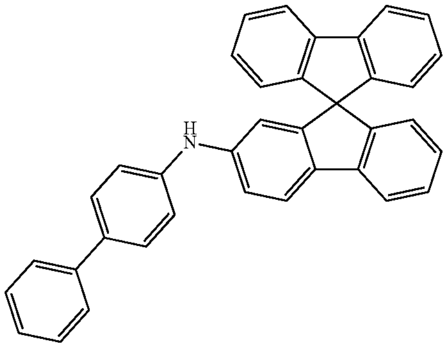
-continued
Sub 4-34
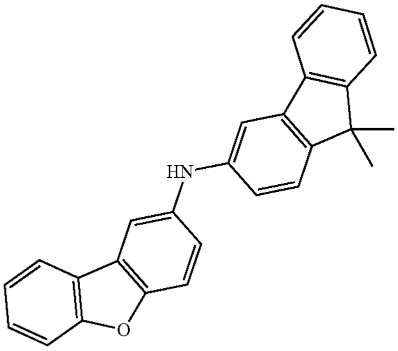
Sub 4-35
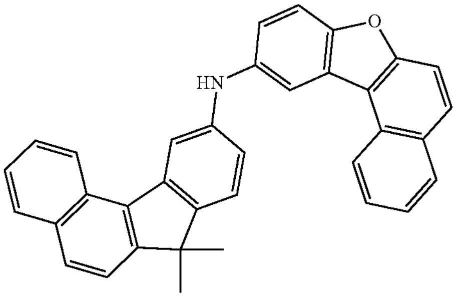
Sub 4-36
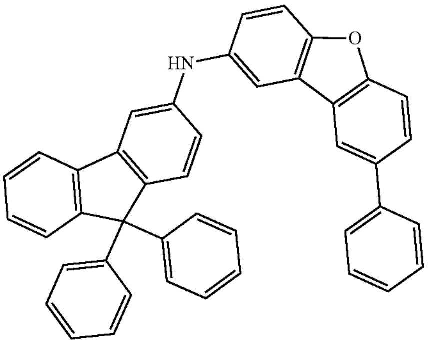
Sub 4-37
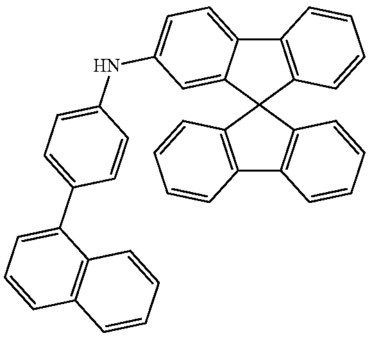

-continued
Sub 4-38
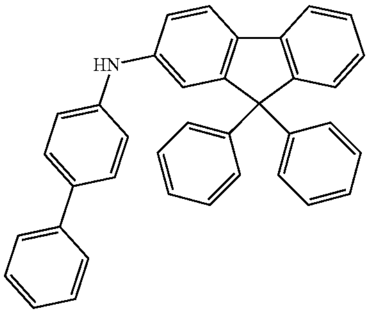
Sub 4-39
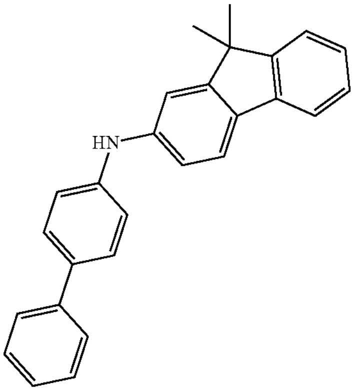
Sub 4-40
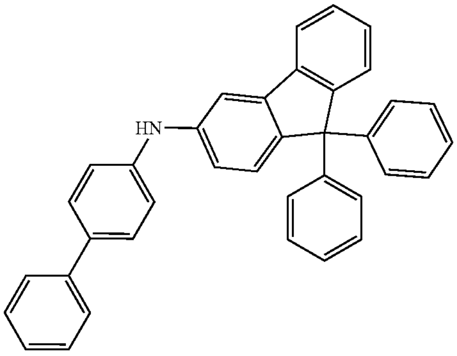
Sub 4-41
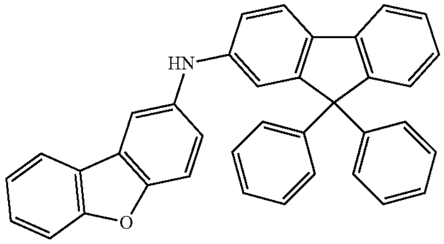
-continued
Sub 4-42
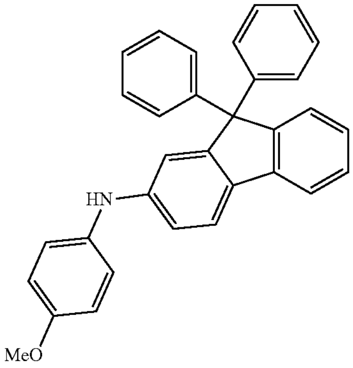
Sub 4-43
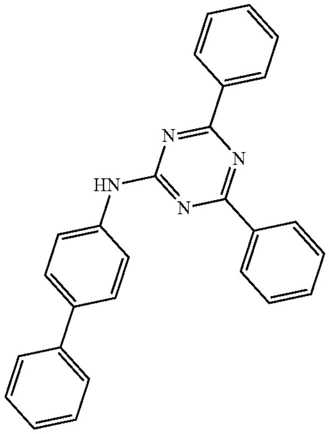
Sub 4-44
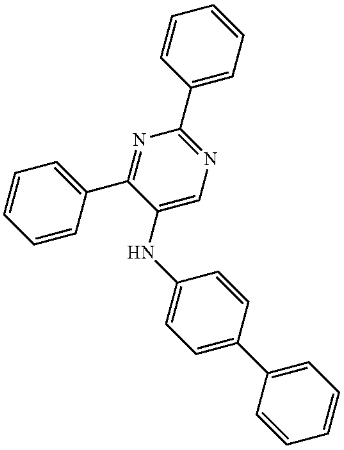
Sub 4-45
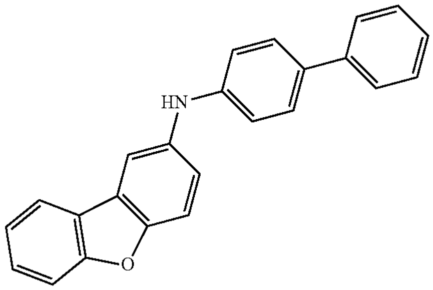

Sub 4-46
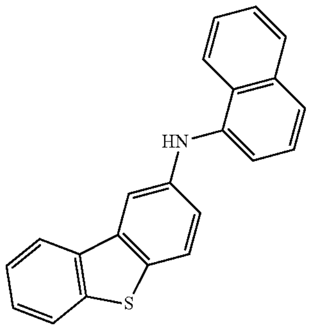
Sub 4-47
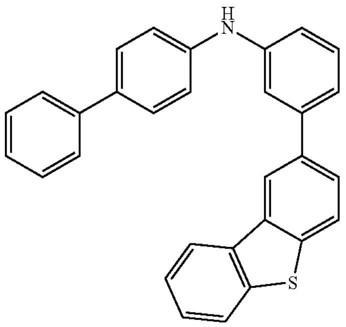
Sub 4-48
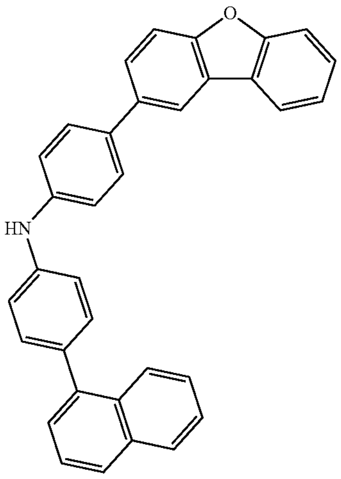
Sub 4-49
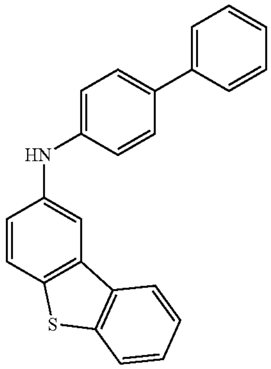
Sub 4-50
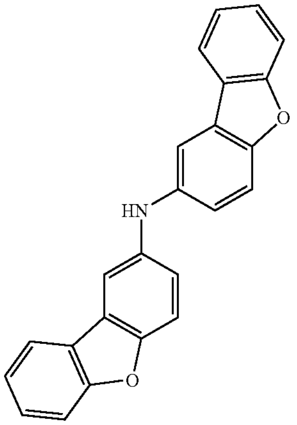
Sub 4-51
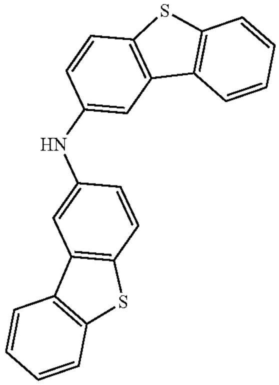
Sub 4-52
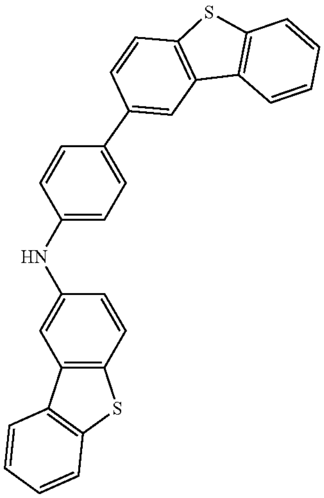

-continued
Sub 4-53
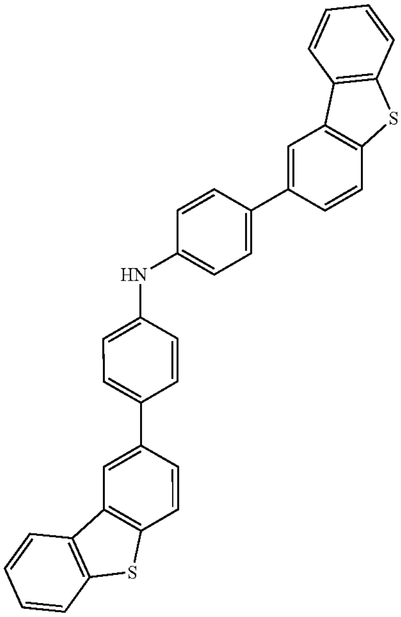
Sub 4-54
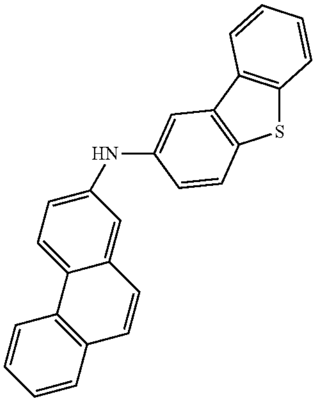
Sub 4-55
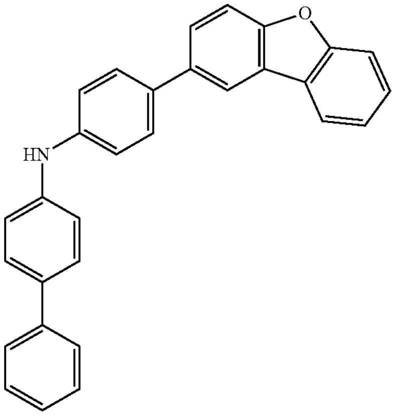
-continued
Sub 4-56
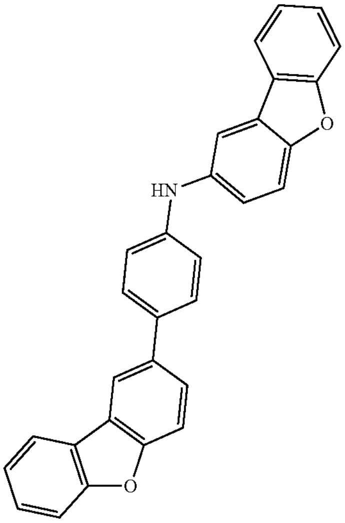
Sub 4-57
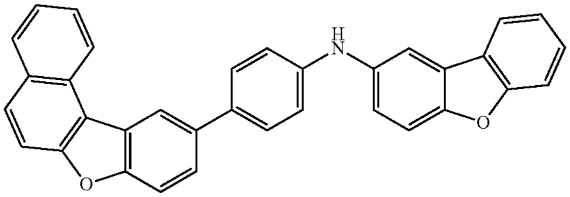
Sub 4-58
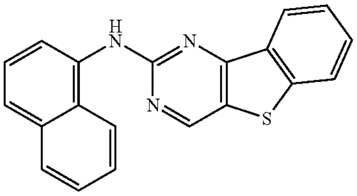
Sub 4-59
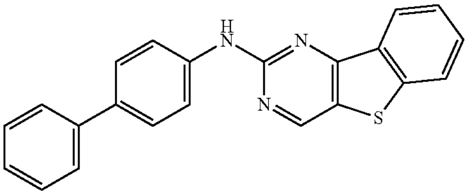
Sub 4-60
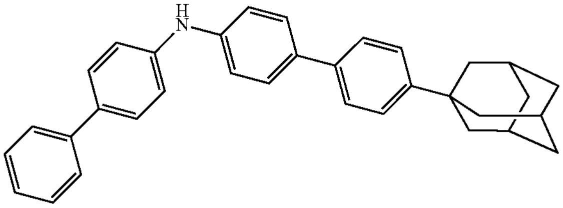
Table 5 shows FD-MS values of the compounds belonging to Sub 4.
TABLE 5
| compound | FD-MS |
| --- | --- |
| Sub 4-1 | m/z = 219.1($C_{16}H_{13}N$ = 219.29) |
| Sub 4-2 | m/z = 295.14($C_{22}H_{17}N$ = 295.39) |
| Sub 4-3 | m/z = 269.12($C_{20}H_{15}N$ = 269.35) |

TABLE 5-continued

| compound | FD-MS |
|---|---|
| Sub 4-4 | m/z = 169.09($C_{12}H_{11}N$ = 169.23) |
| Sub 4-5 | m/z = 245.12($C_{18}H_{15}N$ = 245.33) |
| Sub 4-6 | m/z = 321.15($C_{24}H_{19}N$ = 321.42) |
| Sub 4-7 | m/z = 269.12($C_{20}H_{15}N$ = 269.35) |
| Sub 4-8 | m/z = 345.15($C_{26}H_{19}N$ = 345.45) |
| Sub 4-9 | m/z = 345.15($C_{26}H_{19}N$ = 345.45) |
| Sub 4-10 | m/z = 325.18($C_{24}H_{23}N$ = 325.46) |
| Sub 4-11 | m/z = 245.12($C_{18}H_{15}N$ = 245.33) |
| Sub 4-12 | m/z = 397.18($C_{30}H_{23}N$ = 397.52) |
| Sub 4-13 | m/z = 447.2($C_{34}H_{25}N$ = 447.58) |
| Sub 4-14 | m/z = 371.17($C_{28}H_{21}N$ = 371.48) |
| Sub 4-15 | m/z = 421.18($C_{32}H_{23}N$ = 421.54) |
| Sub 4-16 | m/z = 295.14($C_{22}H_{17}N$ = 295.39) |
| Sub 4-17 | m/z = 397.18($C_{30}H_{23}N$ = 397.52) |
| Sub 4-18 | m/z = 321.15($C_{24}H_{19}N$ = 321.42) |
| Sub 4-19 | m/z = 245.12($C_{18}H_{15}N$ = 245.33) |
| Sub 4-20 | m/z = 321.15($C_{24}H_{19}N$ = 321.42) |
| Sub 4-21 | m/z = 321.15($C_{24}H_{19}N$ = 321.42) |
| Sub 4-22 | m/z = 295.14($C_{22}H_{17}N$ = 295.39) |
| Sub 4-23 | m/z = 313.13($C_{22}H_{16}FN$ = 313.88) |
| Sub 4-24 | m/z = 369.15($C_{28}H_{19}N$ = 369.47) |
| Sub 4-25 | m/z = 473.21($C_{36}H_{27}H$ = 473.62) |
| Sub 4-26 | m/z = 395.17($C_{30}H_{21}N$ = 395.51) |
| Sub 4-27 | m/z = 421.18($C_{32}H_{23}N$ = 421.54) |
| Sub 4-28 | m/z = 371.17($C_{28}H_{21}N$ = 371.48) |
| Sub 4-29 | m/z = 325.15($C_{23}H_{19}NO$ = 325.41) |
| Sub 4-30 | m/z = 561.25($C_{43}H_{31}N$ = 561.73) |
| Sub 4-31 | m/z = 411.2($C_{31}H_{25}N$ = 411.55) |
| Sub 4-32 | m/z = 459.2($C_{35}H_{25}N$ = 459.59) |
| Sub 4-33 | m/z = 483.2($C_{37}H_{25}N$ = 483.61) |
| Sub 4-34 | m/z = 375.16($C_{27}H_{21}NO$ = 375.47) |
| Sub 4-35 | m/z = 475.19($C_{35}H_{25}NO$ = 475.59) |
| Sub 4-36 | m/z = 575.22($C_{43}H_{29}NO$ = 575.71) |
| Sub 4-37 | m/z = 533.21($C_{41}H_{27}N$ = 533.67) |
| Sub 4-38 | m/z = 485.21($C_{37}H_{27}N$ = 485.63) |
| Sub 4-39 | m/z = 361.18($C_{27}H_{23}N$ = 361.49) |
| Sub 4-40 | m/z = 485.21($C_{37}H_{27}N$ = 485.63) |
| Sub 4-41 | m/z = 499.19($C_{37}H_{25}NO$ = 499.61) |
| Sub 4-42 | m/z = 439.19($C_{32}H_{25}NO$ = 439.56) |
| Sub 4-43 | m/z = 400.17($C_{27}H_{20}N4$ = 400.49) |
| Sub 4-44 | m/z = 399.17($C_{28}H_{21}N_3$ = 399.5) |
| Sub 4-45 | m/z = 335.13($C_{24}H_{17}NO$ = 335.41) |
| Sub 4-46 | m/z = 325.09($C_{22}H_{15}NS$ = 325.43) |
| Sub 4-47 | m/z = 427.14($C_{30}H_{21}NS$ = 427.57) |
| Sub 4-48 | m/z = 461.18($C_{34}H23NO$ = 461.56) |
| Sub 4-49 | m/z = 351.11($C_{24}H_{17}NS$ = 351.47) |
| Sub 4-50 | m/z = 349.11($C_{24}H{=}NO_2$ = 349.39) |
| Sub 4-51 | m/z = 381.06($C_{24}H_{15}NS_2$ = 381.51) |
| Sub 4-52 | m/z = 457.1($C_{30}H_{19}NS_2$ = 457.61) |
| Sub 4-53 | m/z = 533.13($C_{36}H_{23}NS_2$ = 533.71) |
| Sub 4-54 | m/z = 375.11($C_{26}H_{17}NS$ = 375.49) |
| Sub 4-55 | m/z = 411.16($C_{30}H_{21}NO$ = 411.5) |
| Sub 4-56 | m/z = 425.14($C_{30}H_{19}NO_2$ = 425.49) |
| Sub 4-57 | m/z = 475.16($C_{34}H_{21}NO_2$ = 475.55) |
| Sub 4-58 | m/z = 327.08($C_{20}H_{13}N_3S$= 327.41) |
| Sub 4-59 | m/z = 353.1($C_{22}H_{15}N_3S$ = 353.44) |
| Sub 4-60 | m/z = 455.26($C_{34}H_{33}N$ = 455.65) |

Sub 4 of the Reaction Scheme 2 can be synthesized according to the reaction routes of the following Reaction Scheme 6, but it is not limited thereto.

<Reaction Scheme 6>

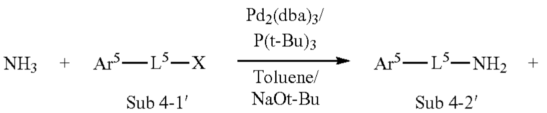

Sub 4-1′
X = Br, I, Cl

Sub 4-2′

-continued

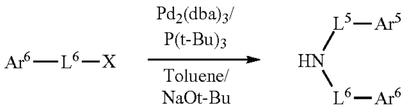

Sub 4-3′
X = Br, I, Cl

Sub 4

Synthesis Example of Sub 4-1

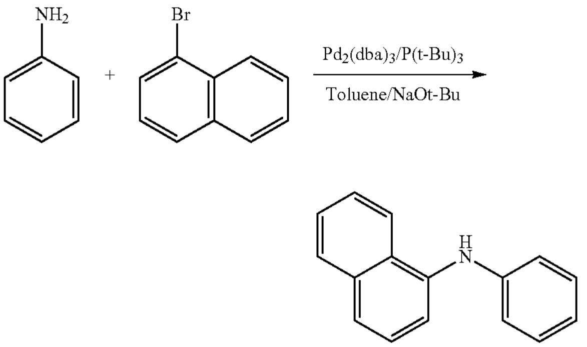

Sub 4-1

Aniline (15 g, 161.1 mmol), 1-bromonaphthalene (36.7 g, 177.2 mmol), $Pd_2(dba)_3$ (7.37 g, 8.05 mmol), $P(t-Bu)_3$ (3.26 g, 16.1 mmol), NaOt-Bu (51.08 g, 531.5 mmol) and toluene (1690 mL) were placed in a round bottom flask and the reaction proceeded at 100° C. When the reaction was completed, the reaction product was extracted with $CH_2Cl_2$ and water, and then the organic layer was dried with $MgSO_4$ and concentrated. Then, the concentrate was applied to silica gel column and recrystallized to obtain 25.4 g (yield: 72%) of Sub 4-1.

Synthesis Example of Sub 4-30

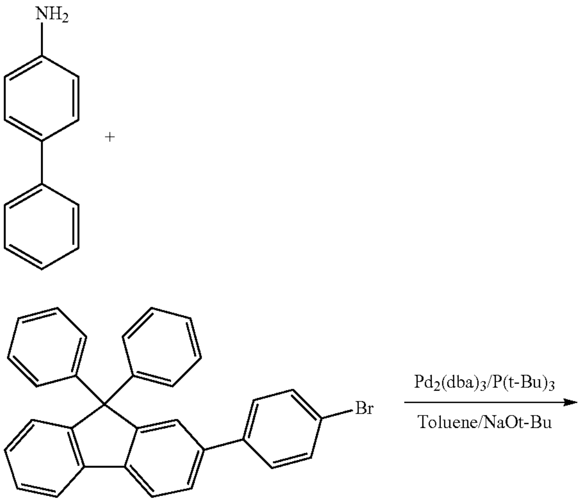

-continued

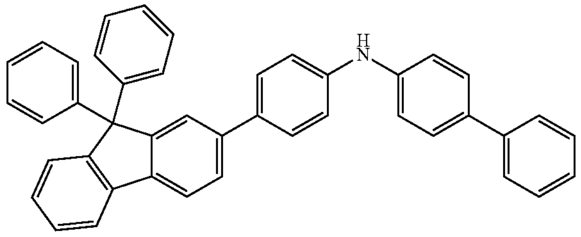

Sub 4-30

After 1,1'-biphenyl]-4-amine (15 g, 88.6 mmol), 2-(4-bromophenyl)-9,9-diphenyl-9H-fluorene (46.2 g, 97.5 mmol), $Pd_2(dba)_3$ (4.06 g, 4.43 mmol), $P(t\text{-}Bu)_3$ (1.8 g, 8.86 mmol), NaOt-Bu (28.1 g, 292.5 mmol) and toluene (931 mL) were placed in a round bottom flask, the reaction was carried out in the same manner as in the synthesis method of Sub 4-1 to obtain 34.9 (yield: 70%) of Sub 4-30.

Synthesis Example of Sub 4-46

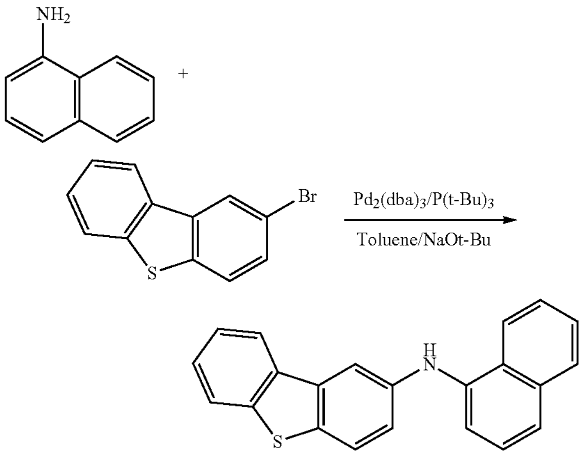

Sub 4-46

After naphthalen-1-amine (15 g, 104.8 mmol), 2-bromodibenzo[b,d]thiophene (30.3 g, 115.2 mmol), $Pd_2(dba)_3$ (4.8 g, 5.24 mmol), $P(t\text{-}Bu)_3$ (2.12 g, 10.48 mmol), NaOt-Bu (33.22 g, 345.7 mmol) and toluene (1100 mL) were placed in a round bottom flask, the reaction was carried out in the same manner as in the synthesis method of Sub 4-1 to obtain 24.9 g (yield: 73%) of Sub 4-46.

Synthesis Example of Sub 4-49

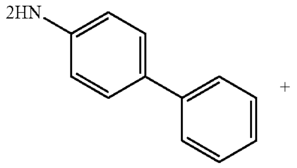

-continued

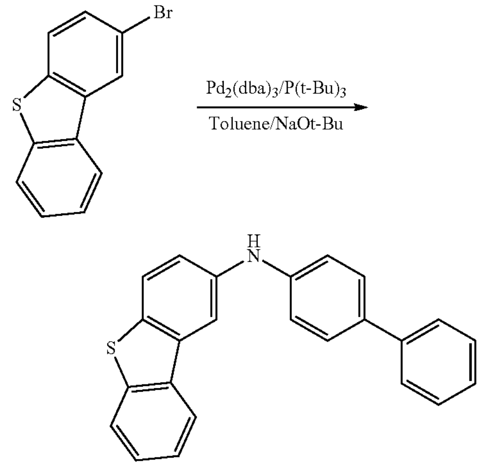

Sub 4-49

After [1,1'-biphenyl]-4-amine (15 g, 88.64 mmol), 2-bromodibenzo[b,d]thiophene (23.32 g, 88.64 mmol), $Pd_2(dba)_3$ (2.4 g, 2.66 mmol), $P(t\text{-}Bu)_3$ (17.93 g, 88.64 mmol), NaOt-Bu (17.04 g, 177.27 mmol) and toluene (886 mL) were placed in a round bottom flask, the reaction was carried out in the same manner as in the synthesis method of Sub 4-1 to obtain 24.61 g (yield: 79%) of Sub 4-49.

Synthesis Example of Sub 4-56

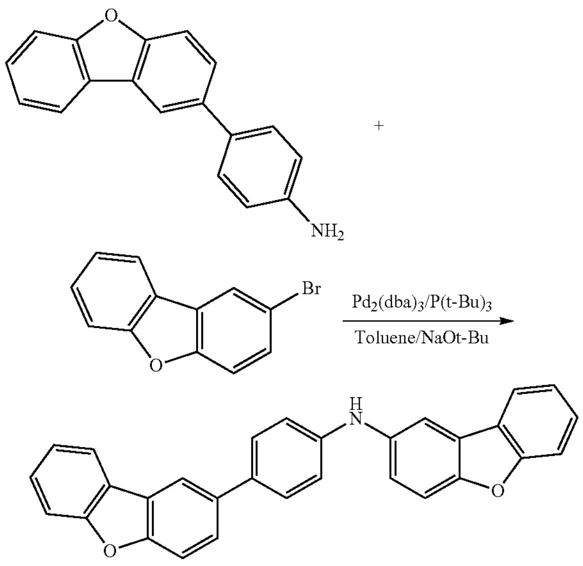

Sub 4-56

After 4-(dibenzo[b,d]furan-2-yl)aniline (15 g, 57.85 mmol), 2-bromodibenzo[b,d]furan (15.7 g, 63.63 mmol), $Pd_2(dba)_3$ (2.65 g, 2.89 mmol), $P(t\text{-}Bu)_3$ (1.17 g, 5.78 mmol), NaOt-Bu (18.35 g, 190.9 mmol) and toluene (607 mL) were placed in a round bottom flask, the reaction was carried out in the same manner as in the synthesis method of Sub 4-1 to obtain 17.2 g (yield: 70%) of Sub Sub 4-56.

3. Synthesis Example of a Final Product

Synthesis of 2-1

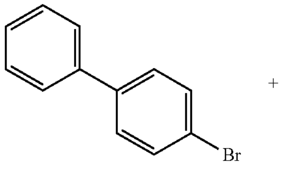

Sub 3-1

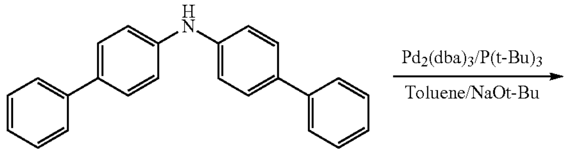

Sub 4-21

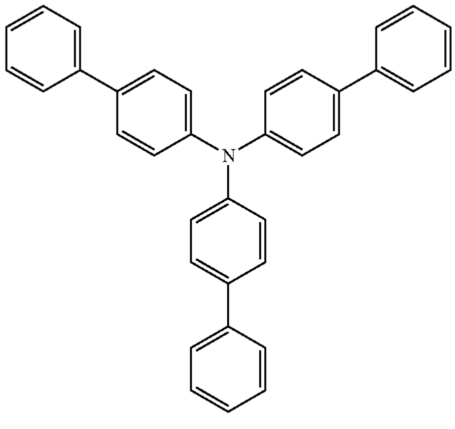

2-1

Sub 3-1 (10 g, 42.9 mmol), Sub 4-21 (13.79 g, 42.9 mmol), $Pd_2(dba)_3$ (1.18 g, 1.29 mmol), $P(t\text{-}Bu)_3$ (8.68 g, 42.9 mmol), NaOt-Bu (8.25 g, 85.80 mmol) and toluene (429 mL) were placed in a round bottom flask and the reaction proceeded at 100° C. When the reaction was completed, the reaction product was extracted with $CH_2Cl_2$ and water, and then the organic layer was dried with $MgSO_4$ and concentrated. Then, the concentrate was applied to silica gel column and recrystallized to obtain 15.6 g (yield: 77%) of the product 2-1.

Synthesis of 2-4

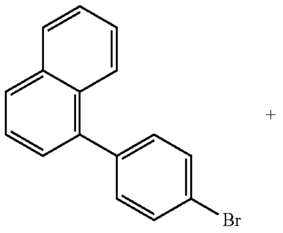

Sub 3-2

-continued

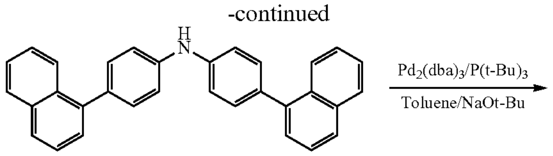

Sub 4-27

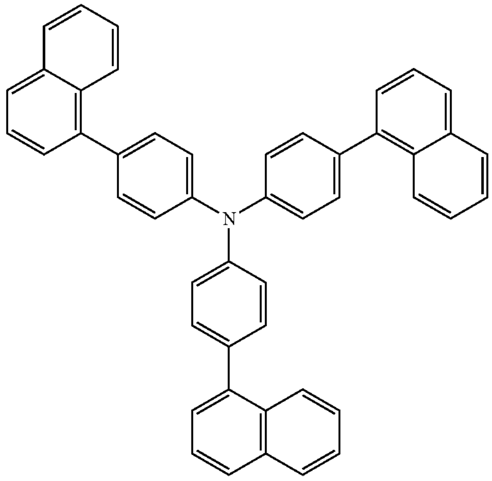

2-4

After Sub 3-2 (10 g, 35.3 mmol), Sub 4-27 (14.8 g, 35.31 mmol), $Pd_2(dba)_3$ (0.97 g, 1.06 mmol), $P(t\text{-}Bu)_3$ (7.14 g, 35.31 mmol), NaOt-Bu (6.79 g, 70.63 mmol) and toluene (353 mL) were placed in a round bottom flask, the reaction was carried out in the same manner as in the synthesis method of 2-1 to obtain 16.9 g (yield: 78%) of the product 2-4.

Synthesis Example of 2-9

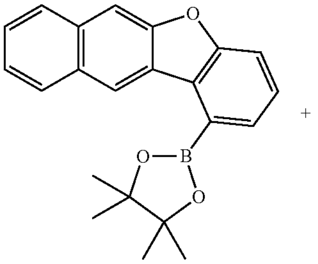

Sub 1-2

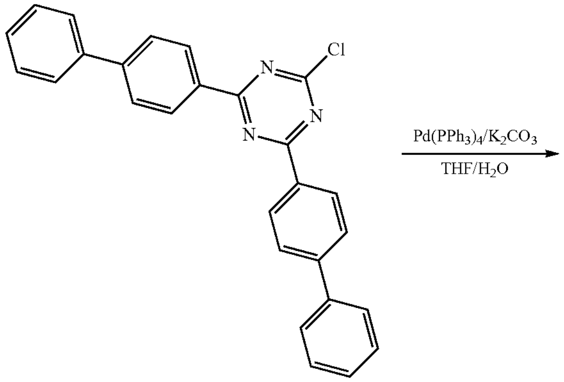

Sub 2-104

-continued

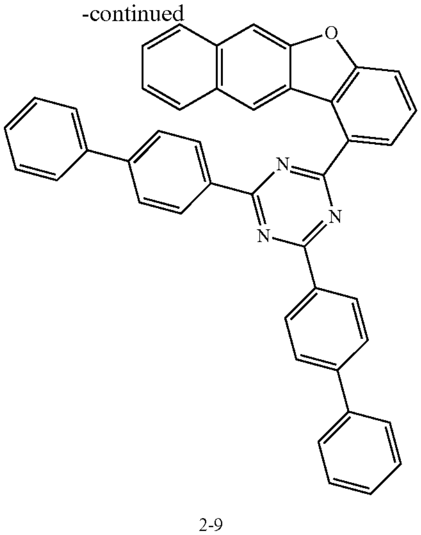

2-9

After adding THF (395 mL), Sub 2-104 (54.3 g, 129.24 mmol), $Pd(PPh_3)_4$ (4.98 g, 4.31 mmol), $K_2CO_3$ (44.66 g, 323.10 mmol) and water (197 mL) to Sub 1-2 (37.1 g, 107.7 mmol), the reaction was carried out in the same manner as in the synthesis method of 1-6 to obtain the product (55.5 g, 81%).

Synthesis of 2-10

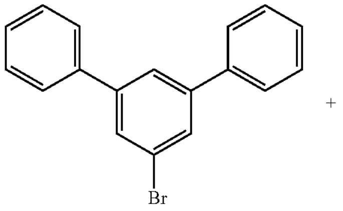

Sub 3-6

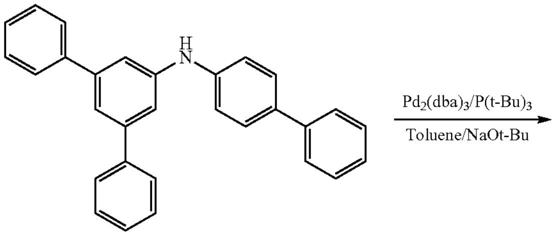

Sub 4-12

-continued

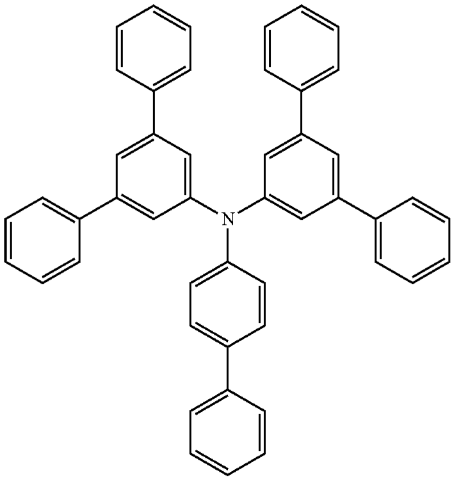

2-10

After Sub 3-6 (10 g, 32.34 mmol), Sub 4-12 (12.86 g, 32.34 mmol), $Pd_2(dba)_3$ (0.89 g, 0.97 mmol), $P(t\text{-}Bu)_3$ (6.54 g, 32.34 mmol), NaOt-Bu (6.22 g, 64.68 mmol) and toluene (323 mL) were placed in a round bottom flask, the reaction was carried out in the same manner as in the synthesis method of 2-1 to obtain 15.1 g (yield: 75%) of the product 2-10.

Synthesis Example of 2-11

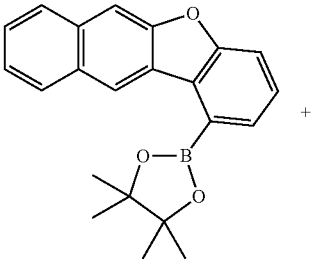

Sub 1-2

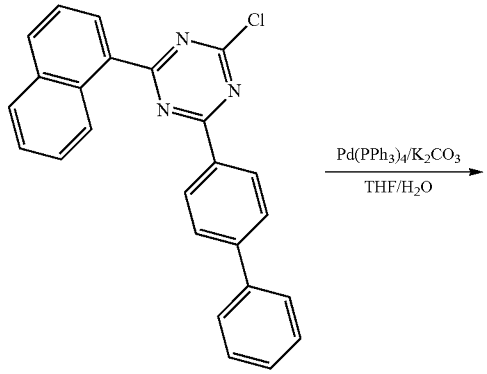

Sub 2-16

-continued

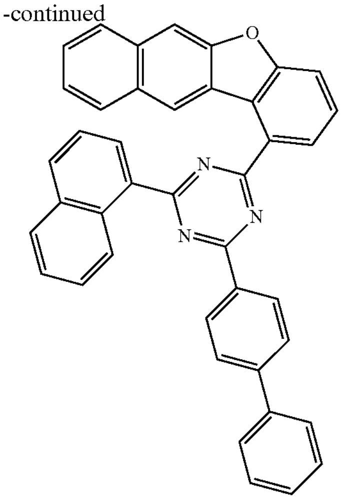

2-11

After adding THF (395 mL), Sub 2-16 (50.9 g, 129.24 mmol), $Pd(PFh_3)_4$ (4.98 g, 4.31 mmol), $K_2CO_3$ (44.66 g, 323.10 mmol) and water (197 mL) to Sub 1-2 (37.1 g, 107.7 mmol), the reaction was carried out in the same manner as in the synthesis method of 1-6 to obtain the product (50.8 g, 82%).

Synthesis of 2-19

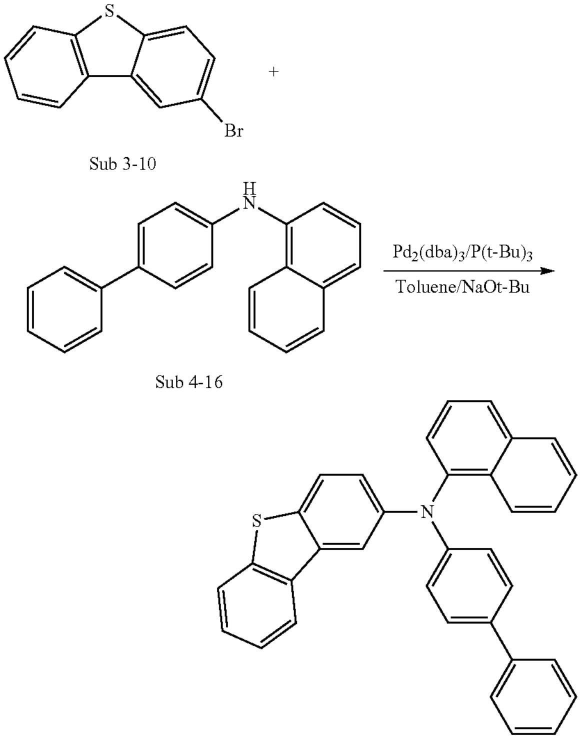

Sub 3-10

Sub 4-16

2-19

After Sub 3-10 (10 g, 38 mmol), Sub 4-16 (11.23 g, 38 mmol), $Pd_2(dba)_3$ (1.04 g, 1.14 mmol), $P(t\text{-}Bu)_3$ (7.69 g, 38 mmol), NaOt-Bu (7.3 g, 76 mmol) and toluene (380 mL) were placed in a round bottom flask, the reaction was carried out in the same manner as in the synthesis method of 2-1 to obtain 13.7 g (yield: 76%) of the product 2-19.

Synthesis of 2-68

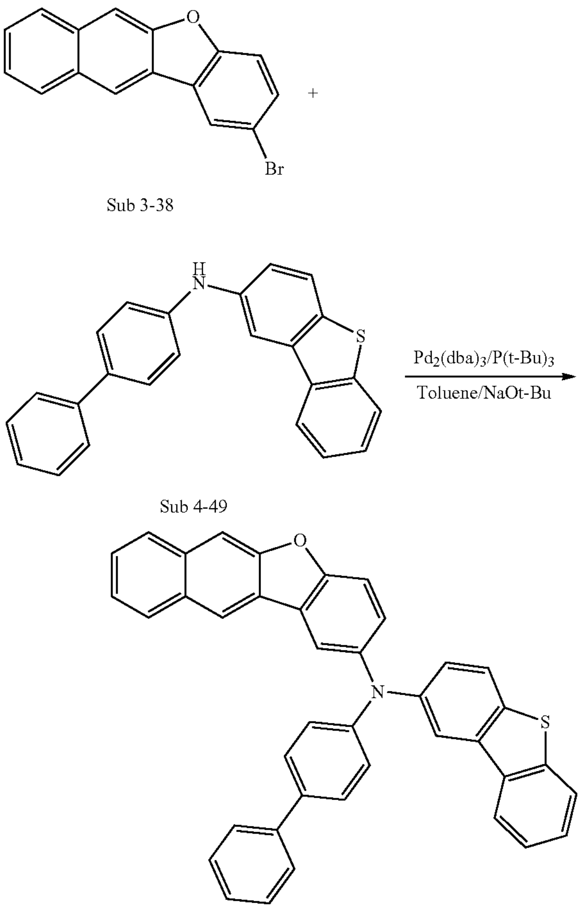

Sub 3-38

Sub 4-49

2-68

After Sub 3-38 (10 g, 33.65 mmol), Sub 4-49 (11.83 g, 33.65 mmol), $Pd_2(dba)_3$ (0.92 g, 1.01 mmol), $P(t\text{-}Bu)_3$ (6.81 g, 33.65 mmol), NaOt-Bu (6.47 g, 67.31 mmol) and toluene (337 mL) were placed in a round bottom flask, the reaction was carried out in the same manner as in the synthesis method of 2-1 to obtain 15.28 g (yield: 80%) of the product 2-68.

Synthesis of 2-24

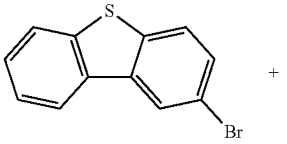

Sub 3-10

-continued

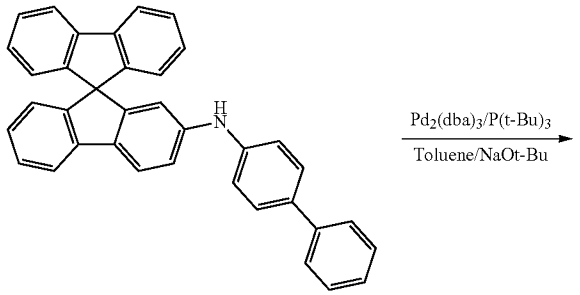

Sub 4-33

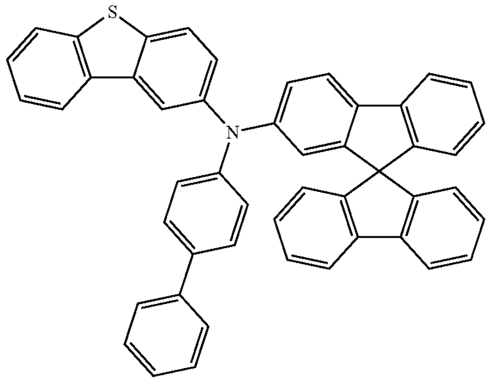

2-24

After Sub 3-10 (10 g, 38 mmol), Sub 4-33 (18.38 g, 38 mmol), $Pd_2(dba)_3$ (1.04 g, 1.14 mmol), $P(t\text{-}Bu)_3$ (7.69 g, 38 mmol), NaOt-Bu (7.3 g, 76 mmol) and toluene (380 mL) were placed in a round bottom flask, the reaction was carried out in the same manner as in the synthesis method of 2-1 to obtain 18.72 g (yield: 74%) of the product.

Synthesis of 2-29

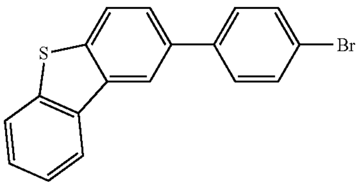

+

Sub 3-11

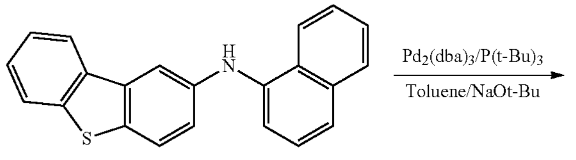

Sub 4-46

-continued

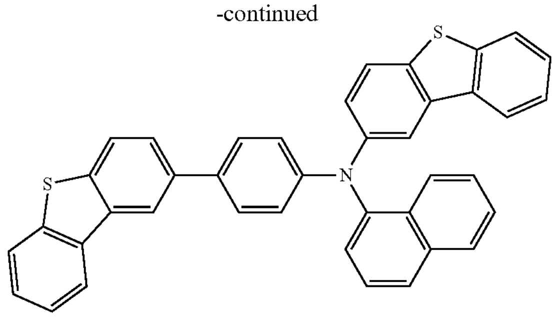

2-29

After Sub 3-11 (10 g, 29.48 mmol), Sub 4-46 (9.59 g, 29.48 mmol), $Pd_2(dba)_3$ (0.81 g, 0.88 mmol), $P(t\text{-}Bu)_3$ (5.96 g, 29.48 mmol), NaOt-Bu (5.67 g, 58.95 mmol) and toluene (295 mL) were placed in a round bottom flask, the reaction was carried out in the same manner as in the synthesis method of 2-1 to obtain 12.39 g (yield 72%) of the product 2-29.

Synthesis of 2-30

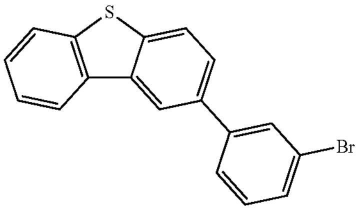

+

Sub 3-14

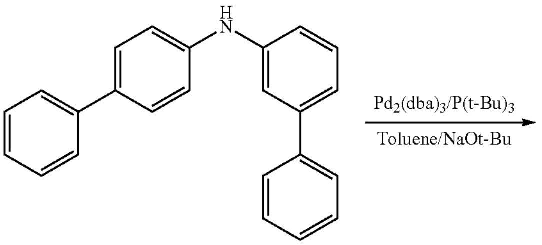

Sub 4-20

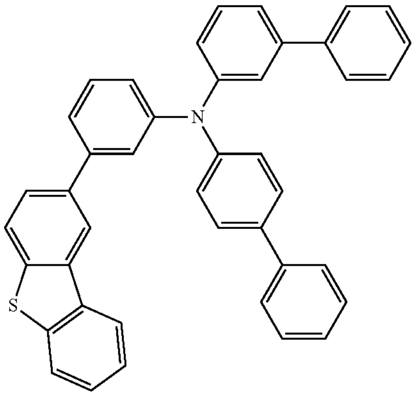

2-30

After Sub 3-14 (10 g, 29.48 mmol), Sub 4-20 (9.47 g, 29.48 mmol), $Pd_2(dba)_3$ (0.81 g, 0.88 mmol), $P(t\text{-}Bu)_3$ (5.96 g, 29.48 mmol), NaOt-Bu (5.67 g, 58.95 mmol) and toluene (295 mL) were placed in a round bottom flask, the reaction was carried out in the same manner as in the synthesis method of 2-1 to obtain 12.13 g (yield: 71%) of the product 2-30.

Synthesis of 2-36

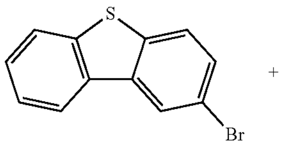

Sub 3-10

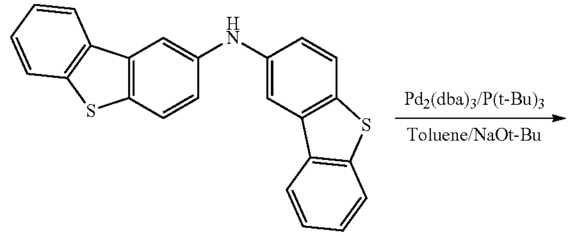

Sub 4-51

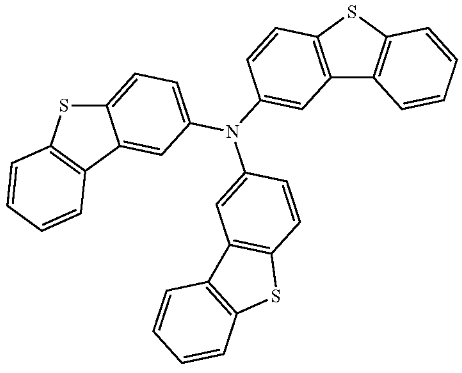

2-36

After Sub 3-10 (10 g, 38 mmol), Sub 4-51 (14.5 g, 38 mmol), $Pd_2(dba)_3$ (1.04 g, 1.14 mmol), $P(t\text{-}Bu)_3$ (7.69 g, 38 mmol), NaOt-Bu (7.30 g, 76 mmol) and toluene (380 mL) were placed in a round bottom flask, the reaction was carried out in the same manner as in the synthesis method of 2-1 to obtain 16.5 g (yield: 77%) of the product 2-36.

Synthesis of 2-50

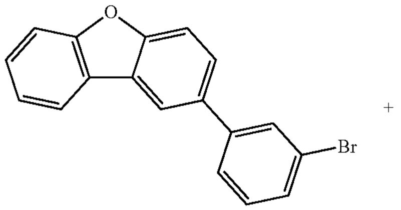

Sub 3-40

-continued

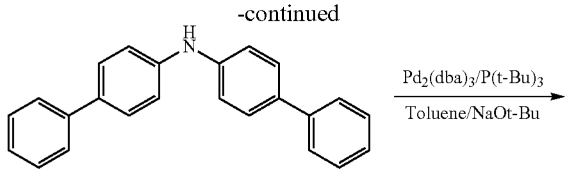

Sub 4-21

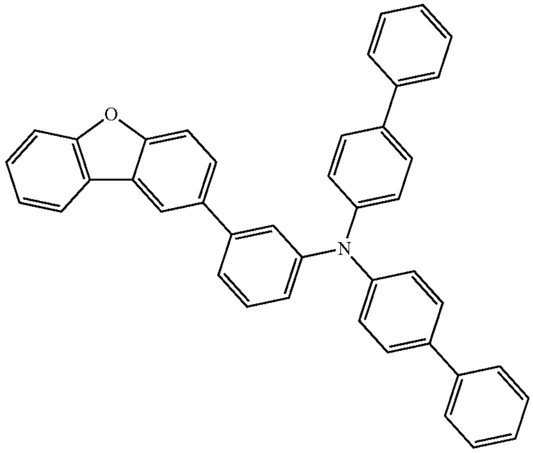

2-50

After Sub 3-40 (10 g, 30.94 mmol), Sub 4-21 (9.95 g, 30.94 mmol), $Pd_2(dba)_3$ (0.85 g, 0.93 mmol), $P(t\text{-}Bu)_3$ (6.26 g, 30.94 mmol), NaOt-Bu (5.95 g, 61.88 mmol) and toluene (309 mL) were placed in a round bottom flask, the reaction was carried out in the same manner as in the synthesis method of 2-1 to obtain 13.26 g (yield: 76%) of the product 2-50.

Synthesis of 2-52

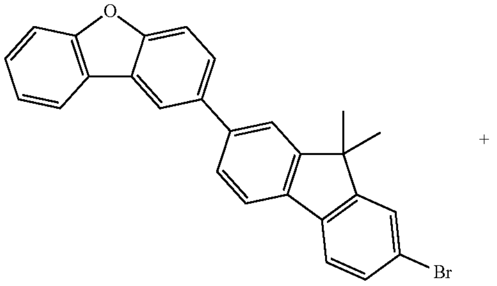

Sub 3-33

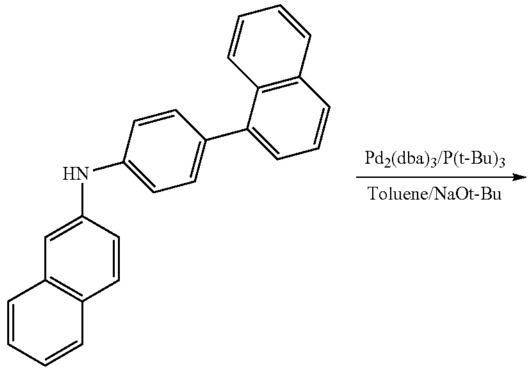

Sub 4-9

-continued

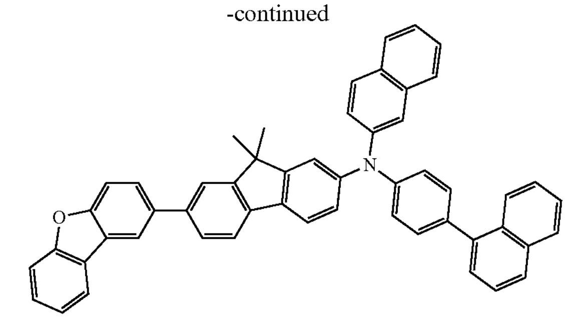

2-52

After Sub 3-33 (10 g, 22.76 mmol), Sub 4-9 (7.86 g, 22.76 mmol), $Pd_2(dba)_3$ (0.63 g, 0.68 mmol), $P(t-Bu)_3$ (4.60 g, 22.76 mmol), NaOt-Bu (4.38 g, 45.52 mmol) and toluene (228 mL) were placed in a round bottom flask, the reaction was carried out in the same manner as in the synthesis method of 2-1 to obtain 11.38 g (yield: 71%) of the product 2-52.

Synthesis of 2-60

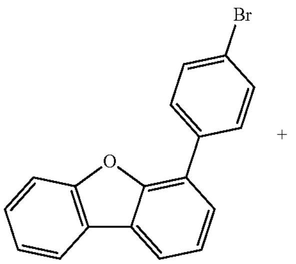

Sub 3-35

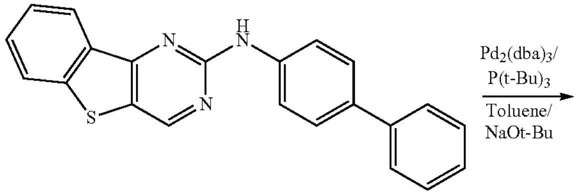

Sub 4-59

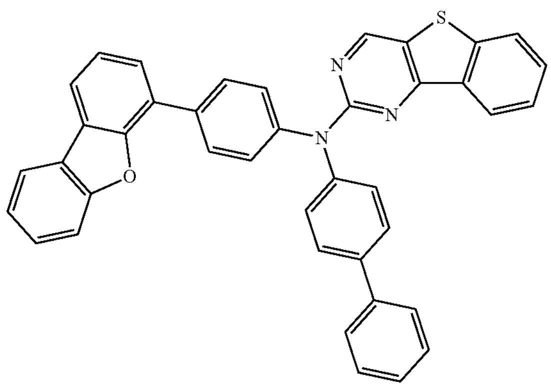

2-60

After Sub 3-35 (10 g, 30.94 mmol), Sub 4-59 (10.94 g, 30.94 mmol), $Pd_2(dba)_3$ (0.85 g, 0.93 mmol), $P(t-Bu)_3$ (6.26 g, 30.94 mmol), NaOt-Bu (5.95 g, 61.88 mmol) and toluene (309 mL) were placed in a round bottom flask, the reaction was carried out in the same manner as in the synthesis method of 2-1 to obtain 13.46 g (yield: 73%) of the product 2-60.

Synthesis of 2-85

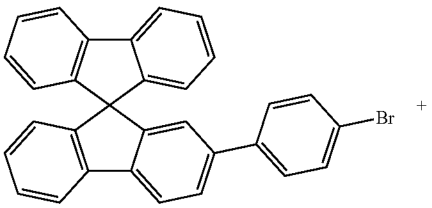

Sub 3-49

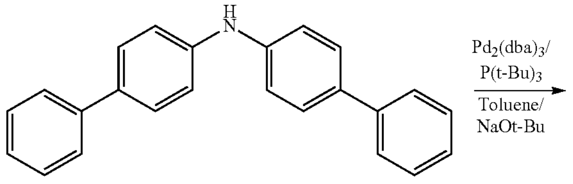

Sub 4-21

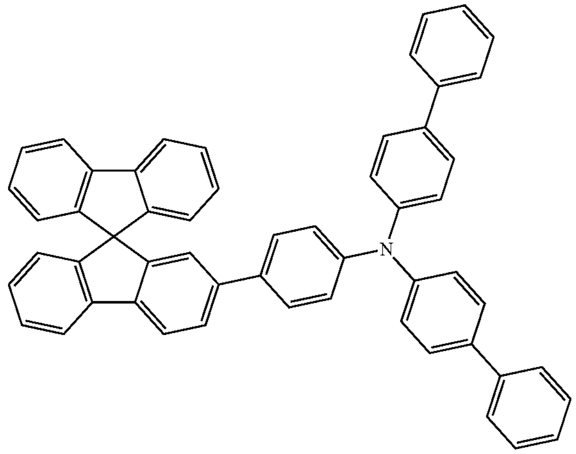

2-85

After Sub 3-49 (10 g, 21.21 mmol), Sub 4-21 (6.82 g, 21.21 mmol), $Pd_2(dba)_3$ (0.58 g, 0.64 mmol), $P(t-Bu)_3$ (4.29 g, 21.21 mmol), NaOt-Bu (4.08 g, 42.43 mmol) and toluene (212 mL) were placed in a round bottom flask, the reaction was carried out in the same manner as in the synthesis method of 2-1 to obtain 10.57 g (yield: 70%) of the product 2-85.

Synthesis of 2-89
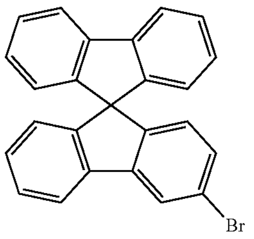
+
Sub 3-50
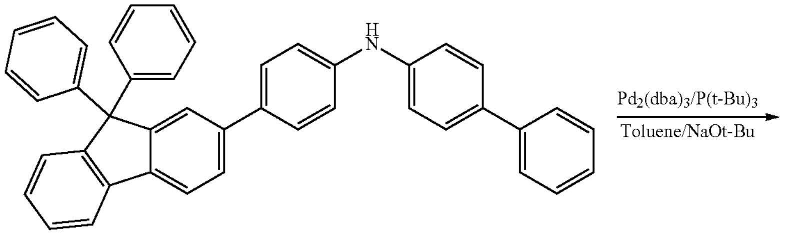
Sub 4-30
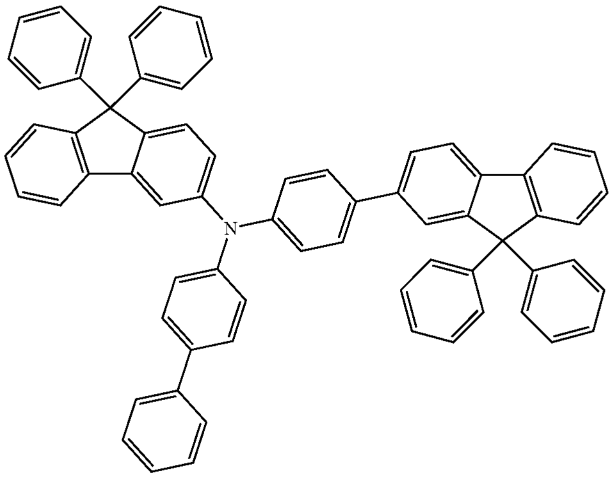
2-89
After Sub 3-50 (10 g, 25.17 mmol), Sub 4-30 (14.14 g, 25.17 mmol), $Pd_2(dba)_3$ (0.69 g, 0.76 mmol), $P(t\text{-}Bu)_3$ (5.09 g, 25.17 mmol), NaOt-Bu (4.84 g, 50.34 mmol) and toluene (252 mL) were placed in a round bottom flask, the reaction was carried out in the same manner as in the synthesis method of 2-1 to obtain 15.91 g (yield: 72%) of the product 2-89.

Synthesis of 3-1

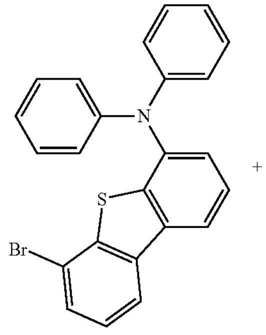

Sub 3-1-1

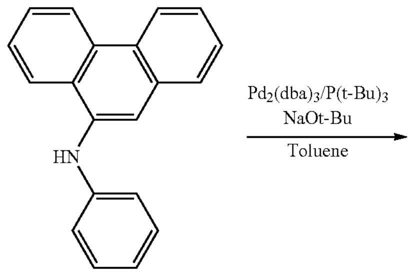

Sub 4-17

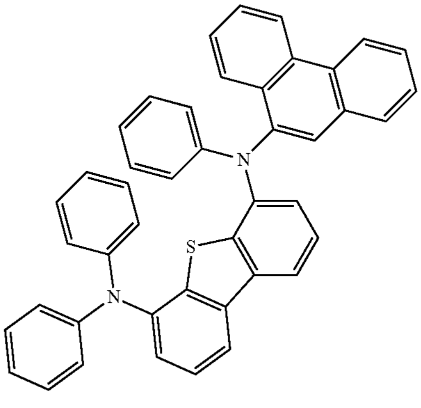

3-1

After dissolving Sub 3-3-1 (5.97 g, 13.87 mmol) in toluene (140 ml), Sub 4-17 (3.74 g, 13.87 mmol), $Pd_2(dba)_3$ (0.38 g, 0.42 mmol), $P(t\text{-}Bu)_3$ (0.28 g, 1.39 mmol) and NaOt-Bu (2.67 g, 27.74 mmol) were added to the solution and the mixture was stirred at 100° C. When the reaction was completed, the reaction product was extracted with $CH_2Cl_2$ and water, and then the organic layer was dried with $MgSO_4$. Then, the concentrate was applied to silica gel column and recrystallized to obtain 6.09 g (yield: 71%) of the product.

Synthesis of 3-2

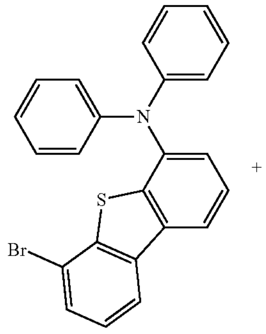

Sub 3-1-1

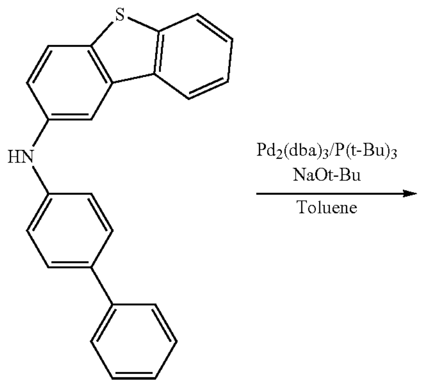

Sub 4-37

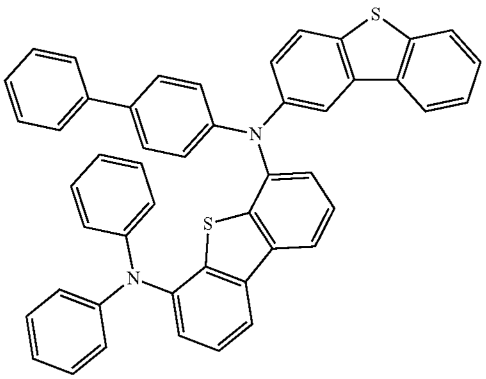

3-2

After adding Sub 4-37 (4.32 g, 12.29 mmol), $Pd_2(dba)_3$ (0.34 g, 0.37 mmol) $P(t\text{-}Bu)_3$ (0.25 g, 1.23 mmol), NaOt-Bu (2.36 g, 24.58 mmol) and toluene (125 ml) to Sub 3-3-1 (5.29 g, 12.29 mmol), the reaction was carried out in the same manner as in the synthesis method of 3-1 to obtain 6.81 g (yield: 79%) of the product.

Synthesis of 3-4
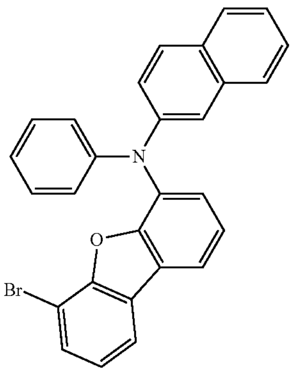
Sub 3-1-3
+
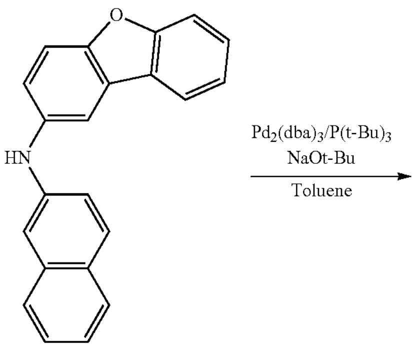
Sub 4-41
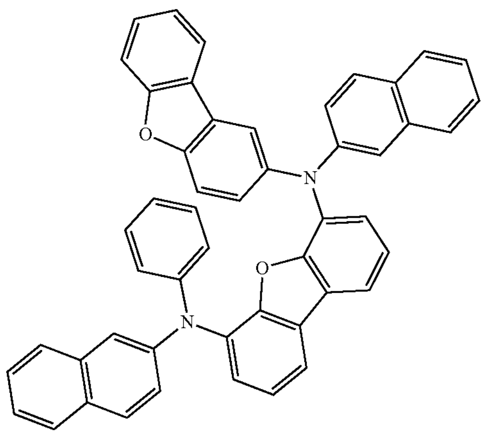
3-4
After adding Sub 4-41 (4.08 g, 13.20 mmol), $Pd_2(dba)_3$ (0.36 g, 0.40 mmol) $P(t\text{-}Bu)_3$ (0.27 g, 1.32 mmol), NaOt-Bu (2.54 g, 26.40 mmol) and toluene (130 ml) to Sub 3-3-3 (6.13 g, 13.20 mmol), the reaction was carried out in the same manner as in the synthesis method of 3-1 to obtain 7.32 g (yield: 80%) of the product.
Synthesis of 3-10
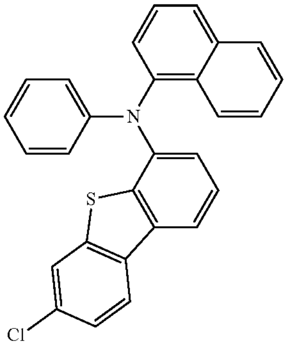
Sub 3-1-5
+
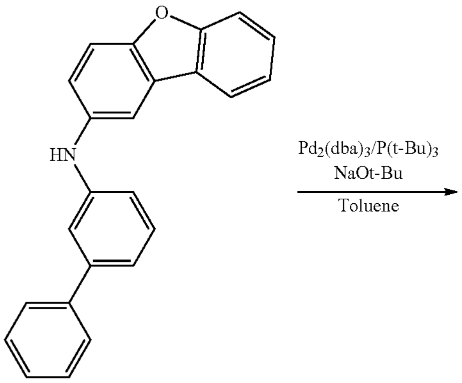
Sub 4-43
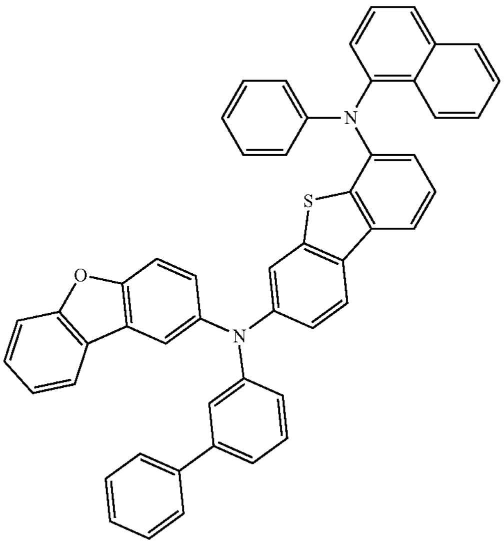
3-10
After adding Sub 4-43 (4.28 g, 12.75 mmol), $Pd_2(dba)_3$ (0.35 g, 0.38 mmol) $P(t\text{-}Bu)_3$ (0.26 g, 1.28 mmol), NaOt-Bu (2.45 g, 25.51 mmol) and toluene (130 ml) to Sub 3-3-5 (5.56 g, 12.75 mmol), the reaction was carried out in the same manner as in the synthesis method of 3-1 to obtain 8.06 g (yield: 86%) of the product.

Synthesis of 3-24

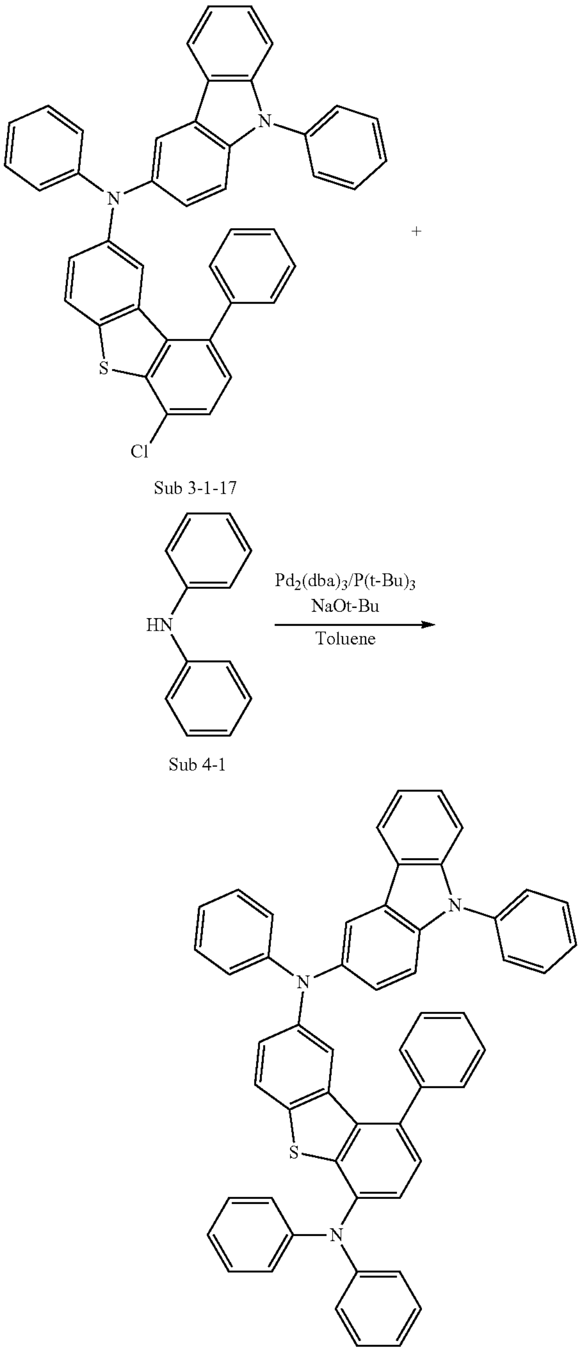

Sub 3-1-17

Sub 4-1

3-24

After adding Sub 4-1 (1.67 g, 9.85 mmol), $Pd_2(dba)_3$ (0.27 g, 0.30 mmol) $P(t\text{-}Bu)_3$ (0.20 g, 0.99 mmol), NaOt-Bu (1.89 g, 19.71 mmol) and toluene (100 ml) to Sub 3-3-17 (6.18 g, 9.85 mmol), the reaction was carried out in the same manner as in the synthesis method of 3-1 to obtain 5.62 g (yield: 75%) of the product.

Synthesis of 3-122

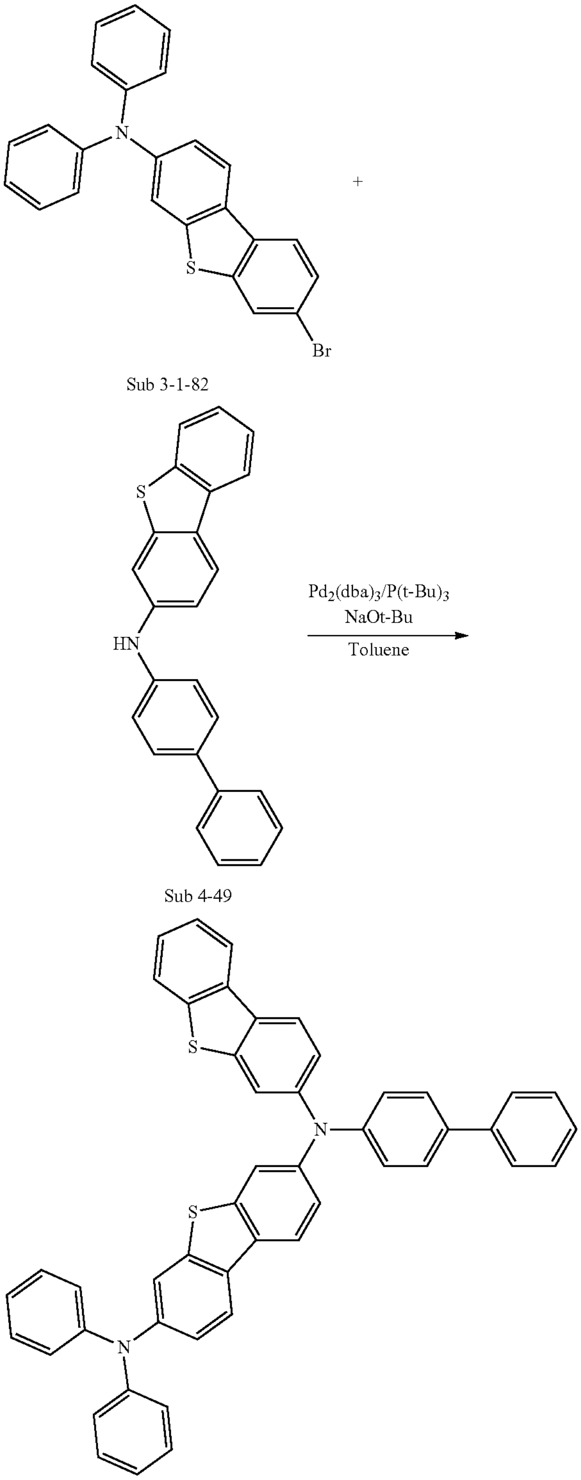

Sub 3-1-82

Sub 4-49

3-122

After adding Sub 4-49 (4.12 g, 11.73 mmol), $Pd_2(dba)_3$ (0.32 g, 0.35 mmol) $P(t\text{-}Bu)_3$ (0.24 g, 1.17 mmol), NaOt-Bu (2.26 g, 23.47 mmol) and toluene (120 ml) to Sub 3-3-82 (5.05 g, 11.73 mmol), the reaction was carried out in the same manner as in the synthesis method of 3-1 to obtain 7.65 g (yield: 93%) of the product.

Synthesis of 3-125

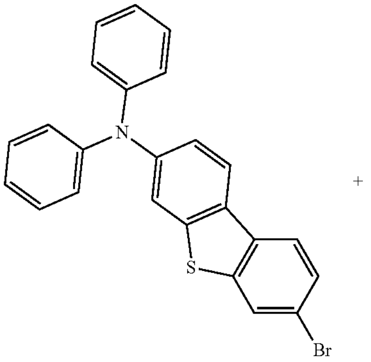

Sub 3-1-82

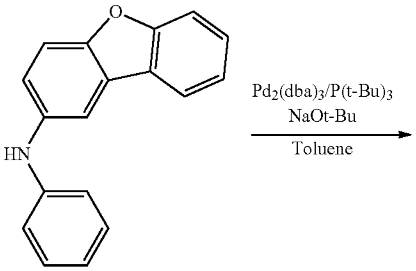

Sub 4-40

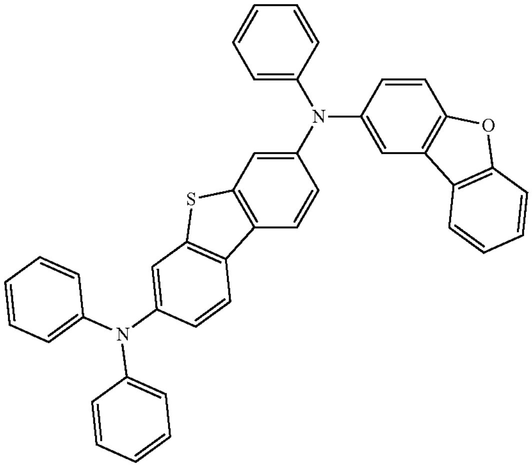

3-125

After adding Sub 4-40 (3.13 g, 12.08 mmol), $Pd_2(dba)_3$ (0.33 g, 0.36 mmol) $P(t\text{-}Bu)_3$ (0.24 g, 1.21 mmol), NaOt-Bu (2.32 g, 24.17 mmol) and toluene (120 ml) to Sub 3-3-82 (5.20 g, 12.08 mmol), the reaction was carried out in the same manner as in the synthesis method of 3-1 to obtain 6.69 g (yield: 91%) of the product.

Synthesis of 3-141

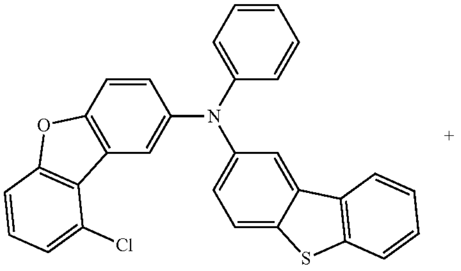

Sub 3-1-102

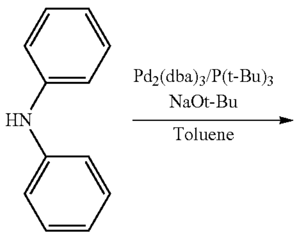

Sub 4-1

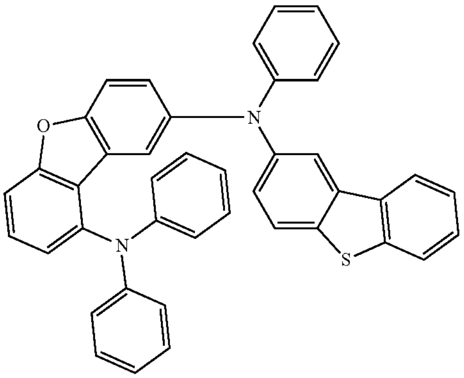

3-141

After adding Sub 4-1 (2.23 g, 13.15 mmol), $Pd_2(dba)_3$ (0.36 g, 0.39 mmol) $P(t\text{-}Bu)_3$ (0.27 g, 1.32 mmol), NaOt-Bu (2.53 g, 26.30 mmol) and toluene (130 ml) to Sub 3-3-102 (6.26 g, 13.15 mmol), the reaction was carried out in the same manner as in the synthesis method of 3-1 to obtain 6.57 g (yield: 82%) of the product.

Synthesis of 3-146

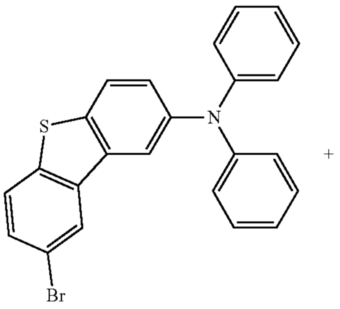

Sub 3-1-104

-continued

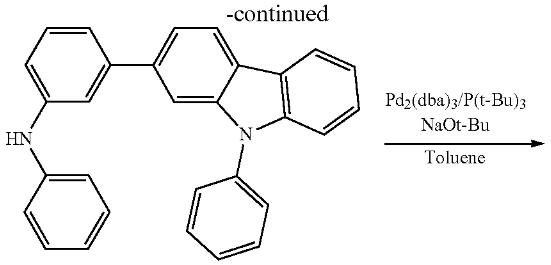

Sub 4-83

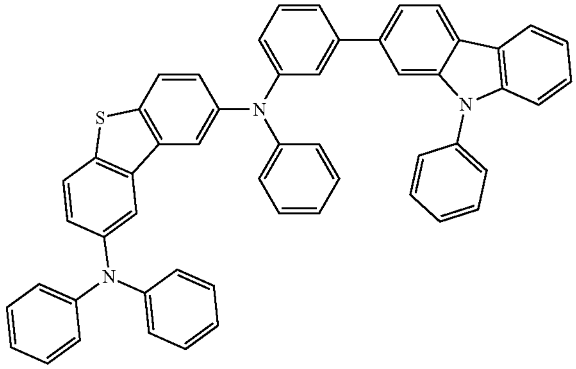

3-146

After adding Sub 4-83 (5.84 g, 14.22 mmol), $Pd_2(dba)_3$ (0.39 g, 0.43 mmol) $P(t\text{-}Bu)_3$ (0.29 g, 1.42 mmol), NaOt-Bu (2.73 g, 28.43 mmol) and toluene (140 ml) to Sub 3-3-104 (6.12 g, 14.22 mmol), the reaction was carried out in the same manner as in the synthesis method of 3-1 to obtain 8.00 g (yield: 74%) of the product.

Synthesis of 3-158

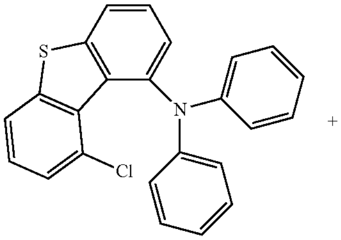

Sub 3-1-112

+

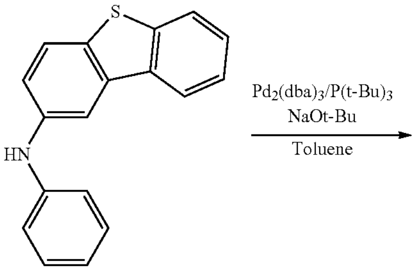

Sub 4-29

-continued

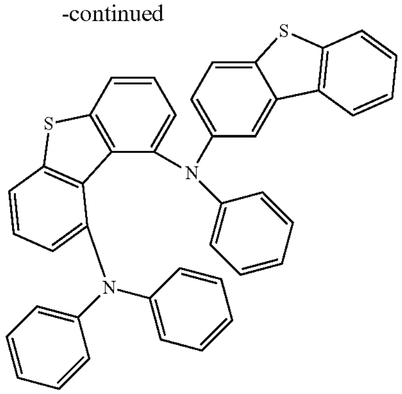

3-158

After adding Sub 4-29 (4.10 g, 14.90 mmol), $Pd_2(dba)_3$ (0.41 g, 0.45 mmol) $P(t\text{-}Bu)_3$ (0.30 g, 1.49 mmol), NaOt-Bu (2.86 g, 29.80 mmol) and toluene (150 ml) to Sub 3-3-112 (5.75 g, 14.90 mmol), the reaction was carried out in the same manner as in the synthesis method of 3-1 to obtain 6.24 g (yield: 67%) of the product.

Synthesis of 3-175

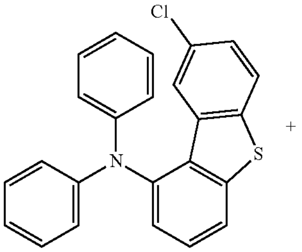

Sub 3-1-175

+

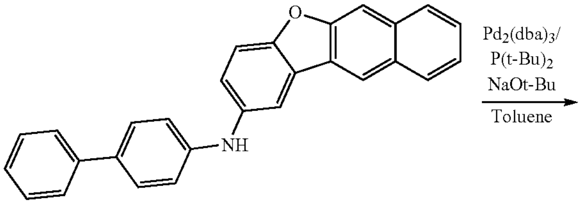

Sub 4-61

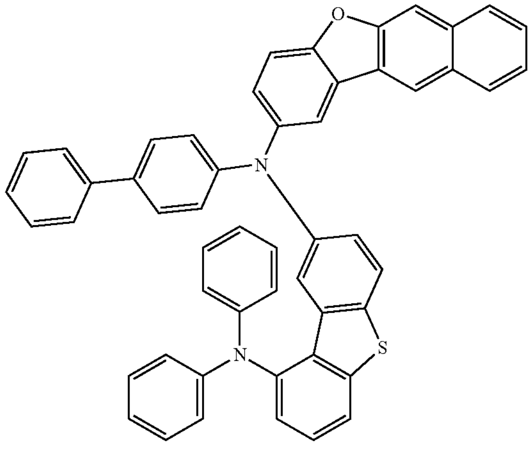

3-175

After adding Sub 4-61 (5.74 g, 14.90 mmol), $Pd_2(dba)_3$ (0.41 g, 0.45 mmol) $P(t-Bu)_3$ (0.30 g, 1.49 mmol), NaOt-Bu (2.86 g, 29.80 mmol) and toluene (150 ml) to Sub 3-3-175 (5.75 g, 14.90 mmol), the reaction was carried out in the same manner as in the synthesis method of 3-1 to obtain 7.67 g (yield: 67%) of the product.

The FD-MS values of the compounds 2-1 to 2-96 and 3-1 to 3-175 prepared according to the above synthesis examples are shown in the following Tables 6 and 7, respectively.

TABLE 6

| compound | FD-MS |
|---|---|
| 2-1 | m/z = 473.21($C_{36}H_{27}N$ = 473.61) |
| 2-2 | m/z = 523.23($C_{40}H_{29}N$ = 523.66) |
| 2-3 | m/z = 573.25($C_{44}H_{31}N$ = 573.72) |
| 2-4 | m/z = 623.26($C_{48}H_{33}N$ = 623.78) |
| 2-5 | m/z = 447.20($C_{34}H_{25}N$ = 447.57) |
| 2-6 | m/z = 371.17($C_{28}H_{21}N$ = 371.47) |
| 2-7 | m/z = 471.20($C_{36}H_{25}N$ = 471.59) |
| 2-8 | m/z = 521.21($C_{40}H_{27}N$ = 521.65) |
| 2-9 | m/z = 549.25($C_{42}H_{31}N$ = 549.70) |
| 2-10 | m/z = 625.28($C_{48}H_{35}N$ = 625.80) |
| 2-11 | m/z = 675.29($C_{52}H_{37}N$ = 675.86) |
| 2-12 | m/z = 473.21($C_{36}H_{27}N$ = 473.61) |
| 2-13 | m/z = 523.23($C_{40}H_{29}N$ = 523.66) |
| 2-14 | m/z = 623.26($C_{48}H_{33}N$ = 623.78) |
| 2-15 | m/z = 549.25($C_{42}H_{31}N$ = 549.70) |
| 2-16 | m/z = 625.28($C_{48}H_{35}N$ = 625.80) |
| 2-17 | m/z = 503.17($C_{38}H_{25}NS$ = 503.66) |
| 2-18 | m/z = 603.20($C_{44}H_{29}NS$ = 603.77) |
| 2-19 | m/z = 477.16($C_{34}H_{23}NS$ = 477.62) |
| 2-20 | m/z = 503.17($C_{36}H_{25}NS$ = 503.66) |
| 2-21 | m/z = 451.14($C_{32}H_{21}NS$ = 451.58) |
| 2-22 | m/z = 593.22($C_{43}H_{31}NS$ = 593.78) |
| 2-23 | m/z = 641.22($C_{47}H_{31}NS$ = 641.82) |
| 2-24 | m/z = 665.22($C_{49}H_{31}NS$ = 665.84) |
| 2-25 | m/z = 503.17($C_{36}H_{25}NS$ = 503.66) |
| 2-26 | m/z = 655.23($C_{48}H_{33}NS$ = 655.85) |
| 2-27 | m/z = 695.26($C_{51}H_{37}NS$ = 695.91) |
| 2-28 | m/z = 593.18($C_{42}H_{27}NOS$ = 593.73) |
| 2-29 | m/z = 583.14($C_{40}H_{25}NS_2$ = 583.76) |
| 2-30 | m/z = 579.20($C_{42}H_{29}NS$ = 579.75) |
| 2-31 | m/z = 685.19($C_{48}H_{31}NS_2$ = 685.90) |
| 2-32 | m/z = 719.23($C_{52}H_{33}NOS$ = 719.89) |
| 2-33 | m/z = 629.22($C_{46}H_{31}NS$ = 629.81) |
| 2-34 | m/z = 629.22($C_{46}H_{31}NS$ = 629.81) |
| 2-35 | m/z = 603.20($C_{46}H_{29}NS$ = 603.77) |
| 2-36 | m/z = 563.08($C_{36}H_{21}NS_3$ = 563.75) |
| 2-37 | m/z = 639.11($C_{42}H_{25}NS_3$ = 639.85) |
| 2-38 | m/z = 715.15($C_{48}H_{29}NS_3$ = 715.95) |
| 2-39 | m/z = 791.18($C_{54}H_{33}NS_3$ = 792.04) |
| 2-40 | m/z = 607.16($C_{42}H_{25}NO_2S$ = 607.72) |
| 2-41 | m/z = 633.21($C_{45}H_{31}NOS$ = 633.80) |
| 2-42 | m/z = 733.24($C_{53}H_{35}NOS$ = 733.92) |
| 2-43 | m/z = 883.29($C_{65}H_{41}NOS$ = 884.09) |
| 2-44 | m/z = 585.13($C_{38}H_{23}N_3S_2$ = 585.74) |
| 2-45 | m/z = 553.19($C_{40}H_{27}NS$ = 553.71) |
| 2-46 | m/z = 603.20($C_{44}H_{29}NS$ = 603.77) |
| 2-47 | m/z = 841.28($C_{63}H_{39}NS$ = 842.06) |
| 2-48 | m/z = 567.17($C_{40}H_{25}NOS$ = 567.71) |
| 2-49 | m/z = 563.22($C_{42}H_{29}NO$ = 563.69) |
| 2-50 | m/z = 563.22($C_{42}H_{29}NO$ = 563.69) |
| 2-51 | m/z = 613.24($C_{46}H_{31}NO$ = 613.74) |
| 2-52 | m/z = 703.29($C_{53}H_{37}NO$ = 703.87) |
| 2-53 | m/z = 587.22($C_{44}H_{29}NO$ = 587.71) |
| 2-54 | m/z = 639.26($C_{48}H_{33}NO$ = 639.78) |
| 2-55 | m/z = 639.26($C_{48}H_{33}NO$ = 639.78) |
| 2-56 | m/z = 653.24($C_{48}H_{31}NO_2$ = 653.77) |
| 2-57 | m/z = 603.26($C_{45}H_{33}NO$ = 603.75) |
| 2-58 | m/z = 727.29($C_{55}H_{37}NO$ = 727.89) |
| 2-59 | m/z = 725.27($C_{55}H_{35}NO$ = 725.87) |
| 2-60 | m/z = 595.17($C_{40}H_{25}N_3OS$ = 595.71) |
| 2-61 | m/z = 567.26($C_{42}H_{33}NO$ = 567.72) |
| 2-62 | m/z = 611.22($C_{46}H_{29}NO$ = 611.73) |
| 2-63 | m/z = 617.18($C_{44}H_{27}NOS$ = 617.76) |
| 2-64 | m/z = 637.24($C_{48}H_{31}NO$ = 637.77) |
| 2-65 | m/z = 667.21($C_{48}H_{29}NO_3$ = 667.75) |
| 2-66 | m/z = 767.25($C_{56}H_{33}NO_3$ = 767.87) |

TABLE 6-continued

| compound | FD-MS |
|---|---|
| 2-67 | m/z = 681.27($C_{50}H_{35}NO_2$ = 681.82) |
| 2-68 | m/z = 567.17($C_{40}H_{25}NOS$ = 567.71 |
| 2-69 | m/z = 658.22($C_{45}H_{30}N_4S$ = 658.82) |
| 2-70 | m/z = 655.23($C_{48}H_{33}NS$ = 655.86) |
| 2-71 | m/z = 744.26($C_{54}H_{36}N_2S$ = 744.96) |
| 2-72 | m/z = 784.27($C_{55}H_{36}N_4S$ = 784.98) |
| 2-73 | m/z = 553.19($C_{40}H_{27}NS$ = 553.72) |
| 2-74 | m/z = 553.19($C_{40}H_{27}NS$ = 553.72) |
| 2-75 | m/z = 543.2($C_{39}H_{29}NS$ = 543.73) |
| 2-76 | m/z = 671.21($C_{48}H_{30}FNS$ = 671.83) |
| 2-77 | m/z = 641.25($C_{46}H_{31}N_3O$ = 641.77) |
| 2-78 | m/z = 639.26($C_{48}H_{33}NO$ = 639.8) |
| 2-79 | m/z = 652.25($C_{48}H_{32}N_2O$ = 652.8) |
| 2-80 | m/z = 667.25($C_{49}H_{33}NO_2$ = 667.81) |
| 2-81 | m/z = 713.31($C_{55}H_{39}N$ = 713.90) |
| 2-82 | m/z = 589.28($C_{45}H_{35}N$ = 589.77) |
| 2-83 | m/z = 639.29($C_{49}H_{37}N$ = 639.82) |
| 2-84 | m/z = 613.28($C_{47}H_{35}N$ = 613.79) |
| 2-85 | m/z = 711.29($C_{56}H_{37}N$ = 711.89) |
| 2-86 | m/z = 637.28($C_{49}H_{35}N$ = 637.81) |
| 2-87 | m/z = 761.31($C_{59}H_{39}N$ = 761.95) |
| 2-88 | m/z = 637.28($C_{49}H_{35}N$ = 637.81) |
| 2-89 | m/z = 877.37($C_{68}H_{47}N$ = 878.11) |
| 2-90 | m/z = 875.36($C_{68}H_{45}N$ = 876.09) |
| 2-91 | m/z = 813.30($C_{62}H_{39}NO$ = 813.98) |
| 2-92 | m/z = 651.26($C_{49}H_{33}NO$ = 651.81) |
| 2-93 | m/z = 591.2($C_{43}H_{29}NS$ = 591.77) |
| 2-94 | m/z = 601.28($C_{46}H_{35}N$ = 601.79) |
| 2-95 | m/z = 677.31($C_{52}H_{39}N$ = 677.89) |
| 2-96 | m/z = 777.3($C_{59}H_{39}NO$ = 777.97) |
| 2-97 | m/z = 647.36($C_{49}H_{45}N$ = 647.91) |

TABLE 7

| compound | FD-MS |
|---|---|
| 3-1 | m/z = 618.21($C_{44}H_{30}N_2S$ = 618.80) |
| 3-2 | m/z = 700.20($C_{48}H_{32}N_2S_2$ = 700.92) |
| 3-3 | m/z = 708.22($C_{50}H_{32}N_2OS$ = 708.88) |
| 3-4 | m/z = 692.25($C_{50}H_{32}N_2O_2$ = 692.82) |
| 3-5 | m/z = 742.30($C_{55}H_{38}N_2O$ = 742.92) |
| 3-6 | m/z = 654.27($C_{48}H_{34}N_2O$ = 654.81) |
| 3-7 | m/z = 700.20($C_{48}H_{32}N_2S_2$ = 700.92) |
| 3-8 | m/z = 760.25($C_{54}H_{36}N_2OS$ = 760.96) |
| 3-9 | m/z = 730.16($C_{48}H_{30}N_2S_3$ = 730.96) |
| 3-10 | m/z = 734.24($C_{52}H_{34}N_2OS$ = 734.92) |
| 3-11 | m/z = 872.32($C_{64}H_{44}N_2S$ = 873.13) |
| 3-12 | m/z = 718.26($C_{52}H_{34}N_2O_2$ = 718.86) |
| 3-13 | m/z = 568.20($C_{40}H_{28}N_2S$ = 568.74) |
| 3-14 | m/z = 624.17($C_{42}H_{28}N_2S_2$ = 624.82) |
| 3-15 | m/z = 658.21($C_{46}H_{30}N_2OS$ = 658.82) |
| 3-16 | m/z = 730.30($C_{56}H_{38}N_2O$ = 730.91) |
| 3-17 | m/z = 698.20($C_{48}H_{30}N_2O_2S$ = 698.84) |
| 3-18 | m/z = 624.17($C_{42}H_{28}N_2S_2$ = 624.82) |
| 3-19 | m/z = 700.20($C_{48}H_{32}N_2S_2$ = 700.92) |
| 3-20 | m/z = 708.22($C_{50}H_{32}N_2OS$ = 708.88) |
| 3-21 | m/z = 750.22($C_{52}H_{34}N_2S_2$ = 750.98) |
| 3-22 | m/z = 776.23($C_{54}H_{36}N_2S_2$ = 777.02) |
| 3-23 | m/z = 867.24($C_{59}H_{37}N_3OS_2$ = 868.09) |
| 3-24 | m/z = 759.27($C_{54}H_{37}N_3S$ = 759.97) |
| 3-25 | m/z = 608.19($C_{42}H_{28}N_2OS$ = 608.76) |
| 3-26 | m/z = 608.19($C_{42}H_{28}N_2OS$ = 608.76) |
| 3-27 | m/z = 692.25($C_{50}H_{32}N_2O_2$ = 692.82) |
| 3-28 | m/z = 894.20($C_{60}H_{34}N_2O_3S_2$ = 895.06) |
| 3-29 | m/z = 618.21($C_{44}H_{30}N_2S$ = 618.80) |
| 3-30 | m/z = 700.20($C_{48}H_{32}N_2S_2$ = 700.92) |
| 3-31 | m/z = 780.17($C_{52}H_{32}N_2S_3$ = 781.02) |
| 3-32 | m/z = 734.24($C_{52}H_{34}N_2OS$ = 734.92) |
| 3-33 | m/z = 834.31($C_{61}H_{52}N_2S$ = 835.08) |
| 3-34 | m/z = 700.20($C_{48}H_{32}N_2S_2$ = 700.92) |
| 3-35 | m/z = 724.25($C_{51}H_{36}N_2OS$ = 724.92) |
| 3-36 | m/z = 624.17($C_{42}H_{28}N_2S_2$ = 624.82) |
| 3-37 | m/z = 700.20($C_{48}H_{32}N_2S_2$ = 700.92) |
| 3-38 | m/z = 700.20($C_{46}H_{32}N_2S_2$ = 700.92) |
| 3-39 | m/z = 674.19($C_{46}H_{30}N_2S_2$ = 674.88) |

TABLE 7-continued

| compound | FD-MS |
|---|---|
| 3-40 | m/z = 700.20($C_{48}H_{32}N_2S_2$ = 700.92) |
| 3-41 | m/z = 608.19($C_{42}H_{28}N_2OS$ = 608.76) |
| 3-42 | m/z = 684.22($C_{48}H_{32}N_2OS$ = 684.86) |
| 3-43 | m/z = 684.22($C_{48}H_{32}N_2OS$ = 684.86) |
| 3-44 | m/z = 624.17($C_{42}H_{28}N_2S_2$ = 624.82) |
| 3-45 | m/z = 674.19($C_{46}H_{30}N_2S_2$ = 674.88) |
| 3-46 | m/z = 700.20($C_{48}H_{32}N_2S_2$ = 700.92) |
| 3-47 | m/z = 826.25($C_{58}H_{18}N_2S_2$ = 827.08) |
| 3-48 | m/z = 608.19($C_{42}H_{38}N_2OS$ = 608.76) |
| 3-49 | m/z = 624.17($C_{42}H_{28}N_2S_2$ = 624.82) |
| 3-50 | m/z = 684.22($C_{48}H_{32}N_2OS$ = 684.86) |
| 3-51 | m/z = 700.20($C_{48}H_{32}N_3S_2$ = 700.92) |
| 3-52 | m/z = 684.22($C_{48}H_{32}N_2OS$ = 684.86) |
| 3-53 | m/z = 730.16($C_{48}H_{30}N_2S_3$ = 730.96) |
| 3-54 | m/z = 826.25($C_{58}H_{38}N_2S_2$ = 827.08) |
| 3-55 | m/z = 806.19($C_{94}H_{54}N_2S_3$ = 807.06) |
| 3-56 | m/z = 674.19($C_{46}H_{30}N_2S_2$ = 674.88) |
| 3-57 | m/z = 674.19($C_{46}H_{10}N_2S_2$ = 674.88) |
| 3-58 | m/z = 674.19($C_{46}H_{50}N_2S_2$ = 674.88) |
| 3-59 | m/z = 674.19($C_{46}H_{30}N_2S_2$ = 674.88) |
| 3-60 | m/z = 674.19($C_{46}H_{30}N_2S_2$ = 674.88) |
| 3-61 | m/z = 638.19($C_{43}H_{30}N_2S_2$ = 638.85) |
| 3-62 | m/z = 638.19($C_{42}H_{30}N_2S_2$ = 638.85) |
| 3-63 | m/z = 638.19($C_{43}H_{30}N_2S_2$ = 638.85) |
| 3-64 | m/z = 622.21($C_{43}H_{30}N_2OS$ = 622.79) |
| 3-65 | m/z = 688.20($C_{47}H_{32}N_2S_2$ = 688.91) |
| 3-66 | m/z = 700.20($C_{48}H_{32}N_2S_2$ = 700.92) |
| 3-67 | m/z = 789.23($C_{54}H_{35}N_3S_2$ = 790.02) |
| 3-68 | m/z = 638.19($C_{43}H_{30}N_2S_2$ = 638.85) |
| 3-69 | m/z = 638.19($C_{43}H_{30}N_2S_2$ = 638.85) |
| 3-70 | m/z = 642.16($C_{42}H_{27}FN_2S_2$ = 642.81) |
| 3-71 | m/z = 638.19($C_{43}H_{30}N_2S_2$ = 638.85) |
| 3-72 | m/z = 714.22($C_{49}H_{34}N_2S_2$ = 714.95) |
| 3-73 | m/z = 716.20($C_{48}H_{32}N_2OS_2$ = 716.92) |
| 3-74 | m/z = 670.24($C_{48}H_{34}N_2S$ = 670.87) |
| 3-75 | m/z = 634.24($C_{45}H_{34}N_2S$ = 634.84) |
| 3-76 | m/z = 759.27($C_{54}H_{37}N_3S$ = 759.97) |
| 3-77 | m/z = 674.19($C_{46}H_{30}N_2S_2$ = 674.88) |
| 3-78 | m/z = 708.22($C_{50}H_{32}N_2OS$ = 708.88) |
| 3-79 | m/z = 674.19($C_{46}H_{30}N_2S_2$ = 674.88) |
| 3-80 | m/z = 748.22($C_{52}H_{32}N_2O_2S$ = 748.90) |
| 3-81 | m/z = 821.29($C_{57}H_{35}D_5N_2S_2$ = 822.11) |
| 3-82 | m/z = 730.16($C_{48}H_{30}N_2S_3$ = 730.96) |
| 3-83 | m/z = 730.16($C_{48}H_{30}N_2S_3$ = 730.96) |
| 3-84 | m/z = 714.18($C_{48}H_{30}N_2OS_2$ = 714.90) |
| 3-85 | m/z = 882.22($C_{60}H_{38}N_2S_3$ = 883.16) |
| 3-86 | m/z = 624.17($C_{42}H_{28}N_2S_2$ = 624.82) |
| 3-87 | m/z = 700.20($C_{48}H_{32}N_2S_2$ = 700.92) |
| 3-88 | m/z = 674.19($C_{46}H_{30}N_2S_2$ = 674.88) |
| 3-89 | m/z = 674.19($C_{46}H_{30}N_2S_2$ = 674.88) |
| 3-90 | m/z = 708.22($C_{50}H_{32}N_2OS$ = 708.88) |
| 3-91 | m/z = 759.27($C_{54}H_{37}N_3S$ = 759.97) |
| 3-92 | m/z = 674.19($C_{46}H_{30}N_2S_2$ = 674.88) |
| 3-93 | m/z = 688.20($C_{47}H_{32}N_2S_2$ = 688.91) |
| 3-94 | m/z = 760.25($C_{54}H_{36}N_2OS$ = 760.96) |
| 3-95 | m/z = 759.27($C_{54}H_{37}N_3S$ = 759.97) |
| 3-96 | m/z = 608.19($C_{42}H_{28}N_2OS$ = 608.76) |
| 3-97 | m/z = 684.22($C_{48}H_{32}N_2OS$ = 684.86) |
| 3-98 | m/z = 622.21($C_{43}H_{30}N_2OS$ = 622.79) |
| 3-99 | m/z = 760.25($C_{54}H_{36}N_2OS$ = 760.96) |
| 3-100 | m/z = 658.21($C_{46}H_{30}N_2OS$ = 658.82) |
| 3-101 | m/z = 658.21($C_{46}H_{30}N_2O_5$ = 658.82) |
| 3-102 | m/z = 692.25($C_{50}H_{32}N_2O_2$ = 692.82) |
| 3-103 | m/z = 628.25($C_{46}H_{32}N_2O$ = 628.78) |
| 3-104 | m/z = 693.28($C_{50}H_{35}N_3O$ = 693.85 |
| 3-105 | m/z = 723.23($C_{50}H_{33}N_3OS$ = 723.89) |
| 3-106 | m/z = 749.29($C_{54}H_{31}D_5N_2S$ = 749.99) |
| 3-107 | m/z = 700.20($C_{48}H_{32}N_2S_2$ = 700.92) |
| 3-108 | m/z = 674.19($C_{46}H_{30}N_2S_2$ = 674.88) |
| 3-109 | m/z = 684.22($C_{48}H_{32}N_2OS$ = 684.86) |
| 3-110 | m/z = 724.25($C_{51}H_{36}N_2OS$ = 724.92) |
| 3-111 | m/z = 674.19($C_{46}H_{30}N_2S_2$ = 674.88) |
| 3-112 | m/z = 674.19($C_{46}H_{30}N_2S_2$ = 674.88) |
| 3-113 | m/z = 780.17($C_{52}H_{32}N_2S_3$ = 781.02) |
| 3-114 | m/z = 684.22($C_{48}H_{32}N_2OS$ = 684.86) |
| 3-115 | m/z = 684.22($C_{48}H_{32}N_2OS$ = 684.86) |
| 3-116 | m/z = 698.20($C_{48}H_{30}N_2O_2S$ = 698.84) |
| 3-117 | m/z = 618.26($C_{42}H_{18}D_{10}N_2OS$ = 618.82) |
| 3-118 | m/z = 757.27($C_{54}H_{35}N_3O_2$ = 757.89) |
| 3-119 | m/z = 668.25($C_{48}H_{32}N_2O_2$ = 668.80) |
| 3-120 | m/z = 720.26($C_{52}H_{36}N_2S$ = 720.93) |
| 3-121 | m/z = 670.24($C_{48}H_{34}N_2S$ = 670.87) |
| 3-122 | m/z = 700.20($C_{48}H_{32}N_2S_2$ = 700.92) |
| 3-123 | m/z = 674.19($C_{46}H_{30}N_2S_2$ = 674.88) |
| 3-124 | m/z = 700.20($C_{48}H_{32}N_2S_2$ = 700.92) |
| 3-125 | m/z = 608.19($C_{42}H_{28}N_2OS$ = 608.76) |
| 3-126 | m/z = 860.25($C_{58}H_{40}N_2O_2S_2$ = 861.09) |
| 3-127 | m/z = 798.27($C_{57}H_{38}N_2OS$ = 799.00) |
| 3-128 | m/z = 734.33($C_{54}H_{42}N_2O$ = 734.94) |
| 3-129 | m/z = 742.26($C_{54}H_{34}N_2O_2$ = 742.88) |
| 3-130 | m/z = 945.37($C_{70}H_{47}N_3O$ = 946.17) |
| 3-131 | m/z = 670.24($C_{48}H_{34}N_2S$ = 670.87) |
| 3-132 | m/z = 624.17($C_{42}H_{28}N_2S_2$ = 624.82) |
| 3-133 | m/z = 700.20($C_{48}H_{32}N_2S_2$ = 700.92) |
| 3-134 | m/z = 724.20($C_{50}H_{32}N_2S_2$ = 724.94) |
| 3-135 | m/z = 816.26($C_{57}H_{40}N_2S_2$ = 817.08) |
| 3-136 | m/z = 760.25($C_{54}H_{36}N_2O_5$ = 760.96) |
| 3-137 | m/z = 674.19($C_{46}H_{30}N_2S_2$ = 674.88) |
| 3-138 | m/z = 730.16($C_{48}H_{30}N_2S_3$ = 730.96) |
| 3-139 | m/z = 881.29($C_{61}H_{43}N_2S_2$ = 882.16) |
| 3-140 | m/z = 704.28($C_{52}H_{36}N_2O$ = 704.87) |
| 3-141 | m/z = 608.19($C_{42}H_{28}N_2OS$ = 608.76) |
| 3-142 | m/z = 682.23($C_{48}H_{30}N_2O_3$ = 682.78) |
| 3-143 | m/z = 670.24($C_{48}H_{34}N_2S$ = 670.87) |
| 3-144 | m/z = 776.23($C_{54}H_{36}N_2S_2$ = 777.02) |
| 3-145 | m/z = 674.19($C_{46}H_{30}N_2S_2$ = 674.88) |
| 3-146 | m/z = 759.27($C_{54}H_{37}N_3S$ = 759.97) |
| 3-147 | m/z = 758.24($C_{54}H_{34}N_2OS$ = 758.94) |
| 3-148 | m/z = 806.28($C_{59}H_{38}N_2S$ = 807.03) |
| 3-149 | m/z = 823.30($C_{59}H_{38}FN_3O$ = 823.97) |
| 3-150 | m/z = 743.29($C_{54}H_{37}N_3O$ = 743.91.) |
| 3-151 | m/z = 998.33($C_{73}H_{46}N_2OS$ = 999.24) |
| 3-152 | m/z = 700.20($C_{48}H_{32}N_2S_2$ = 700.92) |
| 3-153 | m/z = 674.19($C_{46}H_{30}N_2S_2$ = 674.88 |
| 3-154 | m/z = 674.19($C_{46}H_{30}N_2S_2$ = 674.88) |
| 3-155 | m/z = 674.19($C_{46}H_{30}N_2S_2$ = 674.88) |
| 3-156 | m/z = 674.19($C_{46}H_{30}N_2S_2$ = 674.88) |
| 3-157 | m/z = 762.29($C_{50}H_{46}N_2SSi_2$ = 763.16) |
| 3-158 | m/z = 624.17($C_{42}H_{28}N_2S_2$ = 624.82) |
| 3-159 | m/z = 784.25($C_{56}H_{36}N_2OS$ = 784.98) |
| 3-160 | m/z = 810.27($C_{58}H_{38}N_2OS$ = 811.04 |
| 3-161 | m/z = 860.29($C_{62}H_{40}N_2OS$ = 861.08) |
| 3-162 | m/z = 708.22($C_{50}H_{32}N_2OS$ = 708.88) |
| 3-163 | m/z = 742.26($C_{54}H_{34}N_2O_2$ = 742.88) |
| 3-164 | m/z = 828.26($C_{58}H_{40}N_2S_2$ = 829.09) |
| 3-165 | m/z = 708.22($C_{50}H_{32}N_2OS$ = 708.88) |
| 3-166 | m/z = 724.20($C_{50}H_{32}N_2S_2$ = 724.94) |
| 3-167 | m/z = 834.27($C_{60}H_{38}N_2OS$ = 835.04) |
| 3-168 | m/z = 768.28($C_{56}H_{36}N_2O_2$ = 768.92) |
| 3-169 | m/z = 830.19($C_{56}H_{34}N_2S_3$ = 831.08) |
| 3-170 | m/z = 810.27($C_{58}H_{38}N_2OS$ = 811.02) |
| 3-171 | m/z = 810.31($C_{59}H_{42}N_2S$ = 811.06) |
| 3-172 | m/z = 692.25($C_{50}H_{32}N_2O_2$ = 692.82) |
| 3-173 | m/z = 758.24($C_{54}H_{34}N_2OS$ = 758.94) |
| 3-174 | m/z = 708.22($C_{50}H_{32}N_3OS$ = 708.88) |
| 3-175 | m/z = 732.24($C_{52}H_{34}N_2OS$ = 734.92) |

Fabrication and Evaluation of Organic Electronic Element

[Example 1] to [Example 102] Red OLED (Mixed Phosphorescent Host of a Light Emitting Layer After vacuum depositing 4,4',4"-tris[2-naphthyl(phenyl)amino]triphenylamine (abbreviated as "2-TNATA") film on an ITO layer (anode) to form a hole injection layer having a thickness of 60 nm, wherein the ITO layer was formed on a glass substrate, 4,4'-bis[N-(1-napthyl)-N-phenylamino]biphenyl (abbreviated as "NPD") film was vacuum-deposited with a thickness of 55 nm on the hole injection layer to form a hole transport layer.

Next, a light emitting layer with a thickness of 30 nm was formed on the hole transport layer. As shown in Table 8, a mixture of a compound represented by Formula 1 of the present invention (host 1) and a compound represented by Formula 2 of the present invention (host 2) in a weight ratio of 3:7 was used as a host and bis-(1-phenylisoquinolyl) iridium(III) acetylacetonate (abbreviated as "$(piq)_2Ir$ (acac)") was used as a dopant, where the host and dopant were used in a 95:5 weight ratio.

Next, a film of (1,1'-biphenyl-4-olato)bis(2-methyl-8-quinolinolato)aluminum (abbreviated as "BAlq") was vacuum-deposited with a thickness of 10 nm on the light emitting layer to form a hole blocking layer.

Subsequently, after mixing tris-(8-hydroxyquinoline)aluminum (abbreviated as "$Alq_3$") and bis(10-hydroxybenzo[h]quinolinato)beryllium (abbreviated as "$BeBq_2$") in 1:1, the mixture was deposited on the hole blocking layer to form an electron transport layer having a thickness of 45 nm Next, LiF on the electron transport layer was deposited to a thickness of 0.2 nm and then Al was deposited to a thickness of 150 nm to form a cathode. In this way, the OLED was completed.

[Comparative Example 1] to [Comparative Example 4]

The OLEDs were fabricated in the same manner as described in Example 1 except that a single compound represented by Formula 1 of the present invention as listed in the following Table 8 was used as a host of a light emitting layer.

[Comparative Example 5] and [Comparative Example 6]

The OLEDs were fabricated in the same manner as described in Example 1 except that the the mixture of Comparative compounds 1 and 2, the mixture of Comparative compounds 1 and 3 as listed in the following Table 8 were uses as a host of a light emitting layer, respectively.

<Comp. compd 1>

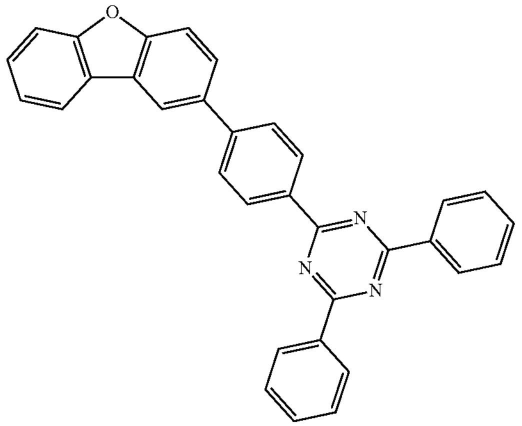

-continued

<Comp. compd 2>

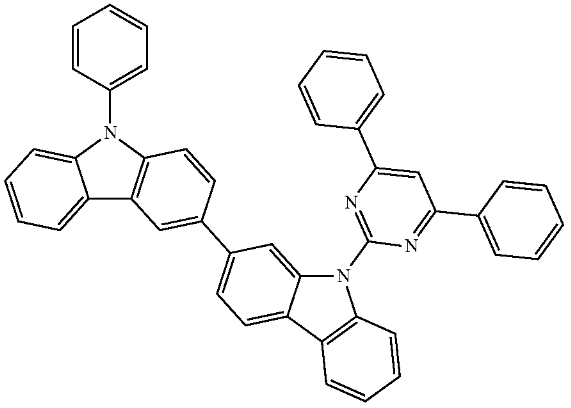

<Comp. compd 3>

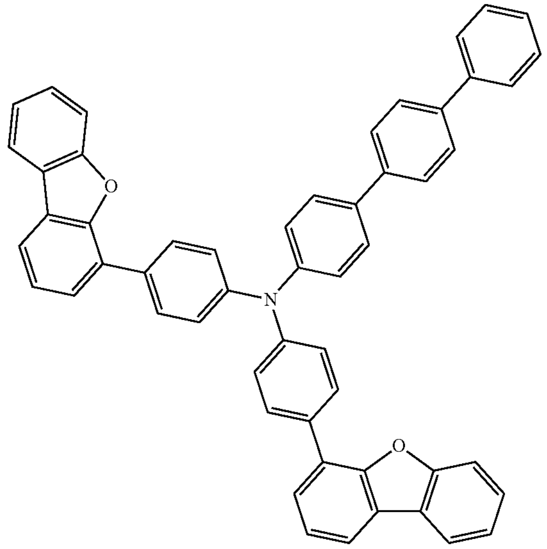

Electroluminescence (EL) characteristics were measured with a PR-650 (Photoresearch) by applying a forward bias DC voltage to the OLEDs prepared in Examples 1 to 102 of the present invention and Comparative Examples 1 to 6. And, the T95 life time was measured using a life time measuring apparatus manufactured by Macscience Inc. at reference brightness of 2500 cd/m$^2$. The measurement results are shown in Tables 8 below.

TABLE 8

| | Host 1 | Host 2 | Voltage (V) | Current Density (mA/cm$^2$) | Brightness (cd/m$^2$) | Efficiency (cd/A) | Lifetime T(95) |
|---|---|---|---|---|---|---|---|
| comp. Ex(1) | Com. 1-61 | | 6.5 | 20.8 | 2500 | 12.0 | 92.5 |
| comp. Ex(2) | Com. 1-92 | | 5.9 | 13.6 | 2500 | 18.4 | 121.2 |
| comp. Ex(3) | Com. 1-145 | | 6.4 | 18.9 | 2500 | 13.2 | 95.4 |
| comp. Ex(4) | Com. 1-160 | | 6.0 | 14.6 | 2500 | 17.1 | 110.4 |
| comp. Ex(5) | ref 1 | ref 2 | 5.8 | 12.3 | 2500 | 20.3 | 123.4 |
| comp. Ex(6) | ref 1 | ref 3 | 5.7 | 12.1 | 2500 | 20.6 | 125.0 |
| Ex. (1) | Com. 1-61 | Com. 2-4 | 4.8 | 9.1 | 2500 | 27.5 | 142.0 |
| Ex. (2) | Com. 1-91 | | 4.9 | 8.5 | 2500 | 29.3 | 142.7 |
| Ex. (3) | Com. 1-92 | | 4.9 | 8.5 | 2500 | 29.5 | 142.9 |
| Ex. (4) | Com. 1-103 | | 4.9 | 8.6 | 2500 | 29.1 | 142.3 |

TABLE 8-continued

| | Host 1 | Host 2 | Voltage (V) | Current Density ($mA/cm^2$) | Brightness ($cd/m^2$) | Efficiency (cd/A) | Lifetime T(95) |
|---|---|---|---|---|---|---|---|
| Ex. (5) | Com. 1-121 | | 4.8 | 8.9 | 2500 | 28.1 | 143.4 |
| Ex. (6) | Com. 1-122 | | 4.9 | 9.0 | 2500 | 27.8 | 143.0 |
| Ex. (7) | Com. 1-145 | | 4.8 | 9.1 | 2500 | 27.6 | 142.1 |
| Ex. (8) | Com. 1-148 | | 4.9 | 8.4 | 2500 | 29.6 | 142.4 |
| Ex. (9) | Com. 1-149 | | 4.9 | 8.4 | 2500 | 29.9 | 142.6 |
| Ex. (10) | Com. 1-151 | | 4.8 | 8.6 | 2500 | 29.1 | 142.3 |
| Ex. (11) | Com. 1-158 | | 4.9 | 8.8 | 2500 | 28.3 | 143.3 |
| Ex. (12) | Com. 1-160 | | 4.9 | 8.7 | 2500 | 28.6 | 143.6 |
| Ex. (13) | Com. 1-172 | | 4.9 | 8.9 | 2500 | 28.0 | 143.1 |
| Ex. (14) | Com. 1-173 | | 4.8 | 8.7 | 2500 | 28.7 | 143.7 |
| Ex. (15) | Com. 1-174 | | 4.8 | 8.7 | 2500 | 28.9 | 144.0 |
| Ex. (16) | Com. 1-61 | Com. 2-45 | 4.8 | 8.3 | 2500 | 30.0 | 143.8 |
| Ex. (17) | Com. 1-91 | | 4.9 | 7.9 | 2500 | 31.8 | 144.5 |
| Ex. (18) | Com. 1-92 | | 4.8 | 7.8 | 2500 | 32.1 | 144.7 |
| Ex. (19) | Com. 1-103 | | 4.8 | 7.9 | 2500 | 31.7 | 144.0 |
| Ex. (20) | Com. 1-121 | | 4.9 | 8.1 | 2500 | 30.8 | 145.3 |
| Ex. (21) | Com. 1-122 | | 4.8 | 8.2 | 2500 | 30.5 | 144.9 |
| Ex. (22) | Com. 1-145 | | 4.9 | 8.3 | 2500 | 30.2 | 143.9 |
| Ex. (23) | Com. 1-148 | | 4.8 | 7.7 | 2500 | 32.3 | 144.2 |
| Ex. (24) | Com. 1-149 | | 4.8 | 7.7 | 2500 | 32.4 | 144.3 |
| Ex. (25) | Com. 1-151 | | 4.8 | 7.9 | 2500 | 31.5 | 143.9 |
| Ex. (26) | Com. 1-158 | | 4.8 | 8.1 | 2500 | 30.9 | 145.2 |
| Ex. (27) | Com. 1-160 | | 4.9 | 8.0 | 2500 | 31.2 | 145.5 |
| Ex. (28) | Com. 1-172 | | 4.9 | 8.1 | 2500 | 30.8 | 145.0 |
| Ex. (29) | Com. 1-173 | | 4.8 | 8.0 | 2500 | 31.3 | 145.7 |
| Ex. (30) | Com. 1-174 | | 4.9 | 7.9 | 2500 | 31.5 | 145.8 |
| Ex. (31) | Com. 1-61 | Com. 2-48 | 4.7 | 6.7 | 2500 | 37.5 | 149.2 |
| Ex. (32) | Com. 1-91 | | 4.6 | 6.4 | 2500 | 39.2 | 150.1 |
| Ex. (33) | Com. 1-92 | | 4.7 | 6.3 | 2500 | 39.4 | 150.3 |
| Ex. (34) | Com. 1-103 | | 4.7 | 6.4 | 2500 | 39.1 | 149.7 |
| Ex. (35) | Com. 1-121 | | 4.7 | 6.6 | 2500 | 38.1 | 150.9 |
| Ex. (36) | Com. 1-122 | | 4.7 | 6.6 | 2500 | 37.8 | 150.4 |
| Ex. (37) | Com. 1-145 | | 4.7 | 6.6 | 2500 | 37.7 | 149.4 |
| Ex. (38) | Com. 1-148 | | 4.6 | 6.3 | 2500 | 39.6 | 149.9 |
| Ex. (39) | Com. 1-149 | | 4.7 | 6.3 | 2500 | 39.9 | 150.0 |
| Ex. (40) | Com. 1-151 | | 4.6 | 6.4 | 2500 | 39.0 | 149.5 |
| Ex. (41) | Com. 1-158 | | 4.6 | 6.5 | 2500 | 38.3 | 150.8 |
| Ex. (42) | Com. 1-160 | | 4.6 | 6.5 | 2500 | 38.5 | 150.9 |
| Ex. (43) | Com. 1-172 | | 4.6 | 6.6 | 2500 | 38.0 | 150.6 |
| Ex. (44) | Com. 1-173 | | 4.7 | 6.5 | 2500 | 38.7 | 151.0 |
| Ex. (45) | Com. 1-174 | | 4.7 | 6.4 | 2500 | 38.8 | 151.2 |
| Ex. (46) | Com. 1-61 | Com. 2-49 | 4.6 | 7.7 | 2500 | 32.5 | 145.6 |
| Ex. (47) | Com. 1-91 | | 4.7 | 7.3 | 2500 | 34.3 | 146.5 |
| Ex. (48) | Com. 1-92 | | 4.7 | 7.2 | 2500 | 34.5 | 146.7 |
| Ex. (49) | Com. 1-103 | | 4.7 | 7.3 | 2500 | 34.2 | 146.1 |
| Ex. (50) | Com. 1-121 | | 4.6 | 7.6 | 2500 | 33.1 | 147.3 |
| Ex. (51) | Com. 1-122 | | 4.6 | 7.6 | 2500 | 32.8 | 146.8 |
| Ex. (52) | Com. 1-145 | | 4.7 | 7.6 | 2500 | 32.7 | 145.8 |
| Ex. (53) | Com. 1-148 | | 4.6 | 7.2 | 2500 | 34.6 | 146.2 |
| Ex. (54) | Com. 1-149 | | 4.7 | 7.2 | 2500 | 34.9 | 146.4 |
| Ex. (55) | Com. 1-151 | | 4.7 | 7.4 | 2500 | 34.0 | 145.9 |
| Ex. (56) | Com. 1-158 | | 4.7 | 7.5 | 2500 | 33.3 | 147.1 |
| Ex. (57) | Com. 1-160 | | 4.6 | 7.5 | 2500 | 33.4 | 147.3 |
| Ex. (58) | Com. 1-172 | | 4.6 | 7.6 | 2500 | 33.0 | 147.0 |
| Ex. (59) | Com. 1-173 | | 4.7 | 7.5 | 2500 | 33.5 | 147.4 |
| Ex. (60) | Com. 1-174 | | 4.7 | 7.4 | 2500 | 33.8 | 147.6 |
| Ex. (61) | Com. 1-61 | Com. 2-57 | 4.7 | 7.1 | 2500 | 35.0 | 147.4 |
| Ex. (62) | Com. 1-91 | | 4.8 | 6.8 | 2500 | 36.9 | 148.2 |
| Ex. (63) | Com. 1-92 | | 4.7 | 6.8 | 2500 | 37.0 | 148.4 |
| Ex. (64) | Com. 1-103 | | 4.8 | 6.8 | 2500 | 36.8 | 147.8 |
| Ex. (65) | Com. 1-121 | | 4.7 | 7.0 | 2500 | 35.8 | 149.0 |
| Ex. (66) | Com. 1-122 | | 4.7 | 7.0 | 2500 | 35.5 | 148.5 |
| Ex. (67) | Com. 1-145 | | 4.8 | 7.1 | 2500 | 35.2 | 147.5 |
| Ex. (68) | Com. 1-148 | | 4.8 | 6.7 | 2500 | 37.2 | 147.9 |
| Ex. (69) | Com. 1-149 | | 4.7 | 6.7 | 2500 | 37.4 | 148.0 |
| Ex. (70) | Com. 1-151 | | 4.8 | 6.8 | 2500 | 36.5 | 147.6 |
| Ex. (71) | Com. 1-158 | | 4.8 | 7.0 | 2500 | 35.8 | 148.8 |
| Ex. (72) | Com. 1-160 | | 4.8 | 7.0 | 2500 | 35.9 | 149.0 |
| Ex. (73) | Com. 1-172 | | 4.8 | 7.0 | 2500 | 35.7 | 148.7 |
| Ex. (74) | Com. 1-173 | | 4.8 | 6.9 | 2500 | 36.1 | 149.1 |
| Ex. (75) | Com. 1-174 | | 4.7 | 6.9 | 2500 | 36.3 | 149.4 |
| Ex. (76) | Com. 1-61 | Com. 2-68 | 4.7 | 6.3 | 2500 | 39.7 | 151.0 |
| Ex. (77) | Com. 1-91 | | 4.6 | 6.0 | 2500 | 41.5 | 151.9 |
| Ex. (78) | Com. 1-92 | | 4.6 | 6.0 | 2500 | 41.7 | 152.1 |
| Ex. (79) | Com. 1-103 | | 4.7 | 6.0 | 2500 | 41.4 | 151.6 |
| Ex. (80) | Com. 1-121 | | 4.7 | 6.2 | 2500 | 40.5 | 152.5 |

TABLE 8-continued

| | Host 1 | Host 2 | Voltage (V) | Current Density ($mA/cm^2$) | Brightness ($cd/m^2$) | Efficiency (cd/A) | Lifetime T(95) |
|---|---|---|---|---|---|---|---|
| Ex. (81) | Com. 1-122 | | 4.7 | 6.2 | 2500 | 40.1 | 152.2 |
| Ex. (82) | Com. 1-145 | | 4.6 | 6.3 | 2500 | 39.9 | 151.1 |
| Ex. (83) | Com. 1-148 | | 4.6 | 6.0 | 2500 | 41.8 | 151.7 |
| Ex. (84) | Com. 1-149 | | 4.6 | 6.0 | 2500 | 42.0 | 151.9 |
| Ex. (85) | Com. 1-151 | | 4.7 | 6.1 | 2500 | 41.3 | 151.4 |
| Ex. (86) | Com. 1-158 | | 4.6 | 6.2 | 2500 | 40.5 | 152.5 |
| Ex. (87) | Com. 1-160 | | 4.6 | 6.1 | 2500 | 40.8 | 152.6 |
| Ex. (88) | Com. 1-172 | | 4.7 | 6.2 | 2500 | 40.3 | 152.4 |
| Ex. (89) | Com. 1-173 | | 4.6 | 6.1 | 2500 | 41.0 | 152.7 |
| Ex. (90) | Com. 1-174 | | 4.6 | 6.1 | 2500 | 41.1 | 153.0 |
| Ex. (91) | Com. (2-101) | Com. (3-36) | 4.4 | 5.7 | 2500.0 | 43.6 | 156.7 |
| Ex. (92) | Com. (2-107) | | 4.5 | 5.7 | 2500.0 | 43.7 | 155.8 |
| Ex. (93) | Com. (2-109) | | 4.5 | 5.8 | 2500.0 | 43.0 | 155.9 |
| Ex. (94) | Com. (2-121) | | 4.4 | 5.7 | 2500.0 | 43.7 | 155.2 |
| Ex. (95) | Com. (2-101) | Com. (3-174) | 4.1 | 5.4 | 2500.0 | 46.0 | 158.8 |
| Ex. (96) | Com. (2-107) | | 3.7 | 5.1 | 2500.0 | 49.1 | 158.9 |
| Ex. (97) | Com. (2-109) | | 4.1 | 5.4 | 2500.0 | 45.9 | 159.6 |
| Ex. (98) | Com. (2-121) | | 4.1 | 5.4 | 2500.0 | 46.1 | 159.3 |
| Ex. (99) | Com. (2-101) | Com. (3-175) | 4.0 | 5.3 | 2500.0 | 47.0 | 159.3 |
| Ex. (100) | Com. (2-107) | | 4.1 | 5.5 | 2500.0 | 45.2 | 159.8 |
| Ex. (101) | Com. (2-109) | | 3.9 | 5.2 | 2500.0 | 48.3 | 162.4 |
| Ex. (102) | Com. (2-121) | | 4.1 | 5.5 | 2500.0 | 45.7 | 158.6 |

From Table 8, it can be seen that the driving voltage, efficiency and lifetime of the element are remarkably improved when the mixture of the compound represented by Formula 1 and the compound represented by Formula 2 of the present invention is used as a phosphorescent host (Examples 1 to 90), compared with the case of using the compound represented by the formula 1 alone (Comparative Examples 1 to 4) or using a mixture of comparative compounds (Comparative Examples 5 to 6).

Comparing Comparative Examples 1 to 6, the characteristics of the element are further improved when the mixture of two kinds of comparative compounds is used (Comparative Examples 5 to 6) than when the compound of the present invention is used alone (Comparative Examples 1 to 4).

In addition, comparing Comparative Examples 5-6 and Examples of the present invention, the driving voltage is lower and the efficiency and lifetime are remarkably improved when the mixture of the compound represented by Formula 1 and the compound represented by Formula 2 of the present invention is used as a host, compared with the case of using the mixture of two kinds of comparative compounds.

From these results, the inventors of the present invention determined that a mixture of the mixture of the compound represented by Formula 1 and the compound represented by Formula 2 had new properties other than those of each compound, and thus, PL lifetime of each of the compounds and the mixture was measured, respectively. As a result, in the case of the mixture of the compound represented by Formula 1 and the compound represented by Formula 2 of the present invention, it was confirmed that a new PL wavelength was formed unlike the case of a single compound.

This is because when the mixture of the compounds of the present invention is used, not only electrons and holes are moved according to the energy levels of the respective materials, but also electrons and holes are moved or energy is transferred according to a novel region with a new energy level formed by mixing and thus the efficiency and lifetime is increased. This is an important example of showing the energy transfer and the emitting process by exciplex of the mixed thin film when the mixture of the compounds of the present invention are used.

In addition, when the polycyclic compound represented by the formula 1 with the high stability for holes as well as electrons and the compound represented by the formula 2 with the strong hole characteristics are mixed, the electrons blocking ability is improved and more holes move quickly and easily into the emitting layer due to the high T1 and LUMO energy values. As a result, as the charge balance increases in the light emitting layer, light is emitted well inside the light emitting layer, not at the hole transport layer interface, and this also reduces the degradation of the HTL interface, thereby the driving voltage, efficiency and lifetime of the element are maximized. That is, when the mixture of the compounds represented by Formulas 1 and 2 is used as a host, the performance of the entire device is greatly improved by electrochemical synergy.

[Example 103] to [Example 106]

An organic electroluminescent element was manufactured in the same manner as in Example 1 except that host 1 and host 2 were mixed at a predetermined ratio as described in Table 8.

Electroluminescence (EL) characteristics were measured with a PR-650 (Photoresearch) by applying a forward bias DC voltage to the OLEDs prepared in Examples 103 to 106. And, the T95 life time was measured using a life time measuring apparatus manufactured by Macscience Inc. at reference brightness of 2500 $cd/m^2$. The measurement results are shown in Tables 9 below. Examples 3 and 80 are the case where the mixture of host 1 and host 2 in a ration of 3:7 like Table 8 is used as host.

TABLE 9

| | Host 1 | Host 2 | Mixing ration (Host 1:Host 2) | Voltage (V) | Current Density (mA/cm$^2$) | Brightness (cd/m$^2$) | Efficiency (cd/A) | Lifetime T(95) |
|---|---|---|---|---|---|---|---|---|
| Ex. (103) | 1-92 | 2-4 | 7:3 | 5.1 | 8.9 | 2500 | 28.2 | 142.1 |
| Ex. (104) | | | 5:5 | 4.9 | 8.6 | 2500 | 29.1 | 142.6 |
| Ex. (3) | | | 3:7 | 4.9 | 8.5 | 2500 | 29.5 | 142.9 |
| Ex. (105) | 1-121 | 2-68 | 7:3 | 5.0 | 7.2 | 2500 | 34.6 | 151.8 |
| Ex. (106) | | | 5:5 | 4.8 | 6.5 | 2500 | 38.4 | 152.2 |
| Ex. (80) | | | 3:7 | 4.7 | 6.2 | 2500 | 40.5 | 152.5 |

Referring to Table 9 above, it can be seen when the first host and the second host are mixed at 3:7, the driving voltage, efficiency, and lifespan are excellent, and as the ratio of the first host increases, the characteristics of the element decrease. This is because the charge balance in the light emitting layer is maximized as the amount of the compound represented by the formula 2 having a stronger hole transport property than the compound represented by the formula 1 is increased.

[Example 107] to [Example 118] Red OLED

After vacuum depositing 2-TNATA film on an ITO layer (anode) to form a hole injection layer having a thickness of 60 nm, wherein the ITO layer was formed on a glass substrate, NPD film was vacuum-deposited with a thickness of 60 nm on the hole injection layer to form a hole transport layer.

Next, a light emitting layer with a thickness of 30 nm was formed on the hole transport layer. As shown in Table 10, the compound represented by Formula 3 of the present invention was used as a host and $(piq)_2Ir$ (acac) was used as a dopant, and dopant was doped so that their weight ratio was 95:5.

Next, BAlq was vacuum-deposited with a thickness of 10 nm on the light emitting layer to form a hole blocking layer. Subsequently, after mixing $Alq_3$ was deposited on the hole blocking layer to form an electron transport layer having a thickness of 40 nm.

Next, LiF on the electron transport layer was deposited to a thickness of 0.2 nm and then Al was deposited to a thickness of 150 nm to form a cathode.

Comparative Example 7

The OLED was fabricated in the same manner as described in Example 107 except that the Comparative compound 4 was used as host of a light emitting layer instead of the compound of the present invention.

<Comparative compound 4>

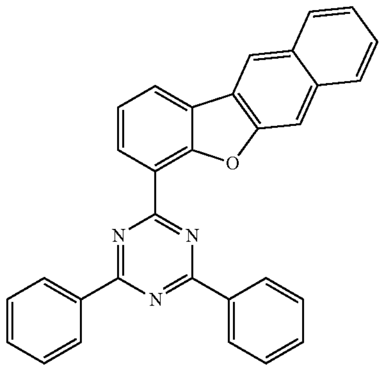

Electroluminescence (EL) characteristics were measured with a PR-650 (Photoresearch) by applying a forward bias DC voltage to the OLEDs prepared in Examples 107 to 118 of the present invention and Comparative Example 7. And, the T95 life time was measured using a life time measuring apparatus manufactured by Macscience Inc. at reference brightness of 2500 cd/m$^2$. The measurement results are shown in Tables 10 below.

TABLE 10

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(7) | comp. Com 4 | 6.3 | 15.3 | 2500.0 | 16.3 | 100.2 | 0.62 | 0.34 |
| Ex. (107) | 2-101 | 5.4 | 12.3 | 2500.0 | 20.4 | 110.6 | 0.63 | 0.32 |
| Ex. (108) | 2-102 | 5.2 | 10.4 | 2500.0 | 24.1 | 117.0 | 0.62 | 0.33 |
| Ex. (109) | 2-103 | 5.1 | 10.0 | 2500.0 | 25.0 | 116.8 | 0.60 | 0.34 |
| Ex. (110) | 2-104 | 5.4 | 11.3 | 2500.0 | 22.1 | 125.0 | 0.61 | 0.32 |
| Ex. (111) | 2-105 | 5.4 | 11.2 | 2500.0 | 22.3 | 120.2 | 0.64 | 0.33 |
| Ex. (112) | 2-106 | 5.4 | 11.3 | 2500.0 | 22.2 | 120.5 | 0.65 | 0.32 |
| Ex. (113) | 2-107 | 5.2 | 10.1 | 2500.0 | 24.8 | 115.4 | 0.61 | 0.34 |
| Ex. (114) | 2-108 | 5.2 | 10.4 | 2500.0 | 24.0 | 119.4 | 0.62 | 0.31 |
| Ex. (115) | 2-109 | 5.3 | 11.2 | 2500.0 | 22.4 | 121.0 | 0.61 | 0.33 |
| Ex. (116) | 2-110 | 5.5 | 11.3 | 2500.0 | 22.0 | 121.1 | 0.62 | 0.33 |
| Ex. (117) | 2-111 | 5.1 | 10.3 | 2500.0 | 24.3 | 115.9 | 0.63 | 0.31 |
| Ex. (118) | 2-112 | 5.2 | 10.3 | 2500.0 | 24.2 | 115.5 | 0.62 | 0.33 |

As can be seen in Table 10, the organic electroluminescent element using the compound of the present invention as a phosphorescent host has improved the driving voltage, efficiency and lifetime compared to the case of using the comparative compound 4.

Comparative compound 4 and the compound of the present invention is different in the bonding position of the triazine substituent bonded to naphthobenzofuran.

When comprehensively judging the device data of Table 10, the driving voltage, efficiency and lifetime of the element are greatly improved when using a compound of the present invention as a host material rather than the comparative compound 4, wherein in the case of Comparative Compound 4, the triazine substituent is substituted at position 4 of naphthobenzofuran, and in the case of the present invention, it is substituted at position 1 of naphthobenzofuran. In particular, when the compound of the present invention comprising a substituent containing naphthyl in the triazine substituent moiety is used as a host material, the driving voltage and efficiency are greatly improved, and when the compound having a biphenyl as a substituent is used, the lifetime is greatly improved.

Figure 4:
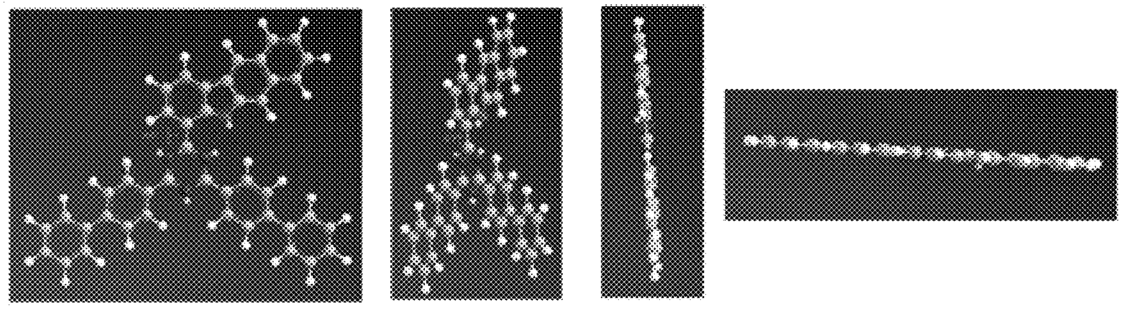
Figure 4:
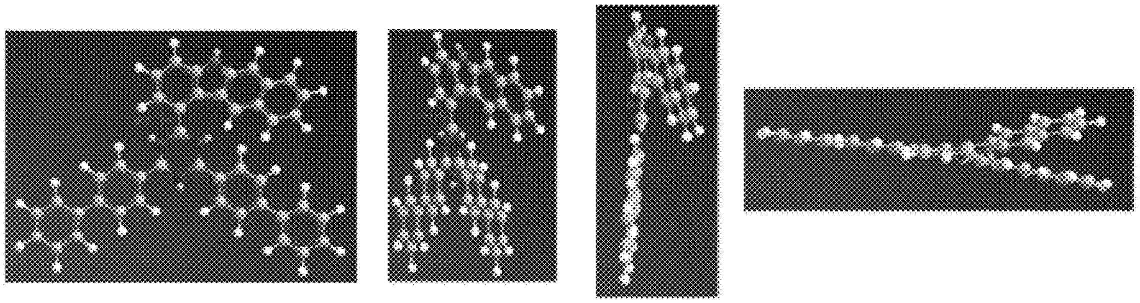

The above results can be seen to be due to the torsion angle. Table 11, as seen as FIG. 4, is a photograph taken from various aspects of the twist angle of 4-naphthobenzofuran such as Comparative Compound 4 and 1-naphthobenzofuran derivative such as Compound 2-109 of the present invention.

In Table 11 (FIG. 4), each drawing shows the image of a three-dimensional structure of Comparative Compound 4 and the compound 2-109 of the present invention in front, horizontal axis 60°, horizontal axis 90°, vertical axis 90° using the Chem3D program MM2 minimize energy method of Perkin Elmer, respectively.

Referring to Table 11 (FIG. 4), 4-naphthobenzofuran derivatives having a torsional angle of 0.9° with triazine, such as Comparative Compound 4, are nearly torsionless and have very high planarity. On the other hand, 1-naphthobenzofuran derivatives such as the present invention have a planarity that is significantly different from that of Comparative Compound 4 since 1-naphthobenzofuran derivatives are more twisted with triazine, wherein a torsion angle is 10.2°.

Therefore, the compound of the present invention which is a relatively steric structure can reduce the degree of electrical polarization by weakening the intermolecular van der Waals force and lower the crystallinity of the thin film by weakening the intermolecular interaction. Moreover, when used as a light emitting layer material, this steric property can cause a certain distance from the electrochemically unstable dopant, which can ultimately increase the stability of the light emitting layer.

These comprehensive characteristics appear to improve the lifetime and characteristics of the element when the material is deposited.

Although exemplary embodiments of the present invention have been described for illustrative purposes, those skilled in the art will appreciate that various modifications, additions and substitutions are possible, without departing from the scope of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. An organic electric element comprising a first electrode, a second electrode, and an organic material layer formed between the first electrode and the second electrode, wherein the organic material layer comprises a phosphorescent light emitting layer, and the phosphorescent light emitting layer comprises as host a first compound represented by Formula 1 and a second compound represented by Formula 2:

[Formula 1]

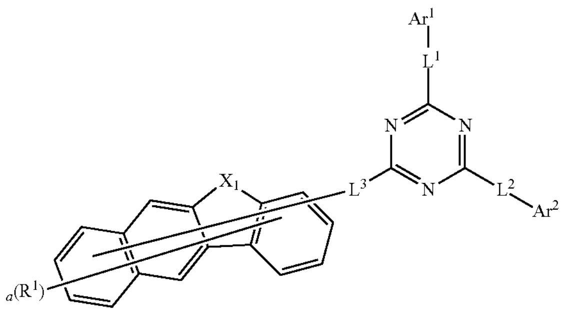

[Formula 2]

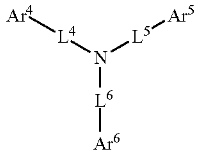

wherein, $X_1$ is O or S, $Ar^1$, $Ar^2$, and $Ar^4$ to $Ar^6$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group, $L^1$ to $L^6$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof, $R^1$ is selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent $R^1$s are not linked to each other to form a ring, a is an integer of 0 to 9, and where a is an integer of 2 or more, a plurality of $R^1$s are the same as or different from each other, L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof, $R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a combination thereof, $Ar^1$ to $Ar^2$, $L^1$ to $L^6$, $R^1$, L', $R_a$, and $R_b$, may be each optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group, and $Ar^4$ to $Ar^6$ may be each optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group, a $C_8$-$C_{20}$ arylalkenyl group and -L'-N($R_a$)($R_b$).

2. The organic electric element of claim 1, wherein $L^1$ to $L^6$ are each independently represented by one of Formulas b-1 to b-13:

<Formula b-1>

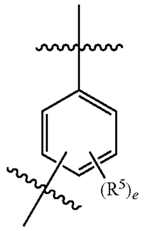

<Formula b-2>

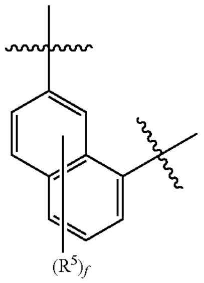

-continued

<Formula b-3>

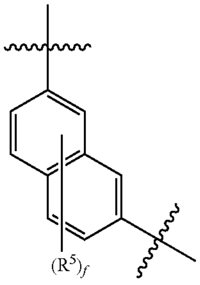

<Formula b-4>

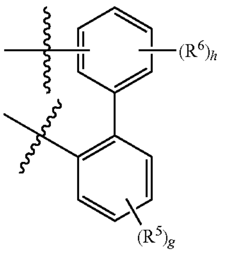

<Formula b-5>

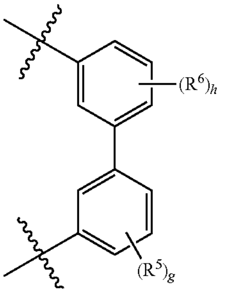

<Formula b-6>

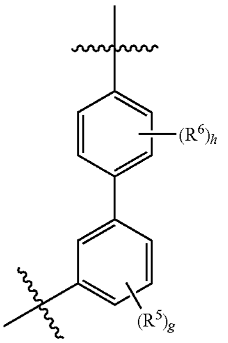

<Formula b-7>

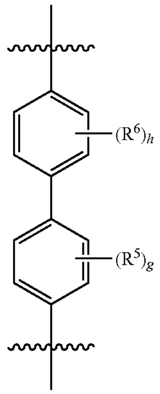

-continued

<Formula b-8>

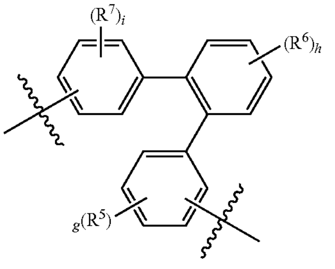

<Formula b-9>

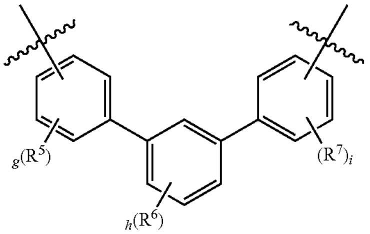

<Formula b-10>

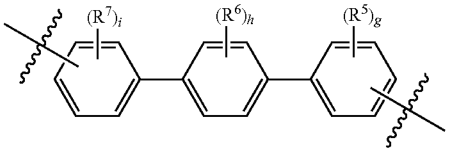

<Formula b-11>

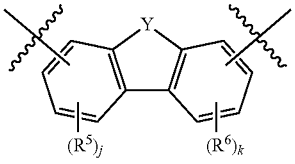

<Formula b-12>

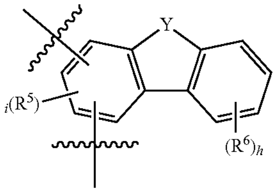

-continued

<Formula b-13>

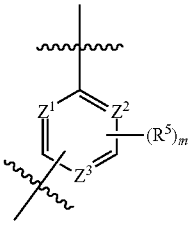

wherein, $R^5$ to $R^7$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, and a $C_6$-$C_{20}$ aryloxy group, Y is N-($L^a$-$Ar^a$), O, S or C(R')(R"), $Z^1$ to $Z^3$ are each independently C, C(R') or N, and at least one of $Z^1$ to $Z^3$ is N, f is an integer of 0 to 6, e, g, h and i are each an integer of 0 to 4, j and k are each an integer of 0 to 3, l is an integer of 0 to 2, m is an integer of 0 to 3, and where they are each an integer of 2 or more, a plurality of $R^5$s, a plurality of $R^6$s, or a plurality of $R^7$s are the same as or different from each other, R' and R" are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group, and -$L^a$-N($R^a$)($R^b$), R' and R" of C(R')(R") may optionally be linked to each other to form a ring, and adjacent R's of C(R') may optionally be linked to each other to form a ring, $Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof, $L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof, $R^a$ and $R^b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

3. The organic electric element of claim 1, wherein Formula 1 is represented by one of Formula 1-A to Formula 1-G:

<Formula 1-A>

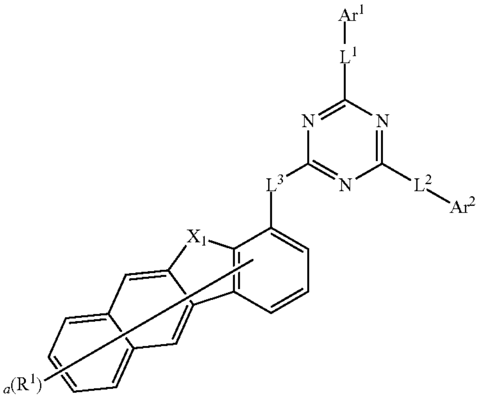

<Formula 1-B>

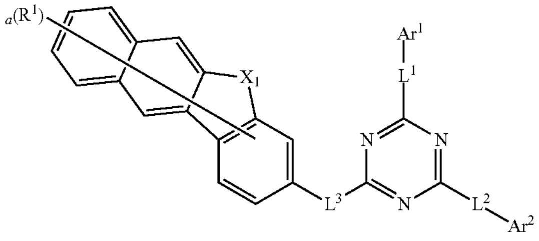

<Formula 1-C>

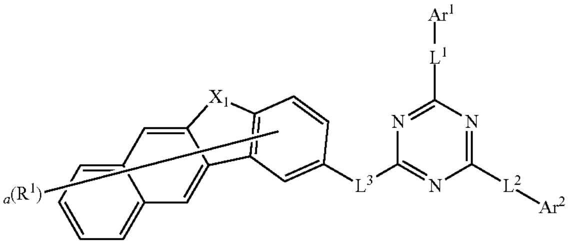

<Formula 1-D>

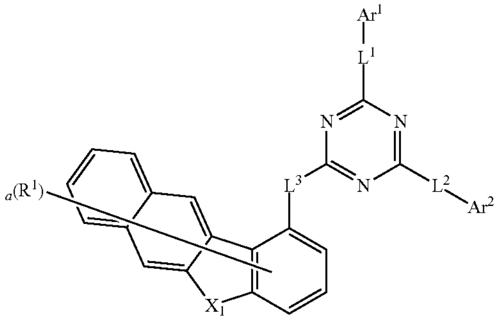

<Formula 1-E>

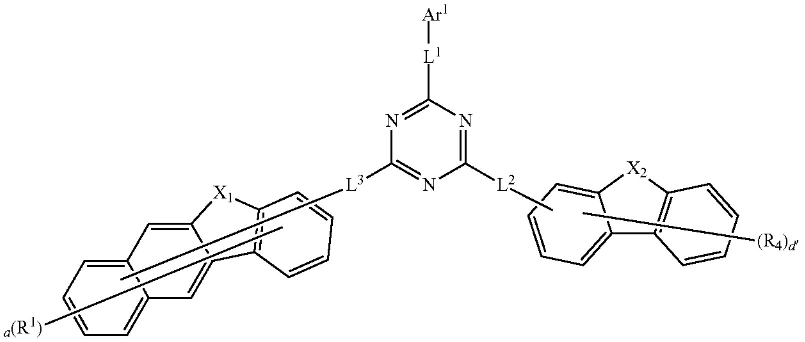

<Formula 1-F>

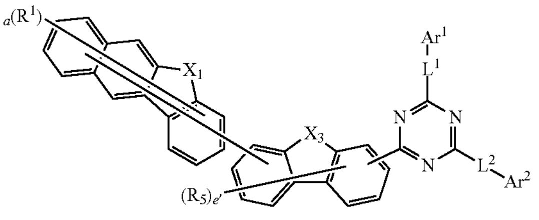

<Formula 1-G>

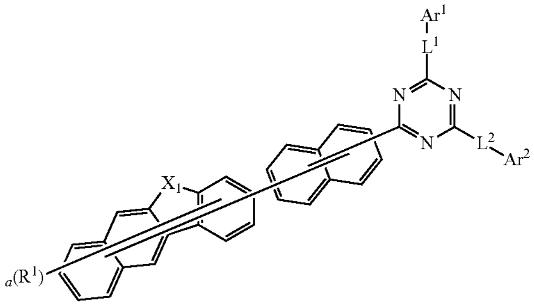

wherein, $Ar^1$, $Ar^2$, $L^1$~$L^3$, $X_1$, $R^1$ and a are the same as defined in claim 1, $X_2$ and $X_3$ are each independently O or S, $R_4$ and $R_5$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, and a $C_6$-$C_{30}$ aryloxy group, and adjacent groups may optionally be linked to each other to form a ring, d' is an integer of 0 to 7, e' is an integer of 0 to 6, and where they are each an integer of 2 or more, a plurality of $R_4$s or a plurality of $R_5$s are the same as or different from each other.

4. The organic electric element of claim 1, wherein Formula 2 is represented by one of Formula 2-A to Formula 2-L:

<Formula 2-A>

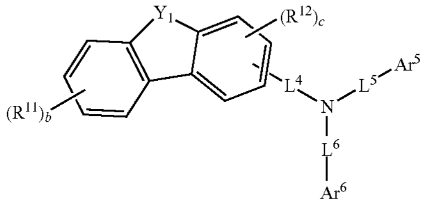

<Formula 2-B>

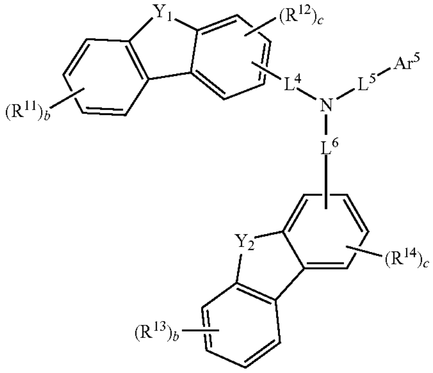

<Formula 2-C>

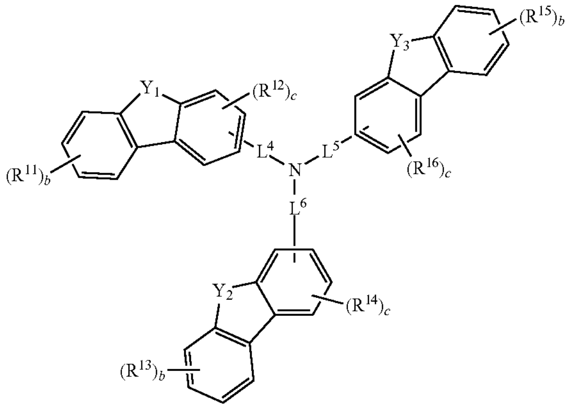

<Formula 2-D>

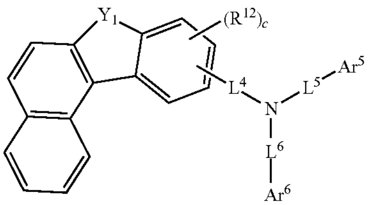

-continued

<Formula 2-E>

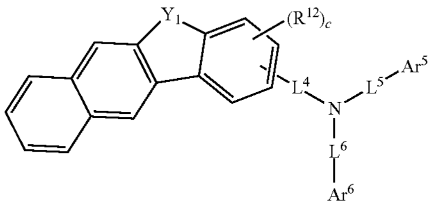

<Formula 2-F>

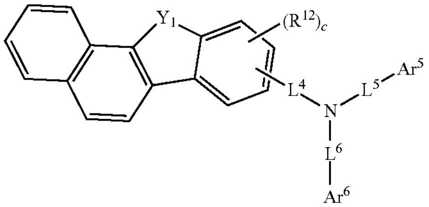

<Formula 2-G>

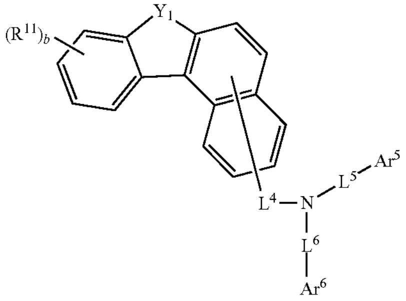

<Formula 2-H>

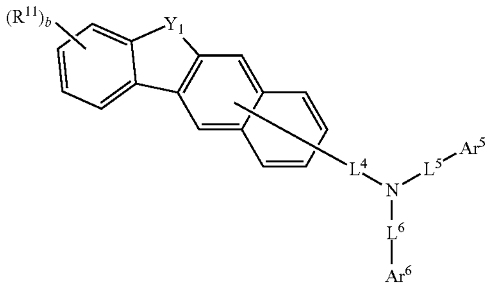

<Formula 2-I>

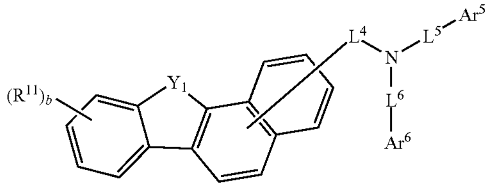

<Formula 2-J>

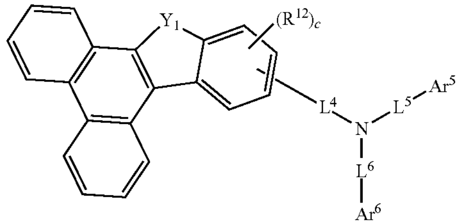

-continued

<Formula 2-K>

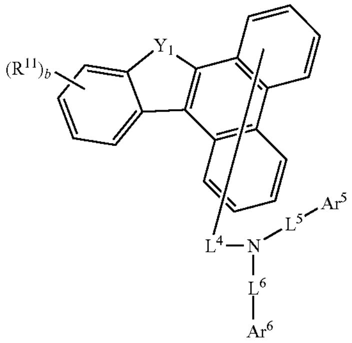

<Formula 2-L>

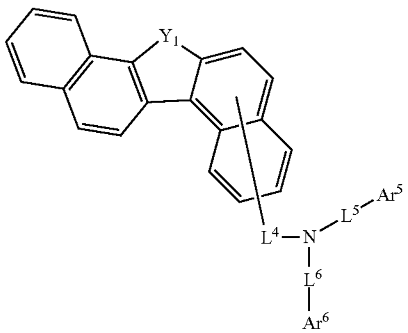

wherein, $Ar^5$, $Ar^6$, and $L^4$~$L^6$ are the same as defined in claim 1, $Y_1$ to $Y_3$ are each independently O, S, or C(R')(R"), $R^{11}$ to $R^{16}$, R' and R" are each independently selected from the group consisting of hydrogen, deuterium, halogen, a silane group substituted or unsubstituted with $C_1$-$C_{20}$ alkyl group or $C_6$-$C_{20}$ aryl group, a cyano group, a nitro group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and -L'-N($R_a$)($R_b$), and adjacent groups may optionally be linked to each other to form a ring, b is an integer of 0 to 4, and where b is an integer of 2 or more, a plurality of $R^{11}$s, a plurality of $R^{13}$s, or a plurality of $R^{15}$s are the same as or different from each other, c is an integer of 0 to 3, and where c is an integer of 2 or more, a plurality of $R^{12}$s, a plurality of $R^{14}$s, or a plurality of $R^{16}$s are the same as or different from each other, L', $R_a$ and $R_b$ are the same as defined in claim 1.

5. The organic electric element of claim 1, wherein the compound represented by Formula 1 is one of the following compounds:

1-1

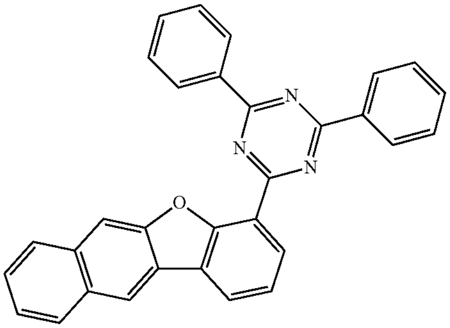

1-2

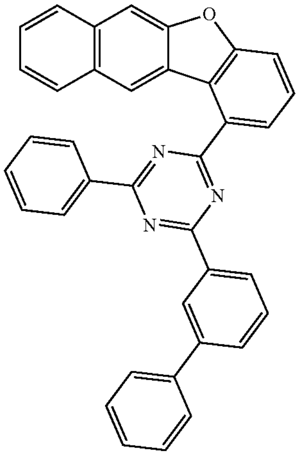

1-3

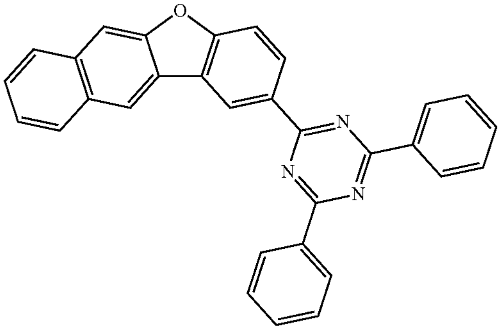

1-4

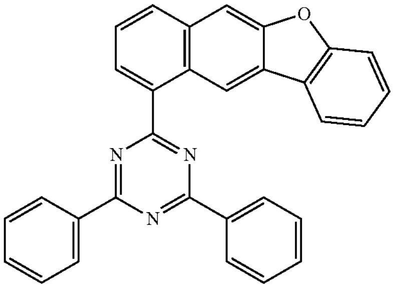

-continued
1-5
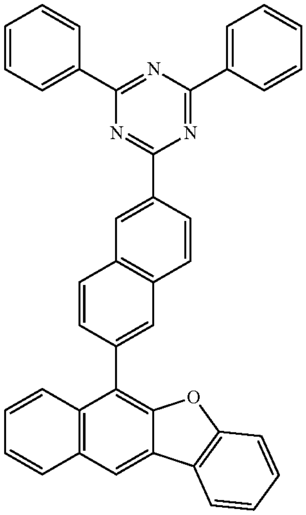
1-6
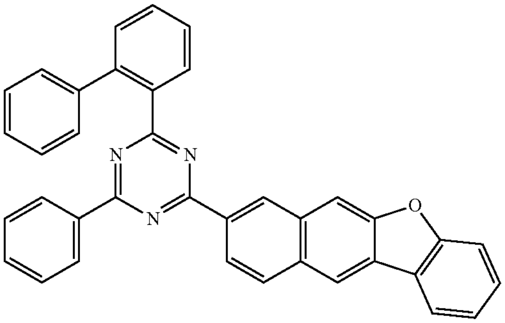
1-7
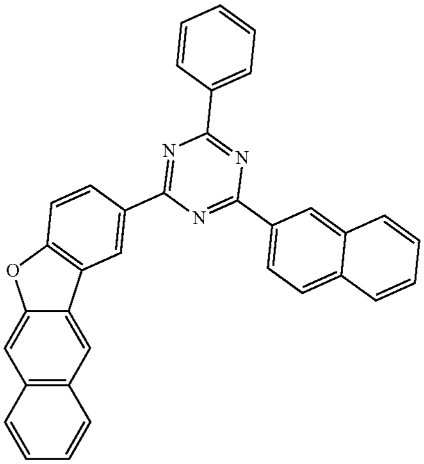
-continued
1-8
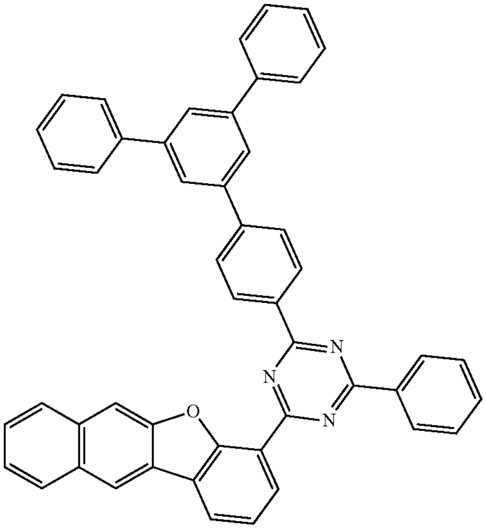
1-9
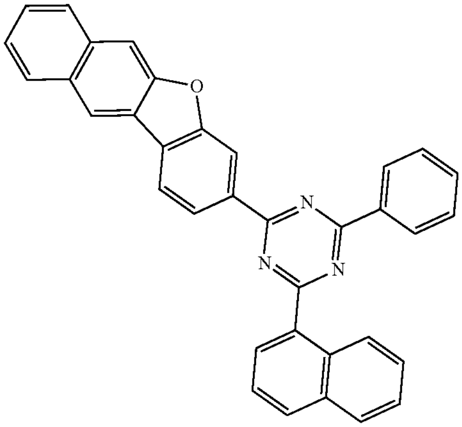
1-10
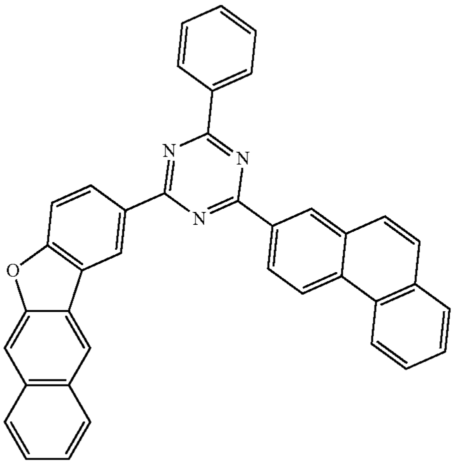

-continued
1-11
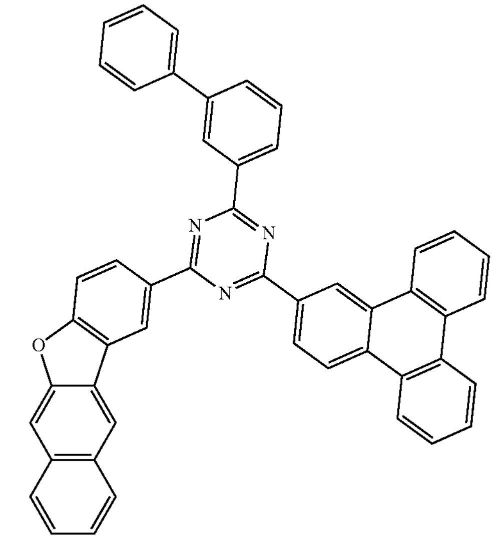
1-12
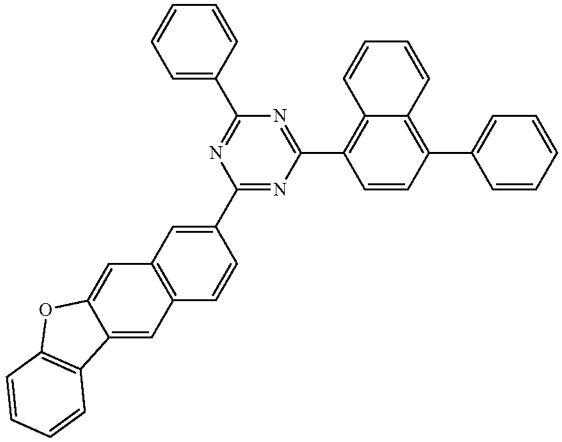
1-13
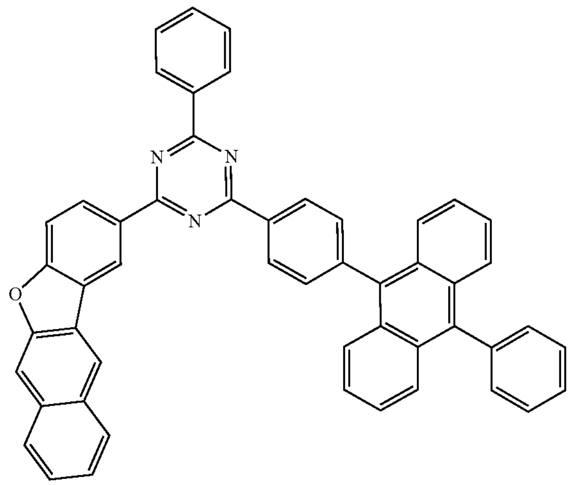
-continued
1-14
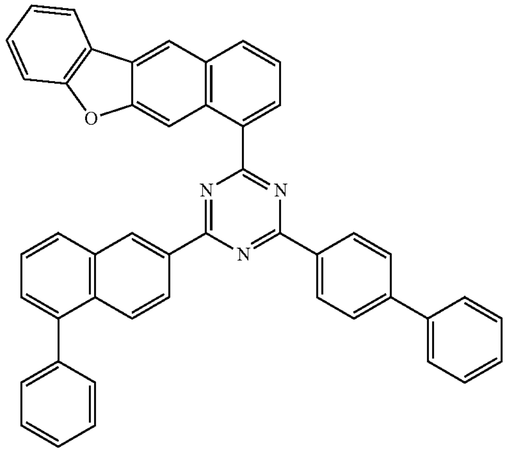
1-15
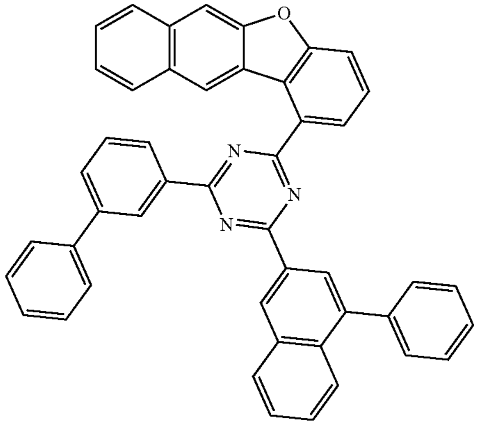
1-16
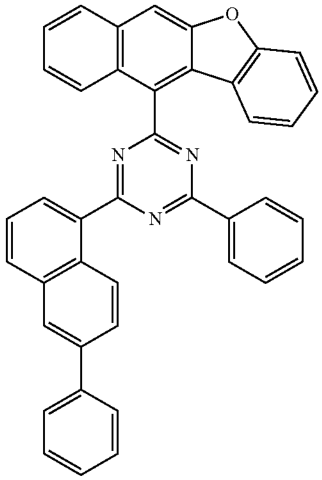

-continued
1-17
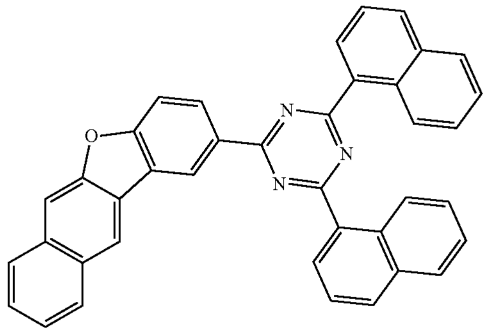
1-18
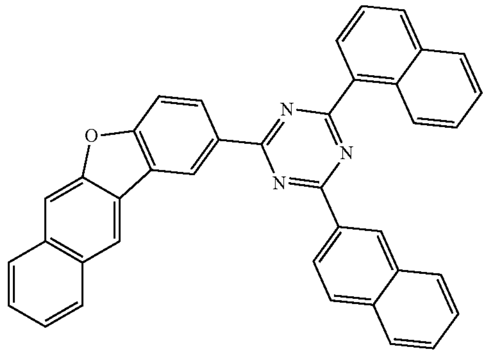
1-19
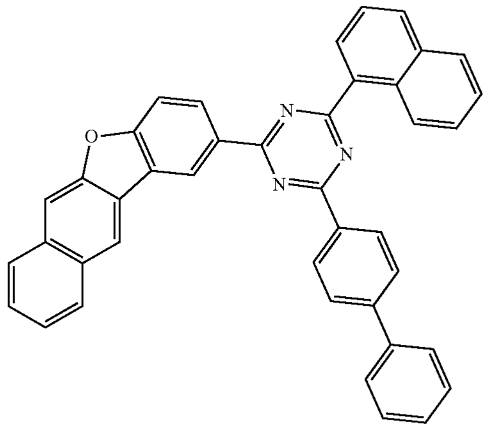
1-20
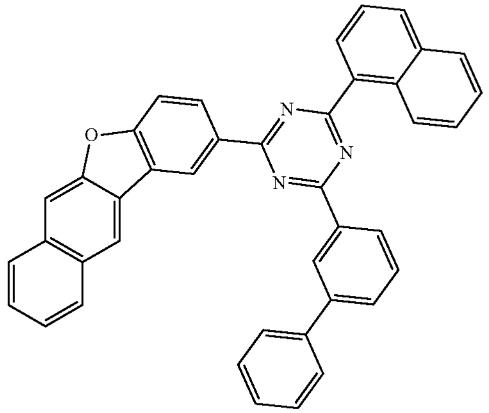
-continued
1-21
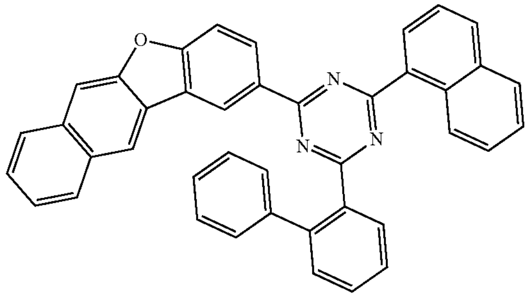
1-22
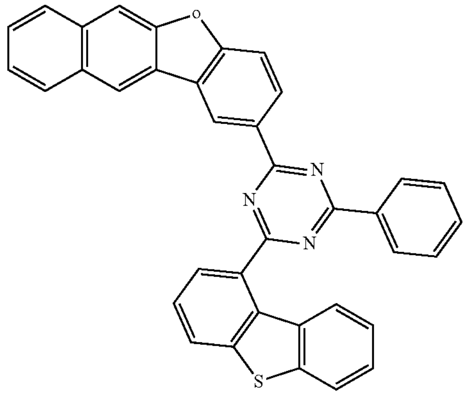
1-23
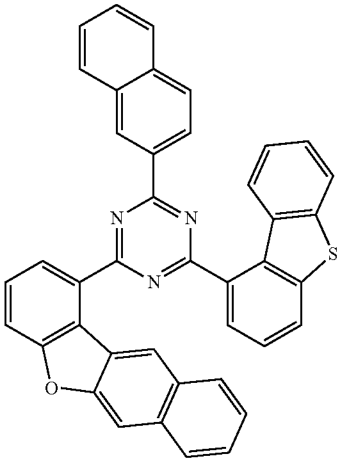
1-24
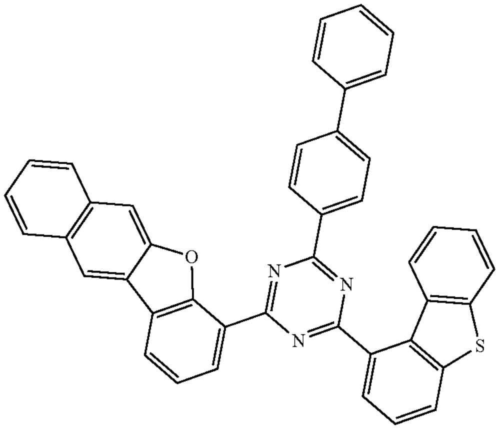

-continued
1-25
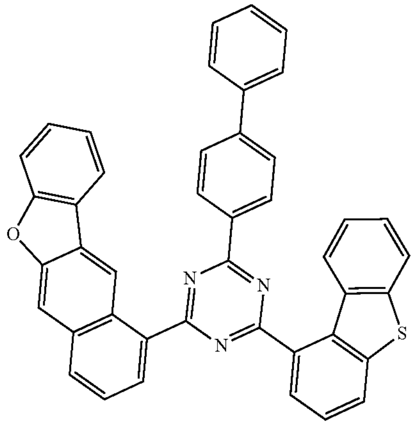
1-26
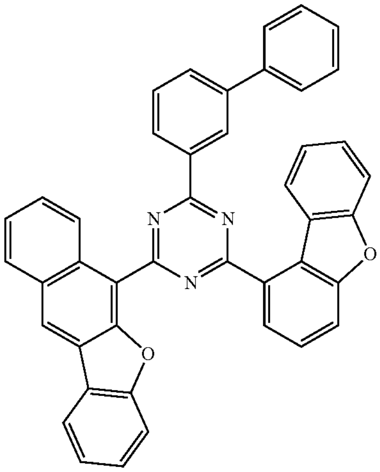
1-27
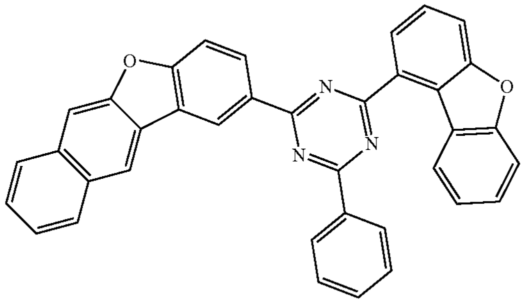
1-28
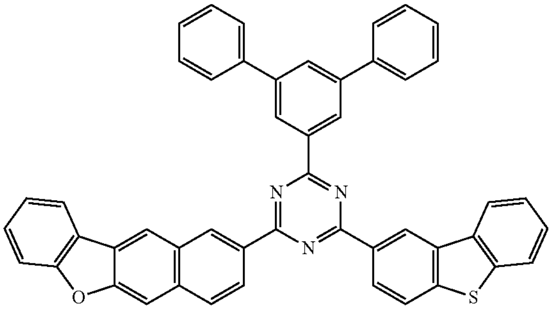
-continued
1-29
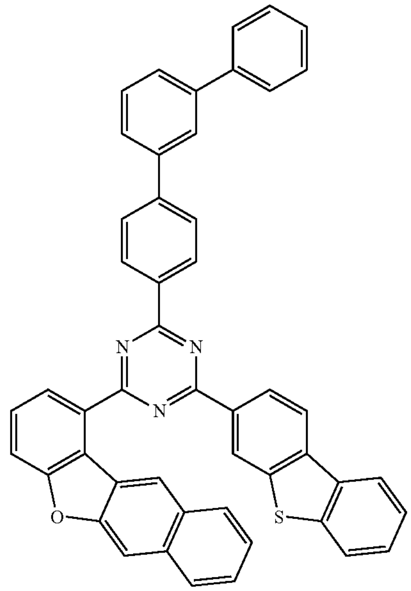
1-30
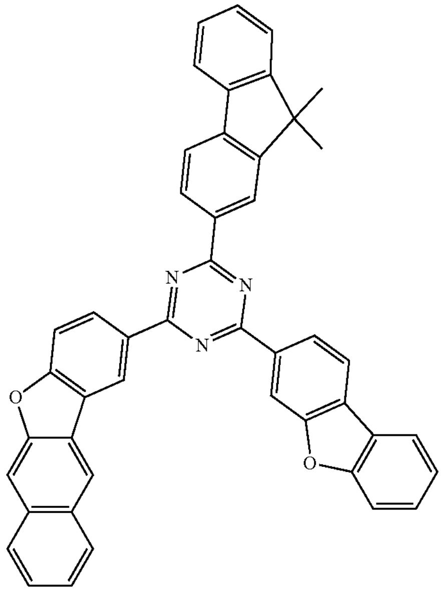
1-31
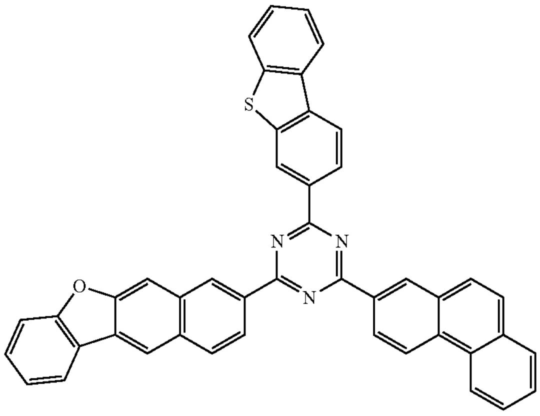

-continued
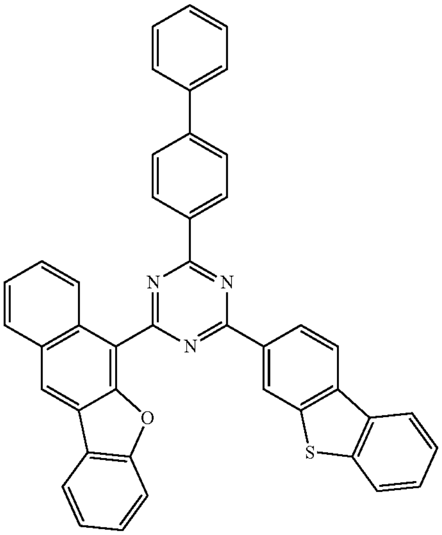
1-32
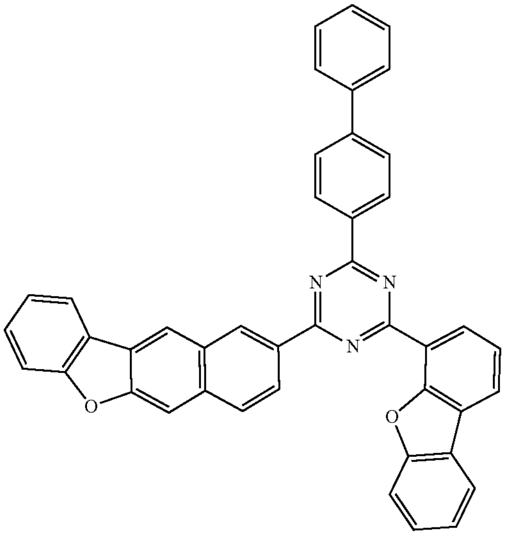
1-33
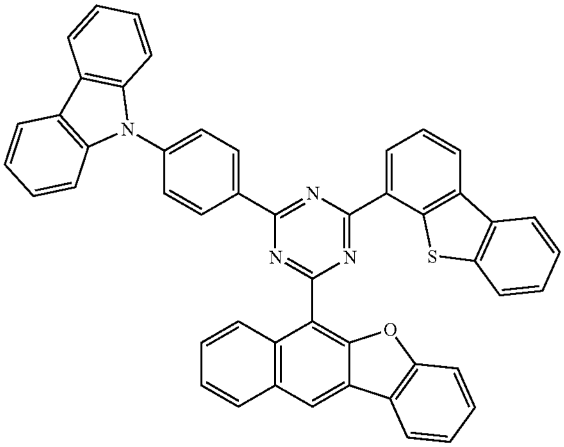
1-34
-continued
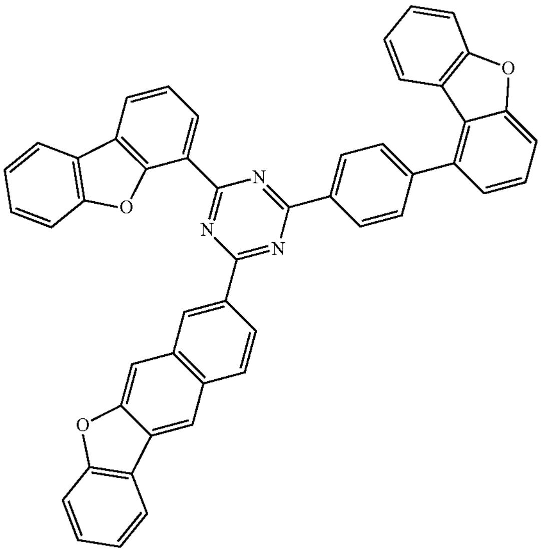
1-35
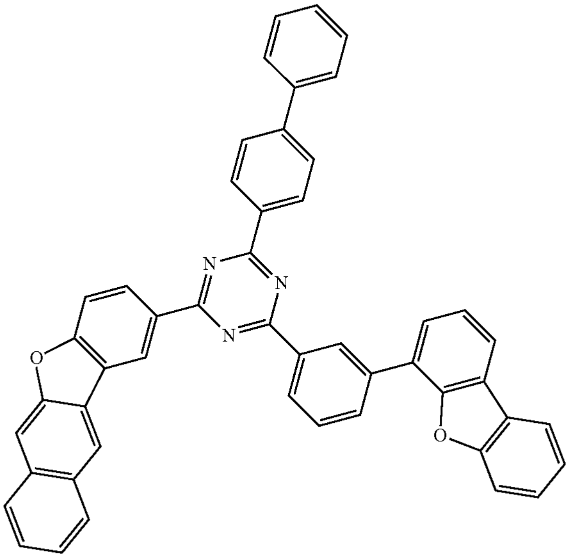
1-36

-continued
1-37
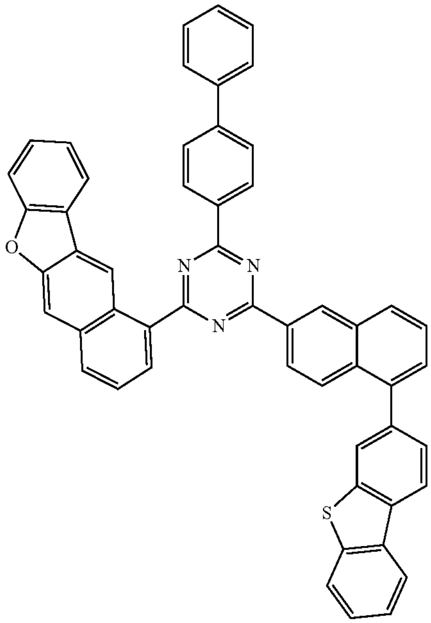
1-38
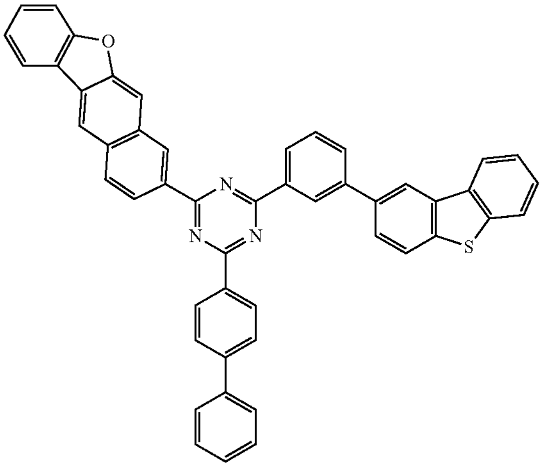
-continued
1-39
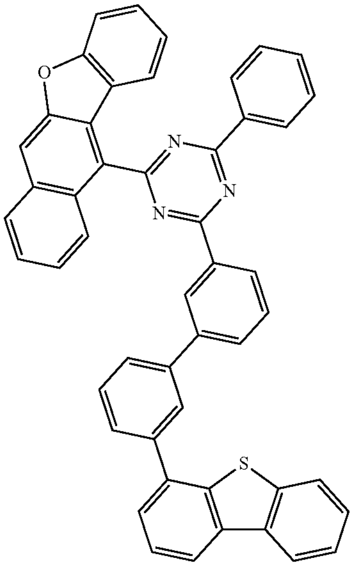
1-40
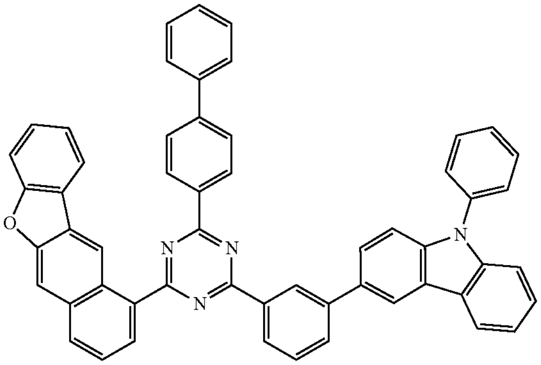
1-41
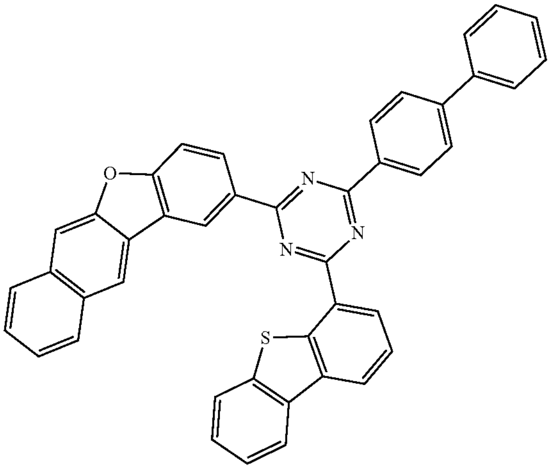

-continued
1-42
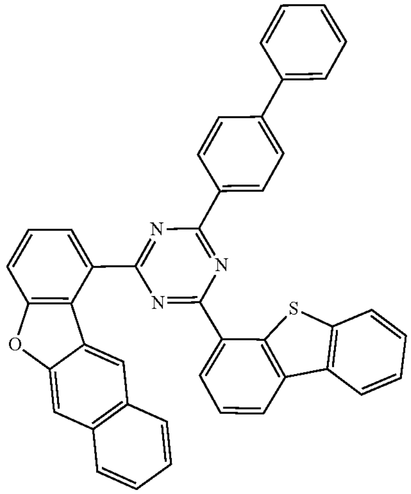
1-43
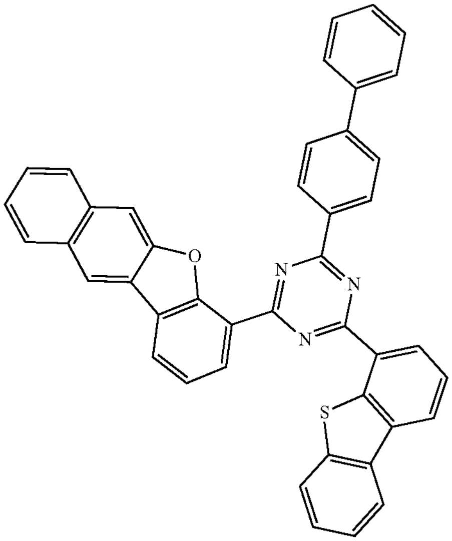
1-44
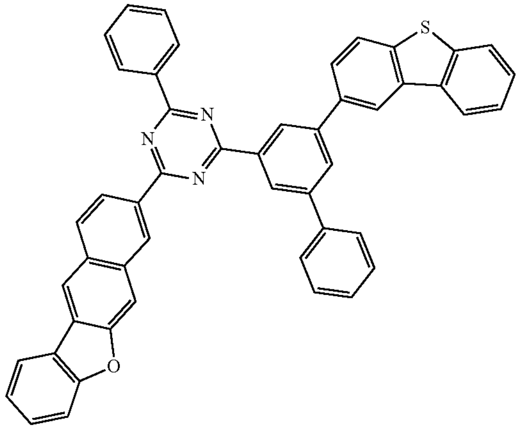
-continued
1-45
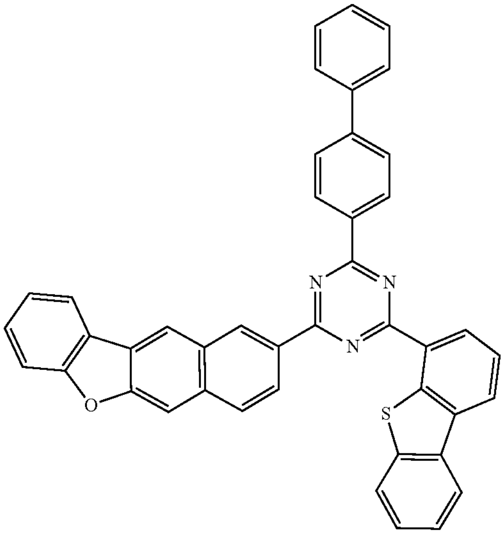
1-46
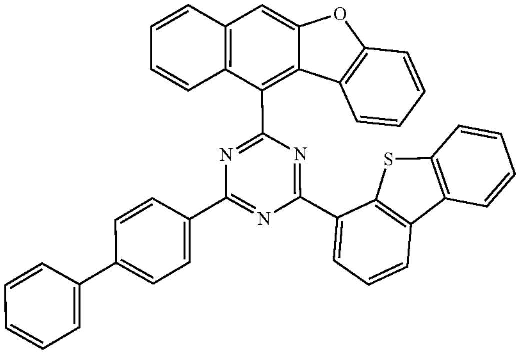
1-47
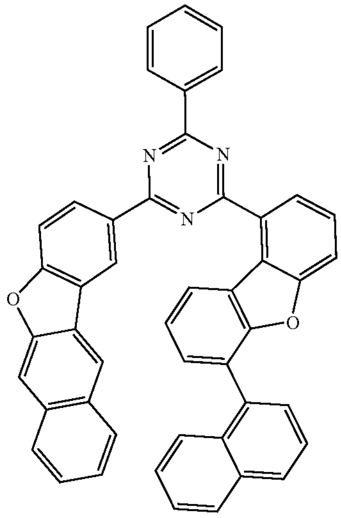

-continued
1-48
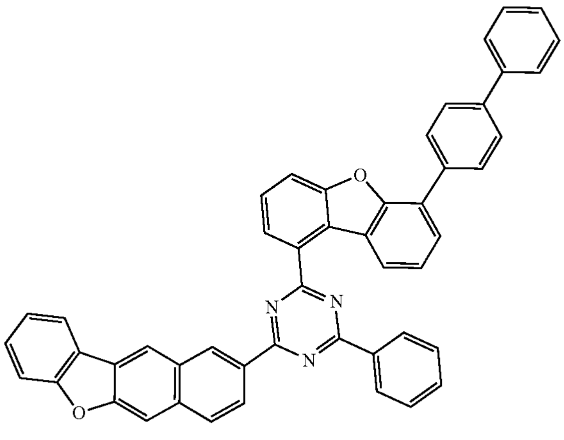
1-49
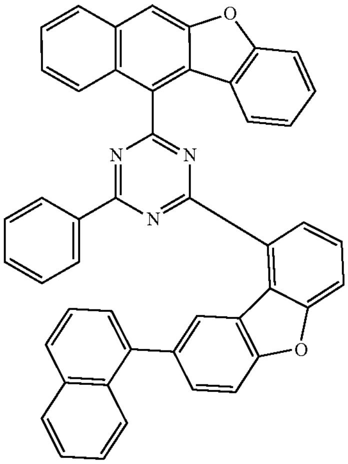
1-50
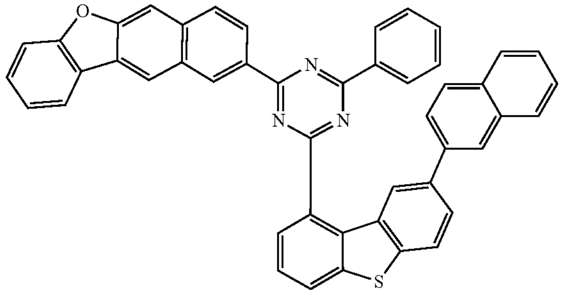
1-51
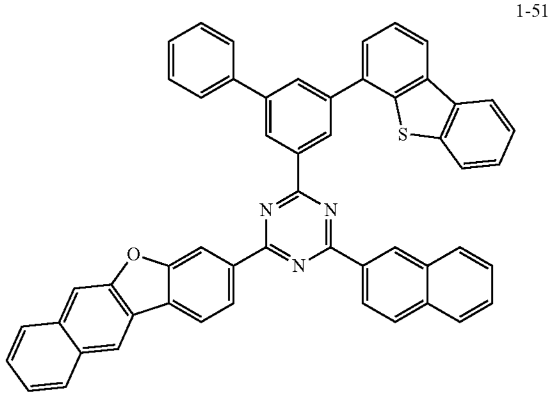
-continued
1-52
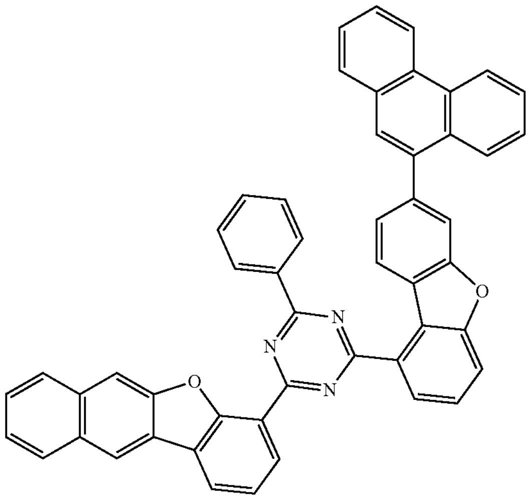
1-53
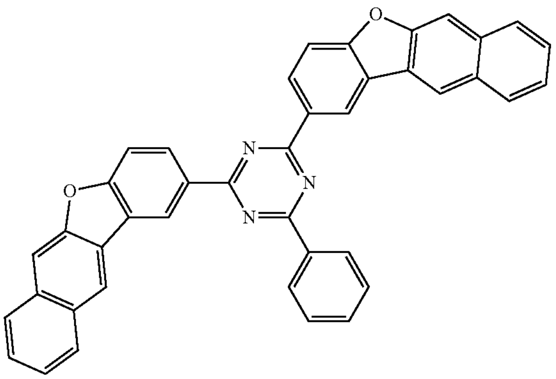
1-54
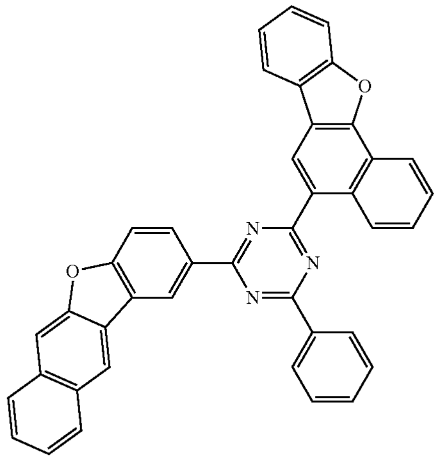

-continued
1-55
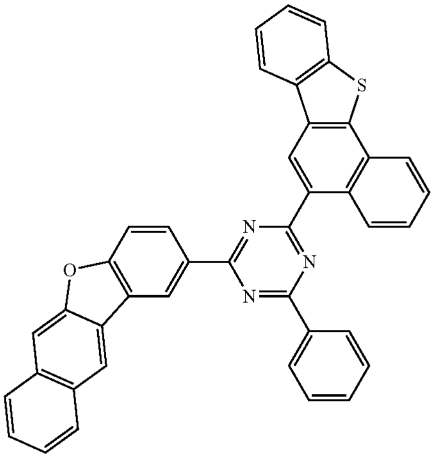
1-56
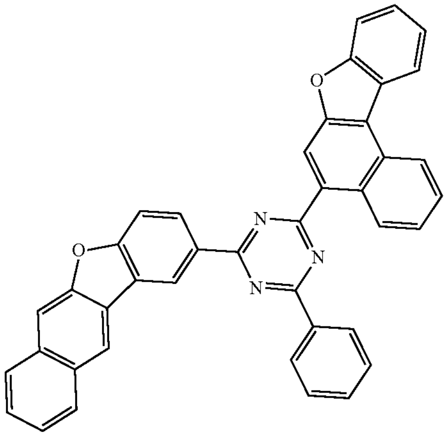
1-57
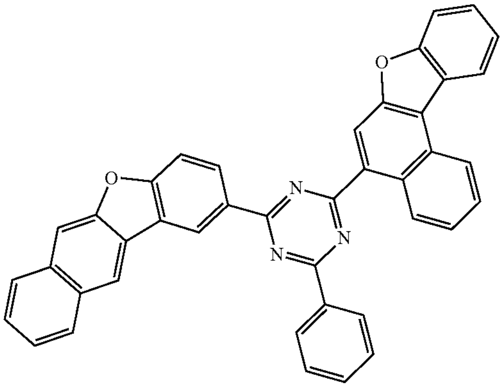
-continued
1-58
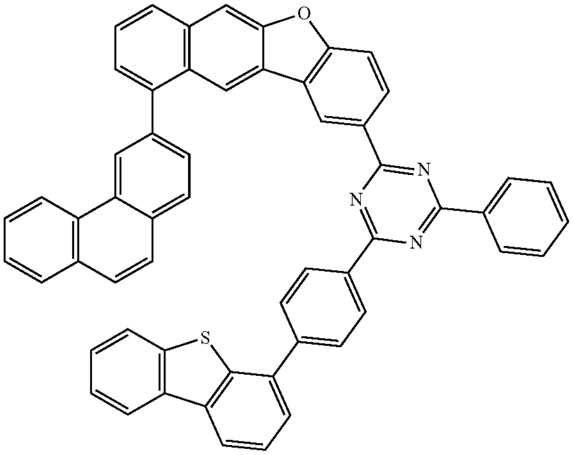
1-59
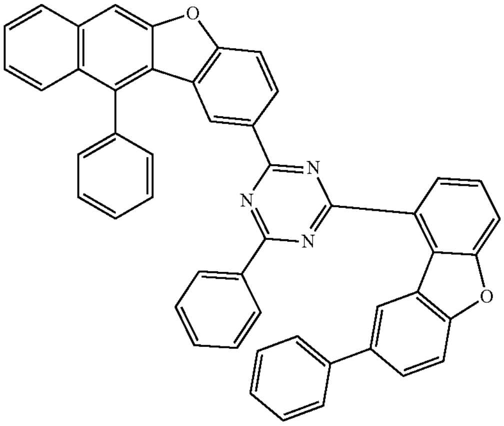
1-60
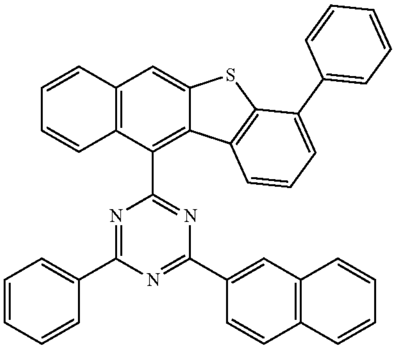
1-61
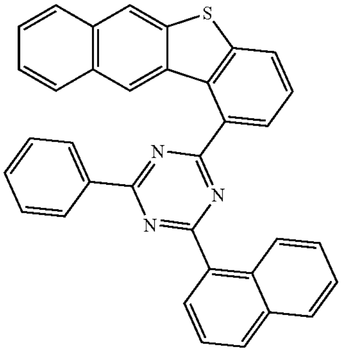

-continued
1-62
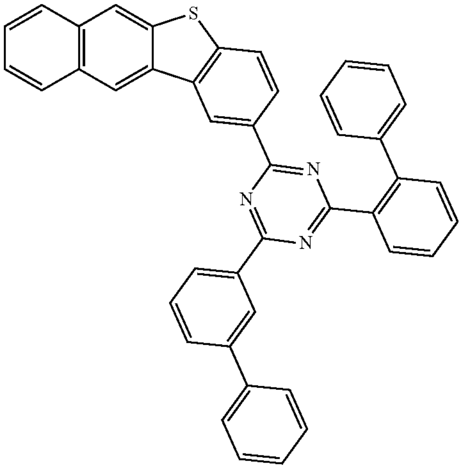
1-63
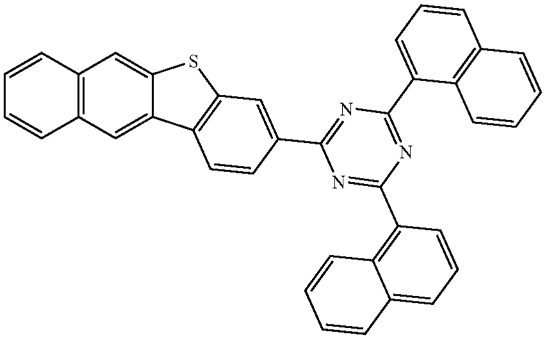
1-64
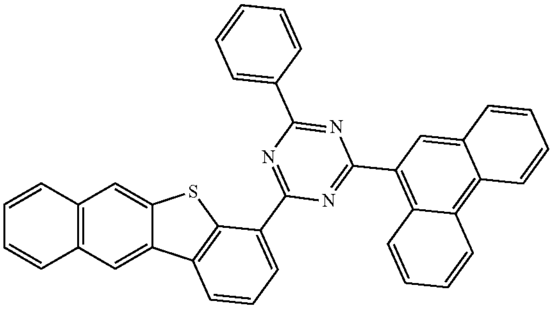
1-65
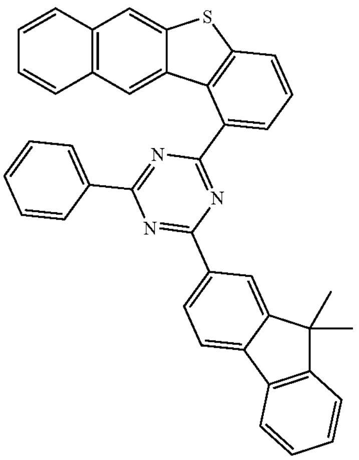
-continued
1-66
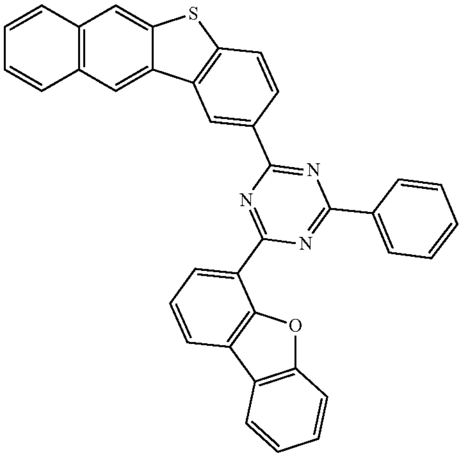
1-67
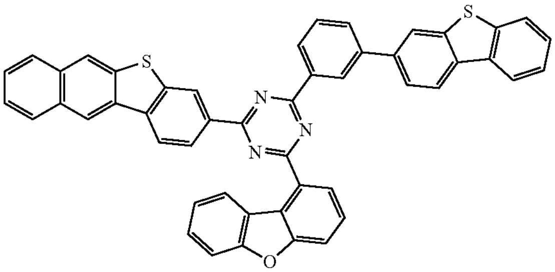
1-68
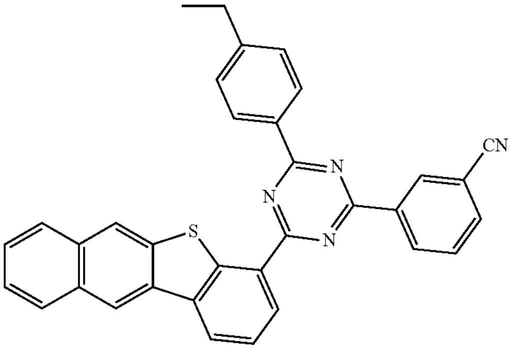
1-69
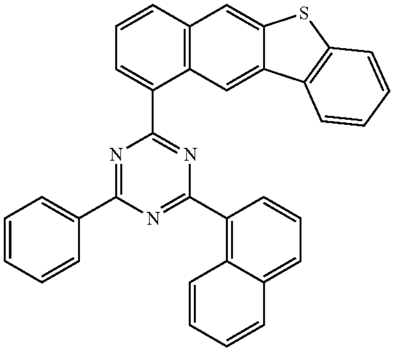

-continued
1-70
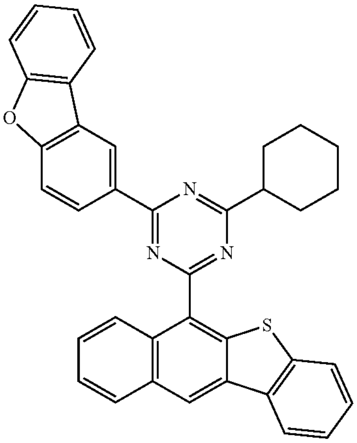
1-71
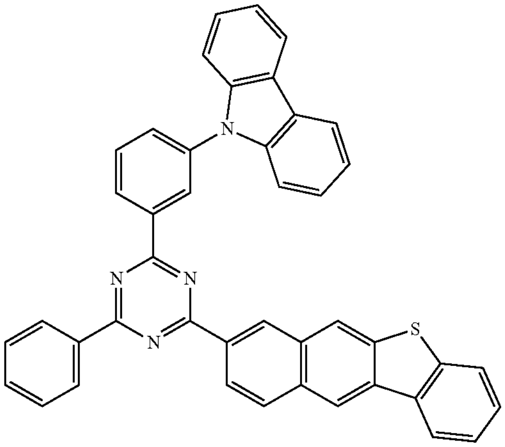
1-72
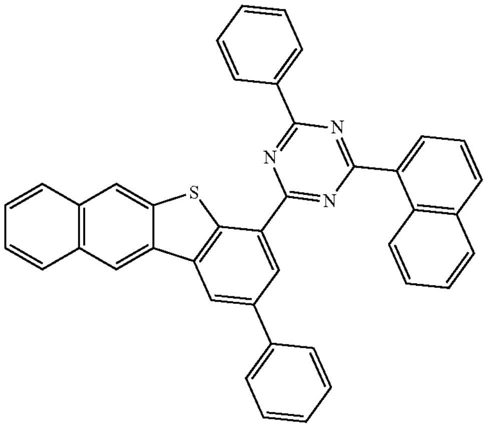
-continued
1-73
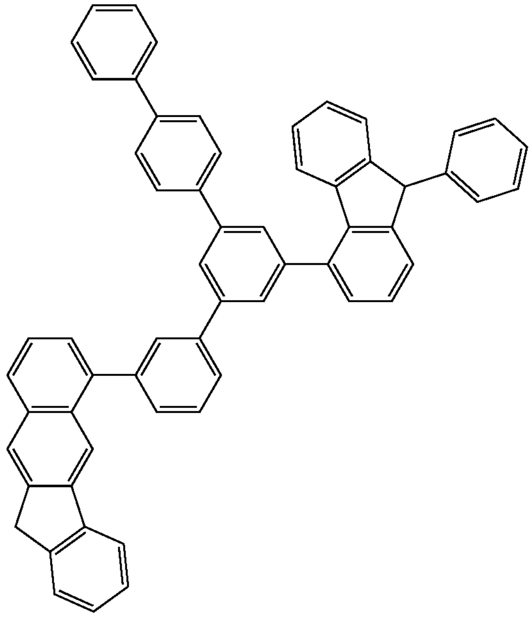
1-74
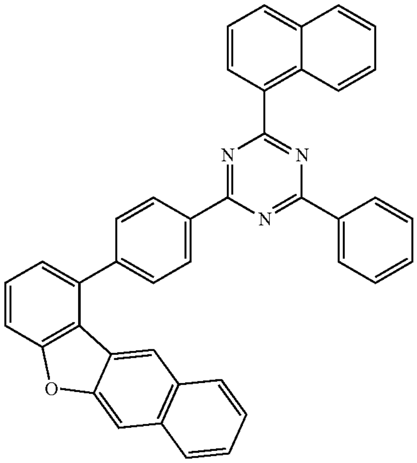
1-75
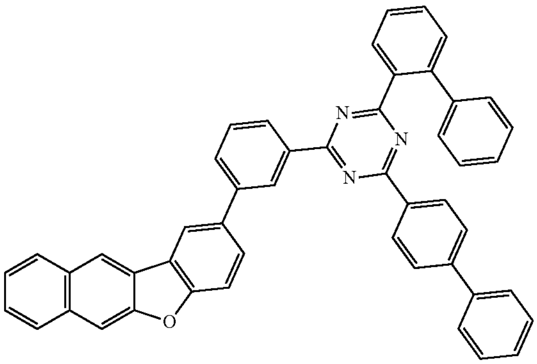

-continued
1-76
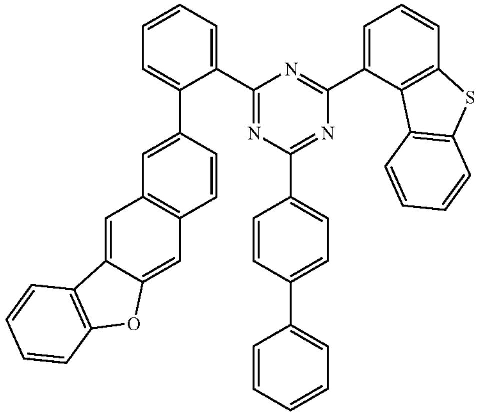
1-77
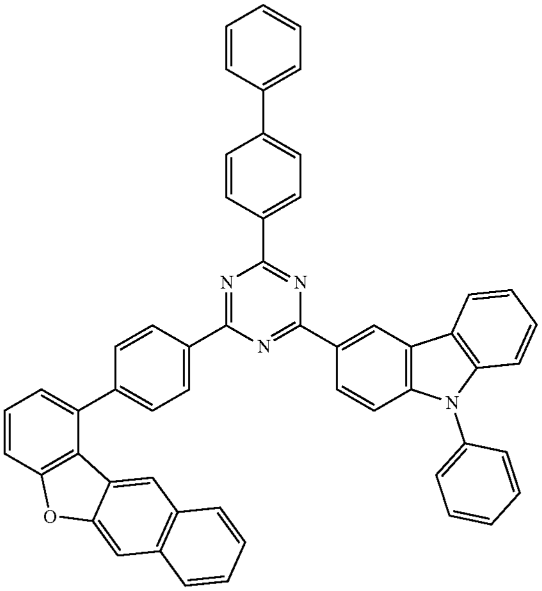
1-78
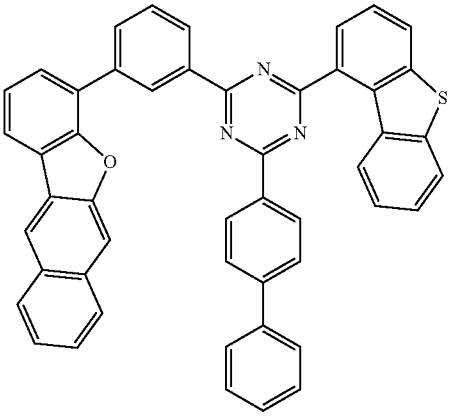
-continued
1-79
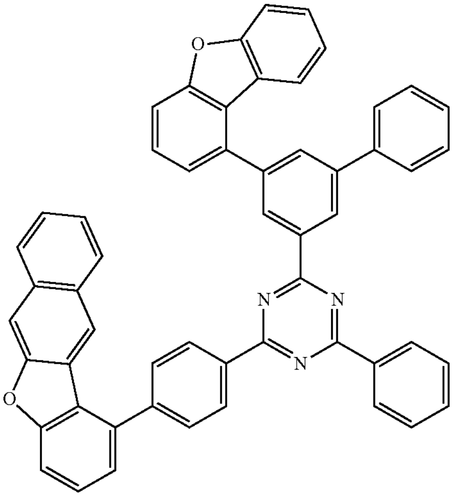
1-80
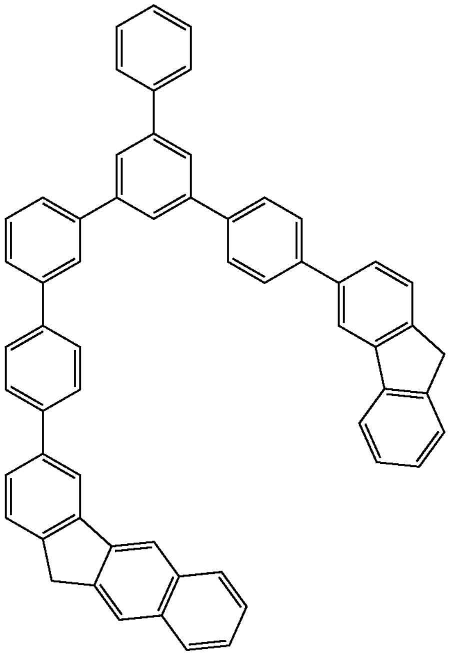
1-81
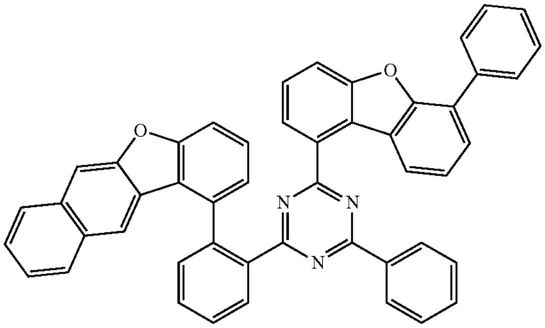

-continued
1-82
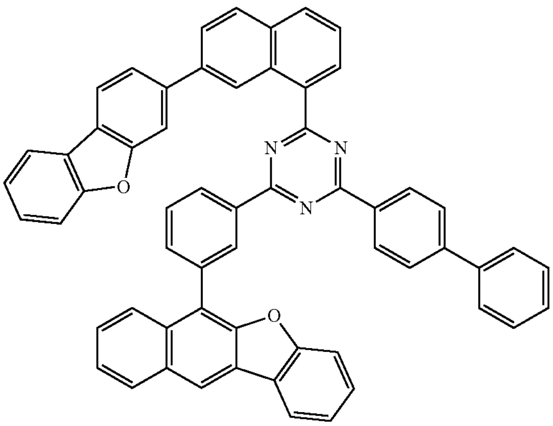
1-83
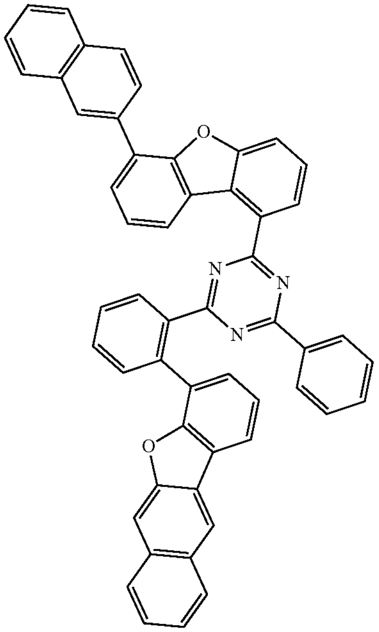
1-84
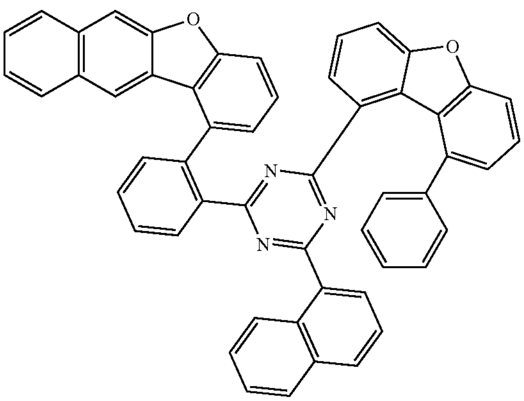
-continued
1-85
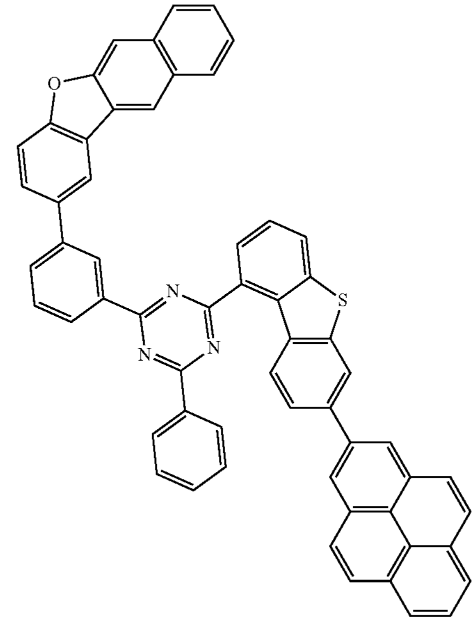
1-86
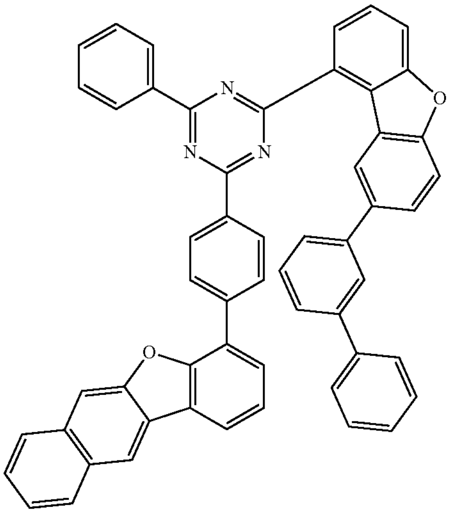
1-87
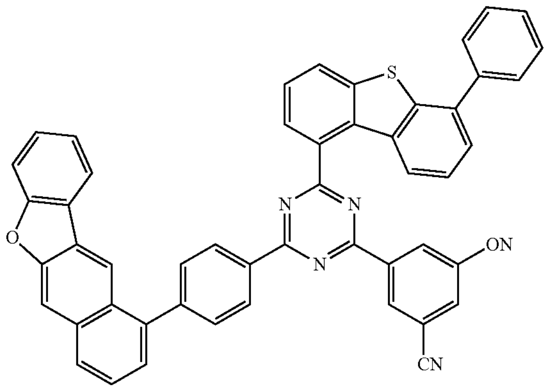

-continued
1-88
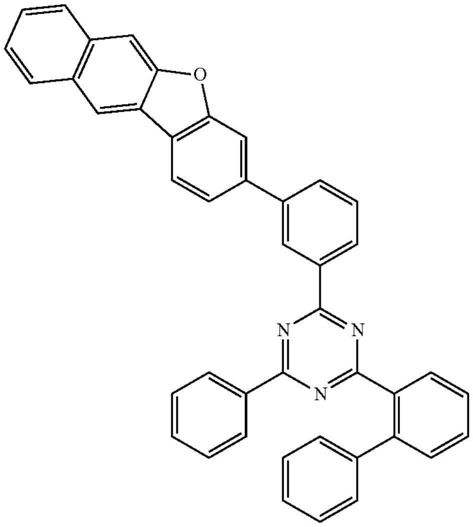
1-89
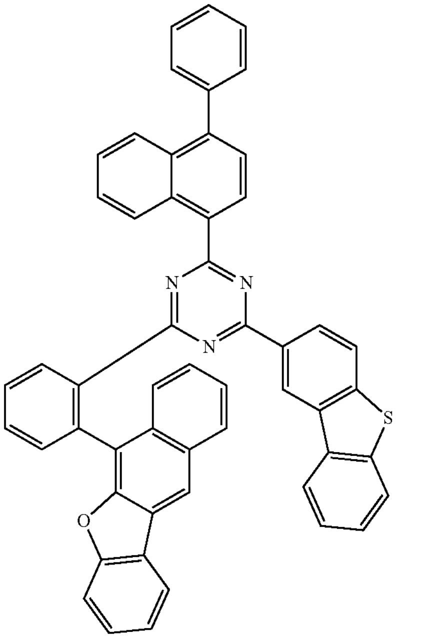
-continued
1-90
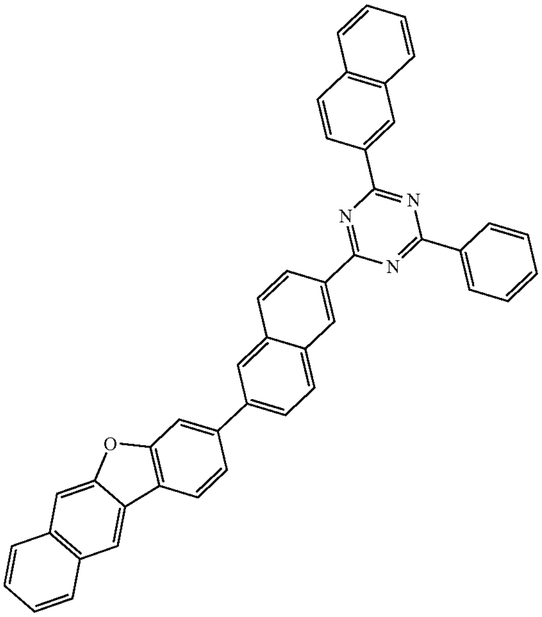
1-91
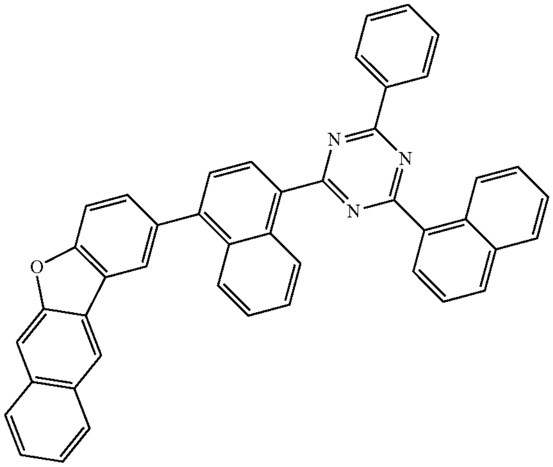
1-92
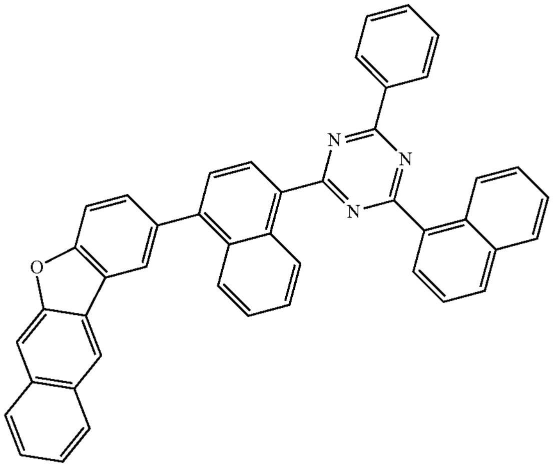

-continued
1-93
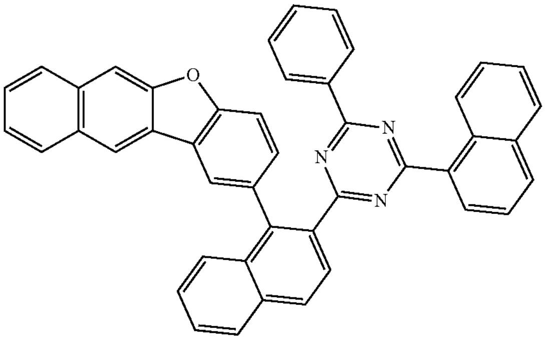
1-94
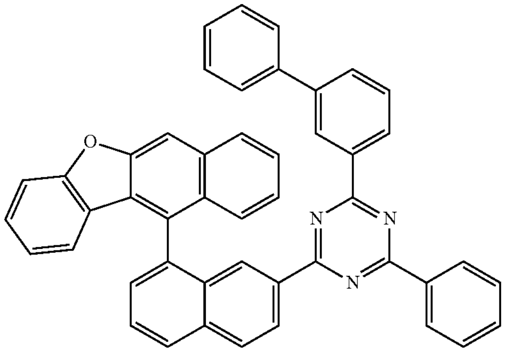
1-95
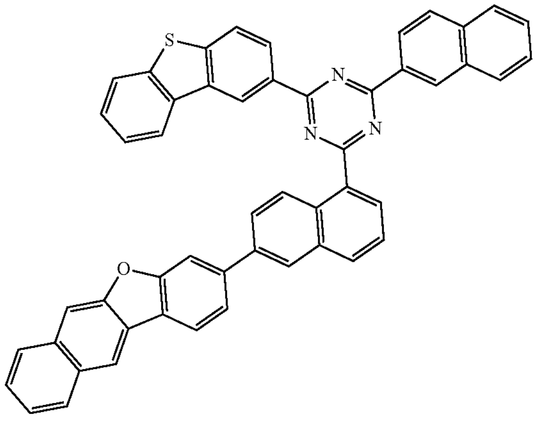
-continued
1-96
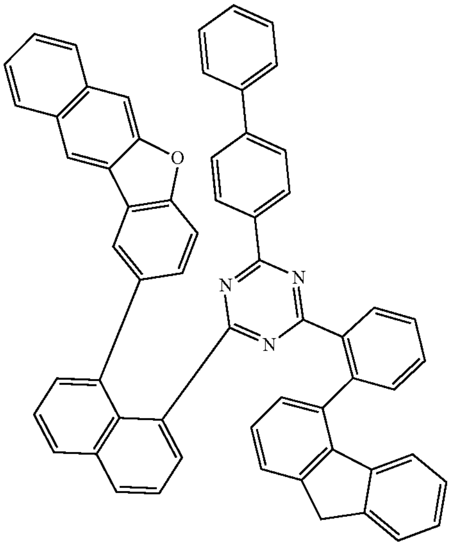
1-97
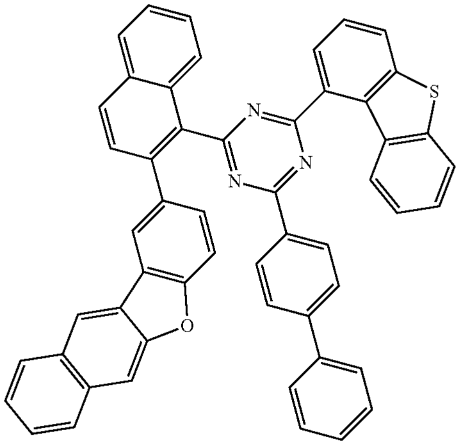
1-98
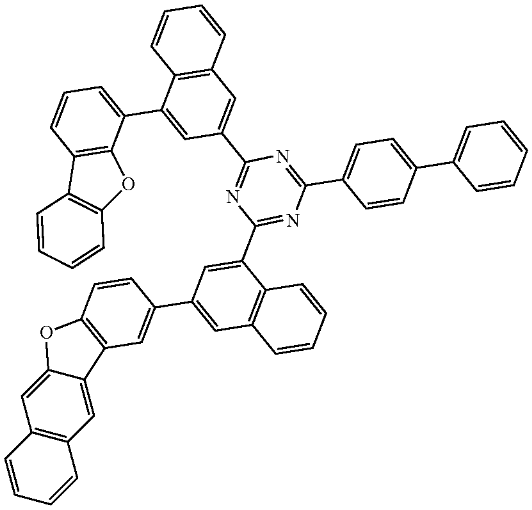

-continued
1-99
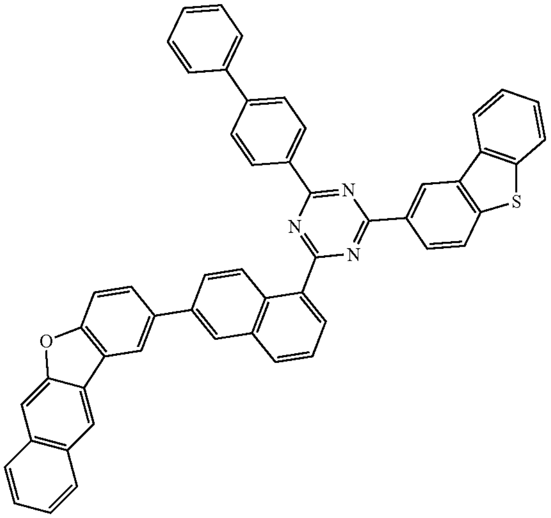
1-100
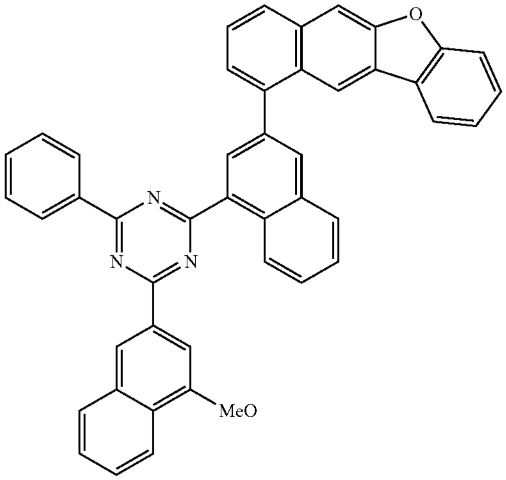
1-101
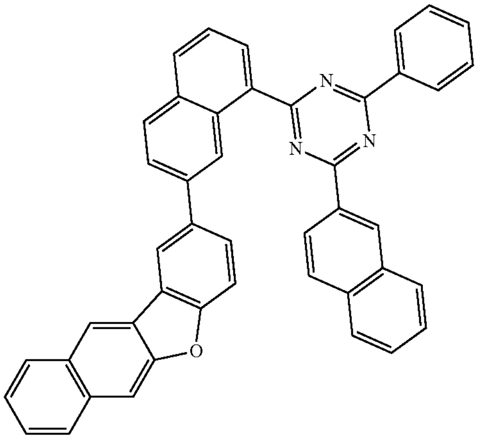
-continued
1-102
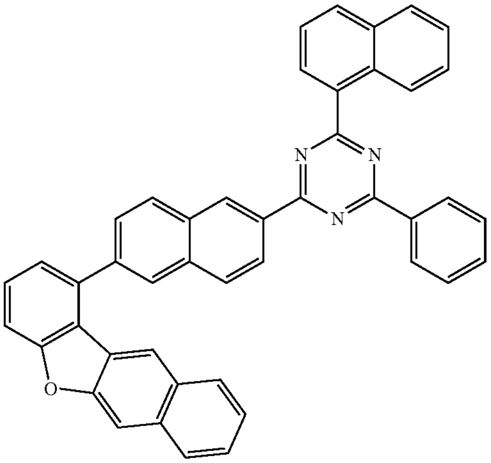
1-103
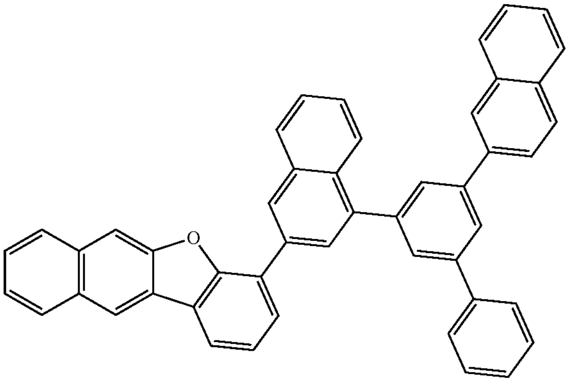
1-104
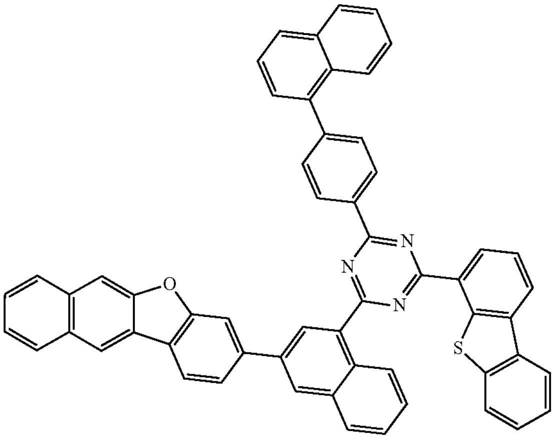

1-105
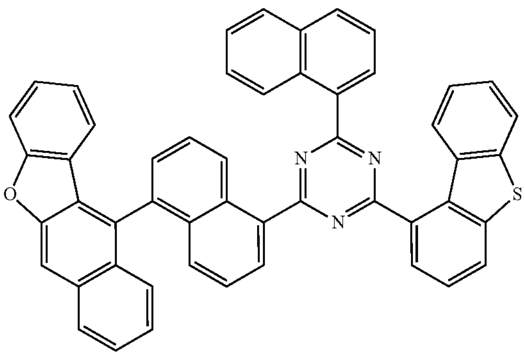
1-106
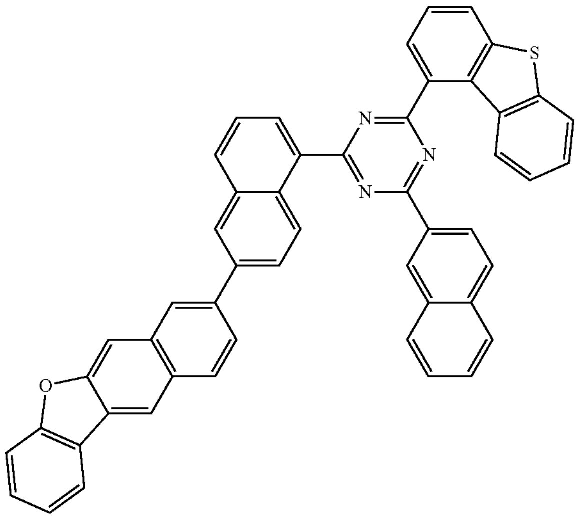
1-107
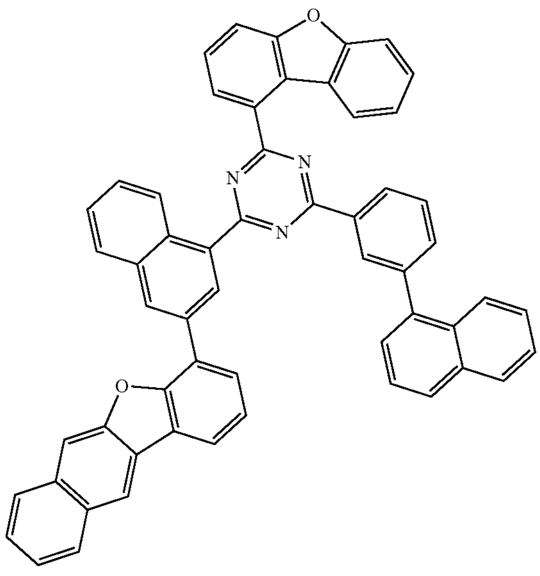
1-108
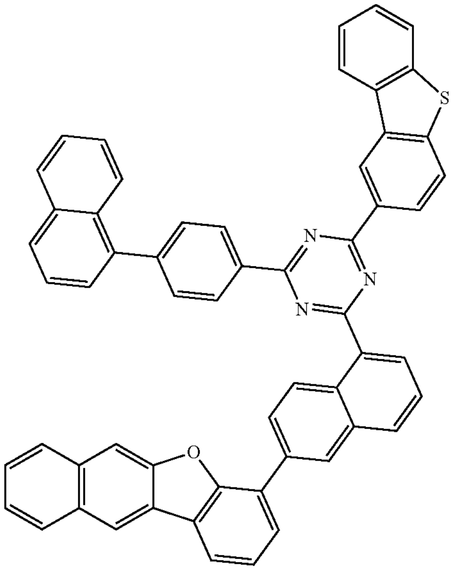
1-109
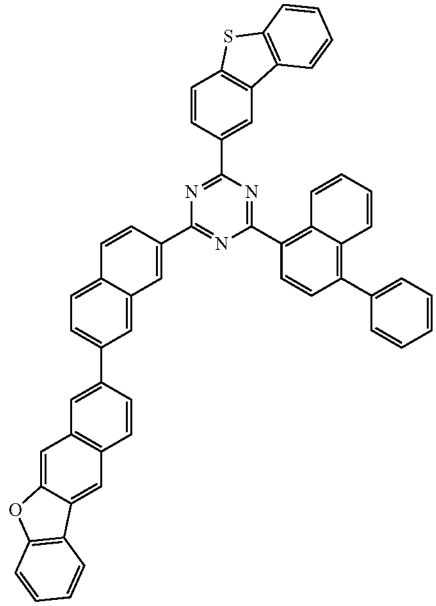
1-110
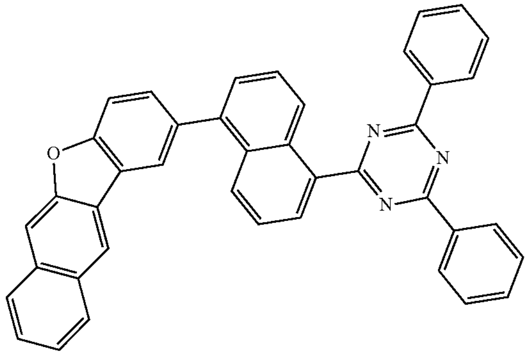

-continued
1-111
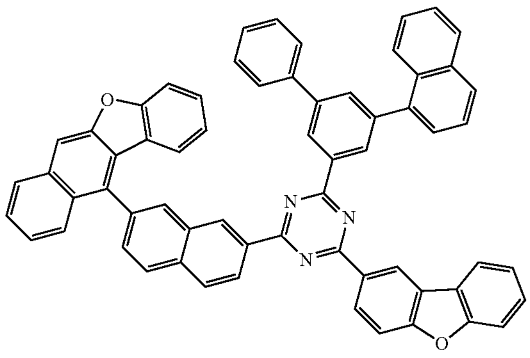
1-112
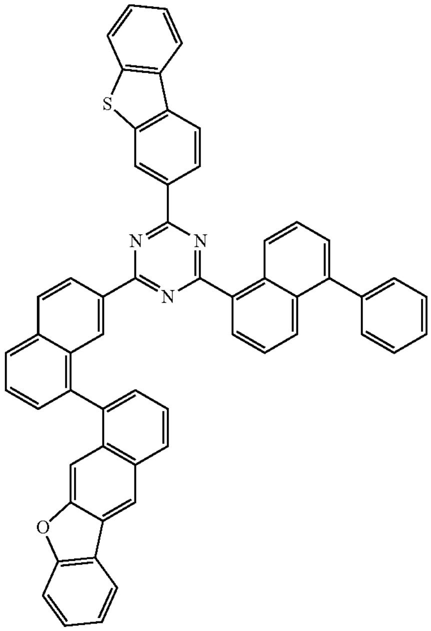
1-113
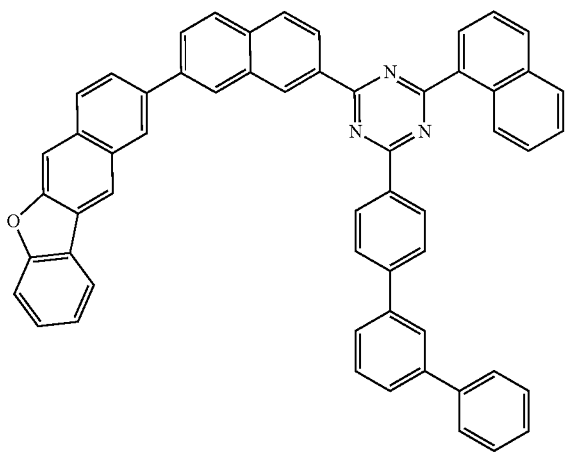
-continued
1-114
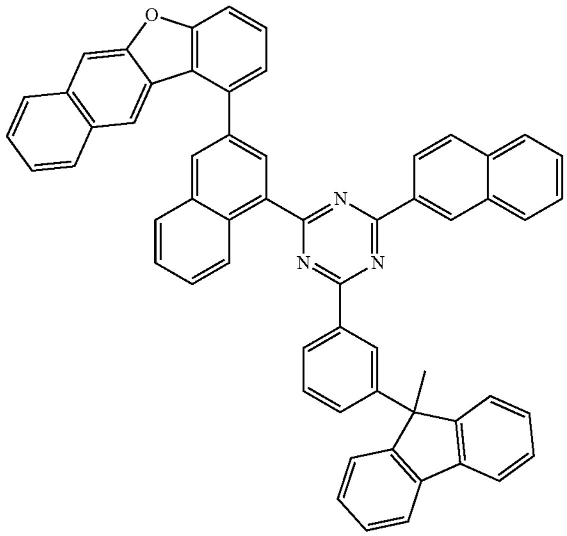
1-115
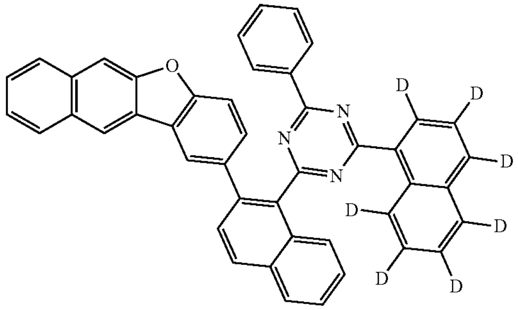
1-116
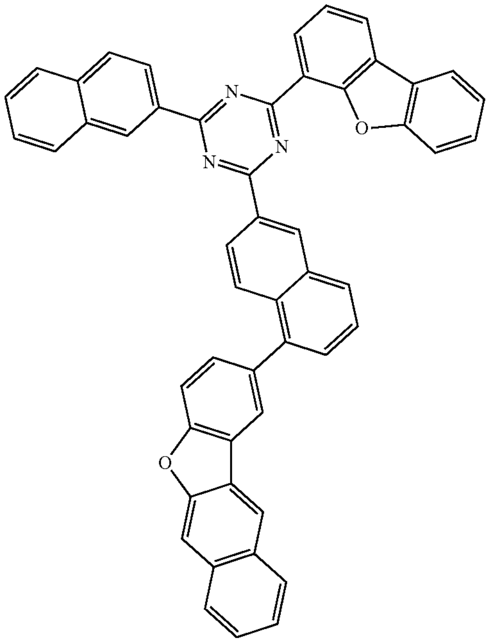

-continued
1-117
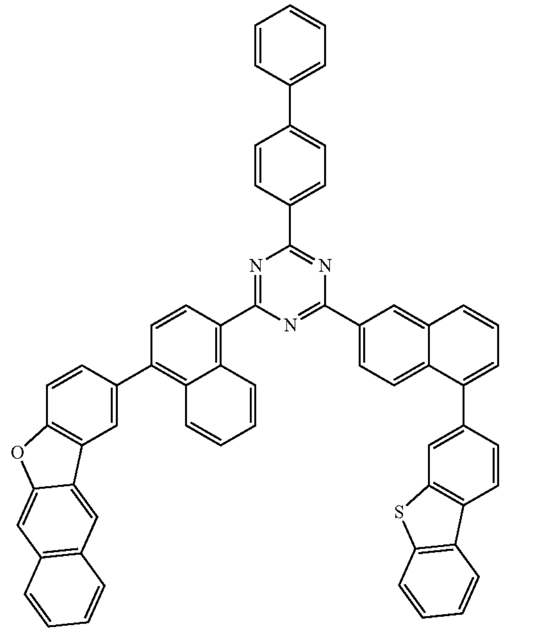
1-118
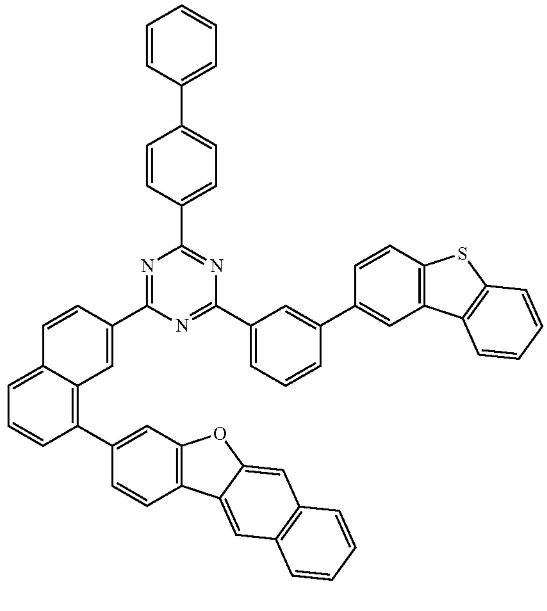
-continued
1-119
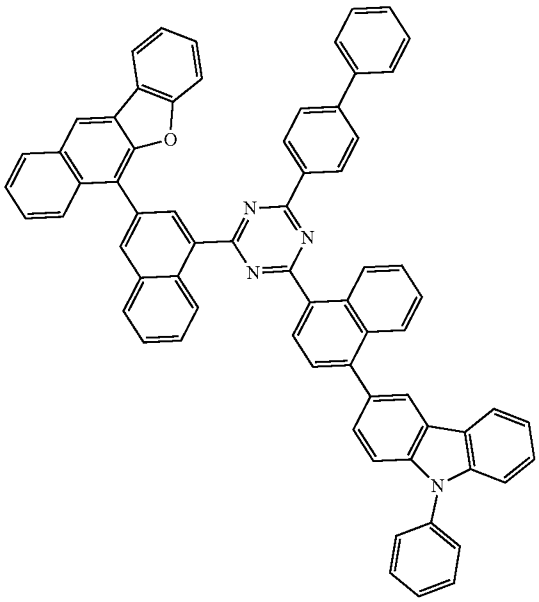
1-120
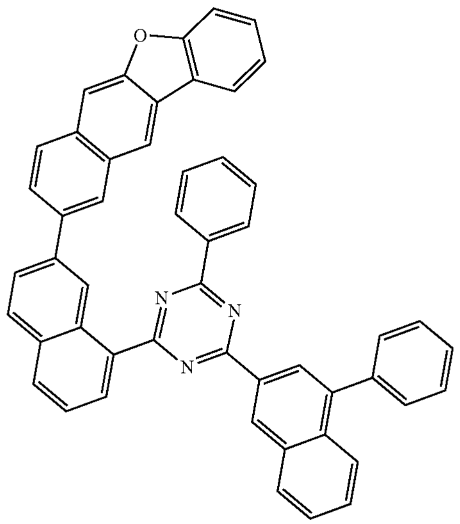
1-121
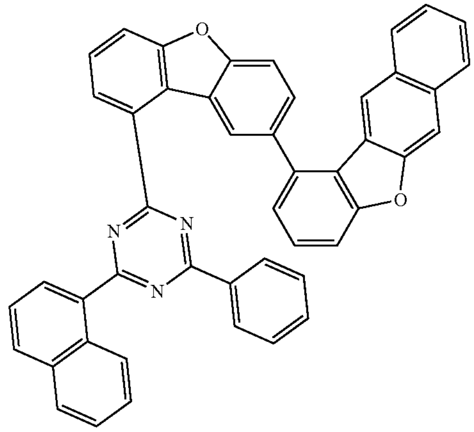

-continued
1-122
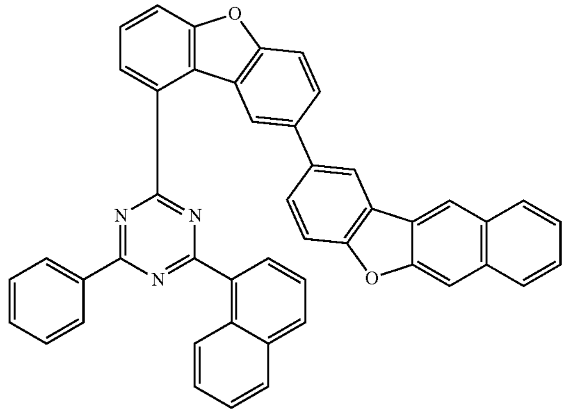
1-123
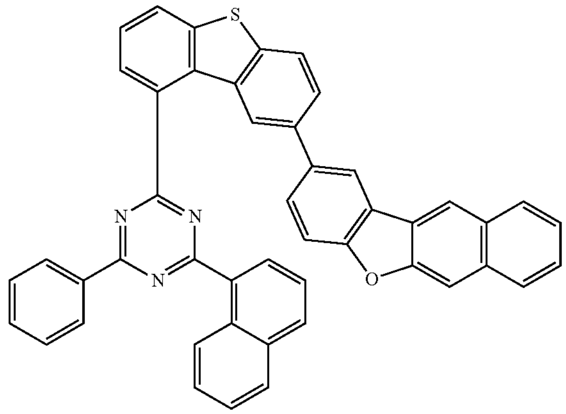
1-124
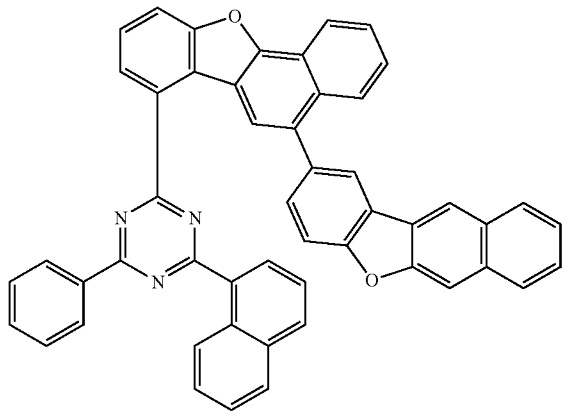
-continued
1-125
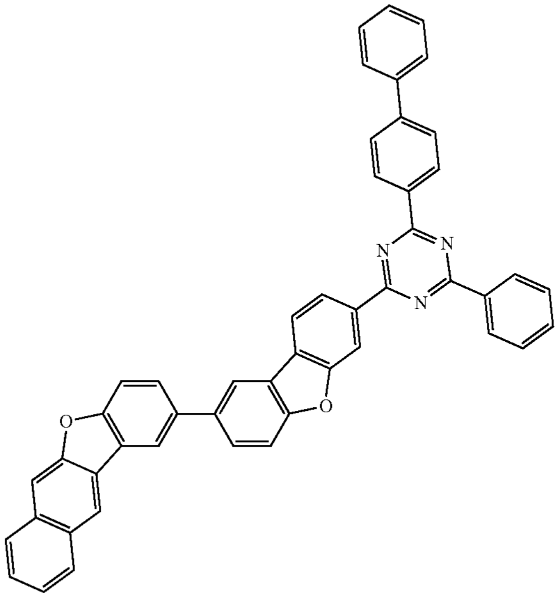
1-126
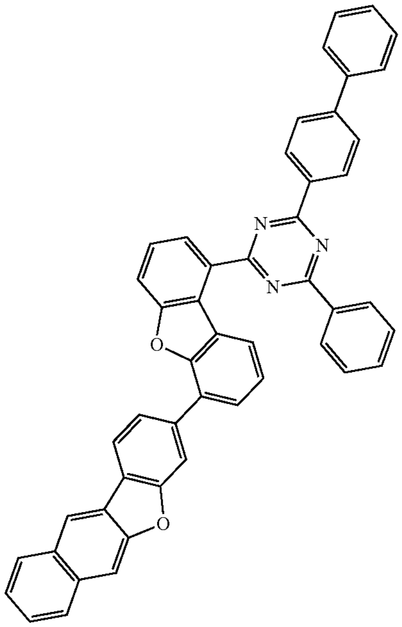

-continued
1-128
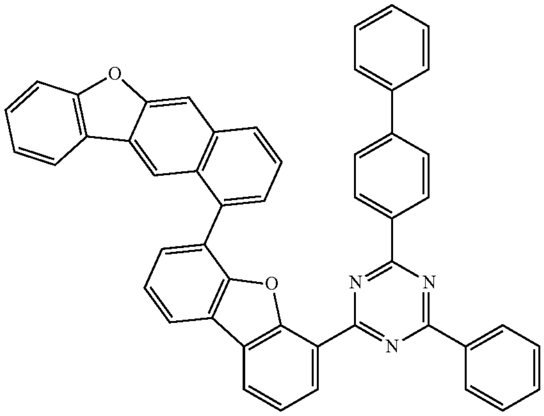
1-129
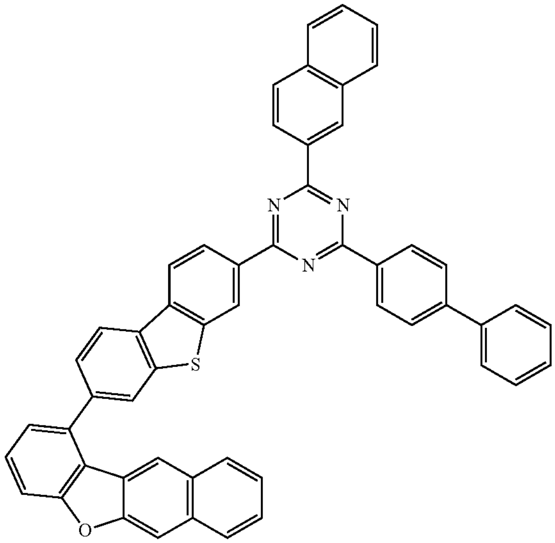
1-130
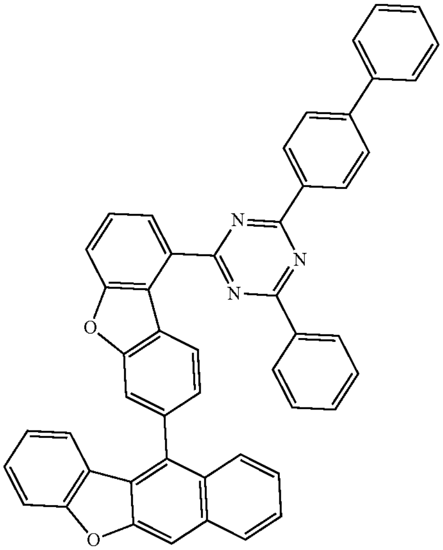
-continued
1-131
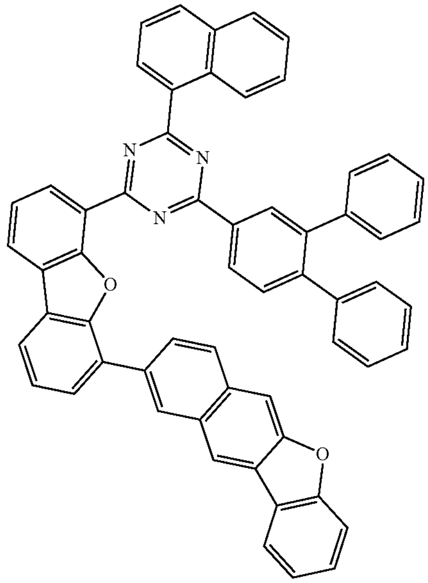
1-132
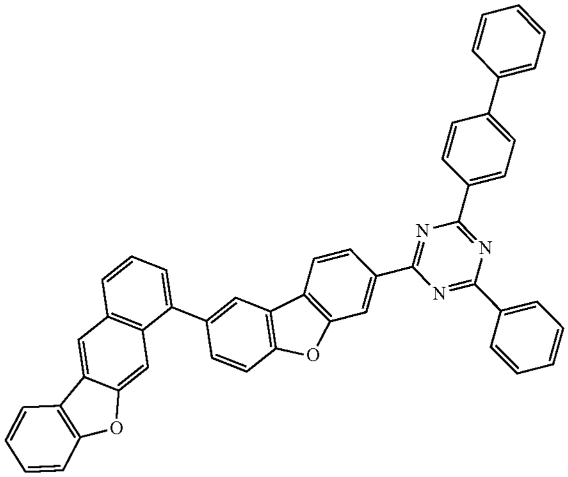

-continued
1-133
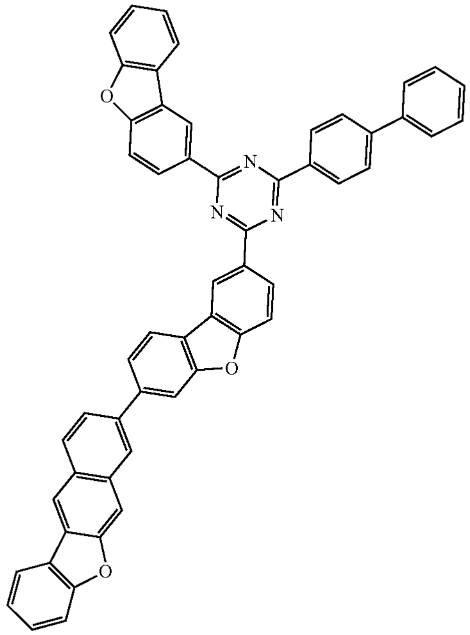
1-134
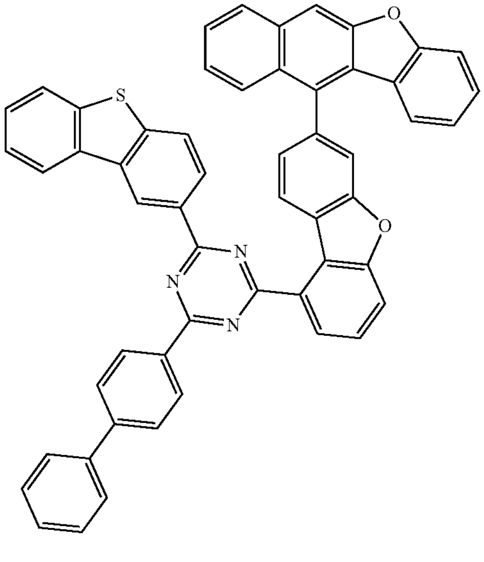
-continued
1-136
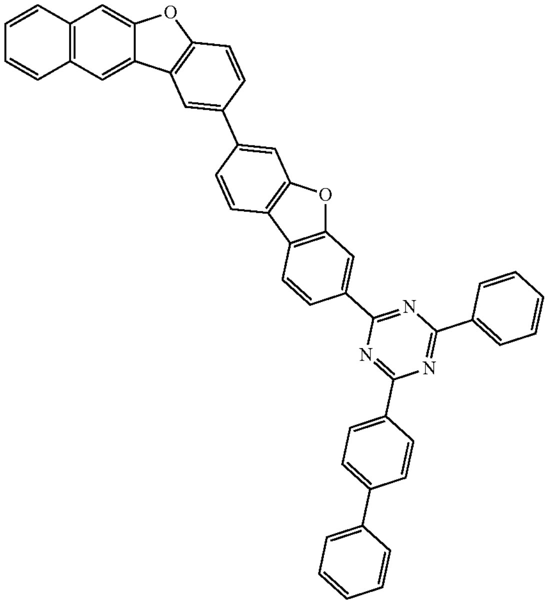
1-137
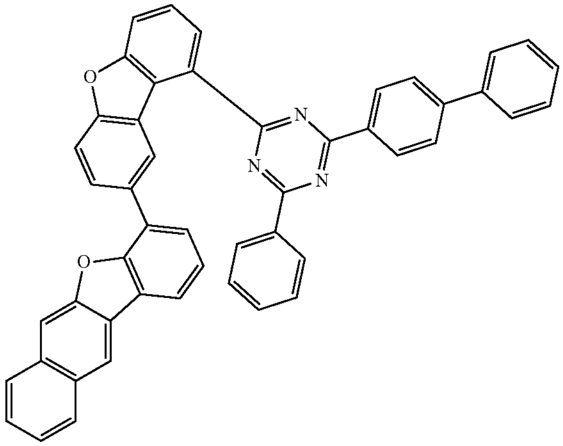
1-138
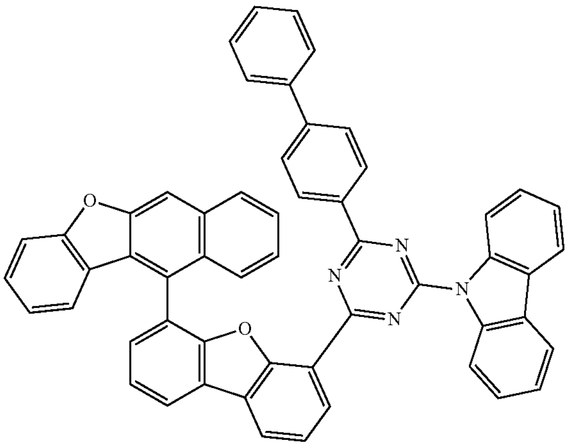

-continued
1-139
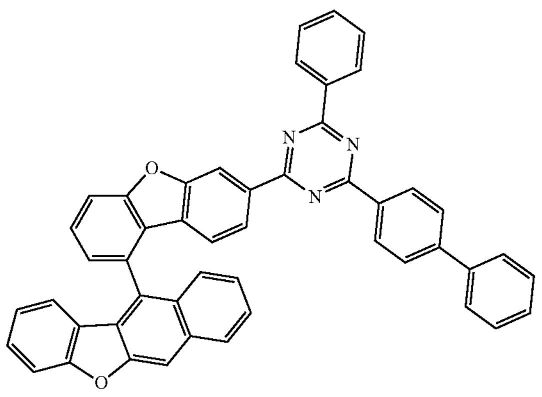
1-140
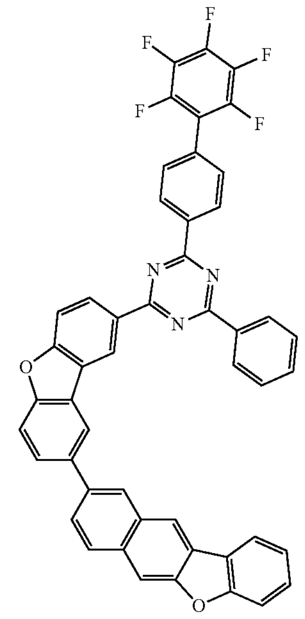
1-141
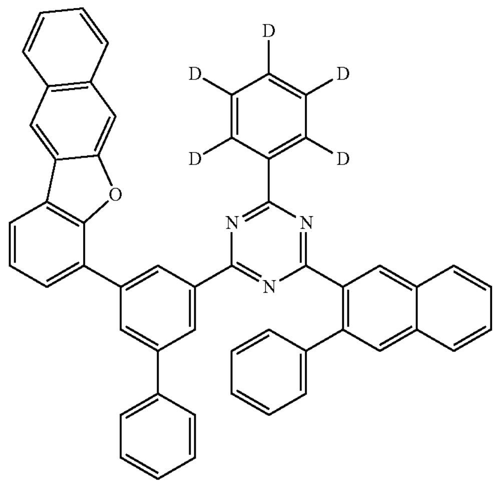
-continued
1-142
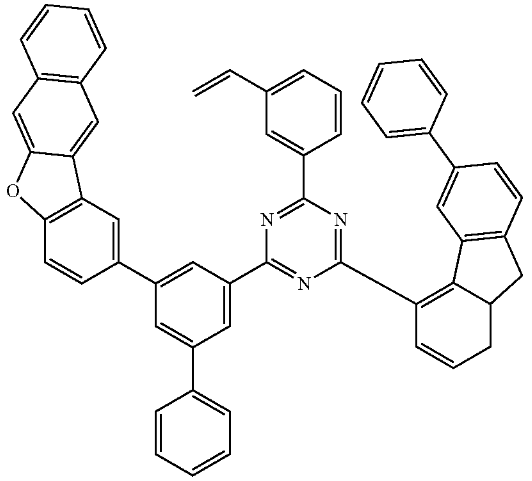
1-143
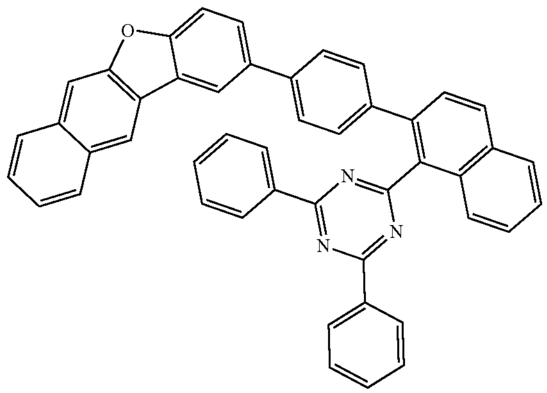
1-144
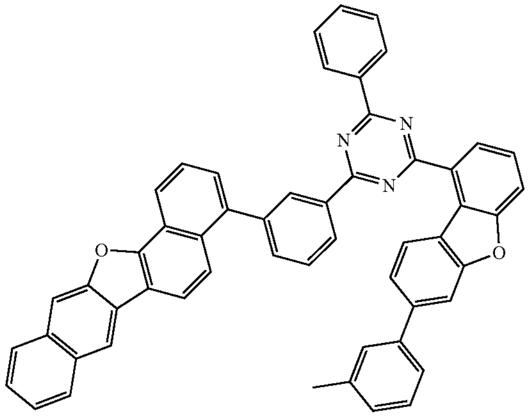

-continued
1-145
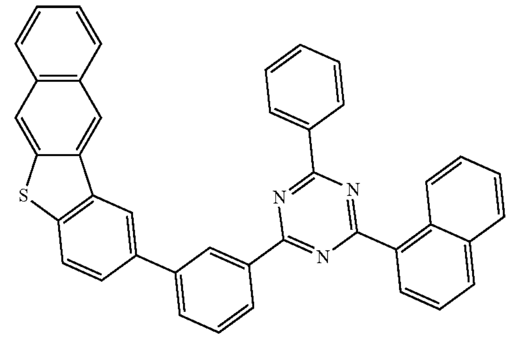
1-146
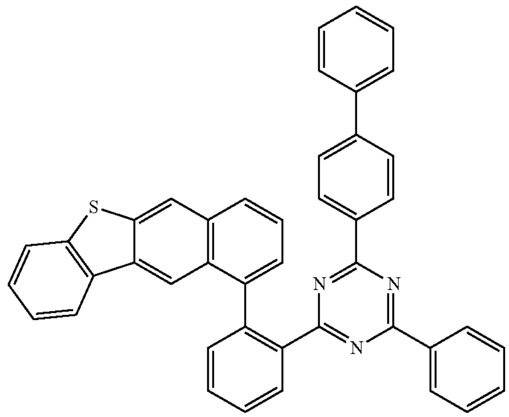
1-147
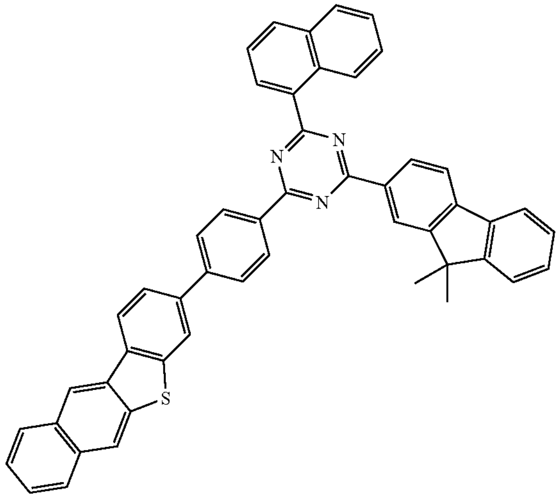
-continued
1-148
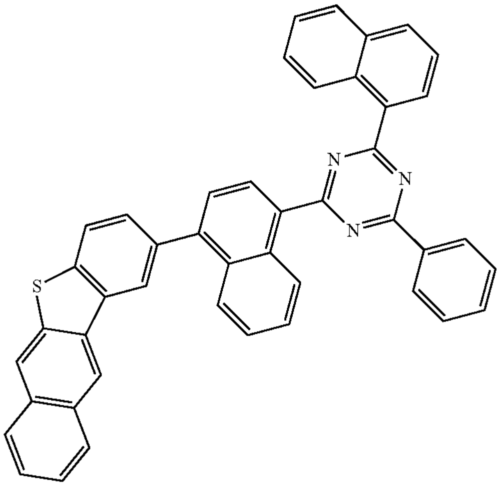
1-149
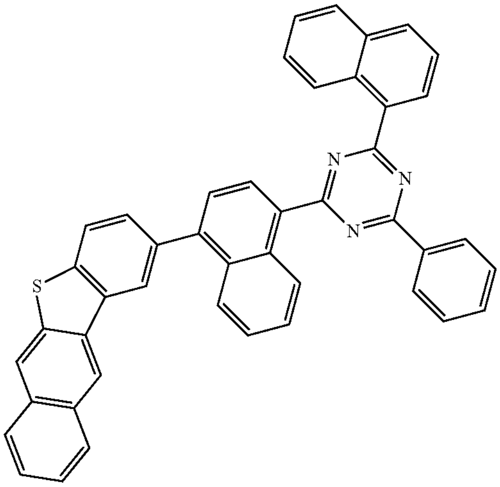
1-150
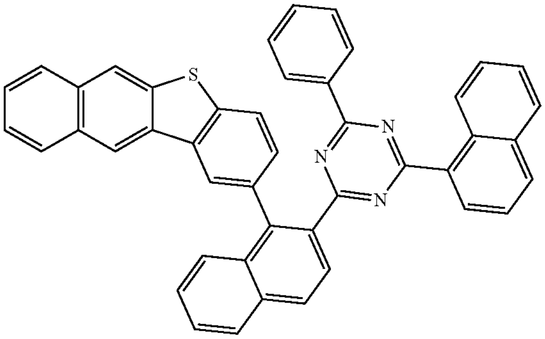

-continued
1-151
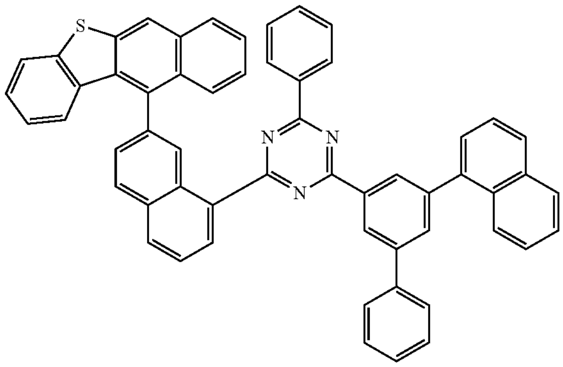
1-152
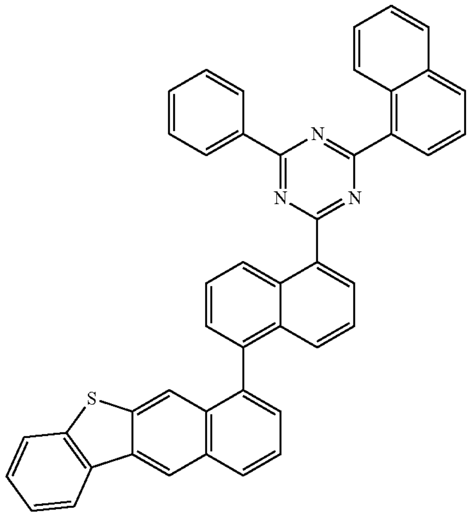
1-153
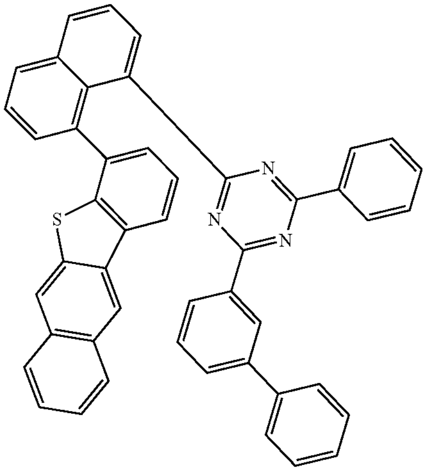
-continued
1-154
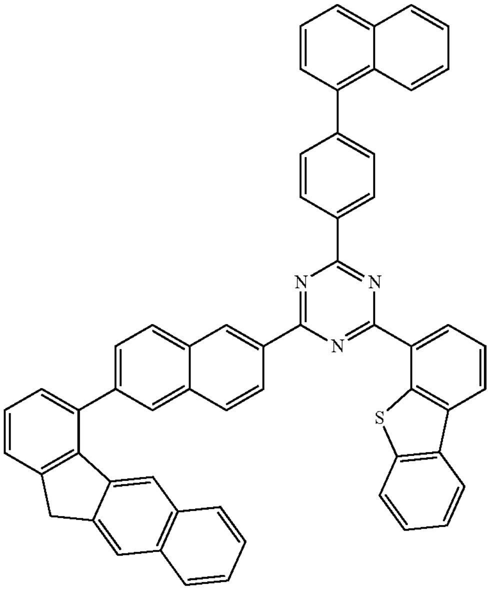
1-155
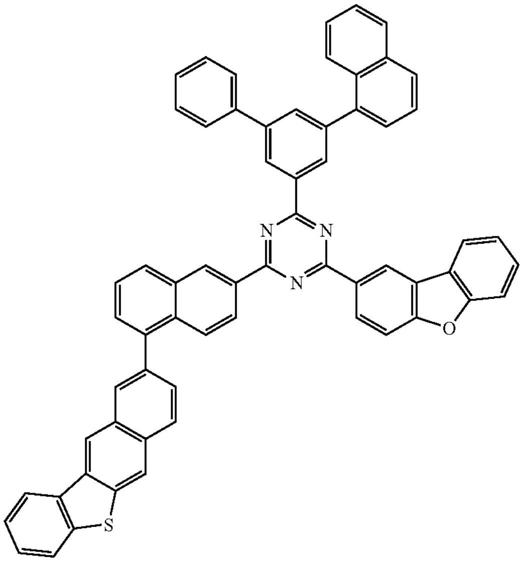
1-156
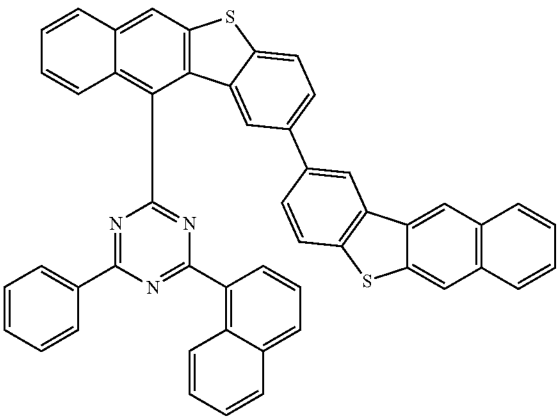

-continued
1-157
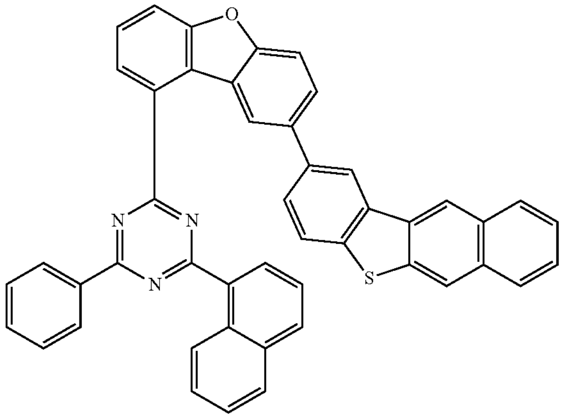
1-158
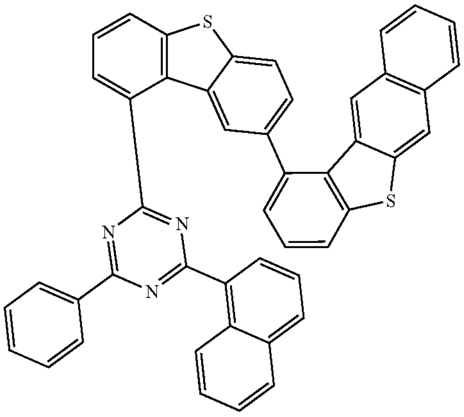
1-159
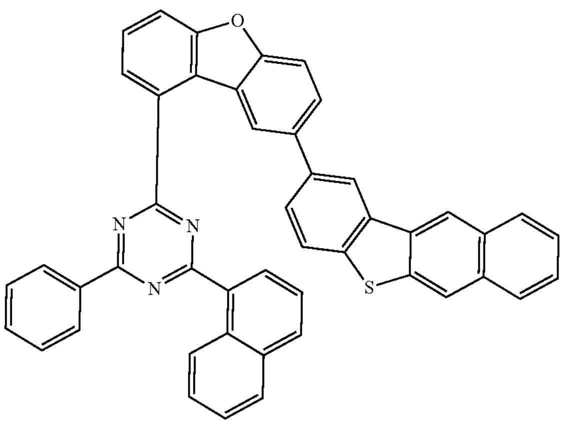
-continued
1-160
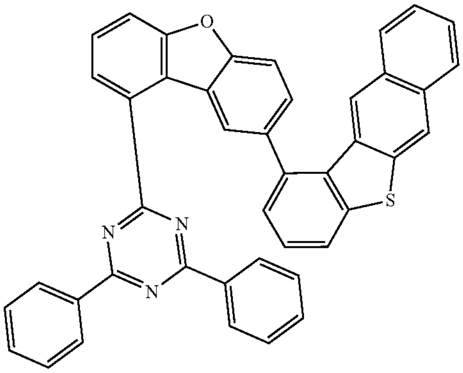
1-162
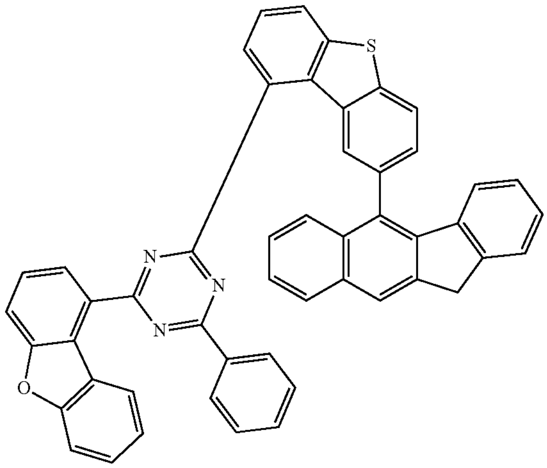
1-163
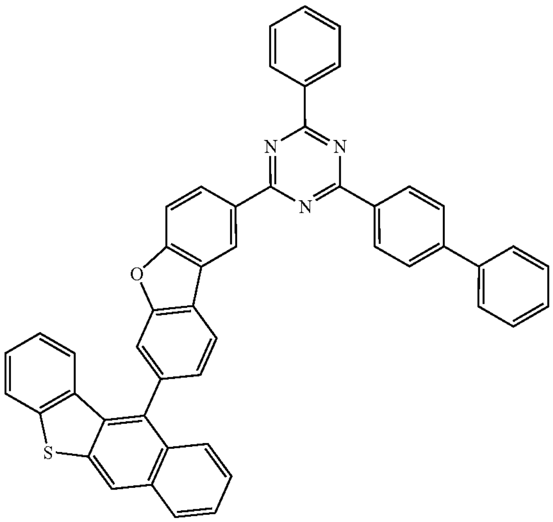

-continued
1-164
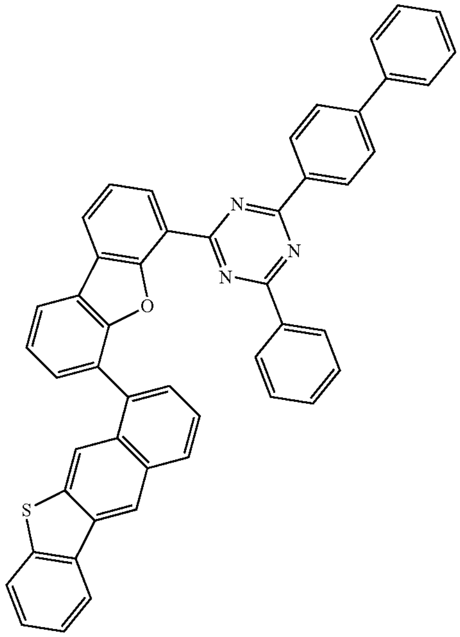
1-165
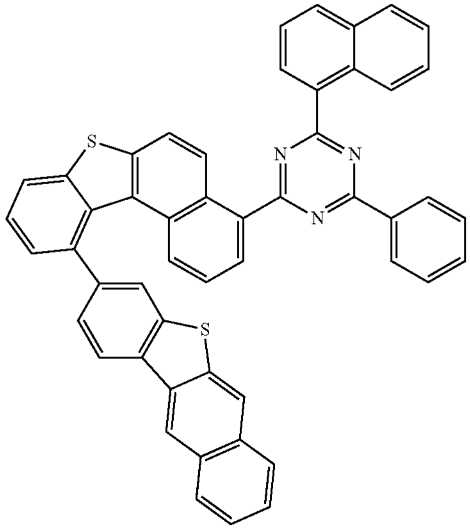
-continued
1-166
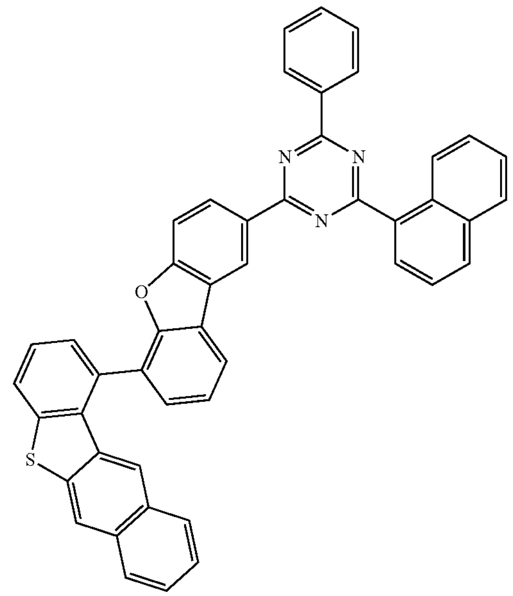
1-167
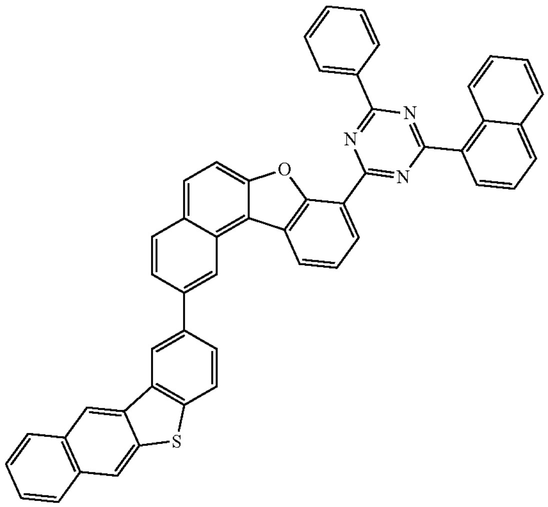

-continued
1-168
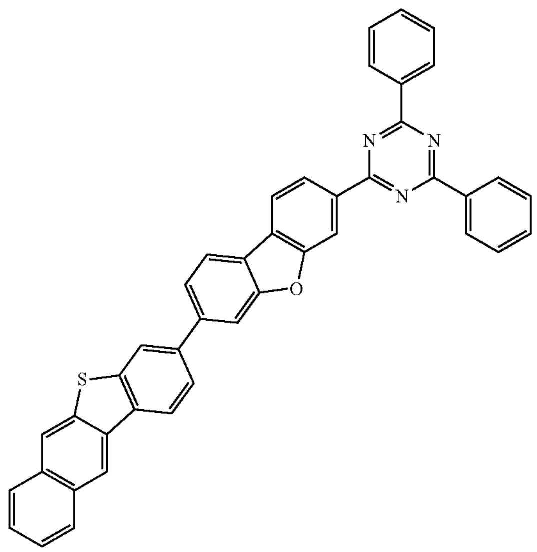
1-169
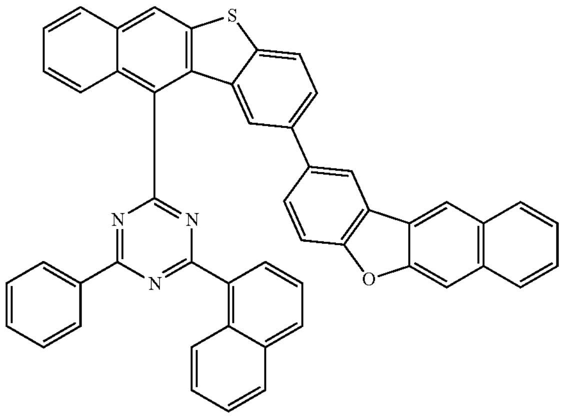
1-170
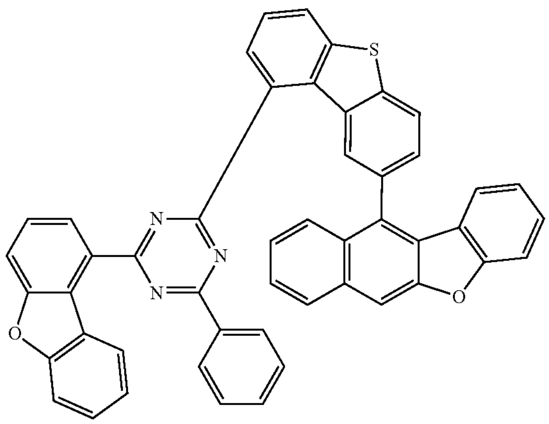
-continued
1-171
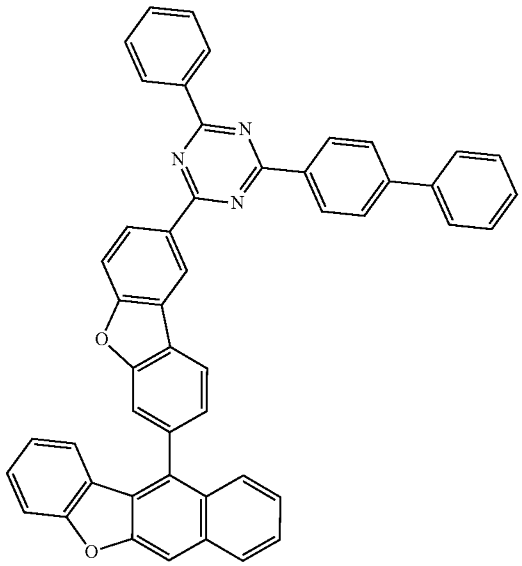
1-172
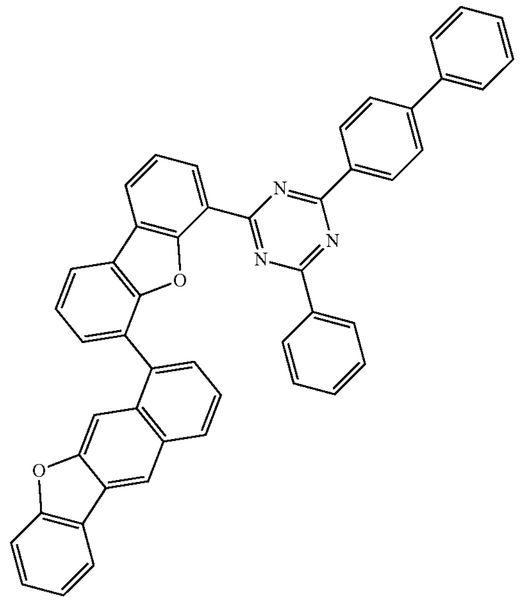
1-173
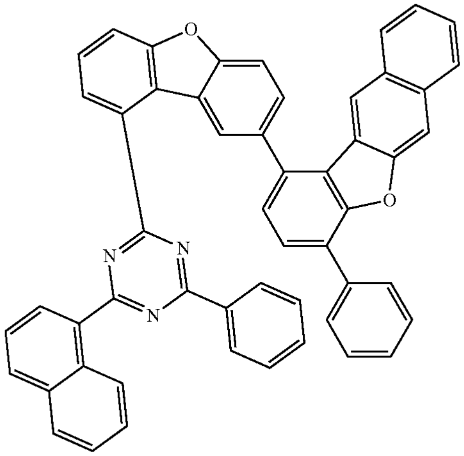

-continued
1-174
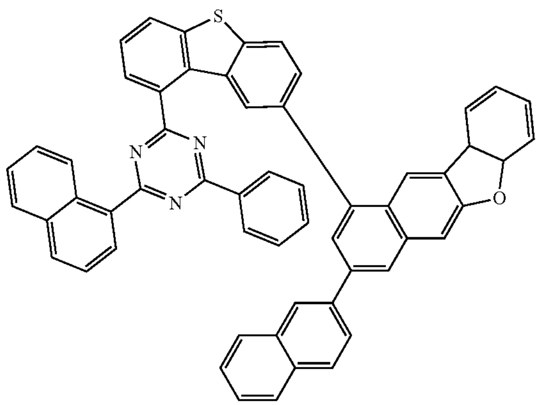
1-175
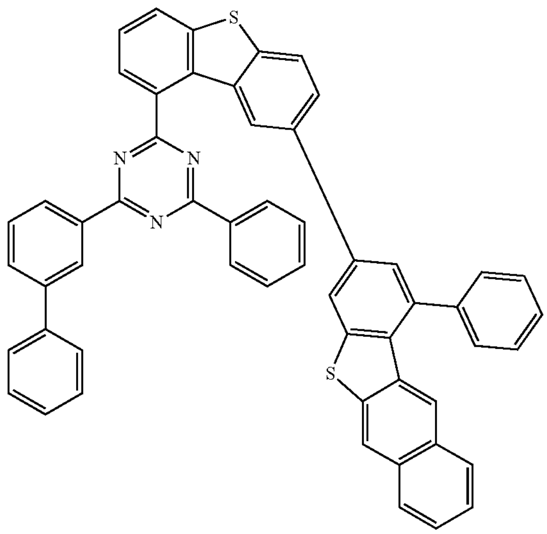
1-176
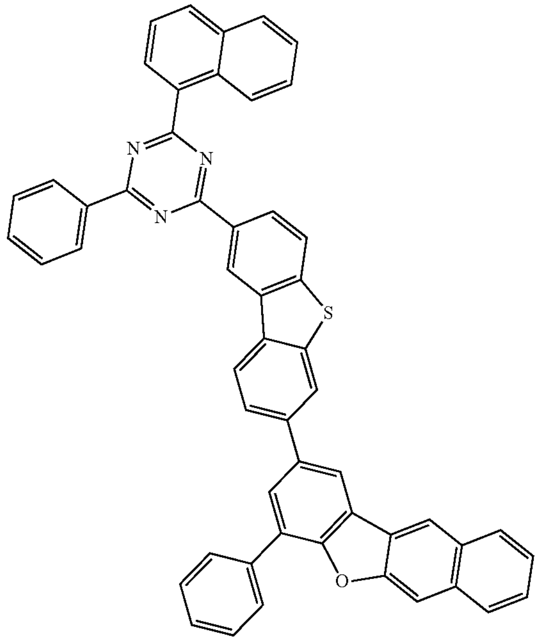
-continued
2-101
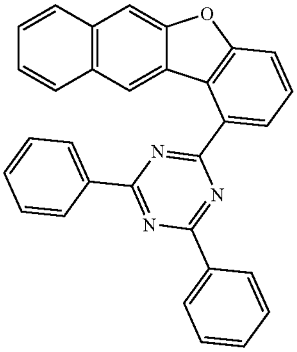
2-102
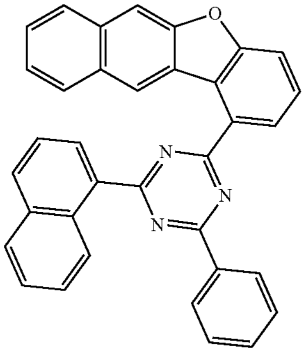
2-103
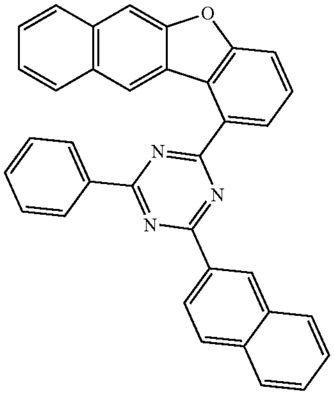
2-104
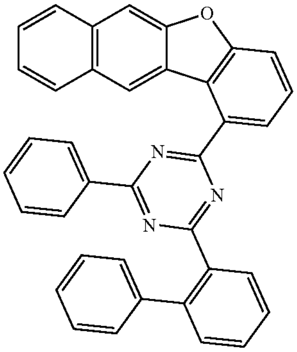

-continued
2-105
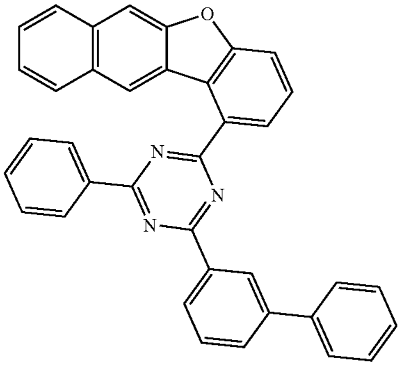
2-106
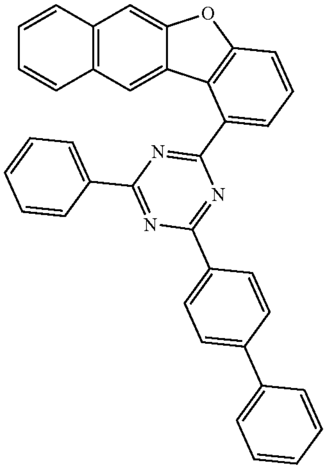
2-107
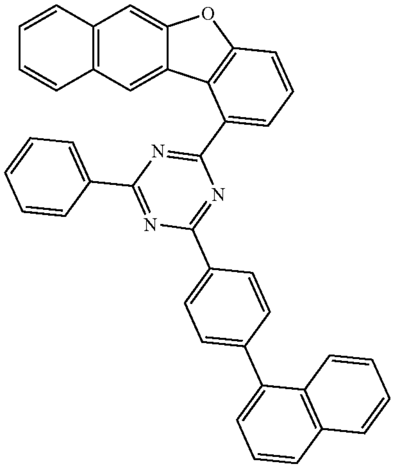
-continued
2-108
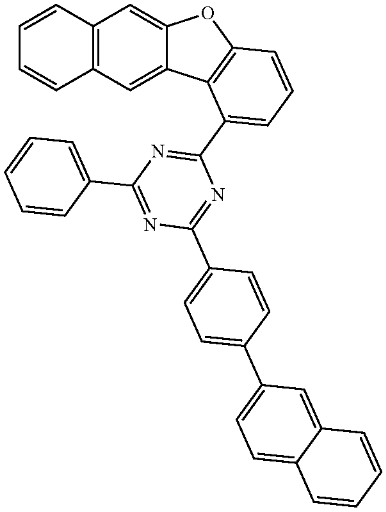
2-109
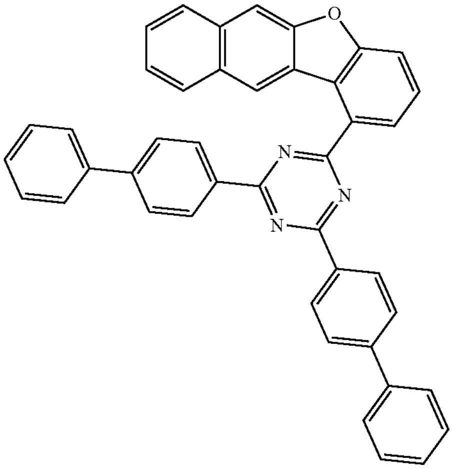
2-110
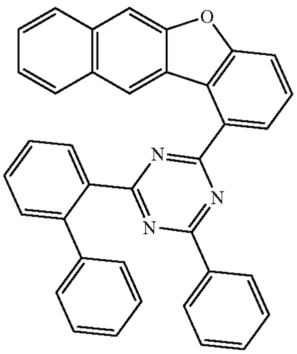

-continued
2-111
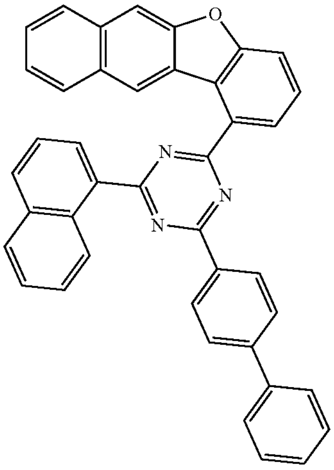
2-112
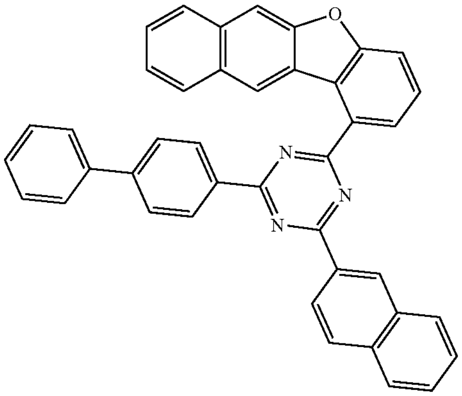
2-113
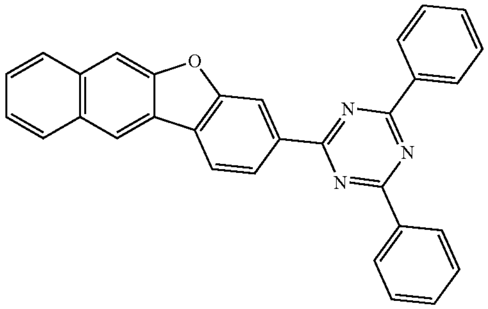
2-114
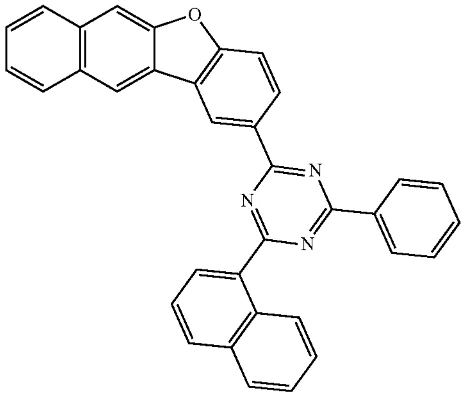
-continued
2-115
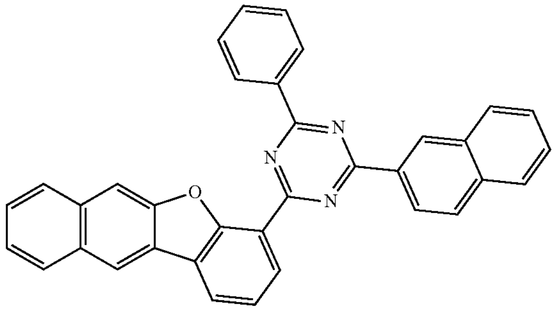
2-116
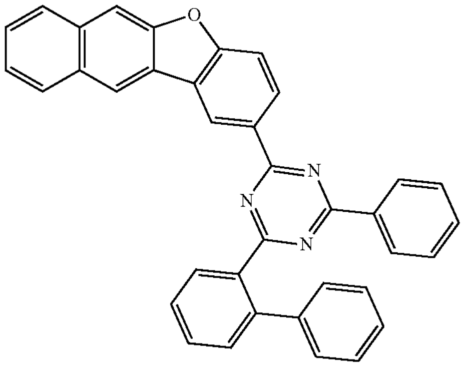
2-117
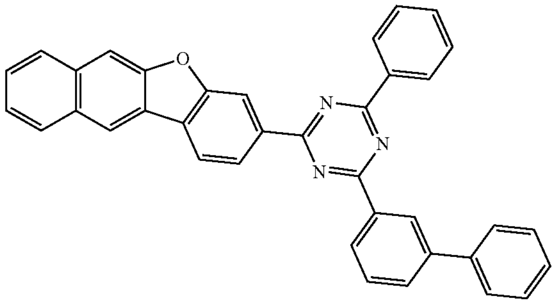
2-118
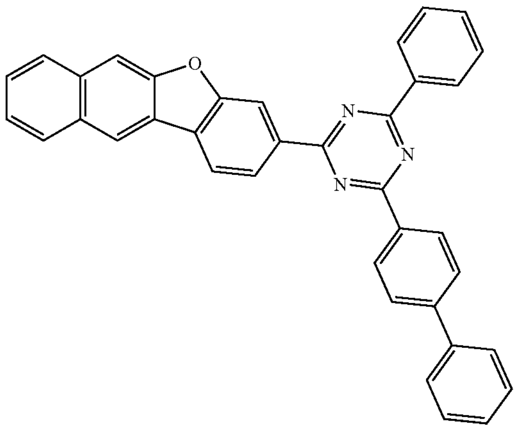

-continued
2-119
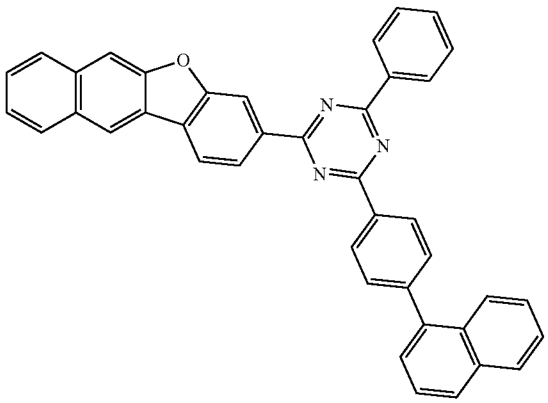
2-120
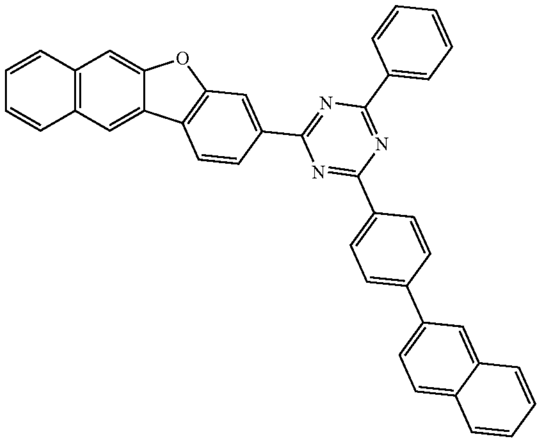
2-121
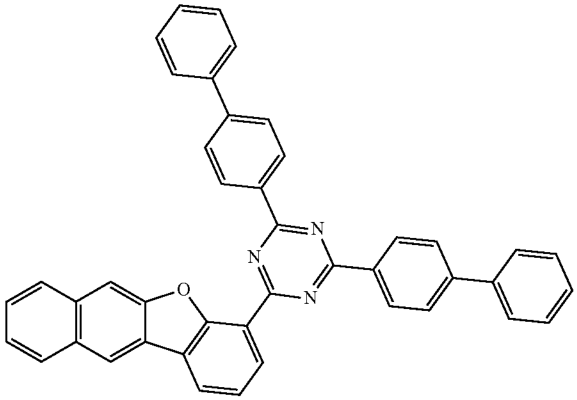
-continued
2-122
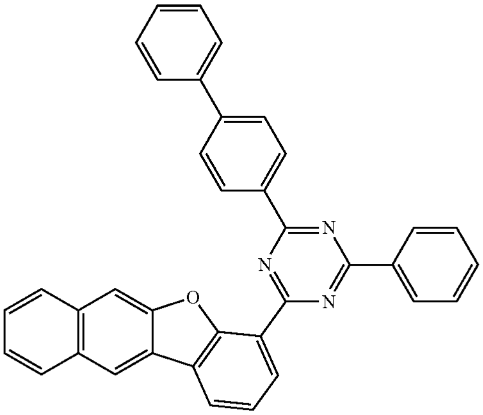
2-123
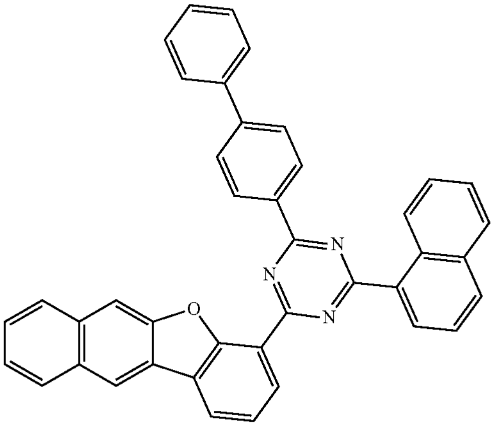
2-124
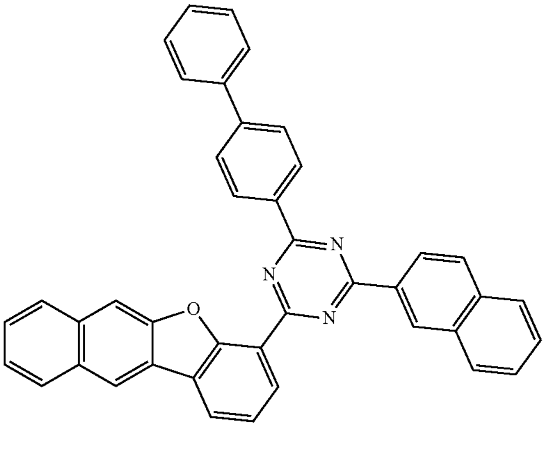
.
6. The organic electric element of claim 1, wherein the compound represented by Formula 2 is one of the following compounds:

-continued
2-1
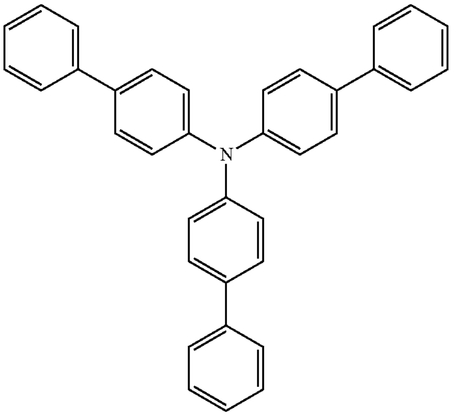
2-2
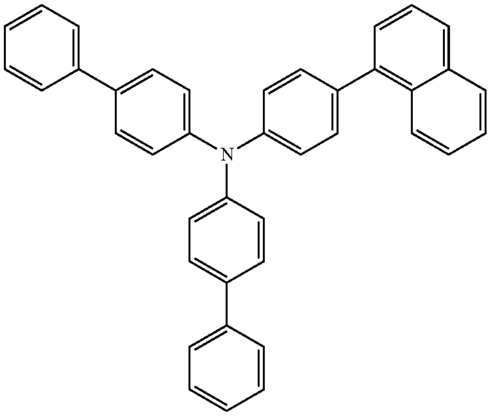
2-3
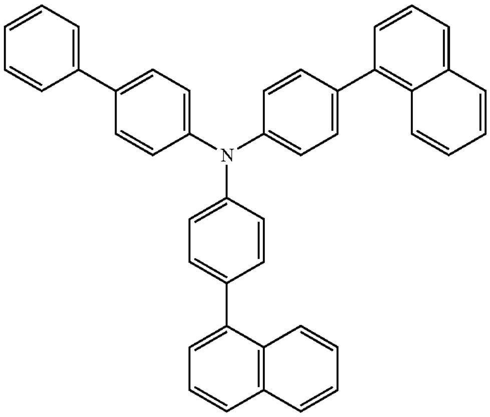
2-4
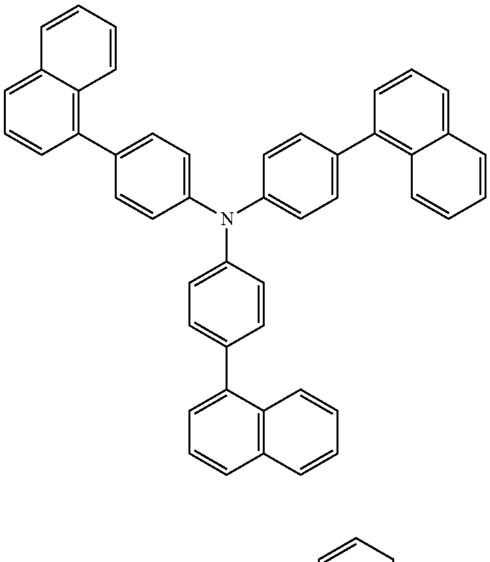
2-5
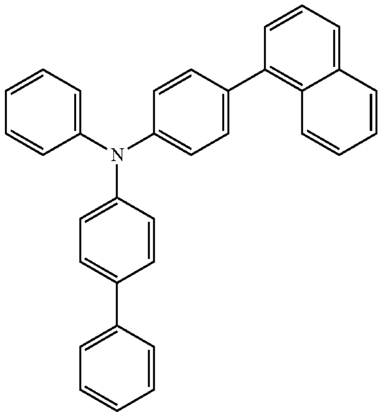
2-6
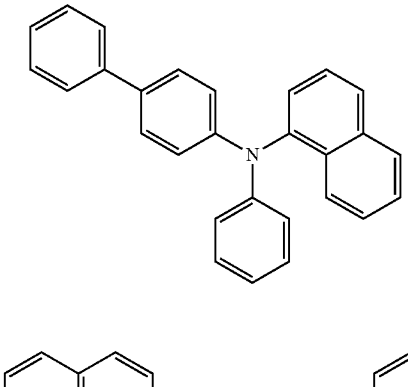
2-7
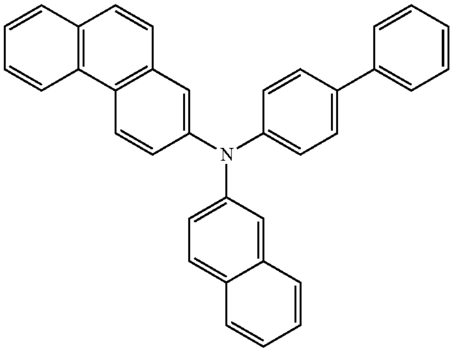

-continued
2-8
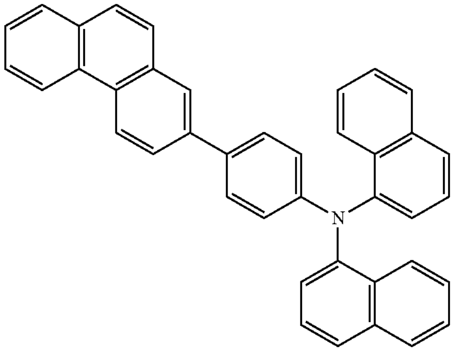
2-9
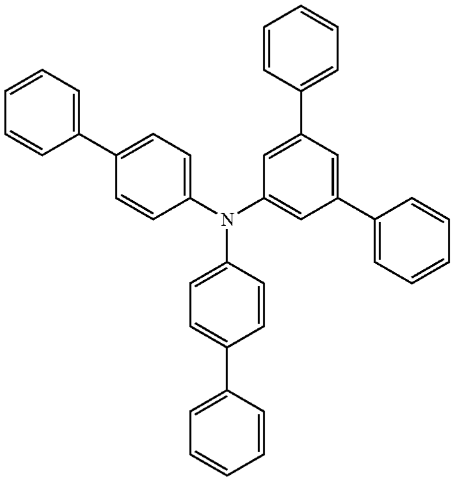
2-10
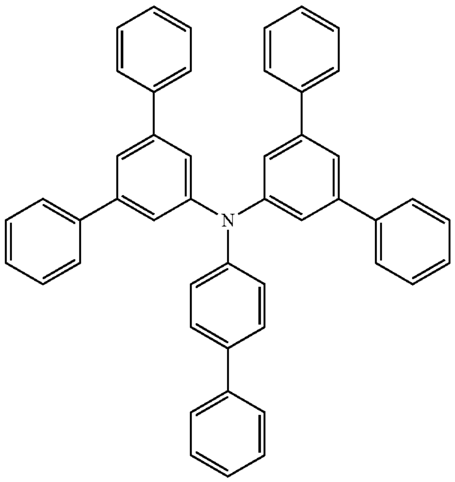
-continued
2-11
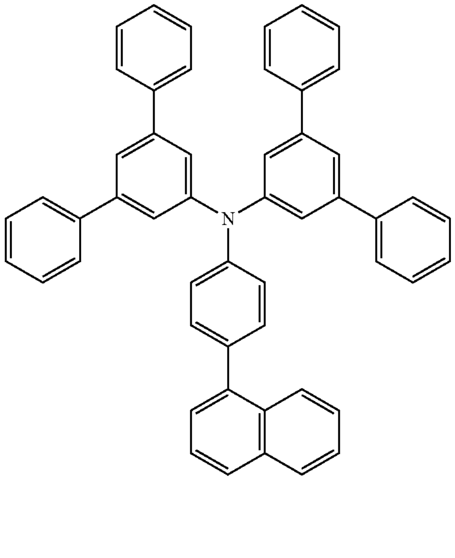
2-12
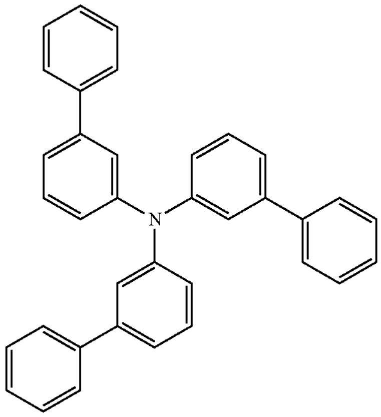
2-13
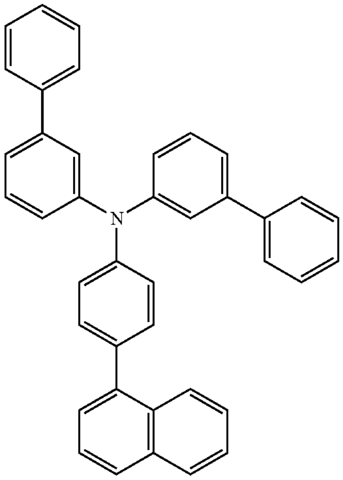

-continued
2-14
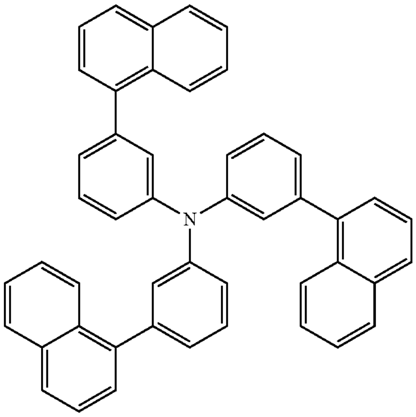
2-15
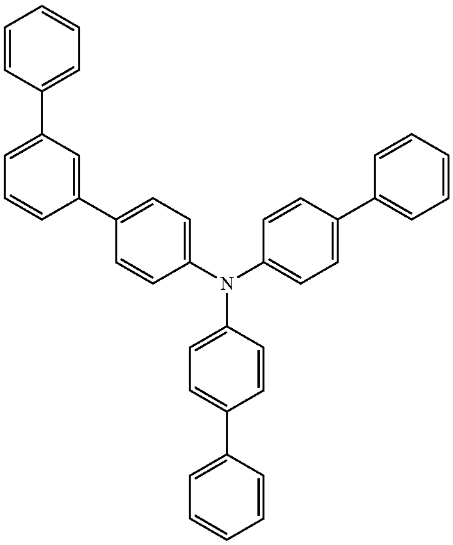
2-16
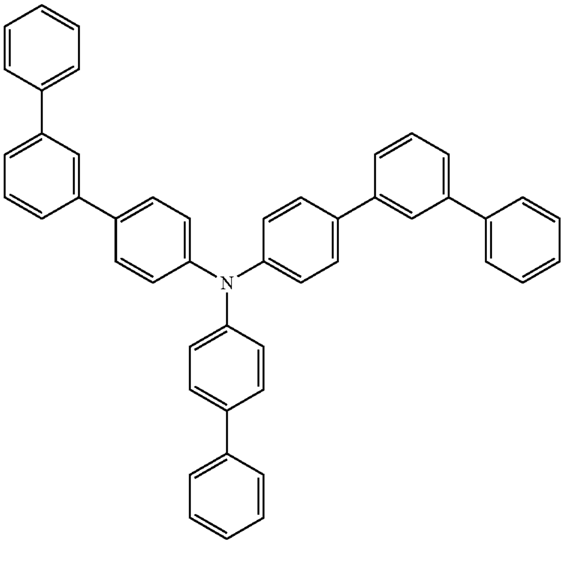
-continued
2-17
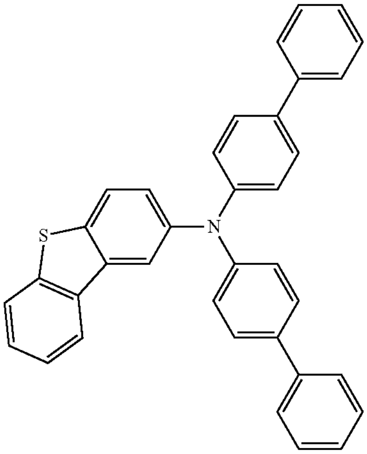
2-18
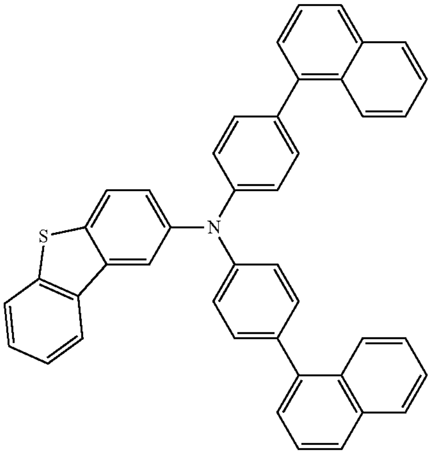
2-19
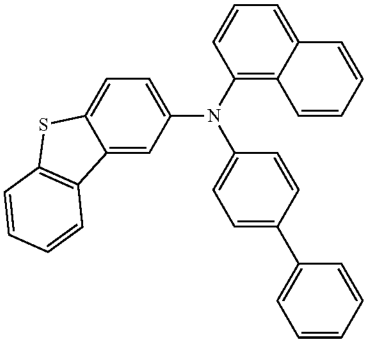
2-20
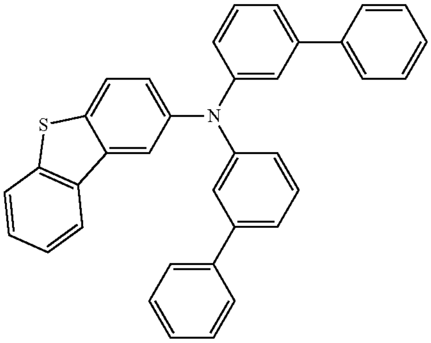

-continued
2-21
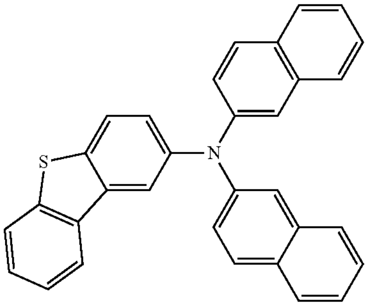
2-22
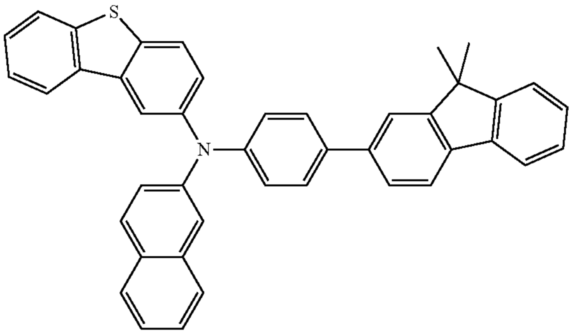
2-23
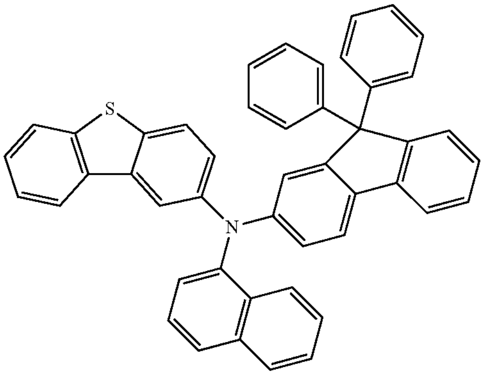
2-24
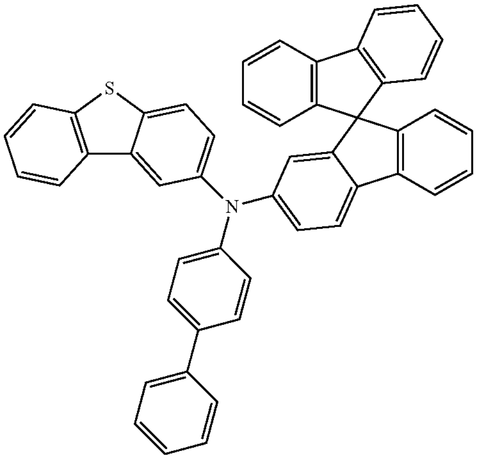
-continued
2-25
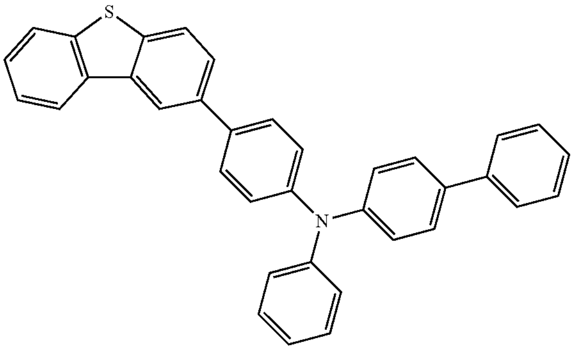
2-26
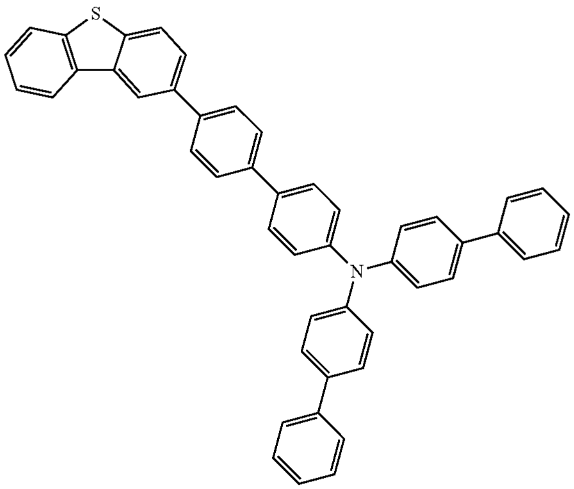
2-27
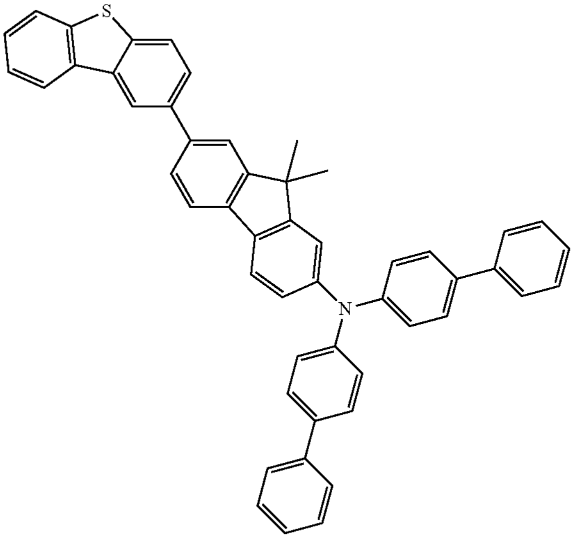

-continued
2-28
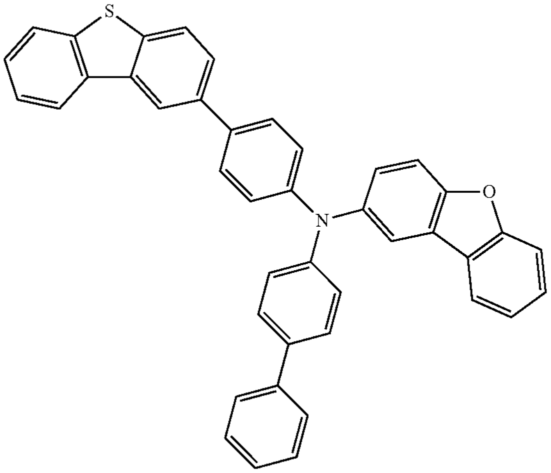
2-29
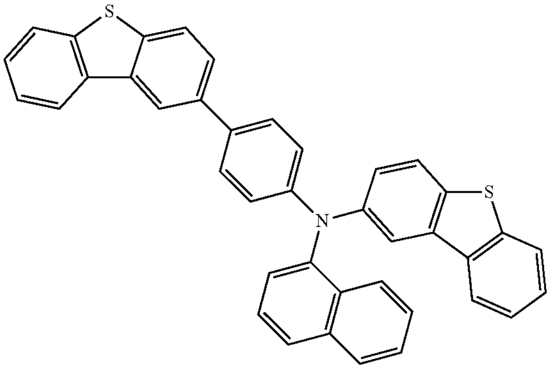
2-30
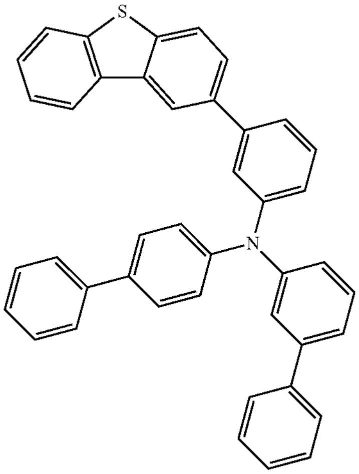
-continued
2-31
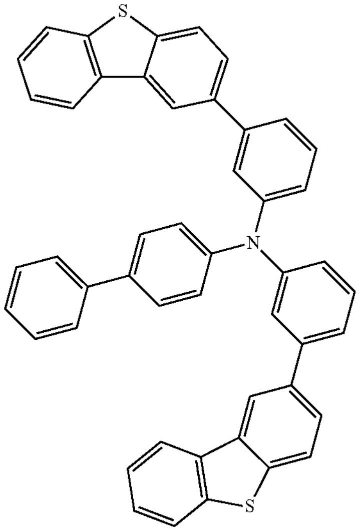
2-32
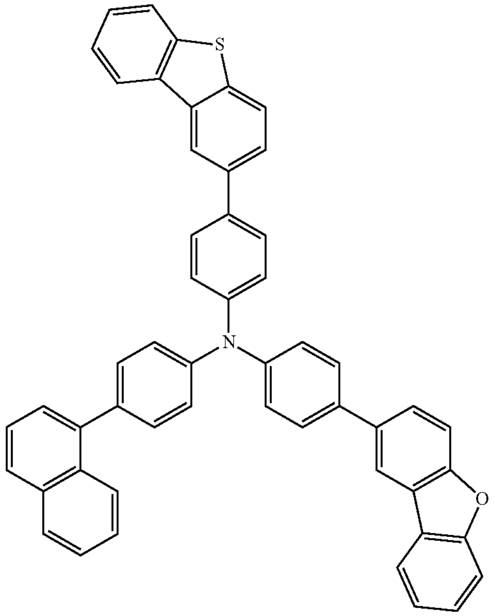
2-33
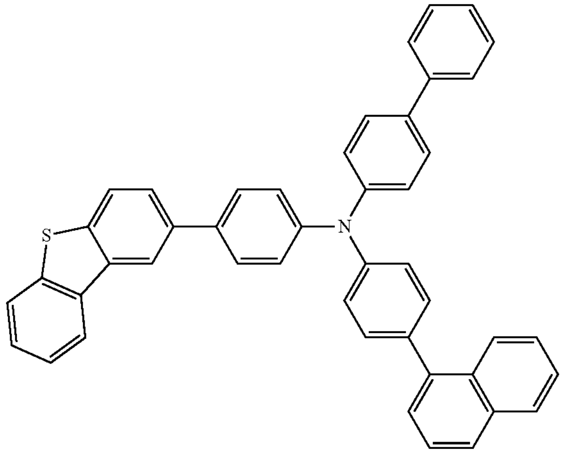

-continued
2-34
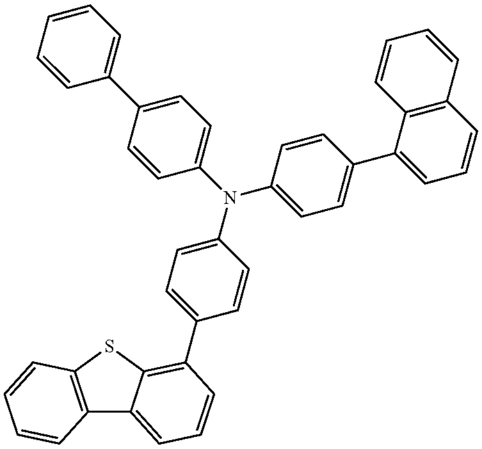
2-35
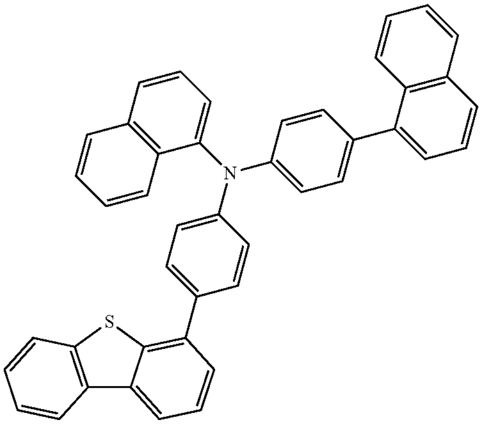
2-36
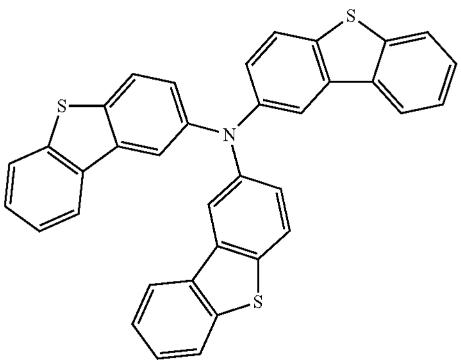
-continued
2-37
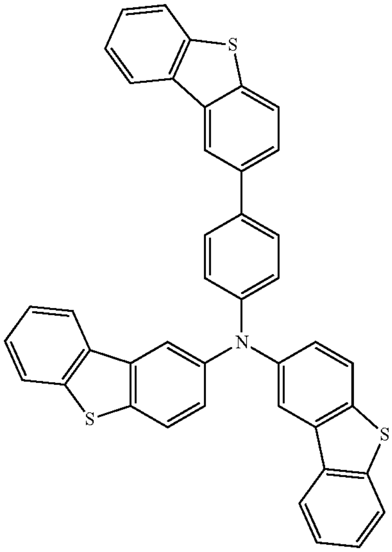
2-38
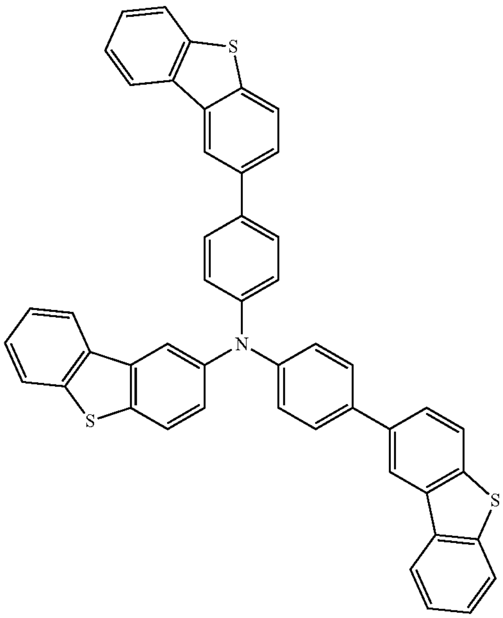

2-39
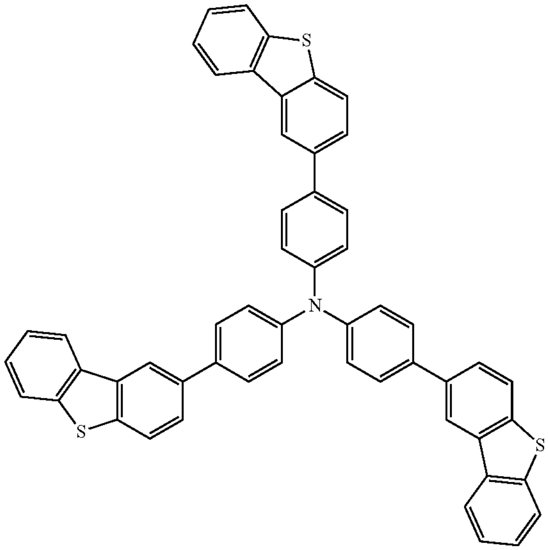
2-40
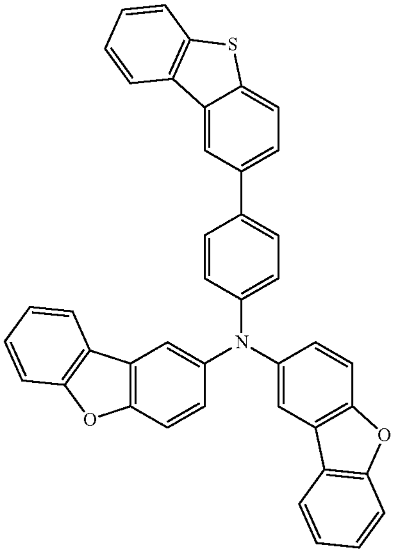
2-41
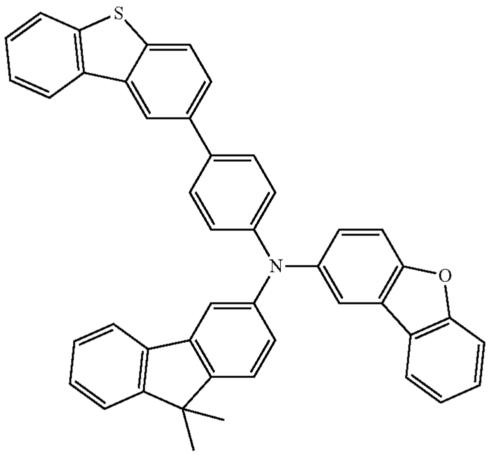
2-42
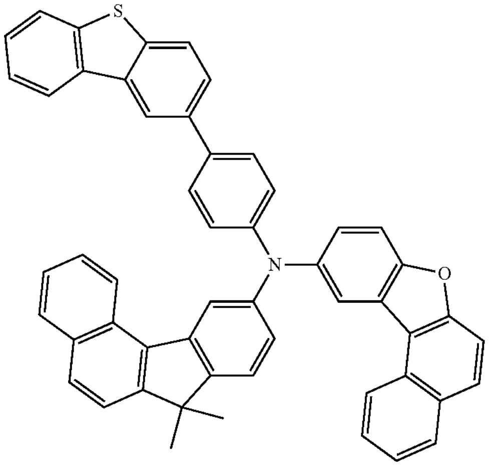
2-43
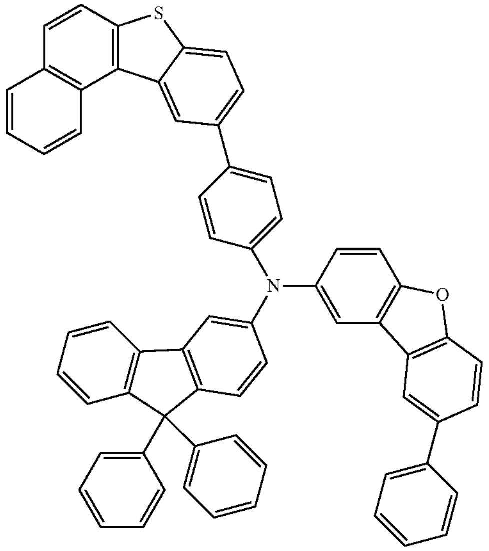
2-44
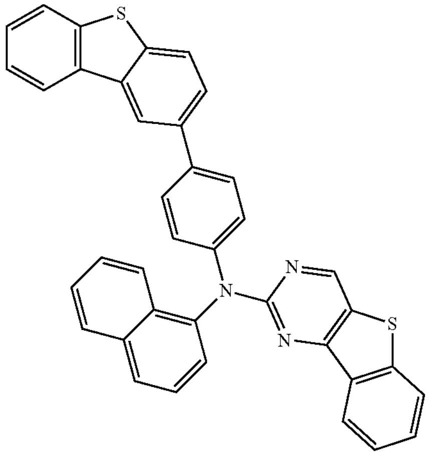

-continued
2-45
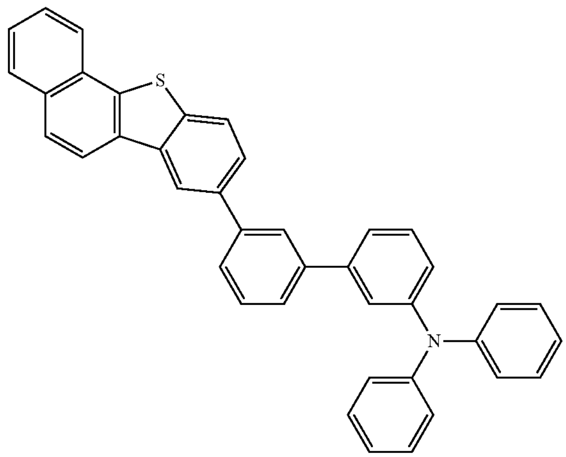
2-46
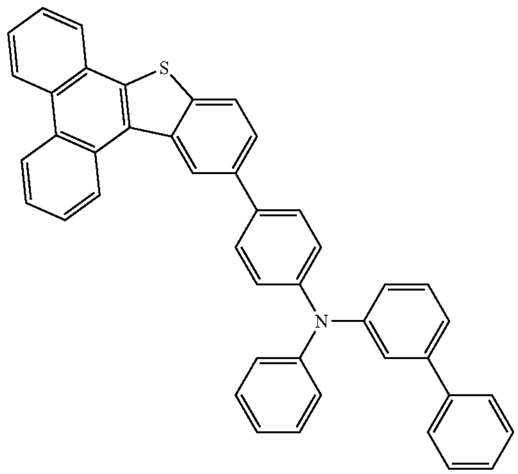
2-47
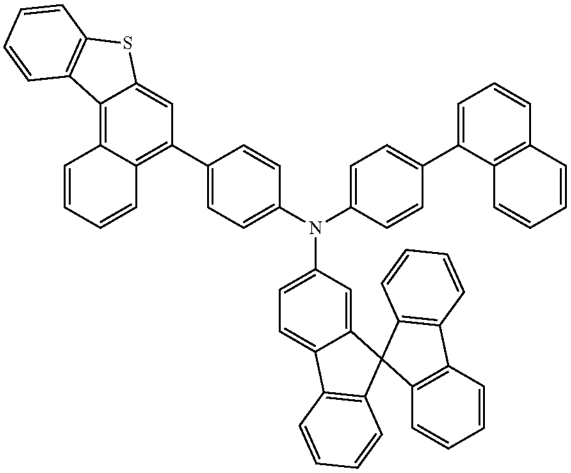
-continued
2-48
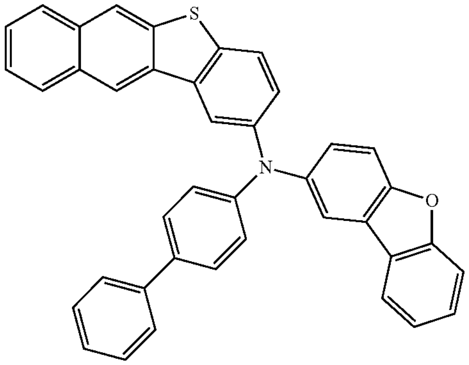
2-49
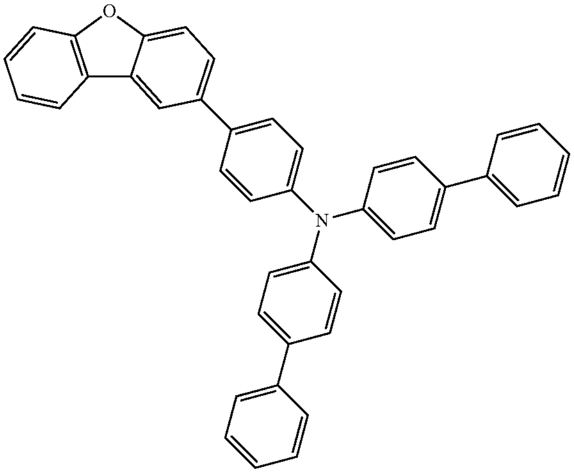
2-50
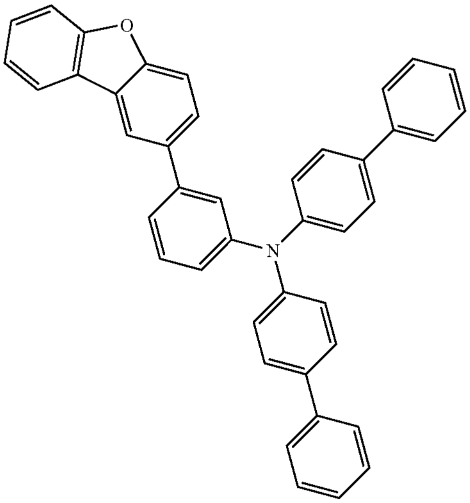

-continued
2-51
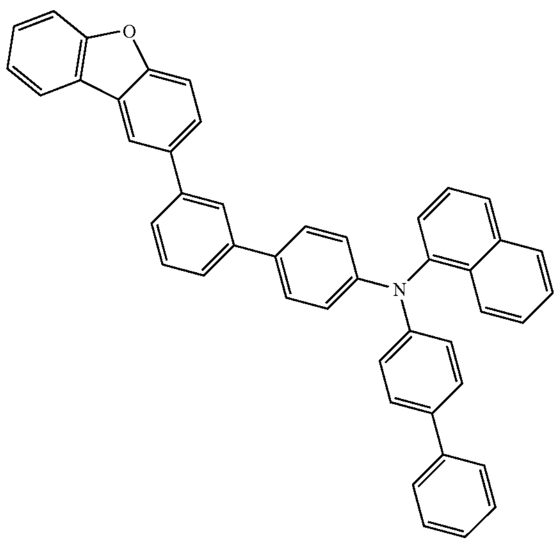
2-52
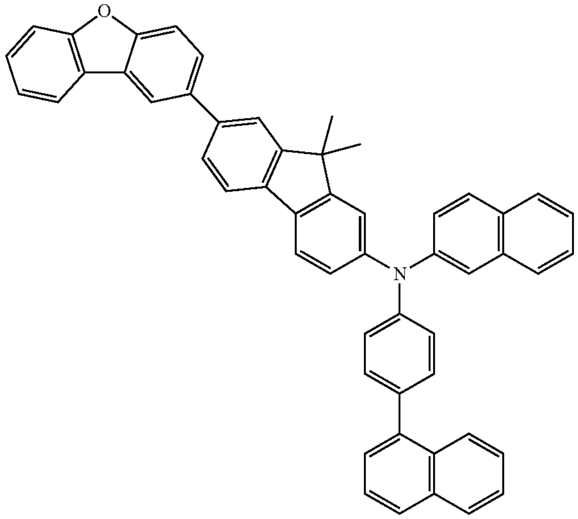
2-53
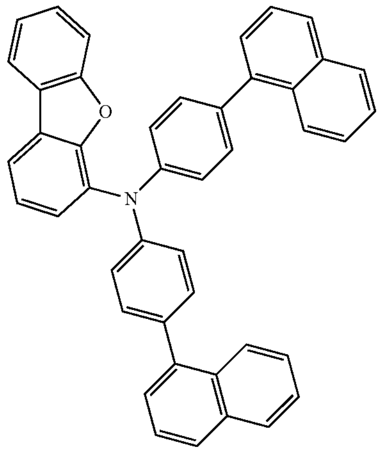
-continued
2-54
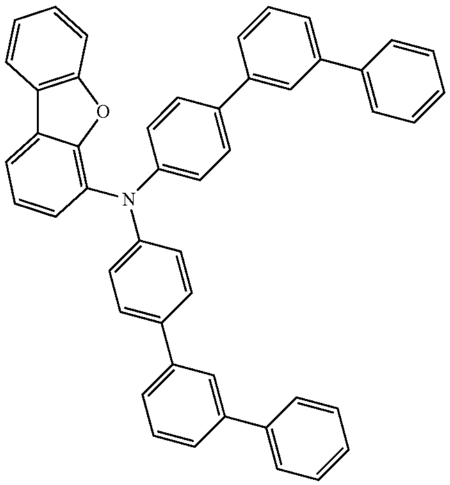
2-55
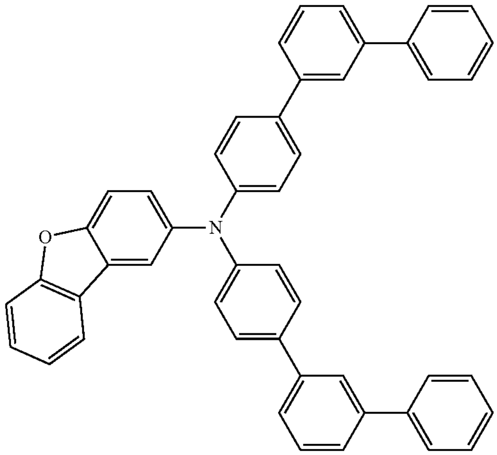
2-56
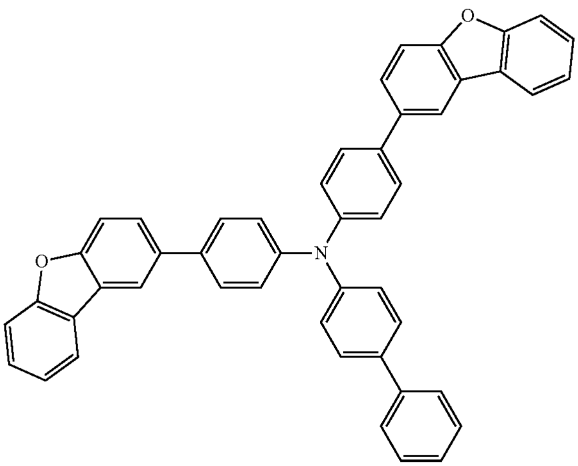

-continued
2-57
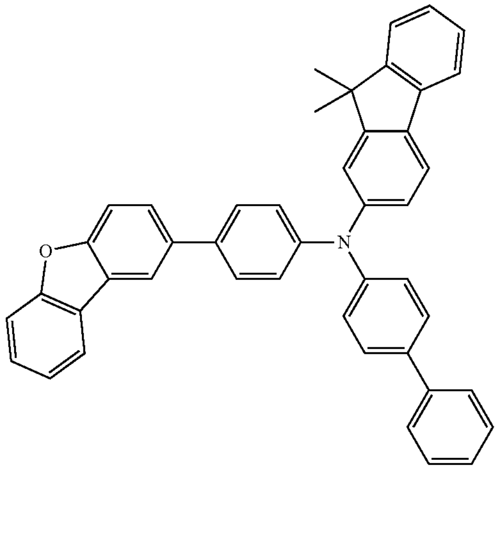
2-58
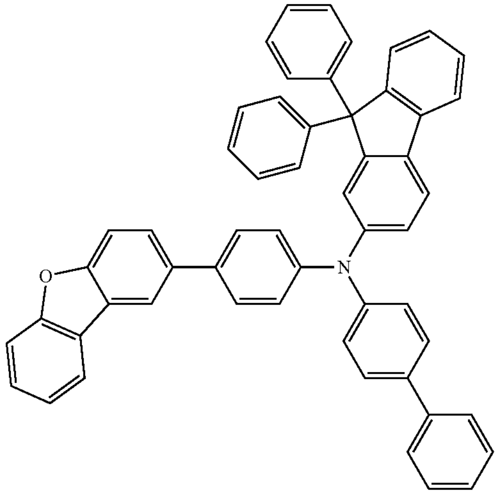
2-59
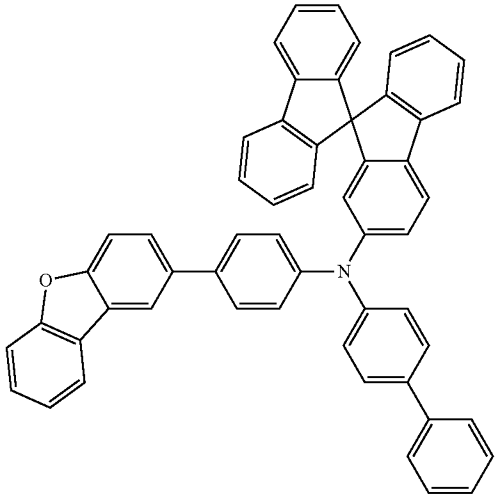
-continued
2-60
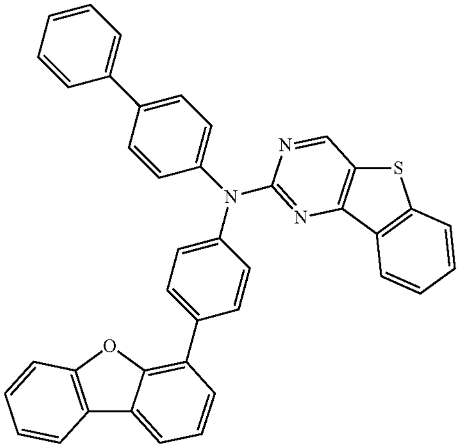
2-61
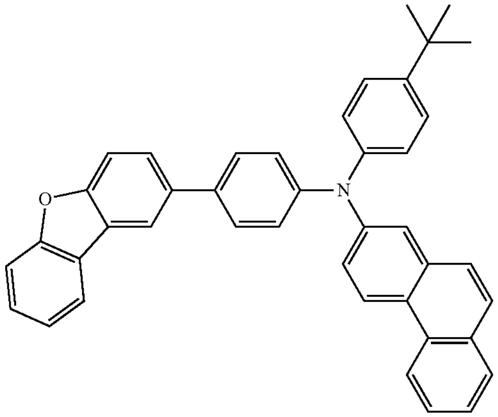
2-62
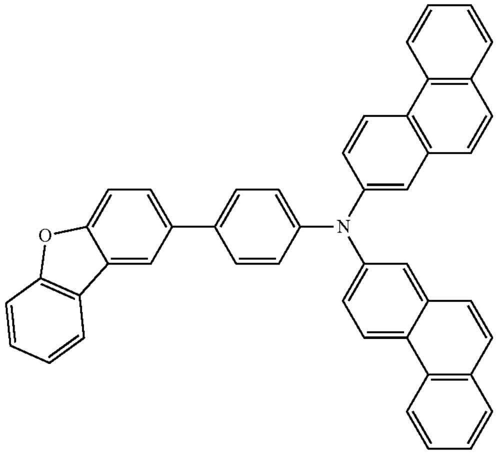

-continued
2-63
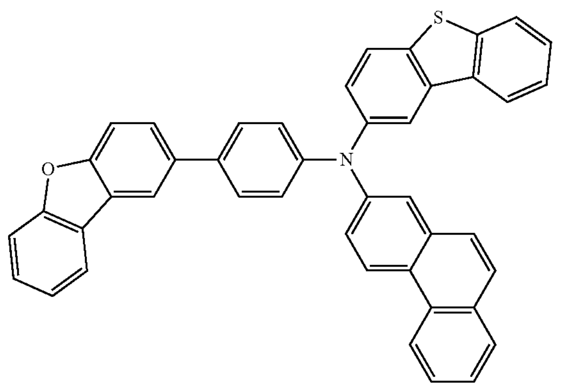
2-64
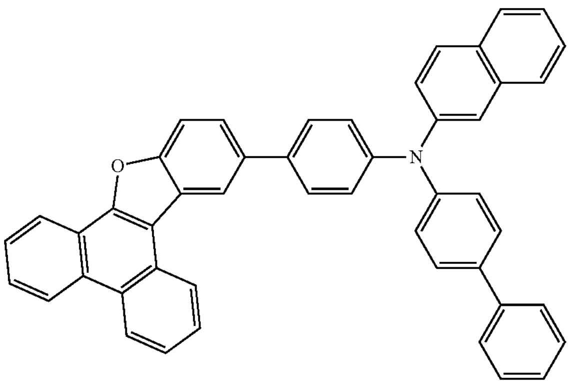
2-65
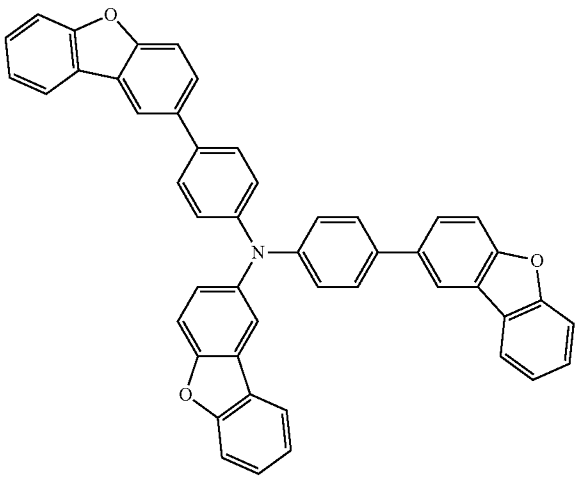
-continued
2-66
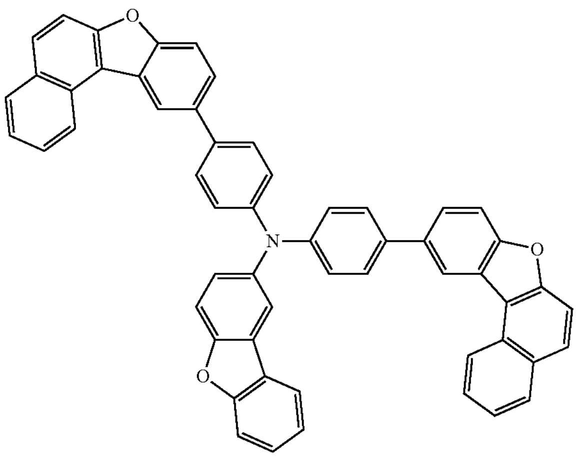
2-67
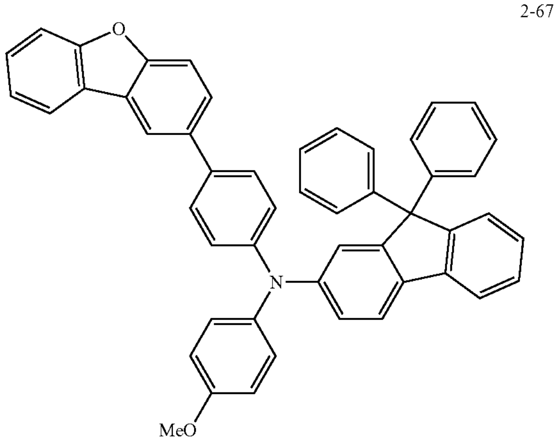
2-68
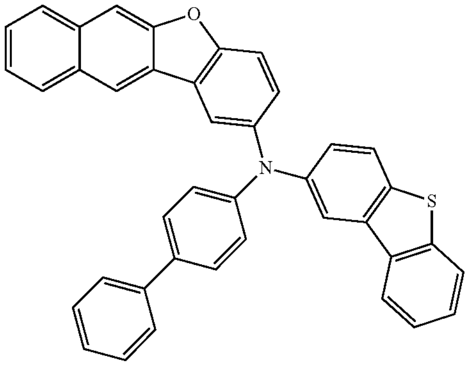

2-69
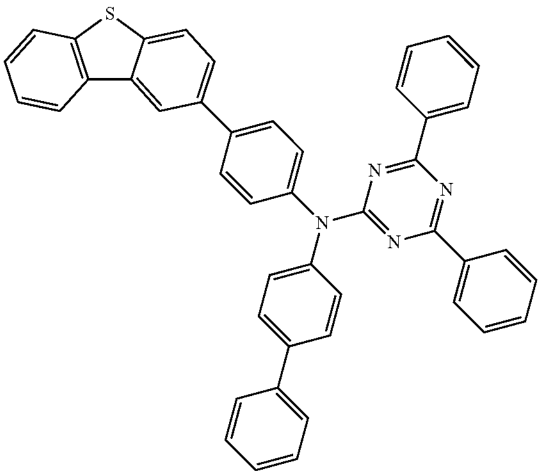
2-70
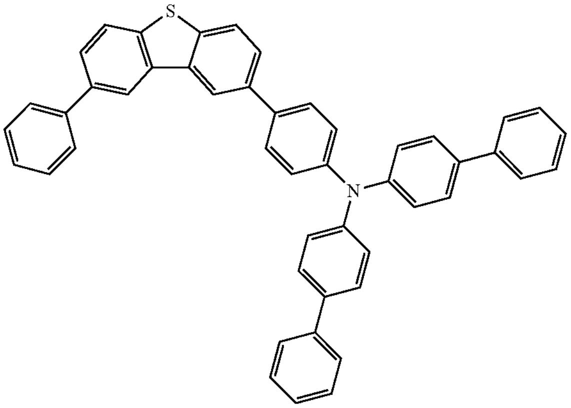
2-71
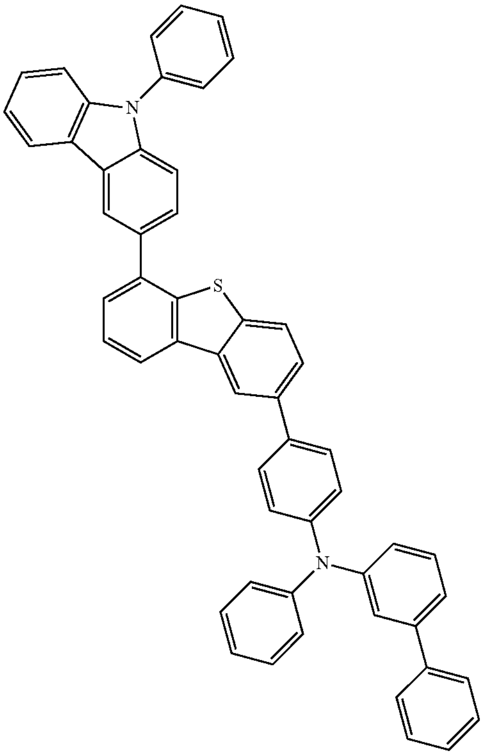
2-72
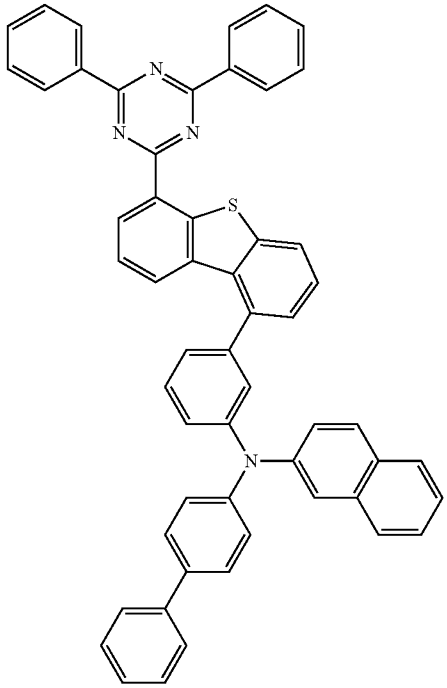

-continued
2-73
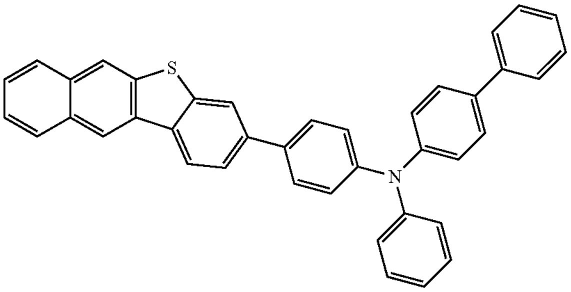
2-74
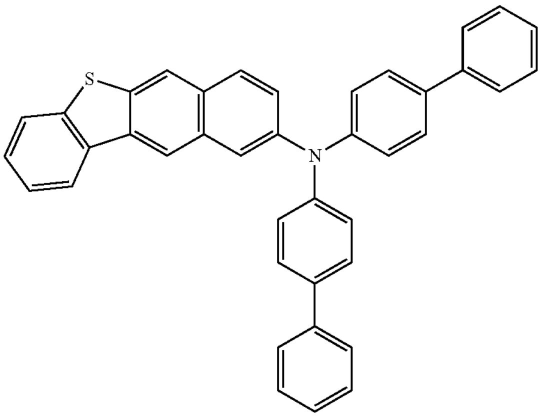
2-75
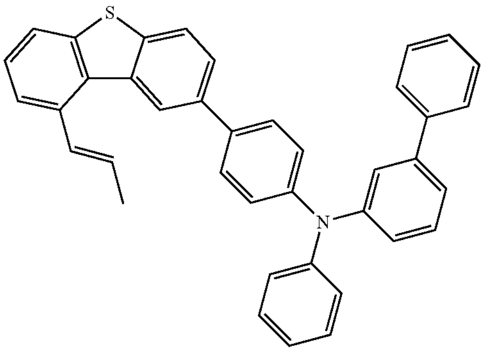
2-76
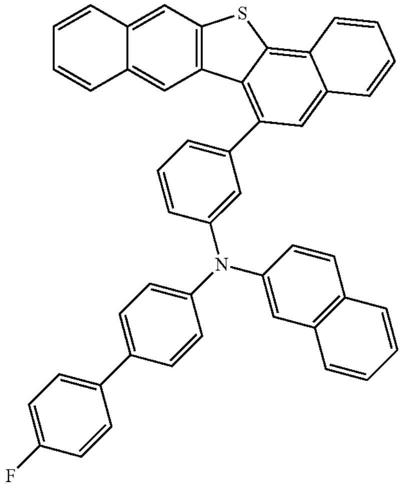
-continued
2-77
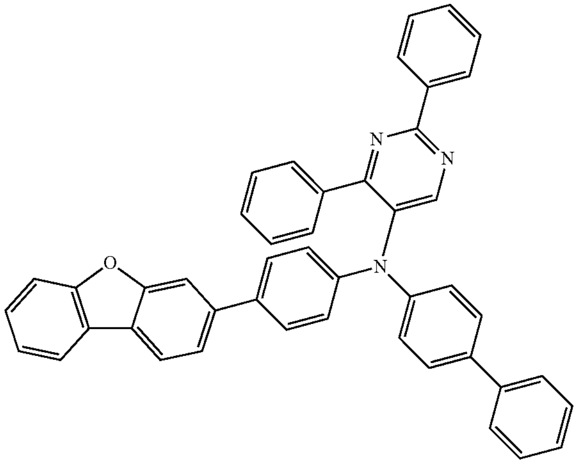
2-78
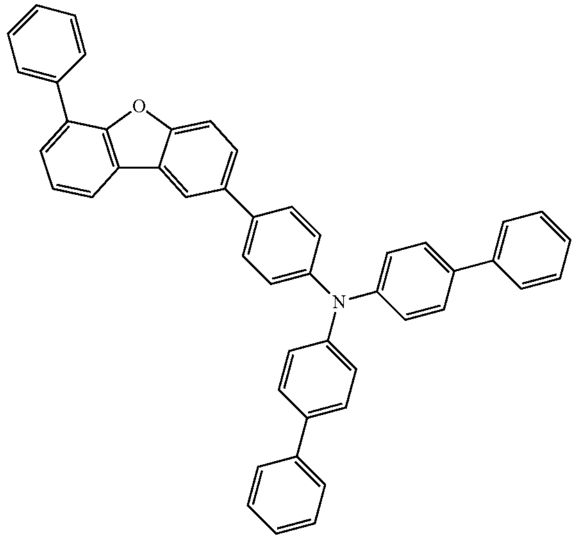
2-79
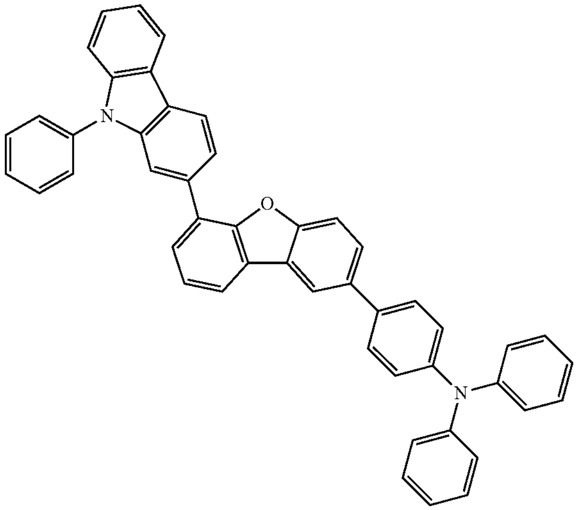

-continued
2-80
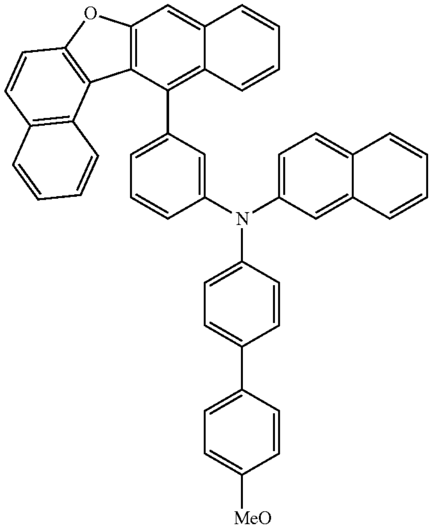
2-81
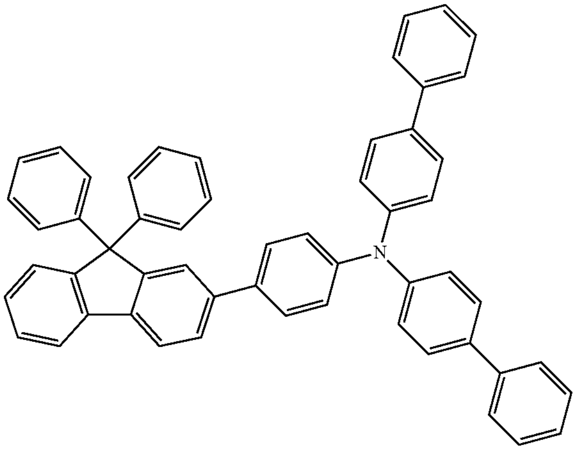
2-82
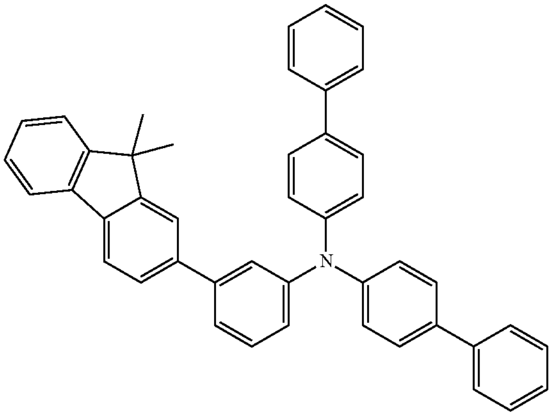
-continued
2-83
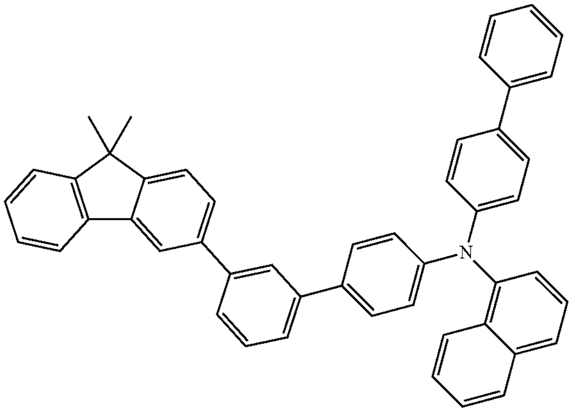
2-84
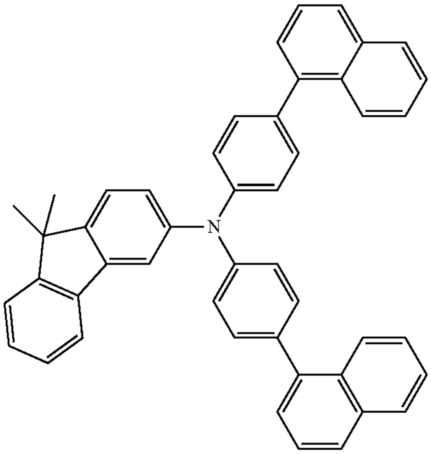
2-85
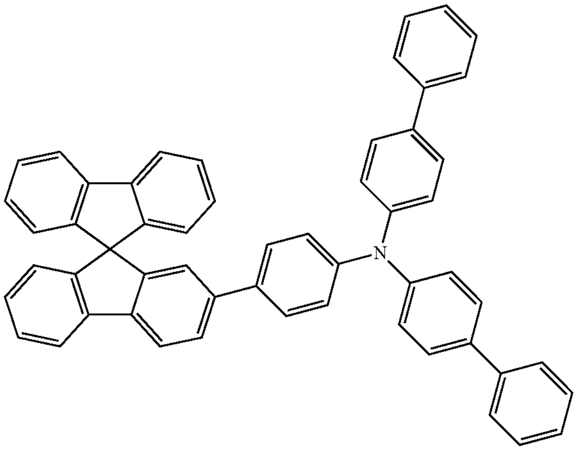

-continued
2-86
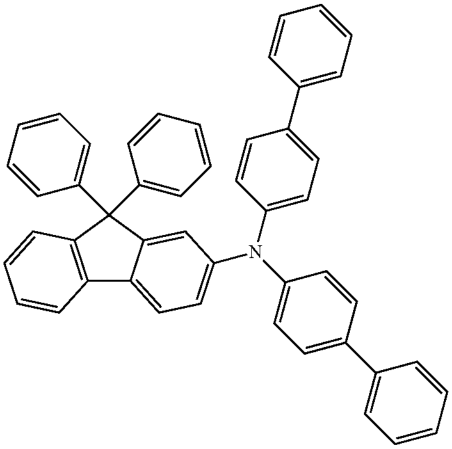
2-87
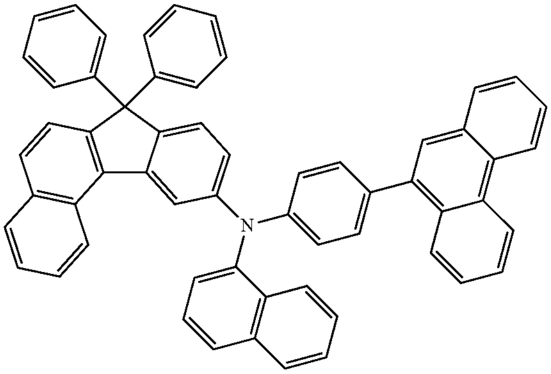
2-88
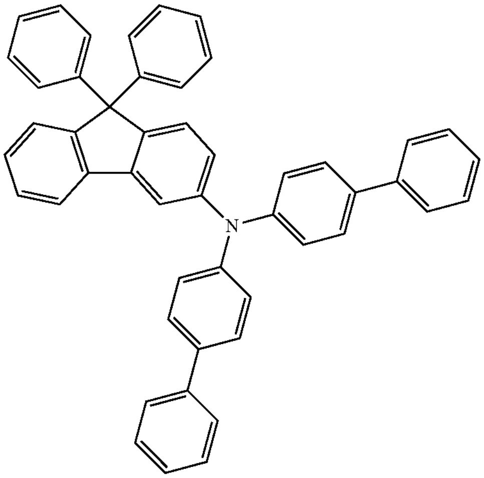
-continued
2-89
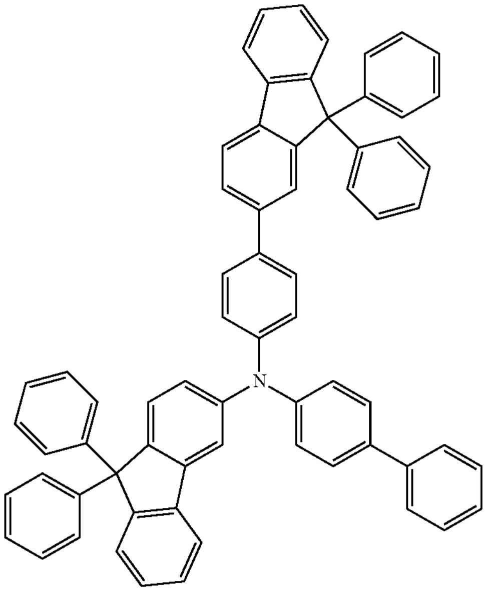
2-90
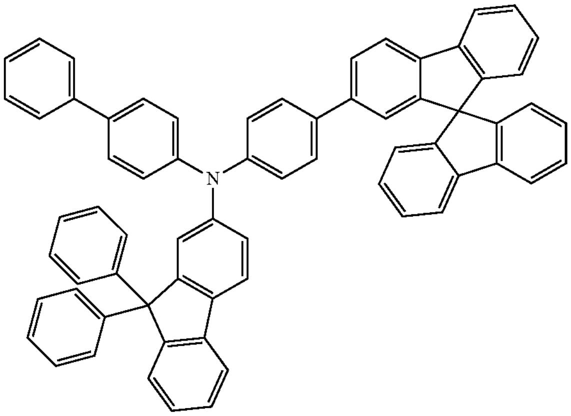
2-91
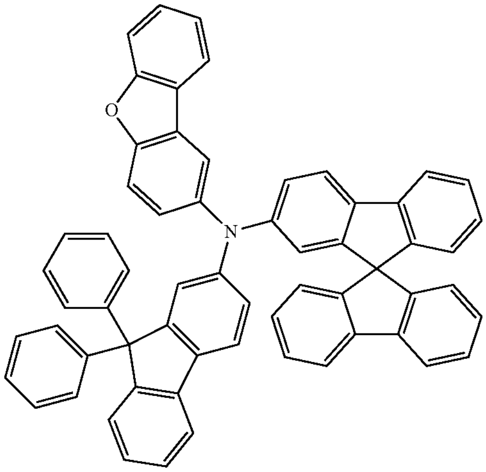

-continued
2-92
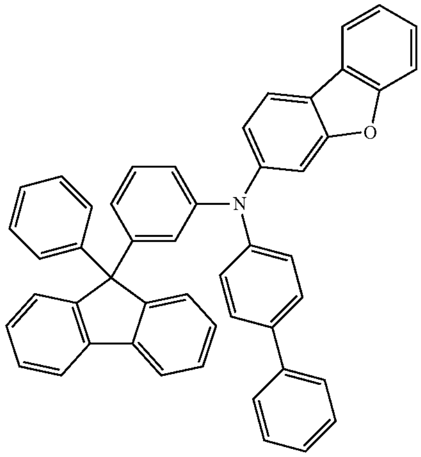
2-93
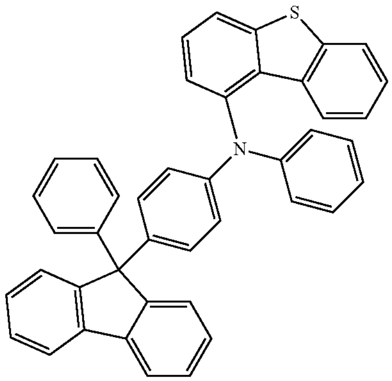
2-94
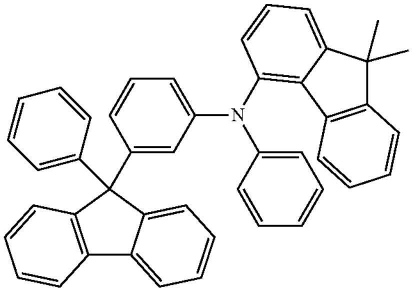
2-95
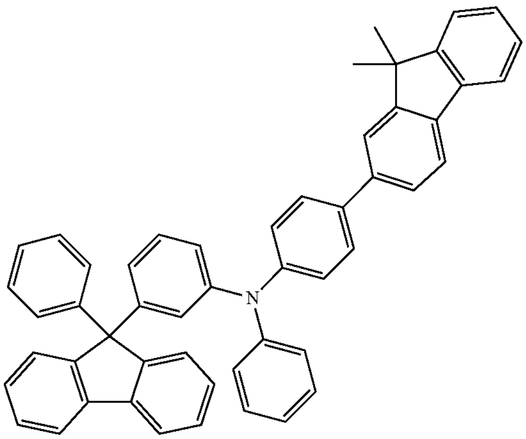
-continued
2-96
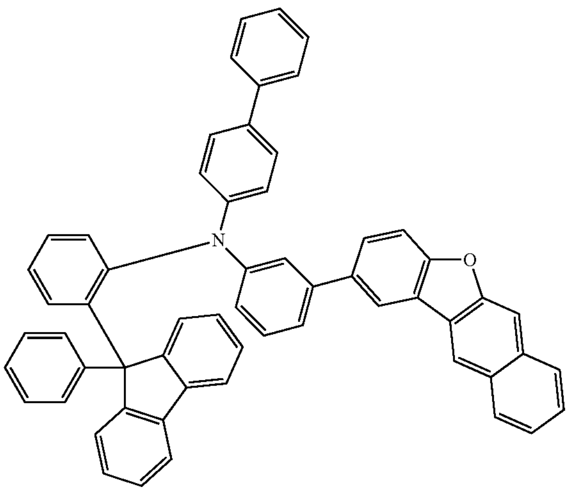
2-97
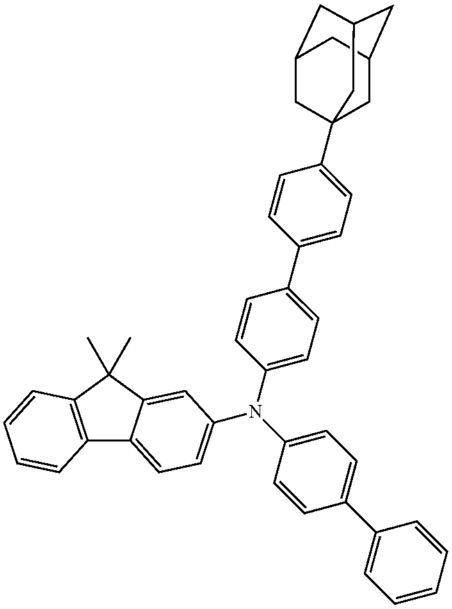
3-1
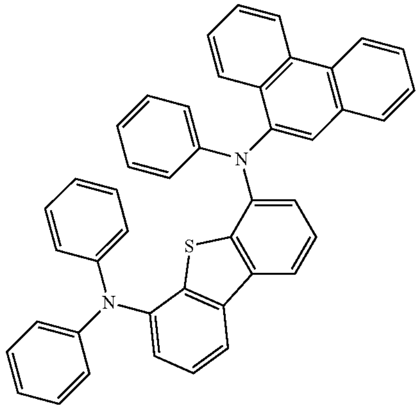

3-2
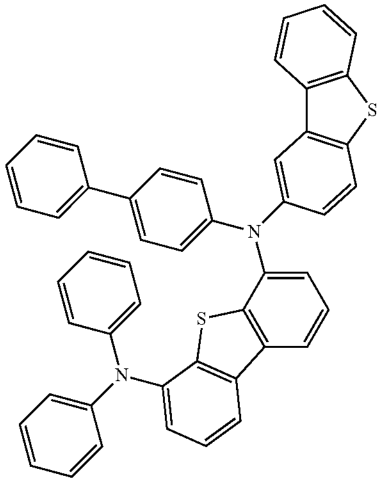
3-3
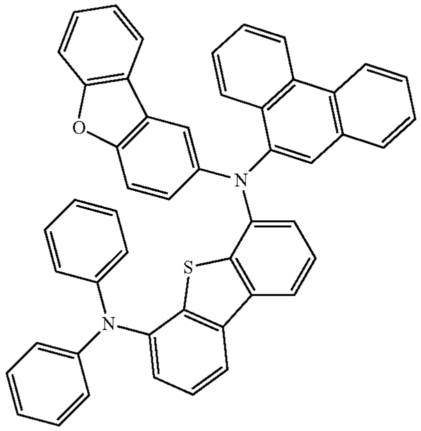
3-4
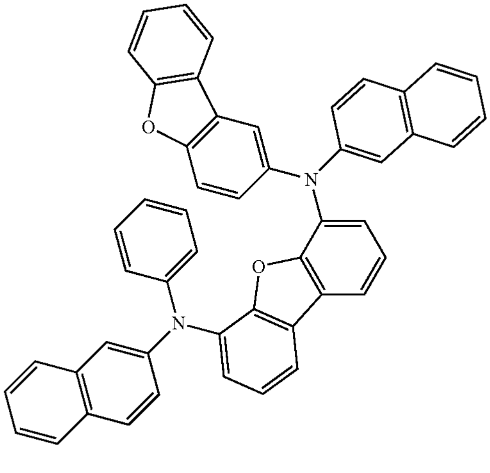
3-5
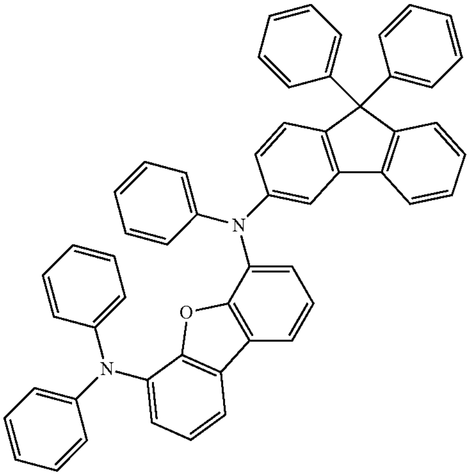
3-6
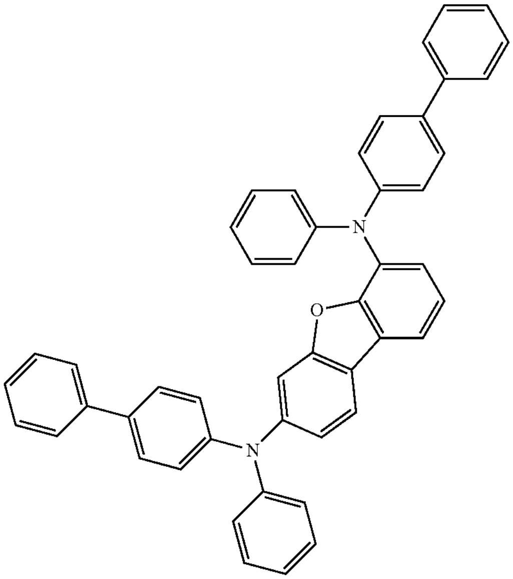
3-7
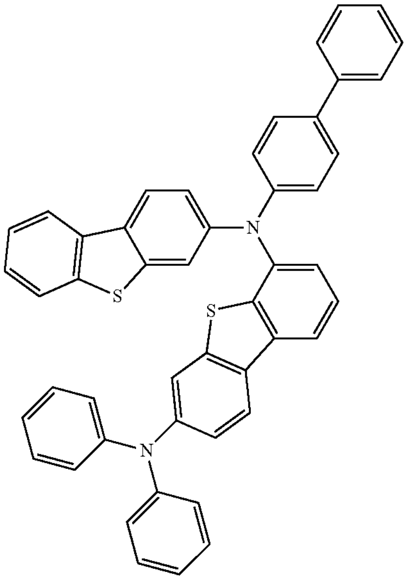

-continued
3-8
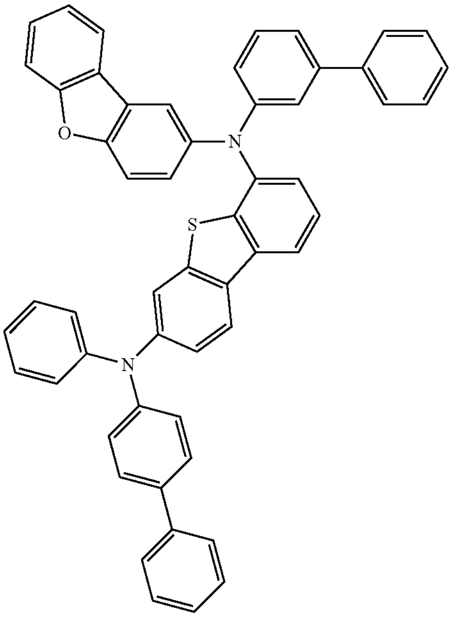
3-9
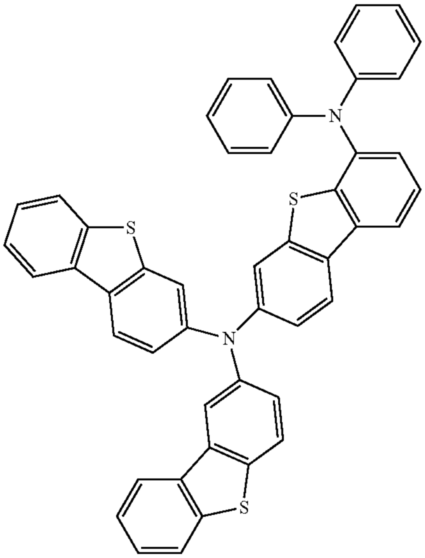
-continued
3-10
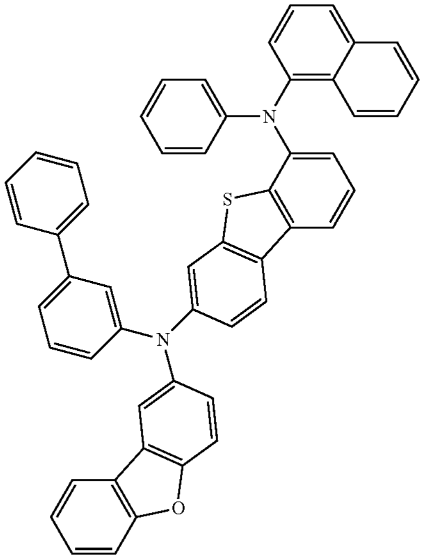
3-11
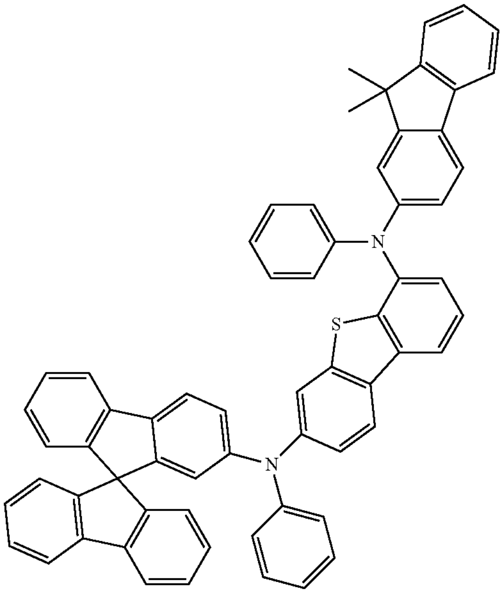

-continued
3-12
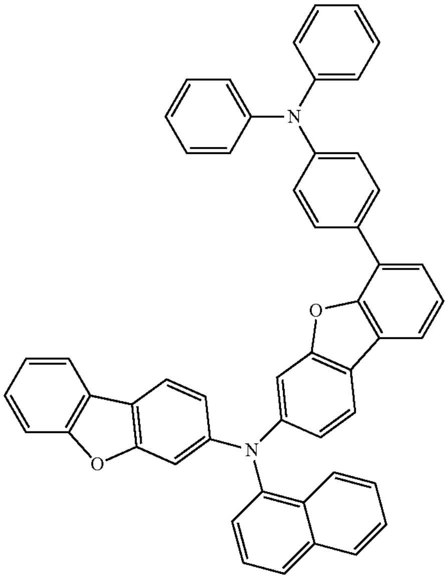
3-13
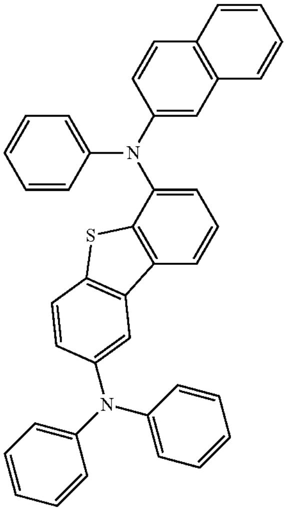
3-14
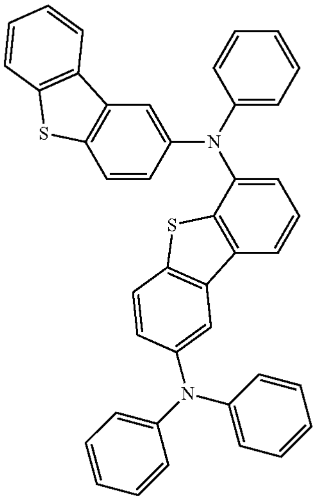
-continued
3-15
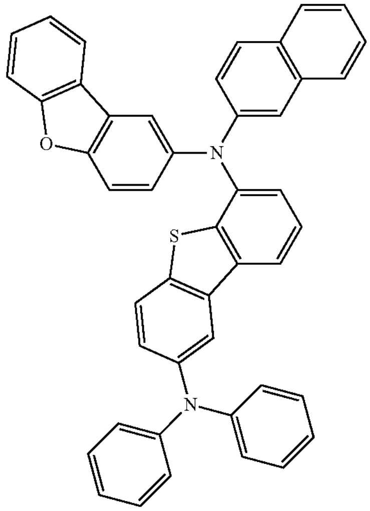
3-16
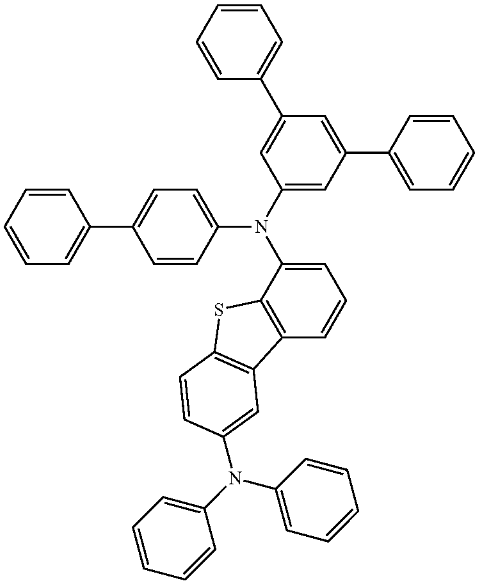

-continued
3-17
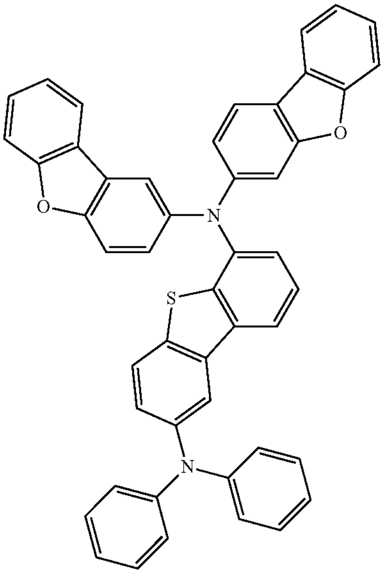
3-18
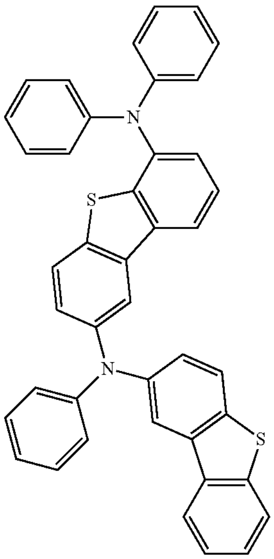
-continued
3-19
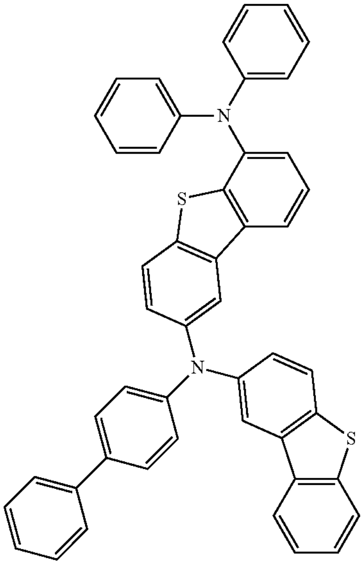
3-20
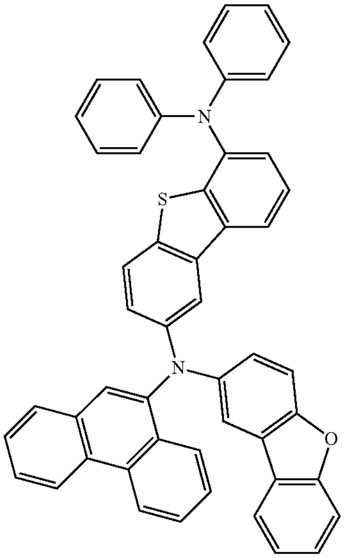

-continued
3-21
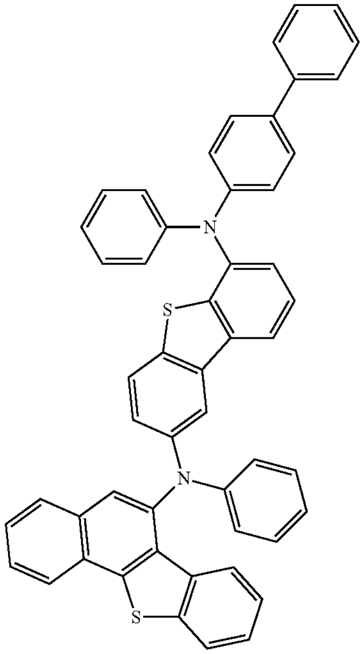
3-22
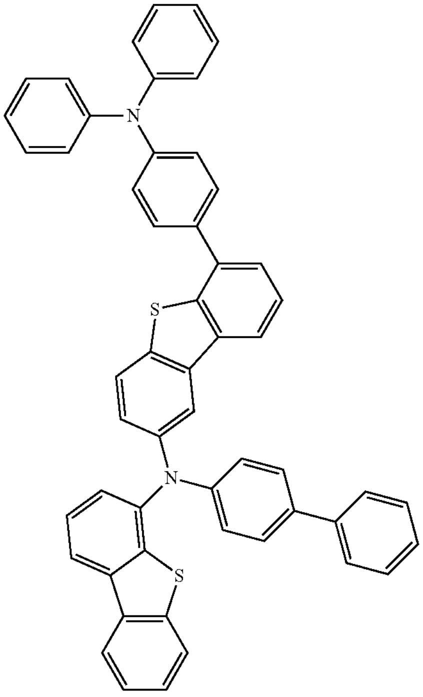
-continued
3-23
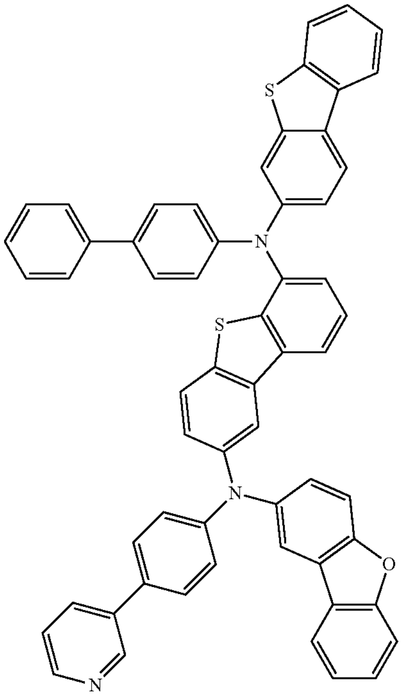
3-24
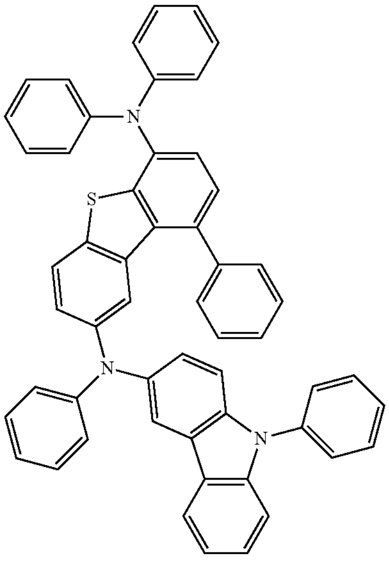

-continued
3-25
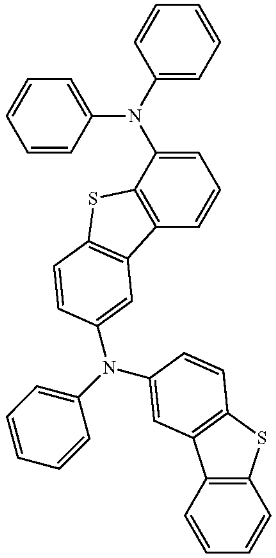
3-26
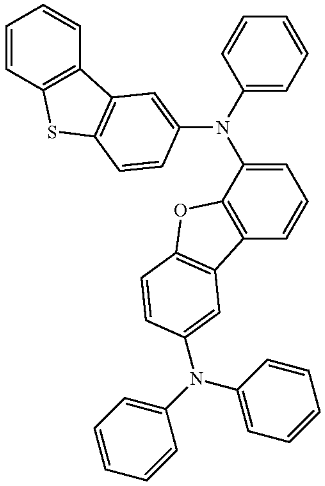
3-27
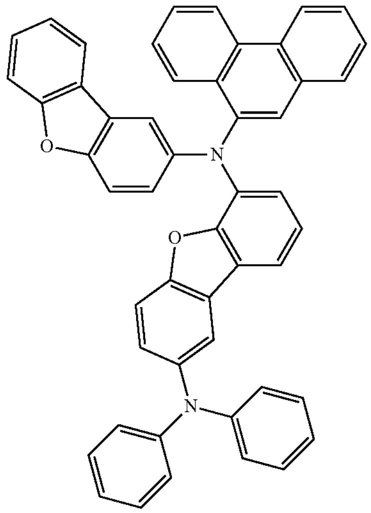
-continued
3-28
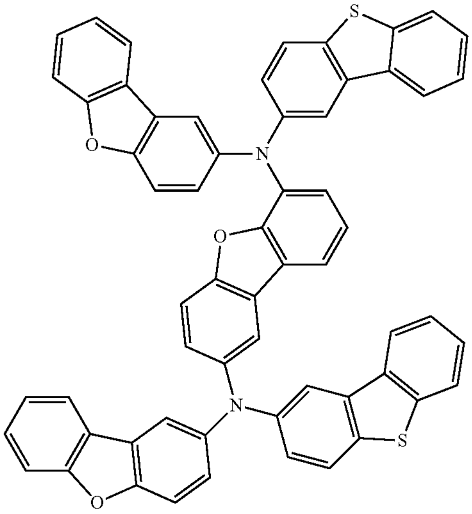
3-29
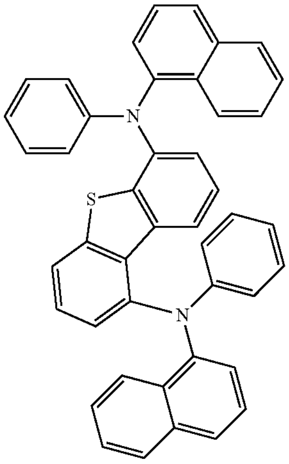
3-30
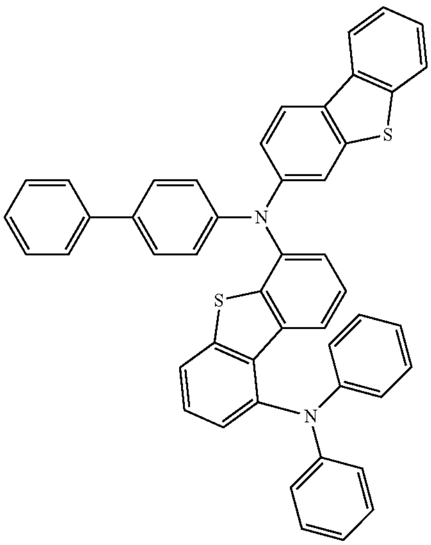

-continued
3-31
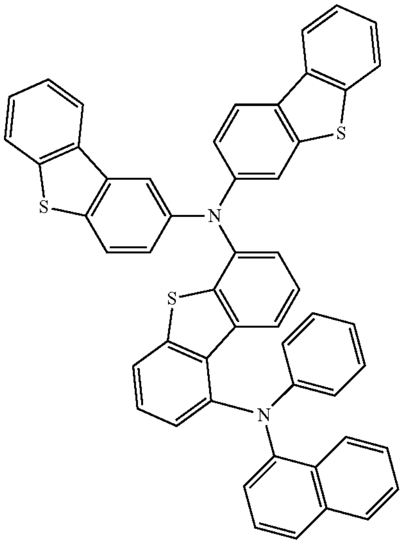
3-32
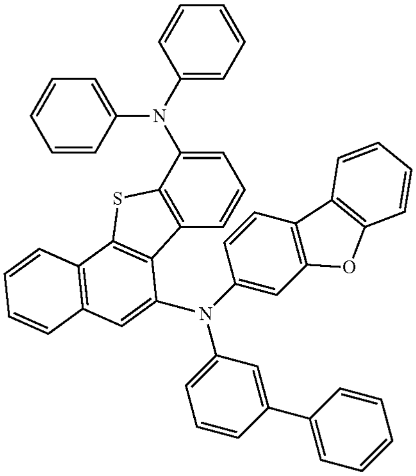
3-33
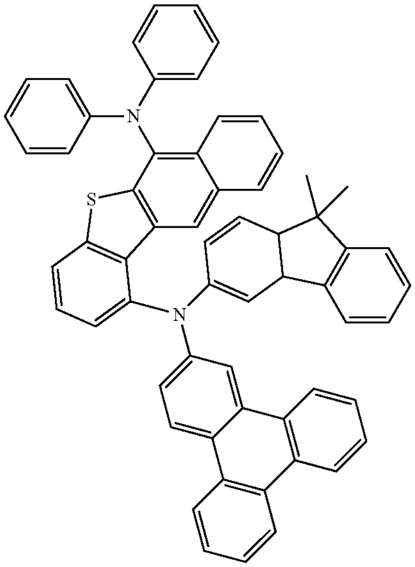
-continued
3-34
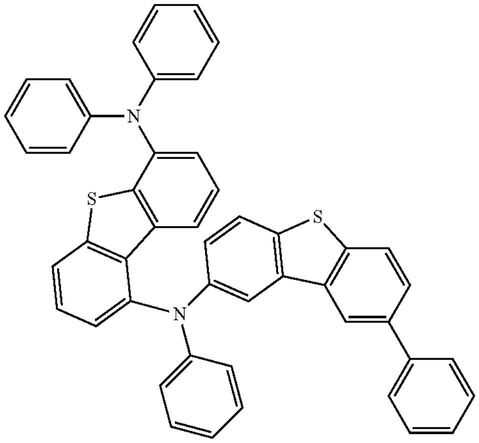
3-35
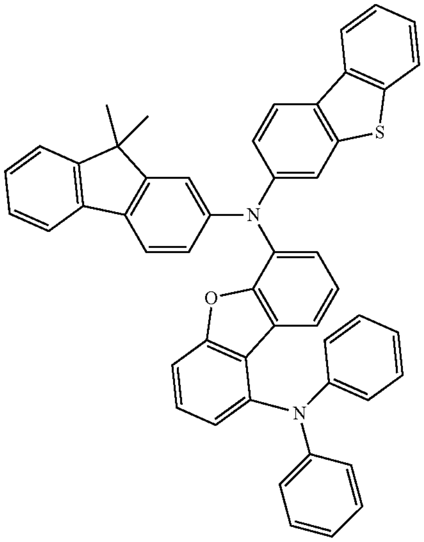
3-36
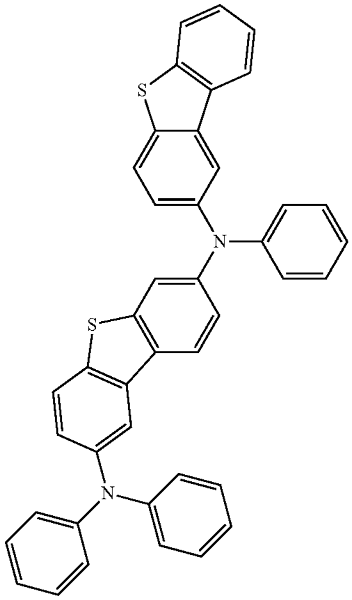

-continued
3-37
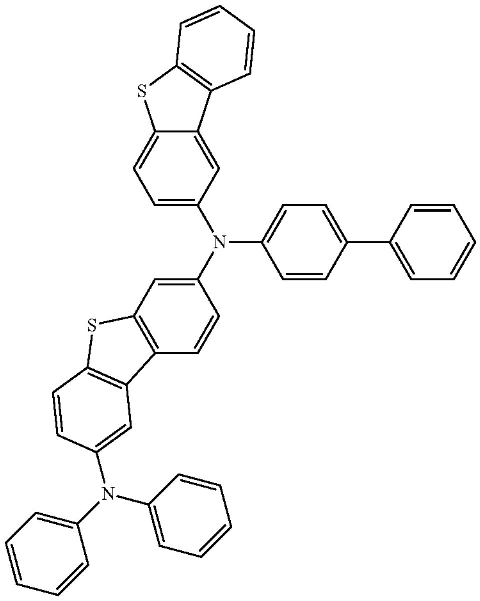
3-38
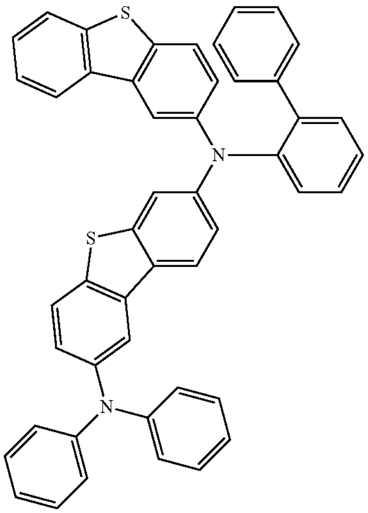
-continued
3-39
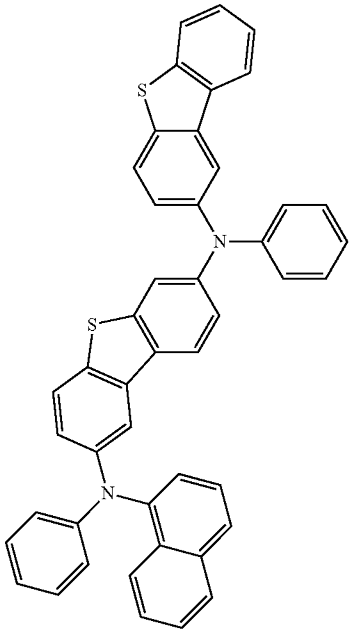
3-40
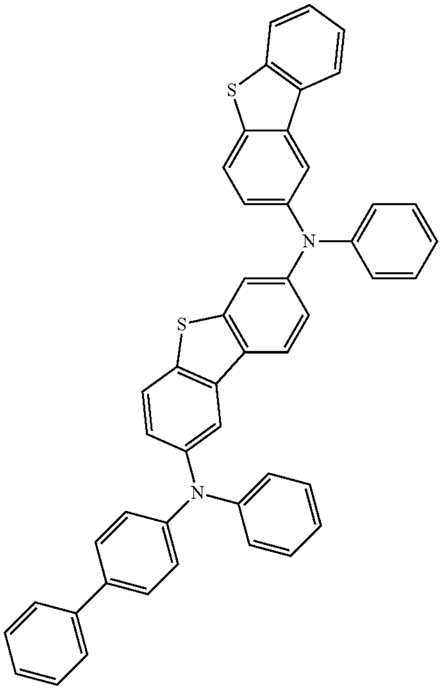

-continued
3-41
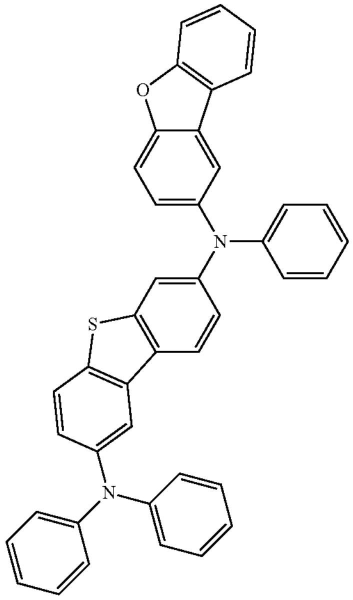
3-42
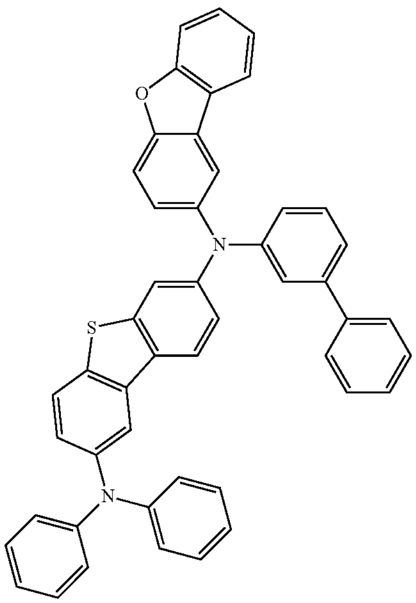
-continued
3-43
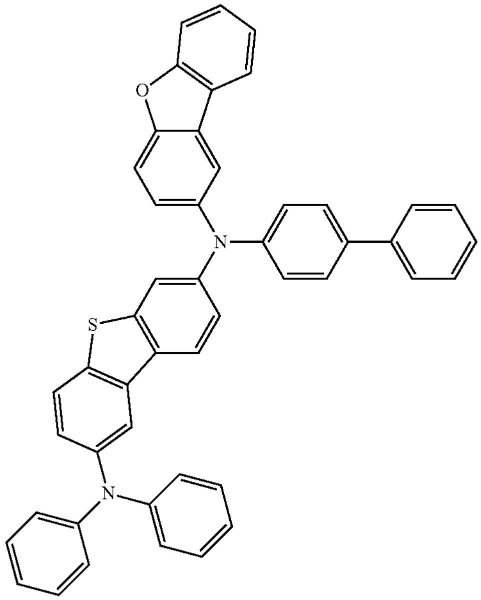
3-44
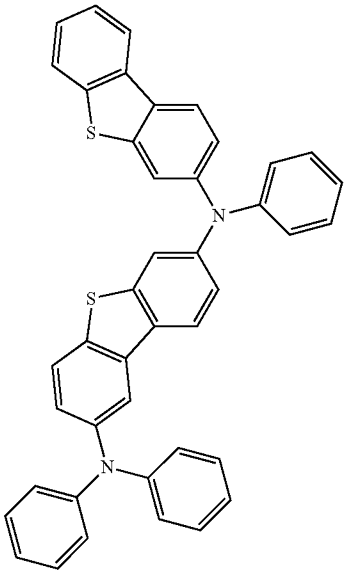

-continued
3-45
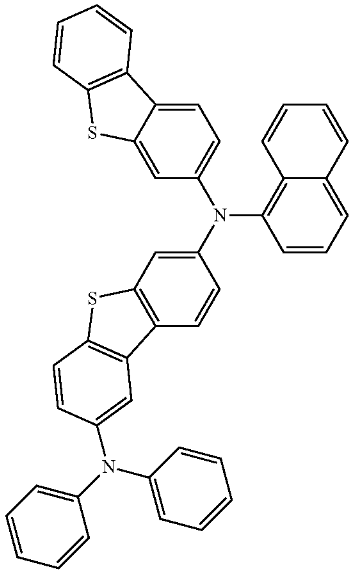
3-46
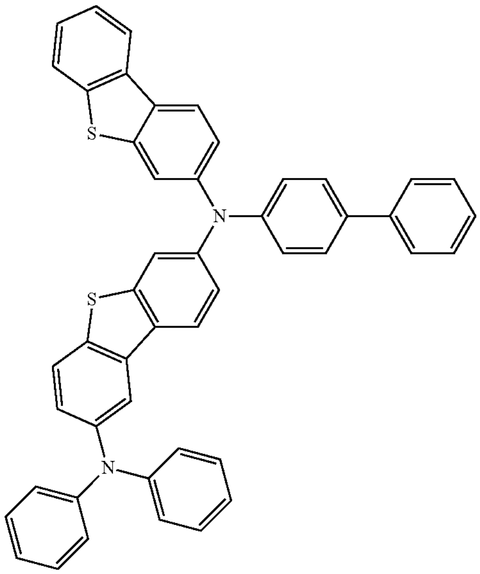
-continued
3-47
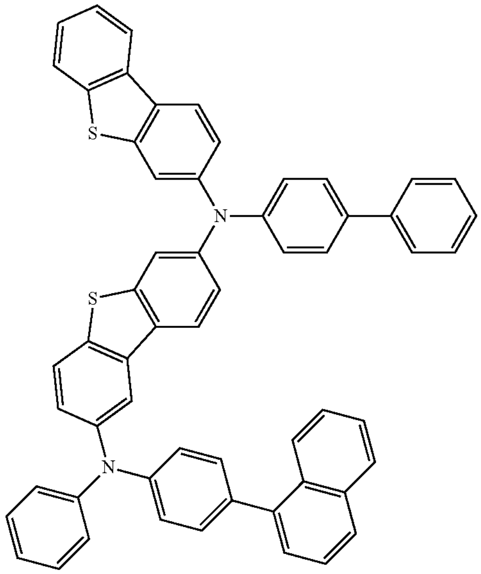
3-48
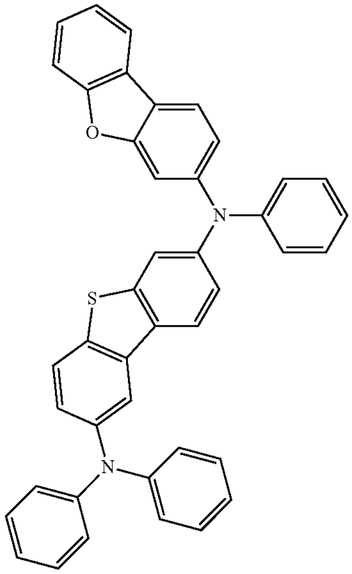
3-49
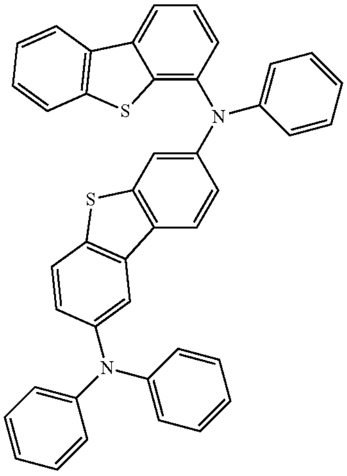

-continued
3-50
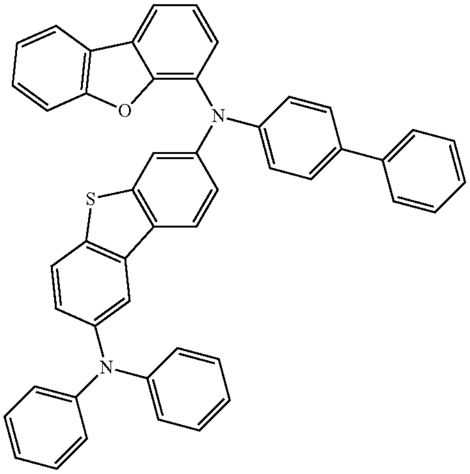
3-51
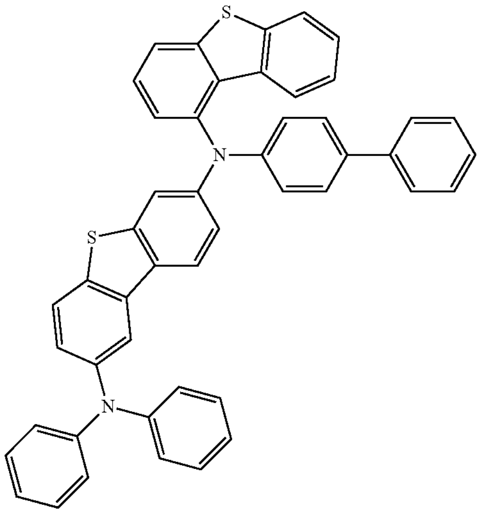
3-52
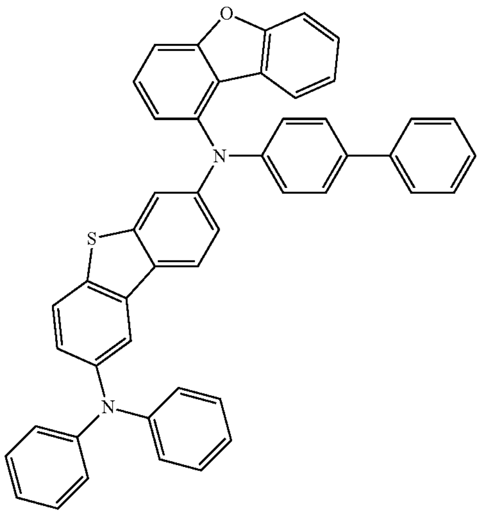
-continued
3-53
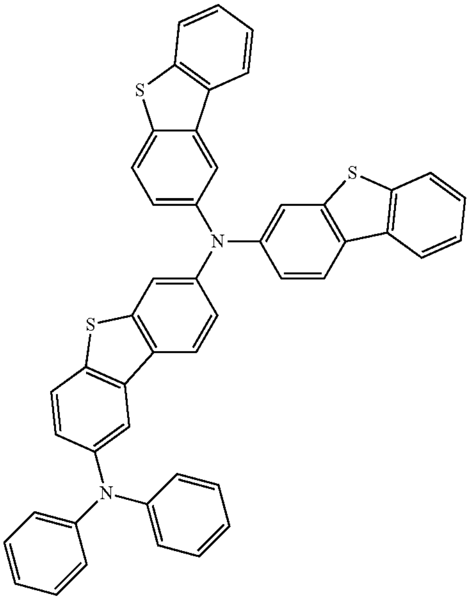
3-54
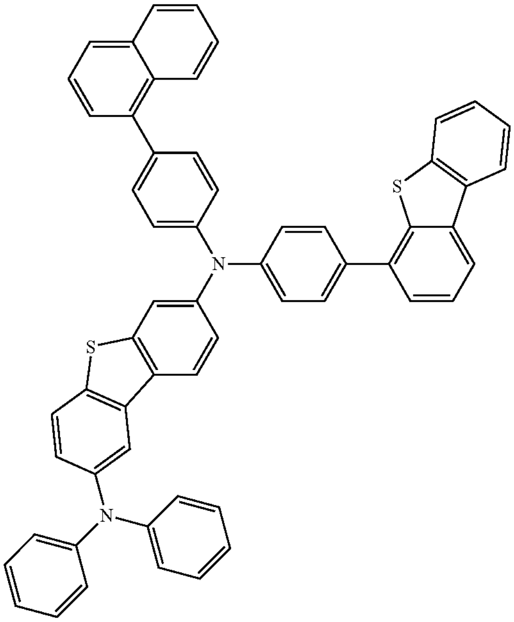

-continued
3-55
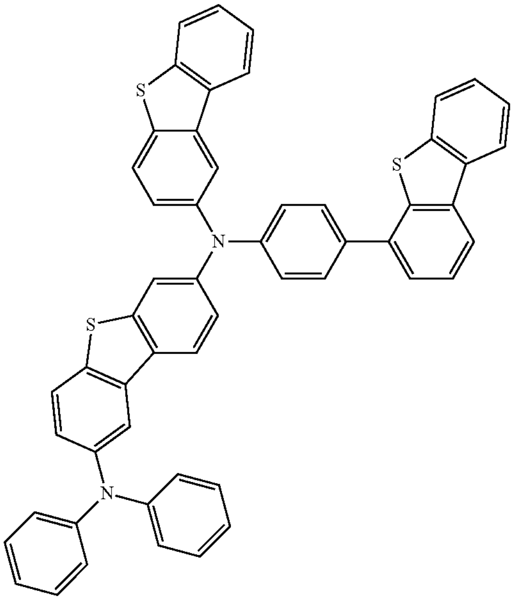
3-56
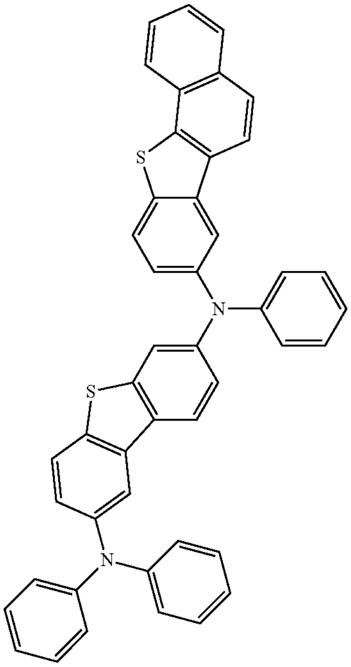
-continued
3-57
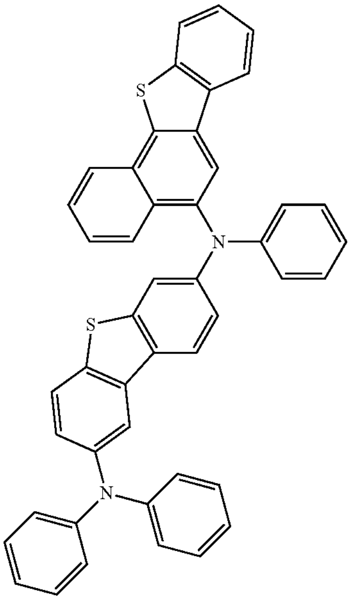
3-58
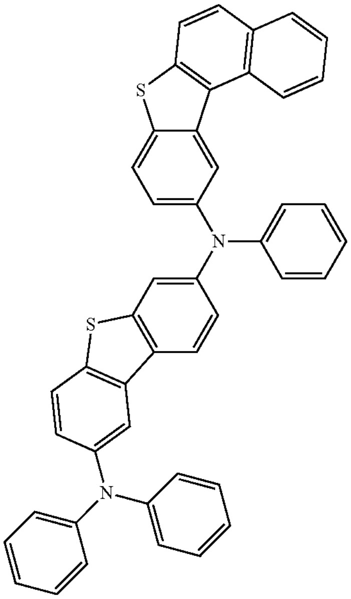

-continued
3-59
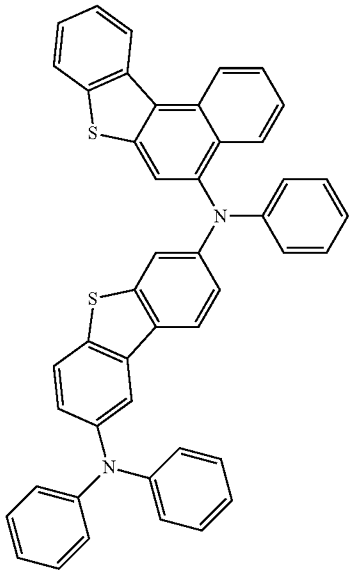
3-60
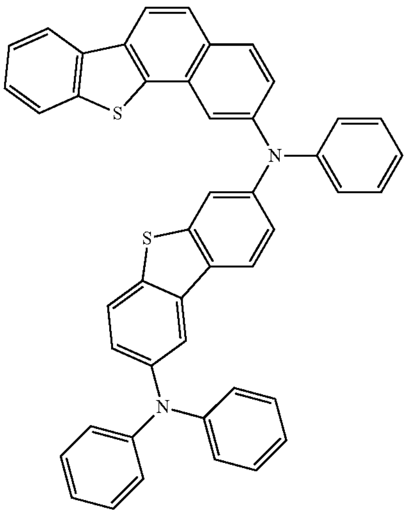
-continued
3-61
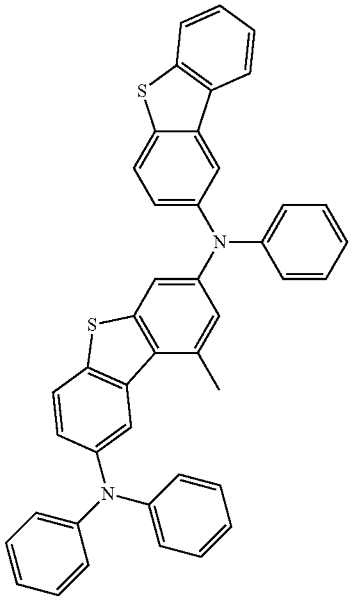
3-62
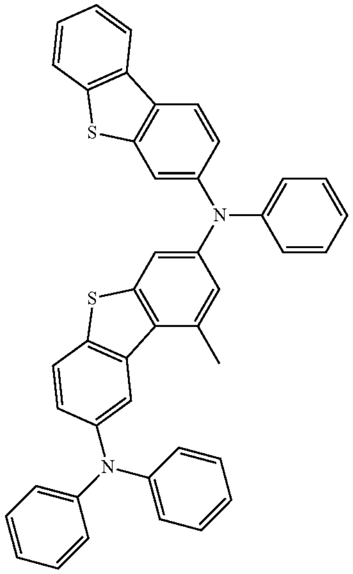

-continued
3-63
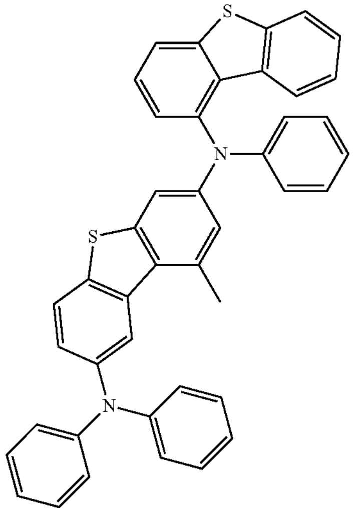
3-64
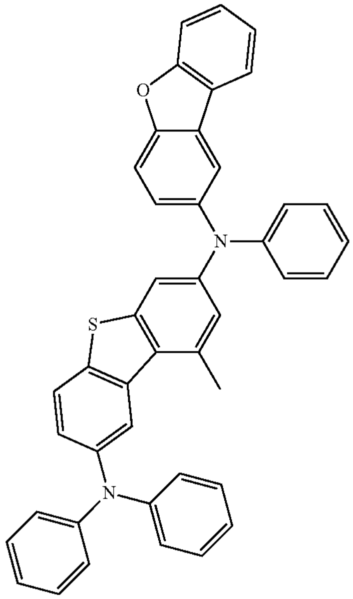
-continued
3-65
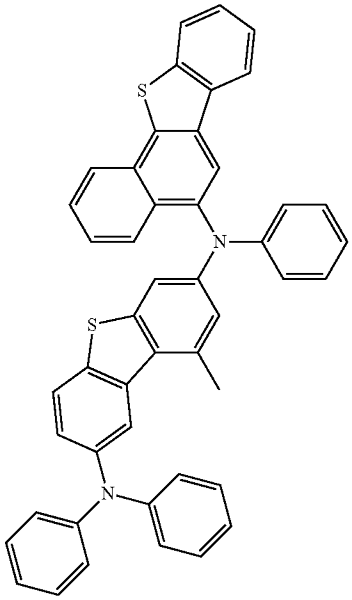
3-66
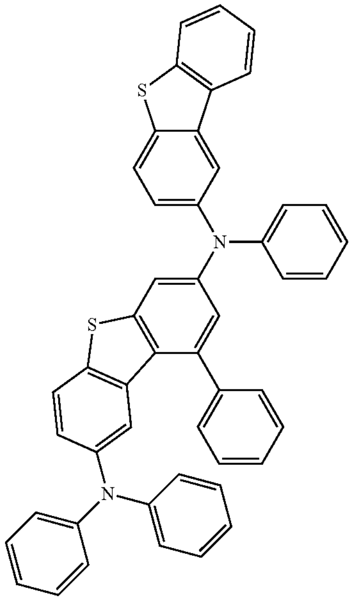

-continued
3-67
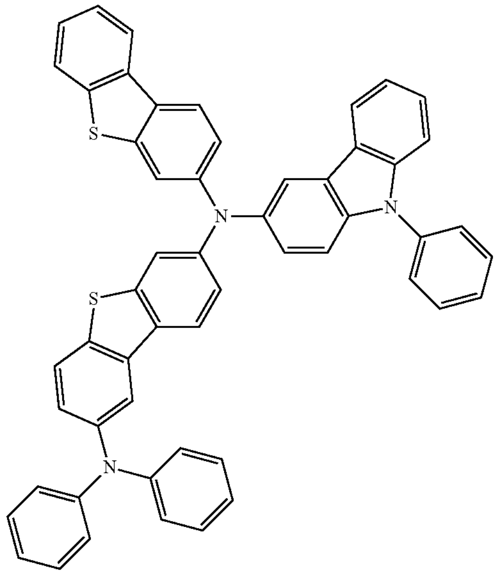
3-68
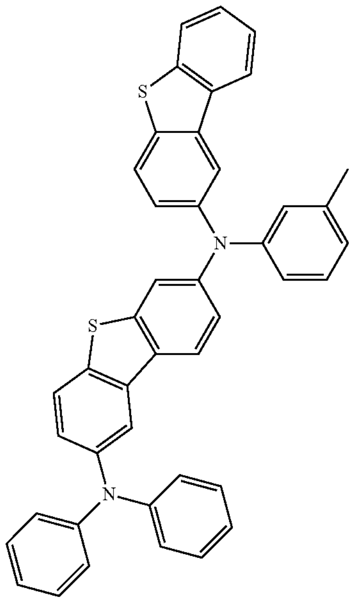
-continued
3-69
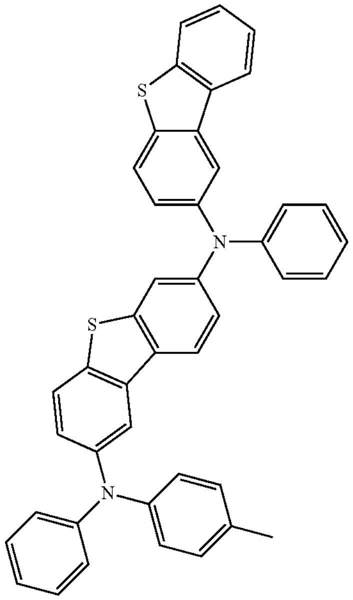
3-70
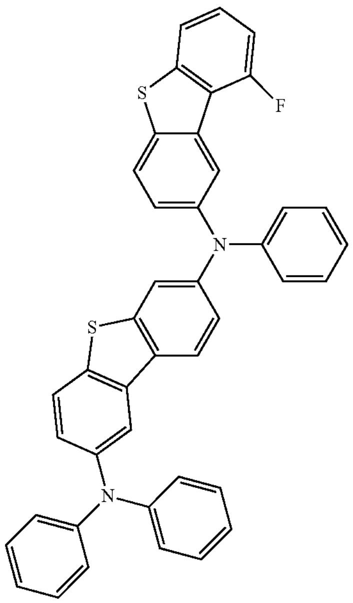

-continued
3-71
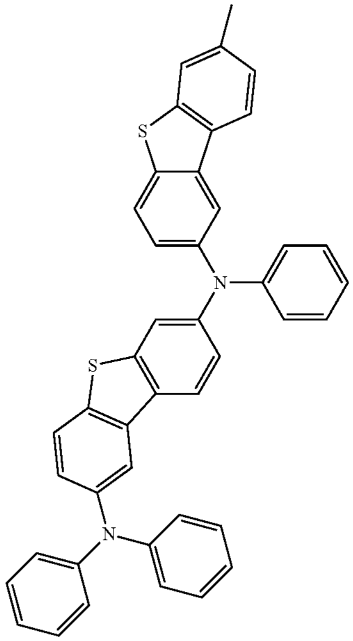
3-72
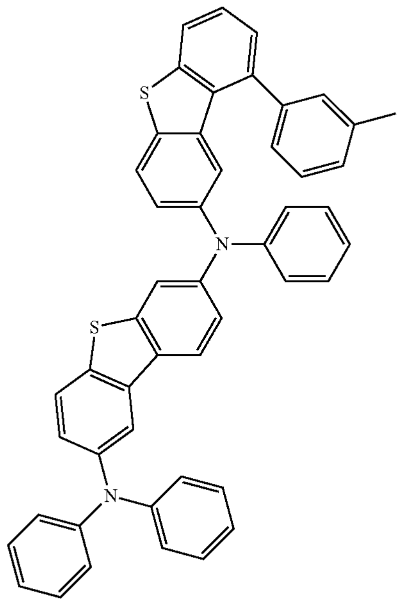
-continued
3-73
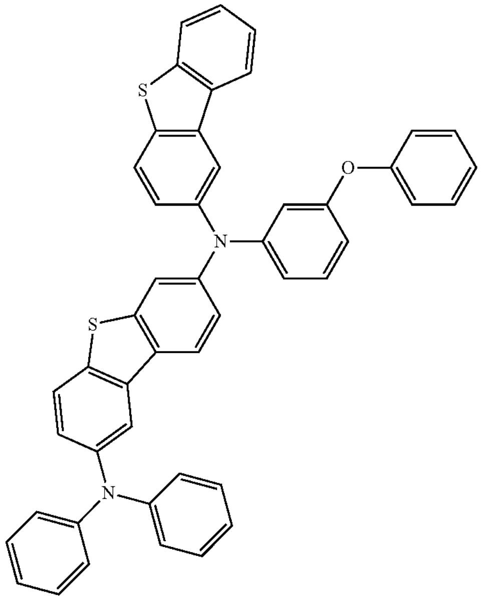
3-74
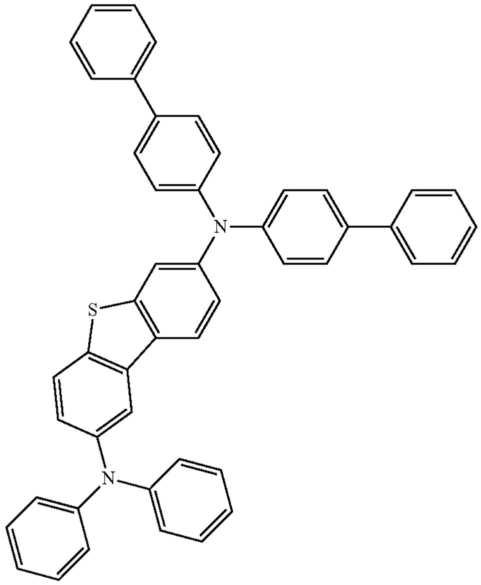
3-75
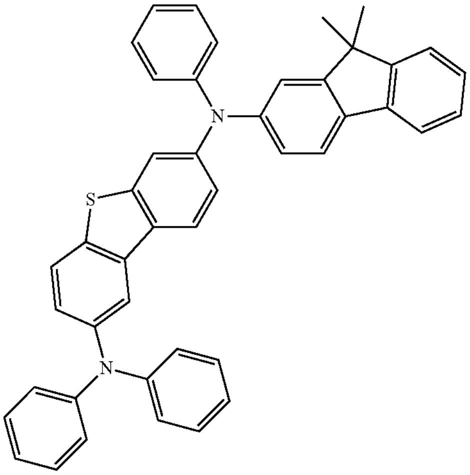

-continued
3-76
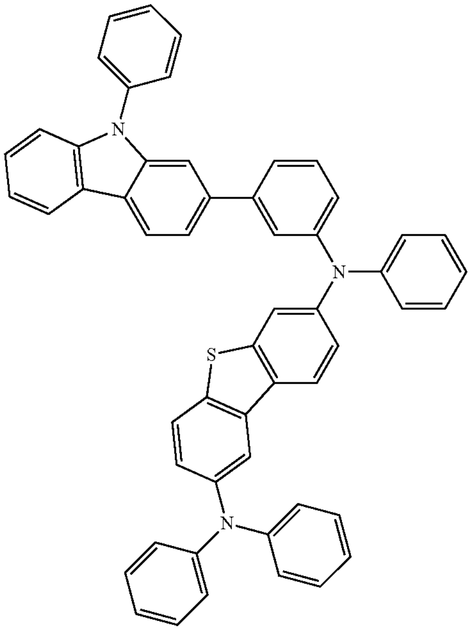
3-77
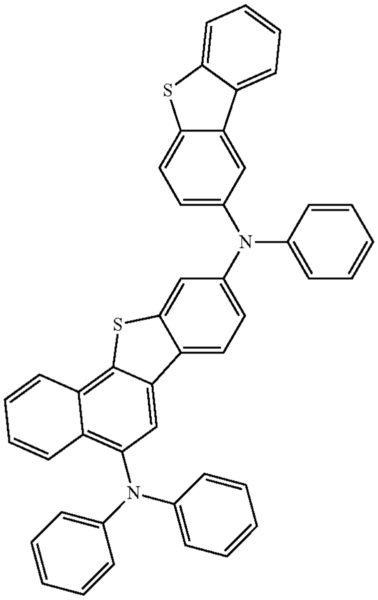
-continued
3-78
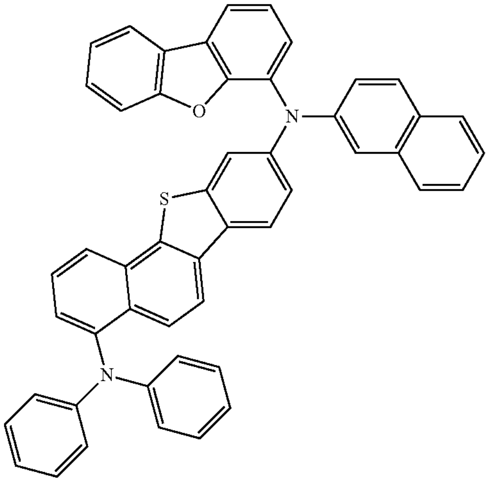
3-79
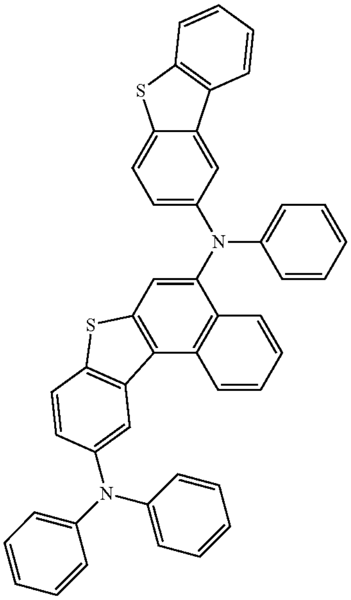

-continued
3-80
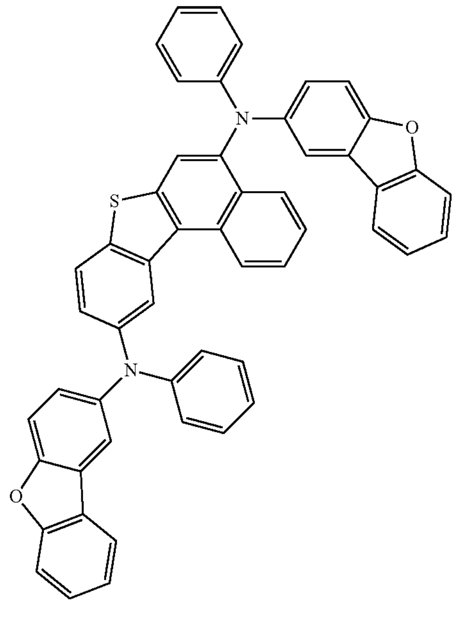
3-81
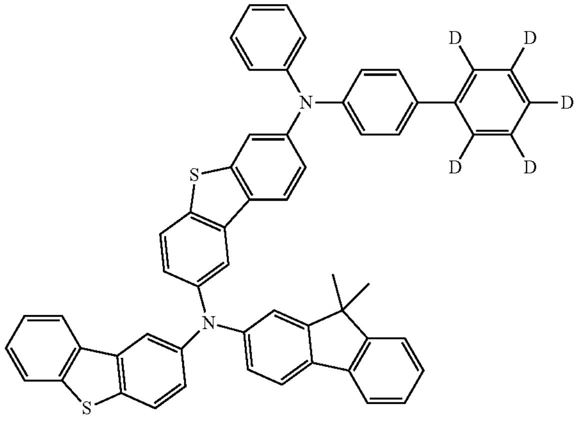
3-82
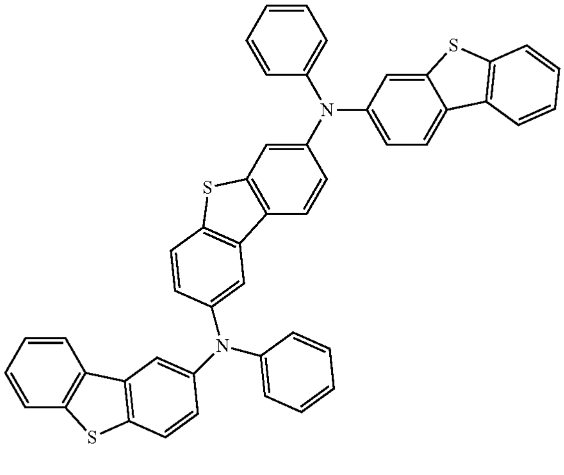
-continued
3-83
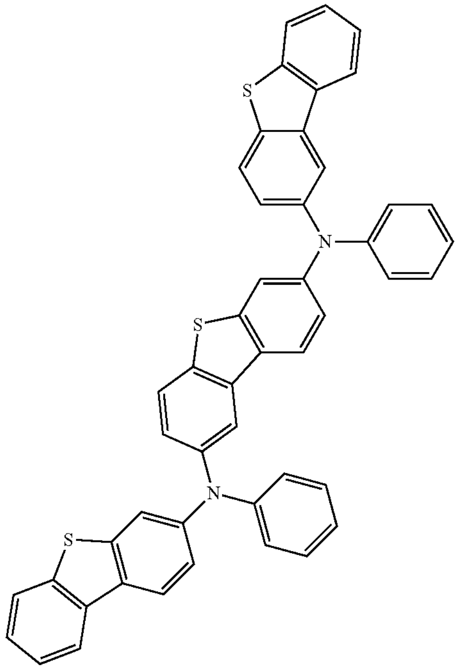
3-84
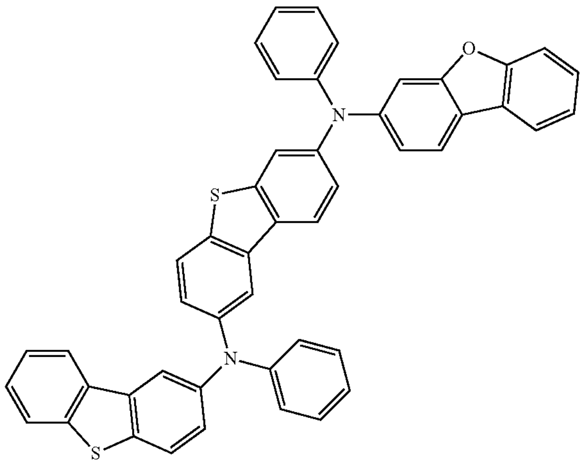

-continued
3-85
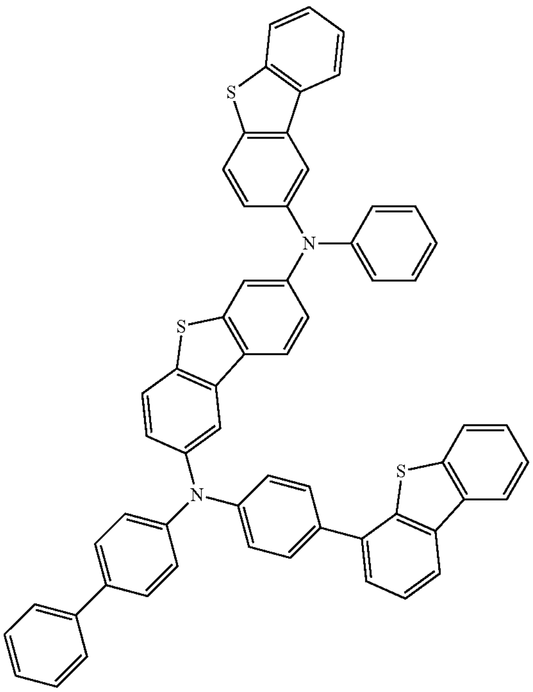
3-86
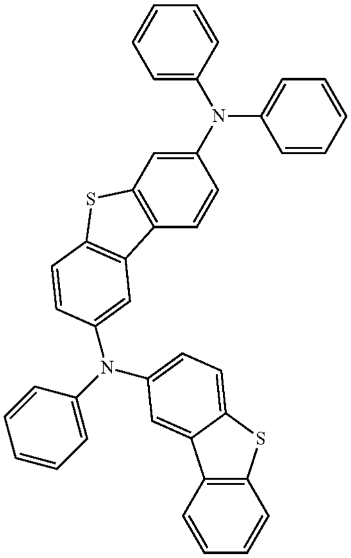
-continued
3-87
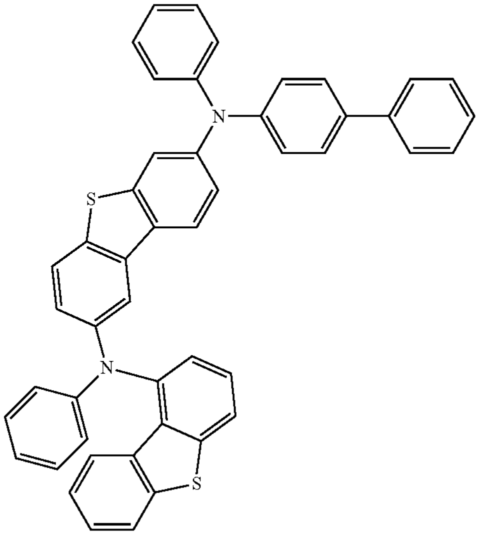
3-88
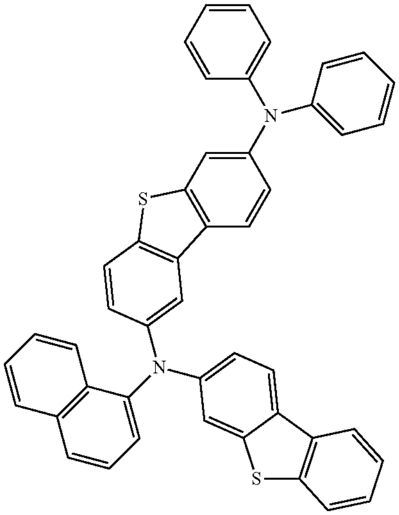
3-89
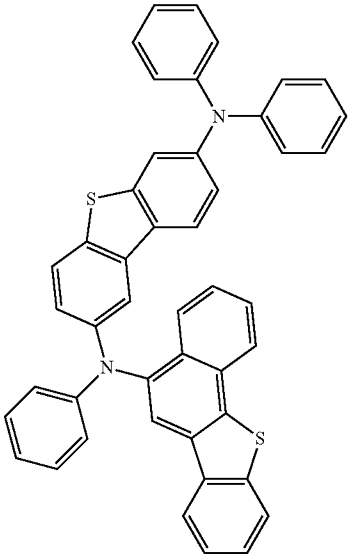

-continued
3-90
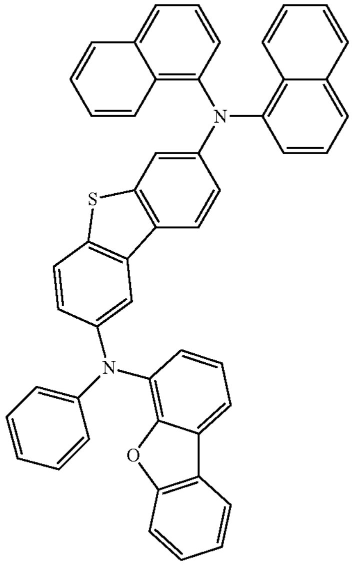
3-91
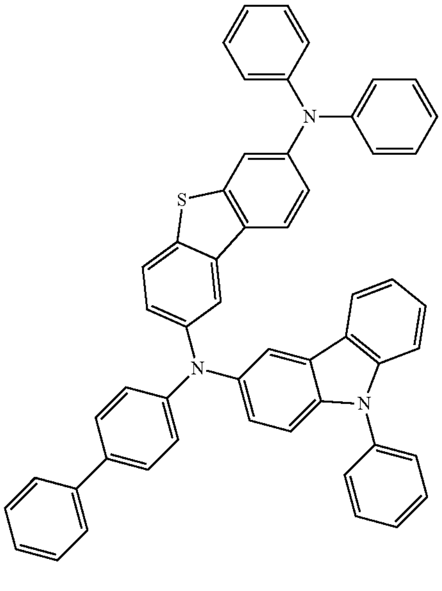
-continued
3-92
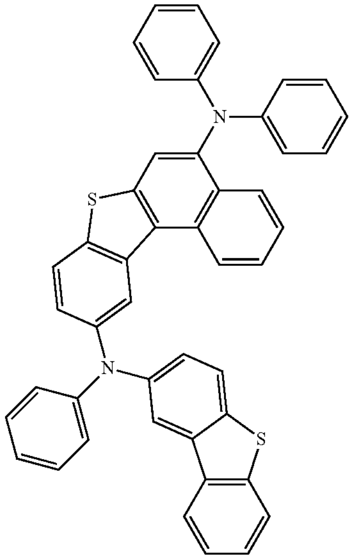
3-93
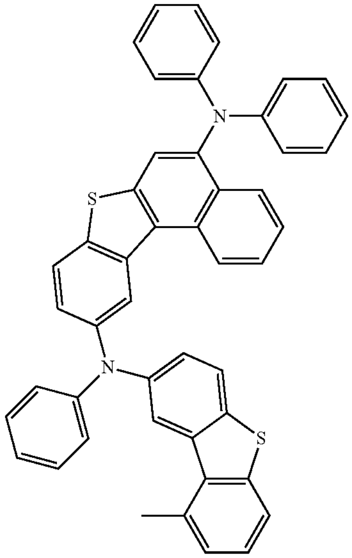

-continued
3-94
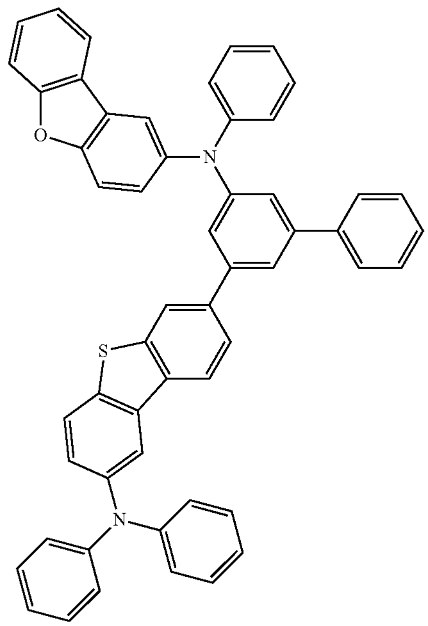
3-95
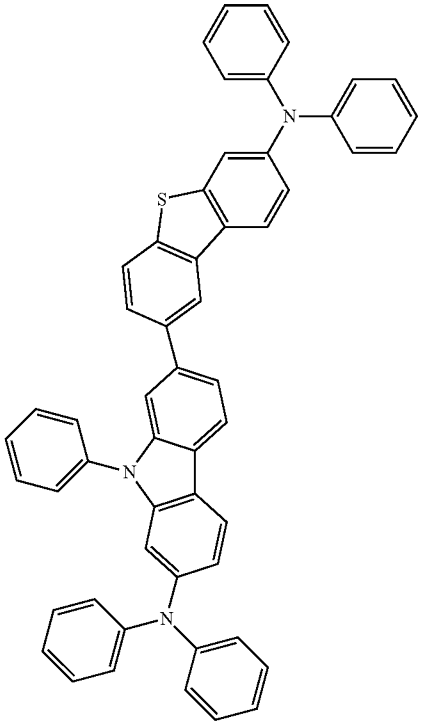
-continued
3-96
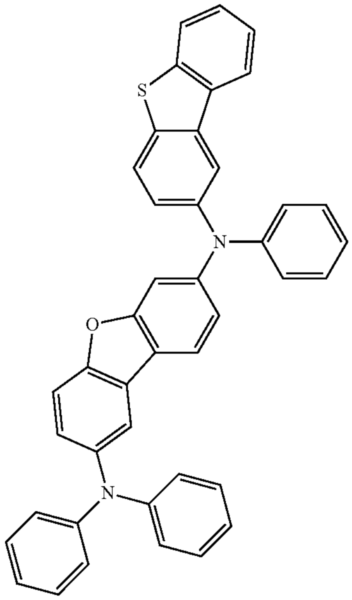
3-97
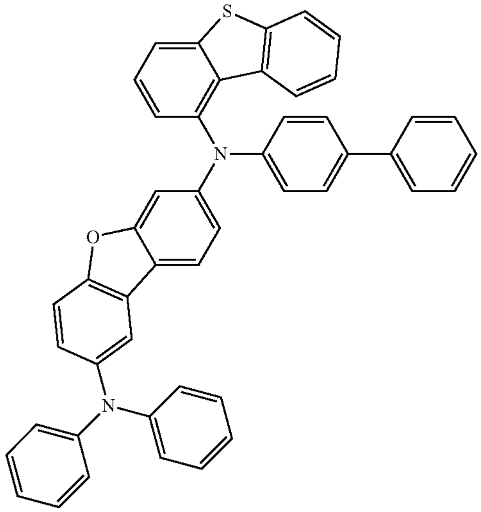

-continued
3-98
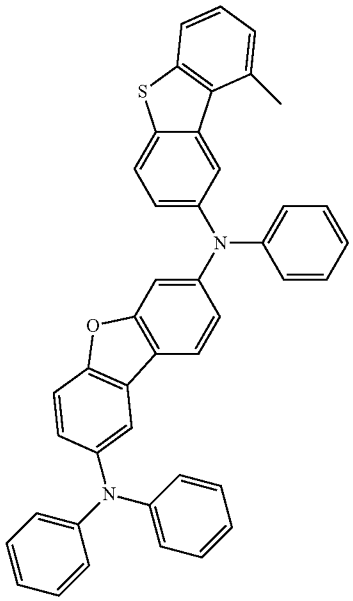
3-99
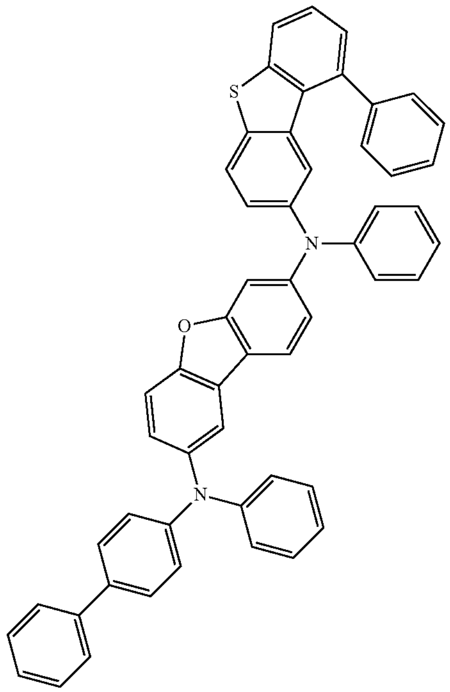
-continued
3-100
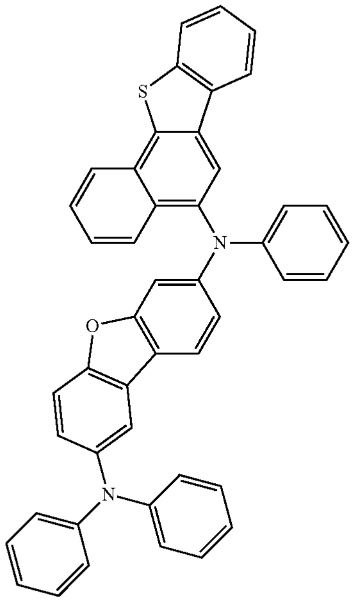
3-101
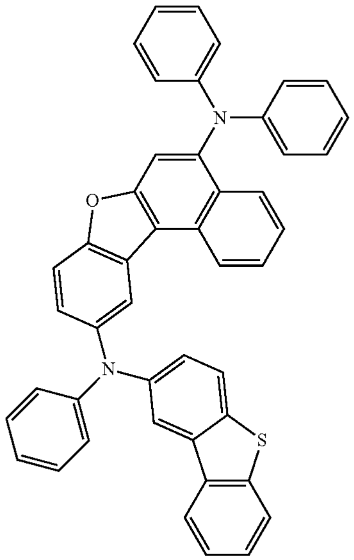

-continued
3-102
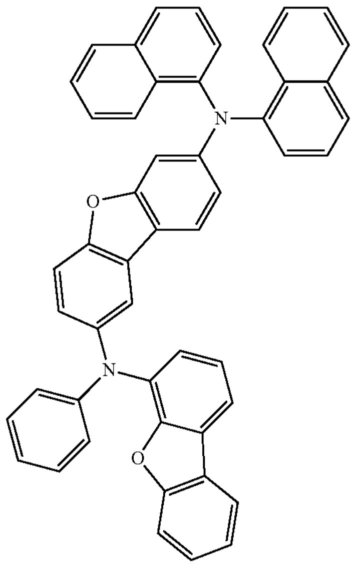
3-103
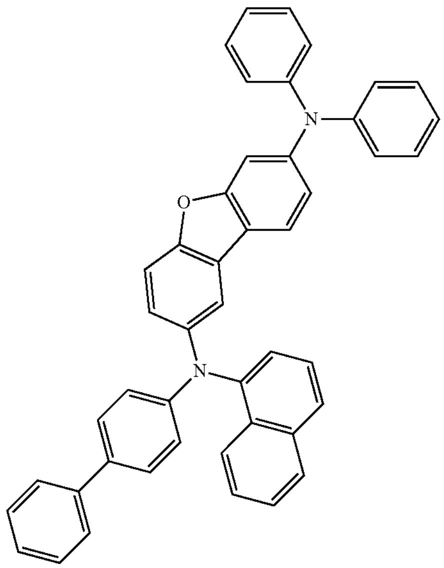
-continued
3-104
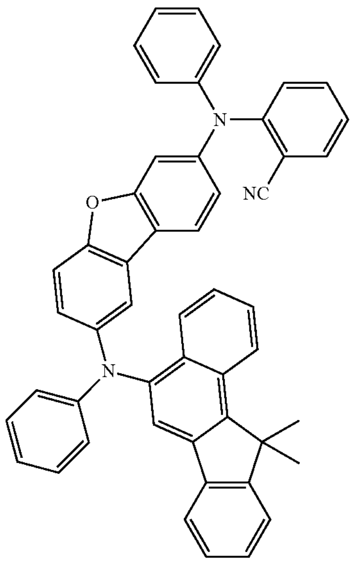
3-105
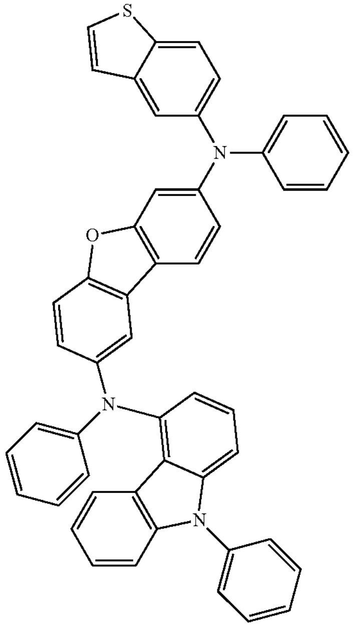

-continued
3-106
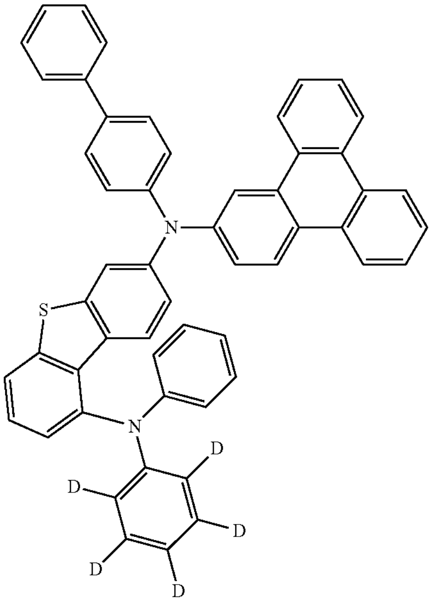
3-107
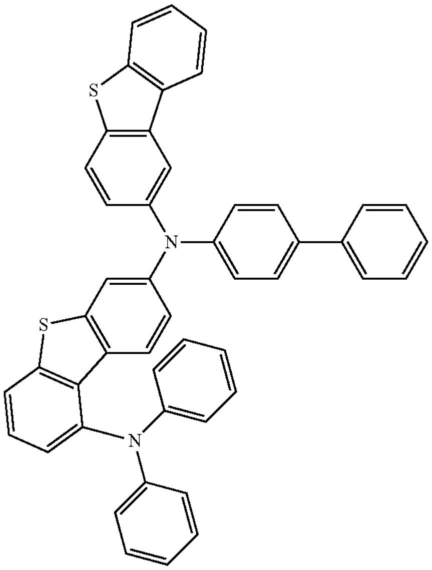
-continued
3-108
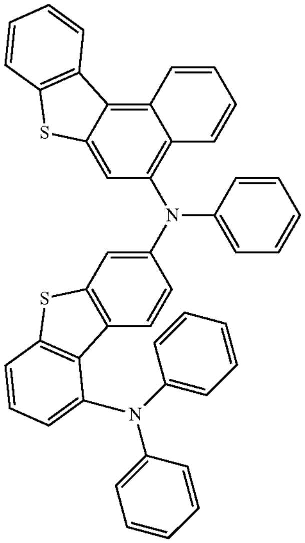
3-109
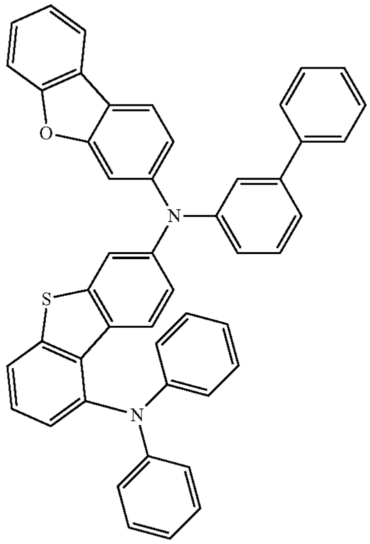
3-110
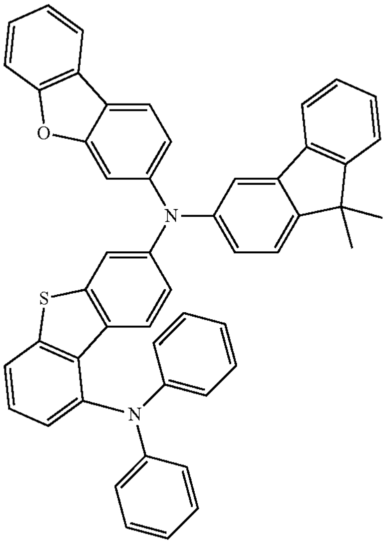

-continued
3-111
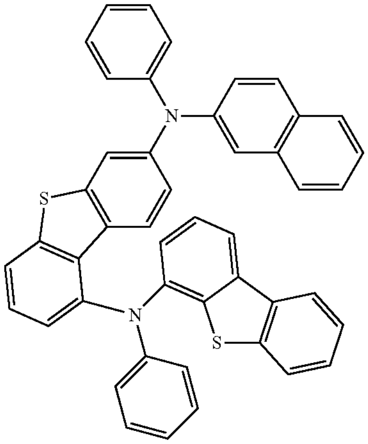
3-112
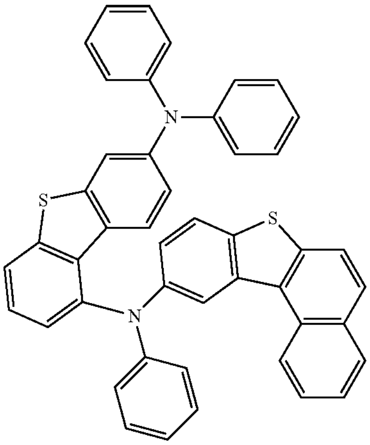
3-113
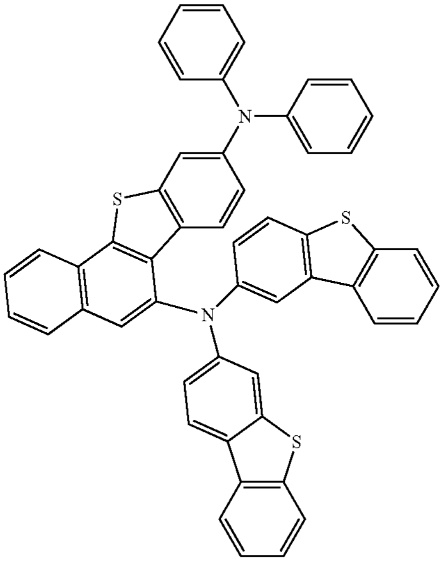
-continued
3-114
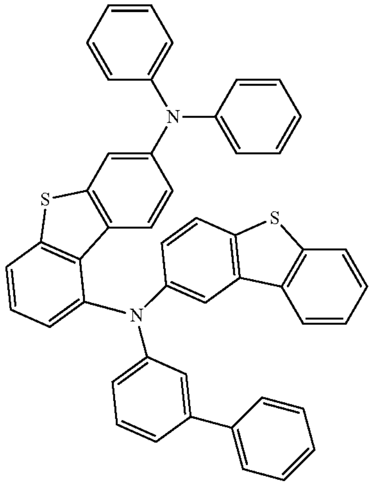
3-115
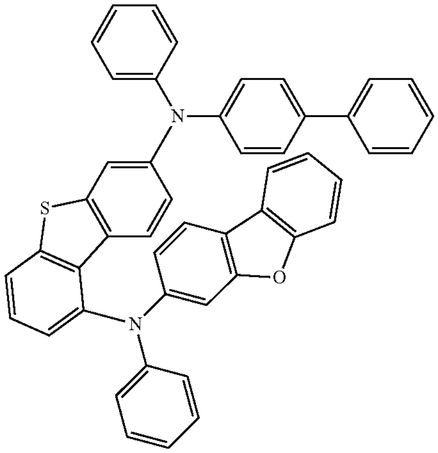
3-116
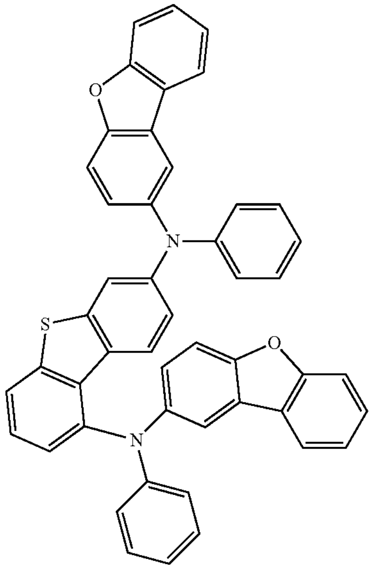

3-117
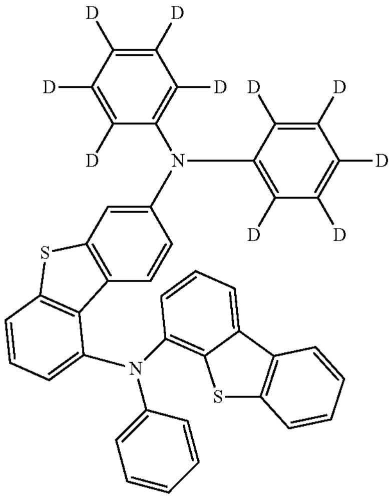
3-118
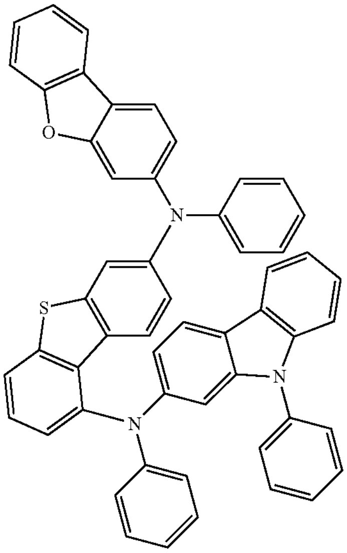
3-119
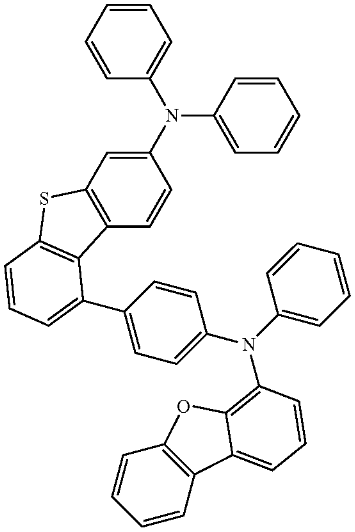
3-120
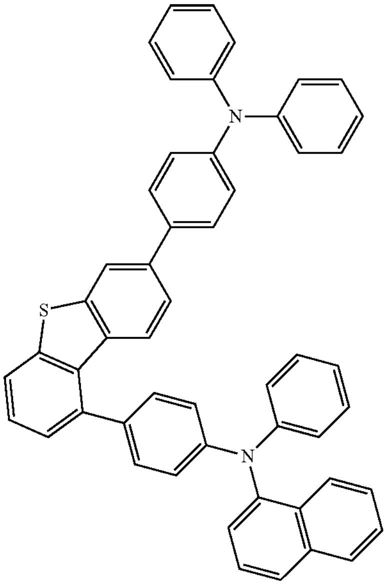
3-121
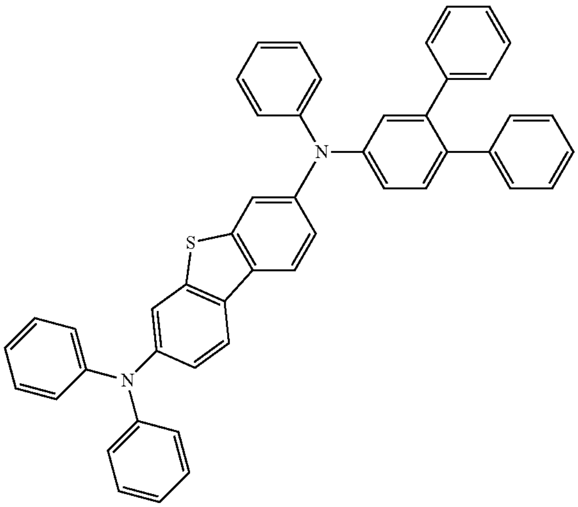

-continued
3-122
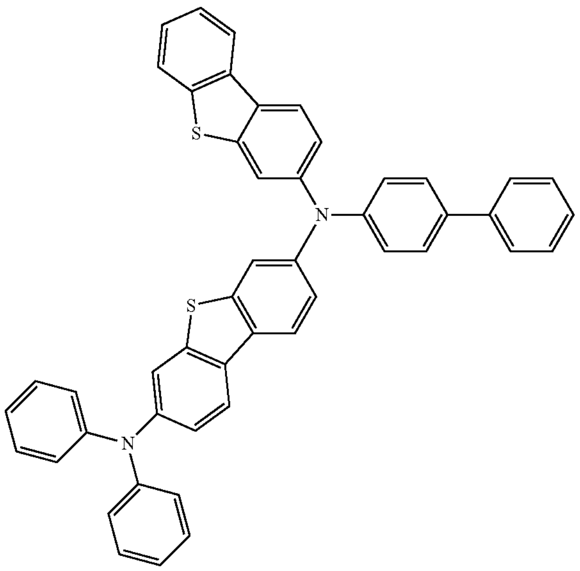
3-123
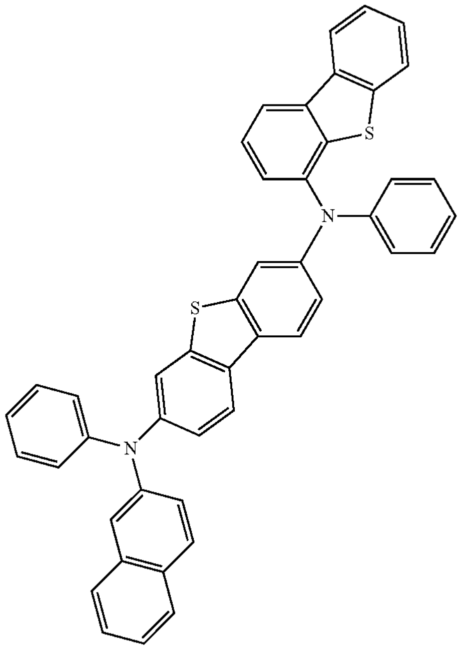
-continued
3-124
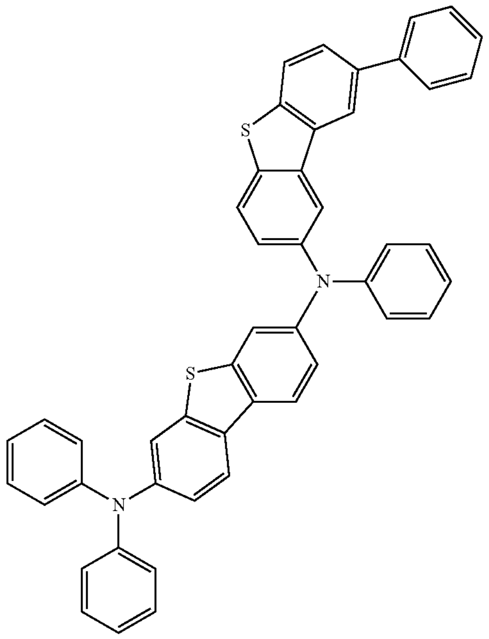
3-125
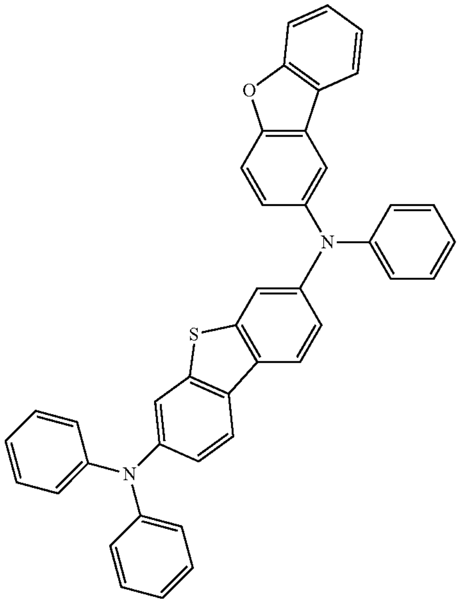

-continued
3-126
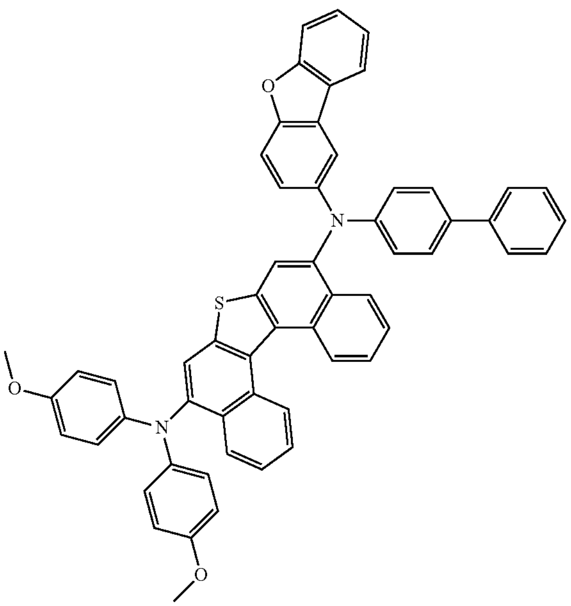
3-127
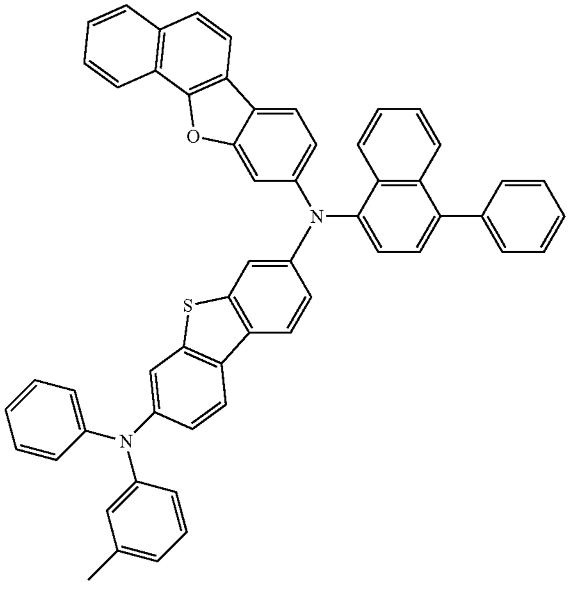
-continued
3-128
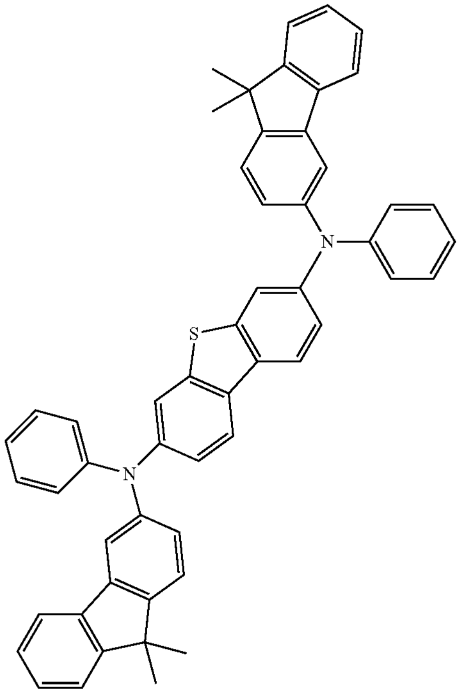
3-129
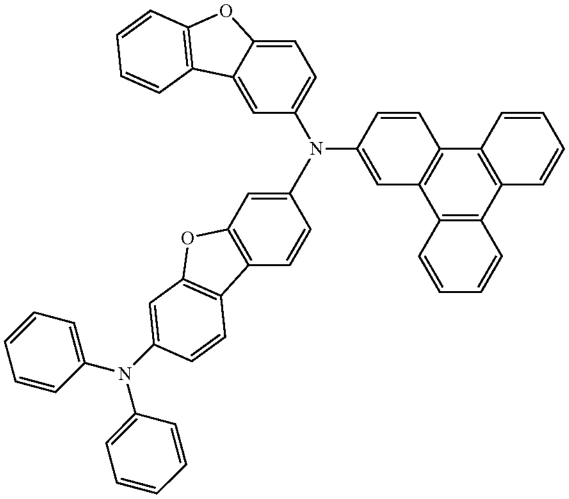

-continued
3-130
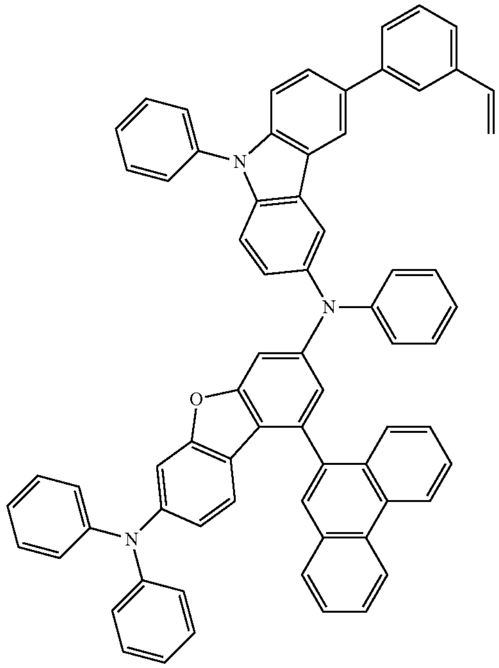
3-131
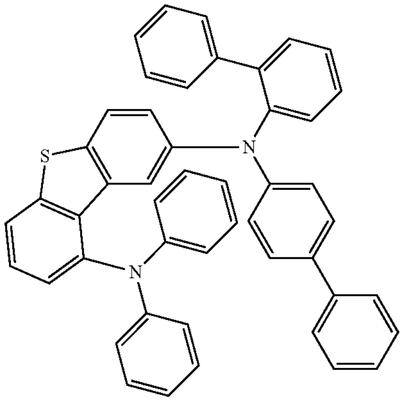
3-132
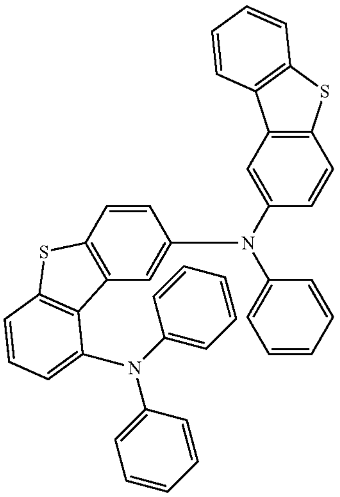
-continued
3-133
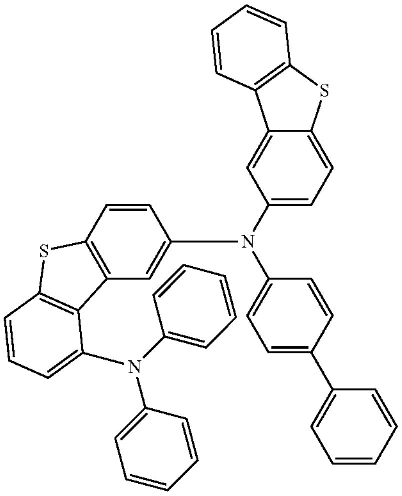
3-134
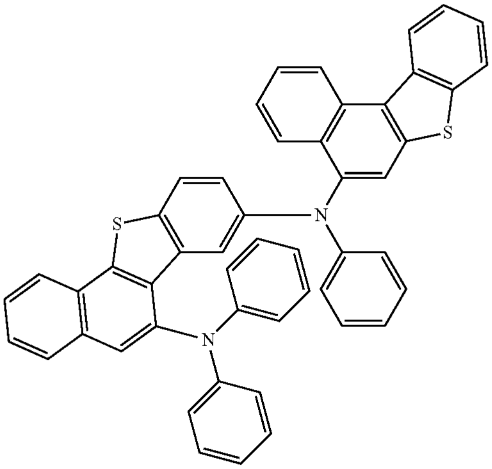
3-135
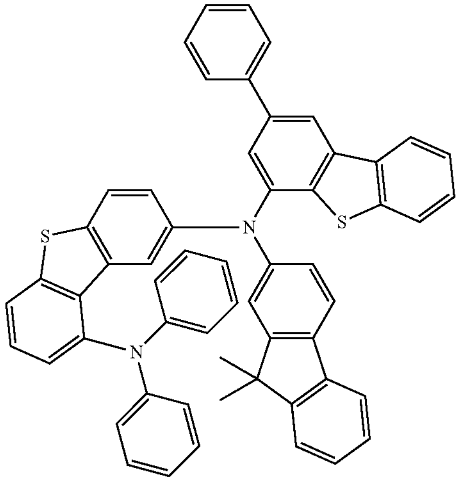

-continued
3-136
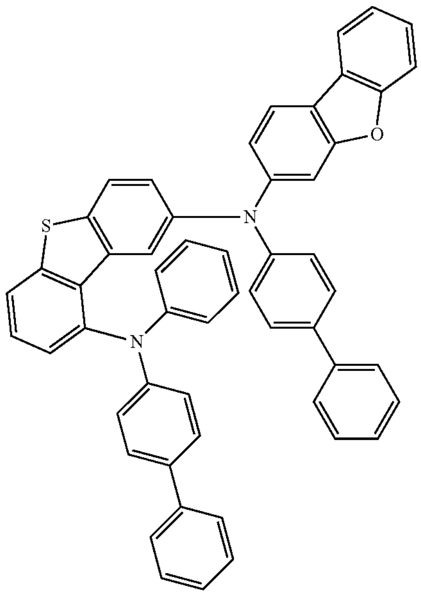
3-137
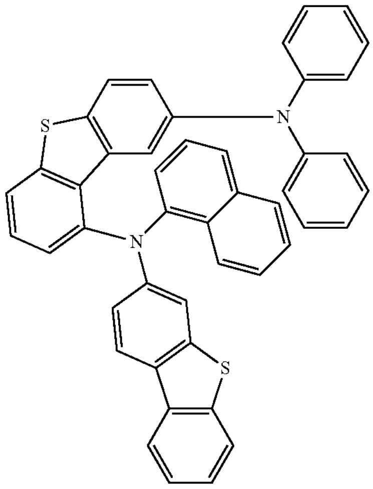
3-138
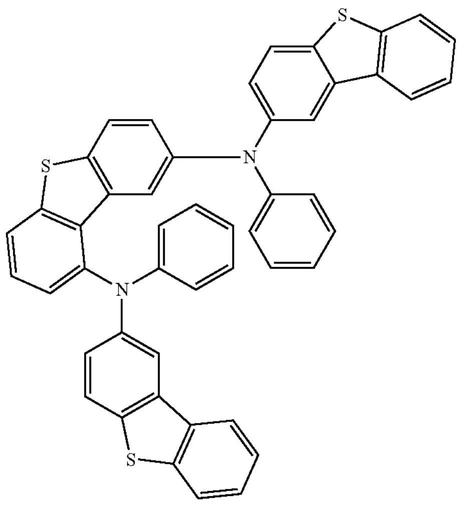
-continued
3-139
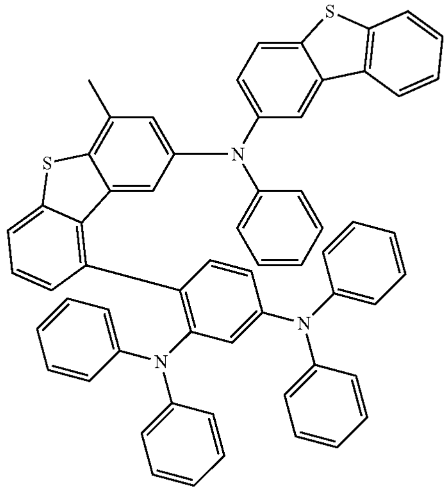
3-140
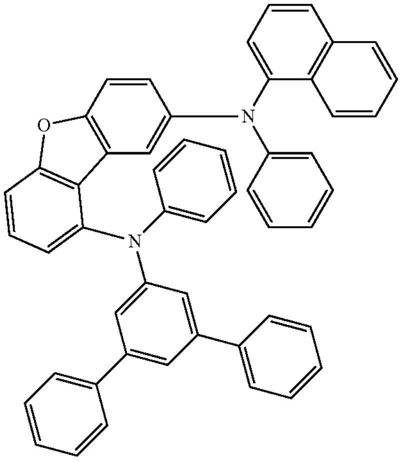
3-141
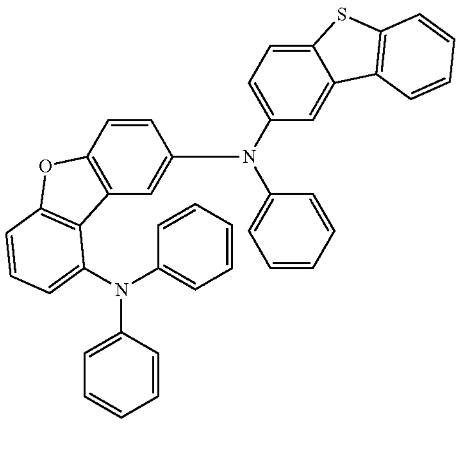

-continued
3-142
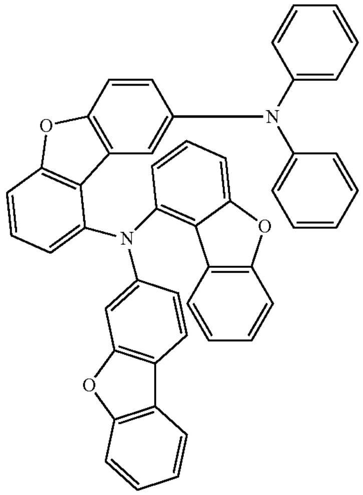
3-143
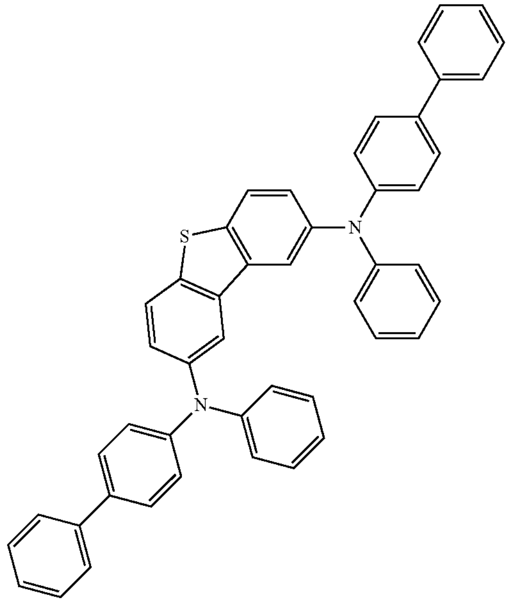
3-144
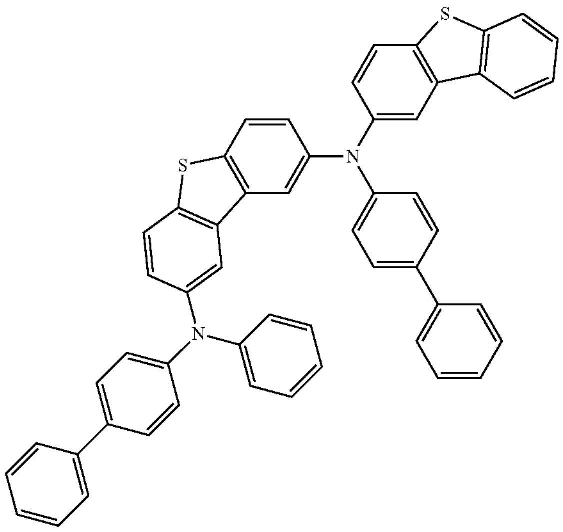
-continued
3-145
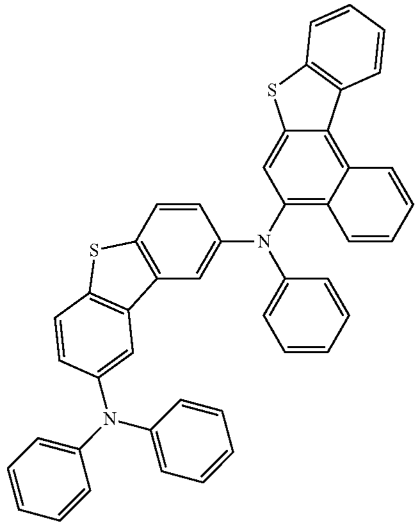
3-146
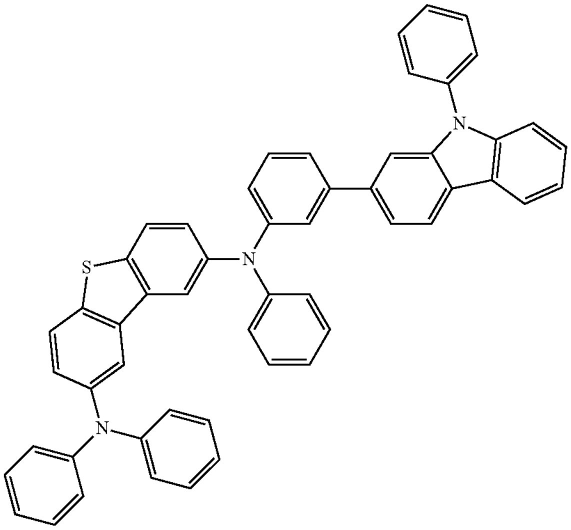
3-147
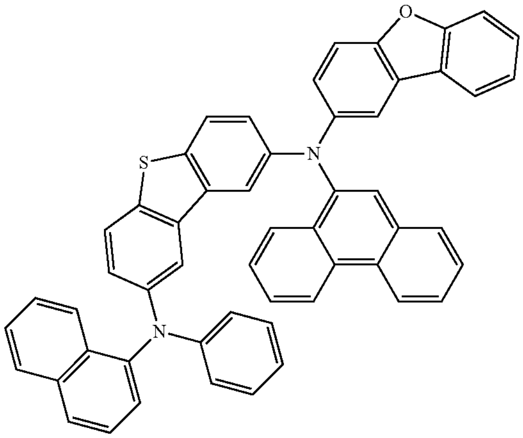

-continued
3-148
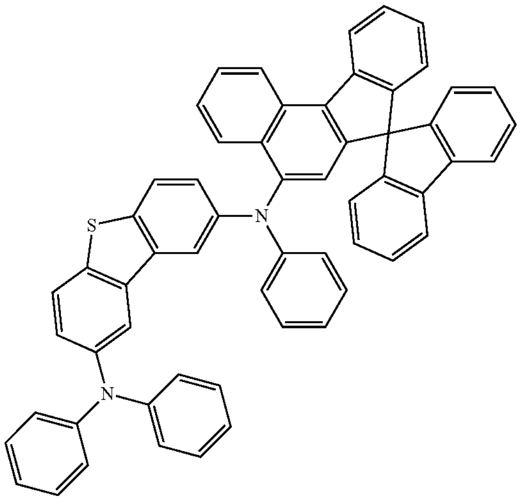
3-149
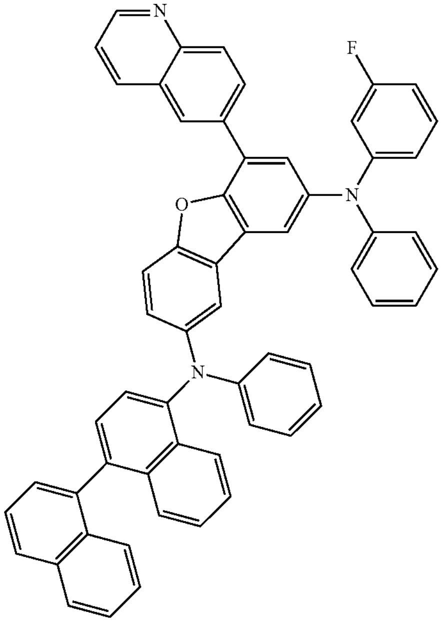
-continued
3-150
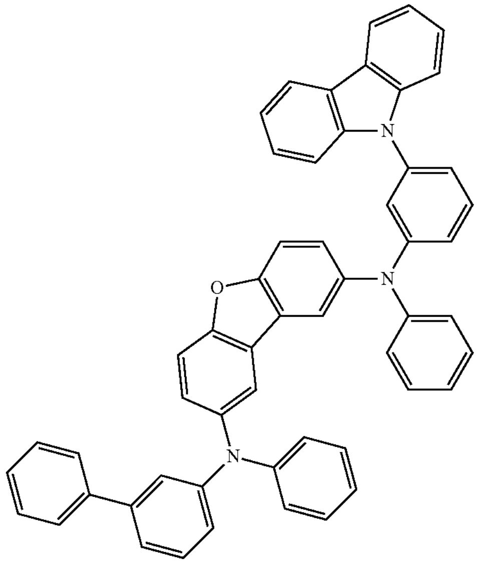
3-151
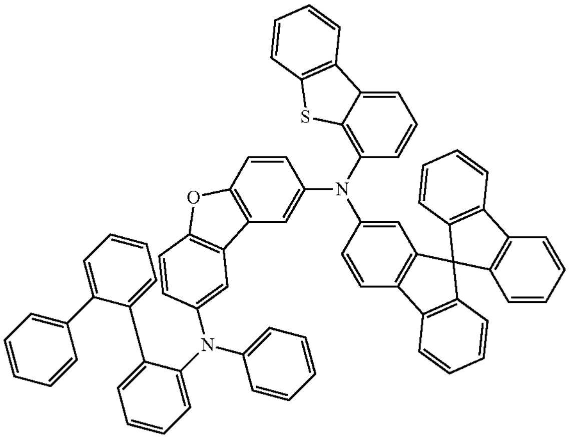
3-152
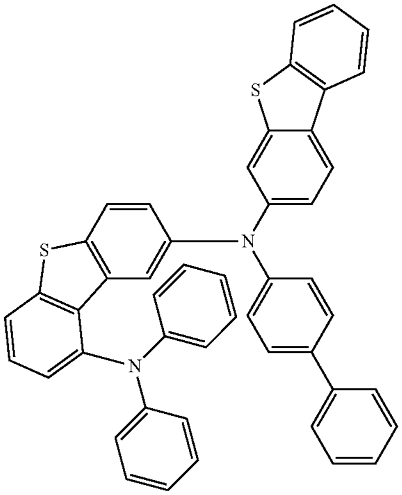

-continued
3-153
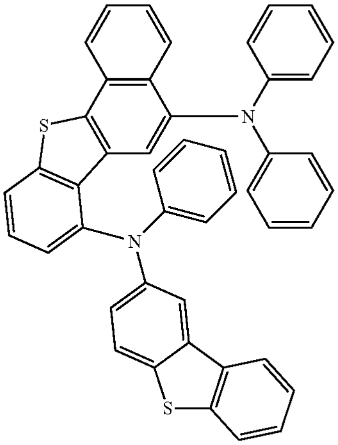
3-154
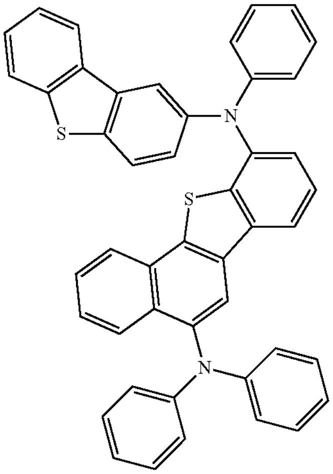
3-155
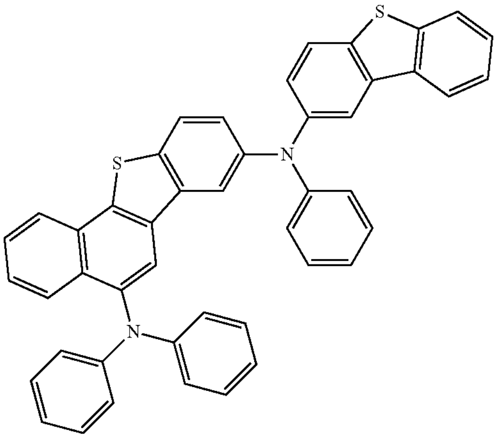
-continued
3-156
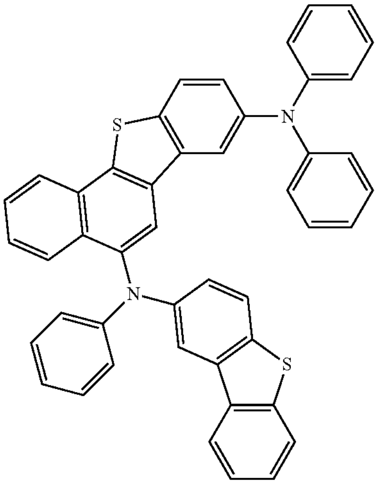
3-157
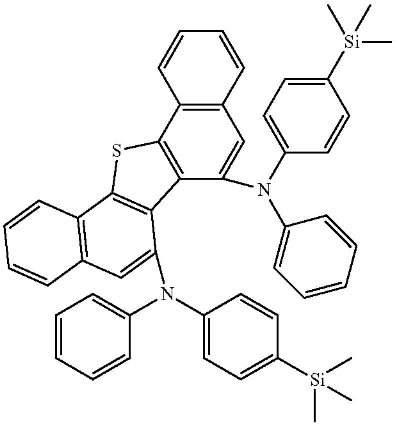
3-158
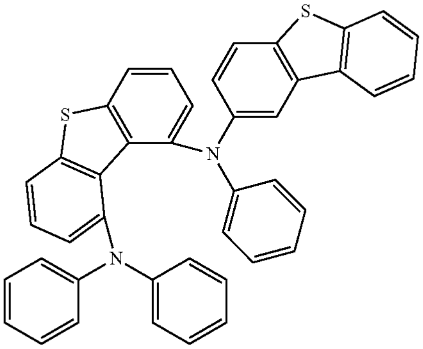
3-159
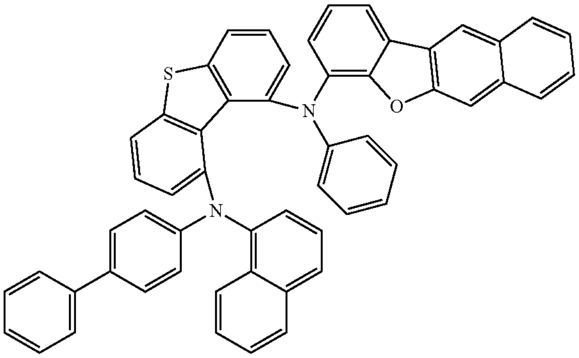

-continued
3-160
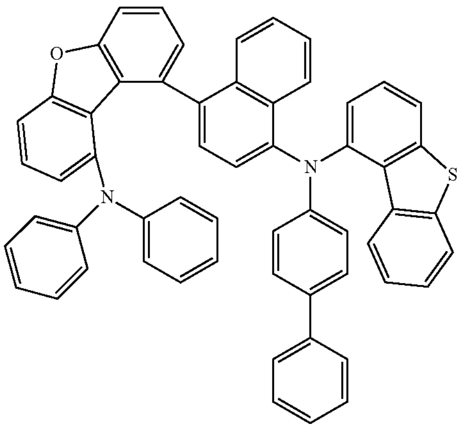
3-161
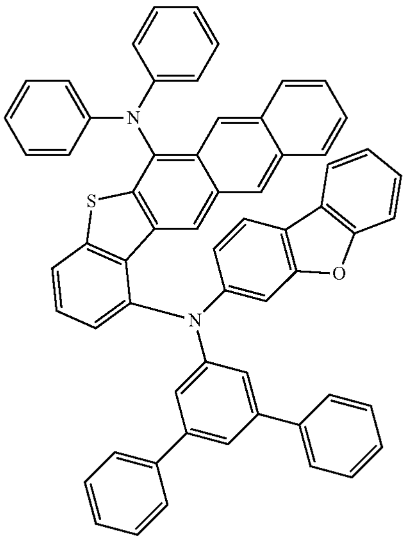
3-162
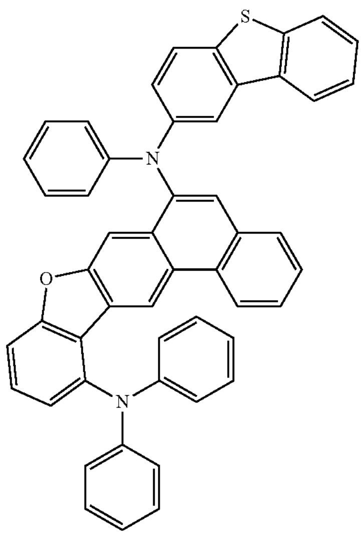
-continued
3-163
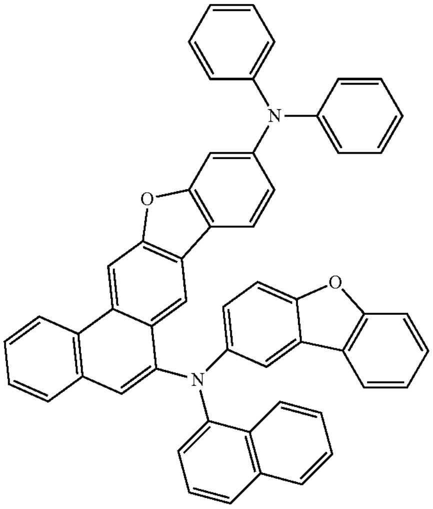
3-164
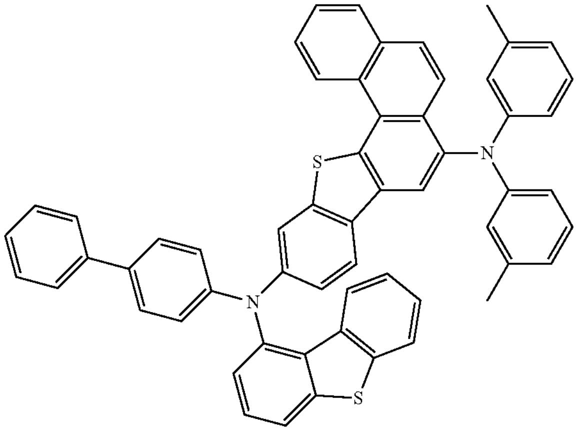
3-165
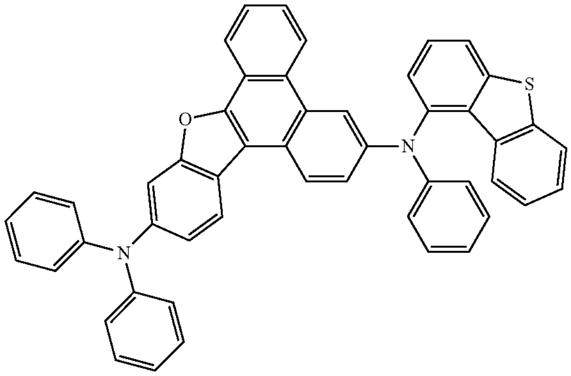

-continued
3-166
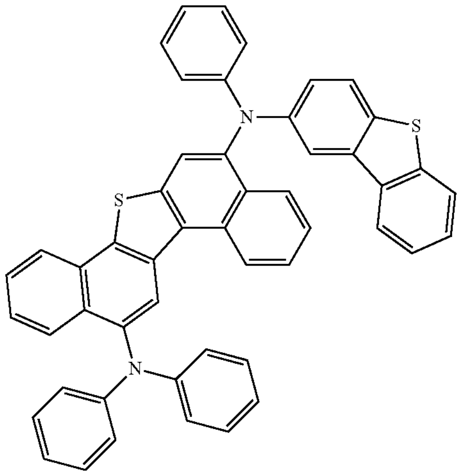
3-167
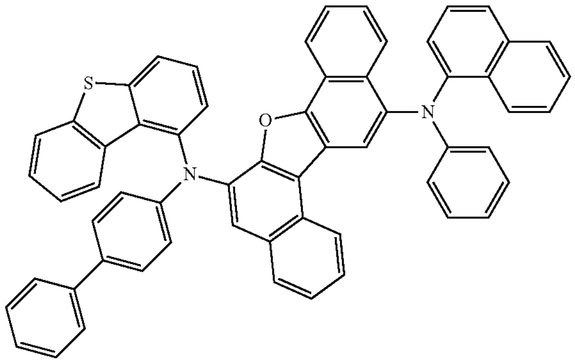
3-168
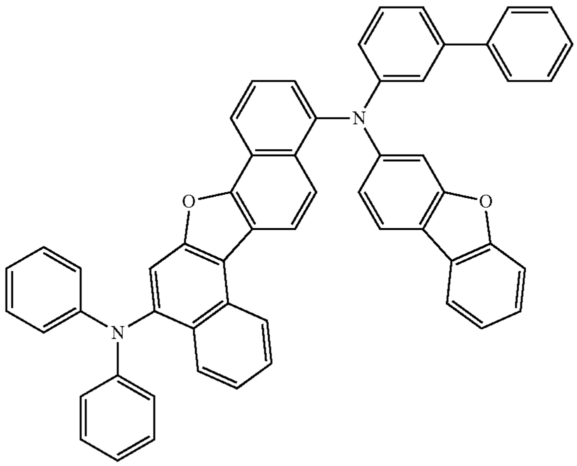
-continued
3-169
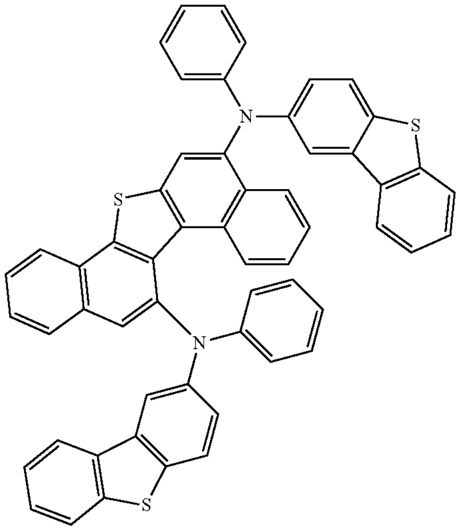
3-170
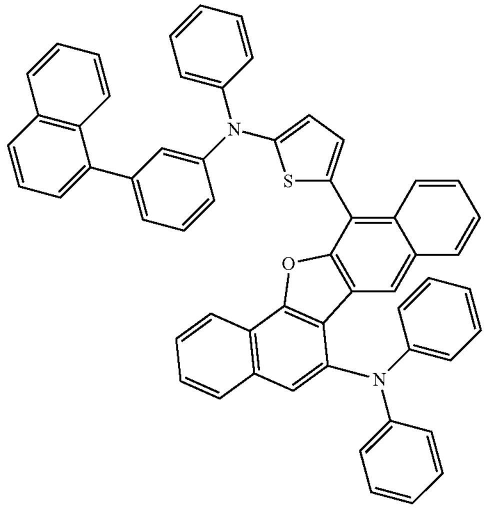
3-171
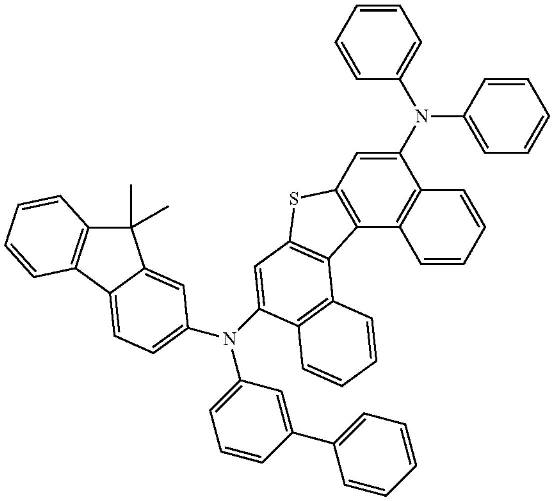

-continued 3-172

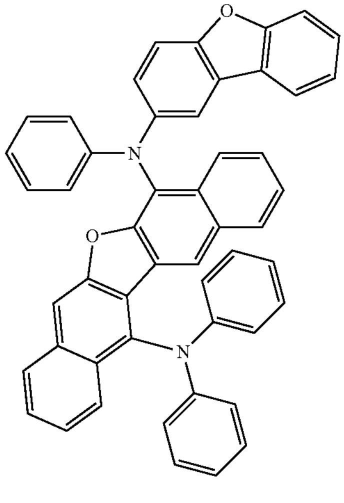

3-173

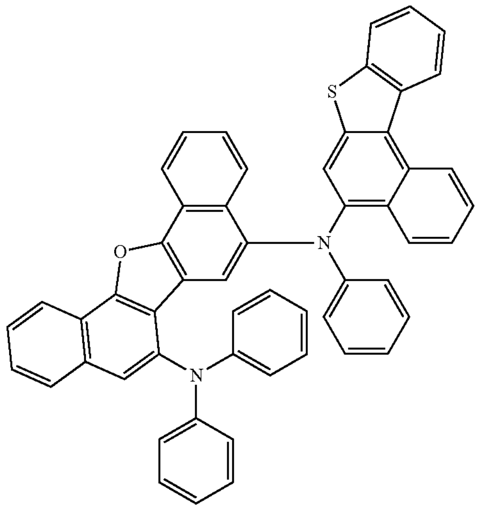

3-174

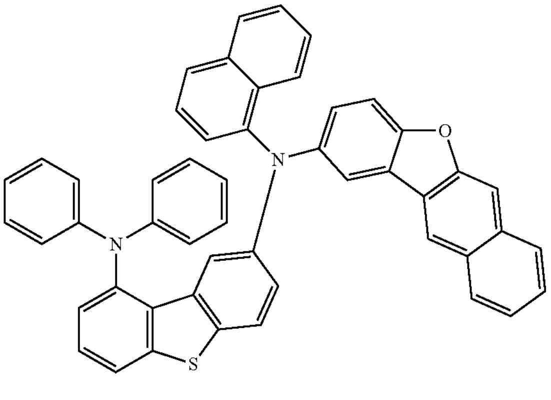

-continued 3-175

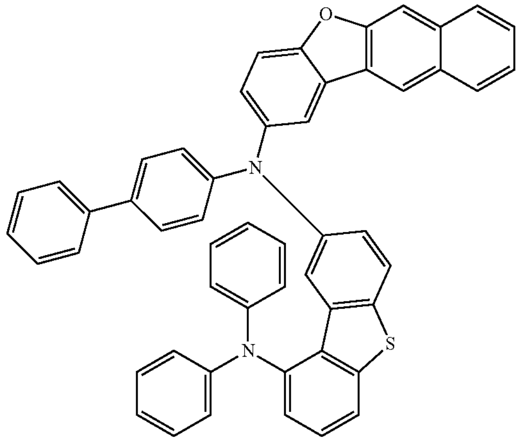

.

7. The organic electric element of claim 1, further comprising a layer for improving luminous efficiency formed on one side of the first electrode or one side of the second electrode, the side not facing the organic material layer.

8. The organic electric element of claim 1, wherein the organic material layer comprises two or more stacks, the stacks comprising a hole transport layer, a light emitting layer, and an electron transport layer in sequence formed on the anode.

9. The organic electric element of claim 8, wherein the organic material layer further comprises a charge generation layer formed between the two or more stacks.

10. An electronic device comprising a display device and a control unit for driving the display device, wherein the display device comprises the organic electric element of claim 1.

11. The electronic device of claim 10, wherein the organic electric element is selected from the group consisting of an organic light emitting diode, an organic solar cell, an organic photo conductor, an organic transistor, an element for monochromatic illumination and a quantum dot display.

12. A compound of Formula 1:

<Formula 1>

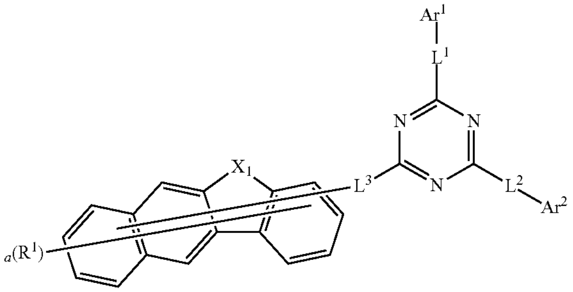

wherein, $X_1$ is O or S, $Ar^1$ and $Ar^2$ are each independently selected from the group consisting of a $C_6$-$C_{14}$ aryl group, a fluorenyl group, a $C_6$-$C_{13}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group, $L^1$ to $L^3$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof, $R^1$ is selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{30}$ aliphatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, and -L'-N($R_a$)($R_b$), and adjacent $R^1$s are not linked to each other to form a ring, a is an integer of 0 to 9, and where a is an integer of 2 or more, a plurality of $R^1$s are the same as or different from each other, L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof, $R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a combination thereof, $Ar^1$ to $Ar^2$, $L^1$ to $L^3$, $R^1$, L', $R_a$, and $R_b$ and may be each optionally substituted with one or more substituents selected from the group consisting of deuterium, halogen, a silane group substituted or unsubstituted with $C_1$-$C_{20}$ alkyl group or $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group.

13. The compound of claim 12, wherein Formula 1 is represented by Formula 3:

<Formula 3>

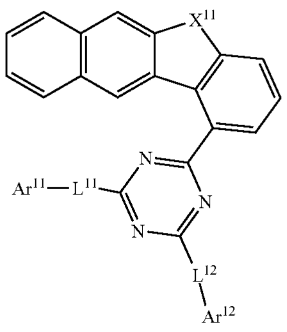

wherein, $X^{11}$ is O or S, $L^{11}$ and $L^{12}$ are each independently a single bond or a $C_6$-$C_{30}$ arylene group, and $Ar^{11}$ and $Ar^{12}$ are each independently a $C_6$-$C_{14}$ aryl group.

14. The compound of claim 13, wherein $L^{11}$ and $L^{12}$ are each independently a single bond or a $C_6$-$C_{15}$ arylene group, and $Ar^{11}$ and $Ar^{12}$ are each independently a $C_6$-$C_{14}$ aryl group.

15. The compound of claim 13, wherein Formula 3 is represented by one of Formulas 3-1, 3-A or 3-B:

<Formula 3-1>

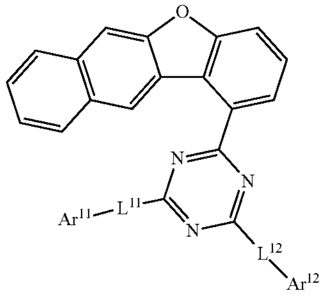

<Formula 3-A>

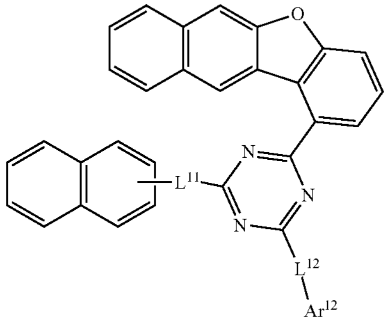

<Formula 3-B>

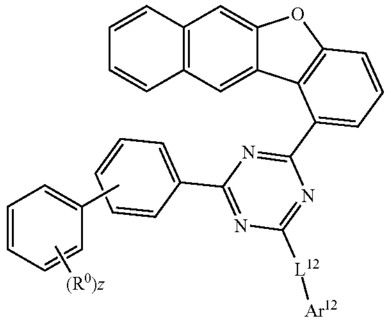

wherein $Ar^{11}$, $Ar^{12}$, $L^{11}$ and $L^{12}$ are the same as defined in claim 13, $R^0$ is defined to be the same as $Ar^{11}$, z is an integer of 0 to 5, and where z is an integer of 2 or more, a plurality of $R^0$s are the same as or different from each other.

16. The compound of claim 13, wherein the compound represented by Formula 3 is one of the following compounds:

1-2
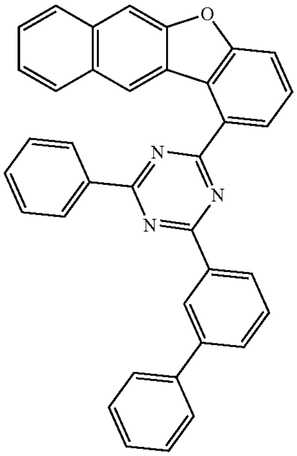
1-15
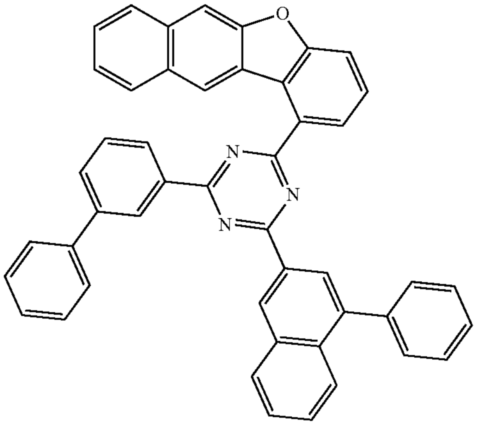
1-61
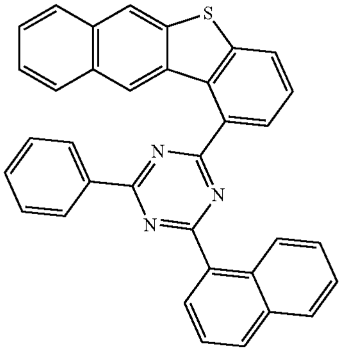
-continued
1-65
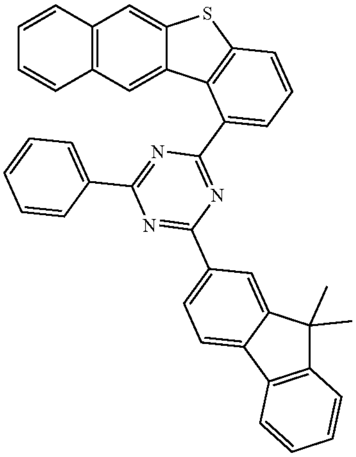
2-101
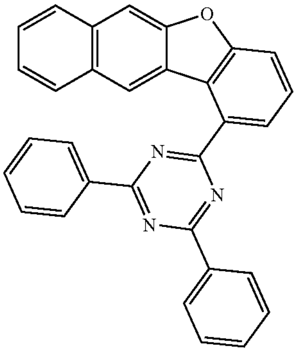
2-102
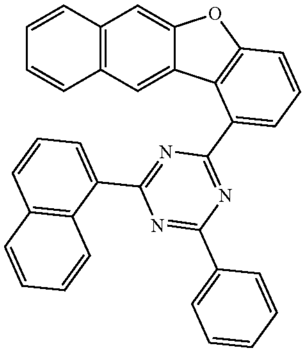
2-103
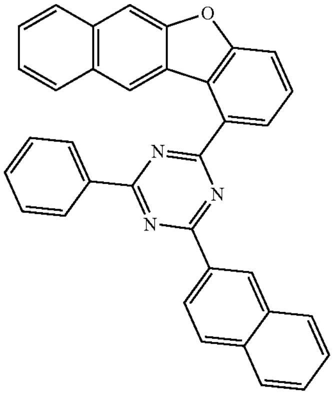

-continued
2-104
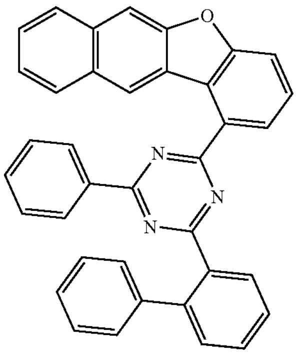
2-105
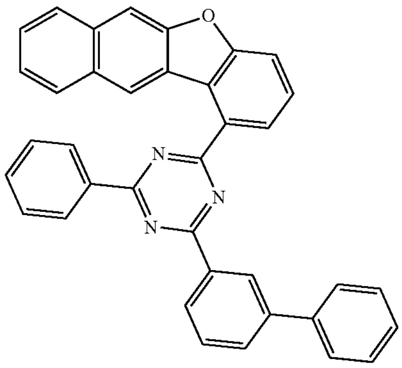
2-106
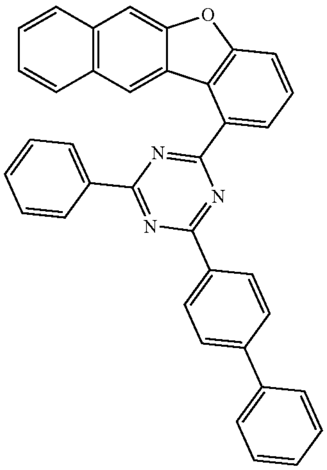
-continued
2-107
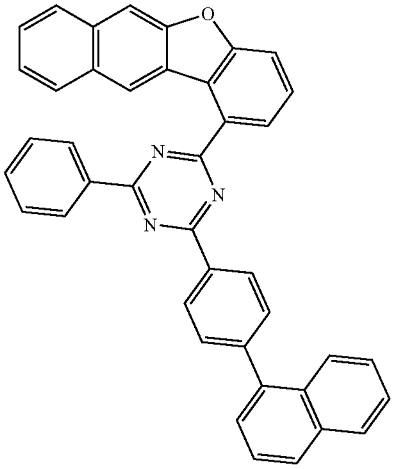
2-108
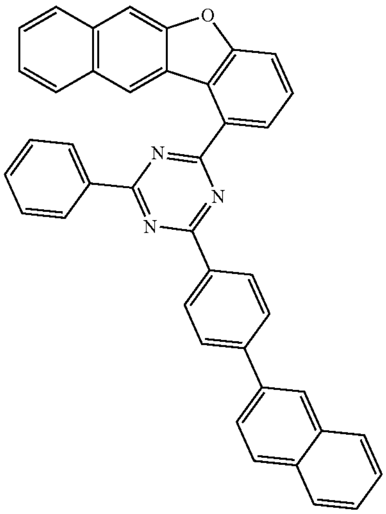
2-109
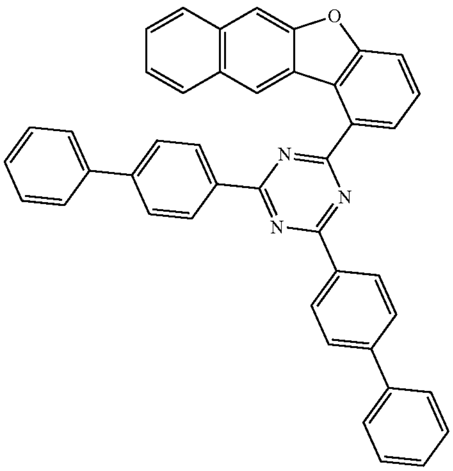

-continued 2-110

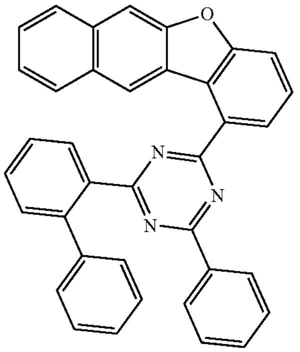

2-111

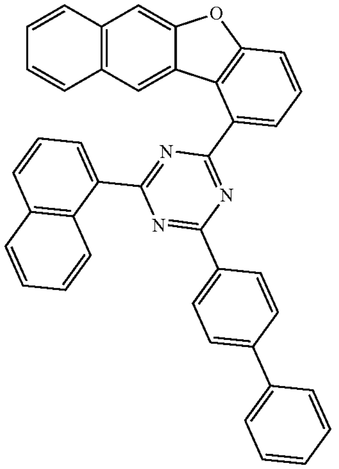

2-112

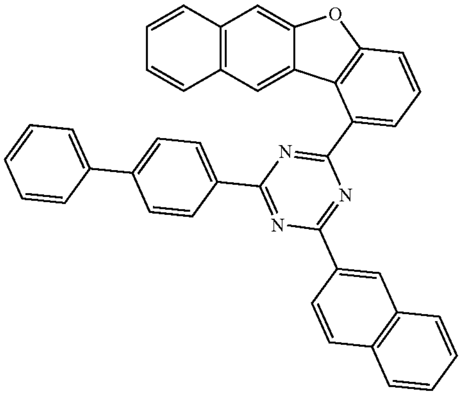

17. An organic electric element comprising a first electrode, a second electrode, and an organic material layer formed between the first electrode and the second electrode, wherein the organic material layer comprises the compound represented by Formula 3 of claim 13.

18. The organic electric element of claim 17, wherein the organic material layer comprises a light emitting layer or an emission-auxiliary layer, and the compound represented by Formula 3 is comprised in the light emitting layer or the emission-auxiliary layer.

19. The organic electric element of claim 17, wherein the organic material layer comprises a light emitting layer, and the light emitting layer comprises the compound represented by Formula 3 and a compound represented by Formula 4:

<Formula 4>

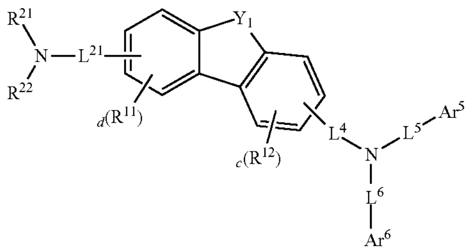

wherein, $Y_1$ is O, S or C(R')(R"), $Ar^5$ and $Ar^6$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{30}$ alkyl group, a $C_2$-$C_{30}$ alkenyl group, a $C_2$-$C_{30}$ alkynyl group, a $C_1$-$C_{30}$ alkoxyl group and a $C_6$-$C_{30}$ aryloxy group, $L^4$ to $L^6$, and $L^{21}$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring and a combination thereof, $R^{11}$, $R^{12}$, $R^{21}$, $R^{22}$, R' and R" are each independently selected from the group consisting of hydrogen, deuterium, halogen, a silane group substituted or unsubstituted with $C_1$-$C_{20}$ alkyl group or $C_6$-$C_{20}$ aryl group, a cyano group, a nitro group, a $C_1$-$C_{20}$ alkoxyl group, a $C_6$-$C_{30}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring and -L'-N($R_a$)($R_b$), and adjacent groups may optionally be linked to each other to form a ring, c and d are each an integer of 0 to 3, and where c or d is an integer of 2 or more, a plurality of $R^{12}$s are the same as or different from each other, L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a combination thereof, $R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a combination thereof, $Ar^5$, $Ar^6$, $L^4$ to $L^6$, $L^{21}$, $R^{11}$, $R^{12}$, $R^{21}$, $R^{22}$, R', R", L', $R_a$, $R_b$ and the ring formed by adjacent groups may be each optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_7$-$C_{20}$ arylalkyl group and a $C_8$-$C_{20}$ arylalkenyl group.

20. The organic electric element of claim 19, wherein the compound of Formula 4 is represented by one of Formulas 4-1 to 4-9:

<Formula 4-1>

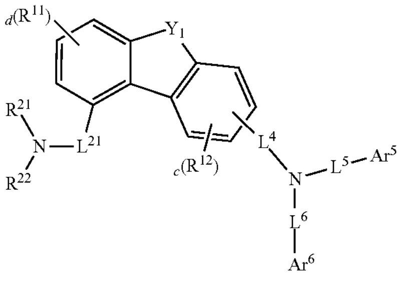

<Formula 4-2>

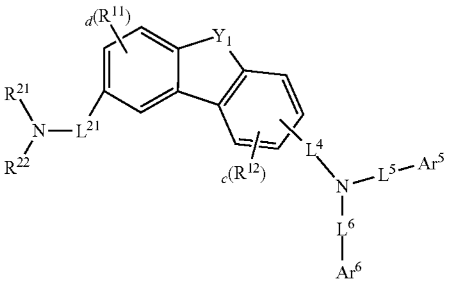

<Formula 4-3>

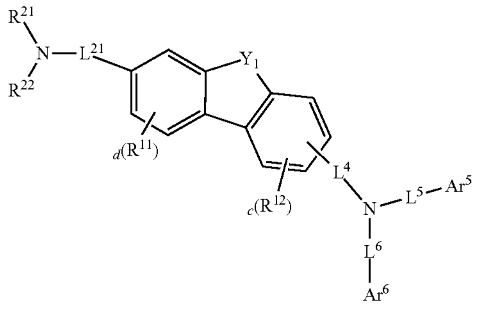

<Formula 4-4>

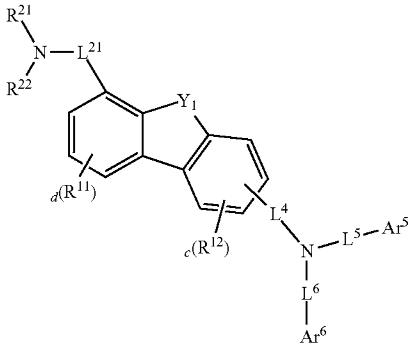

<Formula 4-5>

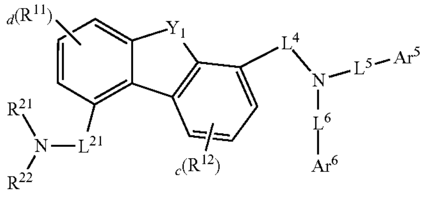

-continued

<Formula 4-6>

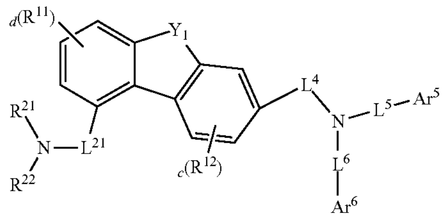

<Formula 4-7>

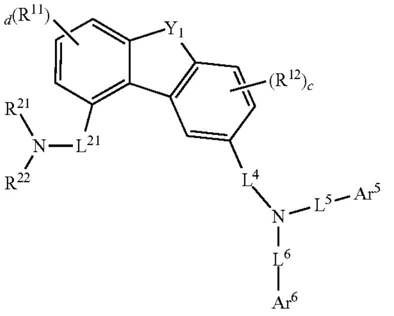

<Formula 4-8>

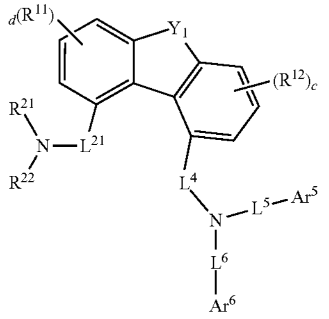

<Formula 4-9>

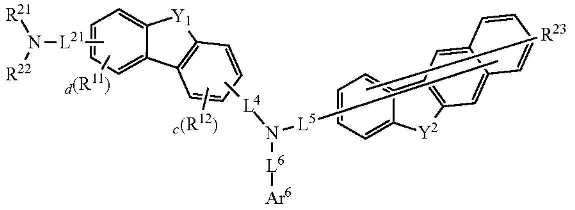

wherein, $Y_1$, $Ar^5$, $Ar^6$, $L^4$ to $L^6$, $L^{21}$, $R^{11}$, $R^{12}$, $R^{21}$, $R^{22}$, c and d are the same as defined in claim 19, $Y^2$ is O or S, and $R^{23}$ is defined to be the same as $R^{11}$.

21. The organic electric element of claim 19, wherein the organic material layer comprises an emission-auxiliary layer, and the emission-auxiliary layer comprises the compound represented by Formula 4.

22. The organic electric element of claim 19, wherein the compound represented by Formula 4 is one of the following compounds:

-continued
3-1
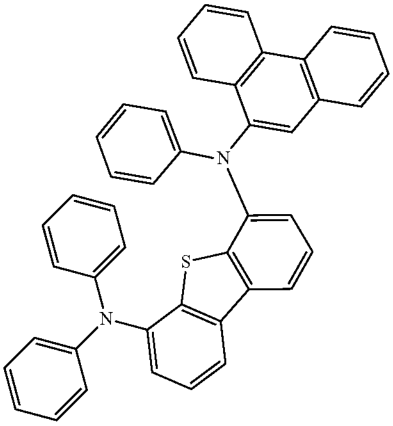
3-2
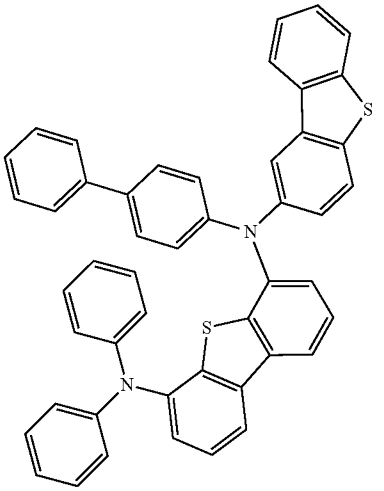
3-3
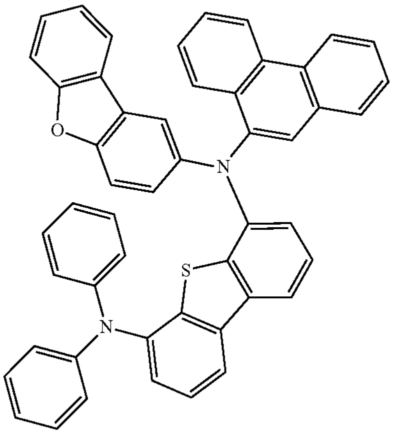
3-4
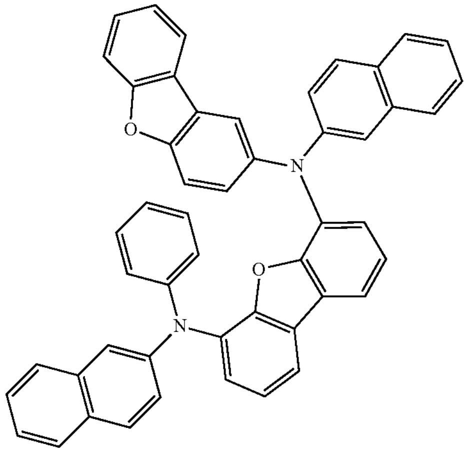
3-5
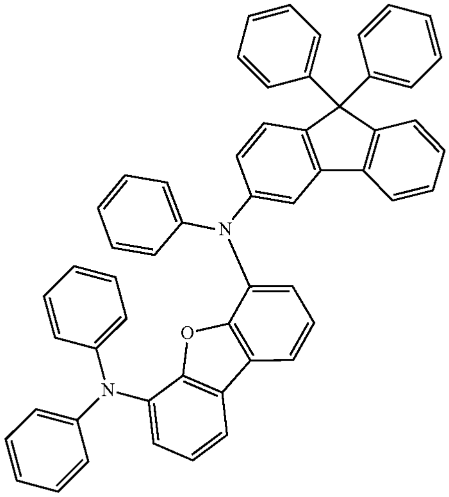
3-6
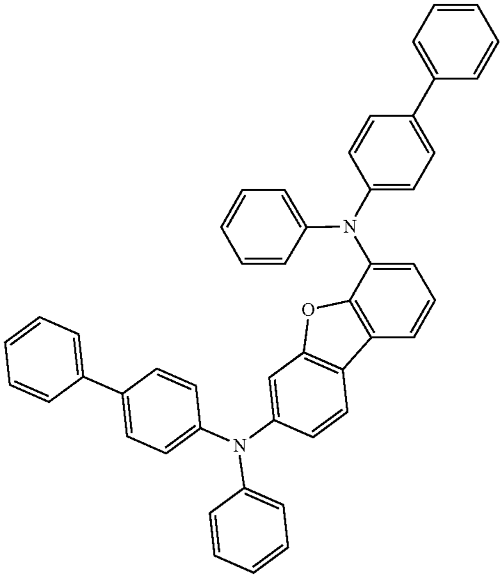

-continued
3-7
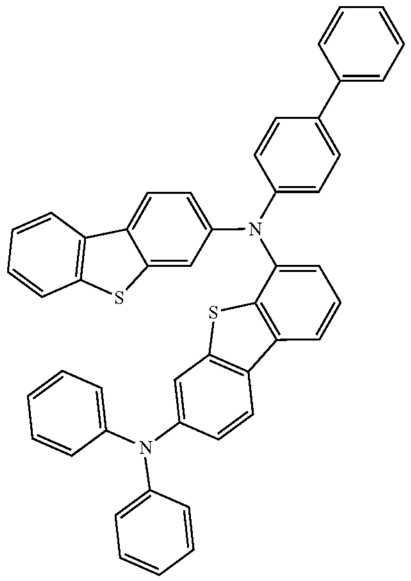
3-8
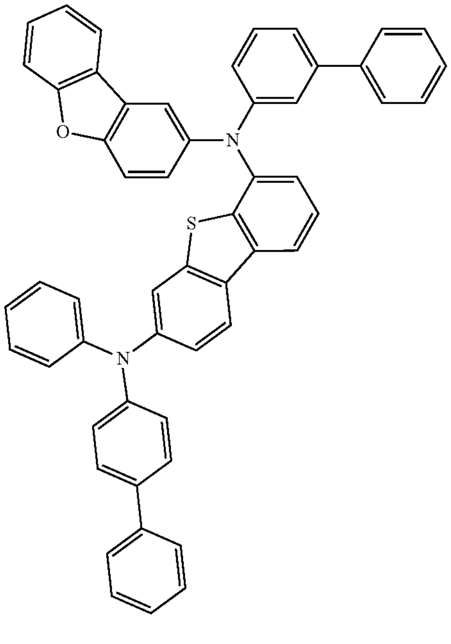
-continued
3-9
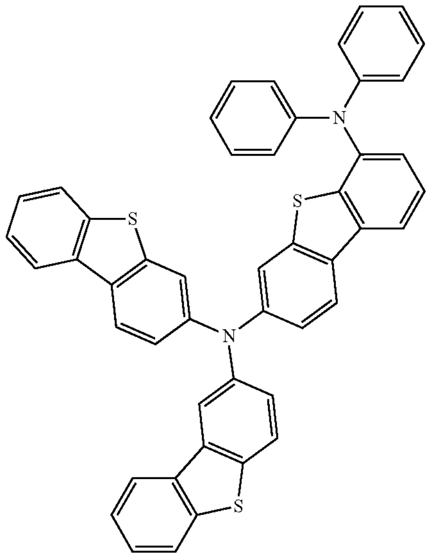
3-10
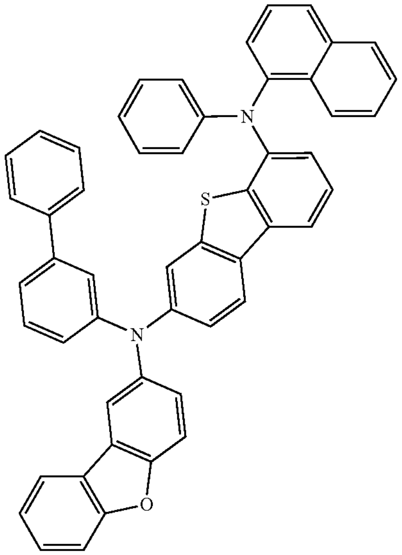

-continued
3-11
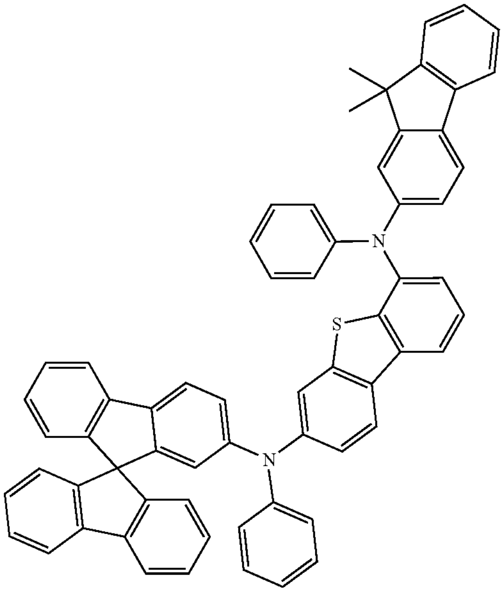
3-12
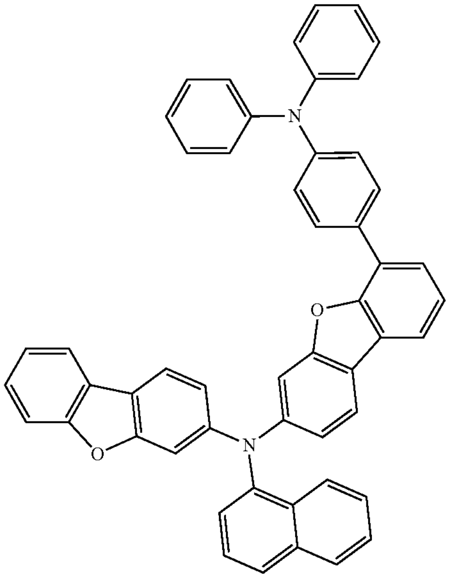
-continued
3-13
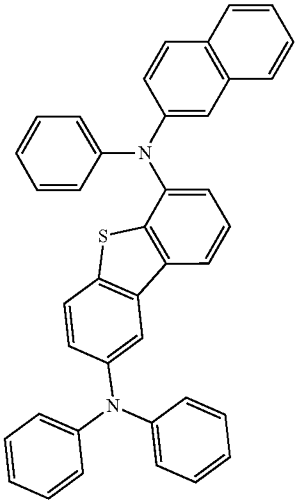
3-14
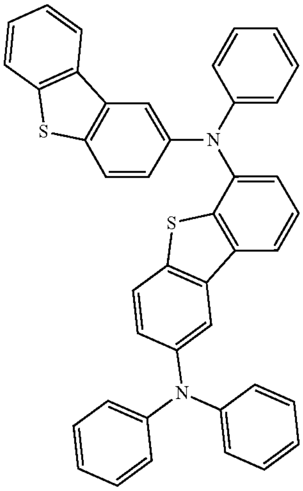
3-15
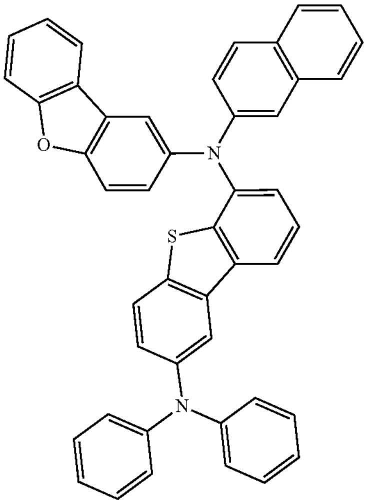

-continued
3-16
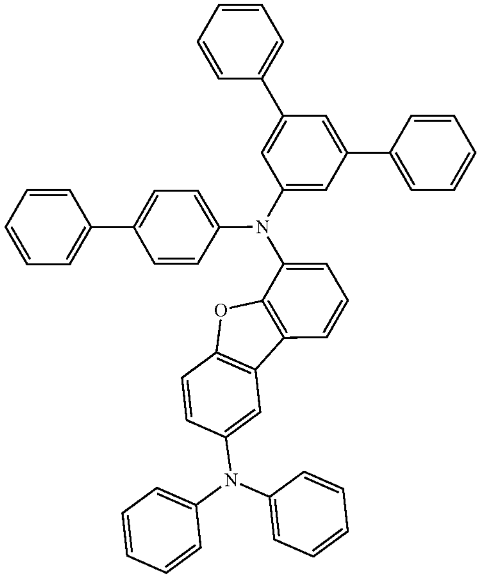
3-17
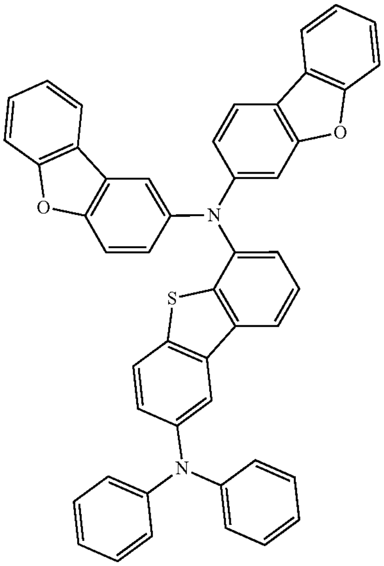
-continued
3-18
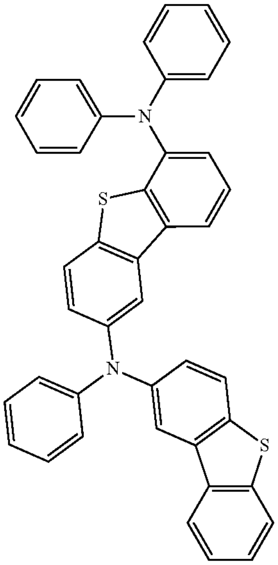
3-19
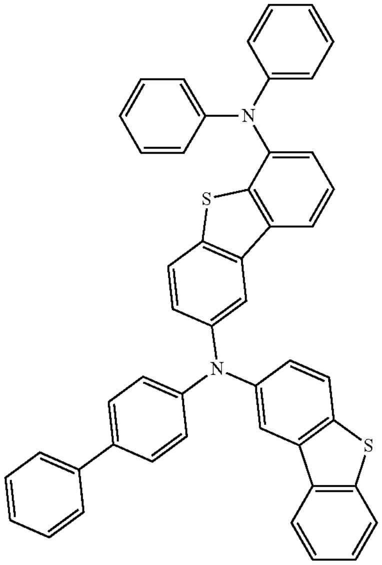

-continued
3-20
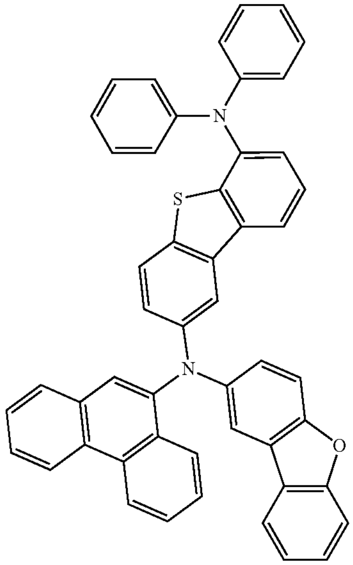
3-21
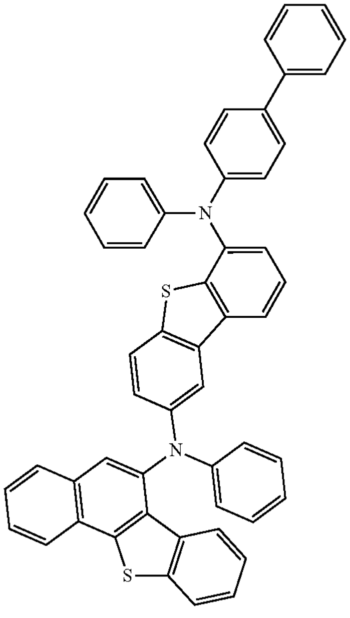
-continued
3-22
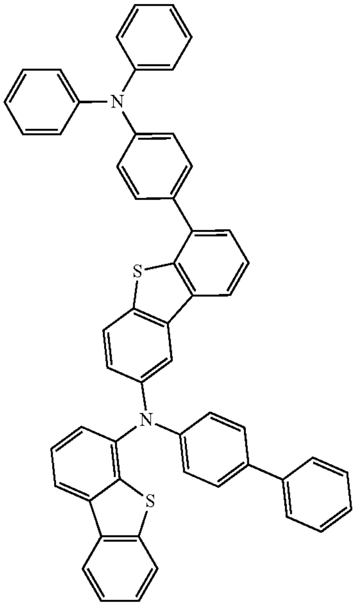
3-23
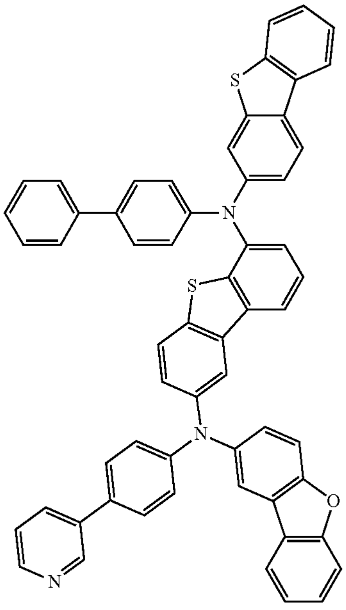

-continued
3-24
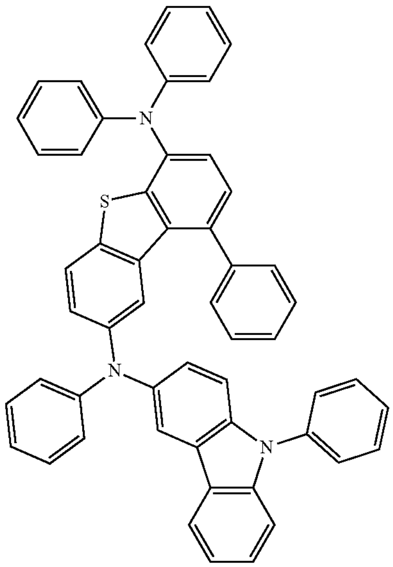
3-25
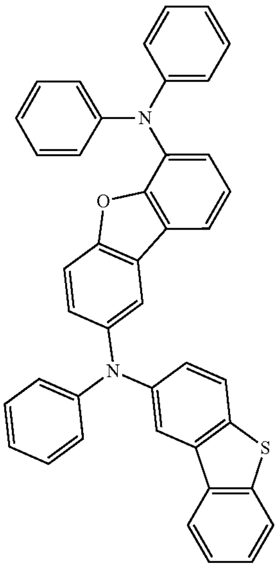
3-26
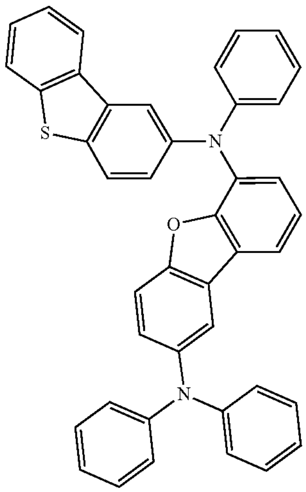
-continued
3-27
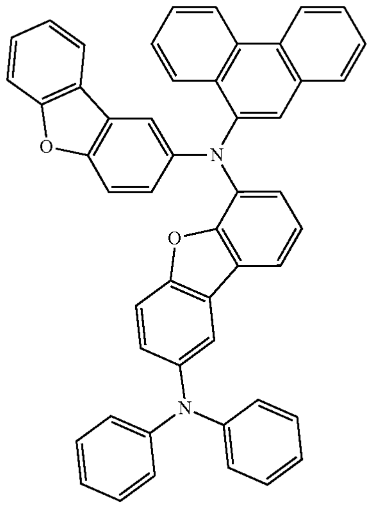
3-28
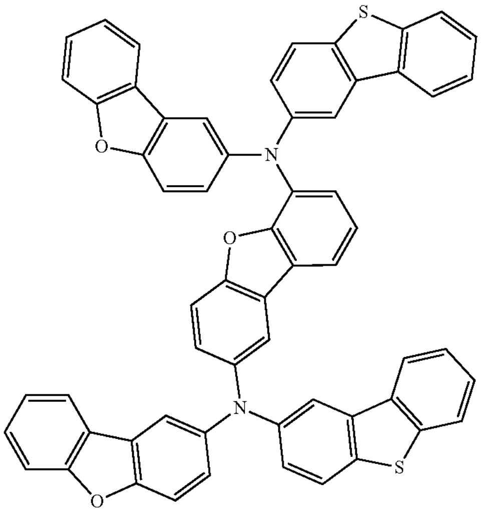
3-29
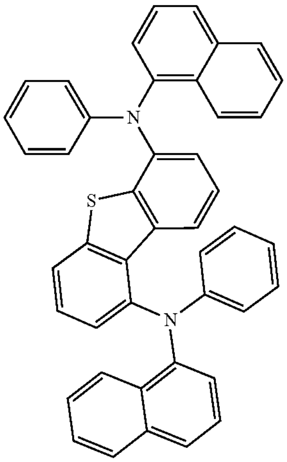

-continued
3-30
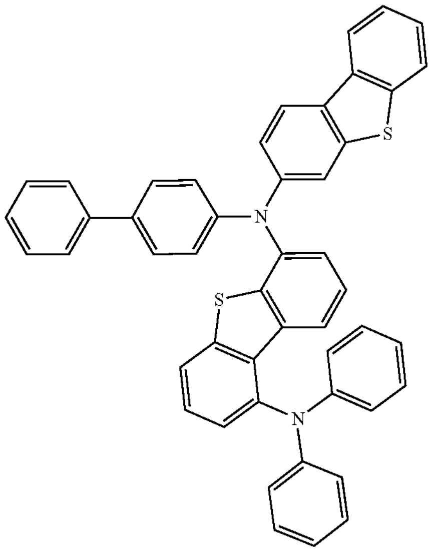
3-31
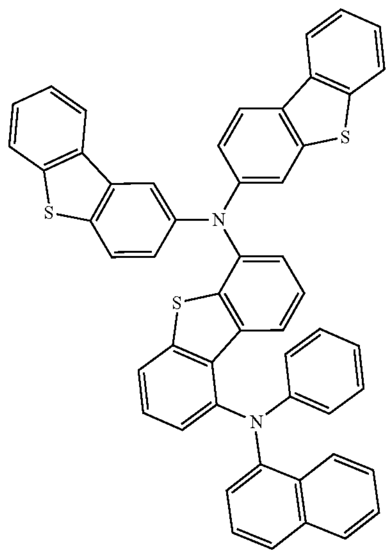
3-32
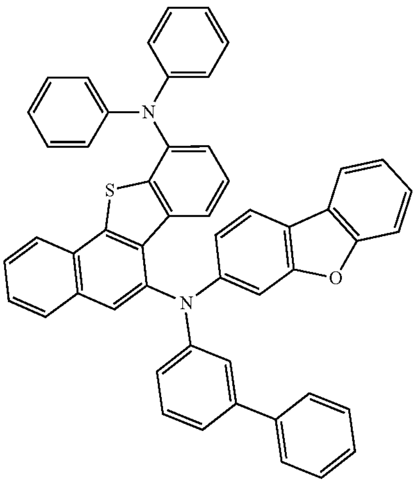
-continued
3-33
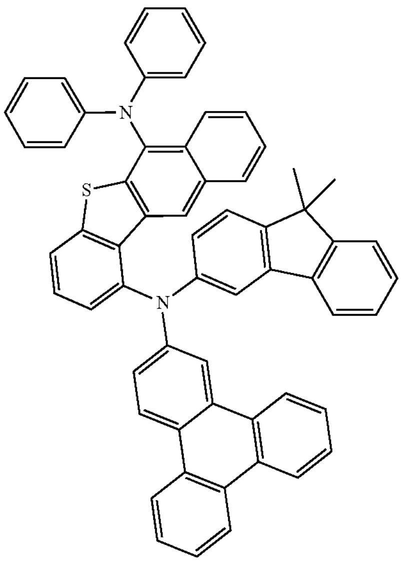
3-34
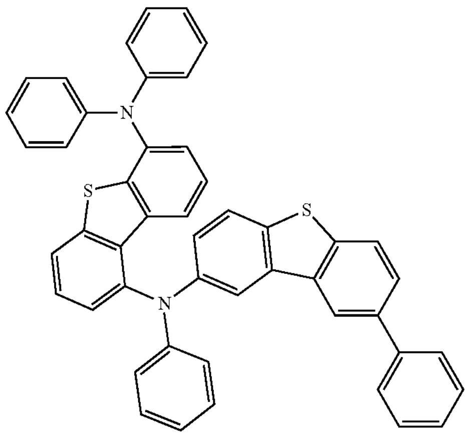
3-35
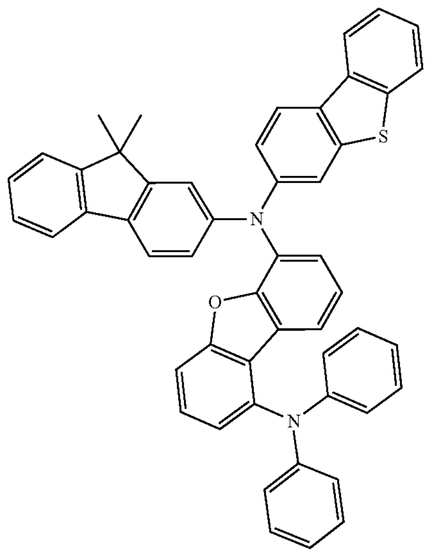

-continued
3-36
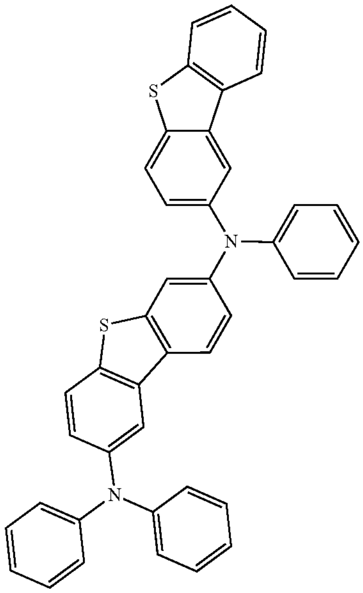
3-37
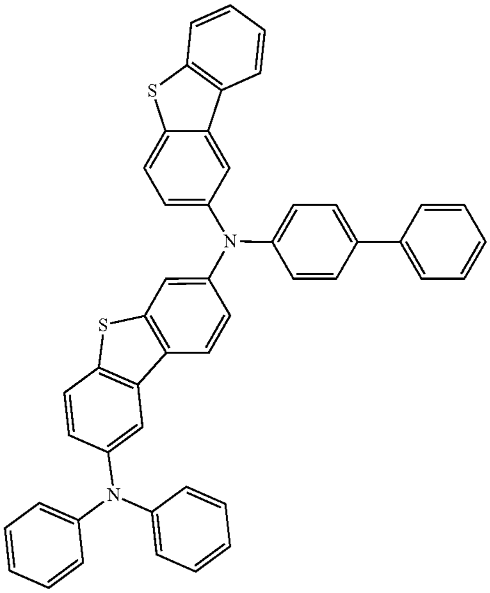
-continued
3-38
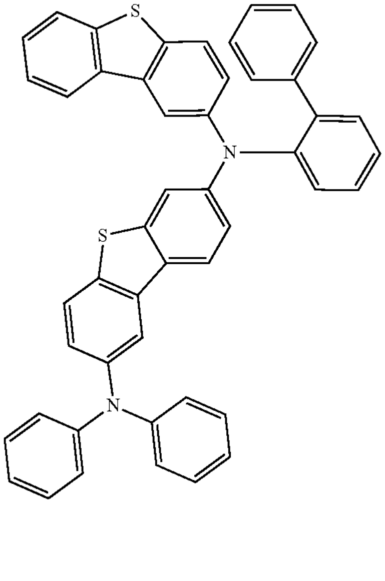
3-39
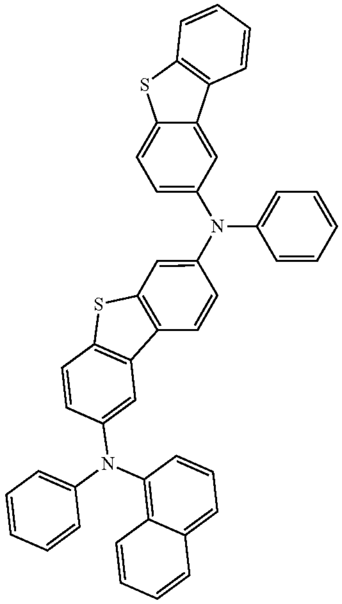

-continued
3-40
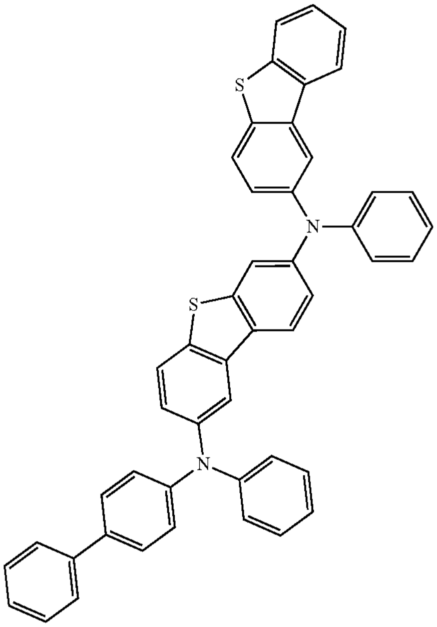
3-41
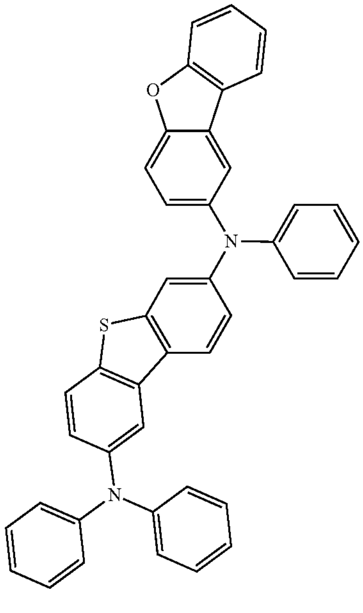
-continued
3-42
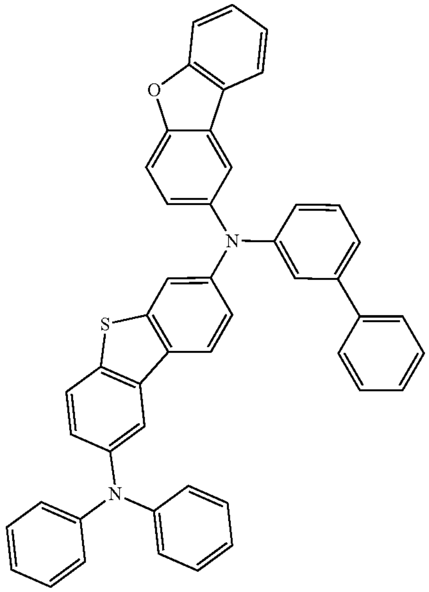
3-43
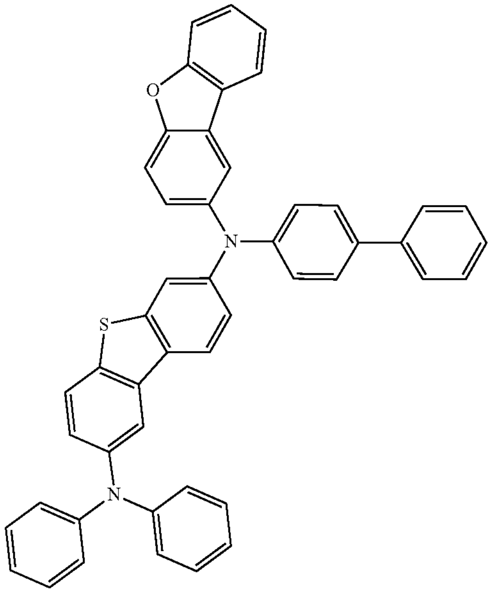

-continued
3-44
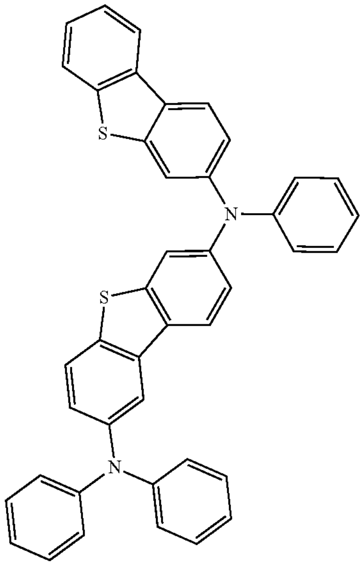
3-45
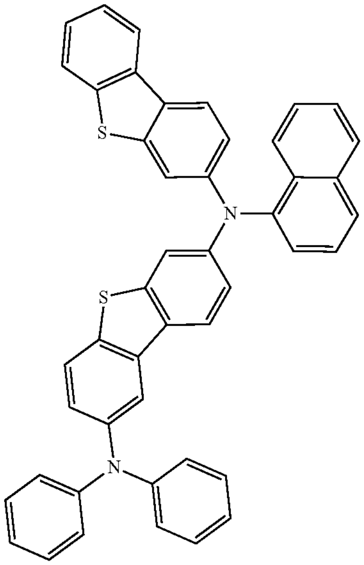
-continued
3-46
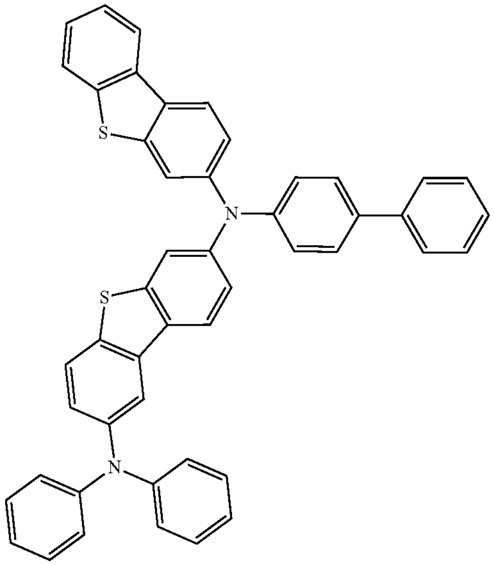
3-47
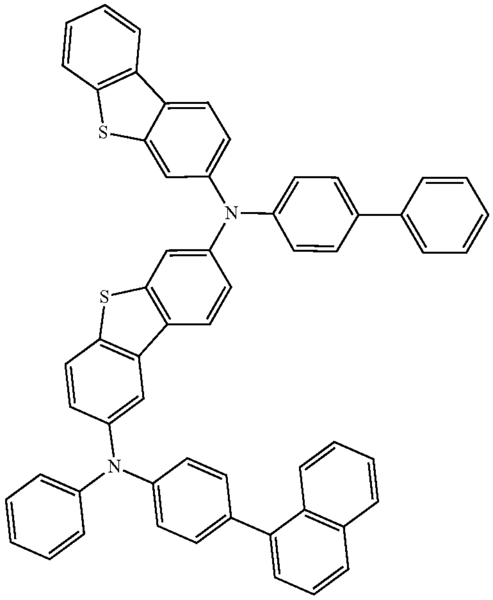

-continued
3-48
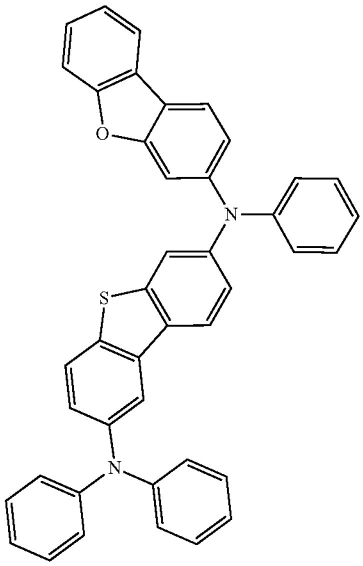
3-49
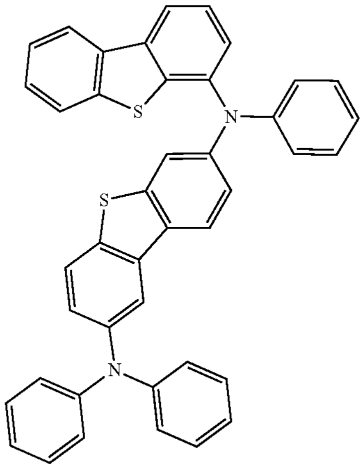
3-50
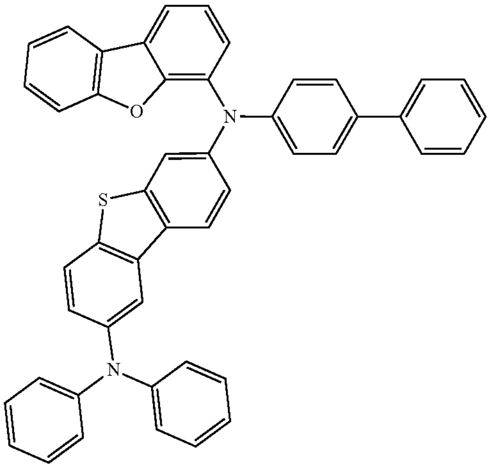
-continued
3-51
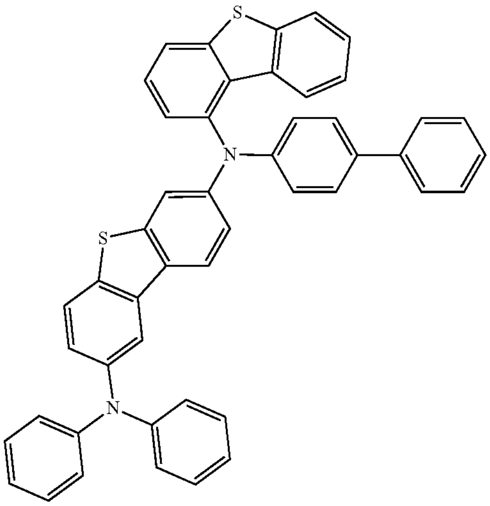
3-52
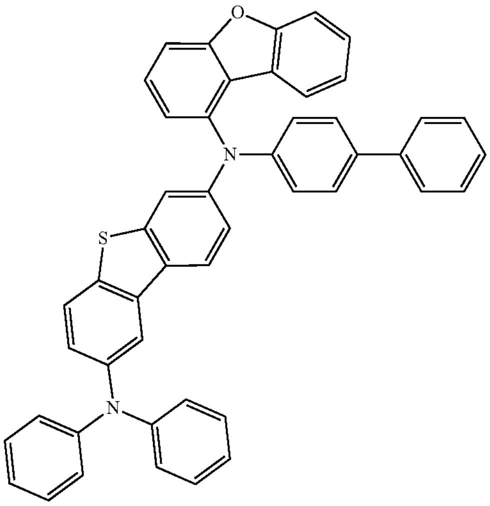
3-53
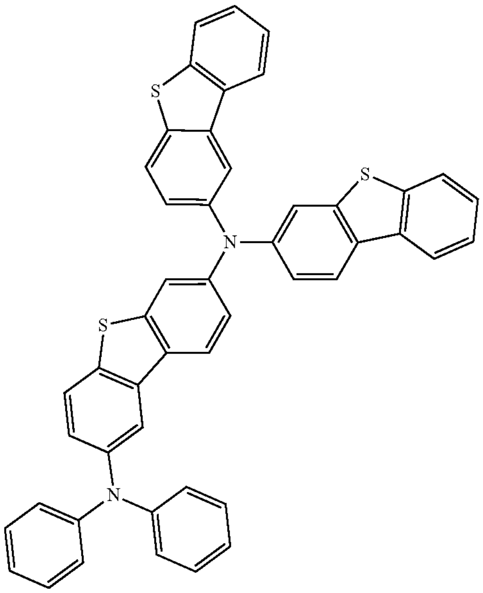

3-54
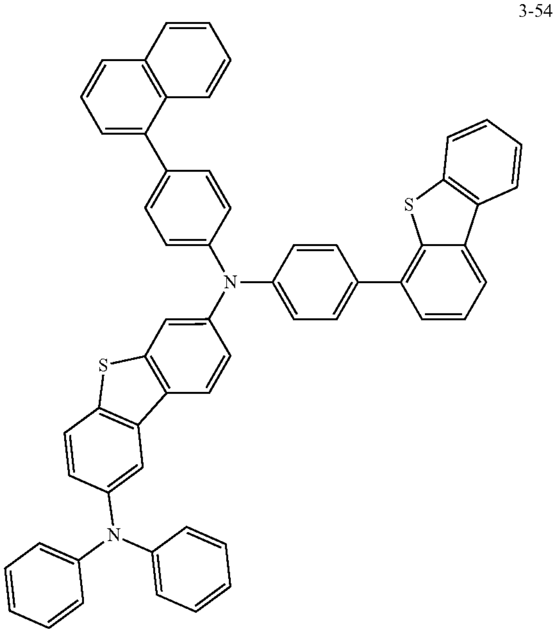
3-55
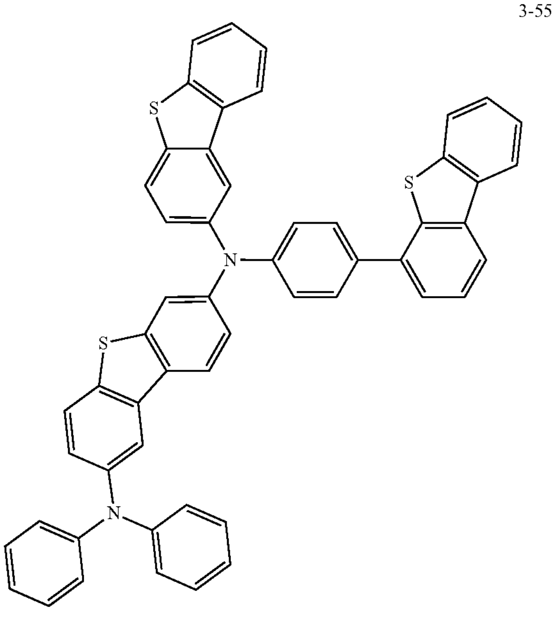
3-56
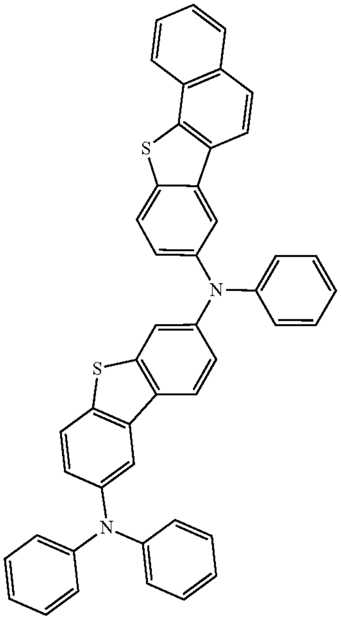
3-57
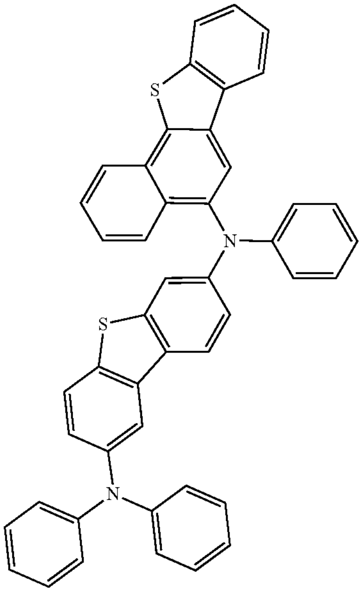

-continued
3-58
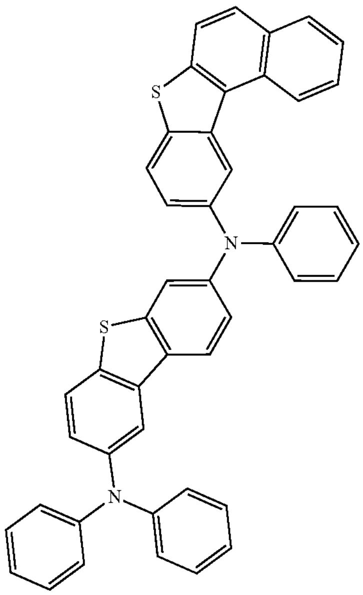
3-59
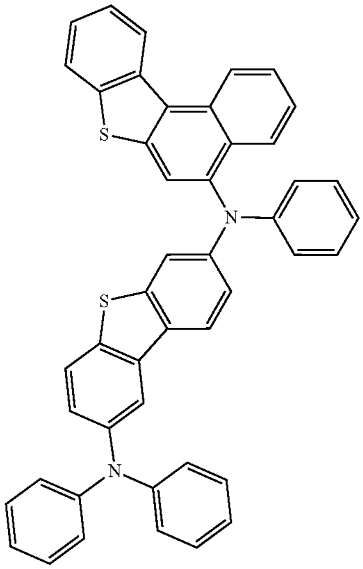
3-60
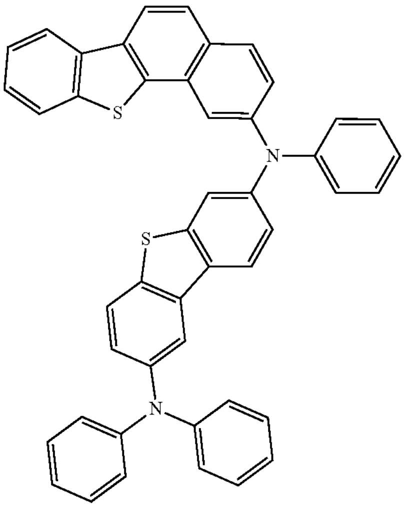
-continued
3-61
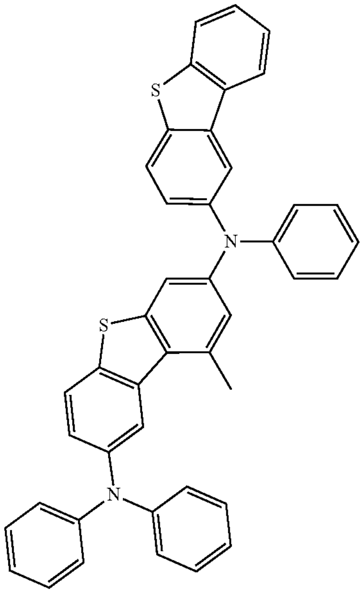
3-62
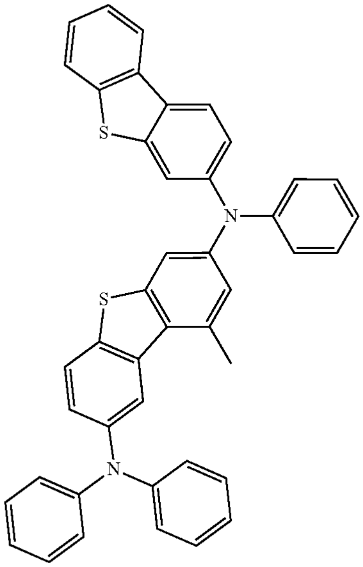
3-63
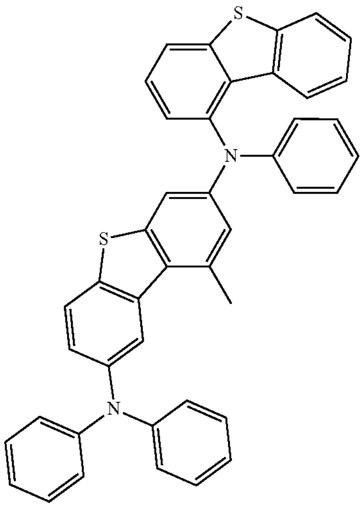

-continued
3-64
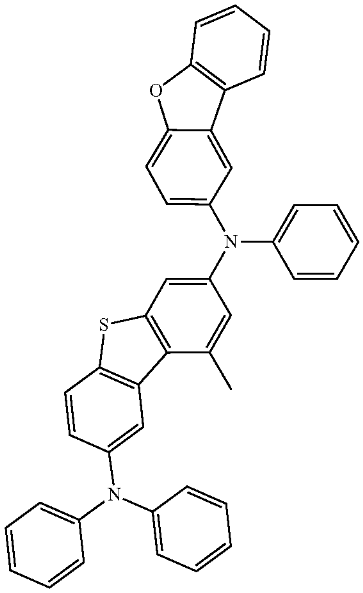
3-65
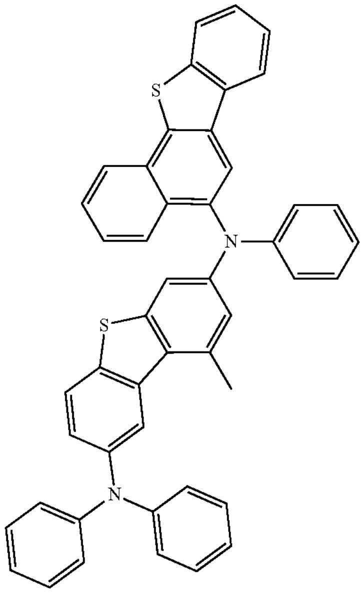
-continued
3-66
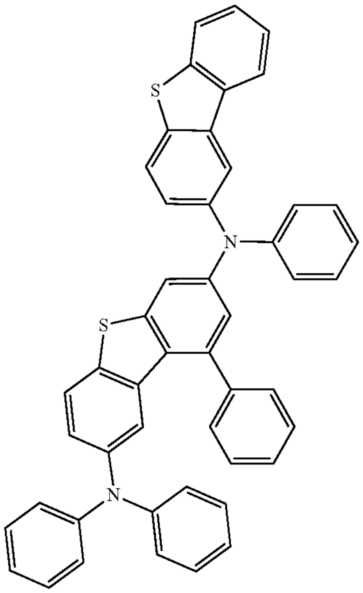
3-67
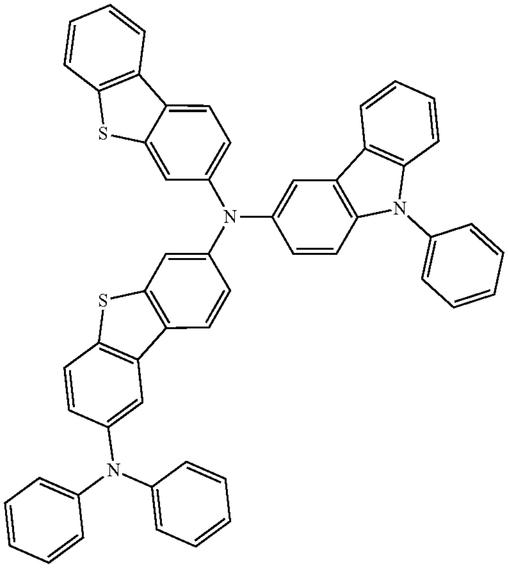

-continued
3-68
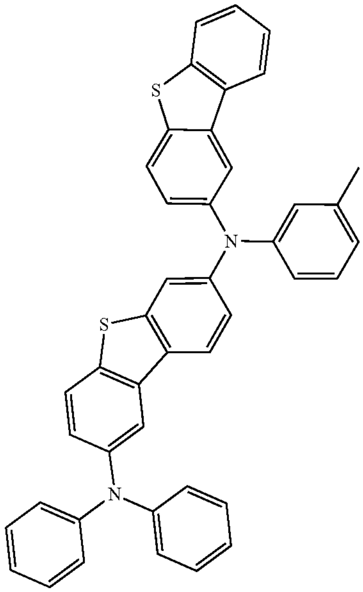
3-70
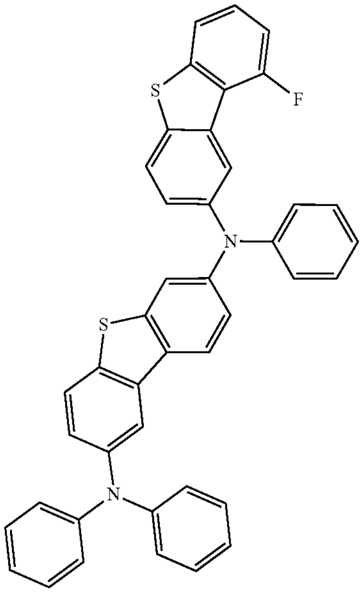
3-69
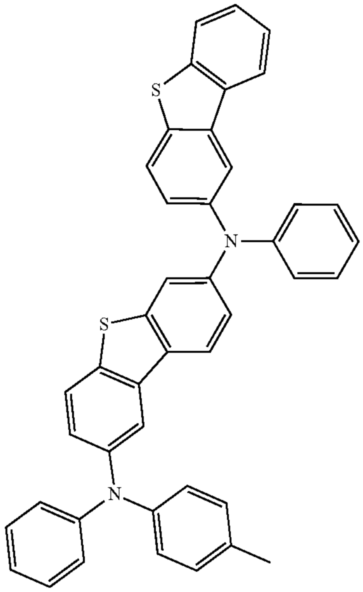
3-71
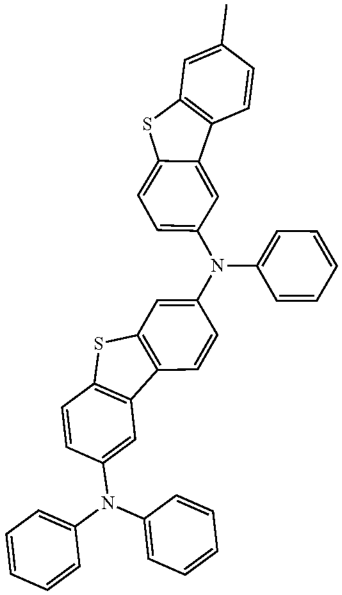

-continued
3-72
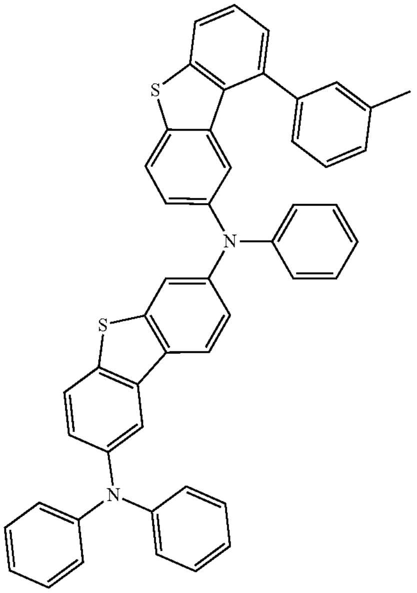
3-73
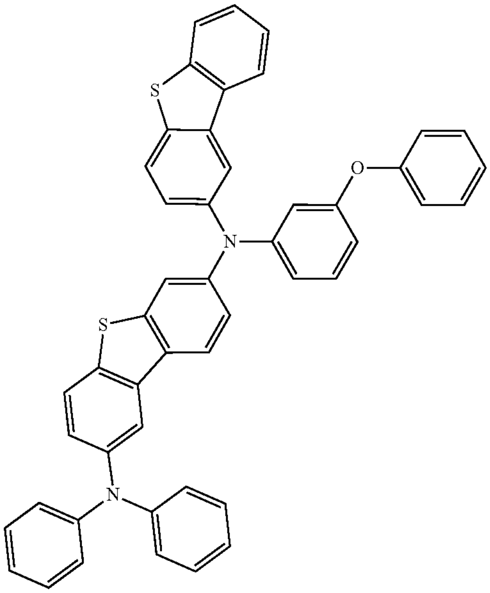
-continued
3-74
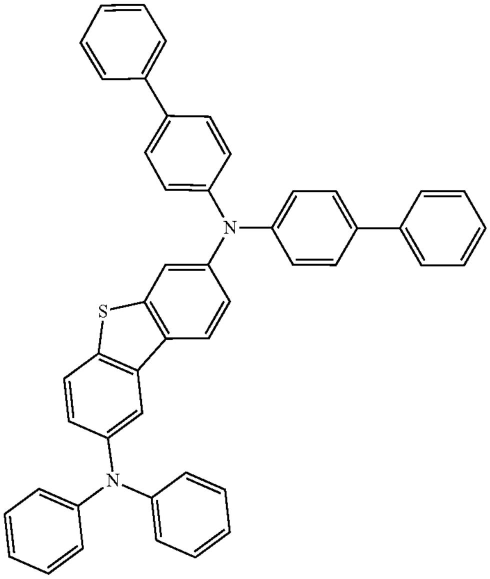
3-75
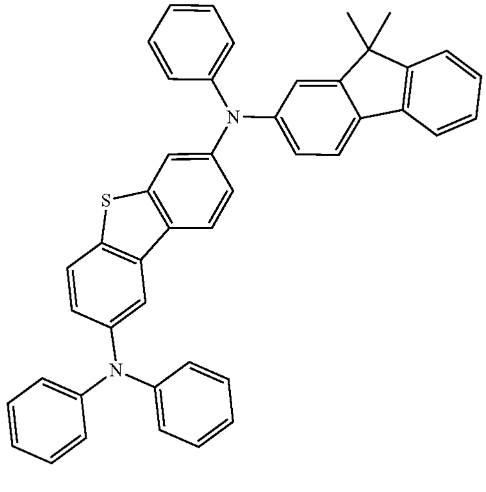

-continued
3-76
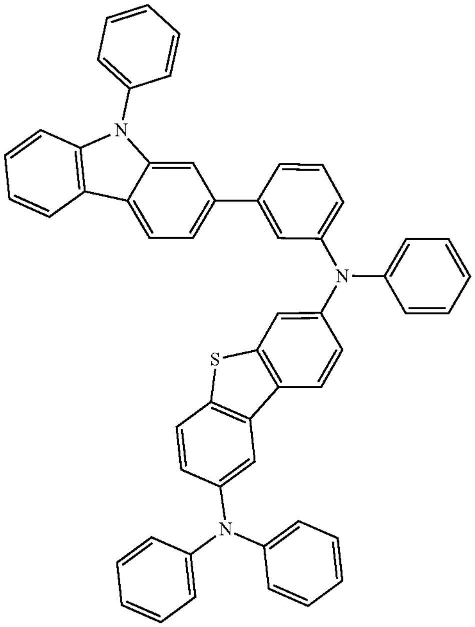
3-77
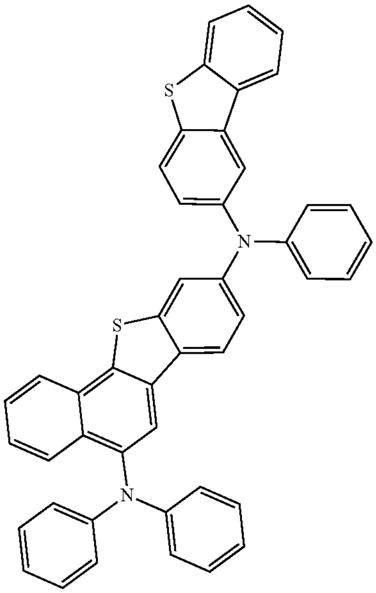
-continued
3-78
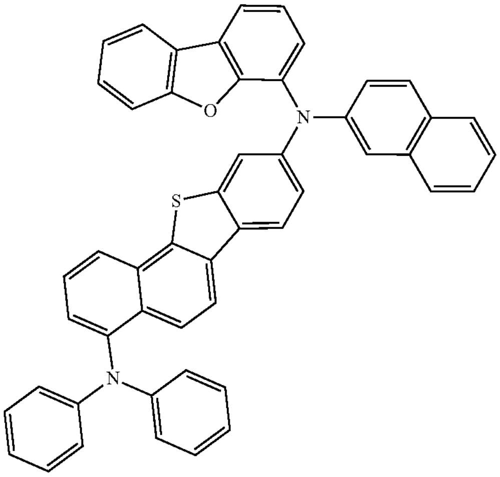
3-79
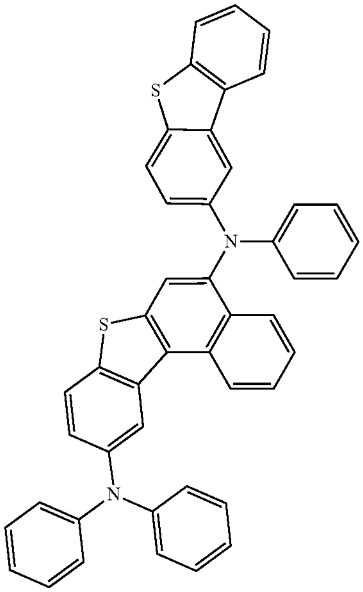
3-80
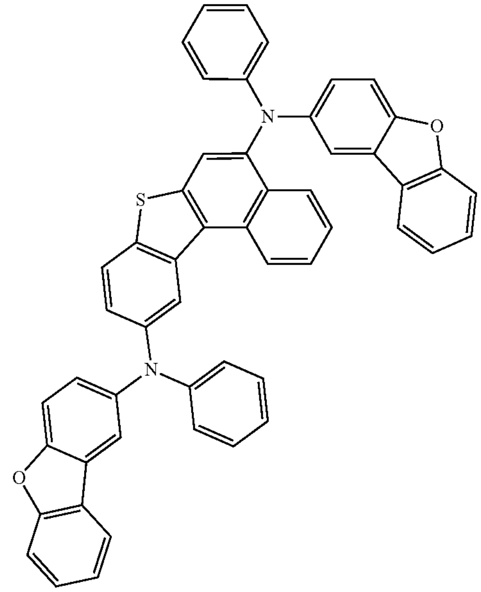

-continued
3-81
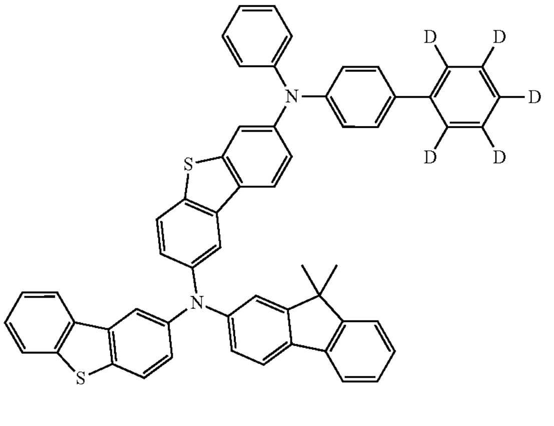
3-82
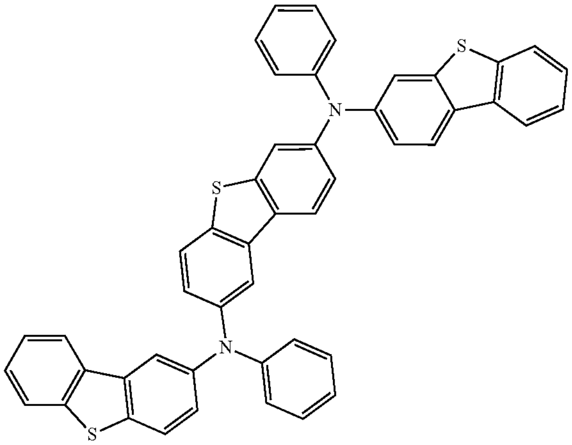
3-83
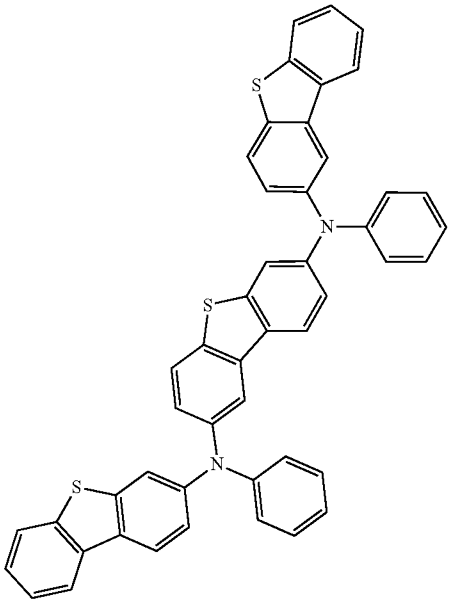
-continued
3-84
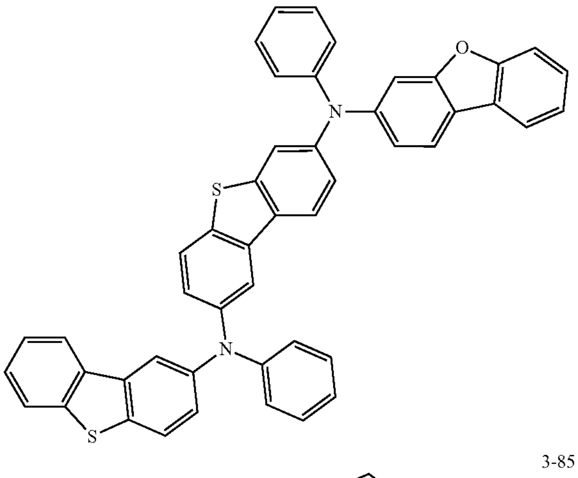
3-85
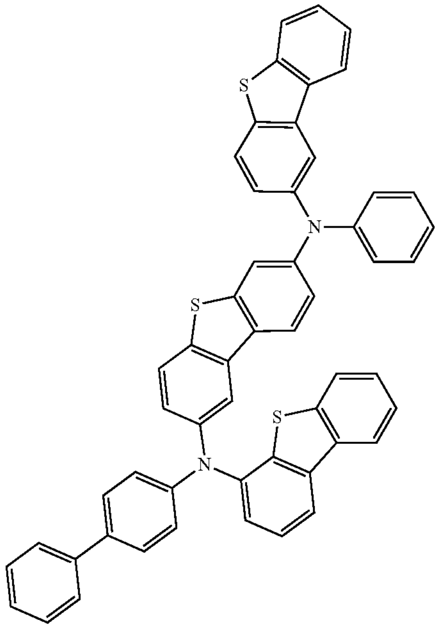
3-86
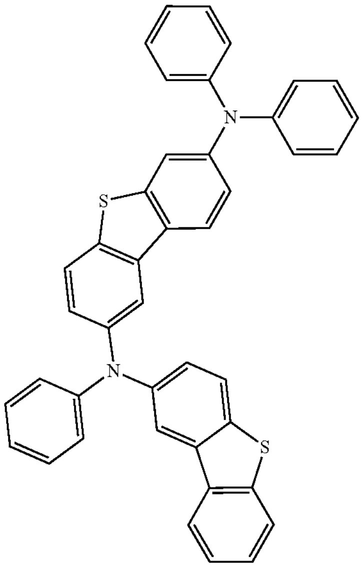

-continued
3-87
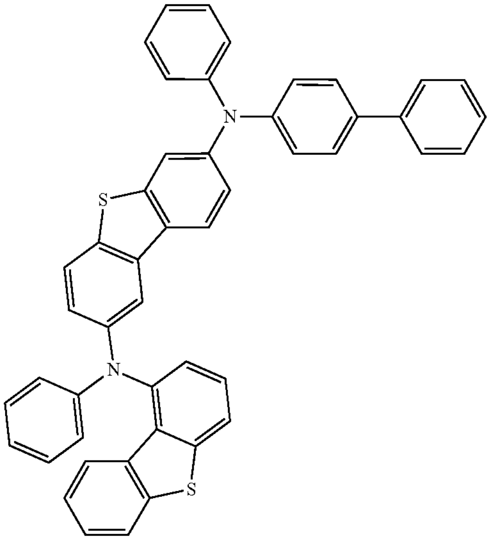
3-88
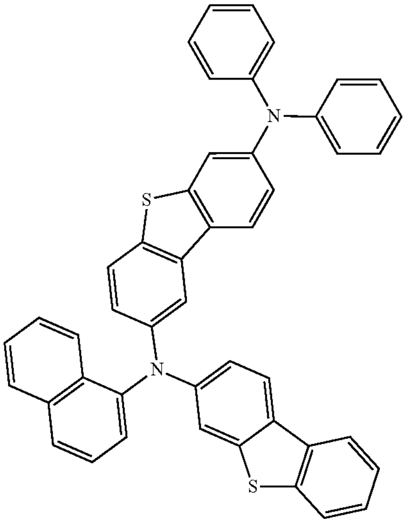
3-89
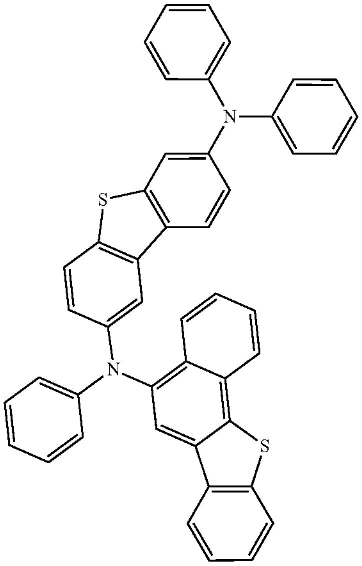
-continued
3-90
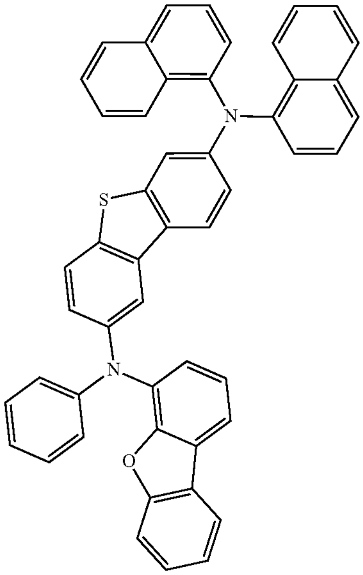
3-91
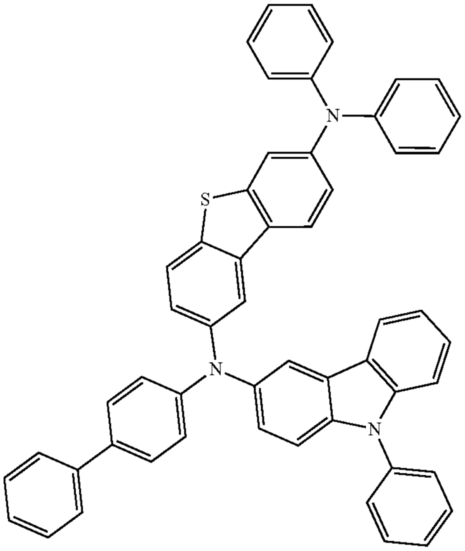

-continued
3-92
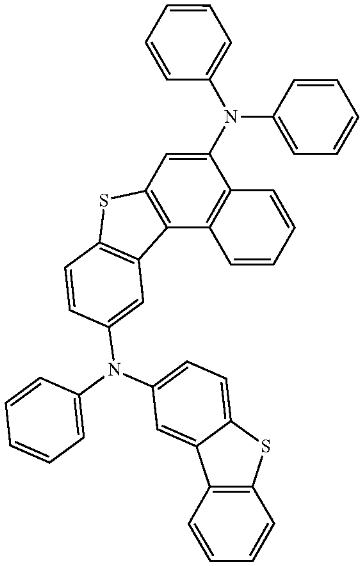
3-93
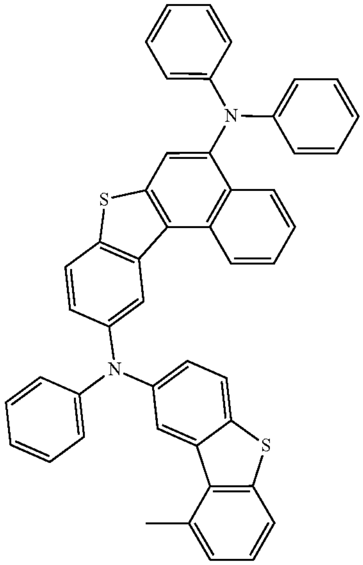
-continued
3-94
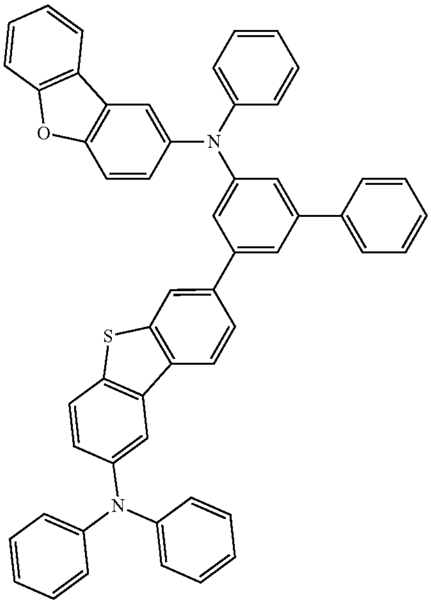
3-95
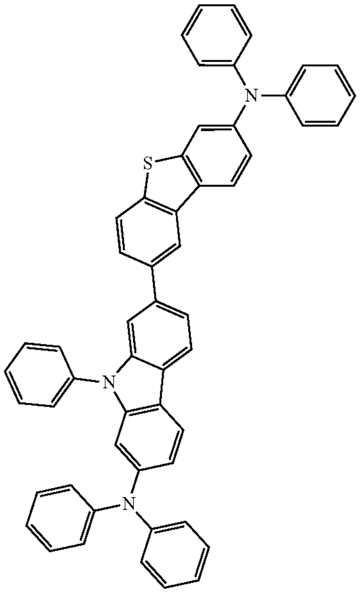

-continued
3-96
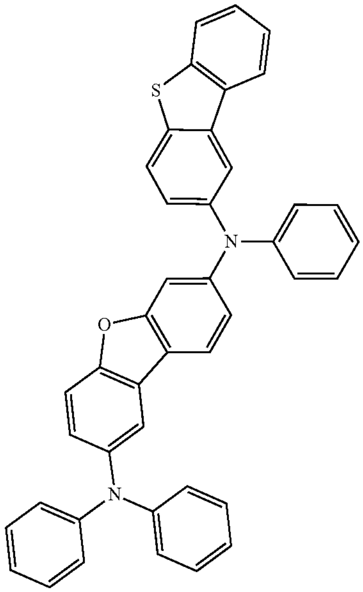
3-97
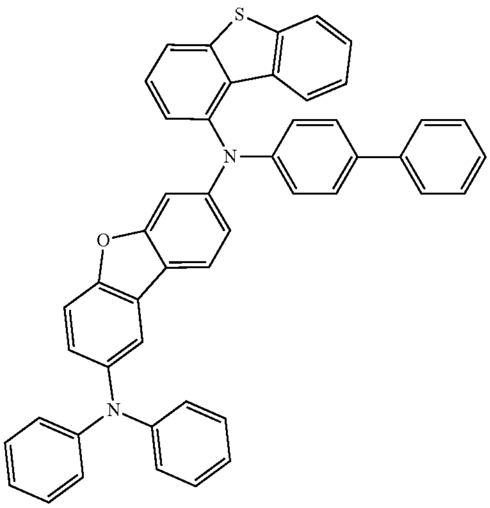
-continued
3-98
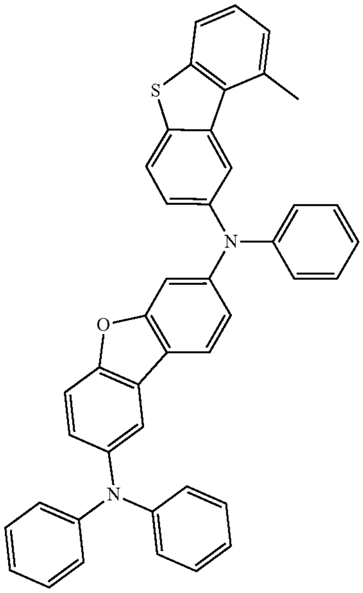
3-99
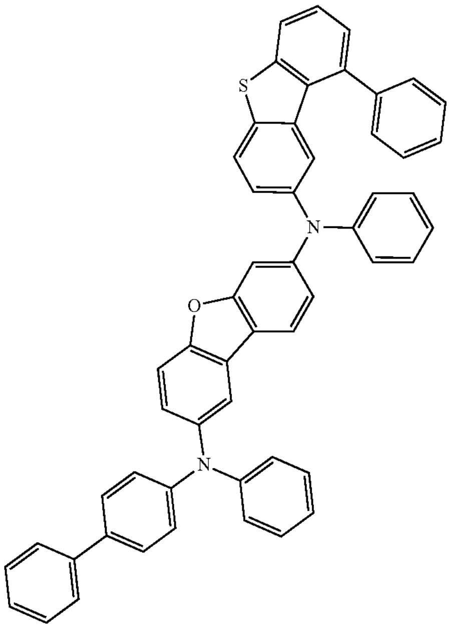

-continued
3-100
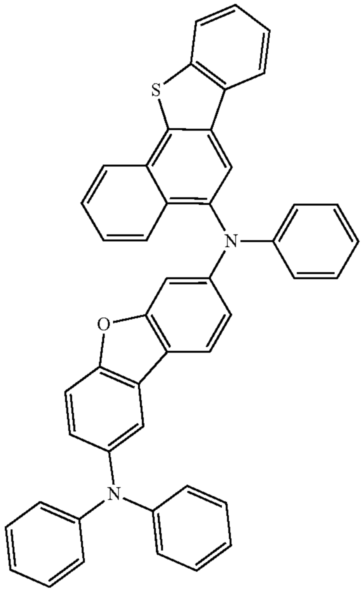
3-101
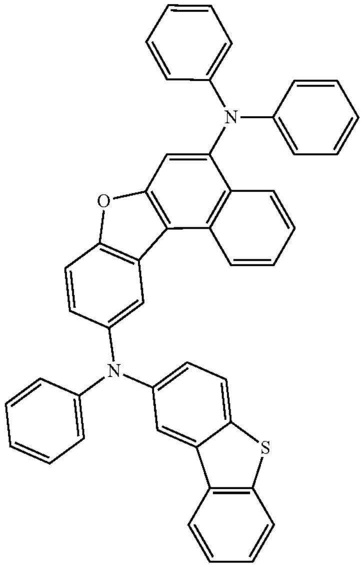
-continued
3-102
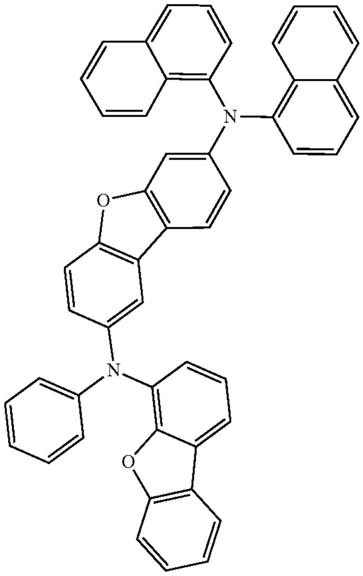
3-103
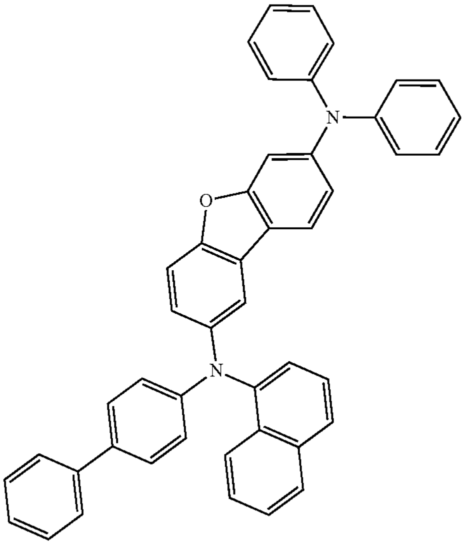

-continued
3-104
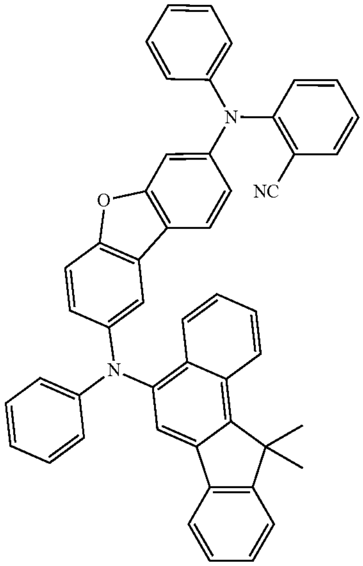
3-105
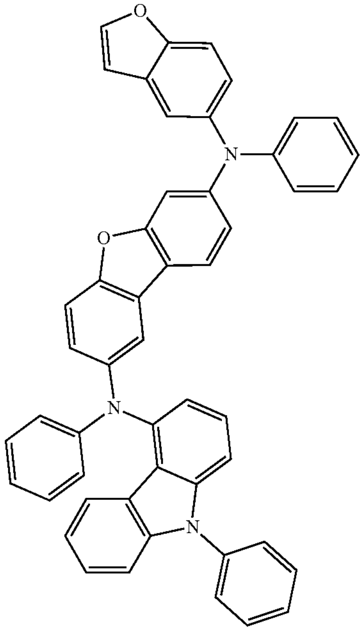
-continued
3-106
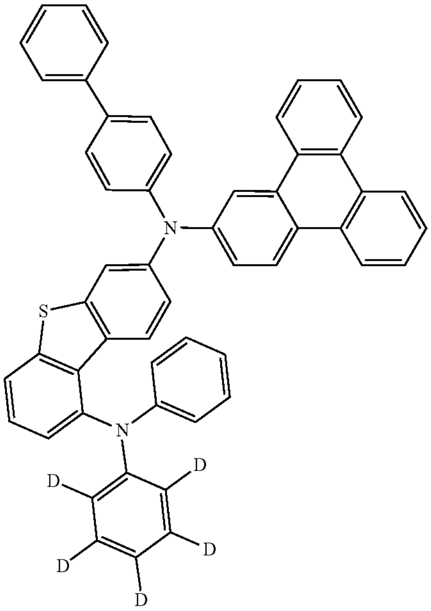
3-107
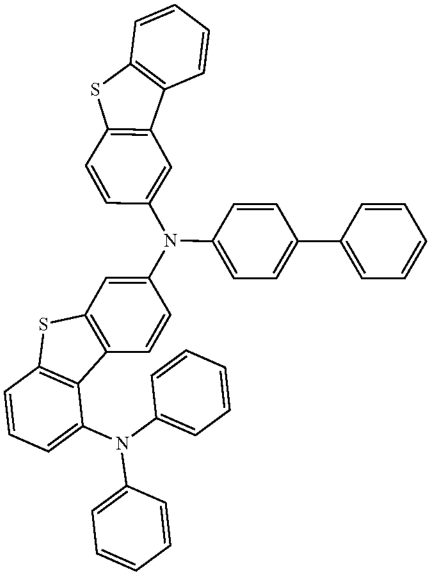

-continued
3-108
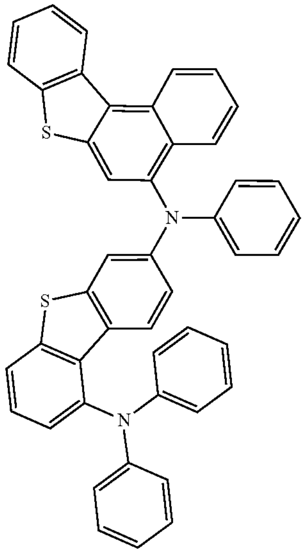
3-109
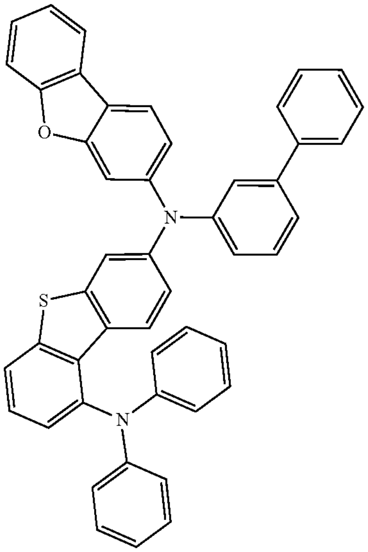
3-110
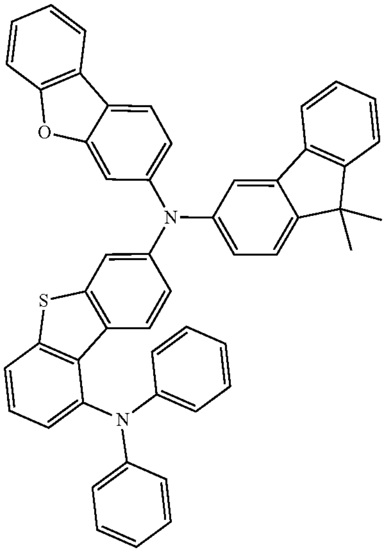
-continued
3-111
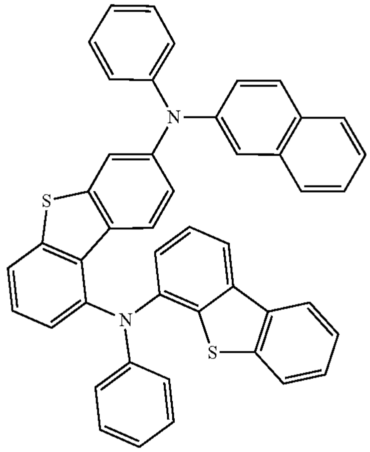
3-112
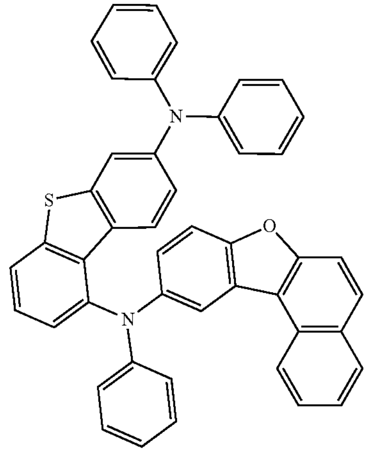
3-113
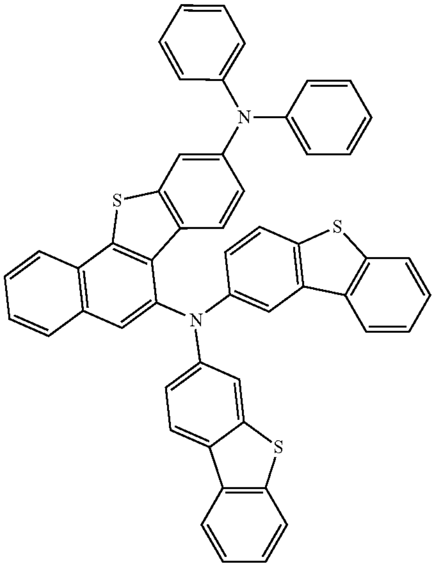

3-114
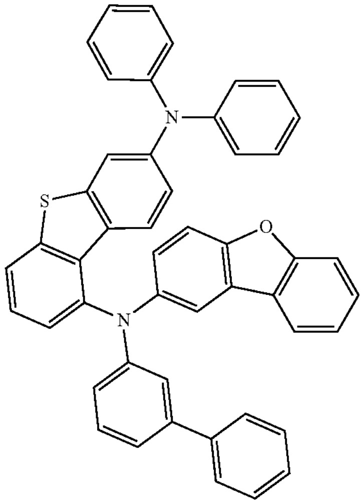
3-115
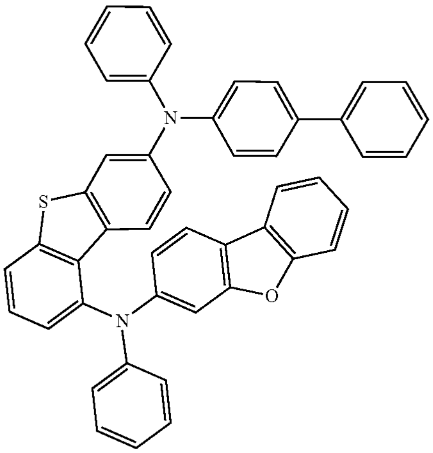
3-116
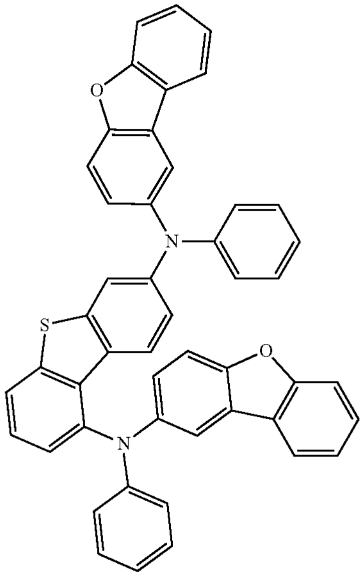
3-117
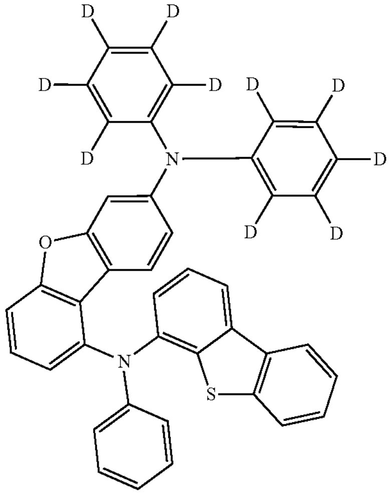
3-118
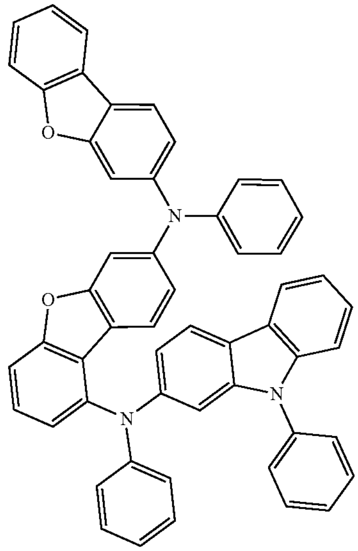
3-119
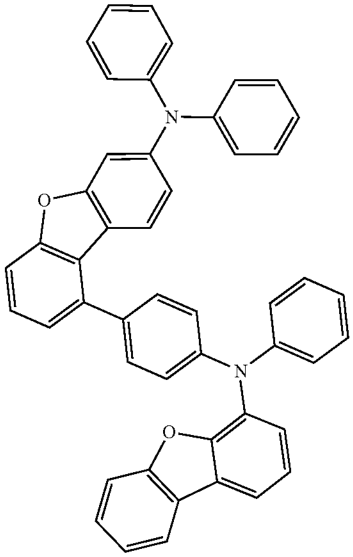

-continued
3-120
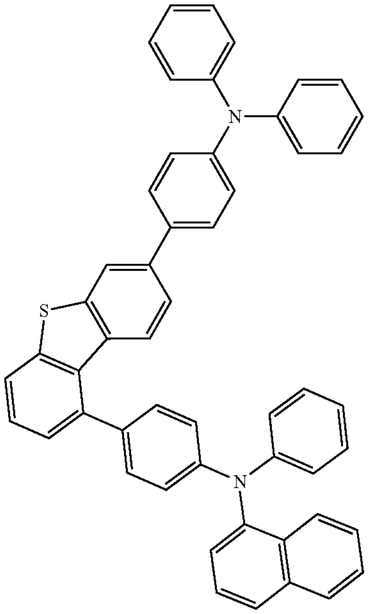
3-121
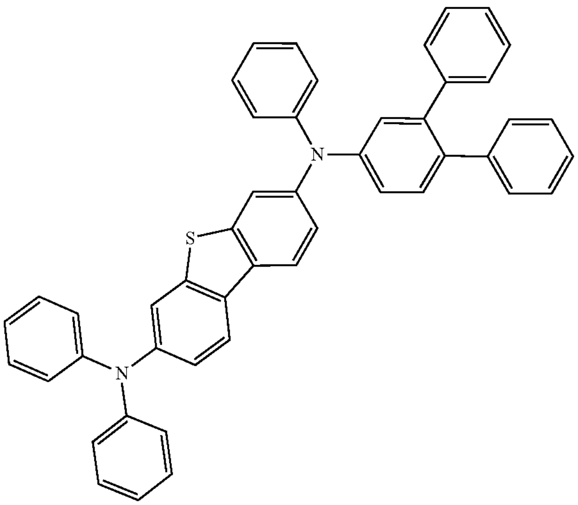
-continued
3-122
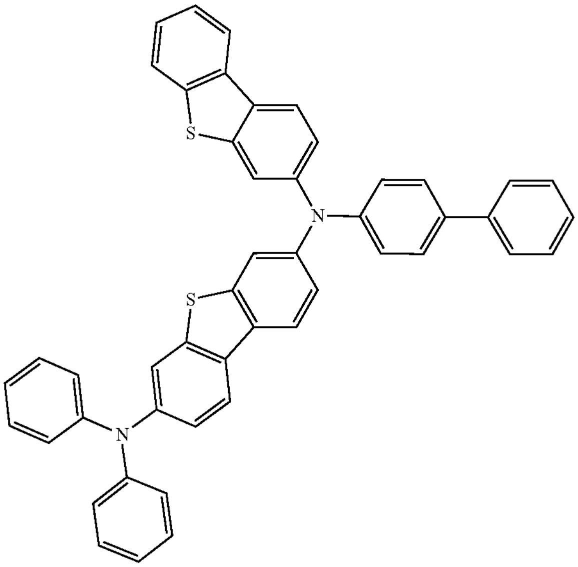
3-123
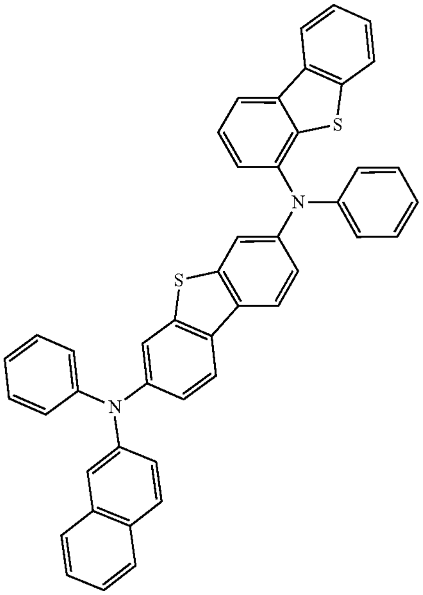

-continued
3-124
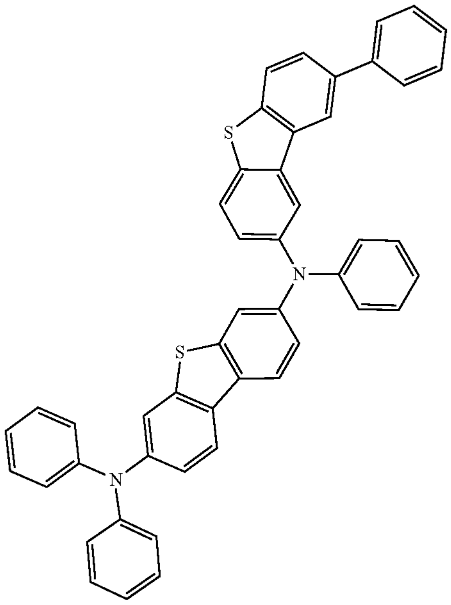
3-125
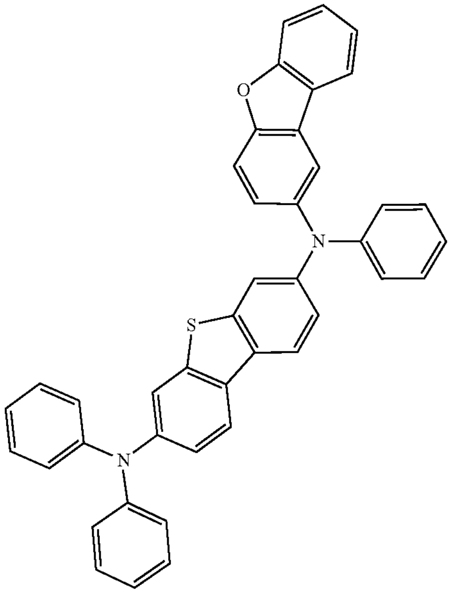
-continued
3-126
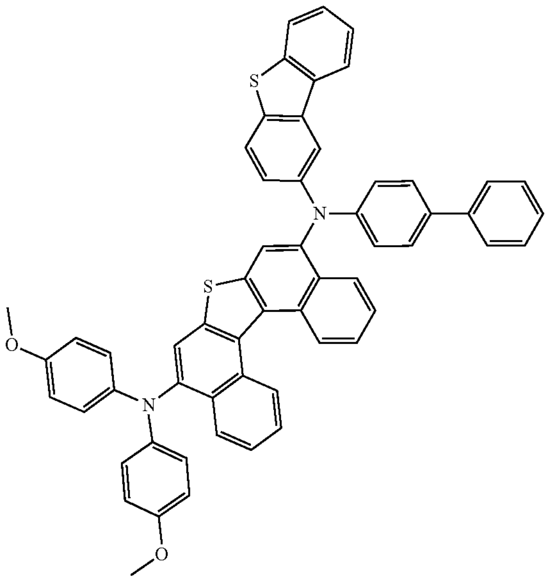
3-127
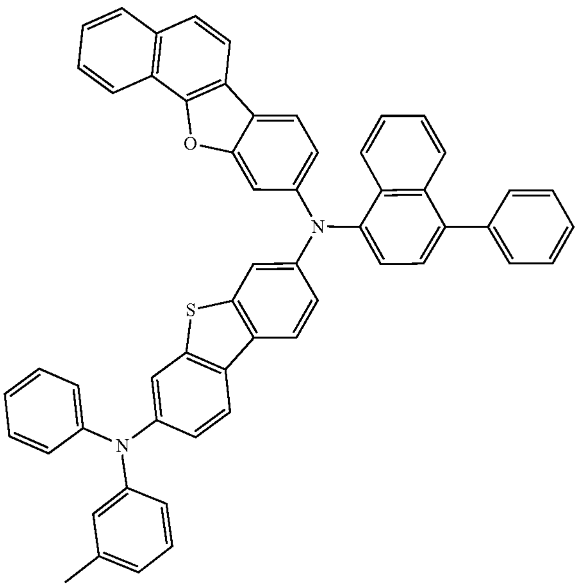

-continued
3-128
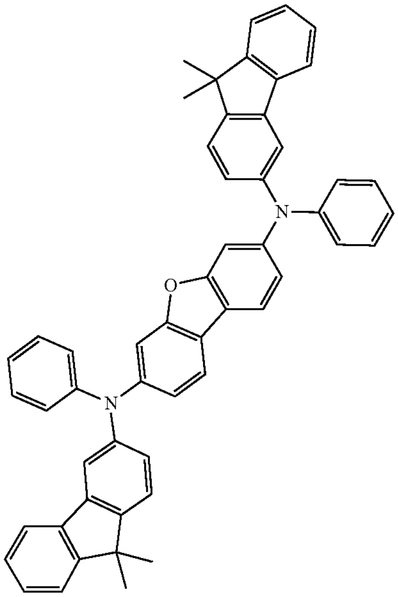
3-129
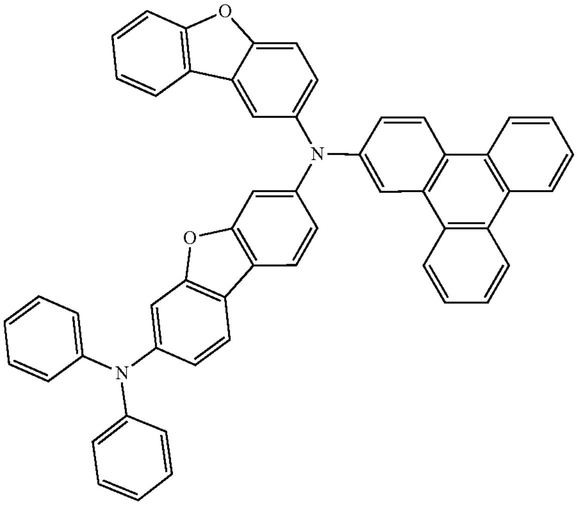
-continued
3-130
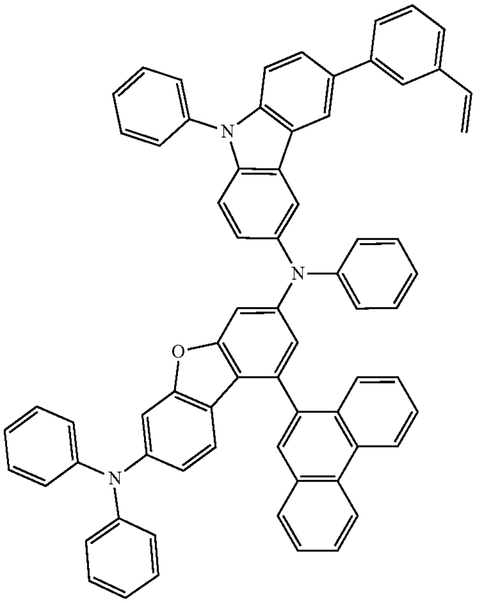
3-131
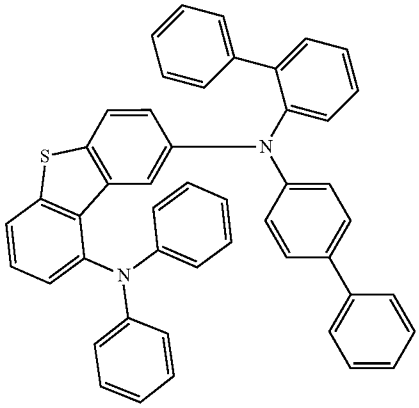
3-132
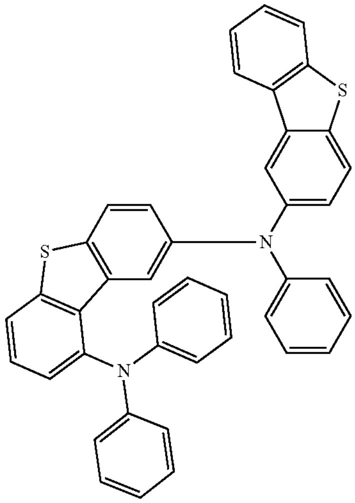

-continued
3-133
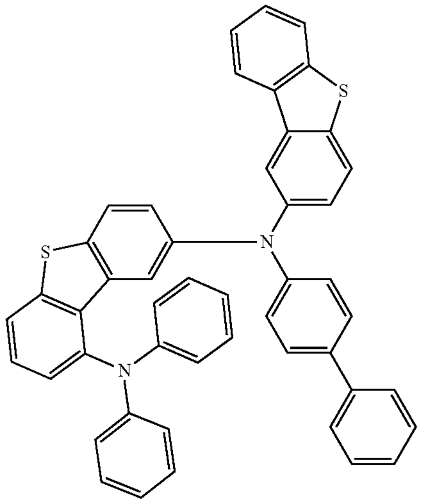
3-134
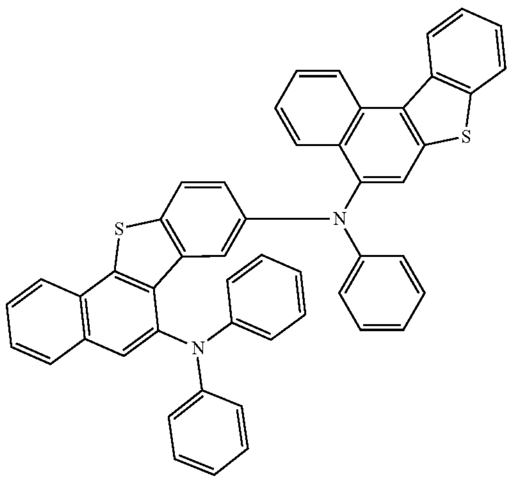
3-135
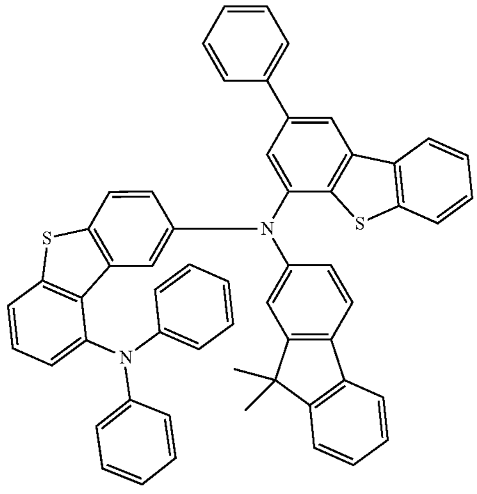
-continued
3-136
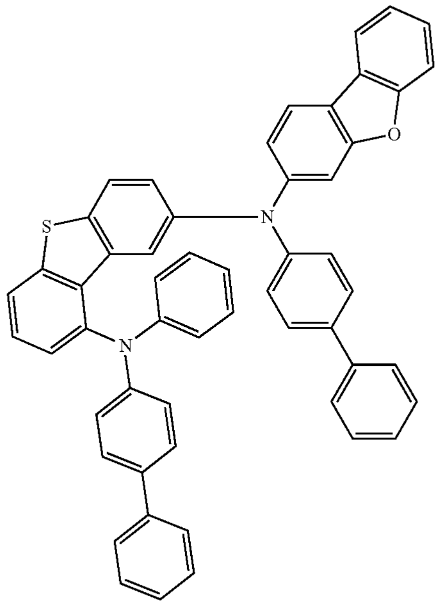
3-137
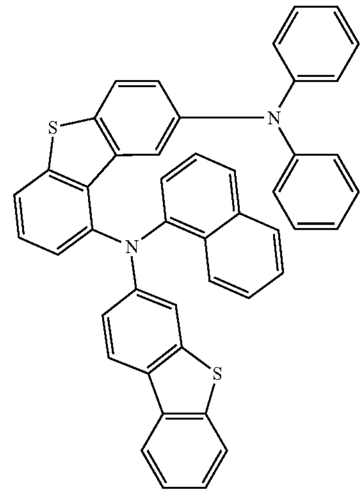
3-138
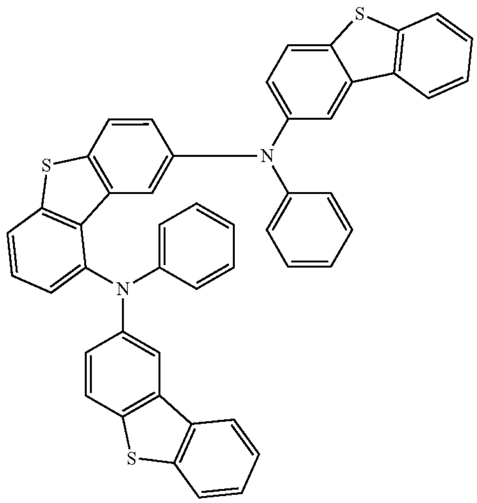

-continued
3-139
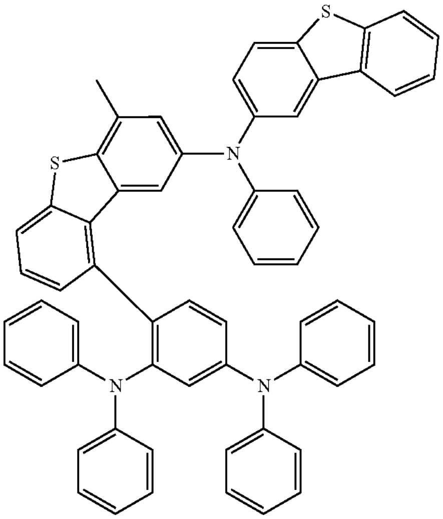
3-140
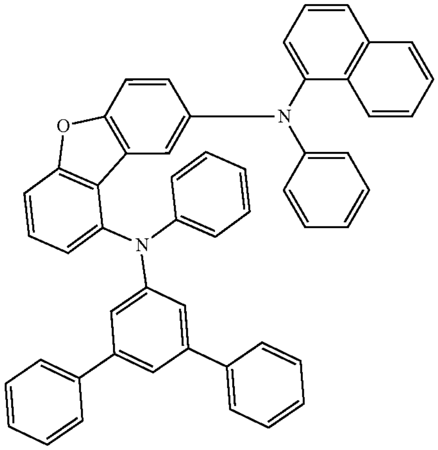
3-141
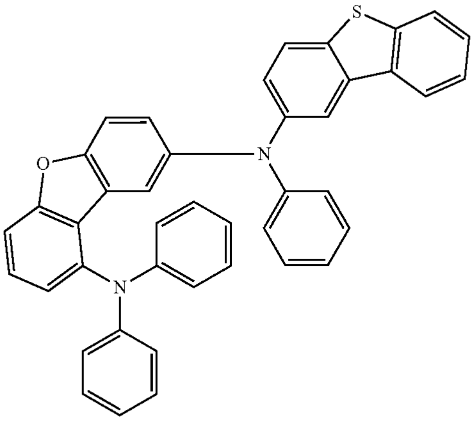
-continued
3-142
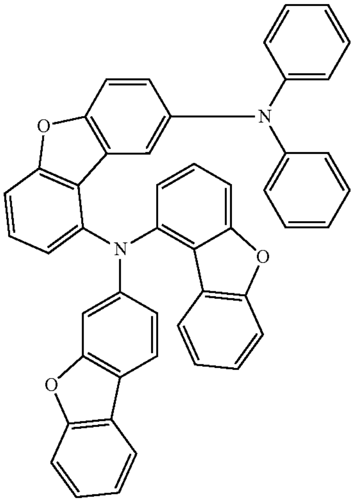
3-143
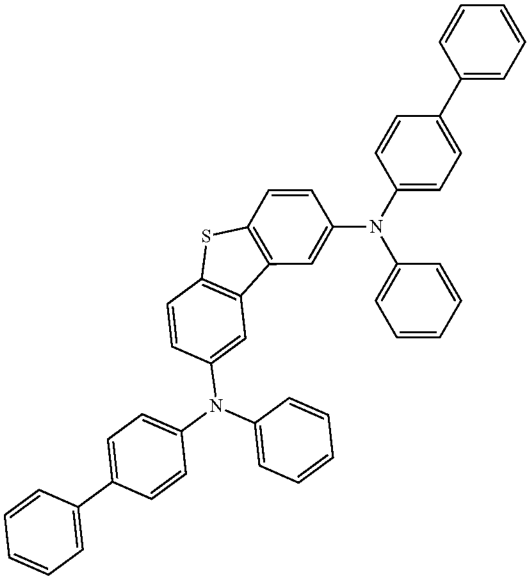
3-144
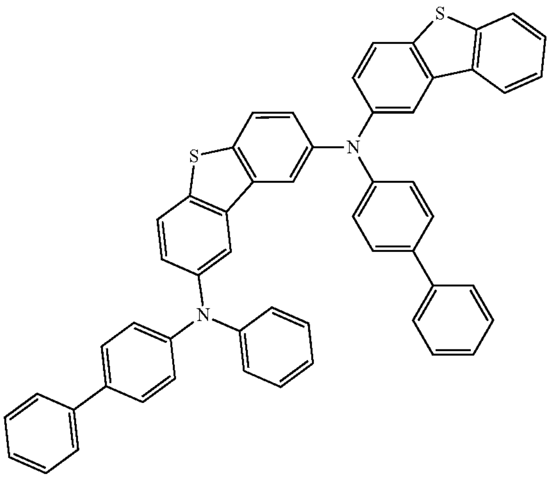

-continued
3-145
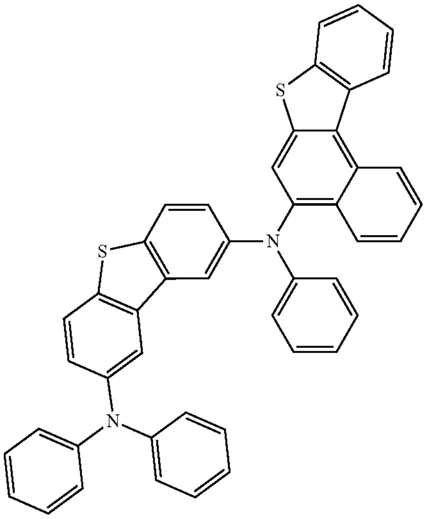
3-146
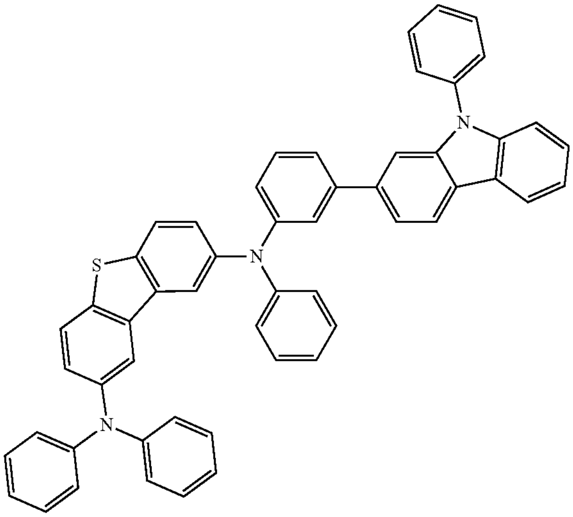
3-147
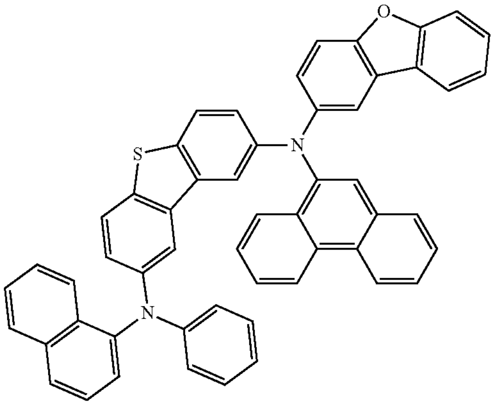
-continued
3-148
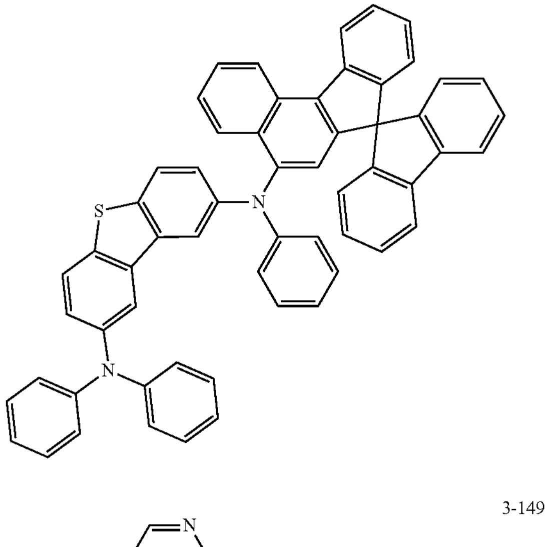
3-149
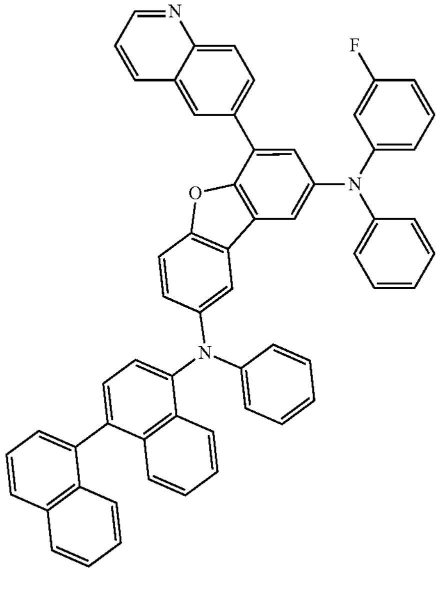
3-150
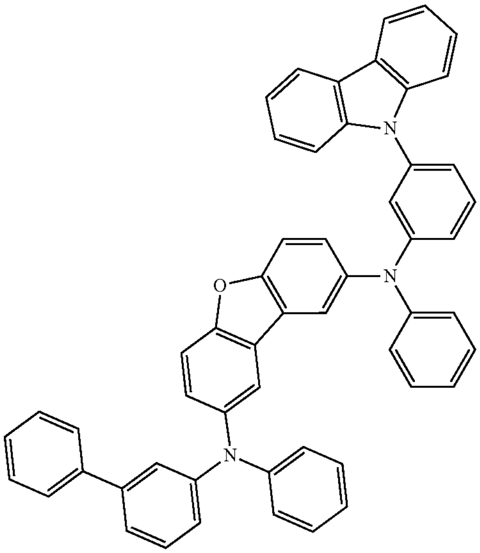

-continued
3-151
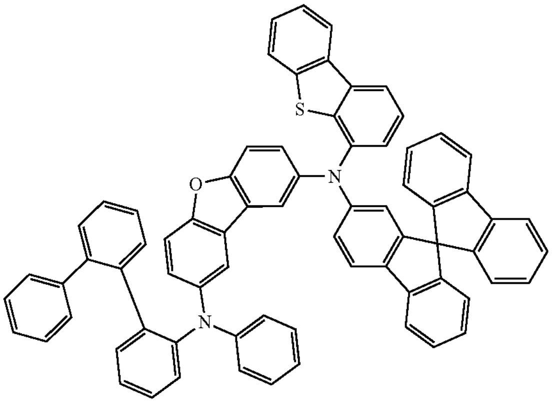
3-152
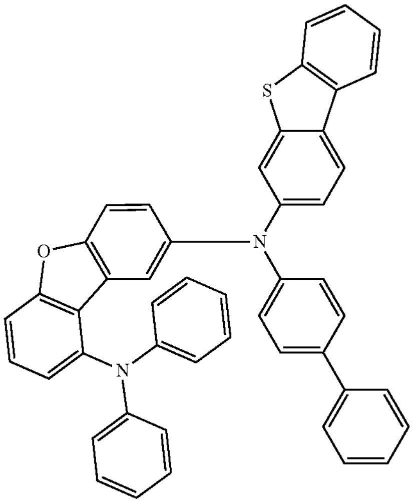
3-153
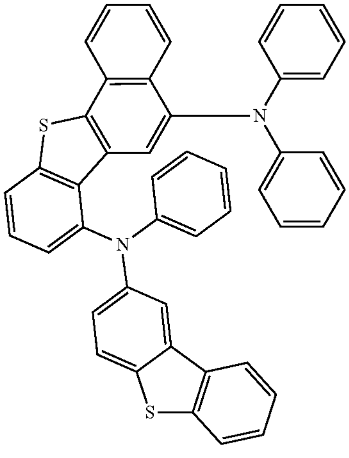
-continued
3-154
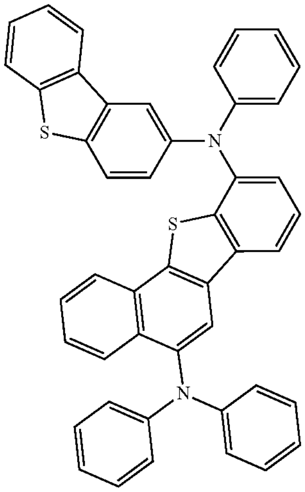
3-155
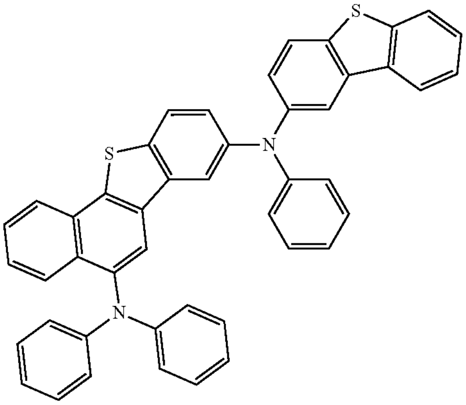
3-156
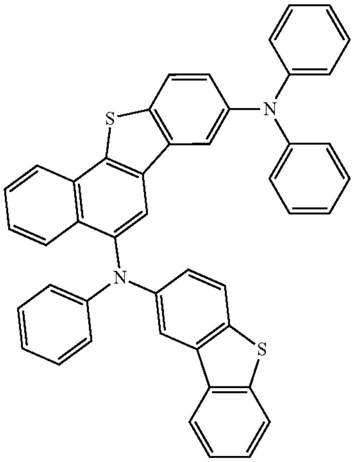

-continued
3-157
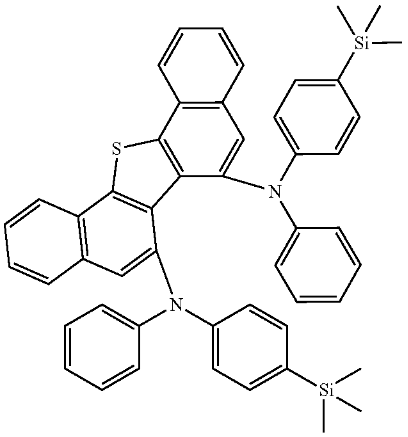
3-158
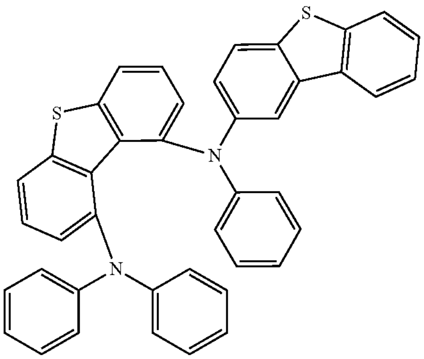
3-159
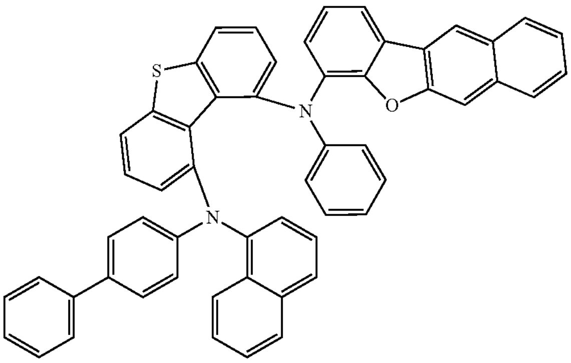
3-160
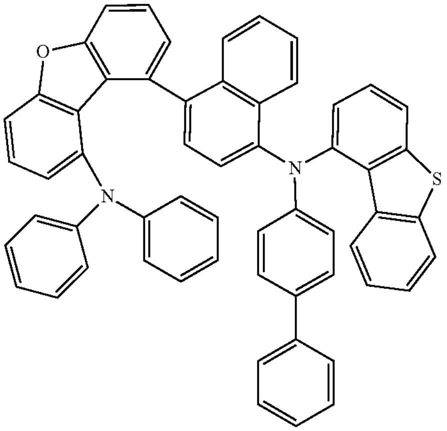
-continued
3-161
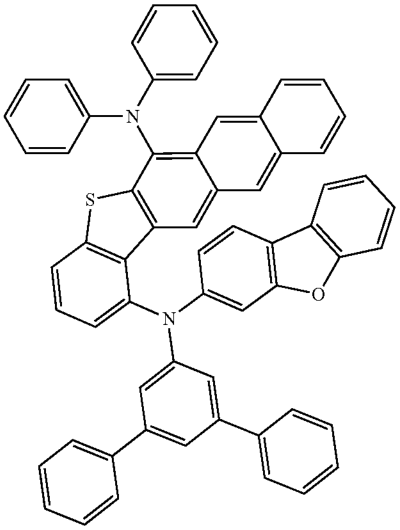
3-162
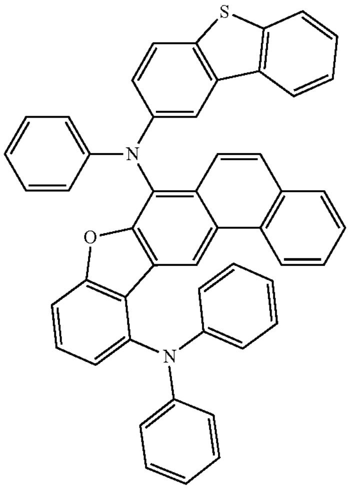
3-163
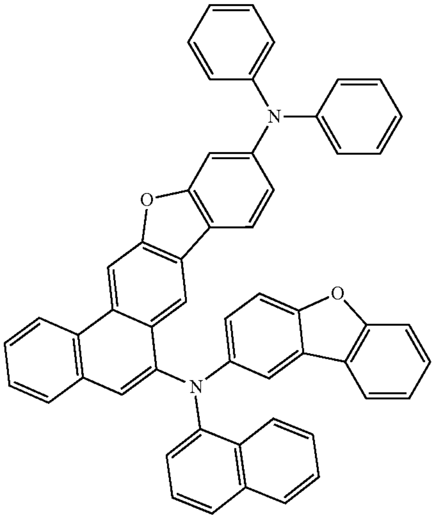

3-164
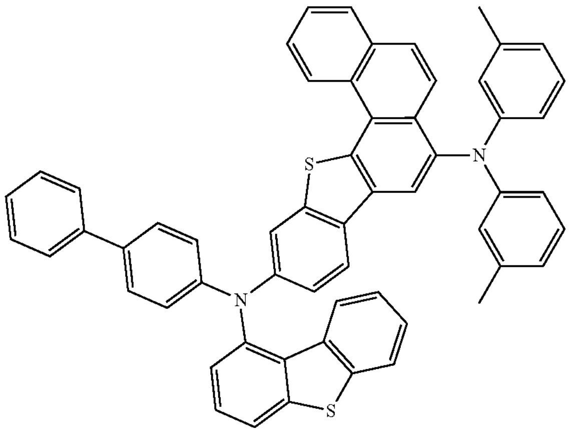
3-165
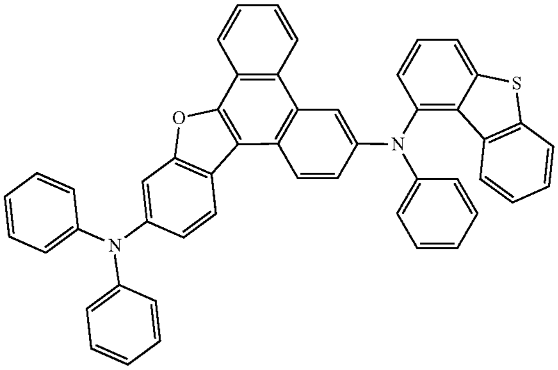
3-166
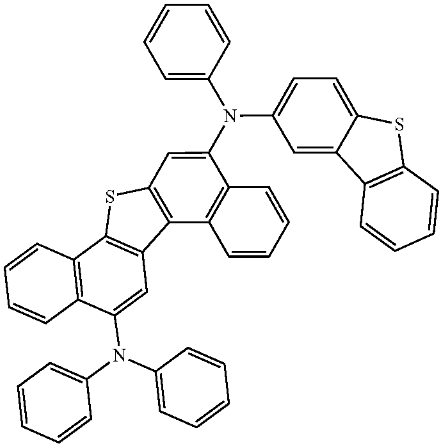
3-167
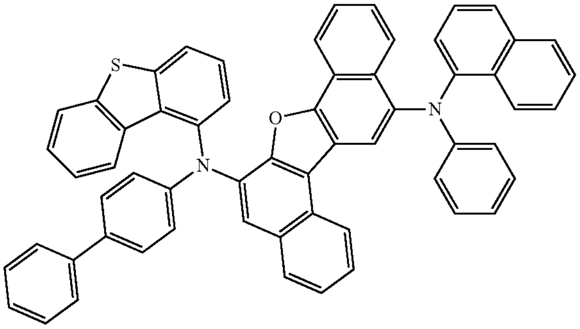
3-168
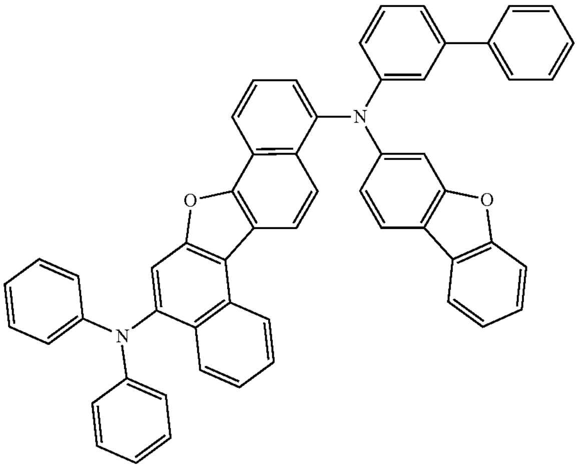
3-169
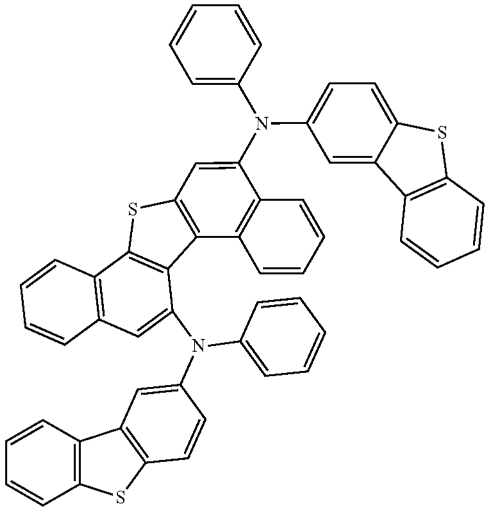
3-170
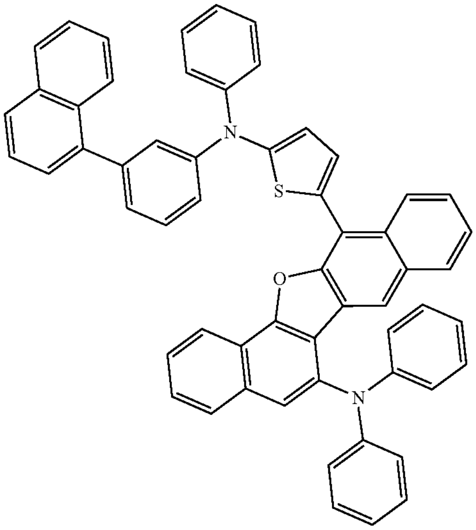

-continued 3-171

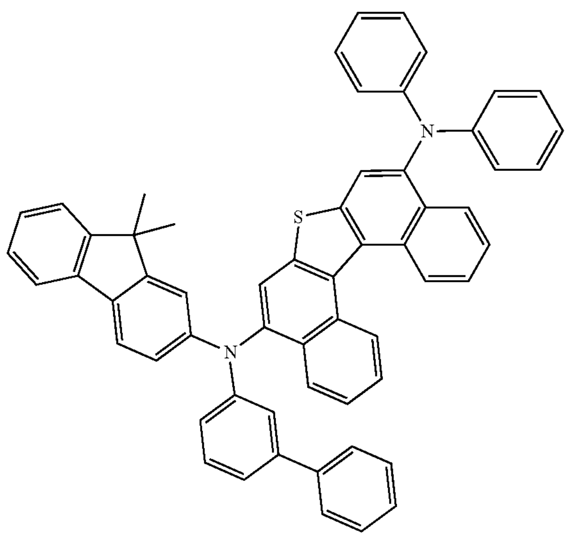

3-172

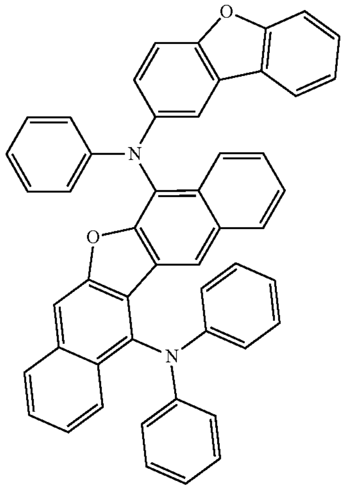

3-173

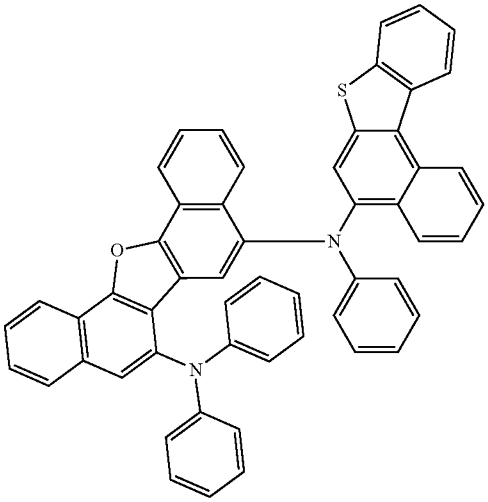

-continued 3-174

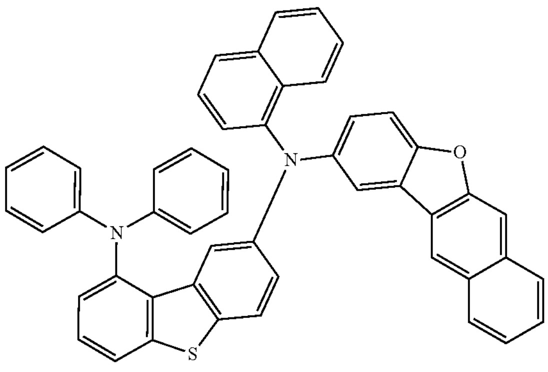

3-175

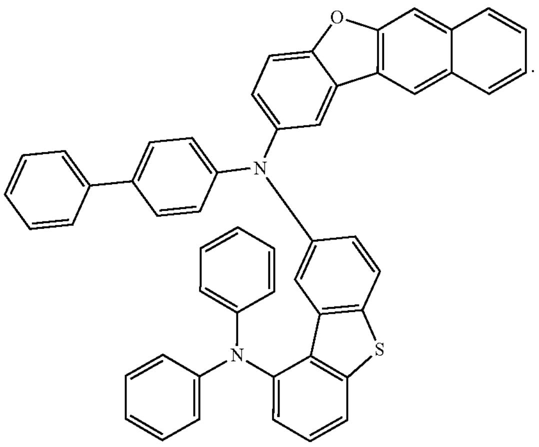

23. The organic electric element of claim 17, further comprising a layer for improving luminous efficiency formed on one side of the first electrode or one side of the second electrode, the side not facing the organic material layer.

24. The organic electric element of claim 17, wherein the organic material layer comprises two or more stacks, the stacks comprising a hole transport layer, a light emitting layer, and an electron transport layer in sequence formed on the anode.

25. The organic electric element of claim 24, wherein the organic material layer further comprises a charge generation layer formed between the two or more stacks.

26. An electronic device comprising a display device and a control unit for driving the display device, wherein the display device comprises the organic electric element of claim 17.

27. The electronic device of claim 26, wherein the organic electric element is selected from the group consisting of an organic light emitting diode, an organic solar cell, an organic photo conductor, an organic transistor, an element for monochromatic illumination and a quantum dot display.

* * * * *